US008802661B2

(12) United States Patent
Regueiro-Ren et al.

(10) Patent No.: US 8,802,661 B2
(45) Date of Patent: Aug. 12, 2014

(54) C-28 AMIDES OF MODIFIED C-3 BETULINIC ACID DERIVATIVES AS HIV MATURATION INHIBITORS

(75) Inventors: Alicia Regueiro-Ren, Middletown, CT (US); Zheng Liu, Beacon Falls, CT (US); Jacob Swidorski, Southington, CT (US); Nicholas A. Meanwell, East Hampton, CT (US); Sing-Yuen Sit, Meriden, CT (US); Jie Chen, Madison, CT (US); Yan Chen, Guilford, CT (US); Ny Sin, East Hampton, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 284 days.

(21) Appl. No.: 13/151,722

(22) Filed: Jun. 2, 2011

(65) Prior Publication Data

US 2012/0142653 A1   Jun. 7, 2012

Related U.S. Application Data

(60) Provisional application No. 61/351,332, filed on Jun. 4, 2010.

(51) Int. Cl.
*A61K 31/56* (2006.01)
*A61K 31/58* (2006.01)
*C07J 53/00* (2006.01)

(52) U.S. Cl.
USPC ............. 514/169; 514/172; 514/176; 540/47; 552/510

(58) Field of Classification Search
USPC .................... 514/169, 172, 176, 183; 540/47; 544/58.2, 106, 358, 383; 546/184, 242, 546/245; 548/146, 152, 267.6, 300.1, 400; 549/76; 552/510; 564/161
See application file for complete search history.

(56) References Cited

U.S. PATENT DOCUMENTS

| 5,679,828 | A | 10/1997 | Lee et al. |
| 7,354,924 | B2 | 4/2008 | Wang et al. |
| 7,365,221 | B2 | 4/2008 | Allaway et al. |
| 7,745,625 | B2 | 6/2010 | Ueda et al. |
| 2005/0239748 | A1 | 10/2005 | Power et al. |
| 2008/0207573 | A1 | 8/2008 | Yager et al. |
| 2010/0216751 | A1 | 8/2010 | Jacob et al. |

FOREIGN PATENT DOCUMENTS

| WO | WO 98/51293 | 11/1998 |
| WO | WO 98/51294 | 11/1998 |
| WO | WO 2004/089357 | 10/2004 |
| WO | WO 2006/001964 | 1/2006 |
| WO | WO 2008/097341 | 8/2008 |
| WO | WO 2008/127364 | 10/2008 |
| WO | WO 2009/100532 | 8/2009 |
| WO | WO 2009/114083 | 9/2009 |

OTHER PUBLICATIONS

U.S. Appl. No. 61/537,099, filed Sep. 21, 2011, Liu et al.
U.S. Appl. No. 61/599,040, filed Feb. 15, 2012, Swidorski et al.
U.S. Appl. No. 13/151,706, filed Jun. 2, 2011, Regueiro-Ren et al.
U.S. Appl. No. 13/359,680, filed Jan. 27, 2012, Regueiro-Ren et al.
U.S. Appl. No. 13/359,727, filed Jan. 27, 2012, Regueiro-Ren et al.
Blair, W.S. et al., "HIV-1 entry—an expanding portal for drug discovery", Drug Discovery Today, vol. 5, No. 5, pp. 183-194 (2000).
Hotoda, H., "Small-molecule inhibitors of HIV-1 entry via chemokine receptors", Drugs of the Future, vol. 24, No. 12, pp. 1355-1362 (1999).
Kashiwada, Y. et al., "Betulinic Acid and Dihydrobetulinic Acid Derivatives as Potent Anti-HIV Agents", Journal of Medicinal Chemistry, vol. 39, No. 5, pp. 1016-1017 (1996).
Meanwell, N.A. et al., "Inhibitors of the entry of HIV into host cells", Current Opinion in Drug Discovery & Development, vol. 6, No. 4, pp. 451-461 (2003).
Pokrovskii, A.G. et al., "Synthesis of derivatives of plant triterpenes and study of their antiviral and immunostimulating activity", Khimiya y Interesakh Ustoichivogo Razvitiya, vol. 9, No. 3, pp. 485-491 (2001) (English abstract).
Sodroski, J.G., "HIV-1 Entry Inhibitors in the Side Pocket: Minireview", Cell, vol. 99, pp. 243-246 (1999).
Yu, D. et al., "Anti-AIDS Agents 69. Moronic Acid and Other Triterpene Derivatives as Novel Potent Anti-HIV Agents", Journal of Medicinal Chemistry, vol. 49, No. 18, pp. 5462-5469 (2006).

*Primary Examiner* — Barbara P Badio
(74) *Attorney, Agent, or Firm* — John F. Levis

(57) ABSTRACT

Compounds having drug and bio-affecting properties, their pharmaceutical compositions and methods of use are set forth. In particular, modified C-3 and C-28 betulinic acid derivatives that possess unique antiviral activity are provided as HIV maturation inhibitors. These compounds are useful for the treatment of HIV and AIDS.

22 Claims, No Drawings

US 8,802,661 B2

C-28 AMIDES OF MODIFIED C-3 BETULINIC ACID DERIVATIVES AS HIV MATURATION INHIBITORS

CROSS-REFERENCE TO RELATED APPLICATION

This non-provisional application claims the benefit of U.S. Provisional Application Ser. No. 61/351,332 filed Jun. 4, 2010.

FIELD OF THE INVENTION

The present invention relates to novel compounds useful against HIV, and more particularly, to compounds derived from betulinic acid and other structurally related compounds which are useful as HIV maturation inhibitors, and to pharmaceutical compositions containing same, as well as to methods for their preparation and use.

BACKGROUND OF THE INVENTION

HIV-1 (human immunodeficiency virus-1) infection remains a major medical problem, with an estimated 45 million people infected worldwide at the end of 2007. The number of cases of HIV and AIDS (acquired immunodeficiency syndrome) has risen rapidly. In 2005, approximately 5.0 million new infections were reported, and 3.1 million people died from AIDS. Currently available drugs for the treatment of HIV include nucleoside reverse transcriptase (RT) inhibitors or approved single pill combinations: zidovudine (or AZT or RETROVIR®), didanosine (or VIDEX®), stavudine (or ZERIT®), lamivudine (or 3TC or EPIVIR®), zalcitabine (or DDC or HIVID®), abacavir succinate (or ZIAGEN®), Tenofovir disoproxil fumarate salt (or VIREAD®), emtricitabine (or FTC-EMTRIVA®), COMBIVIR® (contains -3TC plus AZT), TRIZIVIR® (contains abacavir, lamivudine, and zidovudine), EPZICOM® (contains abacavir and lamivudine), TRUVADA® (contains VIREAD® and EMTRIVA®); non-nucleoside reverse transcriptase inhibitors: nevirapine (or VIRAMUNE®), delavirdine (or RESCRIPTOR®) and efavirenz (or SUSTIVA®), ATRIPLA® (TRUVADA®+ SUSTIVA®), and etravirine, and peptidomimetic protease inhibitors or approved formulations: saquinavir, indinavir, ritonavir, nelfinavir, amprenavir, lopinavir, KALETRA® (lopinavir and Ritonavir), darunavir, atazanavir (REYATAZ®) and tipranavir (APTIVUS®), and integrase inhibitors such as raltegravir (ISENTRESS®), and entry inhibitors such as enfuvirtide (T-20) (FUZEON®) and maraviroc (SELZENRY®).

Each of these drugs can only transiently restrain viral replication if used alone. However, when used in combination, these drugs have a profound effect on viremia and disease progression. In fact, significant reductions in death rates among AIDS patients have been recently documented as a consequence of the widespread application of combination therapy. However, despite these impressive results, 30 to 50% of patients may ultimately fail combination drug therapies. Insufficient drug potency, non-compliance, restricted tissue penetration and drug-specific limitations within certain cell types (e.g. most nucleoside analogs cannot be phosphorylated in resting cells) may account for the incomplete suppression of sensitive viruses. Furthermore, the high replication rate and rapid turnover of HIV-1 combined with the frequent incorporation of mutations, leads to the appearance of drug-resistant variants and treatment failures when sub-optimal drug concentrations are present. Therefore, novel anti-HIV agents exhibiting distinct resistance patterns, and favorable pharmacokinetic as well as safety profiles are needed to provide more treatment options. Improved HIV fusion inhibitors and HIV entry coreceptor antagonists are two examples of new classes of anti-HIV agents further being studied by a number of investigators.

HIV attachment inhibitors are a further subclass of antiviral compounds that bind to the HIV surface glycoprotein gp120, and interfere with the interaction between the surface protein gp120 and the host cell receptor CD4. Thus, they prevent HIV from attaching to the human CD4 T-cell, and block HIV replication in the first stage of the HIV life cycle. The properties of HIV attachment inhibitors have been improved in an effort to obtain compounds with maximized utility and efficacy as antiviral agents. In particular, U.S. Pat. No. 7,354,924 and US 2005/0209246 are illustrative of HIV attachment inhibitors.

Another emerging class of HIV treatment compounds are called HIV maturation inhibitors. Maturation is the last of as many as 10 or more steps in HIV replication or the HIV life cycle, in which HIV becomes infectious as a consequence of several HIV protease-mediated cleavage events in the gag protein that ultimately results in release of the caspid (CA) protein. Maturation inhibitors prevent the HIV capsid from properly assembling and maturing, from forming a protective outer coat, or from emerging from human cells. Instead, non-infectious viruses are produced, preventing subsequent cycles of HIV infection.

Certain derivatives of betulinic acid have now been shown to exhibit potent anti-HIV activity as HIV maturation inhibitors. For example, U.S. Pat. No. 7,365,221 discloses monoacylated betulin and dihydrobetuline derivatives, and their use as anti-HIV agents. As discussed in the '221 reference, esterification of betulinic acid (1) with certain substituted acyl groups, such as 3',3'-dimethylglutaryl and 3',3'-dimethylsuccinyl groups produced derivatives having enhanced activity (Kashiwada, Y., et al., J. Med. Chem. 39:1016-1017 (1996)). Acylated betulinic acid and dihydrobetulinic acid derivatives that are potent anti-HIV agents are also described in U.S. Pat. No. 5,679,828. Esterification of the 3 carbon of betulin with succinic acid also produced a compound capable of inhibiting HIV-1 activity (Pokrovskii, A. G., et al., Gos. Nauchnyi Tsentr Virusol. Biotekhnol. "Vector" 9:485-491 (2001)).

Other references to the use of treating HIV infection with compounds derived from betulinic acid include US 2005/0239748 and US 2008/0207573.

One HIV maturation compound that has been in development has been identified as Bevirimat or PA-457, with the chemical formula of $C_{36}H_{56}O_6$ and the IUPAC name of 3β-(3-carboxy-3-methyl-butanoyloxy) lup-20(29)-en-28-oic acid.

Reference is also made herein to the provisional application by Bristol-Myers Squibb entitled "MODIFIED C-3 BETULINIC ACID DERIVATIVES AS HIV MATURATION INHIBITORS," filed on Jun. 4, 2010 and assigned U.S. Ser. No. 61/351,338.

What is now needed in the art are new compounds which are useful as HIV maturation inhibitors, as well as new pharmaceutical compositions containing these compounds.

SUMMARY OF THE INVENTION

The present invention provides compounds of Formulas I, II, and III below, including pharmaceutically acceptable salts thereof, their pharmaceutical formulations, and their use in patients suffering from or susceptible to a virus such as HIV. The compounds of Formulas I-III are effective antiviral agents, particularly as inhibitors of HIV. They are useful for the treatment of HIV and AIDS.

One embodiment of the present invention is directed to a compound, including pharmaceutically acceptable salts thereof, which is selected from the group of:

a compound of formula I

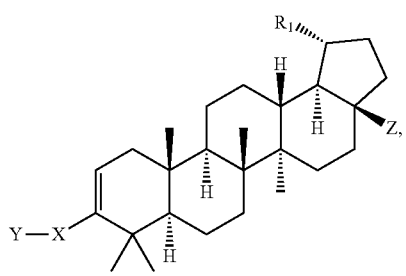

Formula I a compound of formula II

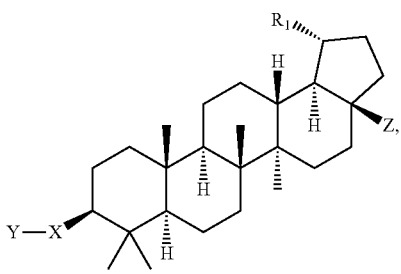

Formula II a compound of formula III

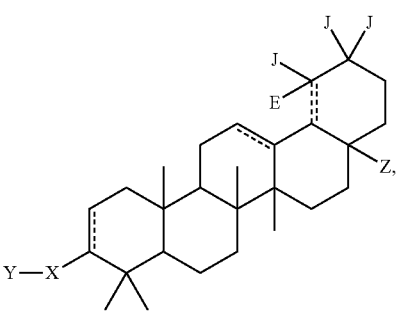

Formula III wherein $R_1$ is isopropenyl or isopropyl;
J and E are —H or —CH$_3$;
E is absent when the double bond is present;
X is a phenyl or heteroaryl ring substituted with A, wherein A is at least one member selected from the group of —H, -halo, -alkyl, -alkoxy, —COOR$_2$ and -hydroxyl wherein $R_2$ is —H—C$_{1-6}$ alkyl or substituted —C$_{1-6}$ alkyl;
Y is selected from the group of —COOR$_2$, —C(O)NR$_2$SO$_2$R$_3$, —C(O)NR$_2$SO$_2$NR$_2$R$_2$, —SO$_2$NR$_2$R$_2$, —NR$_2$SO$_2$R$_2$, —C$_{1-6}$ cycloalkyl-COOR$_2$, —C$_{1-6}$ alkenyl-COOR$_2$, —C$_{1-6}$ alkynyl-COOR$_2$, —C$_{1-6}$ alkyl-COOR$_2$, —NHC(O)(CH$_2$)$_n$—COOR$_2$, —SO$_2$NR$_2$C(O)R$_2$, -tetrazole, B(OH)$_2$ and —CONHOH, wherein n=1-6 and wherein $R_3$ is C$_{1-6}$ alkyl; and
Z is —CONR$_4$R$_5$;

$R_4$ is selected from the group of H, C$_{1-6}$ alkyl, and C$_{1-6}$ alkyl-OH;
$R_5$ is selected from the group of H, C$_{1-6}$ alkyl, substituted-alkyl, C$_{1-6}$ alkyl-R$_6$, C$_{2-6}$ alkyl-R$_7$, SO$_2$R$_8$, SO$_2$NR$_9$R$_{10}$;
$R_6$ is selected from phenyl, substituted phenyl, heteroaryl, substituted heteroaryl, SO$_2$R$_{11}$, SO$_2$NR$_{12}$R$_{13}$, C$_{1-6}$ cycloalkyl, substituted C$_{1-6}$ cycloalkyl, SO$_3$H, COOR$_{14}$, C(O)NR$_{15}$R$_{16}$;
$R_7$ is selected from OR$_{17}$, N$^+$(O$^-$)R$_{18}$R$_{19}$, NR$_{20}$(COR$_{21}$) and NR$_{22}$R$_{23}$;
or $R_4$ and $R_5$ are taken together to form a cycle selected from the group of:

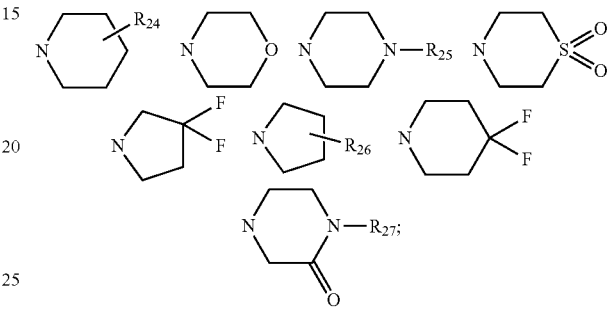

$R_{22}$ and $R_{23}$ are selected from the group of H, C$_{1-6}$ alkyl, substituted-alkyl, C$_{1-6}$ alkyl-R$_{32}$, C$_{2-6}$ alkyl-R$_{33}$, SO$_2$R$_8$, SO$_2$NR$_9$R$_{10}$;
$R_{32}$ is selected from phenyl, substituted phenyl, heteroaryl, substituted heteroaryl, SO$_2$R$_{11}$, SO$_2$NR$_{12}$R$_{13}$, C$_{1-6}$ cycloalkyl, substituted C$_{1-6}$ cycloalkyl, SO$_3$H, COOR$_{14}$, C(O)NR$_{15}$R$_{16}$,
$R_{33}$ is selected from the group of OR$_{17}$, N$^+$(O$^-$)R$_{18}$R$_{19}$, NR$_{20}$(COR$_{21}$) and NR$_9$R$_{10}$,
or $R_{22}$ and $R_{23}$ are taken together to form a cycle selected from the group of:

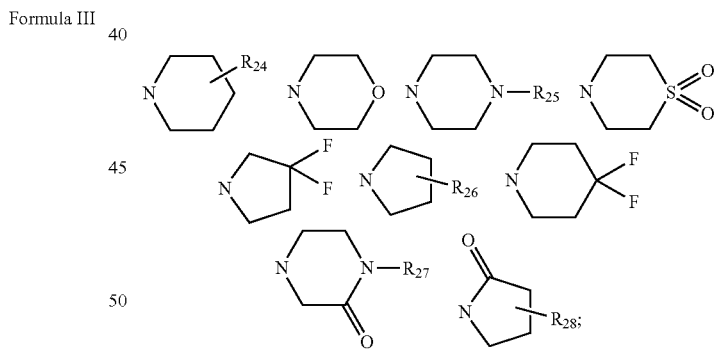

$R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{27}$, $R_{29}$, $R_{30}$ and $R_{31}$ are each independently selected from the group of H, C$_{1-6}$ alkyl, substituted-alkyl, C$_{1-6}$ cycloalkyl and substituted C$_{1-6}$ cycloalkyl;
$R_{24}$, $R_{26}$ and $R_{28}$ are selected from the group of H, alkyl, substituted alkyl, COOR$_{29}$, COONR$_{30}$R$_{31}$; and
$R_{25}$ is selected from the group of alkyl, substituted alkyl, COOR$_{29}$, COONR$_{30}$R$_{31}$.

In a further embodiment, there is provided a method for treating mammals infected with a virus, especially wherein said virus is HIV, comprising administering to said mammal an antiviral effective amount of a compound which is selected from the group of compounds of Formulas I, II, III above, and one or more pharmaceutically acceptable carriers, excipients or diluents. Optionally, the compound of Formulas I, II, and/or III can be administered in combination with an antiviral effective amount of another—AIDS treatment agent selected from the group consisting of: (a) an AIDS antiviral agent; (b) an anti-infective agent; (c) an immunomodulator; and (d) other HIV entry inhibitors.

Another embodiment of the present invention is a pharmaceutical composition comprising an antiviral effective amount of a compound which is selected from the group of compounds of Formulas I, II, and III, and one or more pharmaceutically acceptable carriers, excipients, and diluents; and optionally in combination with an antiviral effective amount of another AIDS treatment agent selected from the group consisting of: (a) an AIDS antiviral agent; (b) an anti-infective agent; (c) an immunomodulator; and (d) other HIV entry inhibitors.

In another embodiment of the invention there is provided one or more methods for making the compounds of Formulas I, II, and III.

The present invention is directed to these, as well as other important ends, hereinafter described.

DETAILED DESCRIPTION OF THE EMBODIMENTS

Since the compounds of the present invention may possess asymmetric centers and therefore occur as mixtures of diastereomers and enantiomers, the present disclosure includes the individual diastereoisomeric and enantiomeric forms of the compounds of Formulas I, II and III in addition to the mixtures thereof.

The terms "C-3" and "C-28" refer to certain positions of a triterpene core as numbered in accordance with IUPAC rules (positions depicted below with respect to an illustrative triterpene: betulin):

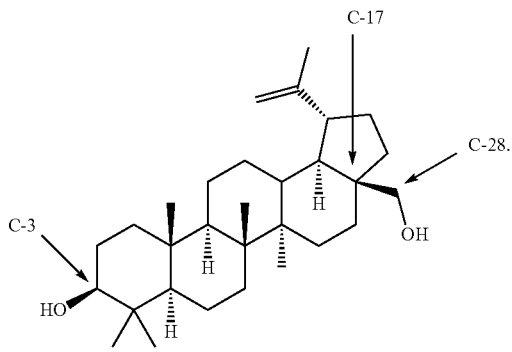

The same numbering is maintained when referring to the compound series in schemes and general descriptions of methods.

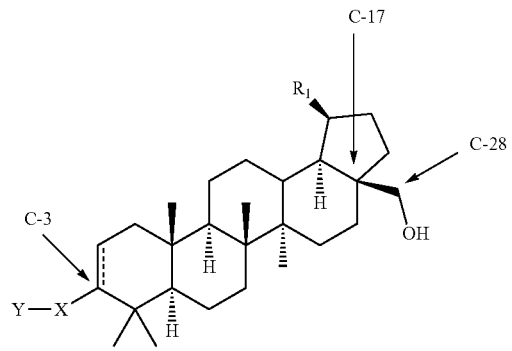

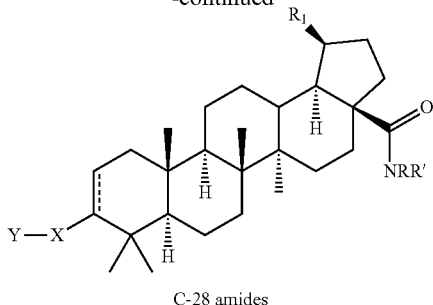

C-28 amides

DEFINITIONS

Unless otherwise specifically set forth elsewhere in the application, one or more of the following terms may be used herein, and shall have the following meanings:

"H" refers to hydrogen, including its isotopes, such as deuterium.

The term "$C_{1-6}$ alkyl" as used herein and in the claims (unless specified otherwise) mean straight or branched chain alkyl groups such as methyl, ethyl, propyl, isopropyl, butyl, isobutyl, t-butyl, amyl, hexyl and the like.

"$C_1$-$C_4$ fluoroalkyl" refers to F-substituted $C_1$-$C_4$ alkyl wherein at least one H atom is substituted with F atom, and each H atom can be independently substituted by F atom;

"Halogen" refers to chlorine, bromine, iodine or fluorine.

An "aryl" or "Ar" group refers to an all carbon monocyclic or fused-ring polycyclic (i.e., rings which share adjacent pairs of carbon atoms) groups having a completely conjugated pi-electron system. Examples, without limitation, of aryl groups are phenyl, napthalenyl and anthracenyl. The aryl group may be substituted or unsubstituted. When substituted the substituted group(s) is preferably one or more selected from alkyl, cycloalkyl, aryl, heteroaryl, heteroalicyclic, hydroxy, alkoxy, aryloxy, heteroaryloxy, heteroalicycloxy, thiohydroxy, thioaryloxy, thioheteroaryloxy, thioheteroalicycloxy, cyano, halogen, nitro, carbonyl, O-carbamyl, N-carbamyl, C-amido, N-amido, C-carboxy, O-carboxy, sulfinyl, sulfonyl, sulfonamido, trihalomethyl, ureido, amino and —$NR^xR^y$, wherein $R^x$ and $R^y$ are independently selected from the group consisting of hydrogen, alkyl, cycloalkyl, aryl, carbonyl, C-carboxy, sulfonyl, trihalomethyl, and, combined, a five- or six-member heteroalicyclic ring.

As used herein, a "heteroaryl" group refers to a monocyclic or fused ring (i.e., rings which share an adjacent pair of atoms) group having in the ring(s) one or more atoms selected from the group consisting of nitrogen, oxygen and sulfur and, in addition, having a completely conjugated pi-electron system. Unless otherwise indicated, the heteroaryl group may be attached at either a carbon or nitrogen atom within the heteroaryl group. It should be noted that the term heteroaryl is intended to encompass an N-oxide of the parent heteroaryl if such an N-oxide is chemically feasible as is known in the art. Examples, without limitation, of heteroaryl groups are furyl, thienyl, benzothienyl, thiazolyl, imidazolyl, oxazolyl, oxadiazolyl, thiadiazolyl, benzothiazolyl, triazolyl, tetrazolyl, isoxazolyl, isothiazolyl, pyrrolyl, pyranyl, tetrahydropyranyl, pyrazolyl, pyridyl, pyrimidinyl, quinolinyl, isoquinolinyl, purinyl, carbazolyl, benzoxazolyl, benzimidazolyl, indolyl, isoindolyl, pyrazinyl. diazinyl, pyrazine, triazinyl, tetrazinyl, and tetrazolyl. When substituted the substituted group(s) is preferably one or more selected from alkyl, cycloalkyl, aryl, heteroaryl, heteroalicyclic, hydroxy, alkoxy, aryloxy, heteroaryloxy, heteroalicycloxy, thioalkoxy, thiohydroxy, thioaryloxy, thioheteroaryloxy, thioheteroalicycloxy, cyano, halogen, nitro, carbonyl, O-carbamyl, N-carbamyl, C-amido, N-amido, C-carboxy, O-carboxy, sulfinyl, sulfonyl, sulfonamido, trihalomethyl, ureido, amino, and —$NR^xR^y$, wherein $R^x$ and $R^y$ are as defined above.

As used herein, a "heteroalicyclic" group refers to a monocyclic or fused ring group having in the ring(s) one or more atoms selected from the group consisting of nitrogen, oxygen and sulfur. Rings are selected from those which provide stable arrangements of bonds and are not intended to encompass systems which would not exist. The rings may also have one or more double bonds. However, the rings do not have a completely conjugated pi-electron system. Examples, without limitation, of heteroalicyclic groups are azetidinyl, piperidyl, piperazinyl, imidazolinyl, thiazolidinyl, 3-pyrrolidin-1-yl, morpholinyl, thiomorpholinyl and tetrahydropyranyl. When substituted the substituted group(s) is preferably one or more selected from alkyl, cycloalkyl, aryl, heteroaryl, heteroalicyclic, hydroxy, alkoxy, aryloxy, heteroaryloxy, heteroalicycloxy, thiohydroxy, thioalkoxy, thioaryloxy, thioheteroaryloxy, thioheteroalicycloxy, cyano, halogen, nitro, carbonyl, thiocarbonyl, O-carbamyl, N-carbamyl, O-thiocarbamyl, N-thiocarbamyl, C-amido, C-thioamido, N-amido, C-carboxy, O-carboxy, sulfinyl, sulfonyl, sulfonamido, trihalomethanesulfonamido, trihalomethanesulfonyl, silyl, guanyl, guanidino, ureido, phosphonyl, amino and —NR$^x$R$^y$, wherein R$^x$ and R$^y$ are as defined above.

An "alkyl" group refers to a saturated aliphatic hydrocarbon including straight chain and branched chain groups. Preferably, the alkyl group has 1 to 20 carbon atoms (whenever a numerical range; e.g., "1-20", is stated herein, it means that the group, in this case the alkyl group may contain 1 carbon atom, 2 carbon atoms, 3 carbon atoms, etc. up to and including 20 carbon atoms). More preferably, it is a medium size alkyl having 1 to 10 carbon atoms. Most preferably, it is a lower alkyl having 1 to 4 carbon atoms. The alkyl group may be substituted or unsubstituted. When substituted, the substituent group(s) is preferably one or more individually selected from trihaloalkyl, cycloalkyl, aryl, heteroaryl, heteroalicyclic, hydroxy, alkoxy, aryloxy, heteroaryloxy, heteroalicycloxy, thiohydroxy, thioalkoxy, thioaryloxy, thioheteroaryloxy, thioheteroalicycloxy, cyano, halo, nitro, carbonyl, thiocarbonyl, O-carbamyl, N-carbamyl, O-thiocarbamyl, N-thiocarbamyl, C-amido, C-thioamido, N-amido, C-carboxy, O-carboxy, sulfinyl, sulfonyl, sulfonamido, trihalomethanesulfonamido, trihalomethanesulfonyl, and combined, a five- or six-member heteroalicyclic ring.

A "cycloalkyl" group refers to an all-carbon monocyclic or fused ring (i.e., rings which share and adjacent pair of carbon atoms) group wherein one or more rings does not have a completely conjugated pi-electron system. Examples, without limitation, of cycloalkyl groups are cyclopropane, cyclobutane, cyclopentane, cyclopentene, cyclohexane, cyclohexene, cycloheptane, cycloheptene and adamantane. A cycloalkyl group may be substituted or unsubstituted. When substituted, the substituent group(s) is preferably one or more individually selected from alkyl, aryl, heteroaryl, heteroalicyclic, hydroxy, alkoxy, aryloxy, heteroaryloxy, heteroalicycloxy, thiohydroxy, thioalkoxy, thioaryloxy, thioheteroaryloxy, thioheteroalicycloxy, cyano, halo, nitro, carbonyl, thiocarbonyl, O-carbamyl, N-carbamyl, O-thiocarbamyl, N-thiocarbamyl, C-amido, C-thioamido, N-amido, C-carboxy, O-carboxy, sulfinyl, sulfonyl, sulfonamido, trihalomethanesulfonamido, trihalomethanesulfonyl, silyl, amidino, guanidino, ureido, phosphonyl, amino and —NR$^x$R$^Y$ with R$^x$ and R$^Y$ as defined above.

An "alkenyl" group refers to an alkyl group, as defined herein, having at least two carbon atoms and at least one carbon-carbon double bond.

An "alkynyl" group refers to an alkyl group, as defined herein, having at least two carbon atoms and at least one carbon-carbon triple bond.

A "hydroxy" group refers to an —OH group.

An "alkoxy" group refers to both an —O-alkyl and an —O-cycloalkyl group as defined herein.

An "aryloxy" group refers to both an —O-aryl and an —O-heteroaryl group, as defined herein.

A "heteroaryloxy" group refers to a heteroaryl-O— group with heteroaryl as defined herein.

A "heteroalicycloxy" group refers to a heteroalicyclic-O— group with heteroalicyclic as defined herein.

A "thiohydroxy" group refers to an —SH group.

A "thioalkoxy" group refers to both an S-alkyl and an —S-cycloalkyl group, as defined herein.

A "thioaryloxy" group refers to both an —S-aryl and an —S-heteroaryl group, as defined herein.

A "thioheteroaryloxy" group refers to a heteroaryl-S— group with heteroaryl as defined herein.

A "thioheteroalicycloxy" group refers to a heteroalicyclic-S— group with heteroalicyclic as defined herein.

A "carbonyl" group refers to a —C(=O)—R" group, where R" is selected from the group consisting of hydrogen, alkyl, alkenyl, alkynyl, cycloalkyl, aryl, heteroaryl (bonded through a ring carbon) and heteroalicyclic (bonded through a ring carbon), as each is defined herein.

An "aldehyde" group refers to a carbonyl group where R" is hydrogen.

A "thiocarbonyl" group refers to a —C(=S)—R" group, with R" as defined herein.

A "Keto" group refers to a —CC(=O)C— group wherein the carbon on either or both sides of the C=O may be alkyl, cycloalkyl, aryl or a carbon of a heteroaryl or heteroalicyclic group.

A "trihalomethanecarbonyl" group refers to a Z$_3$CC(=O)— group with said Z being a halogen.

A "C-carboxy" group refers to a —C(=O)O—R" groups, with R" as defined herein.

An "O-carboxy" group refers to a R"C(=O)O-group, with R" as defined herein.

A "carboxylic acid" group refers to a C-carboxy group in which R" is hydrogen.

A "trihalomethyl" group refers to a —CZ$_3$, group wherein Z is a halogen group as defined herein.

A "trihalomethanesulfonyl" group refers to an Z$_3$CS(=O)$_2$— groups with Z as defined above.

A "trihalomethanesulfonamido" group refers to a Z$_3$CS(=O)$_2$NR$^x$— group with Z as defined above and R$^x$ being H or (C$_{1-6}$)alkyl.

A "sulfinyl" group refers to a —S(=O)—R" group, with R" being (C$_{1-6}$)alkyl.

A "sulfonyl" group refers to a —S(=O)$_2$R" group with R" being (C$_{1-6}$)alkyl.

A "S-sulfonamido" group refers to a —S(=O)$_2$NR$^X$R$^Y$, with R$^X$ and R$^Y$ independently being H or (C$_{1-6}$)alkyl.

A "N-Sulfonamido" group refers to a R"S(=O)$_2$NR$_x$— group, with R$_x$ being H or (C$_{1-6}$)alkyl.

A "O-carbamyl" group refers to a —OC(=O)NR$^x$R$^y$ group, with R$^X$ and R$^Y$ independently being H or (C$_{1-6}$)alkyl.

A "N-carbamyl" group refers to a R$^x$OC(=O)NR$^y$ group, with R$^x$ and R$^y$ independently being H or (C$_{1-6}$)alkyl.

A "O-thiocarbamyl" group refers to a —OC(=S)NR$^x$R$^Y$ group, with R$^x$ and R$^Y$ independently being H or (C$_{1-6}$)alkyl.

A "N-thiocarbamyl" group refers to a R$^x$OC(=S)NR$^y$— group, with R$^x$ and R$^y$ independently being H or (C$_{1-6}$)alkyl.

An "amino" group refers to an —NH$_2$ group.

A "C-amido" group refers to a —C(=O)NR$^x$R$^y$ group, with R$^x$ and R$^y$ independently being H or (C$_{1-6}$)alkyl.

A "C-thioamido" group refers to a —C(=S)NR$^x$R$^y$ group, with R$^x$ and R$^y$ independently being H or (C$_{1-6}$)alkyl.

A "N-amido" group refers to a R$^x$C(=O)NR$^y$— group, with R$^x$ and R$^y$ independently being H or (C$_{1-6}$)alkyl.

An "ureido" group refers to a —NR$^x$C(=O)NR$^y$R$^{y2}$ group, with R$^x$, R$^y$, and R$^{y2}$ independently being H or (C$_{1-6}$)alkyl.

A "guanidino" group refers to a —R$^x$NC(=N)NR$^y$R$^{y2}$ group, with R$^x$, R$^y$, and R$^{y2}$ independently being H or (C$_{1-6}$)alkyl.

A "amidino" group refers to a R$^x$R$^y$NC(=N)— group, with R$^x$ and R$^y$ independently being H or (C$_{1-6}$)alkyl.

A "cyano" group refers to a —CN group.

A "silyl" group refers to a —Si(R")$_3$, with R" being (C$_{1-6}$)alkyl or phenyl.

A "phosphonyl" group refers to a P(=O)(OR$^x$)$_2$ with R$^x$ being (C$_{1-6}$)alkyl.

A "hydrazino" group refers to a —NR$^x$NR$^y$R$^{y2}$ group, with R$^x$, R$^y$, and R$^{y2}$ independently being H or (C$_{1-6}$)alkyl.

A "4, 5, or 6 membered ring cyclic N-lactam" group refers to

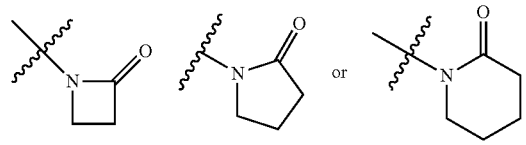

Any two adjacent R groups may combine to form an additional aryl, cycloalkyl, heteroaryl or heterocyclic ring fused to the ring initially bearing those R groups.

It is known in the art that nitrogen atoms in heteroaryl systems can be "participating in a heteroaryl ring double bond", and this refers to the form of double bonds in the two tautomeric structures which comprise five-member ring heteroaryl groups. This dictates whether nitrogens can be substituted as well understood by chemists in the art. The disclosure and claims of the present disclosure are based on the known general principles of chemical bonding. It is understood that the claims do not encompass structures known to be unstable or not able to exist based on the literature.

Pharmaceutically acceptable salts and prodrugs of compounds disclosed herein are within the scope of the invention. The term "pharmaceutically acceptable salt" as used herein and in the claims is intended to include nontoxic base addition salts. Suitable salts include those derived from organic and inorganic acids such as, without limitation, hydrochloric acid, hydrobromic acid, phosphoric acid, sulfuric acid, methanesulfonic acid, acetic acid, tartaric acid, lactic acid, sulfinic acid, citric acid, maleic acid, fumaric acid, sorbic acid, aconitic acid, salicylic acid, phthalic acid, and the like. The term "pharmaceutically acceptable salt" as used herein is also intended to include salts of acidic groups, such as a carboxylate, with such counterions as ammonium, alkali metal salts, particularly sodium or potassium, alkaline earth metal salts, particularly calcium or magnesium, and salts with suitable organic bases such as lower alkylamines (methylamine, ethylamine, cyclohexylamine, and the like) or with substituted lower alkylamines (e.g. hydroxyl-substituted alkylamines such as diethanolamine, triethanolamine or tris(hydroxymethyl)-aminomethane), or with bases such as piperidine or morpholine.

As stated above, the compounds of the invention also include "prodrugs". The term "prodrug" as used herein encompasses both the term "prodrug esters" and the term "prodrug ethers". The term "prodrug esters" as employed herein includes esters and carbonates formed by reacting one or more hydroxyls of compounds of Formula I with either alkyl, alkoxy, or aryl substituted acylating agents or phosphorylating agent employing procedures known to those skilled in the art to generate acetates, pivalates, methylcarbonates, benzoates, amino acid esters, phosphates, half acid esters such as malonates, succinates or glutarates, and the like. In certain embodiments, amino acid esters may be especially preferred.

Examples of such prodrug esters include

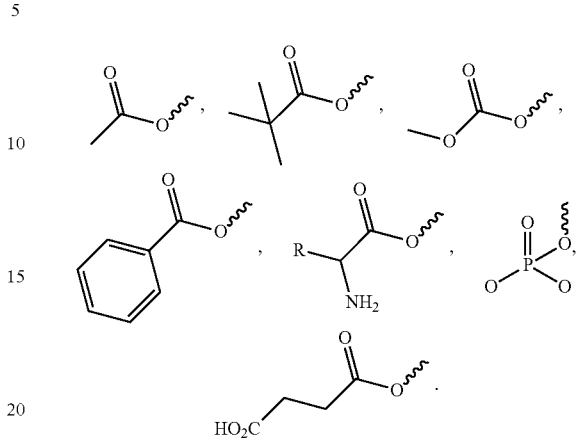

The term "prodrug ethers" include both phosphate acetals and O-glucosides. Representative examples of such prodrug ethers include

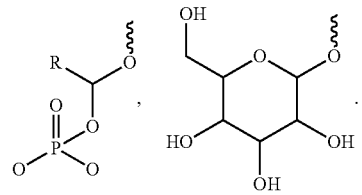

As set forth above, the invention is directed to a compound, including pharmaceutically acceptable salts thereof, which is selected from the group of:

a compound of formula I

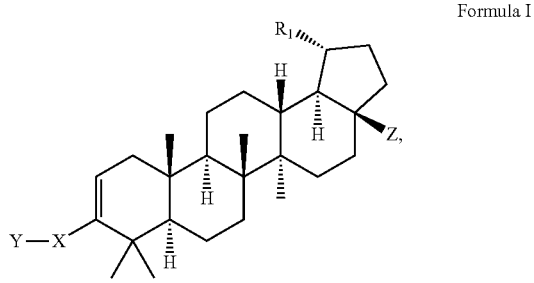

Formula I a compound of formula II

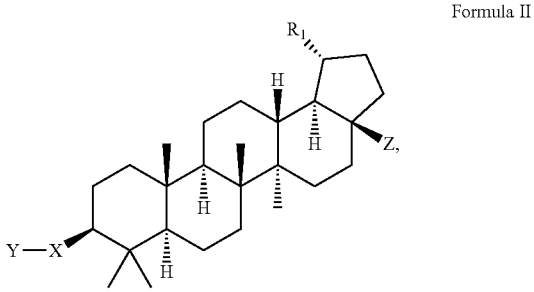

Formula II a compound of formula III

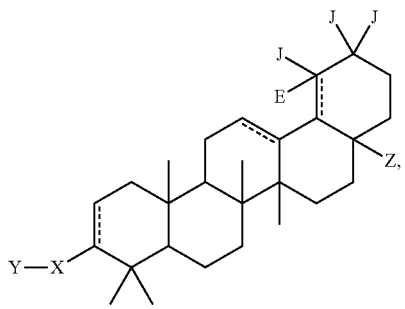

Formula III wherein $R_1$ is isopropenyl or isopropyl;
J and E are —H or —CH$_3$;
E is absent when the double bond is present;
X is a phenyl or heteroaryl ring substituted with A, wherein A is at least one member selected from the group of —H, -halo, -alkyl, -alkoxy, —COOR$_2$ and -hydroxyl wherein $R_2$ is —H—C$_{1-6}$ alkyl, or substituted —C$_{1-6}$ alkyl;
Y is selected from the group of —COOR$_2$, —C(O)NR$_2$SO$_2$R$_3$, —C(O)NR$_2$SO$_2$NR$_2$R$_2$, —SO$_2$NR$_2$R$_2$, —NR$_2$SO$_2$R$_2$, —C$_{1-6}$ cycloalkyl-COOR$_2$, —C$_{1-6}$ alkenyl-COOR$_2$, —C$_{1-6}$ alkynyl-COOR$_2$, —C$_{1-6}$ alkyl-COOR$_2$, —NHC(O)(CH$_2$)$_n$—COOR$_2$, —SO$_2$NR$_2$C(O)R$_2$, -tetrazole, B(OH)$_2$ and —CONHOH wherein n=1-6 and wherein $R_3$ is C$_{1-6}$ alkyl; and
Z is —CONR$_4$R$_5$;
$R_4$ is selected from the group of H, C$_{1-6}$ alkyl, and C$_{1-6}$ alkyl-OH;
$R_5$ is selected from the group of H, C$_{1-6}$ alkyl, substituted-alkyl, C$_{1-6}$ alkyl-R$_6$, C$_{2-6}$ alkyl-R$_7$, SO$_2$R$_8$, SO$_2$NR$_9$R$_{10}$;
$R_6$ is selected from phenyl, substituted phenyl, heteroaryl, substituted heteroaryl, SO$_2$R$_{11}$, SO$_2$NR$_{12}$R$_{13}$, C$_{1-6}$ cycloalkyl, substituted C$_{1-6}$ cycloalkyl, SO$_3$H, COOR$_{14}$, C(O)NR$_{15}$R$_{16}$;
$R_7$ is selected from OR$_{12}$, N$^+$(O$^-$)R$_{18}$R$_{19}$, NR$_{20}$(COR$_{21}$) and NR$_{22}$R$_{23}$;
or $R_4$ and $R_5$ are taken together to form a cycle selected from the group of:

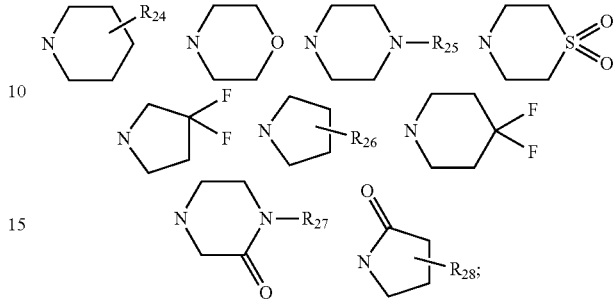

$R_{22}$ and $R_{23}$ are selected from the group of H, C$_{1-6}$ alkyl, substituted-alkyl, C$_{1-6}$ alkyl-R$_{32}$, C$_{2-6}$ alkyl-R$_{33}$, SO$_2$R$_8$, SO$_2$NR$_9$R$_{10}$;
$R_{32}$ is selected from phenyl, substituted phenyl, heteroaryl, substituted heteroaryl, SO$_2$R$_{11}$, SO$_2$NR$_{12}$R$_{13}$, C$_{1-6}$ cycloalkyl, substituted C$_{1-6}$ cycloalkyl, SO$_3$H, COOR$_{14}$, C(O)NR$_{15}$R$_{16}$;

$R_{33}$ is selected from OR$_{12}$, N$^+$(O$^-$)R$_{18}$R$_{19}$, NR$_{20}$(COR$_{21}$) and NR$_9$R$_{10}$;
or $R_{22}$ and $R_{23}$ are taken together to form a cycle selected from the group of:

$R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{27}$, $R_{29}$, $R_{30}$ and $R_{31}$ are each independently selected from the group of H, C$_{1-6}$ alkyl, substituted-alkyl, C$_{1-6}$ cycloalkyl and substituted C$_{1-6}$ cycloalkyl;
$R_{24}$, $R_{26}$ and $R_{28}$ are selected from the group of H, alkyl, substituted alkyl, —COOR$_{29}$, —COONR$_{30}$R$_{31}$; and
$R_{25}$ is selected from the group of alkyl, substituted alkyl, —COOR$_{29}$, —COONR$_{30}$R$_{31}$.

More preferred compounds include those which are encompassed by Formula I. Of these, those wherein X is a phenyl ring are even more preferred. Even more preferred are compounds of Formula I wherein X is a phenyl ring and Y is in the para position.

Also preferred are compounds of Formula I wherein A is at least one member selected from the group of —H, —OH, -halo, —C$_{1-3}$ alkyl, and —C$_{1-3}$ alkoxy, wherein -halo is selected from the group of —Cl, —F and —Br, with —F being more preferred.

Also preferred are compounds of Formula I wherein Y is —COOH.

In another preferred embodiment there is provided a compound of Formula Ia below wherein X is a phenyl ring and Y is —COOH in the para position:

Formula Ia

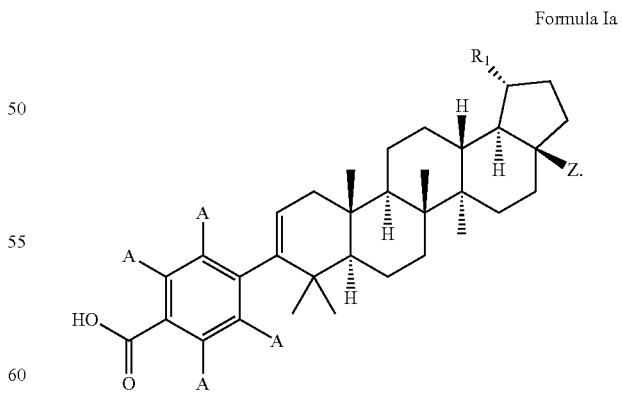

In this embodiment, it is also preferred that A is at least one member selected from the group of —H, -halo, —OH, —C$_{1-3}$ alkyl and —C$_{1-3}$ alkoxy. It is particularly preferred that A is at least one member selected from the group of —H, -fluoro, -chloro, —OH, -methyl and -methoxy.

Other compounds encompassed by Formula I which are preferred as part of the invention
include 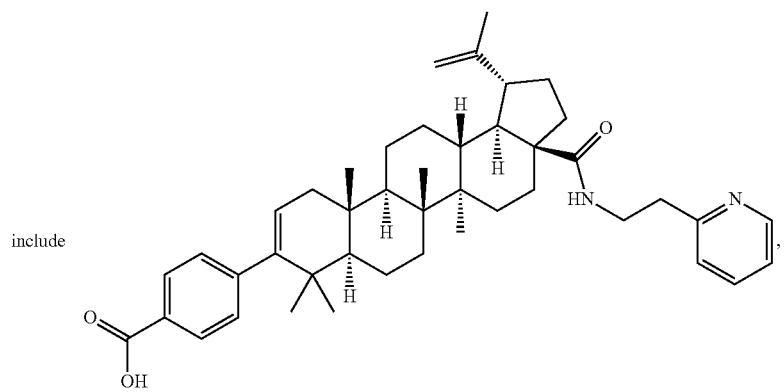,
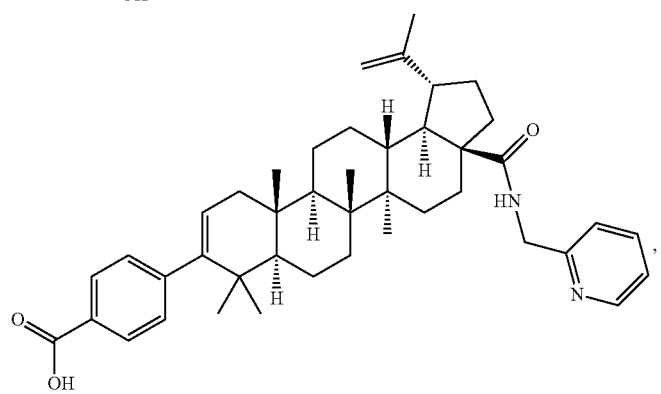,
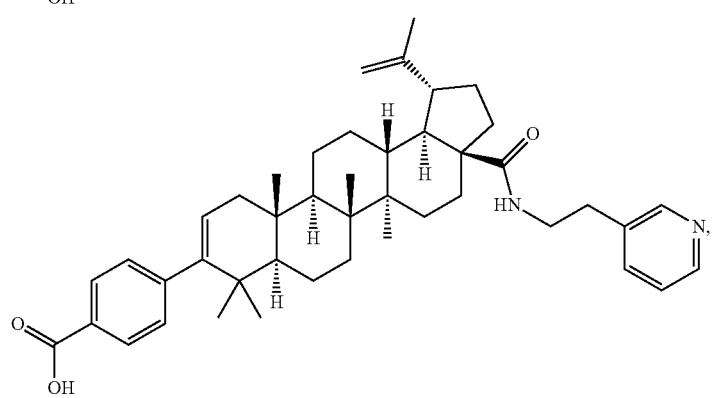,
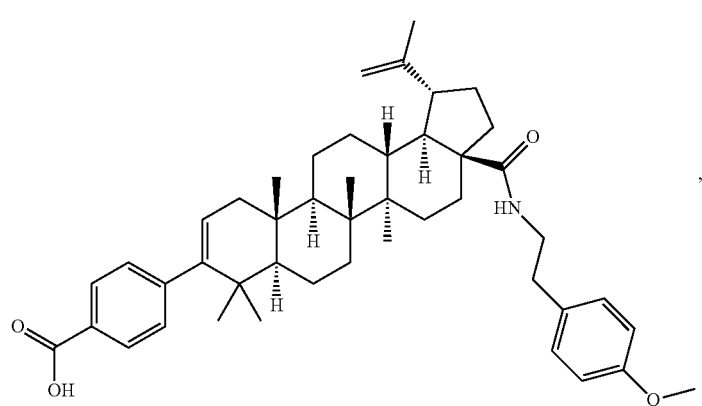, -continued
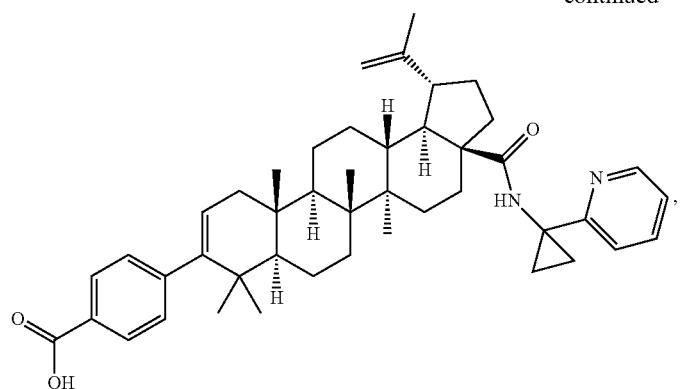
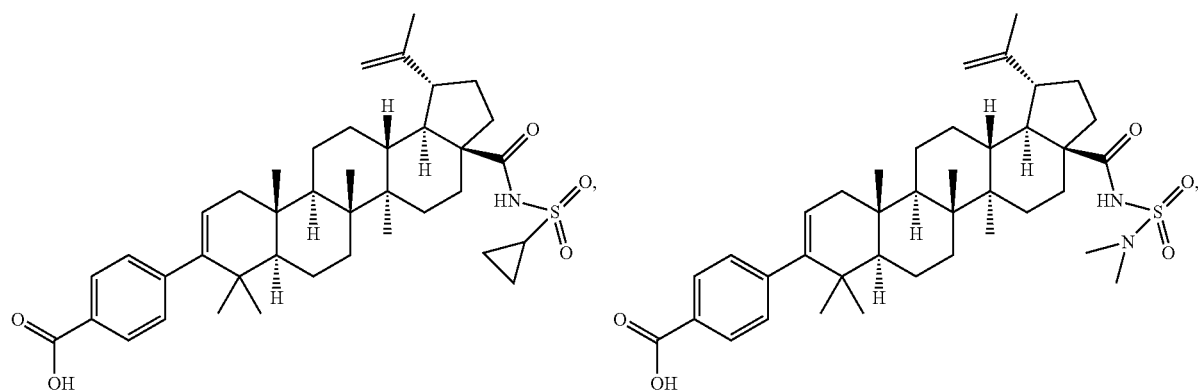
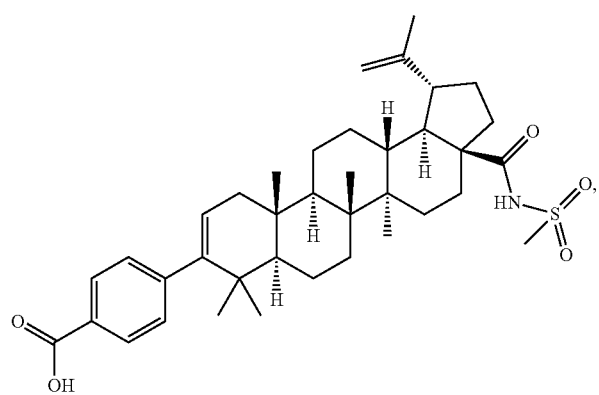
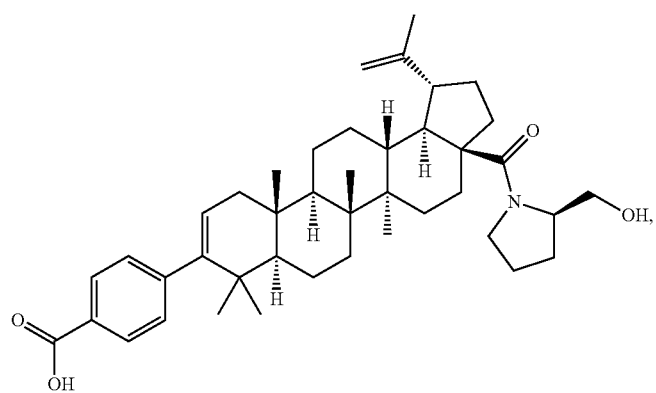

-continued
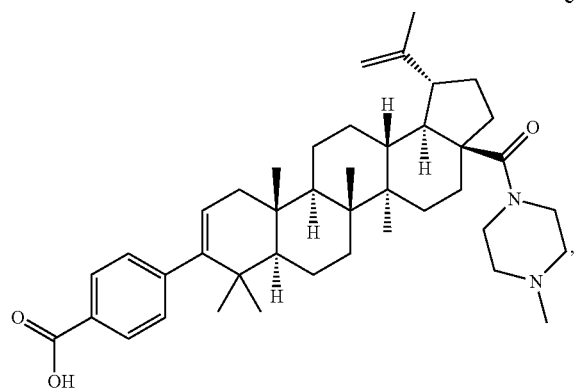
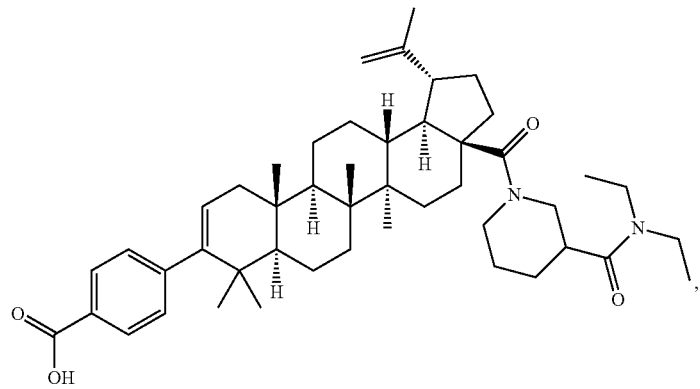
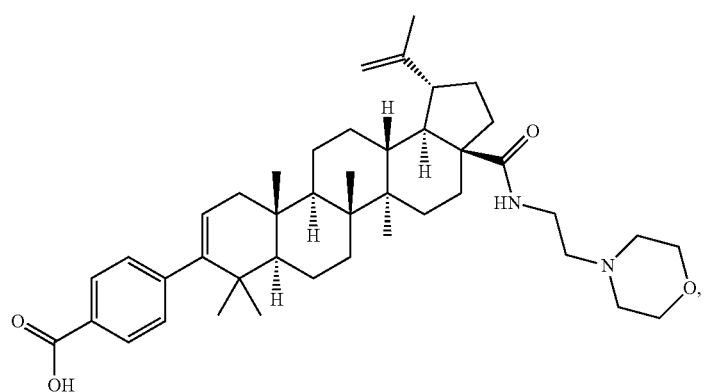
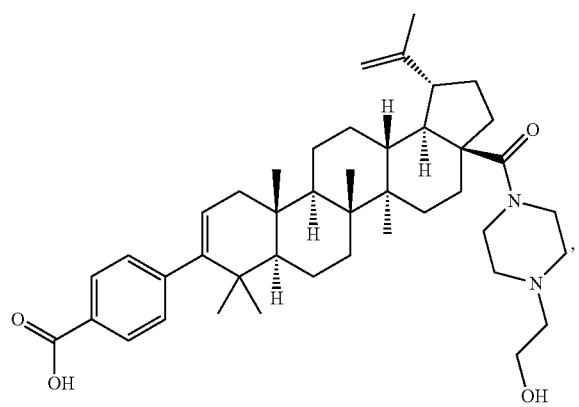

-continued
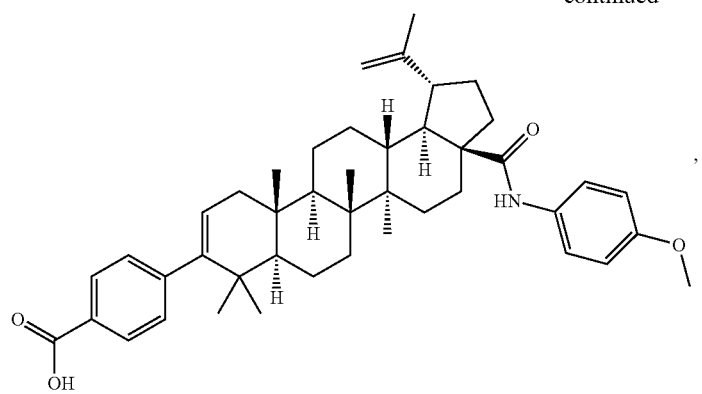
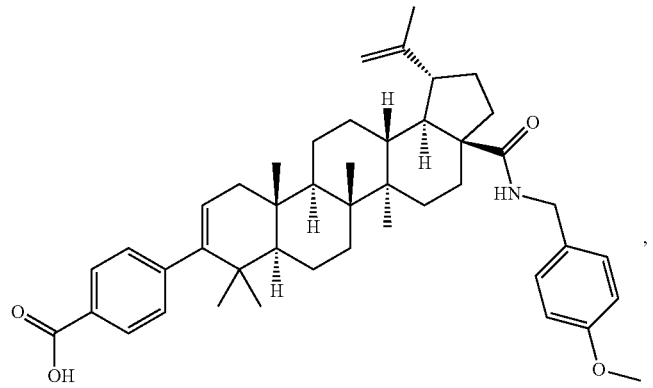
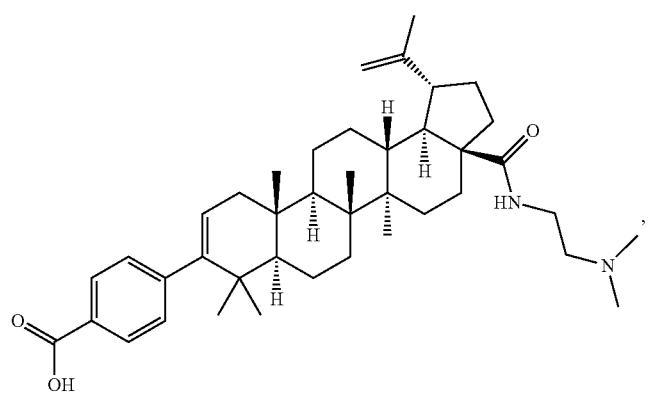
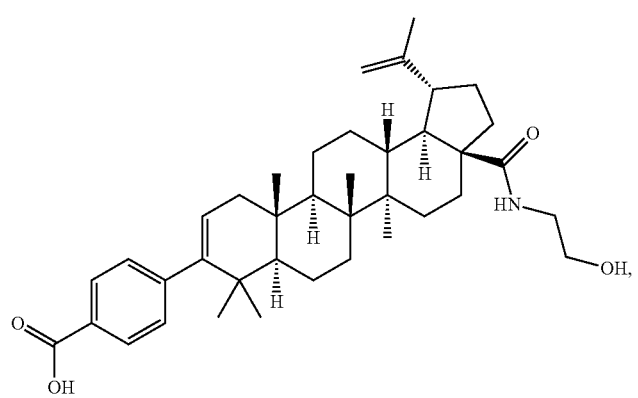

-continued
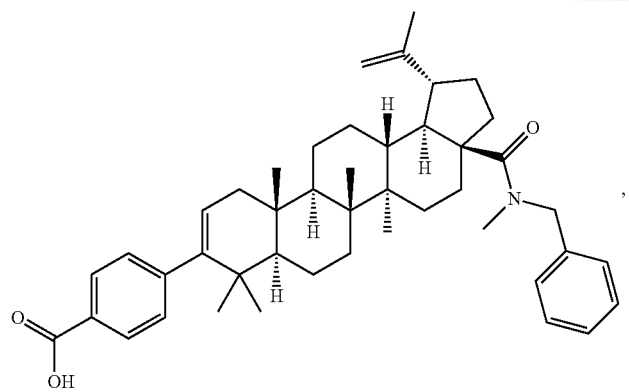
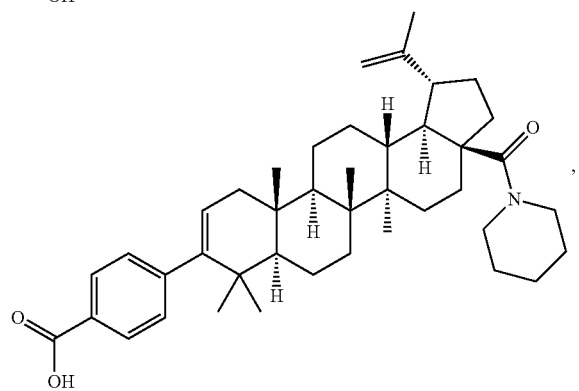
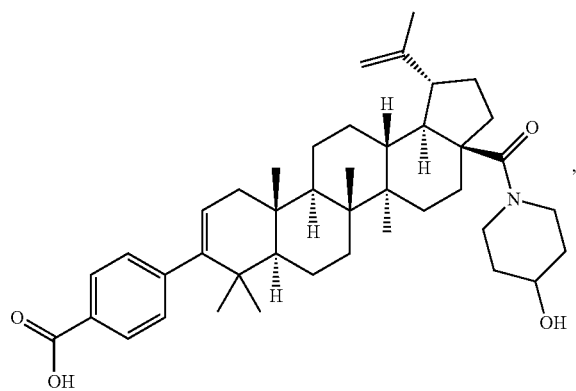
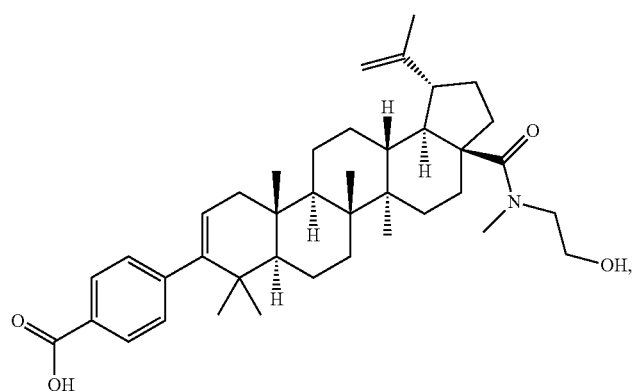
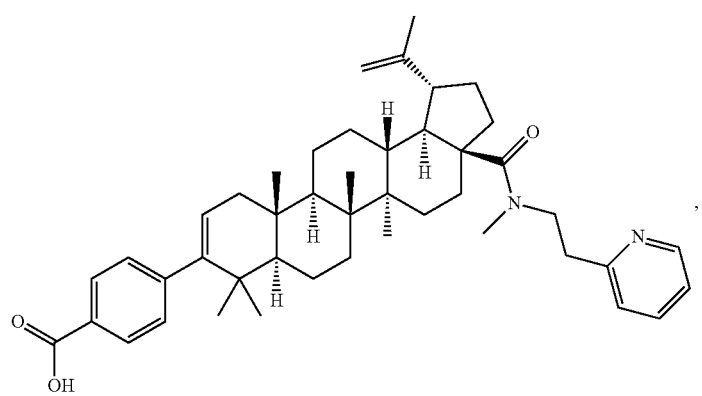

-continued
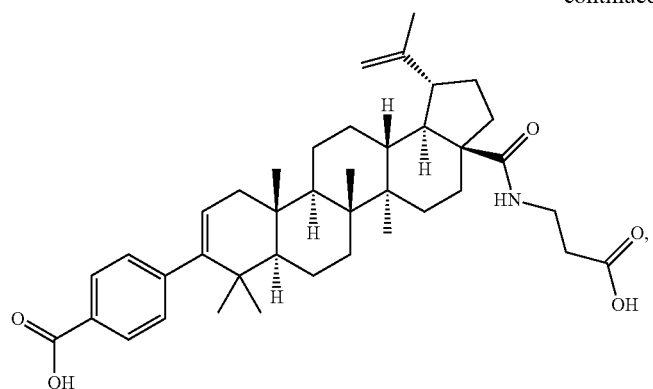
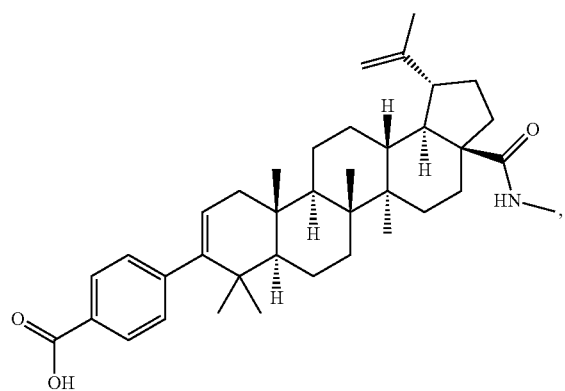
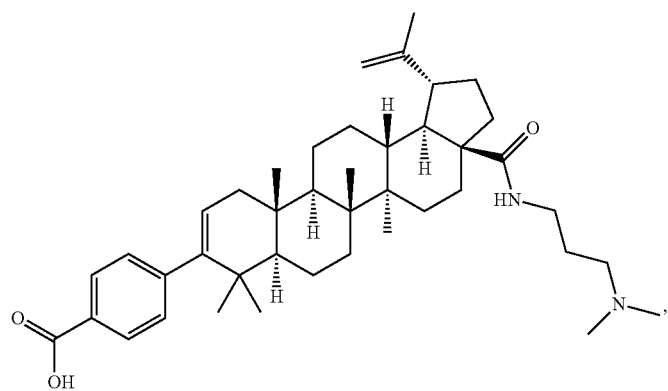
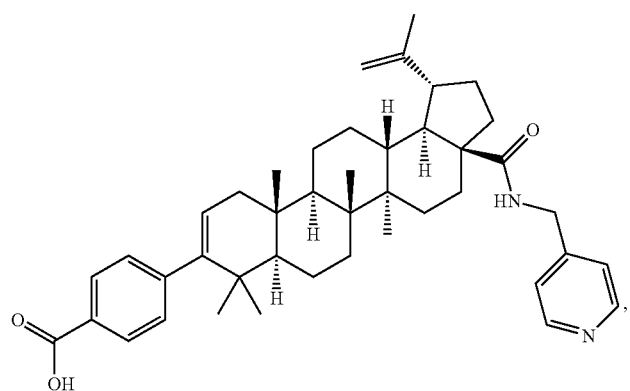

-continued
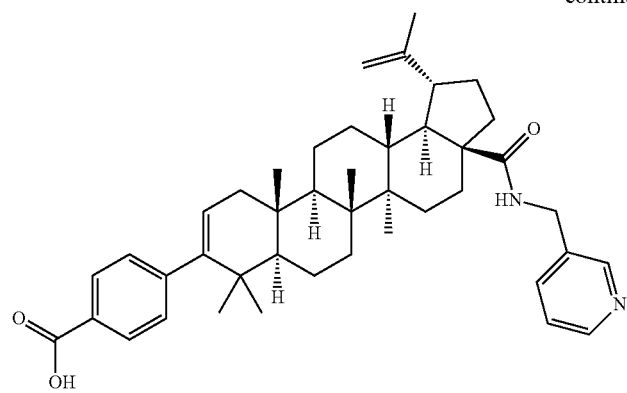
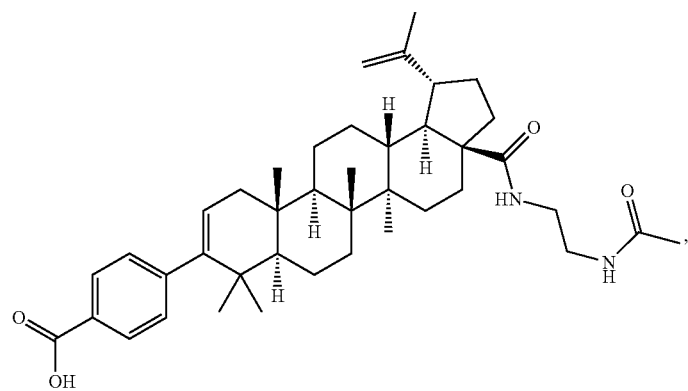
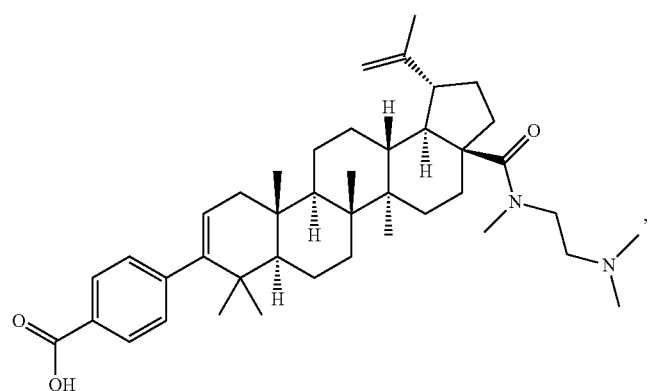
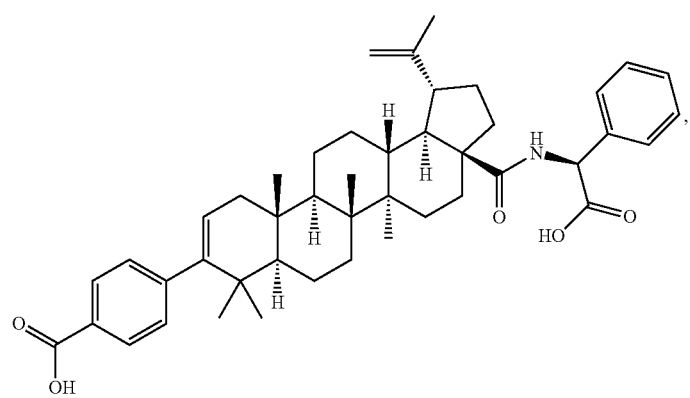

-continued
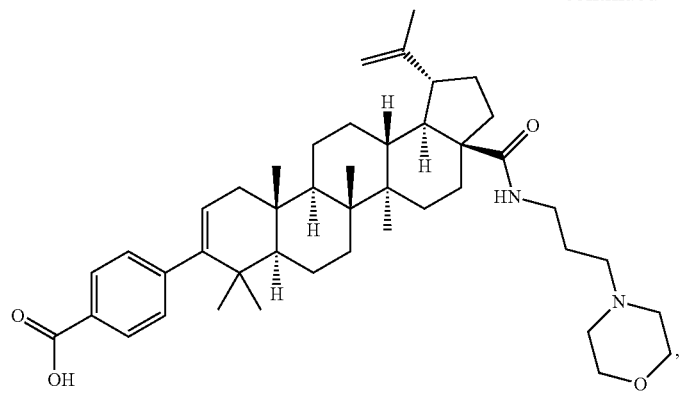
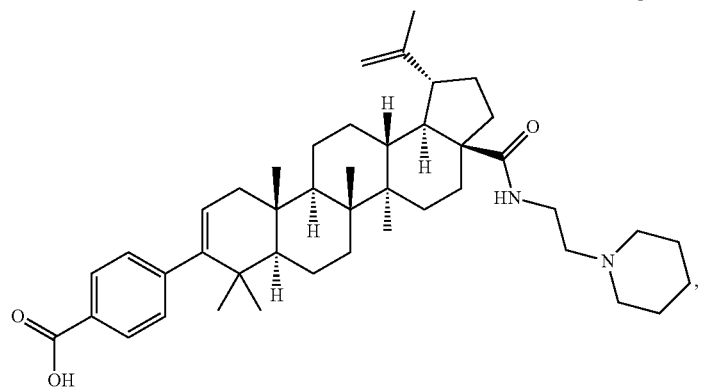
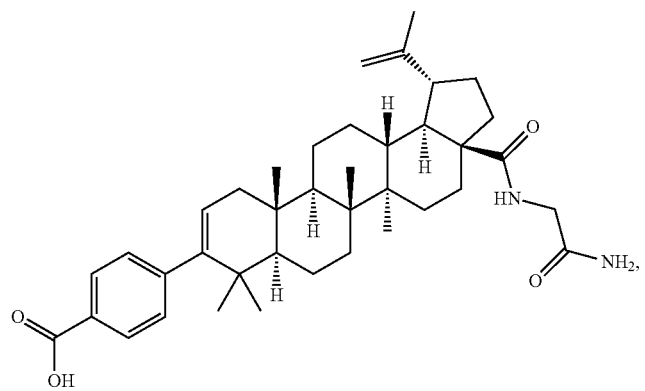
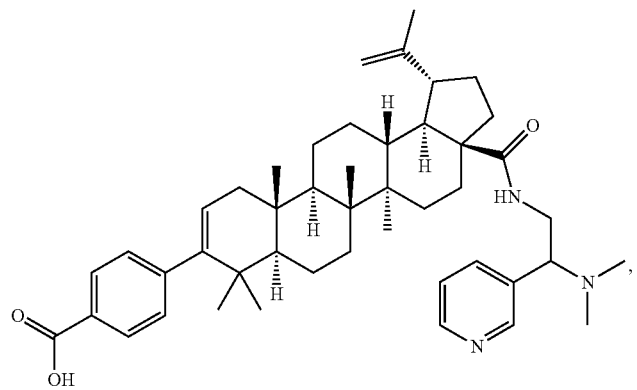

-continued
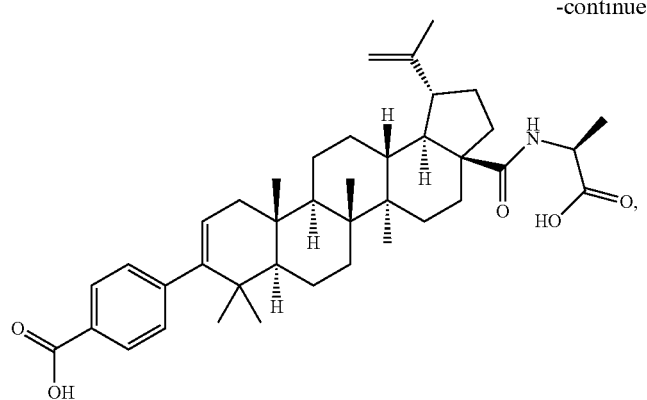
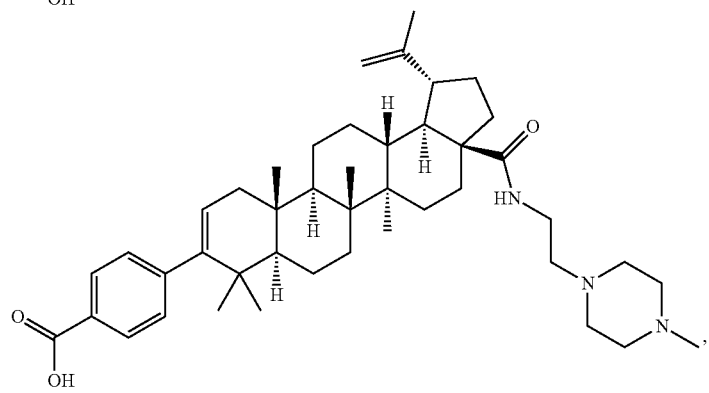
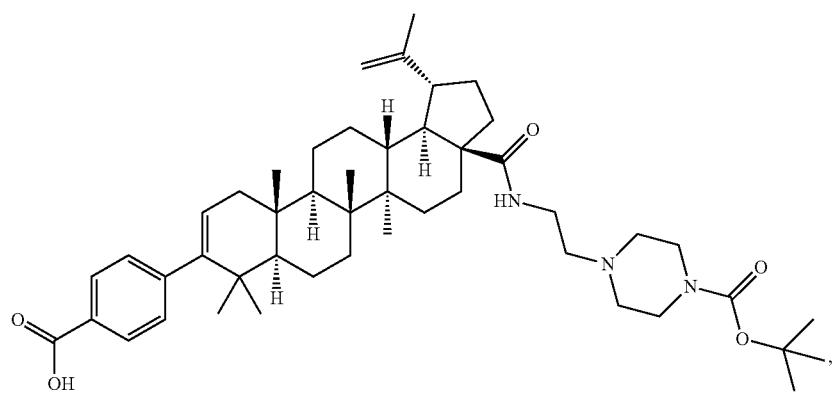
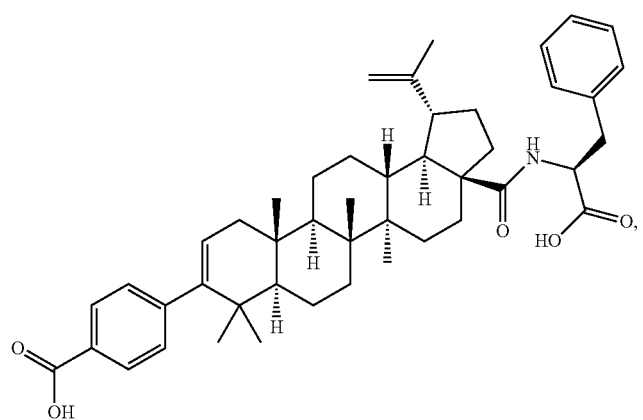

-continued
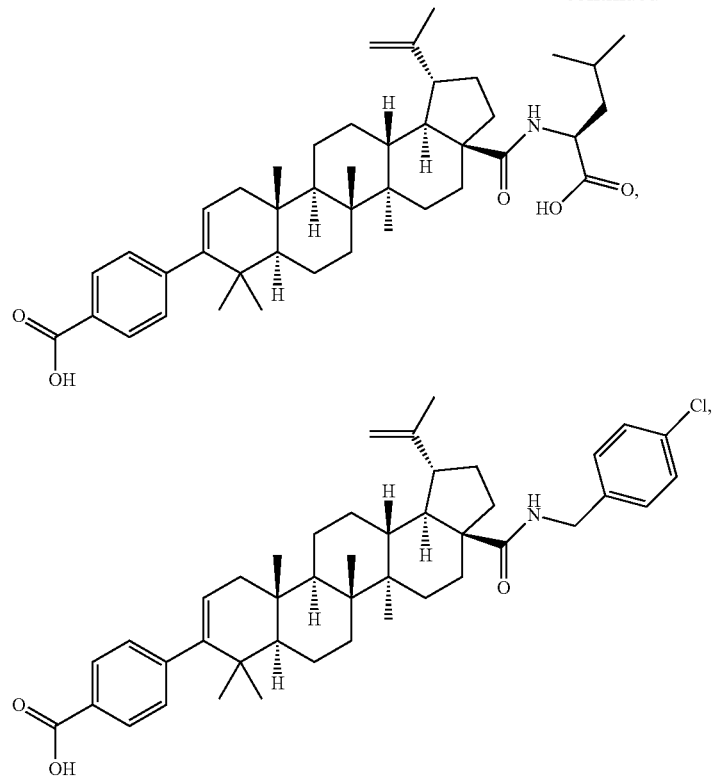
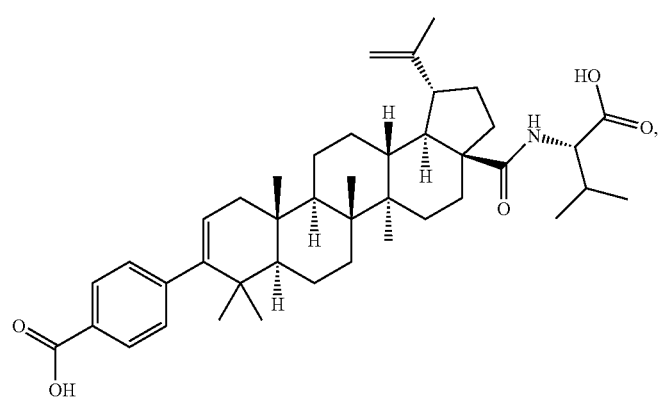
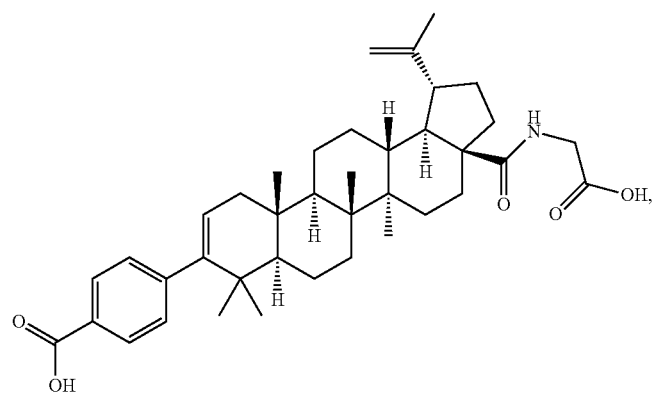

-continued
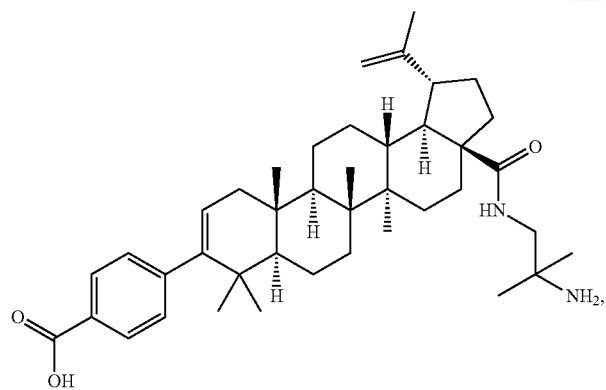
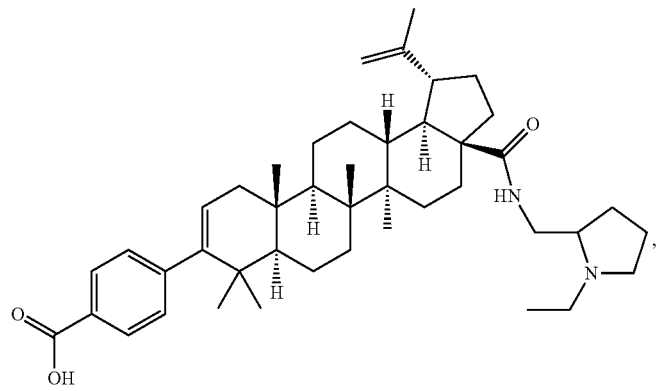
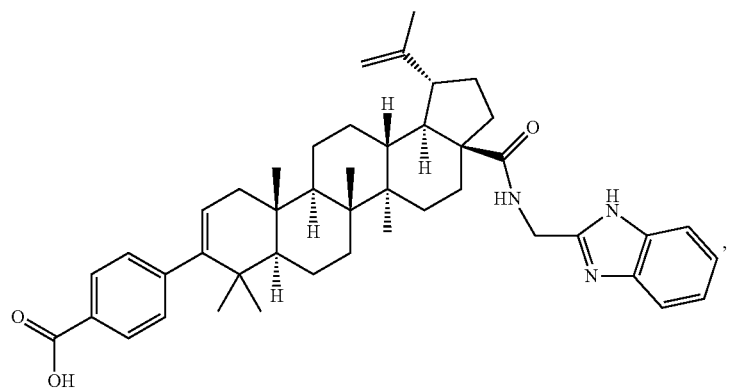
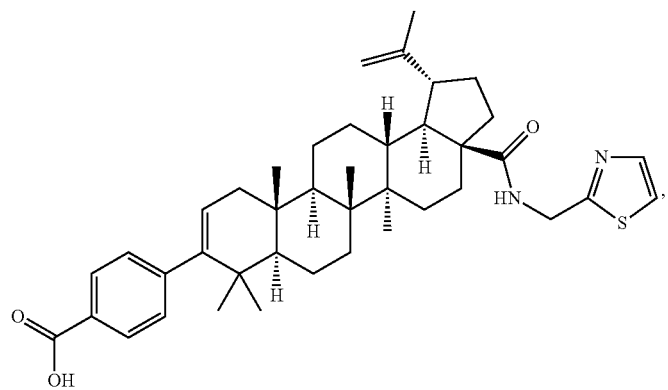

-continued
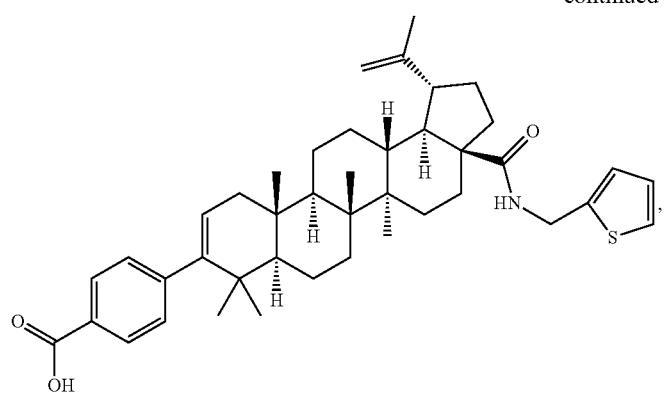
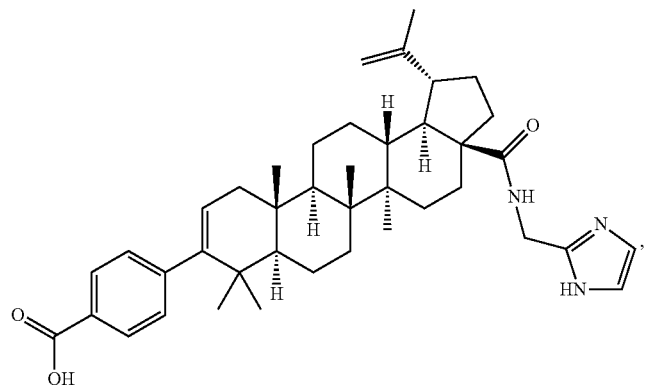
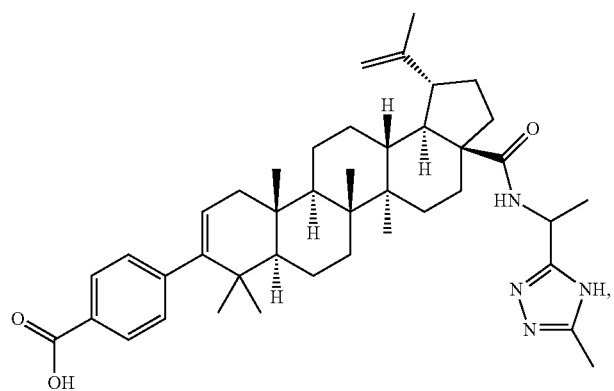
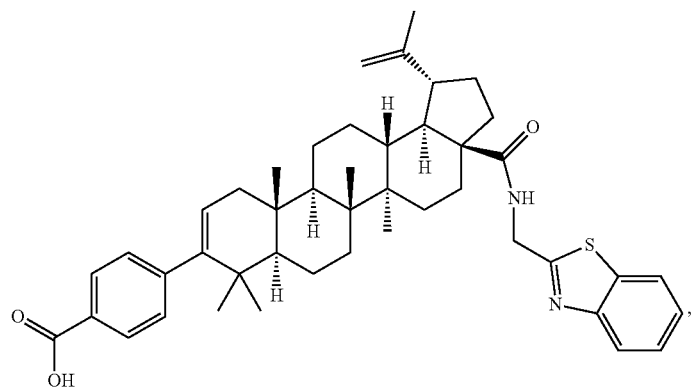

-continued
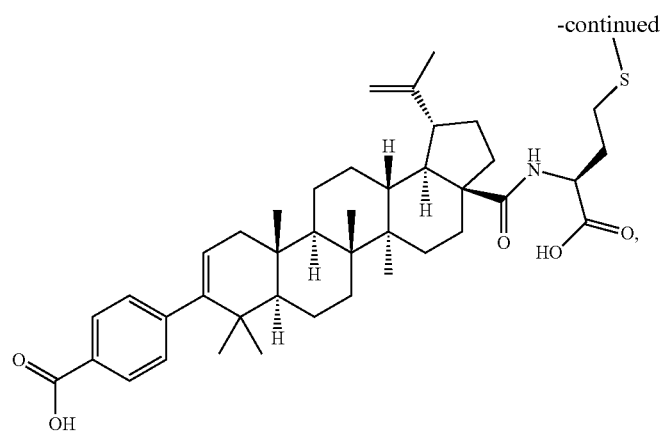
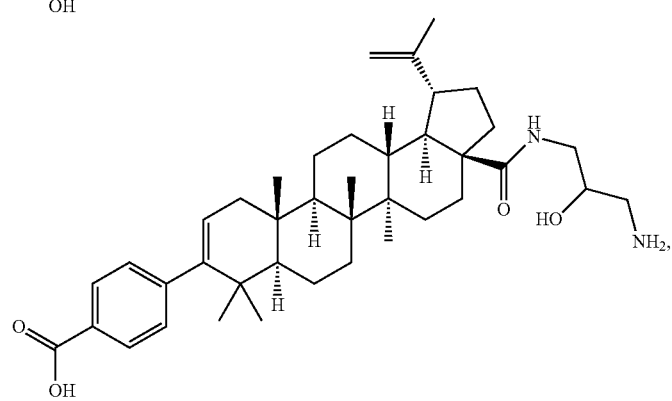
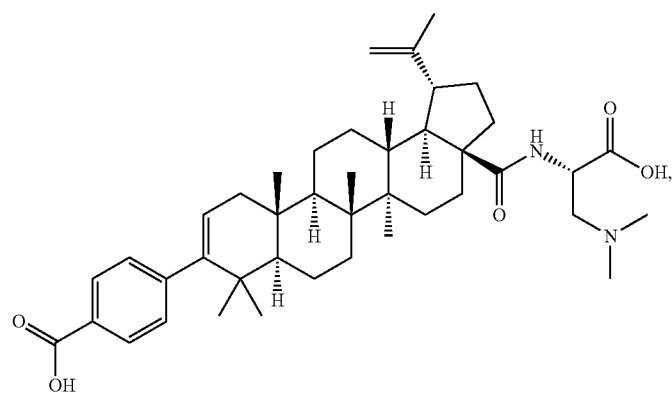
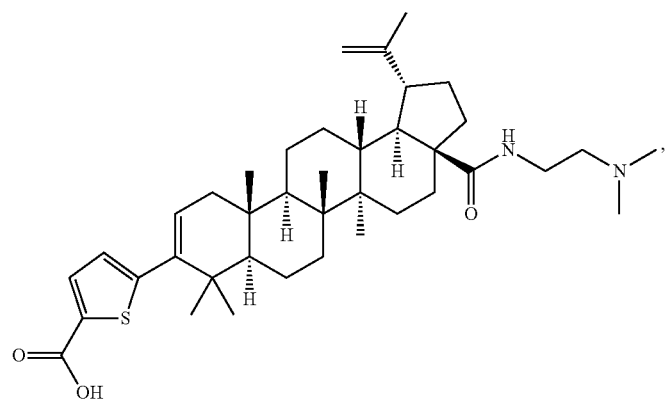

-continued
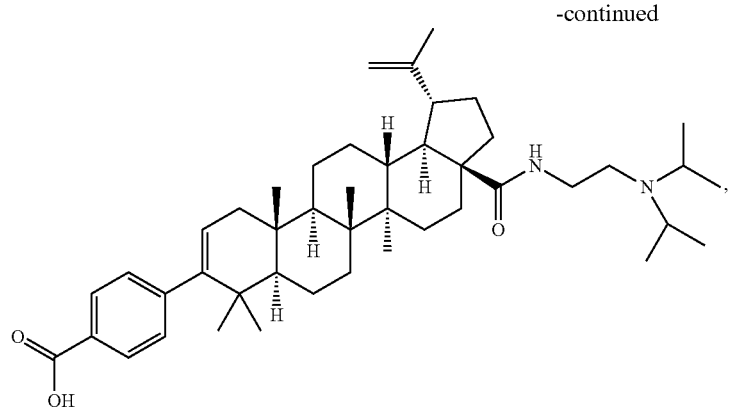
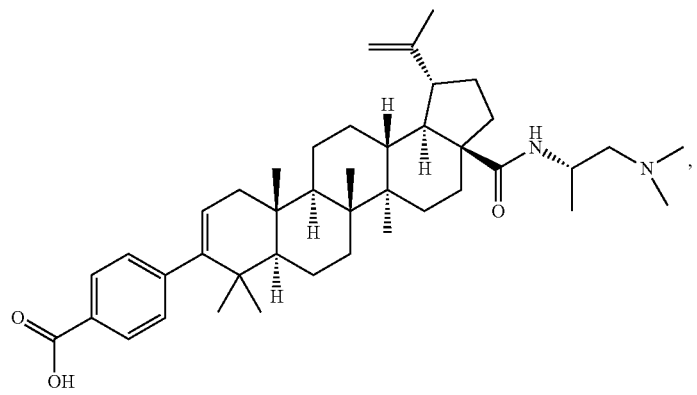
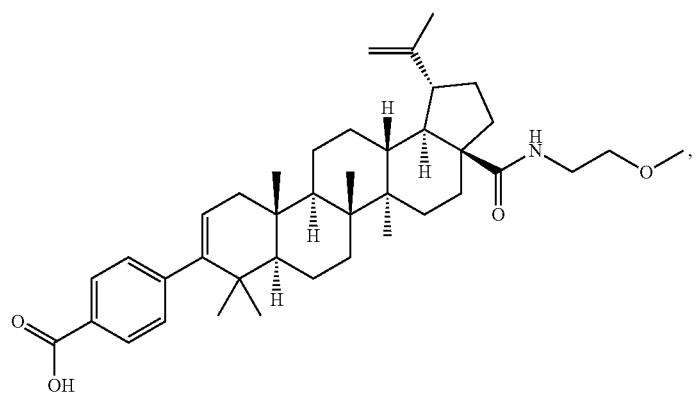
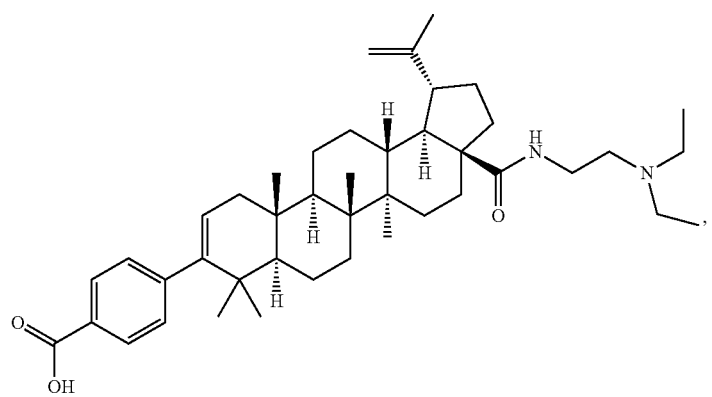

-continued
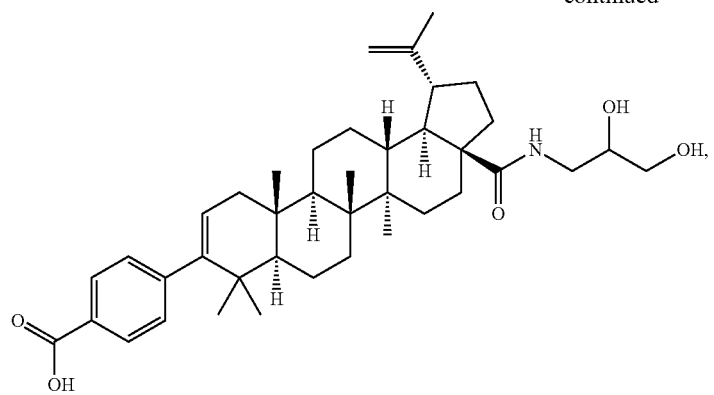
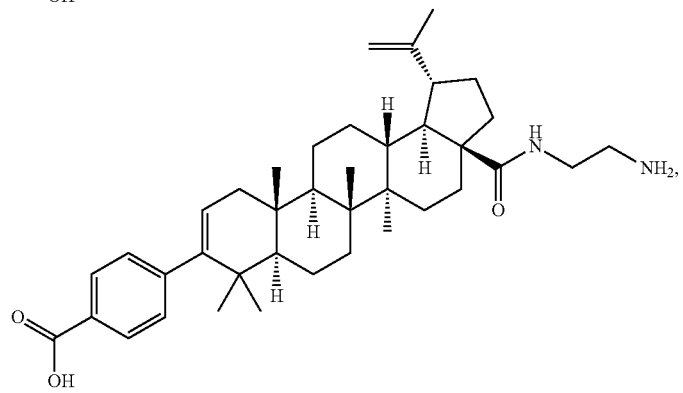
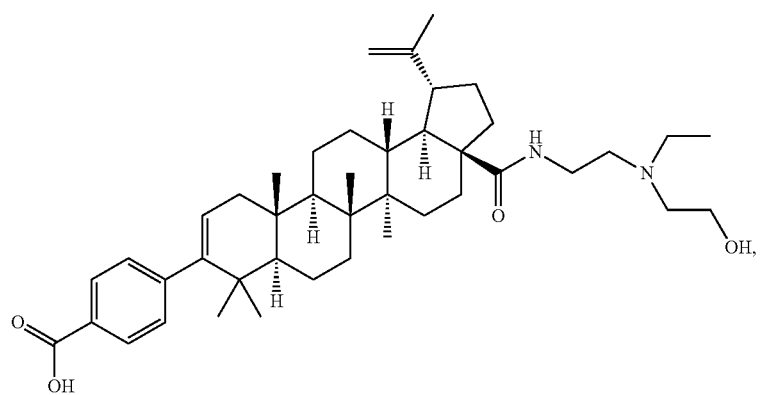
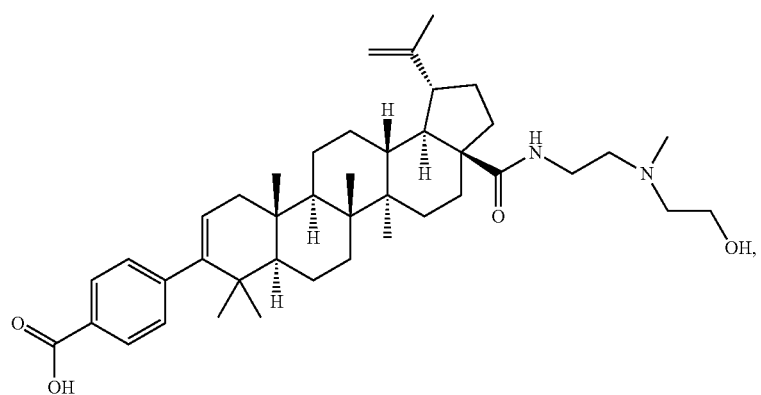

-continued
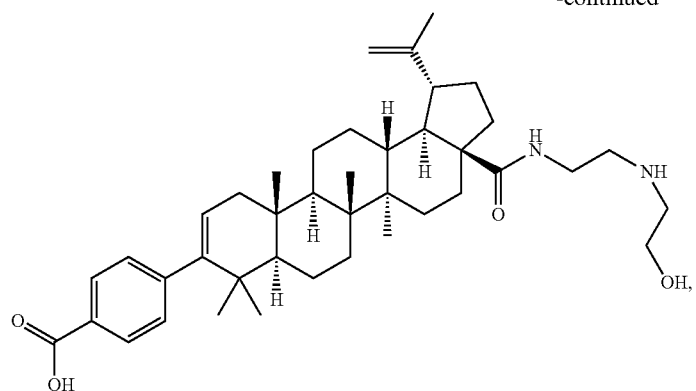
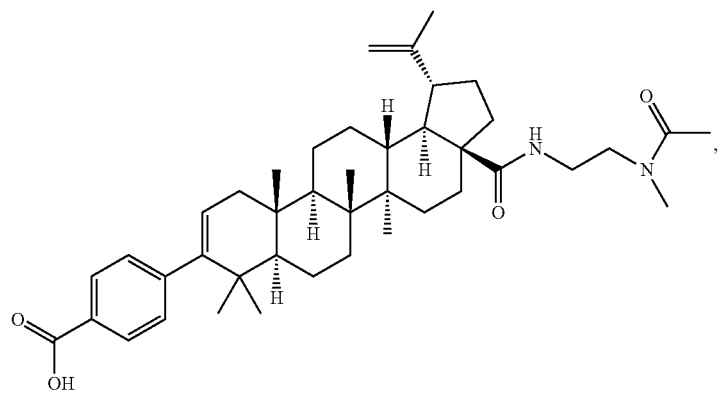
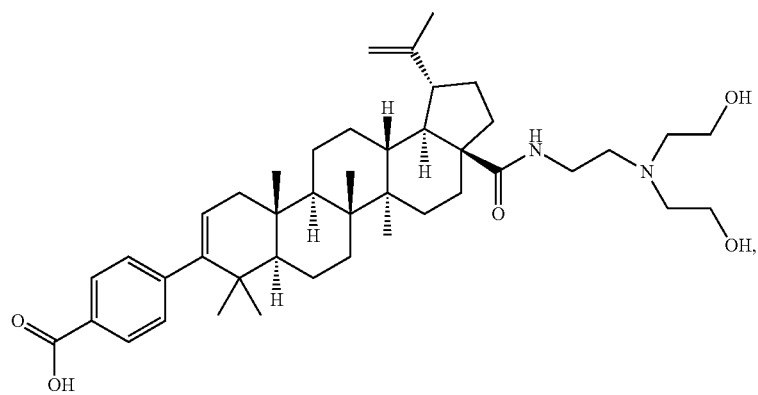
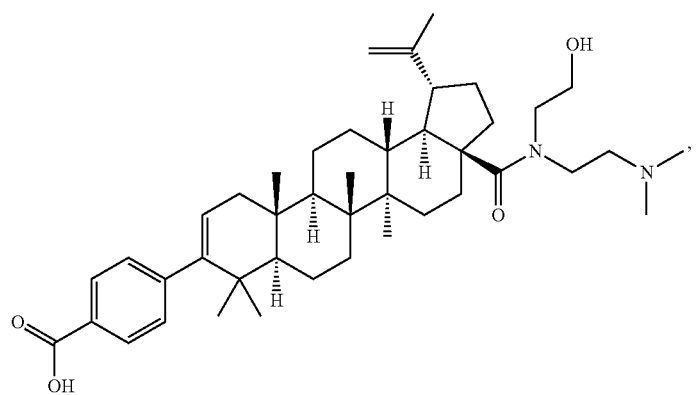

-continued
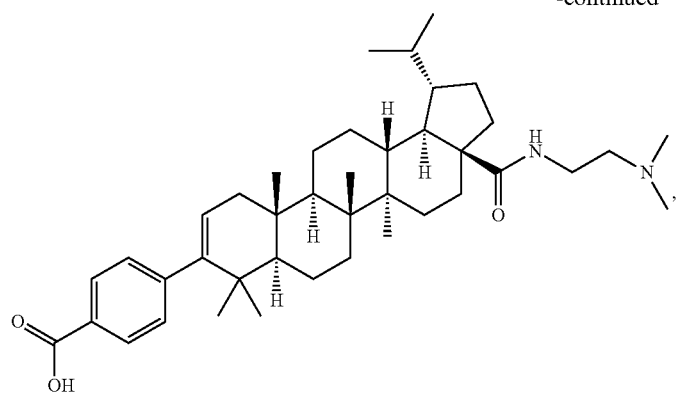
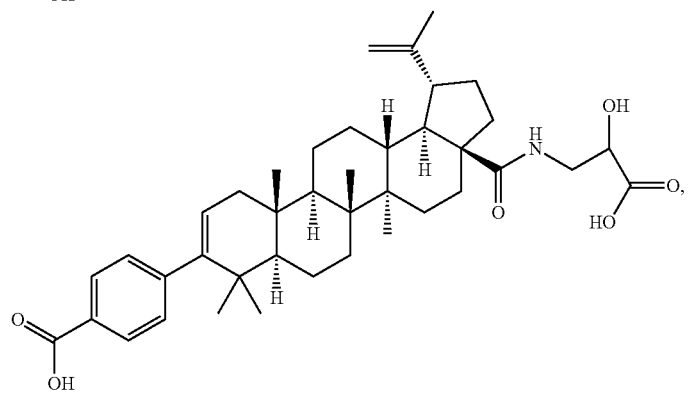
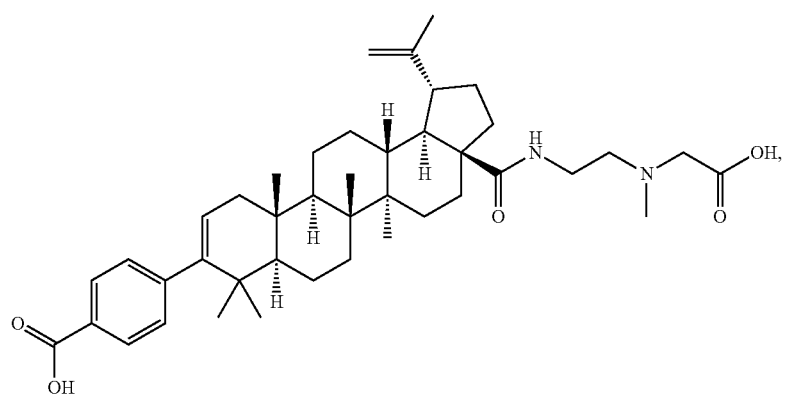
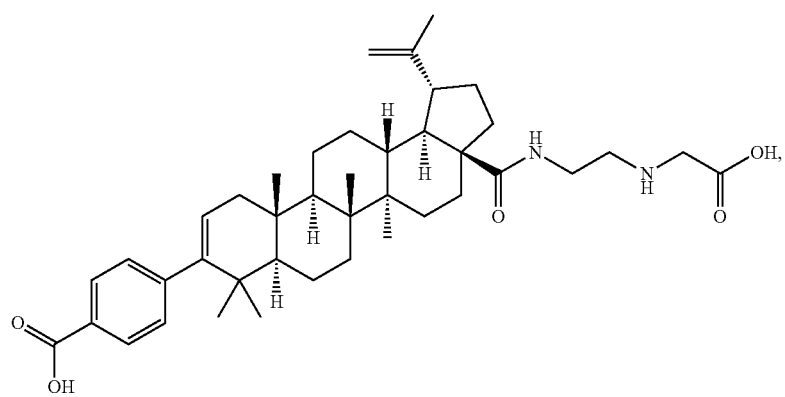

-continued
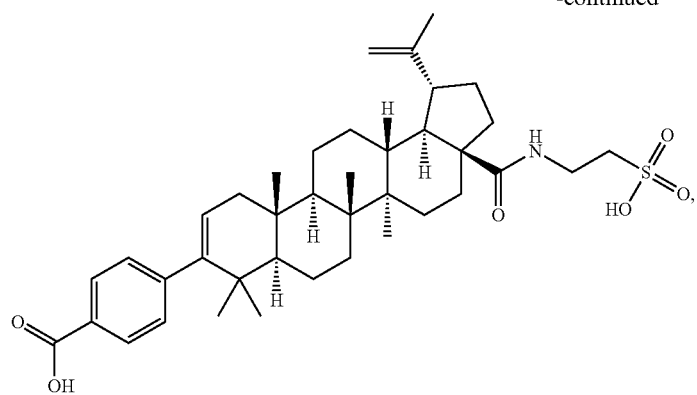
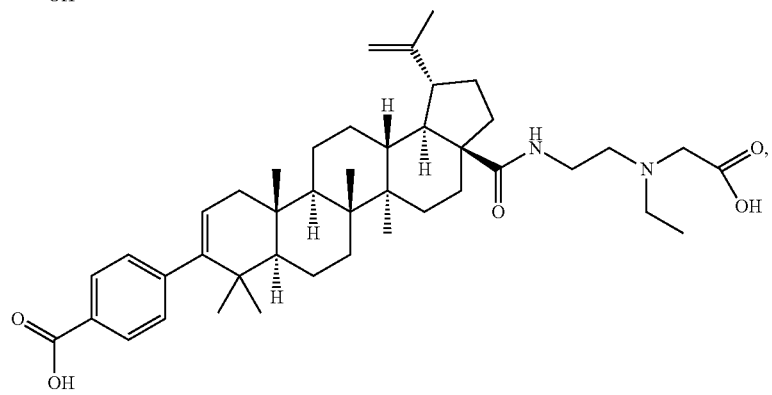
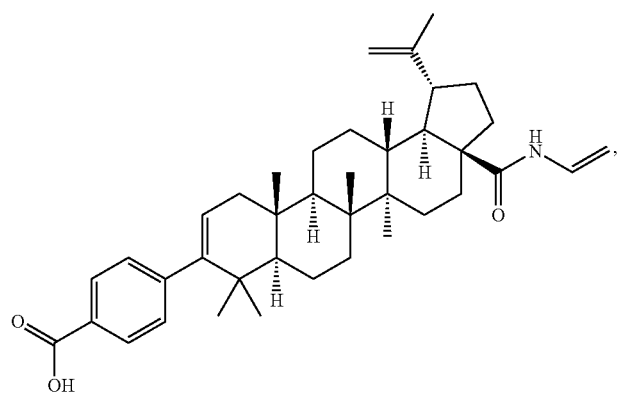
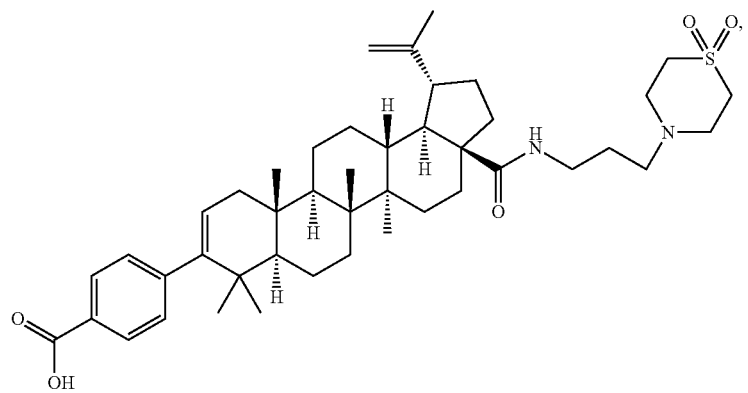

-continued
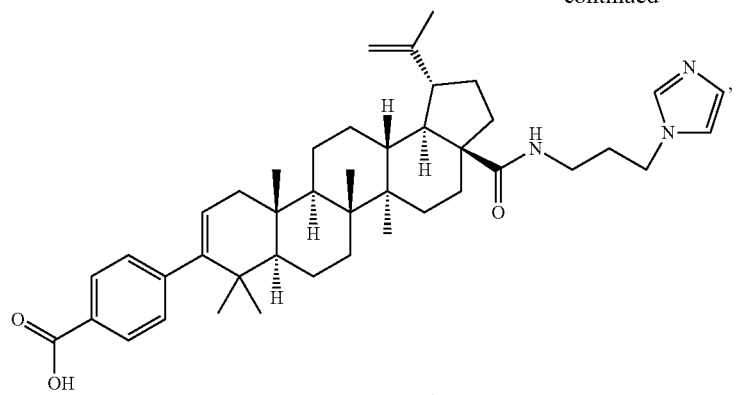
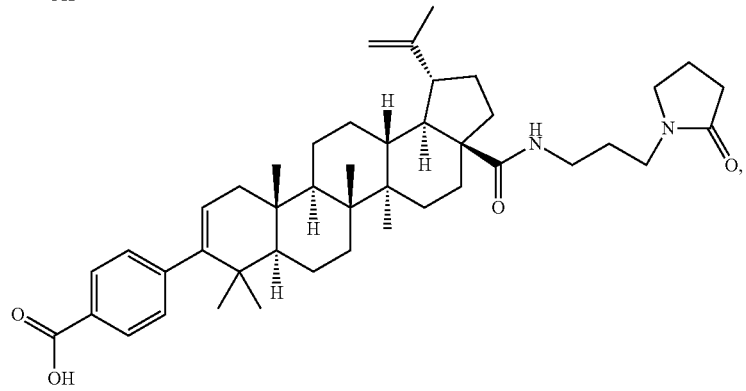
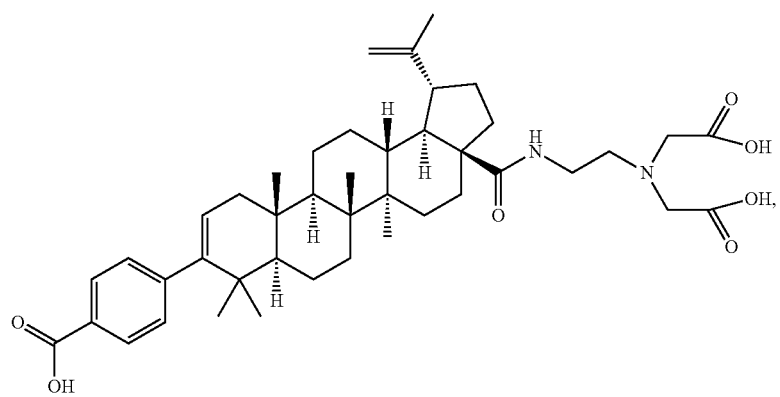
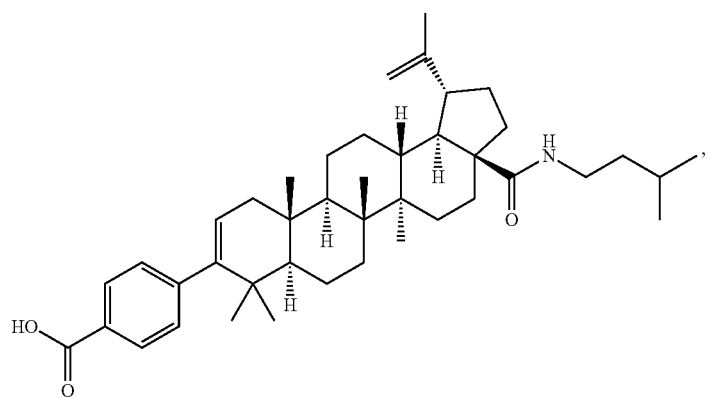

-continued
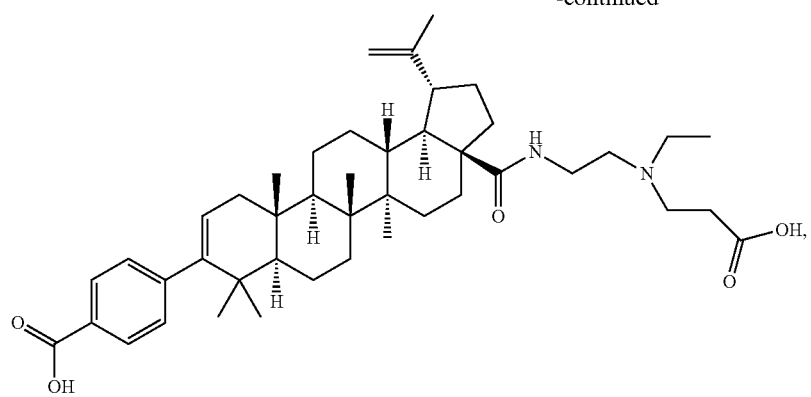
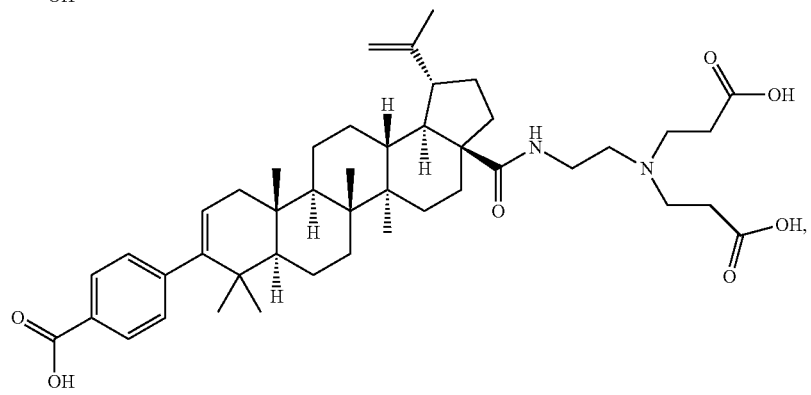
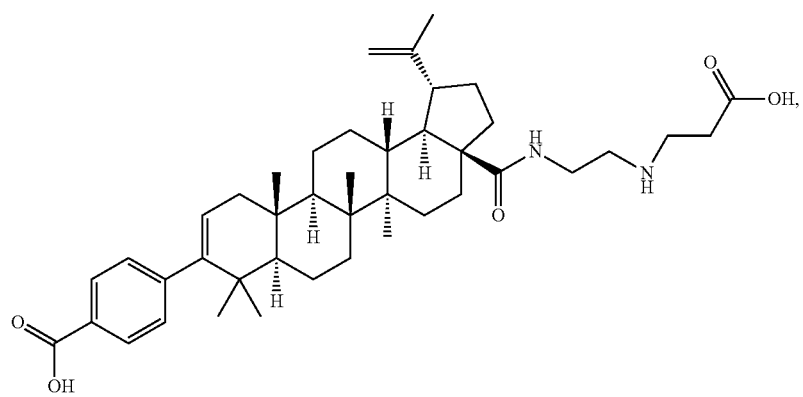
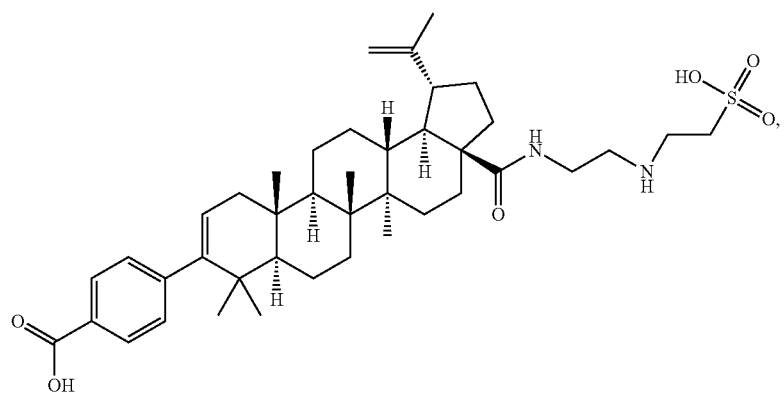

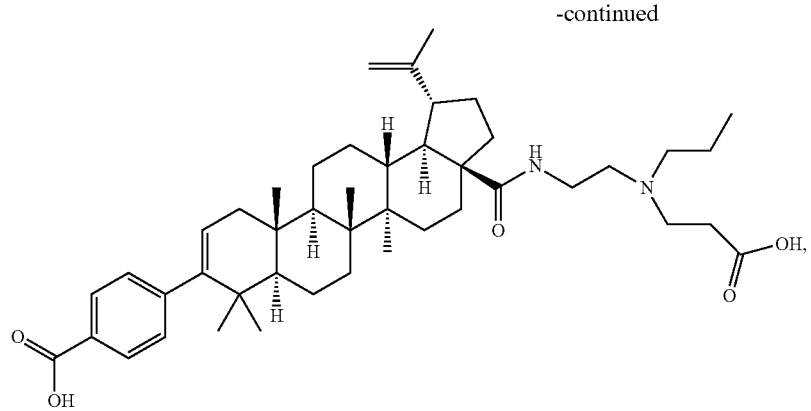
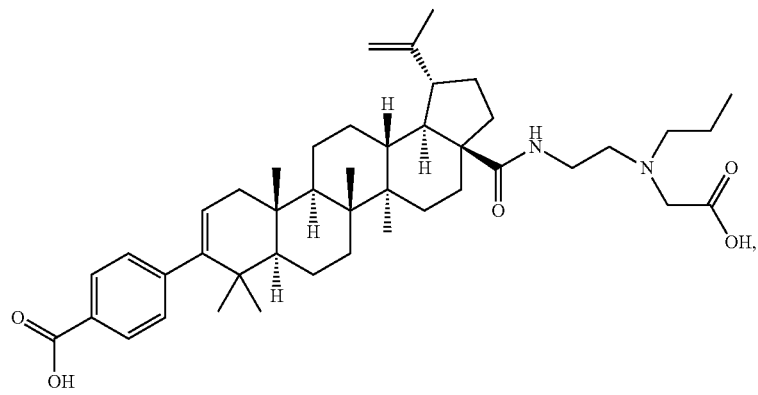
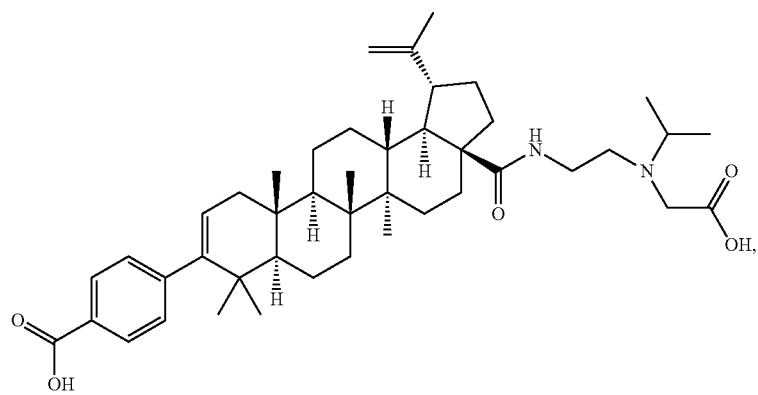
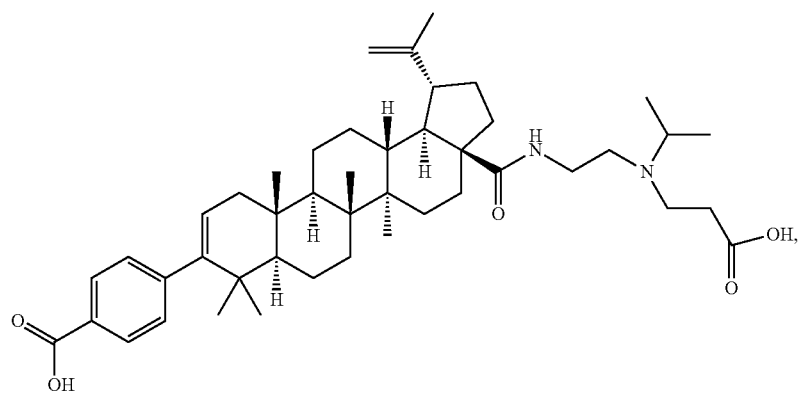

-continued
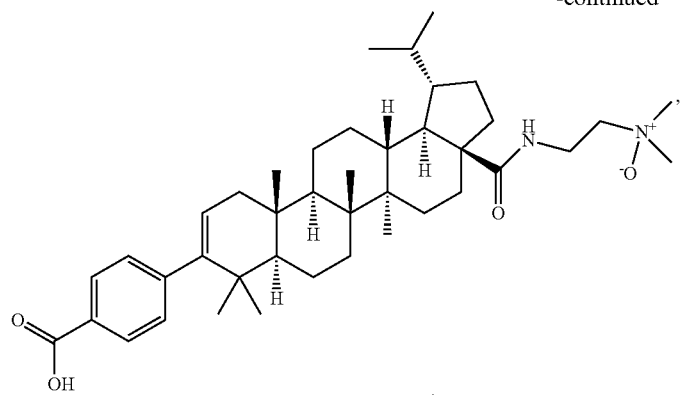
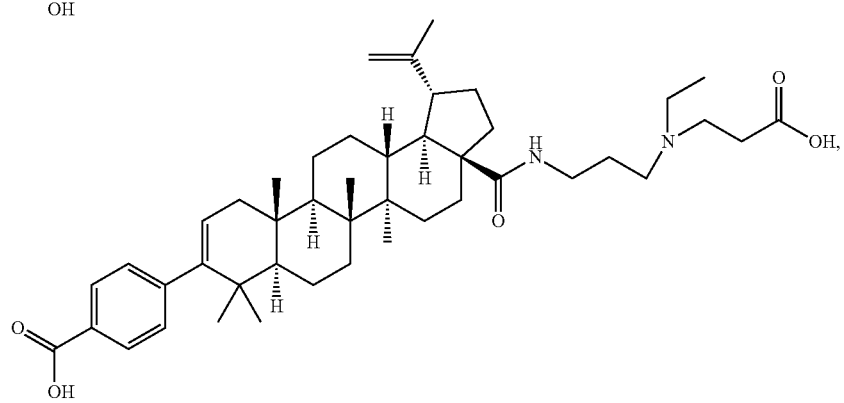
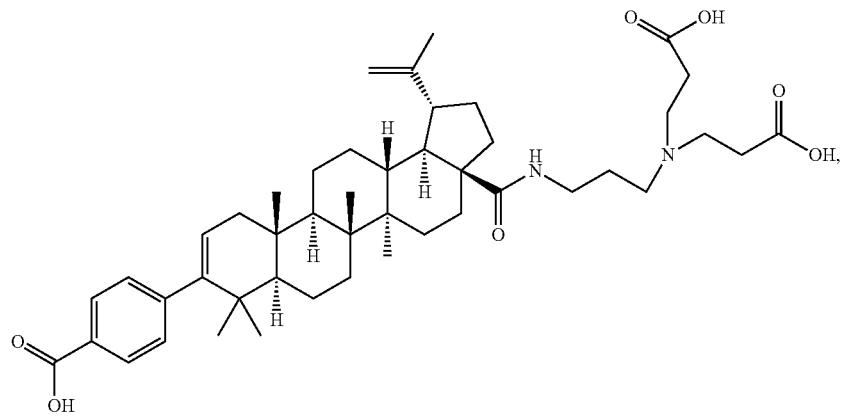
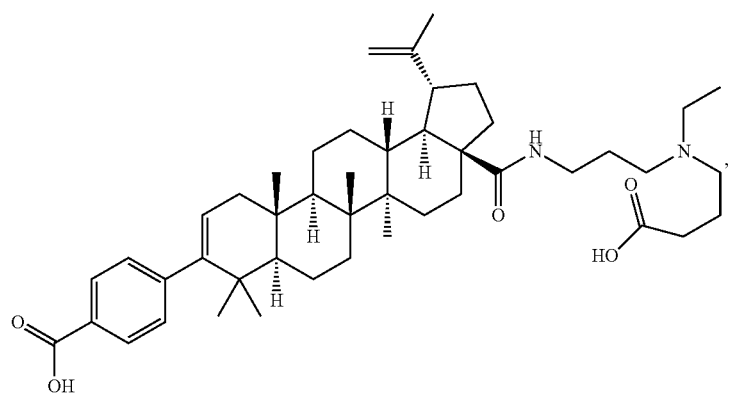

-continued
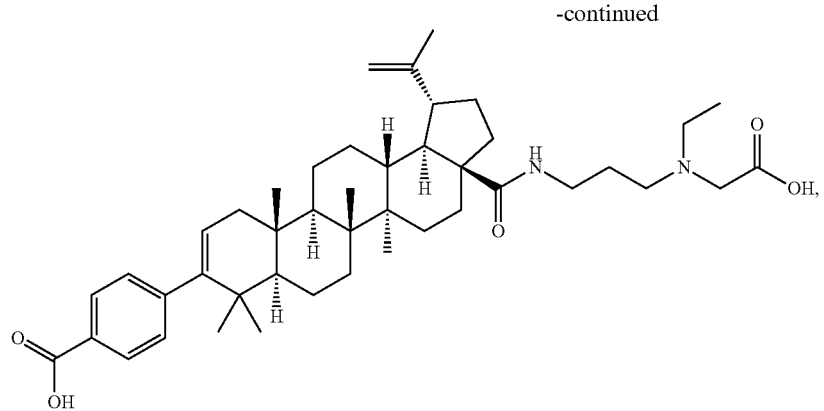
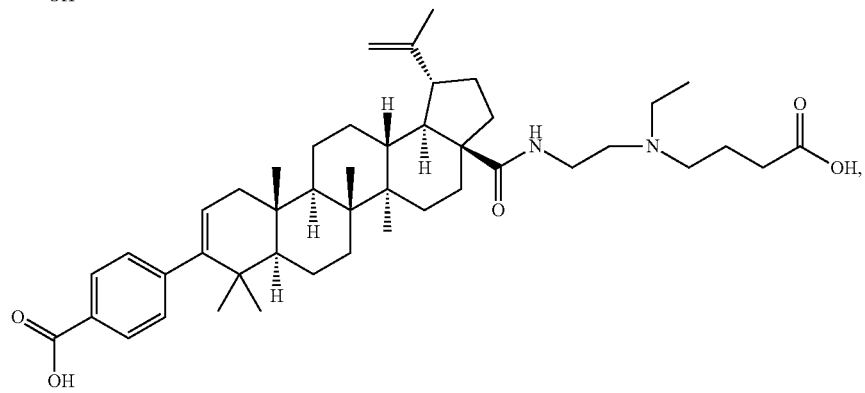
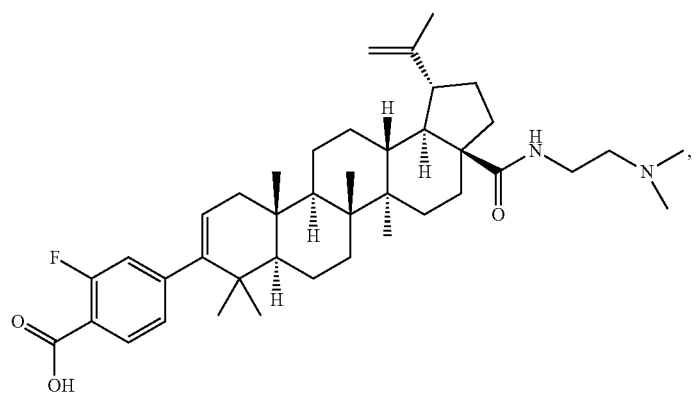
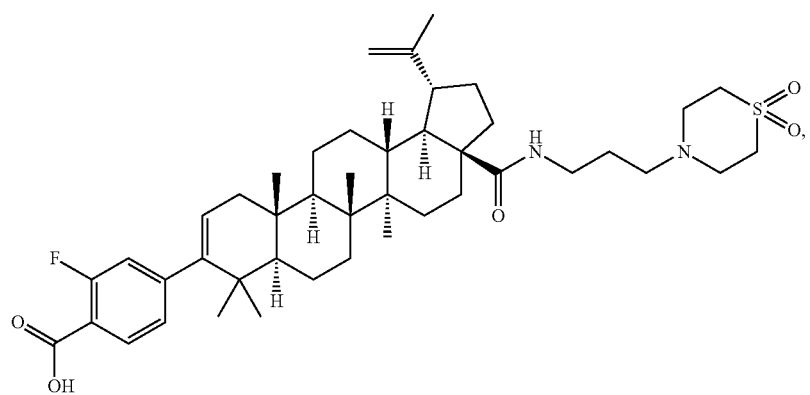

-continued
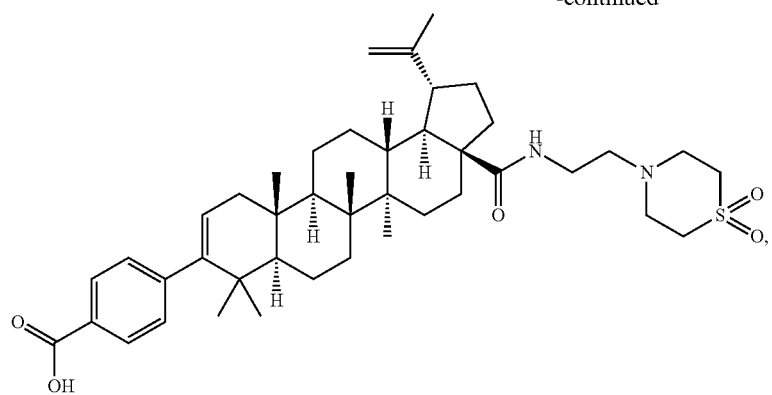
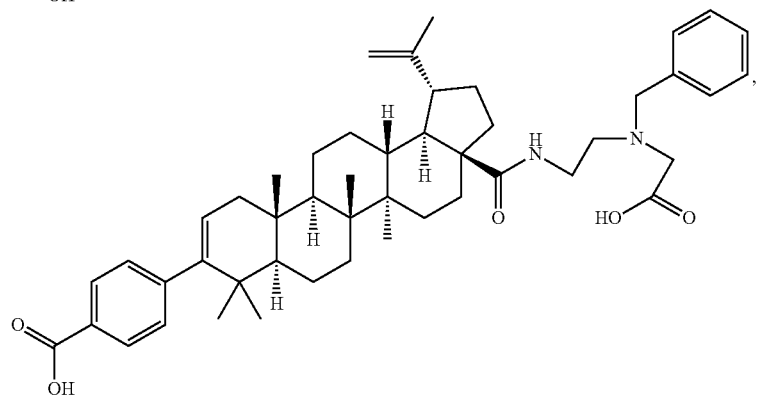
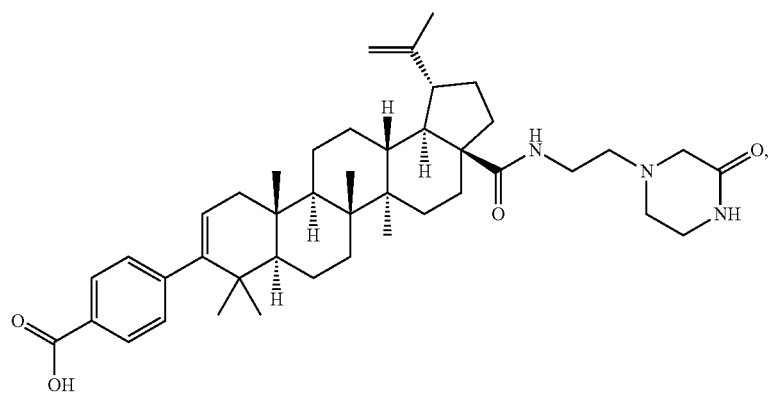
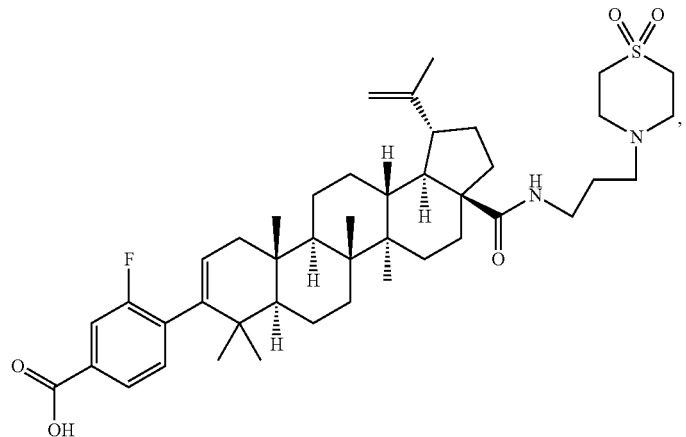

-continued
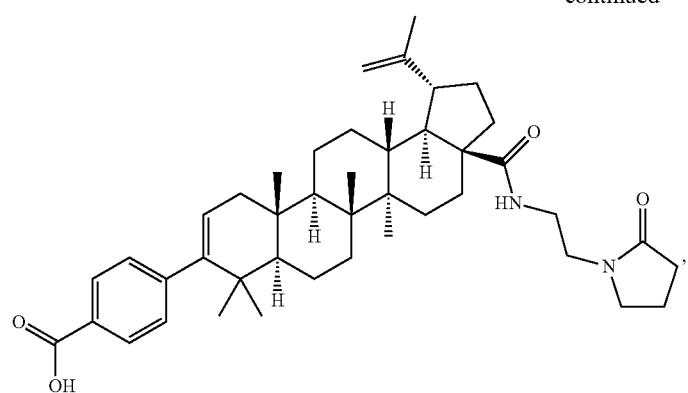
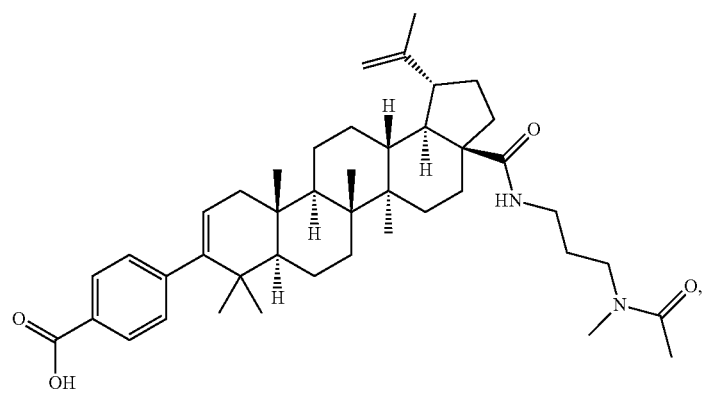
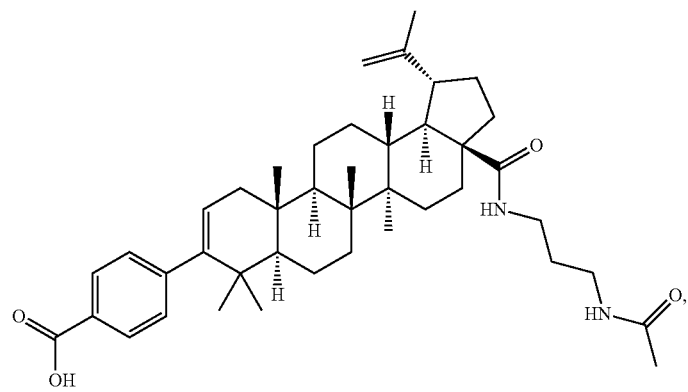
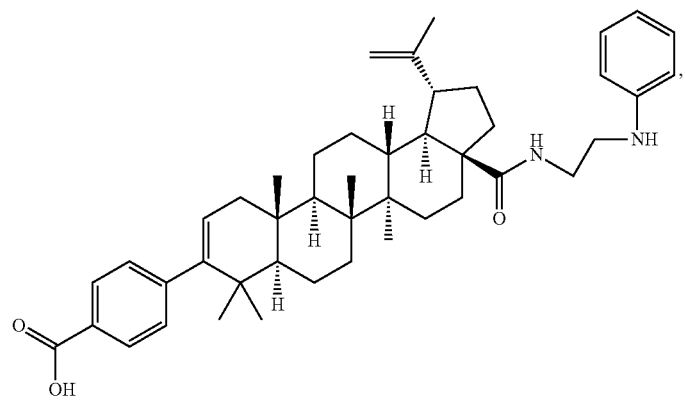

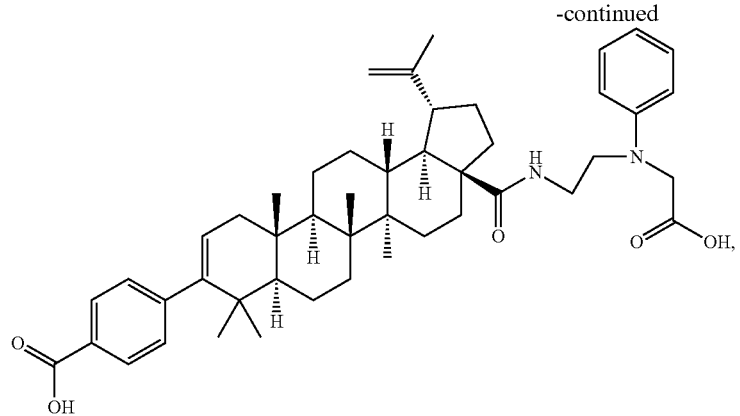
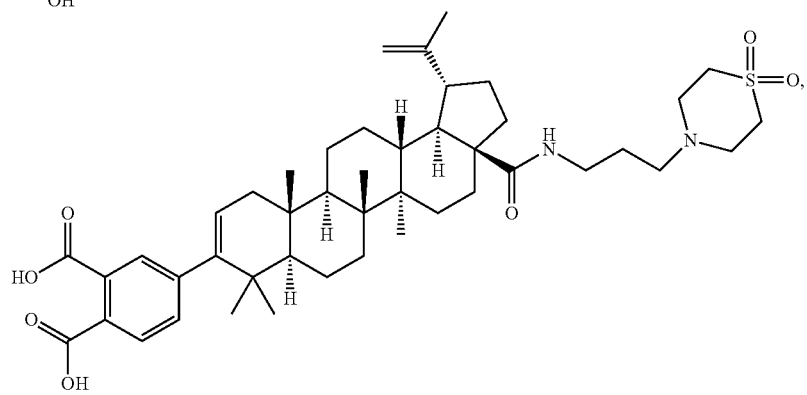
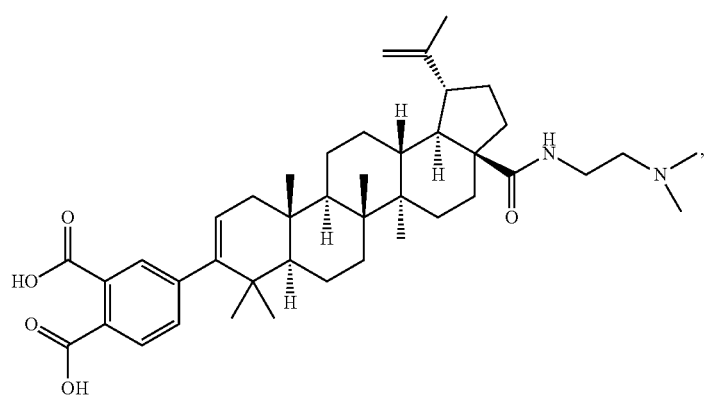
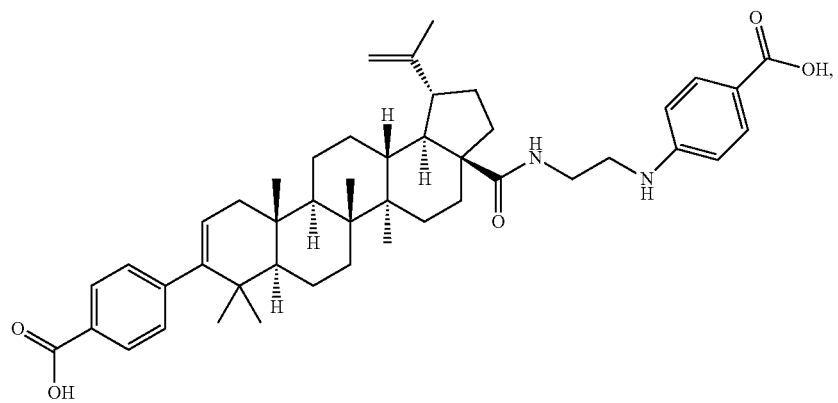

-continued
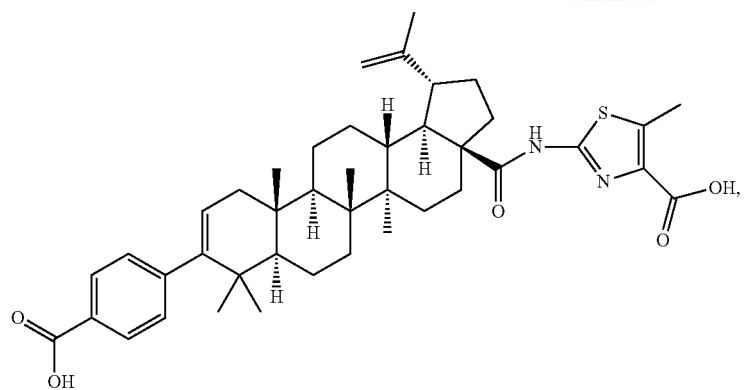
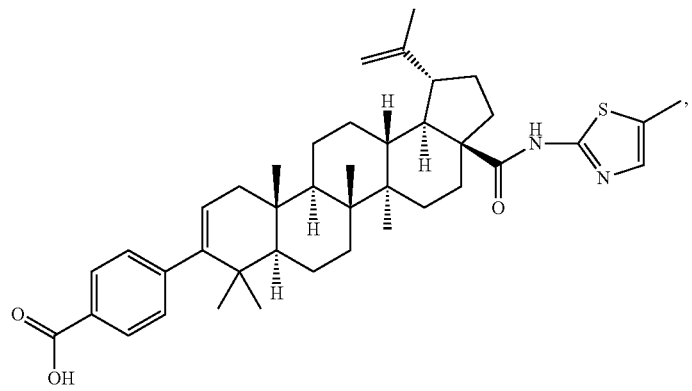
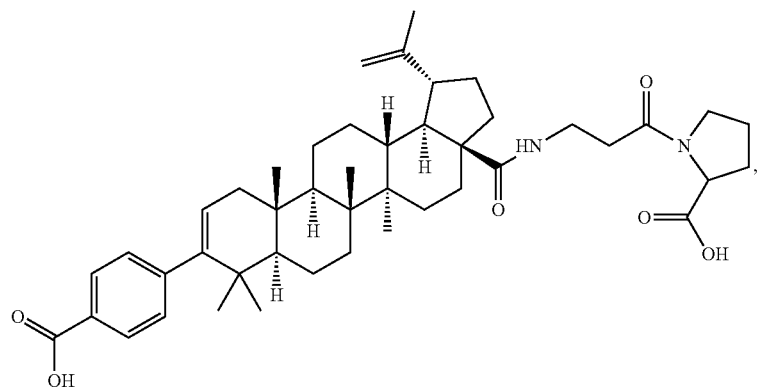
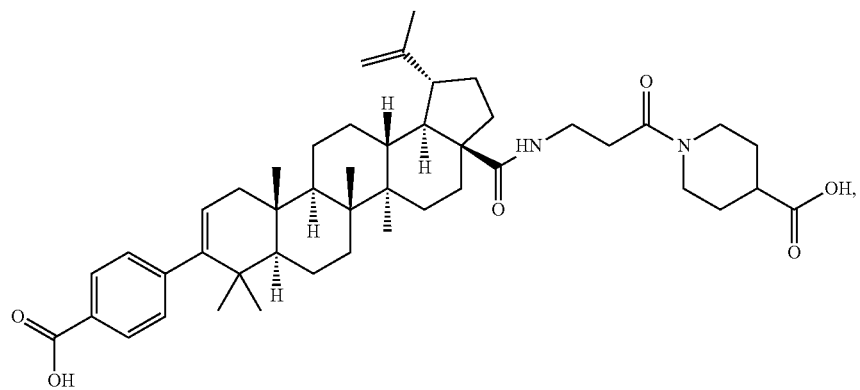

-continued
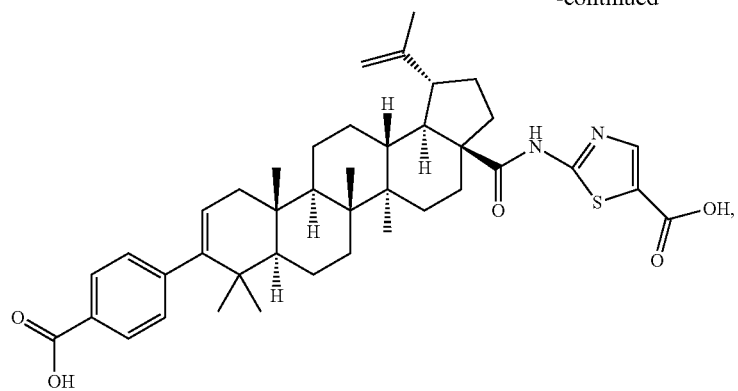
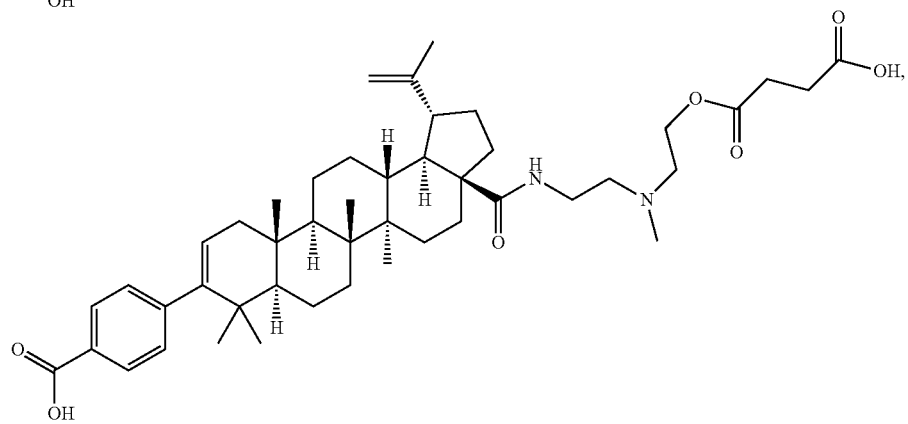
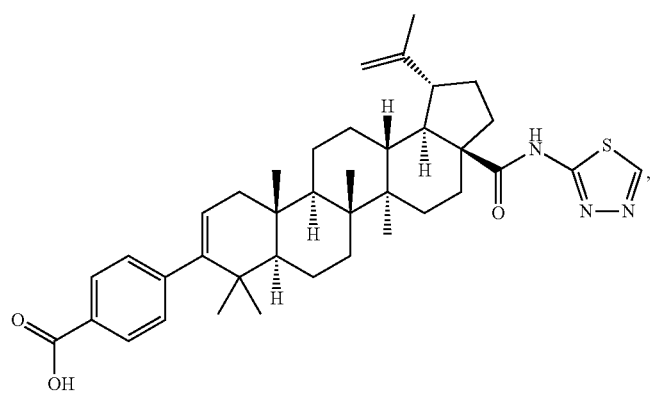
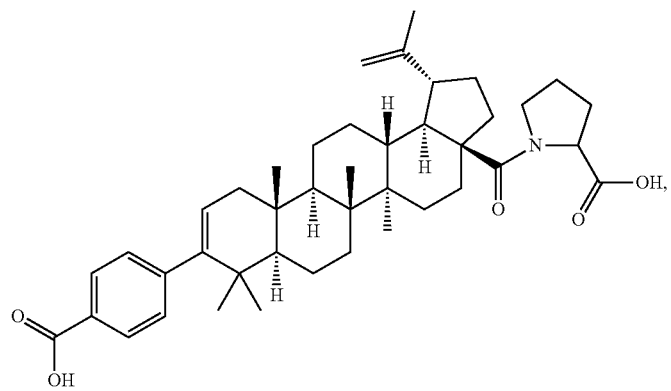

-continued
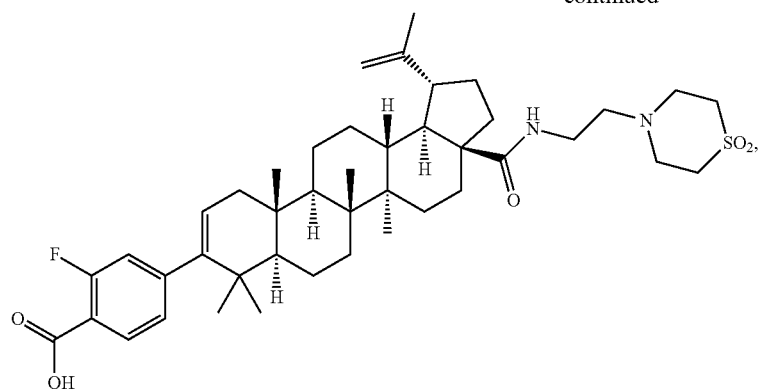
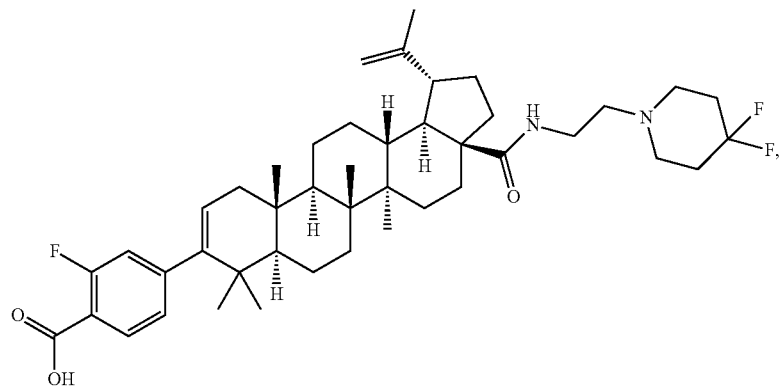
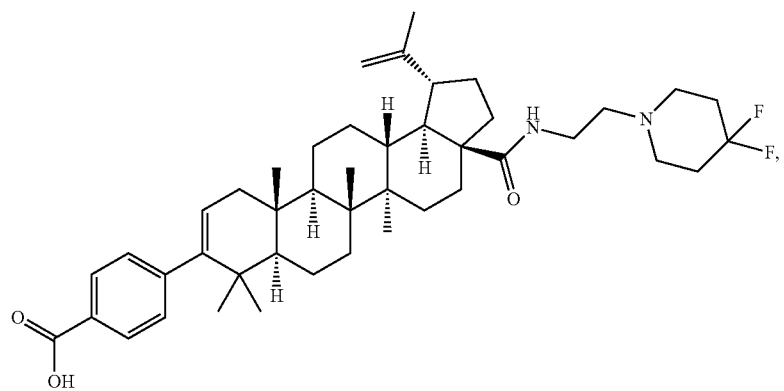
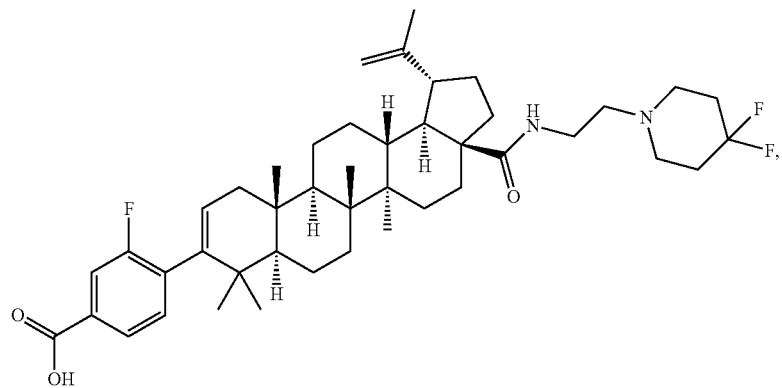

-continued
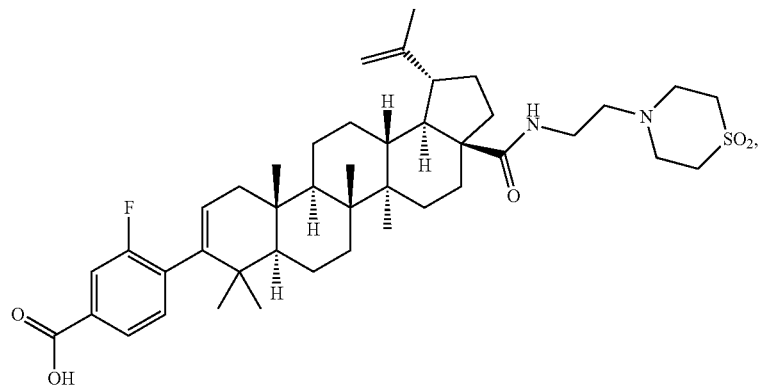
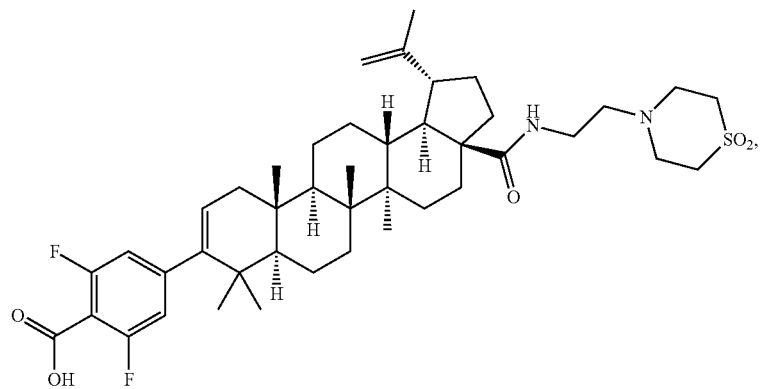
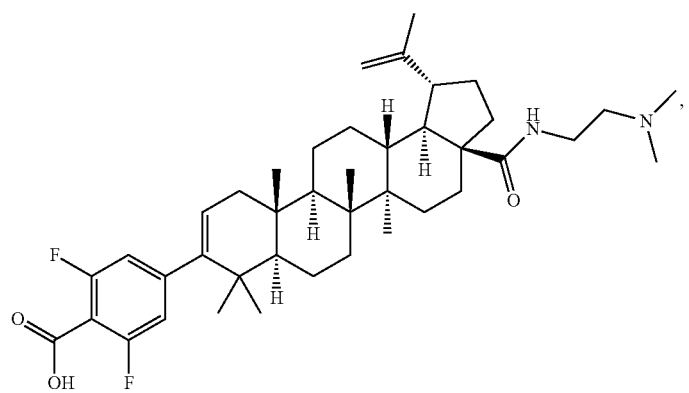
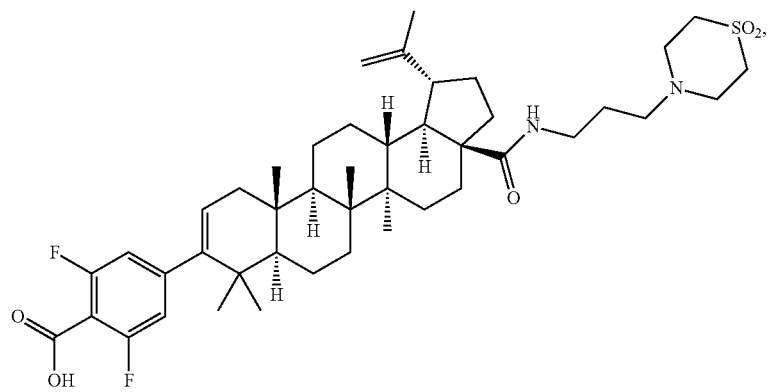

-continued
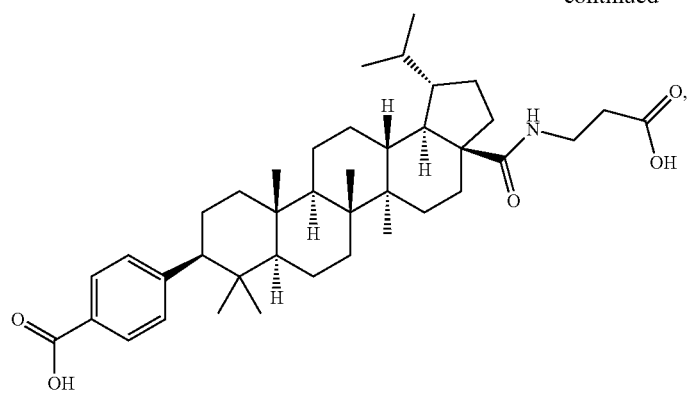
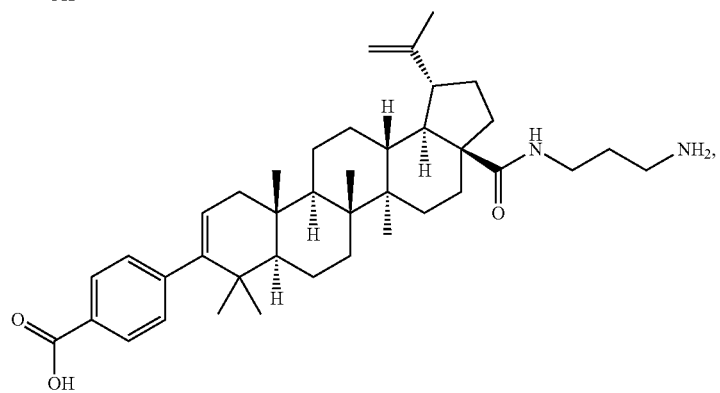
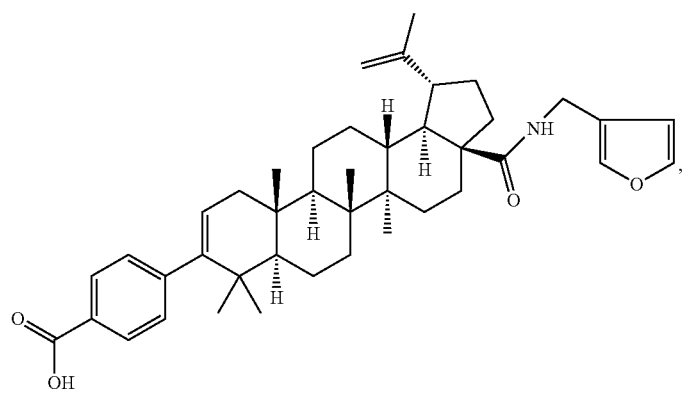
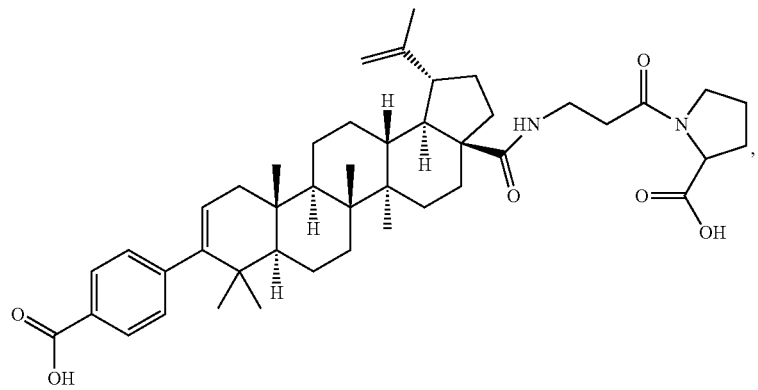

-continued
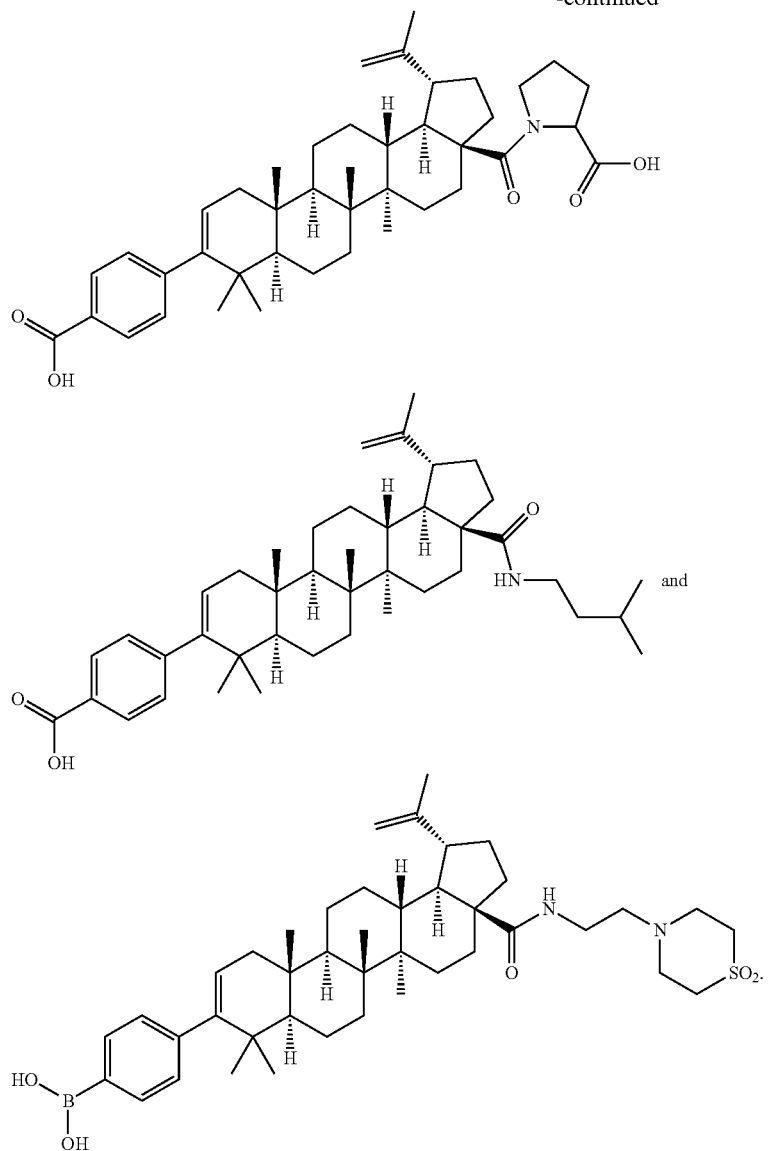
Of the foregoing, the following compounds are particularly preferred:
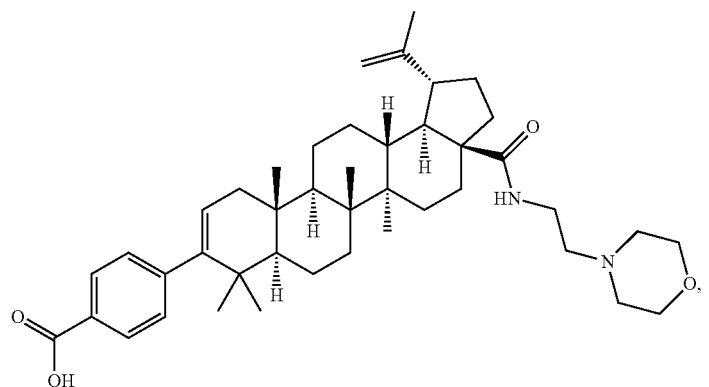

-continued
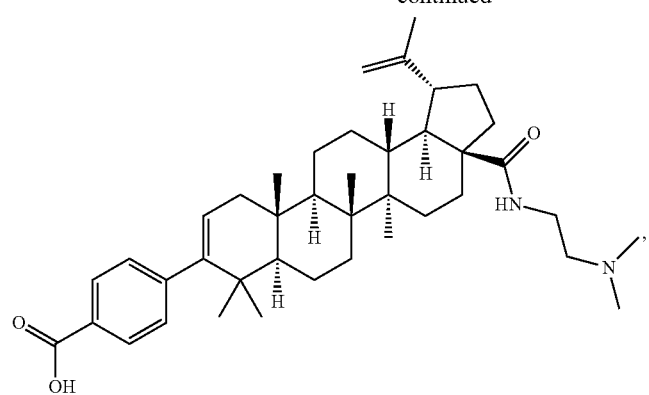
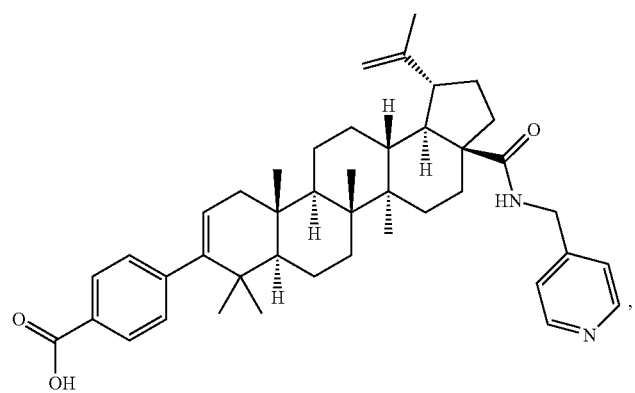
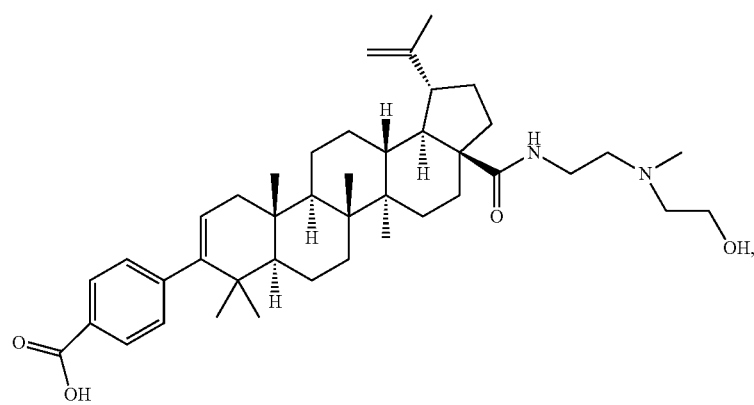
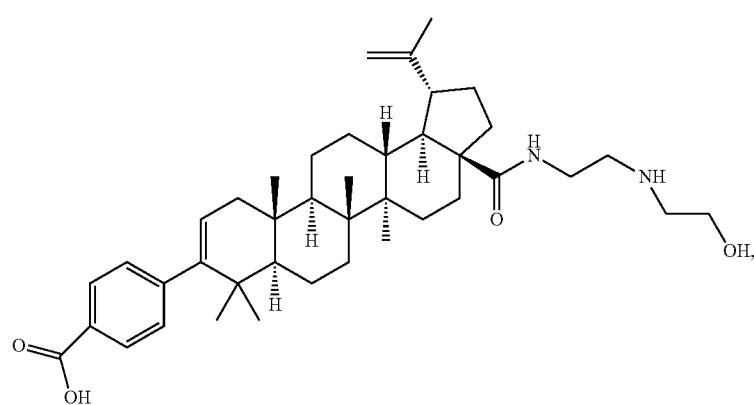

-continued
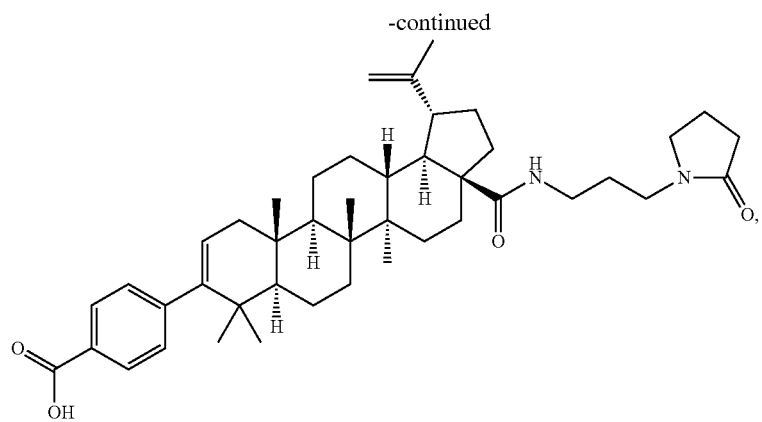
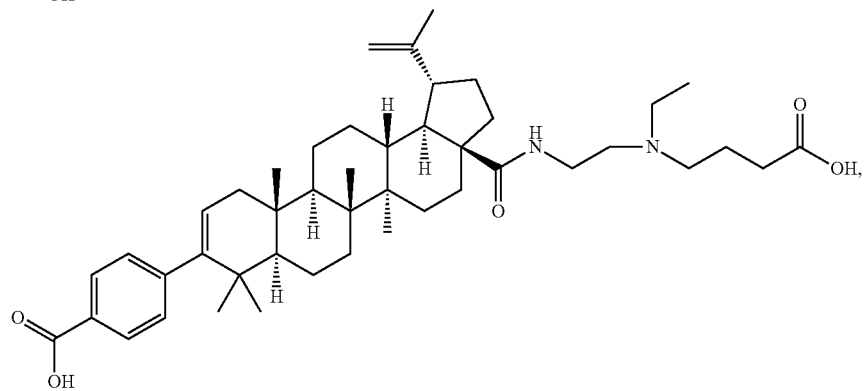
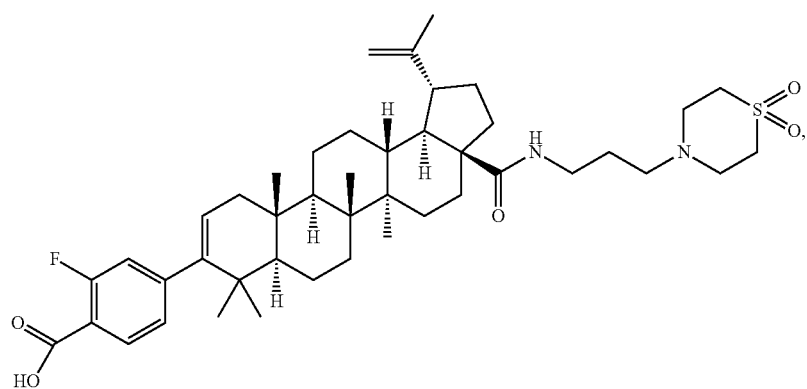
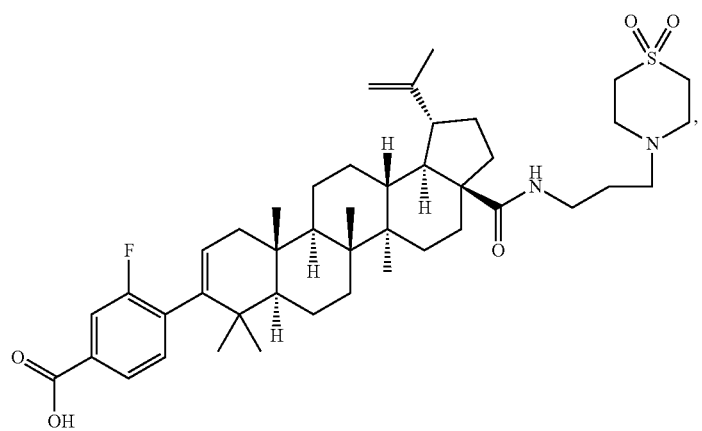

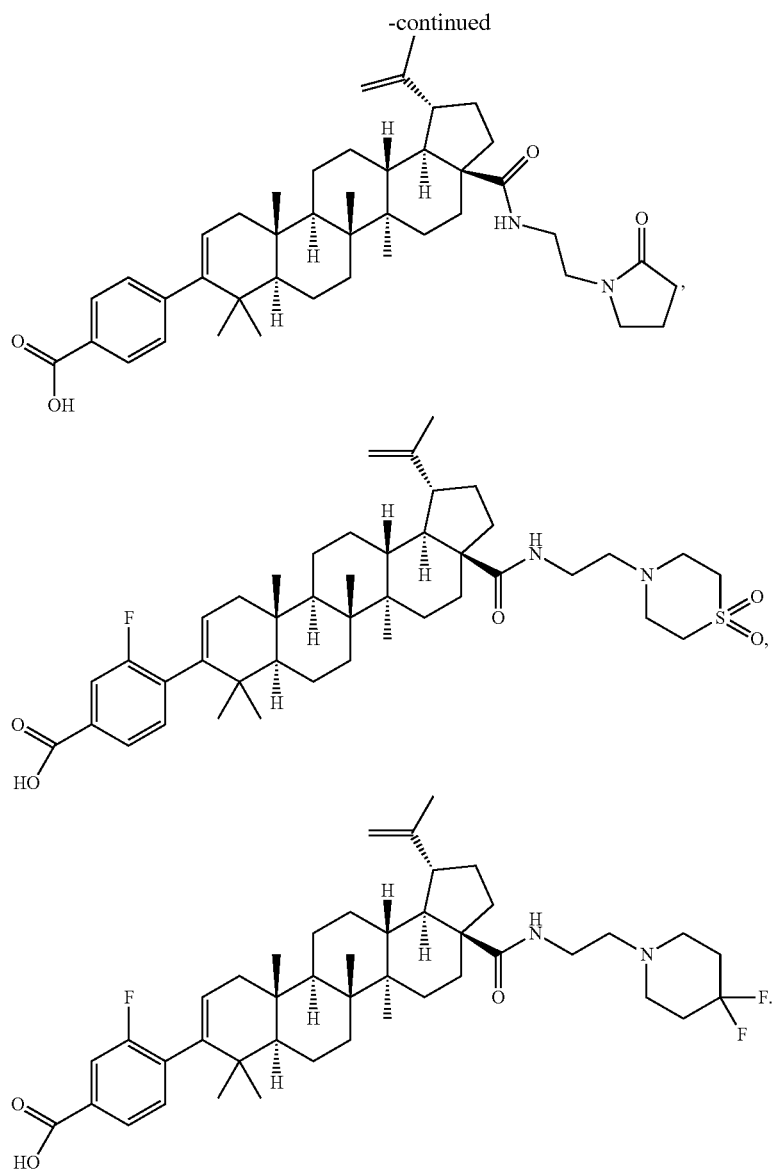

Also preferred as part of the invention are the compounds of Formula I wherein X is 5 or 6-membered heteroaryl ring. In particular, the compounds of Formula I wherein X is a 5-membered heteroaryl ring having the following structure are particularly preferred:

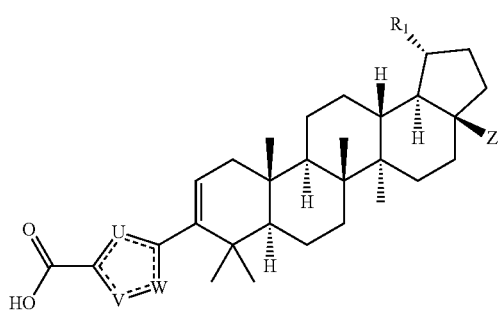

wherein each of U, V and W is selected from the group consisting of C, N, O and S, with the proviso that at least one of U, V and W is other than C. Of these, the compounds wherein X is selected from the group of thiophene, pyrazole, isoxaxole, and oxadiazole groups are particularly preferred, with thiophene being even more preferred.

Also preferred are the compounds of Formula I wherein X is a 6-membered heteroaryl ring selected from the group of pyridyl and pyrimidine rings.

Other preferred compounds of the invention include those which are encompassed by Formula II as set forth above. Of these, the compounds wherein X is a phenyl group and Y is —COOH in the para position (and wherein A is as previously set forth) according to Formula IIa below are particularly preferred:

Formula IIa
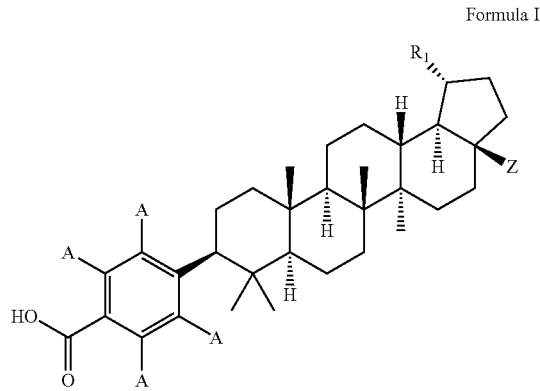
Preferred examples of the compounds of Formula IIa include the following:
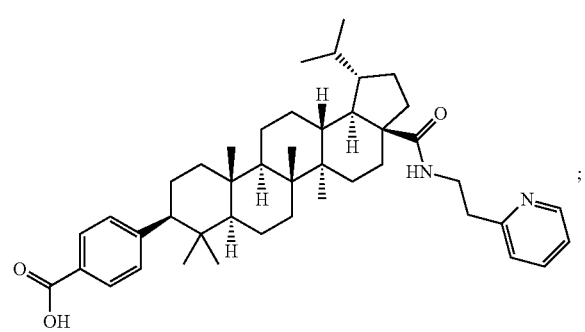
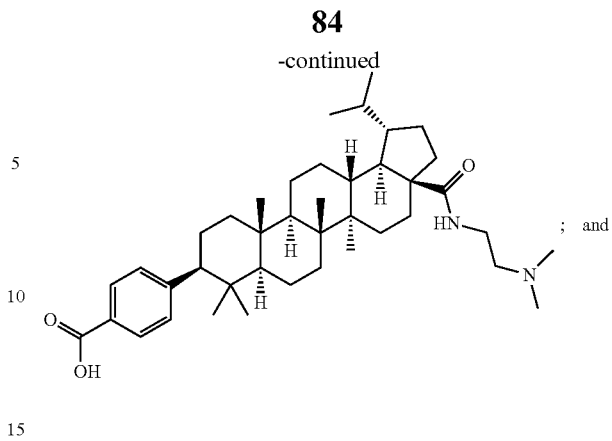
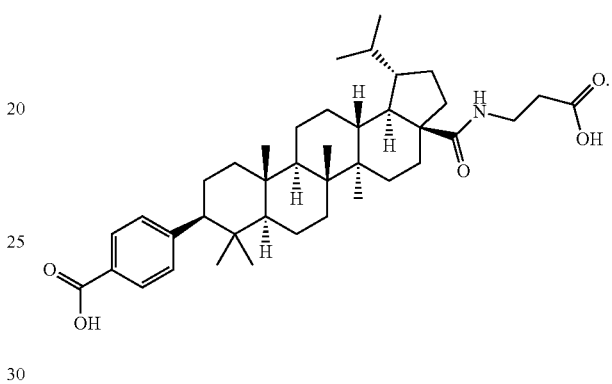
In addition, preferred examples of the compounds of Formula III include the following:
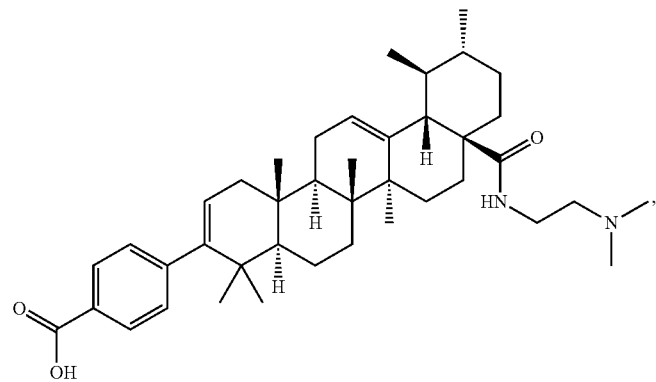
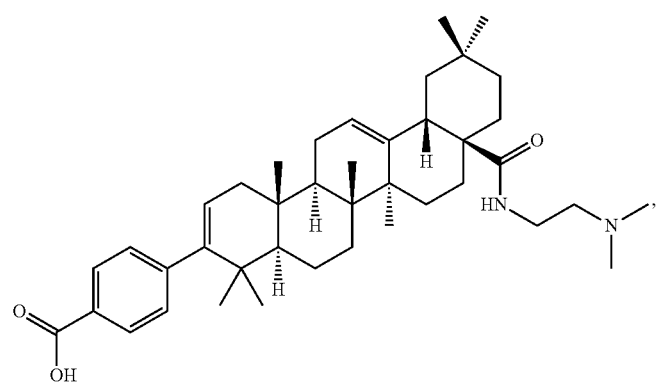

-continued

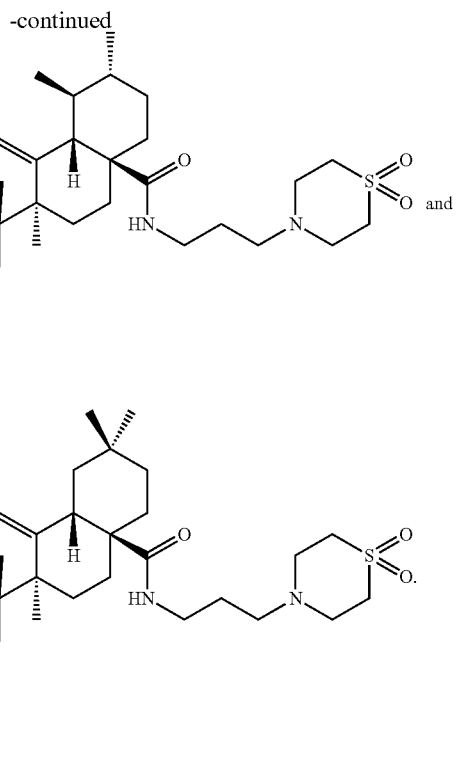

and.

The compounds of the present invention, according to all the various embodiments described above, may be administered orally, parenterally (including subcutaneous injections, intravenous, intramuscular, intrasternal injection or infusion techniques), by inhalation spray, or rectally, and by other means, in dosage unit formulations containing non-toxic pharmaceutically acceptable carriers, excipients and diluents available to the skilled artisan. One or more adjuvants may also be included.

Thus, in accordance with the present invention, there is further provided a method of treatment, and a pharmaceutical composition, for treating viral infections such as HIV infection and AIDS. The treatment involves administering to a patient in need of such treatment a pharmaceutical composition which contains an antiviral effective amount of one or more of the compounds of Formulas I, II, and/or III, together with one or more pharmaceutically acceptable carriers, excipients or diluents. As used herein, the term "antiviral effective amount" means the total amount of each active component of the composition and method that is sufficient to show a meaningful patient benefit, i.e., inhibiting, ameliorating, or healing of acute conditions characterized by inhibition of the HIV infection. When applied to an individual active ingredient, administered alone, the term refers to that ingredient alone. When applied to a combination, the term refers to combined amounts of the active ingredients that result in the therapeutic effect, whether administered in combination, serially or simultaneously. The terms "treat, treating, treatment" as used herein and in the claims means preventing, ameliorating or healing diseases associated with HIV infection.

The pharmaceutical compositions of the invention may be in the form of orally administrable suspensions or tablets; as well as nasal sprays, sterile injectable preparations, for example, as sterile injectable aqueous or oleaginous suspensions or suppositories. Pharmaceutically acceptable carriers, excipients or diluents may be utilized in the pharmaceutical compositions, and are those utilized in the art of pharmaceutical preparations.

When administered orally as a suspension, these compositions are prepared according to techniques typically known in the art of pharmaceutical formulation and may contain microcrystalline cellulose for imparting bulk, alginic acid or sodium alginate as a suspending agent, methylcellulose as a viscosity enhancer, and sweeteners/flavoring agents known in the art. As immediate release tablets, these compositions may contain microcrystalline cellulose, dicalcium phosphate, starch, magnesium stearate and lactose and/or other excipients, binders, extenders, disintegrants, diluents, and lubricants known in the art.

The injectable solutions or suspensions may be formulated according to known art, using suitable non-toxic, parenterally acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

The compounds herein set forth can be administered orally to humans in a dosage range of about 1 to 100 mg/kg body weight in divided doses, usually over an extended period, such as days, weeks, months, or even years. One preferred dosage range is about 1 to 10 mg/kg body weight orally in divided doses. Another preferred dosage range is about 1 to 20 mg/kg body weight in divided doses. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Also contemplated herein are combinations of the compounds of Formulas I, II, and/or III herein set forth, together with one or more other agents useful in the treatment of AIDS. For example, the compounds of this disclosure may be effectively administered, whether at periods of pre-exposure and/or post-exposure, in combination with effective amounts of the AIDS antivirals, immunomodulators, antiinfectives, or vaccines, such as those in the following non-limiting table:

| Drug Name | Manufacturer | Indication |
|---|---|---|
| ANTIVIRALS | | |
| 097 | Hoechst/Bayer | HIV infection, AIDS, ARC (non-nucleoside reverse transcriptase (RT) inhibitor) |
| Amprenavir 141 W94 GW 141 | Glaxo Wellcome | HIV infection, AIDS, ARC (protease inhibitor) |
| Abacavir (1592U89) GW 1592 | Glaxo Wellcome | HIV infection, AIDS, ARC (RT inhibitor) |
| Acemannan | Carrington Labs (Irving, TX) | ARC |
| Acyclovir | Burroughs Wellcome | HIV infection, AIDS, ARC |
| AD-439 | Tanox Biosystems | HIV infection, AIDS, ARC |
| AD-519 | Tanox Biosystems | HIV infection, AIDS, ARC |
| Adefovir dipivoxil | Gilead Sciences | HIV infection ARC, |
| AL-721 | Ethigen (Los Angeles, CA) | PGL HIV positive, AIDS |
| Alpha Interferon | Glaxo Wellcome | Kaposi's sarcoma, HIV in combination w/Retrovir |
| Ansamycin LM 427 | Adria Laboratories (Dublin, OH) Erbamont (Stamford, CT) | ARC |
| Antibody which Neutralizes pH Labile alpha aberrant Interferon | Advanced Biotherapy Concepts (Rockville, MD) | AIDS, ARC |
| AR177 | Aronex Pharm | HIV infection, AIDS, ARC |
| Beta-fluoro-ddA | Nat'l Cancer Institute | AIDS-associated diseases |
| BMS-234475 (CGP-61755) | Bristol-Myers Squibb/ Novartis | HIV infection, AIDS, ARC (protease inhibitor) |
| CI-1012 | Warner-Lambert | HIV-1 infection |
| Cidofovir | Gilead Science | CMV retinitis, herpes, papillomavirus |
| Curdlan sulfate | AJI Pharma USA | HIV infection |
| Cytomegalovirus Immune globin | MedImmune | CMV retinitis |
| Cytovene Ganciclovir | Syntex | Sight threatening CMV peripheral CMV retinitis |
| Darunavir | Tibotec- J & J | HIV infection, AIDS, ARC (protease inhibitor) |
| Delaviridine | Pharmacia-Upjohn | HIV infection, AIDS, ARC (RT inhibitor) |
| Dextran Sulfate | Ueno Fine Chem. Ind. Ltd. (Osaka, Japan) | AIDS, ARC, HIV positive asymptomatic |
| ddC Dideoxycytidine | Hoffman-La Roche | HIV infection, AIDS, ARC |
| ddI Dideoxyinosine | Bristol-Myers Squibb | HIV infection, AIDS, ARC; combination with AZT/d4T |
| DMP-450 | AVID (Camden, NJ) | HIV infection, AIDS, ARC (protease inhibitor) |
| Efavirenz (DMP 266, SUSTIVA ®) (−)6-Chloro-4-(S)-cyclopropylethynyl-4(S)-trifluoro-methyl-1,4-dihydro-2H-3,1-benzoxazin-2-one, STOCRINE | Bristol Myers Squibb | HIV infection, AIDS, ARC (non-nucleoside RT inhibitor) |

-continued

| Drug Name | Manufacturer | Indication |
| --- | --- | --- |
| EL10 | Elan Corp, PLC (Gainesville, GA) | HIV infection |
| Etravirine | Tibotec/J & J | HIV infection, AIDS, ARC (non-nucleoside reverse transcriptase inhibitor) |
| Famciclovir | Smith Kline | herpes zoster, herpes simplex |
| GS 840 | Gilead | HIV infection, AIDS, ARC (reverse transcriptase inhibitor) |
| HBY097 | Hoechst Marion Roussel | HIV infection, AIDS, ARC (non-nucleoside reverse transcriptase inhibitor) |
| Hypericin | VIMRx Pharm. | HIV infection, AIDS, ARC |
| Recombinant Human Interferon Beta | Triton Biosciences (Almeda, CA) | AIDS, Kaposi's sarcoma, ARC |
| Interferon alfa-n3 | Interferon Sciences | ARC, AIDS |
| Indinavir | Merck | HIV infection, AIDS, ARC, asymptomatic HIV positive, also in combination with AZT/ddI/ddC |
| ISIS 2922 | ISIS Pharmaceuticals | CMV retinitis |
| KNI-272 | Nat'l Cancer Institute | HIV-assoc. diseases |
| Lamivudine, 3TC | Glaxo Wellcome | HIV infection, AIDS, ARC (reverse transcriptase inhibitor); also with AZT |
| Lobucavir | Bristol-Myers Squibb | CMV infection |
| Nelfinavir | Agouron Pharmaceuticals | HIV infection, AIDS, ARC (protease inhibitor) |
| Nevirapine | Boeheringer Ingleheim | HIV infection, AIDS, ARC (RT inhibitor) |
| Novapren | Novaferon Labs, Inc. (Akron, OH) | HIV inhibitor |
| Peptide T Octapeptide Sequence | Peninsula Labs (Belmont, CA) | AIDS |
| Trisodium Phosphonoformate | Astra Pharm. Products, Inc. | CMV retinitis, HIV infection, other CMV infections |
| PNU-140690 | Pharmacia Upjohn | HIV infection, AIDS, ARC (protease inhibitor) |
| Probucol | Vyrex | HIV infection, AIDS |
| RBC-CD4 | Sheffield Med. Tech (Houston, TX) | HIV infection, AIDS, ARC |
| Ritonavir | Abbott | HIV infection, AIDS, ARC (protease inhibitor) |
| Saquinavir | Hoffmann-LaRoche | HIV infection, AIDS, ARC (protease inhibitor) |
| Stavudine; d4T Didehydrodeoxy-Thymidine | Bristol-Myers Squibb | HIV infection, AIDS, ARC |
| Tipranavir | Boehringer Ingelheim | HIV infection, AIDS, ARC (protease inhibitor) |
| Valaciclovir | Glaxo Wellcome | Genital HSV & CMV infections |
| Virazole Ribavirin | Viratek/ICN (Costa Mesa, CA) | asymptomatic HIV positive, LAS, ARC |
| VX-478 | Vertex | HIV infection, AIDS, ARC |
| Zalcitabine | Hoffmann-LaRoche | HIV infection, AIDS, ARC, with AZT |
| Zidovudine; AZT | Glaxo Wellcome | HIV infection, AIDS, ARC, Kaposi's sarcoma, in combination with other therapies |
| Tenofovir disoproxil, fumarate salt (VIREAD ®) | Gilead | HIV infection, AIDS, (reverse transcriptase inhibitor) |

-continued

| Drug Name | Manufacturer | Indication |
|---|---|---|
| EMTRIVA ® (Emtricitabine) (FTC) | Gilead | HIV infection, AIDS, (reverse transcriptase inhibitor) |
| Combivir ® | GSK | HIV infection, AIDS, (reverse transcriptase inhibitor) |
| Abacavir succinate (or ZIAGEN ®) | GSK | HIV infection, AIDS, (reverse transcriptase inhibitor) |
| REYATAZ ® (or atazanavir) | Bristol-Myers Squibb | HIV infection AIDs, protease inhibitor |
| FUZEON ® (Enfuvirtide or T-20) | Roche/Trimeris | HIV infection AIDs, viral Fusion inhibitor |
| LEXIVA ® (or Fosamprenavir calcium) | GSK/Vertex | HIV infection AIDs, viral protease inhibitor |
| SELZENTRY ® Maraviroc; (UK 427857) | Pfizer | HIV infection AIDs, (CCR5 antagonist, in development) |
| TRIZIVIR ® | GSK | HIV infection AIDs, (three drug combination) |
| Sch-417690 (vicriviroc) | Schering-Plough | HIV infection AIDs, (CCR5 antagonist, in development) |
| TAK-652 | Takeda | HIV infection AIDs, (CCR5 antagonist, in development) |
| GSK 873140 (ONO-4128) | GSK/ONO | HIV infection AIDs, (CCR5 antagonist, in development) |
| Integrase Inhibitor MK-0518 Raltegravir | Merck | HIV infection AIDs |
| TRUVADA ® | Gilead | Combination of Tenofovir disoproxil fumarate salt (VIREAD ®) and EMTRIVA ® (Emtricitabine) |
| Integrase Inhibitor GS917/JTK-303 Elvitegravir | Gilead/Japan Tobacco | HIV Infection AIDs in development |
| Triple drug combination ATRIPLA ® | Gilead/Bristol-Myers Squibb | Combination of Tenofovir disoproxil fumarate salt (VIREAD ®), EMTRIVA ® (Emtricitabine), and SUSTIVA ® (Efavirenz) |
| 4'-ethynyl-d4T | Bristol-Myers Squibb | HIV infection AIDs in development |
| CMX-157 Lipid conjugate of nucleotide tenofovir | Chimerix | HIV infection AIDs |
| GSK1349572 Integrase inhibitor | GSK | HIV infection AIDs |
| IMMUNOMODULATORS | | |
| AS-101 | Wyeth-Ayerst | AIDS |
| Bropirimine | Pharmacia Upjohn | Advanced AIDS |
| Acemannan | Carrington Labs, Inc. (Irving, TX) | AIDS, ARC |
| CL246,738 | Wyeth Lederle Labs | AIDS, Kaposi's sarcoma |
| FP-21399 | Fuki ImmunoPharm | Blocks HIV fusion with CD4+ cells |
| Gamma Interferon | Genentech | ARC, in combination w/TNF (tumor necrosis factor) |
| Granulocyte Macrophage Colony Stimulating Factor | Genetics Institute Sandoz | AIDS |
| Granulocyte Macrophage Colony Stimulating Factor | Hoechst-Roussel Immunex | AIDS |
| Granulocyte Macrophage Colony Stimulating Factor | Schering-Plough | AIDS, combination w/AZT |
| HIV Core Particle Immunostimulant | Rorer | Seropositive HIV |
| IL-2 Interleukin-2 | Cetus | AIDS, in combination w/AZT |

-continued

| Drug Name | Manufacturer | Indication |
|---|---|---|
| IL-2 Interleukin-2 | Hoffman-LaRoche Immunex | AIDS, ARC, HIV, in combination w/AZT |
| IL-2 Interleukin-2 (aldeslukin) | Chiron | AIDS, increase in CD4 cell counts |
| Immune Globulin Intravenous (human) | Cutter Biological (Berkeley, CA) | Pediatric AIDS, in combination w/AZT |
| IMREG-1 | Imreg (New Orleans, LA) | AIDS, Kaposi's sarcoma, ARC, PGL |
| IMREG-2 | Imreg (New Orleans, LA) | AIDS, Kaposi's sarcoma, ARC, PGL |
| Imuthiol Diethyl Dithio Carbamate | Merieux Institute | AIDS, ARC |
| Alpha-2 Interferon | Schering Plough | Kaposi's sarcoma w/AZT, AIDS |
| Methionine-Enkephalin | TNI Pharmaceutical (Chicago, IL) | AIDS, ARC |
| MTP-PE Muramyl-Tripeptide | Ciba-Geigy Corp. | Kaposi's sarcoma |
| Granulocyte Colony Stimulating Factor | Amgen | AIDS, in combination w/AZT |
| Remune | Immune Response Corp. | Immunotherapeutic |
| rCD4 Recombinant Soluble Human CD4 | Genentech | AIDS, ARC |
| rCD4-IgG hybrids | | AIDS, ARC |
| Recombinant Soluble Human CD4 | Biogen | AIDS, ARC |
| Interferon Alfa 2a | Hoffman-La Roche | Kaposi's sarcoma AIDS, ARC, in combination w/AZT |
| SK&F106528 Soluble T4 | Smith Kline | HIV infection |
| Thymopentin | Immunobiology Research Institute (Annandale, NJ) | HIV infection |
| Tumor Necrosis Factor; TNF | Genentech | ARC, in combination w/gamma Interferon |
| ANTI-INFECTIVES | | |
| Clindamycin with Primaquine | Pharmacia Upjohn | PCP |
| Fluconazole | Pfizer | Cryptococcal meningitis, candidiasis |
| Pastille Nystatin Pastille | Squibb Corp. | Prevention of oral candidiasis |
| Ornidyl Eflornithine | Merrell Dow | PCP |
| Pentamidine Isethionate (IM & IV) | LyphoMed (Rosemont, IL) | PCP treatment |
| Trimethoprim | | Antibacterial |
| Trimethoprim/sulfa | | Antibacterial |
| Piritrexim | Burroughs Wellcome | PCP treatment |
| Pentamidine Isethionate for Inhalation | Fisons Corporation | PCP prophylaxis |
| Spiramycin | Rhone-Poulenc | Cryptosporidial diarrhea |
| Intraconazole-R51211 | Janssen-Pharm. | Histoplasmosis; cryptococcal meningitis |
| Trimetrexate | Warner-Lambert | PCP |
| Daunorubicin | NeXstar, Sequus | Kaposi's sarcoma |
| Recombinant Human Erythropoietin | Ortho Pharm. Corp. | Severe anemia assoc. with AZT therapy |
| Recombinant Human Growth Hormone | Serono | AIDS-related wasting, cachexia |
| Megestrol Acetate | Bristol-Myers Squibb | Treatment of anorexia assoc. W/AIDS |

-continued

| Drug Name | Manufacturer | Indication |
|---|---|---|
| Testosterone | Alza, Smith Kline | AIDS-related wasting |
| Total Enteral Nutrition | Norwich Eaton Pharmaceuticals | Diarrhea and malabsorption related to AIDS |

Additionally, the compounds of the disclosure herein set forth may be used in combination with HIV entry inhibitors. Examples of such HIV entry inhibitors are discussed in DRUGS OF THE FUTURE 1999, 24(12), pp. 1355-1362; CELL, Vol. 9, pp. 243-246, Oct. 29, 1999; and DRUG DISCOVERY TODAY, Vol. 5, No. 5, May 2000, pp. 183-194 and Inhibitors of the entry of HIV into host cells. Meanwell, Nicholas A.; Kadow, John F. Current Opinion in Drug Discovery & Development (2003), 6(4), 451-461. Specifically the compounds can be utilized in combination with attachment inhibitors, fusion inhibitors, and chemokine receptor antagonists aimed at either the CCR5 or CXCR4 coreceptor. HIV attachment inhibitors are also set forth in U.S. Pat. No. 7,354,924 and US 2005/0209246.

It will be understood that the scope of combinations of the compounds of this application with AIDS antivirals, immunomodulators, anti-infectives, HIV entry inhibitors or vaccines is not limited to the list in the above Table but includes, in principle, any combination with any pharmaceutical composition useful for the treatment of AIDS.

Preferred combinations are simultaneous or alternating treatments with a compound of the present disclosure and an inhibitor of HIV protease and/or a non-nucleoside inhibitor of HIV reverse transcriptase. An optional fourth component in the combination is a nucleoside inhibitor of HIV reverse transcriptase, such as AZT, 3TC, ddC or ddI. A preferred inhibitor of HIV protease is REYATAZ® (active ingredient Atazanavir). Typically a dose of 300 to 600 mg is administered once a day. This may be co-administered with a low dose of Ritonavir (50 to 500 mgs). Another preferred inhibitor of HIV protease is KALETRA®. Another useful inhibitor of HIV protease is indinavir, which is the sulfate salt of N-(2 (R)-hydroxy-1-(S)-indanyl)-2(R)-phenylmethyl-4-(S)-hydroxy-5-(1-(4-(3-pyridyl-methyl)-2(S)—N'-(t-butylcarboxamido)-piperazinyl))-pentaneamide ethanolate, and is synthesized according to U.S. Pat. No. 5,413,999. Indinavir is generally administered at a dosage of 800 mg three times a day. Other preferred protease inhibitors are nelfinavir and ritonavir. Another preferred inhibitor of HIV protease is saquinavir which is administered in a dosage of 600 or 1200 mg tid. Preferred non-nucleoside inhibitors of HIV reverse transcriptase include efavirenz. These combinations may have unexpected effects on limiting the spread and degree of infection of HIV. Preferred combinations include those with the following (1) indinavir with efavirenz, and, optionally, AZT and/or 3TC and/or ddI and/or ddC; (2) indinavir, and any of AZT and/or ddI and/or ddC and/or 3TC, in particular, indinavir and AZT and 3TC; (3) stavudine and 3TC and/or zidovudine; (4) tenofovir disoproxil fumarate salt and emtricitabine.

In such combinations the compound of the present invention and other active agents may be administered separately or in conjunction. In addition, the administration of one element may be prior to, concurrent to, or subsequent to the administration of other agent(s).

General Chemistry (Methods of Synthesis)

The present invention comprises compounds of Formulas I, II, and III, their pharmaceutical formulations, and their use in patients suffering from or susceptible to HIV infection. The compounds of Formulas I, II, and III also include pharmaceutically acceptable salts thereof. General procedures to construct compounds of Formulas I, II, and III and intermediates useful for their synthesis are described in the following Schemes (after the Abbreviations).

ABBREVIATIONS

One or more of the following abbreviations, most of which are conventional abbreviations well known to those skilled in the art, may be used throughout the description of the disclosure and the examples:

h=hour(s)
min=minute(s)
rt=room temperature
mol=mole(s)
mmol=millimole(s)
g=gram(s)
mg=milligram(s)
mL=milliliter(s)
TFA=trifluoroacetic Acid
DCE=1,2-Dichloroethane
THF=tetrahydrofuran
DIEA=N,N-diisopropylethylamine
DMAP=4-dimethylaminopyridine
DMF=N,N-dimethylformamide
EDC=1-(3-dimethylaminopropyl)-3-ethyldiimide hydrochloride
KHMDS=potassium hexamethyldisilazide
TMS=trimethylsilyl
DCM=dichloromethane
MeOH=methanol
EtOAc=ethyl acetate
DME=dimethoxyethane
TLC=thin layer chromatography
DMSO=dimethylsulfoxide
PCC=pyridinium chlorochromate
ATM=atmosphere(s)
HOAc=acidic acid
$SOCl_2$=thionylchloride
TBAF=tetrabutylammonium fluoride
TBDPSCl=tertbutyldiphenylchlorosilane
TBTU=o-benzotriazol-1-yl-N,N,N',N'-tetramethyluronium tetrafluoroborate
Hex=hexane(s)
Equiv.=equivalents
Rb=round bottom
Prep HPLC=preparative High performance liquid chromatography Preparation of Compounds of Formulas I, II and III General Chemistry Schemes:

Compounds of Formulas I, II and III can be prepared from commercially available (Aldrich, others) betulinic acid and betulin by chemistry described in the following schemes.

General reaction schemes are set forth as follows:
Schemes A through E can be used for the preparation of compounds of Formula I:
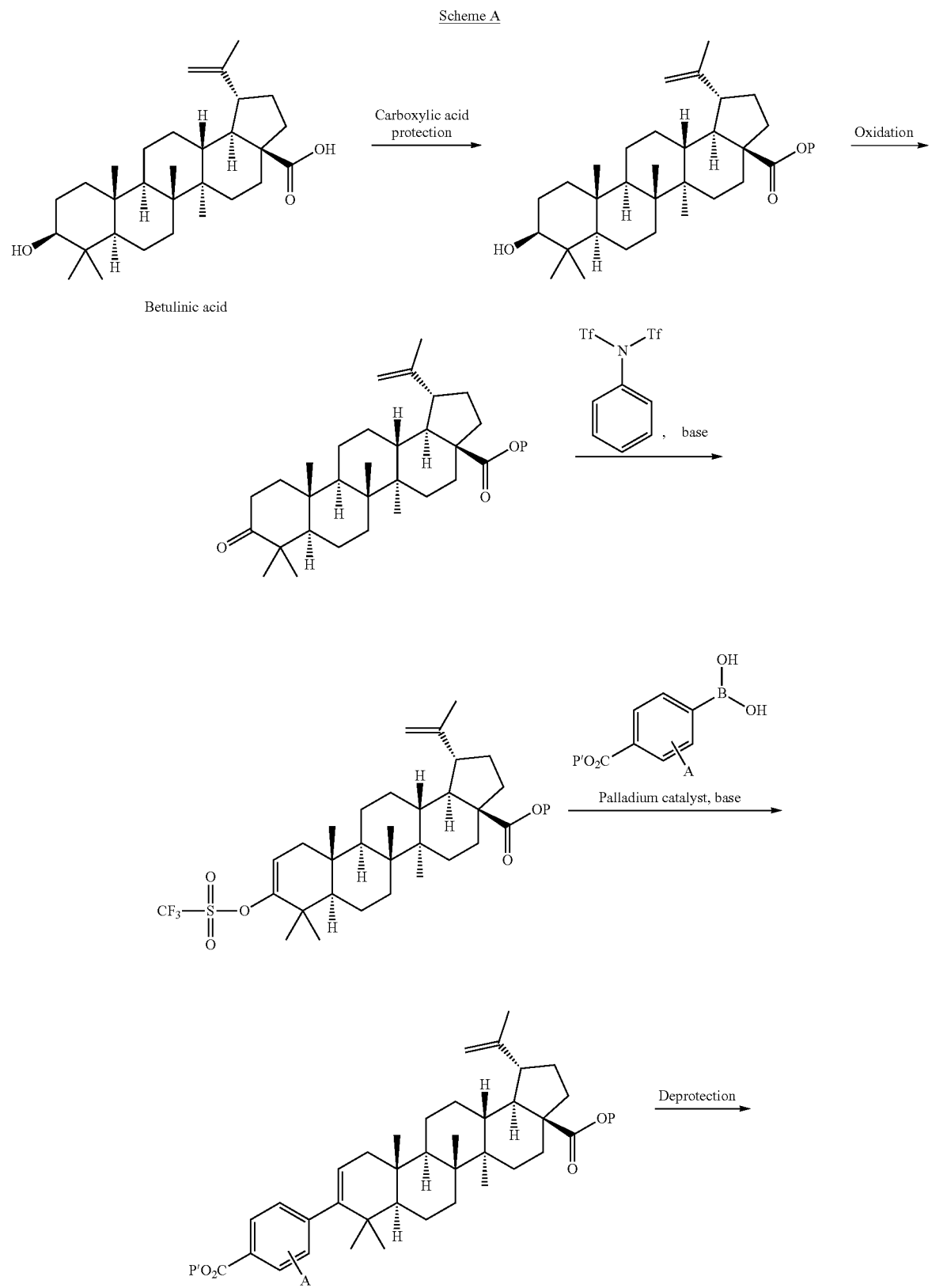
Scheme A -continued
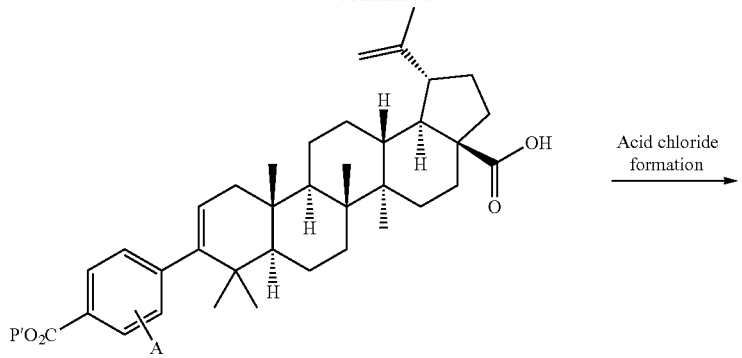
Acid chloride formation →
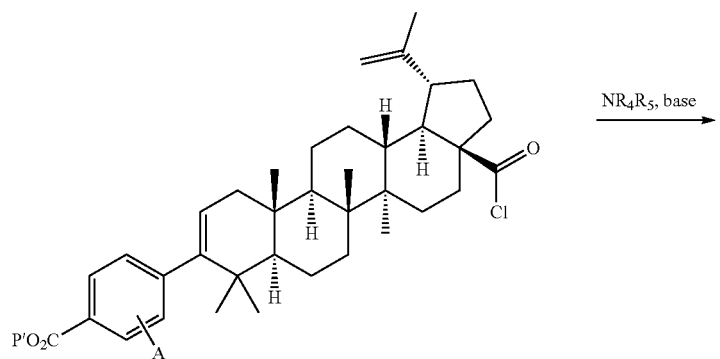
NR₄R₅, base →
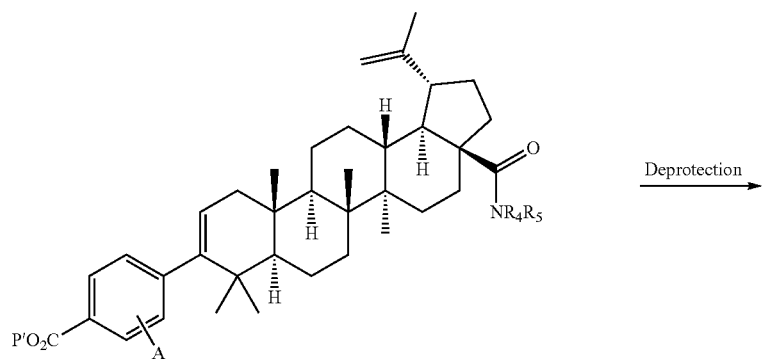
Deprotection →
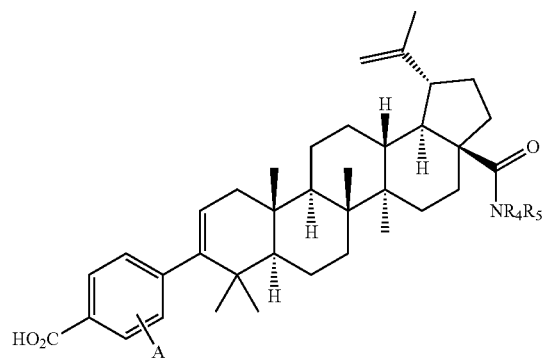

The synthesis starts with introduction of a suitable carboxylic acid protective group. Oxidation of the C-3 alcohol using standard oxidation reagents affords the C-3 ketone which is converted into the triflate by methods available to those skilled in the art. The ketone can be subjected to standard Suzuki couping with boronic acids; Stille coupling using tin reagents can also be used. Selective deprotection of the carboxylic acid in the C-28 position allowed the preparation of the corresponding acid chloride which can be reacted with amines to afford the desired amide. Sometimes the amines can carry a protective group that can be deprotected sequentially or simultaneously with the deprotection of the carboxylic acid.

Alternatively, the C-28 amides can be prepared from the C-28 acid intermediate as shown in scheme B:

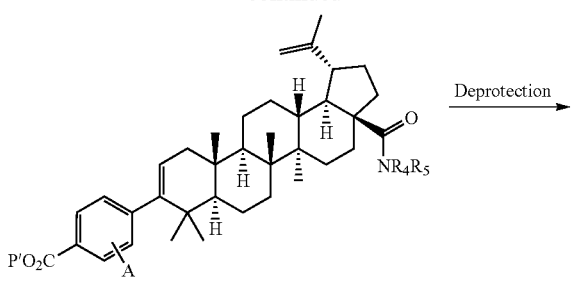

Scheme B

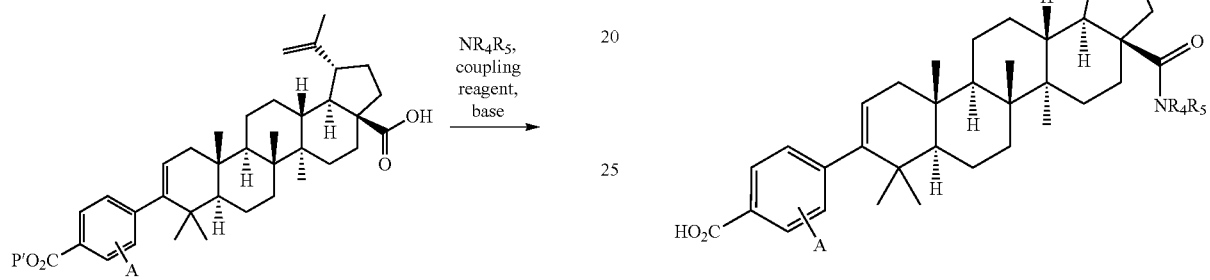

Scheme C

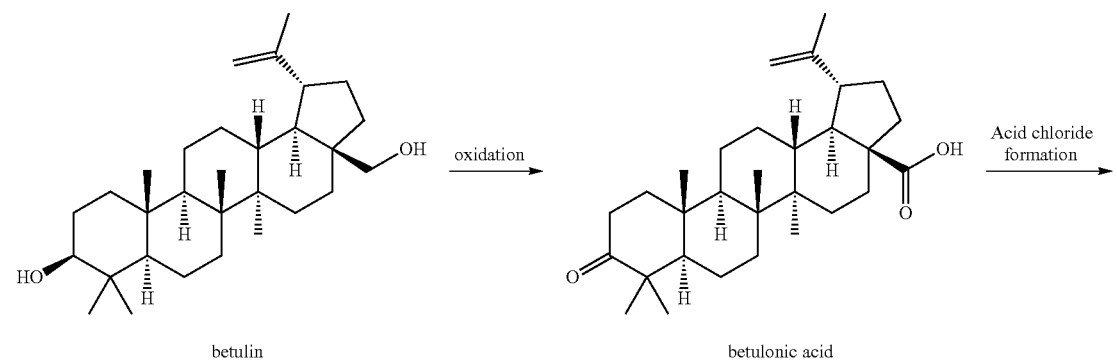

betulin betulonic acid

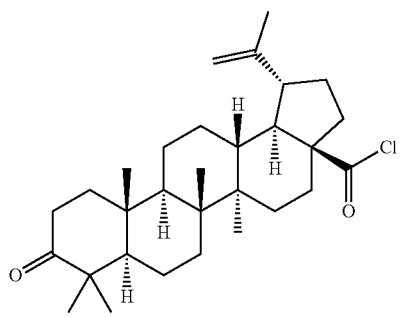

-continued

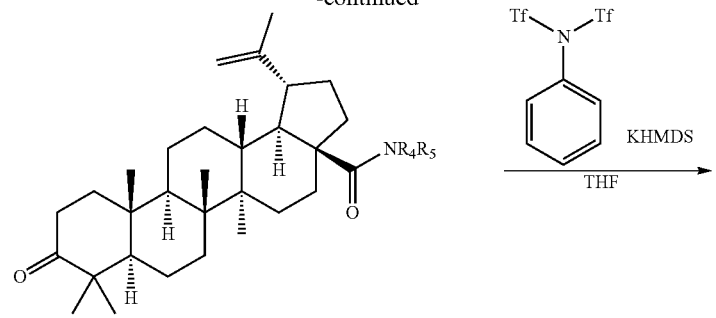

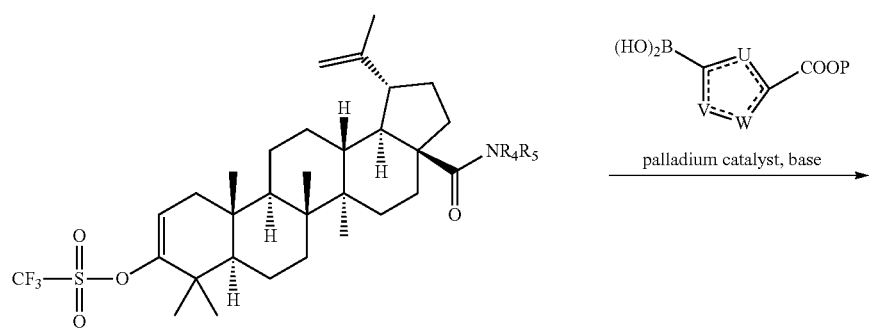

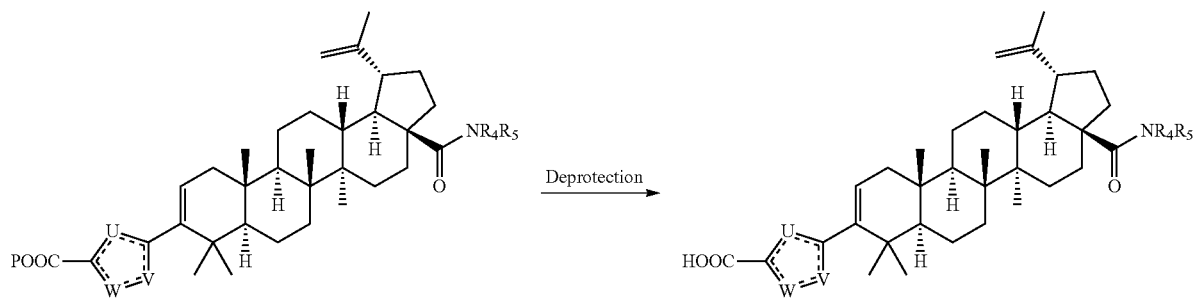

Oxidation of betulin with oxidants such as Jones' reagent can afford betulonic acid which can be further converted into the corresponding acid chloride. Treatment with amine affords the corresponding C-28 amide. Conversion of the C-3 ketone into the triflate followed by Suzuki coupling and deprotection as described above affords the desired compound.

Scheme D

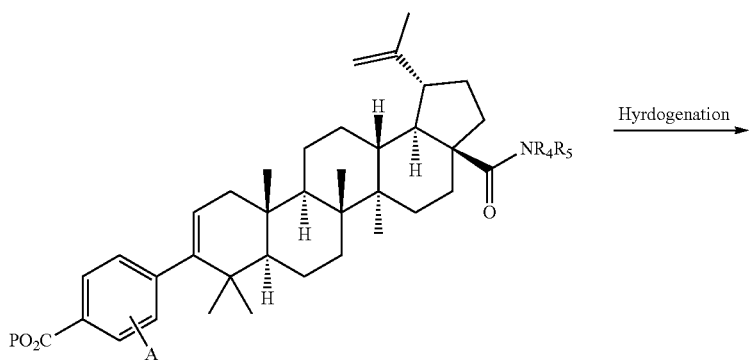

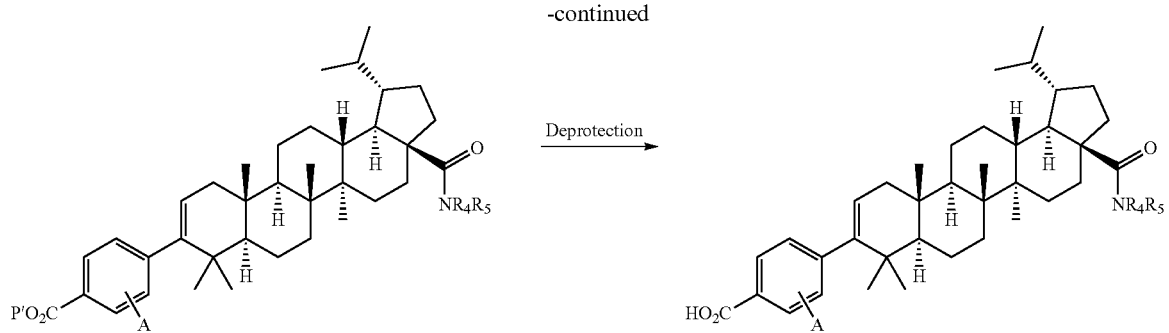
Scheme E
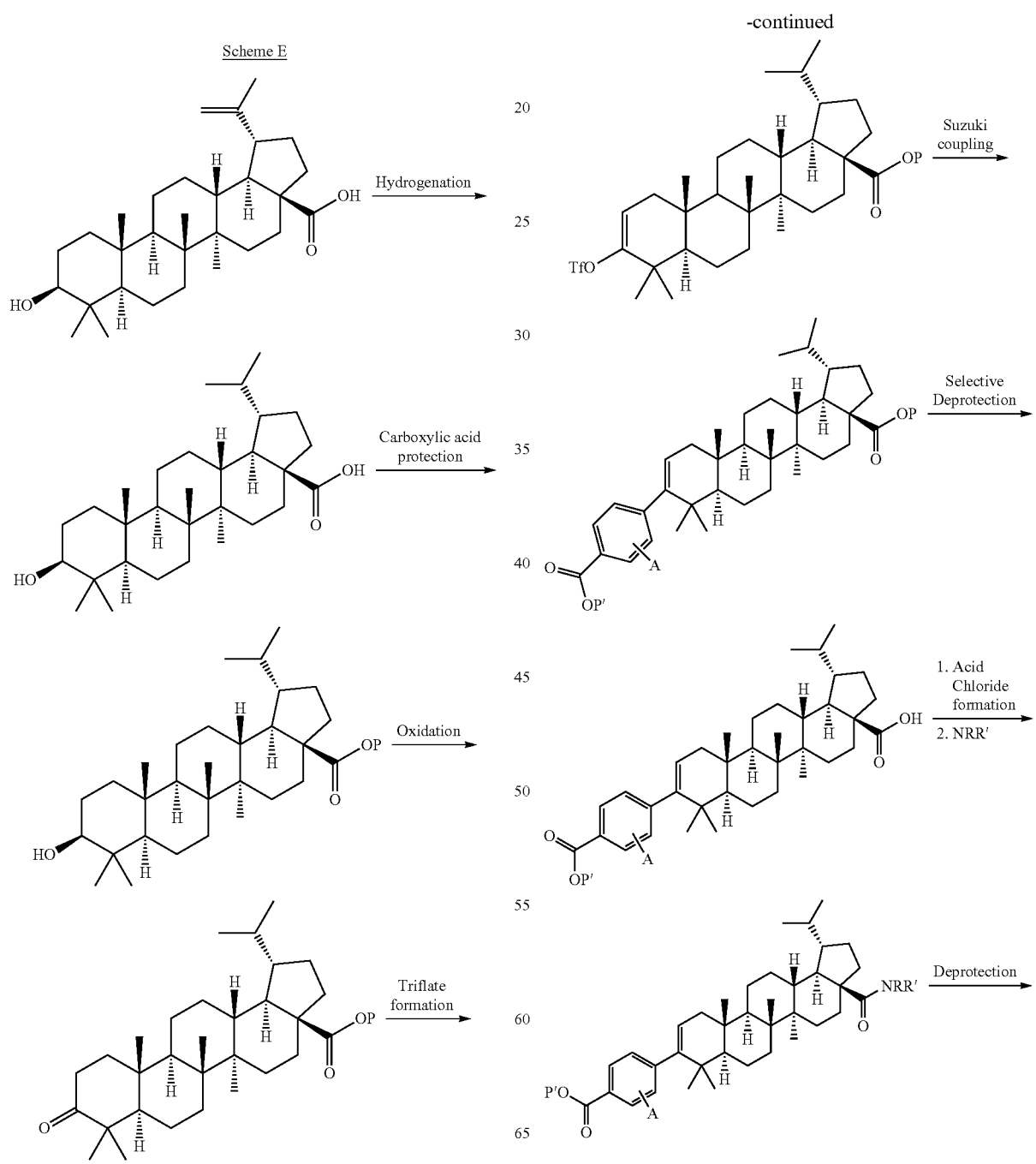

107
-continued
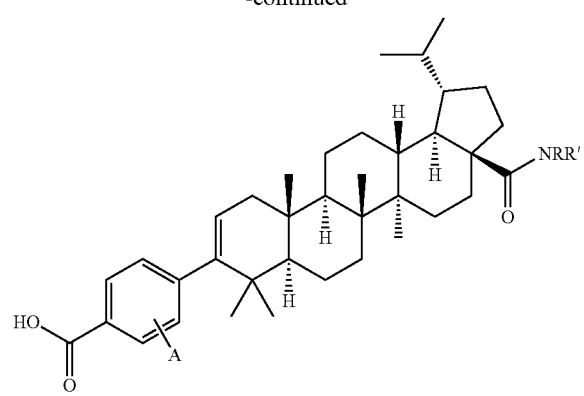
108
-continued
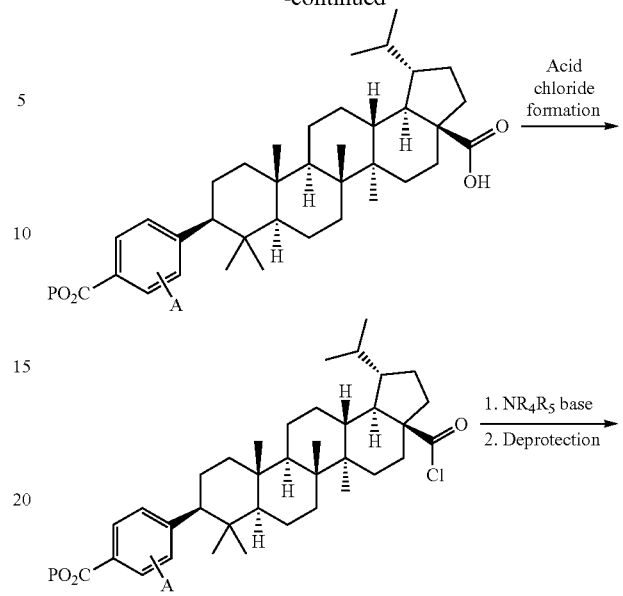
Compounds of formula II can be prepared as shown in schemes F-G:
Scheme F
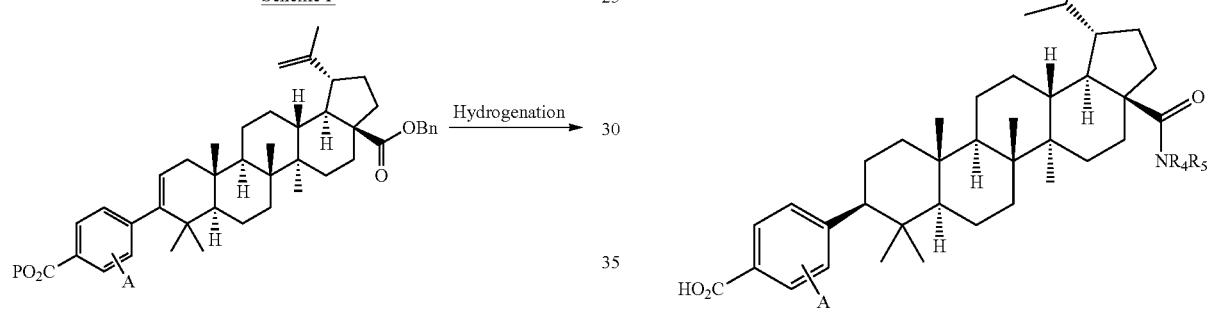
Scheme G
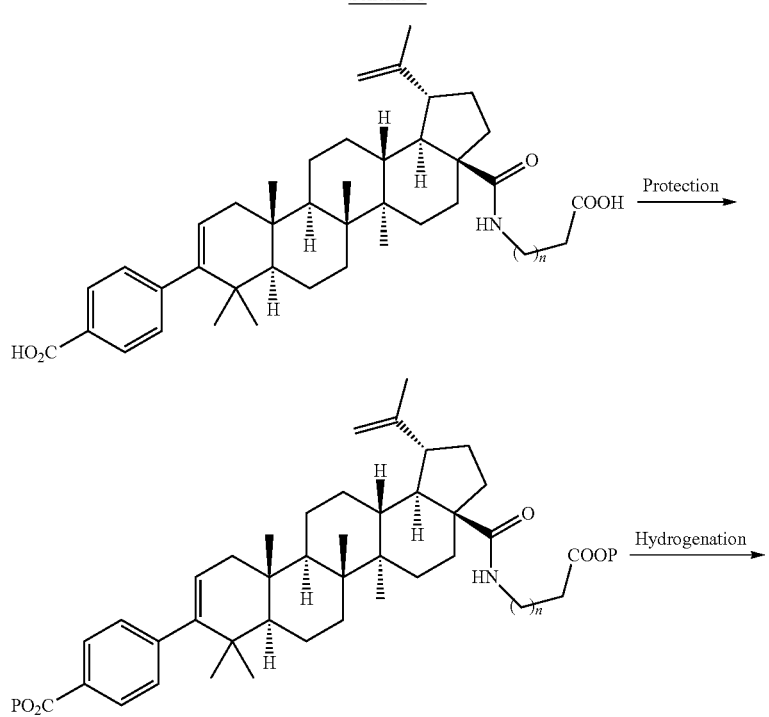

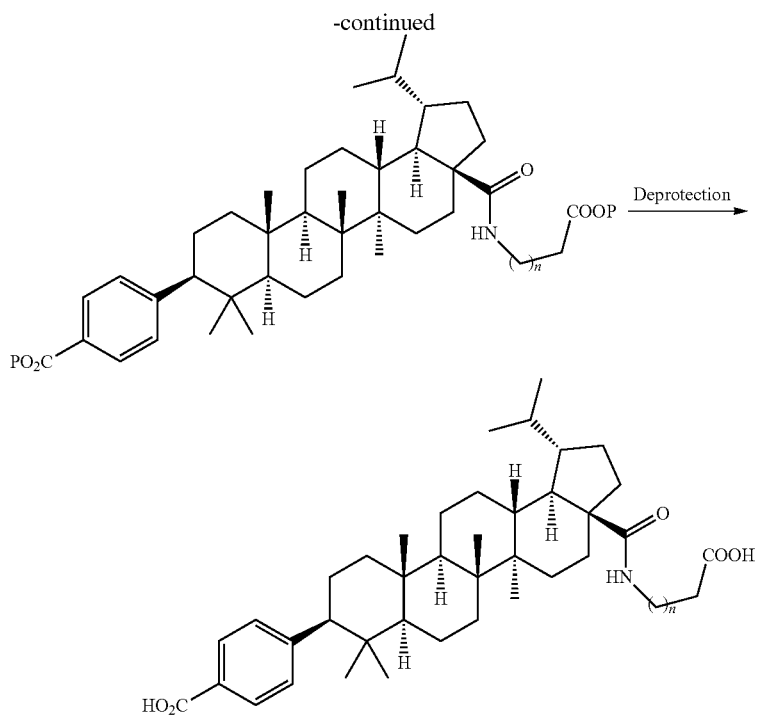

Alternatively, compounds of formula II can be prepared from betulinic acid by hydrogenation of the double bond, followed by protection of the carboxylic acid with a suitable protecting group. Then oxidation of the hydroxyl group to ketone and triflate formation followed by palladium promoted cross coupling such as Suzuki or Stille coupling provide the benzoic ester intermediate. Selective deprotection of the ester in the C-28 position affords the corresponding carboxylic acid which is converted to the acid chloride and reacted with the desired amine to provide the C-28 amide. Deprotection of the benzoic ester provides the final compound.

Some of the amides can be further modified as exemplified in the following schemes:

Scheme 1

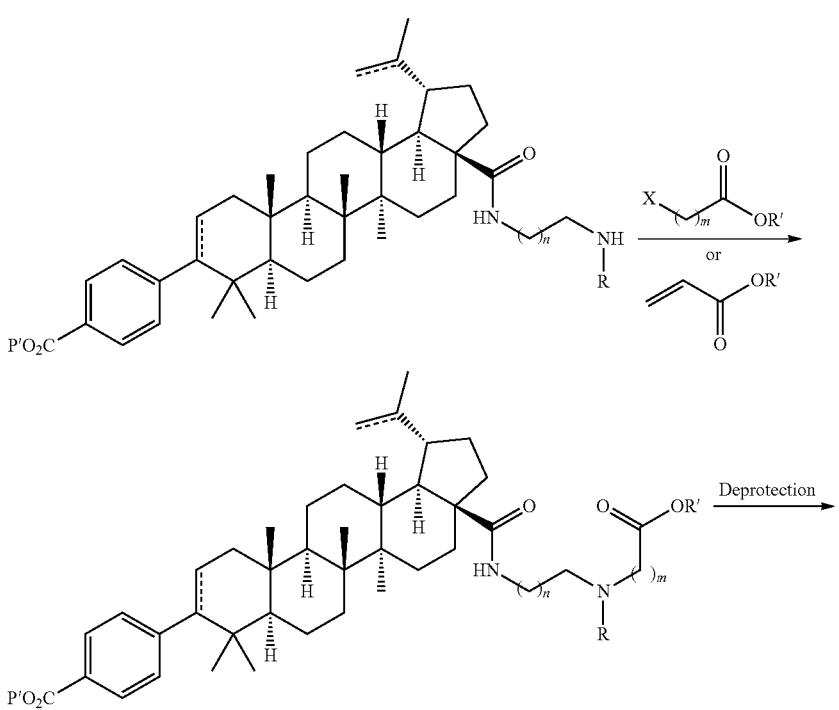

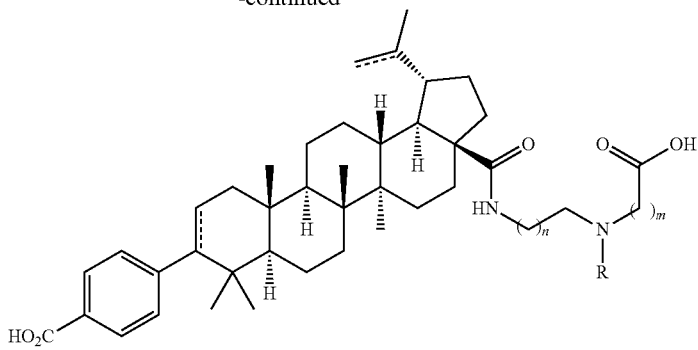

The amine in the amide side chain can be derivatized with an alkylating reagent containing a carboxylic ester or by Michal addition to and α,β-unsaturated carboxylic ester followed by deprotection of the two carboxylic esters.

Scheme 2

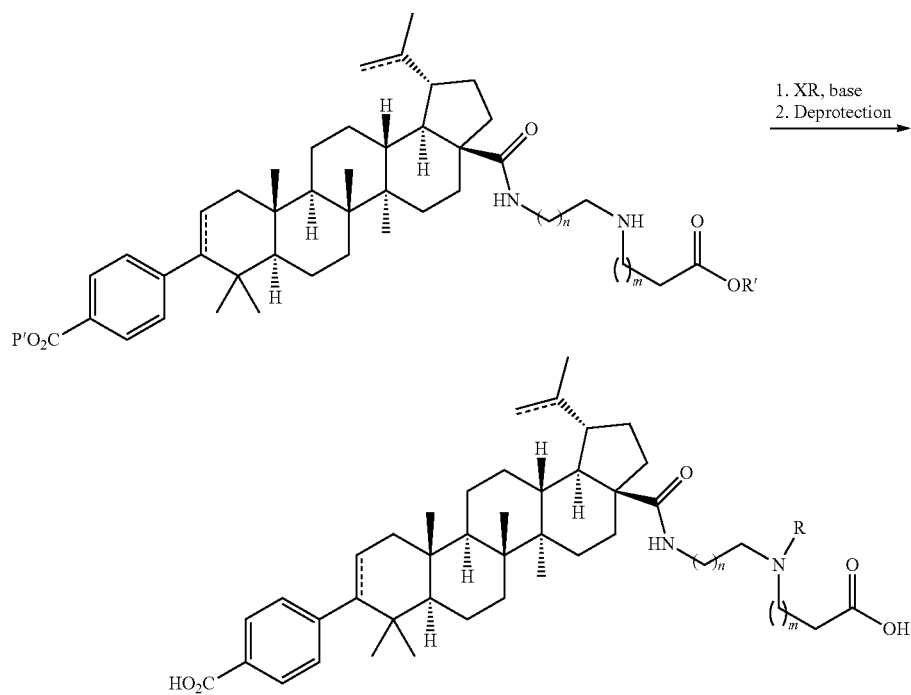

Amides containing amines can be alkylated with an alkyl halide as shown above. Deprotection of the carboxylic esters affords the final compounds.

Scheme 3

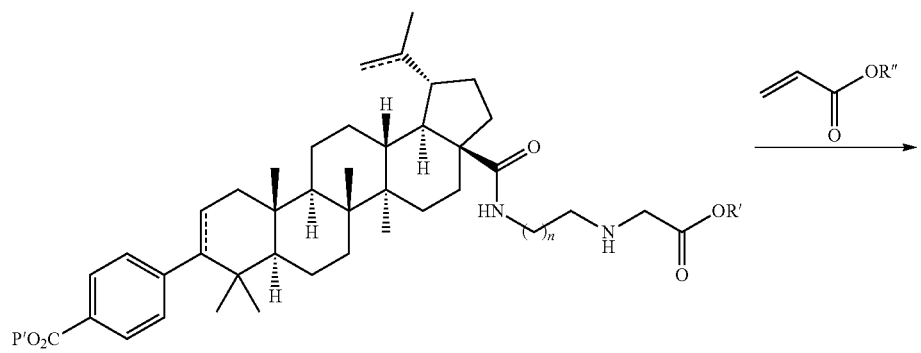

-continued
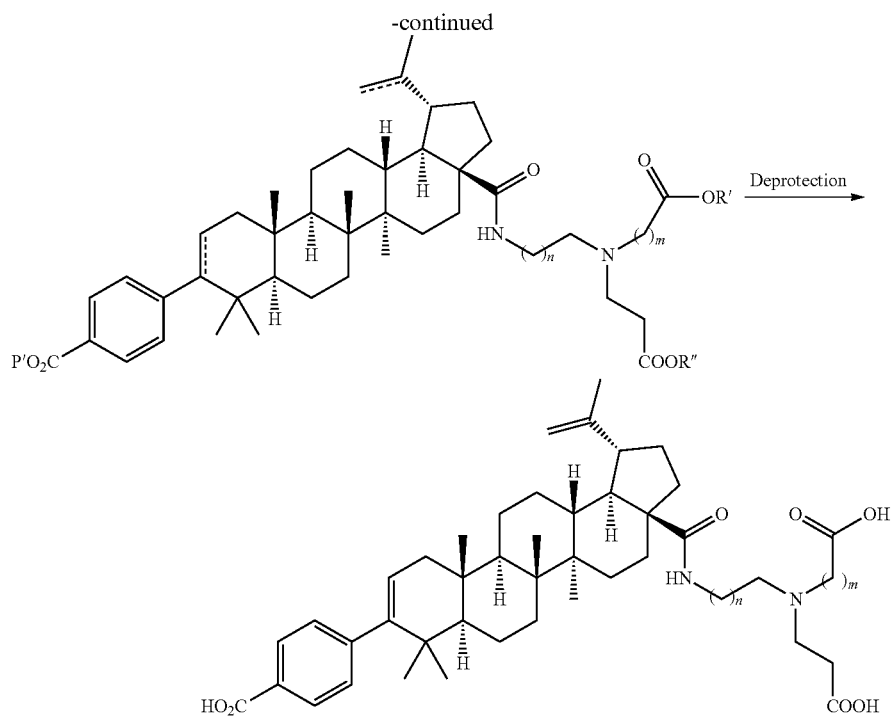
Amides containing amines can be also derivatized using a Michael acceptor as shown above. Deprotection of the carboxylic esters affords the final compounds.
Scheme 4
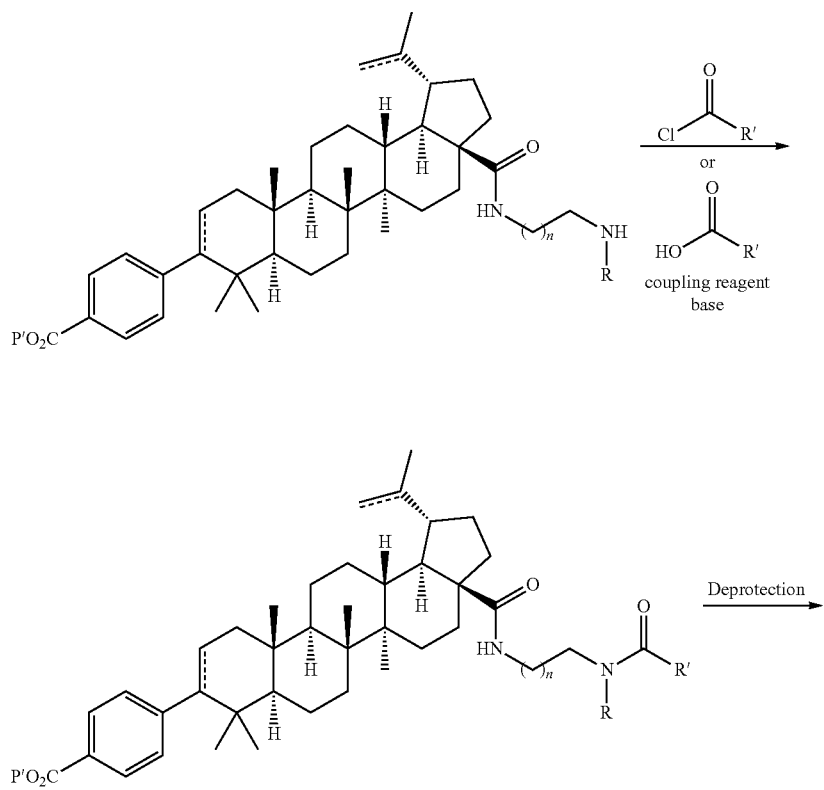

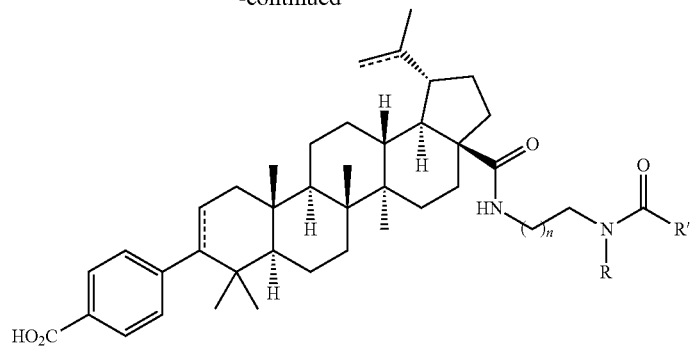

A compound with an amine group can be acylated with and acid chloride or by treatment with a carboxylic acid and the appropriate coupling reagent in the presence of a base to provide an amide. Unmasking of the carboxylic acid afford the final compounds.

The preparation of amides with a pending carboxylic amide can be done as shown above. The C-28 acid chloride can be treated with an amine containing a carboxylic ester. Selective deprotection of this carboxylic ester followed by standard amide coupling and deprotection of the benzoic acid afford the final compounds.

Scheme 5

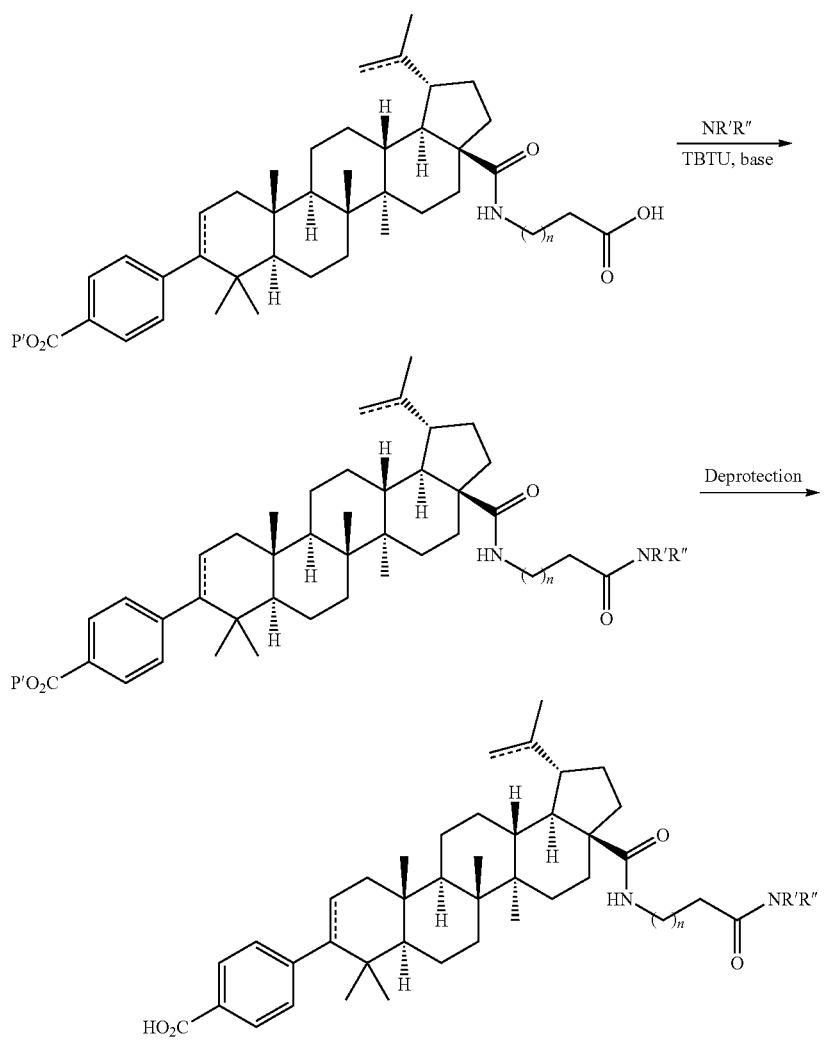

Scheme 6

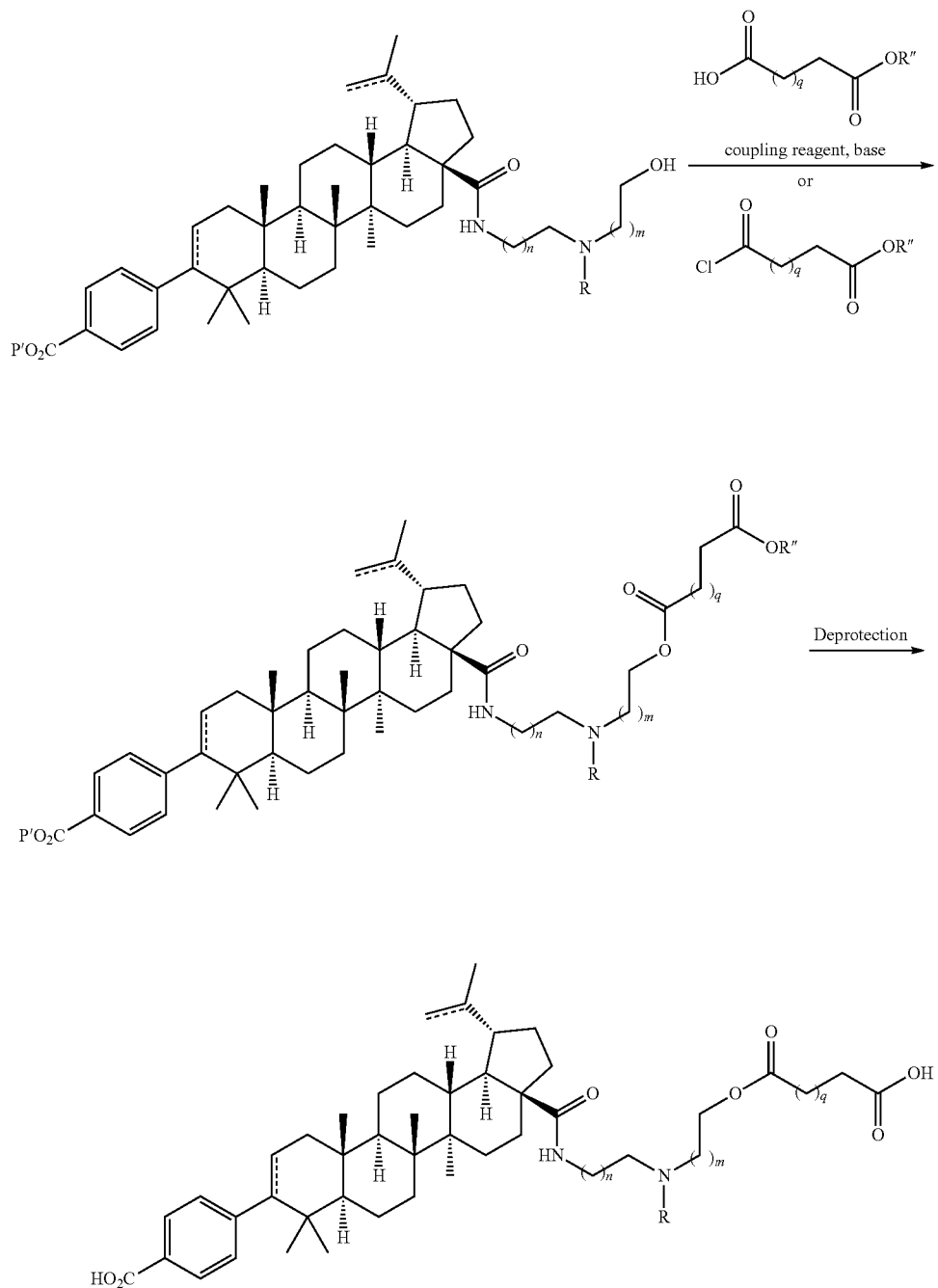

A compound with a hydroxyl group can be acylated with an acid chloride or by treatment with a carboxylic acid and coupling reagent in the presence of a base to provide an ester. Unmasking of the terminal carboxylic acids afford the final compounds. Amides containing an amine can be converted into the corresponding N-oxide under standard oxidation conditions.

The same synthetic methods can be applied to prepare compounds of Formula III using ursolic acid, oleanoic acid or moronic acid (oxidation is not necessary in this case, since the C-3 ketone is already present) as starting material instead of betulinic acid or betulin as shown, for example, in the following scheme:

Scheme 7
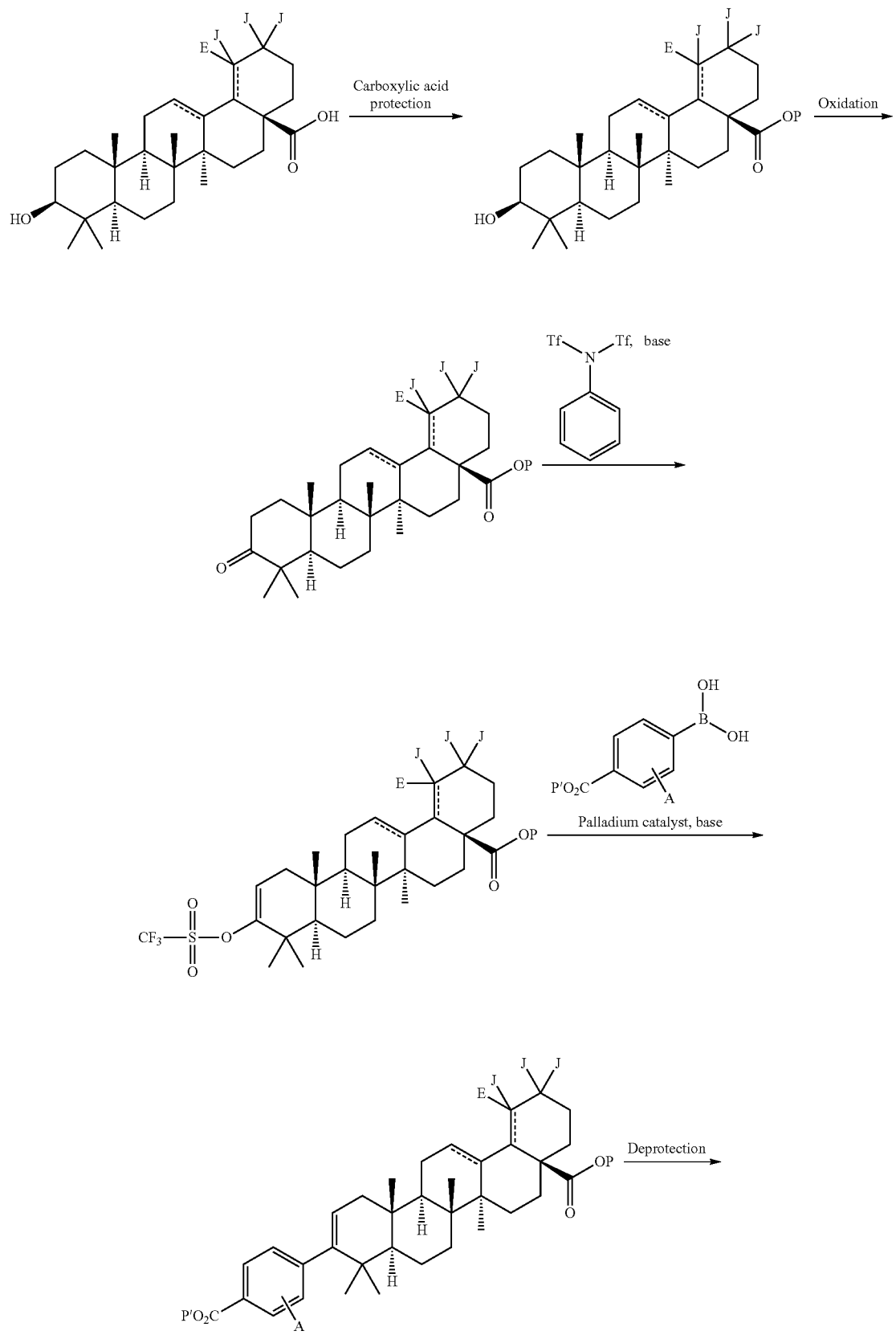

-continued
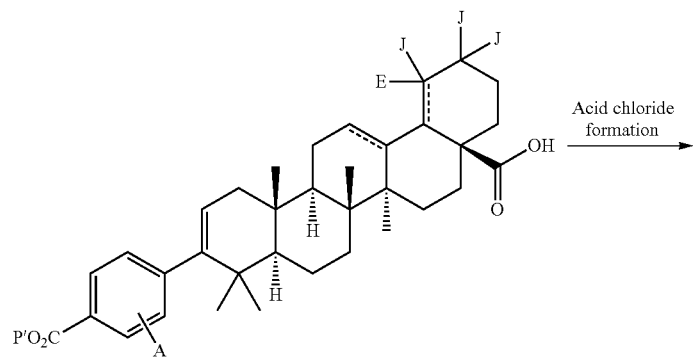 Acid chloride formation →
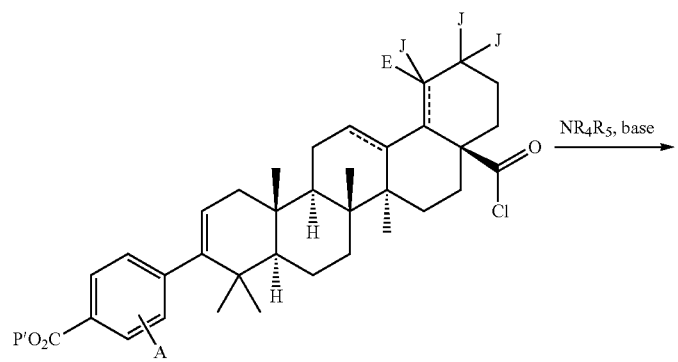 NR₄R₅, base →
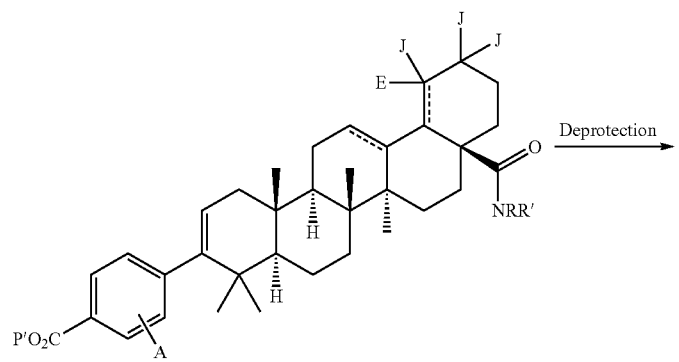 Deprotection →
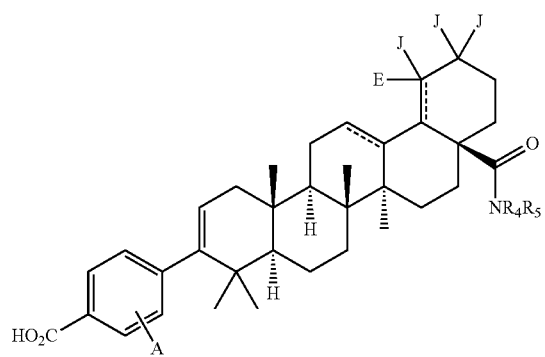

EXAMPLES

The following examples illustrate typical syntheses of the compounds of Formulas I, II and III as described generally above. These examples are illustrative only and are not intended to limit the disclosure in any way. The reagents and starting materials are readily available to one of ordinary skill in the art.

Chemistry

Typical Procedures and Characterization of Selected Examples:

Unless otherwise stated, solvents and reagents were used directly as obtained from commercial sources, and reactions were performed under a nitrogen atmosphere. Flash chromatography was conducted on Silica gel 60 (0.040-0.063 particle size; EM Science supply). $^1$H NMR spectra were recorded on Bruker DRX-500f at 500 MHz (or Bruker AV 400 MHz, Bruker DPX-300B or Varian Gemini 300 at 300 MHz as stated). The chemical shifts were reported in ppm on the δ scale relative to δTMS=0. The following internal references were used for the residual protons in the following solvents: CDCl$_3$ ($\oplus_H$ 7.26), CD$_3$OD ($\delta_H$ 3.30), Acetic-d4 (Acetic Acid d$_4$) ($\delta_H$ 11.6, 2.07), DMSOmix or DMSO-D6_CDCl$_3$ (($_H$ 2.50 and 8.25) (ratio 75%:25%), and DMSO-D6 ($\delta_H$ 2.50). Standard acronyms were employed to describe the multiplicity patterns: s (singlet), br. s (broad singlet), d (doublet), t (triplet), q (quartet), m (multiplet), b (broad), app (apparent). The coupling constant (J) is in Hertz. All Liquid Chromatography (LC) data were recorded on a Shimadzu LC-10AS liquid chromatograph using a SPD-10AV UV-Vis detector with Mass Spectrometry (MS) data determined using a Micromass Platform for LC in electrospray mode.

LC/MS Methods

Method 1
Start % B=0, Final % B=100 over 2 minute gradient
Flow Rate=4 mL/Min
Solvent A=95% Water/5% Methanol/10 mM Ammonium Acetate
Solvent B=5% Water/95% Methanol/10 mM Ammonium Acetate
Column=PHENOMENEX-LUNA 3.0×50 mm Method 2
Start % B=0, Final % B=100 over 2 minute gradient
Flow Rate=1 mL/Min
Solvent A=90% Water/10% Acetonitrile/0.1% TFA
Solvent B=10% Water/90% Acetonitrile/0.1% TFA
Column=PHENOMENEX-LUNA 2.0×30 mm C18, 3u Method 3
Start % B=0, Final % B=100 over 2 minute gradient
Flow Rate=4 mL/Min
Solvent A=95% Water/5% methanol/10 mM Ammonium Acetate
Solvent B=5% Water/95% methanol/10 mM Ammonium Acetate
Column=Xbridge 4.6×50 mm 5u C18

Method 4
Start % B=0, Final % B=100 over 2 minute gradient
Flow Rate=0.8 mL/Min
Solvent A=95% Water/5% methanol/10 mM Ammonium Acetate
Solvent B=5% Water/95% methanol/10 mM Ammonium Acetate
Column=Xbridge 2.1×50 mm 3.5 um C18

Method 5
Start % B=15, Final % B=100 over 2 minute gradient, hold at 100% for 3 minutes
Flow Rate=1 mL/Min
Solvent A=95% Water/5% acetonitrile/10 mM Ammonium Acetate
Solvent B=5% Water/95% acetonitrile/10 mM Ammonium Acetate
Column=PHENOMENEX-LUNA 2.0×30 mm C18, 3u Preparation of Compounds:

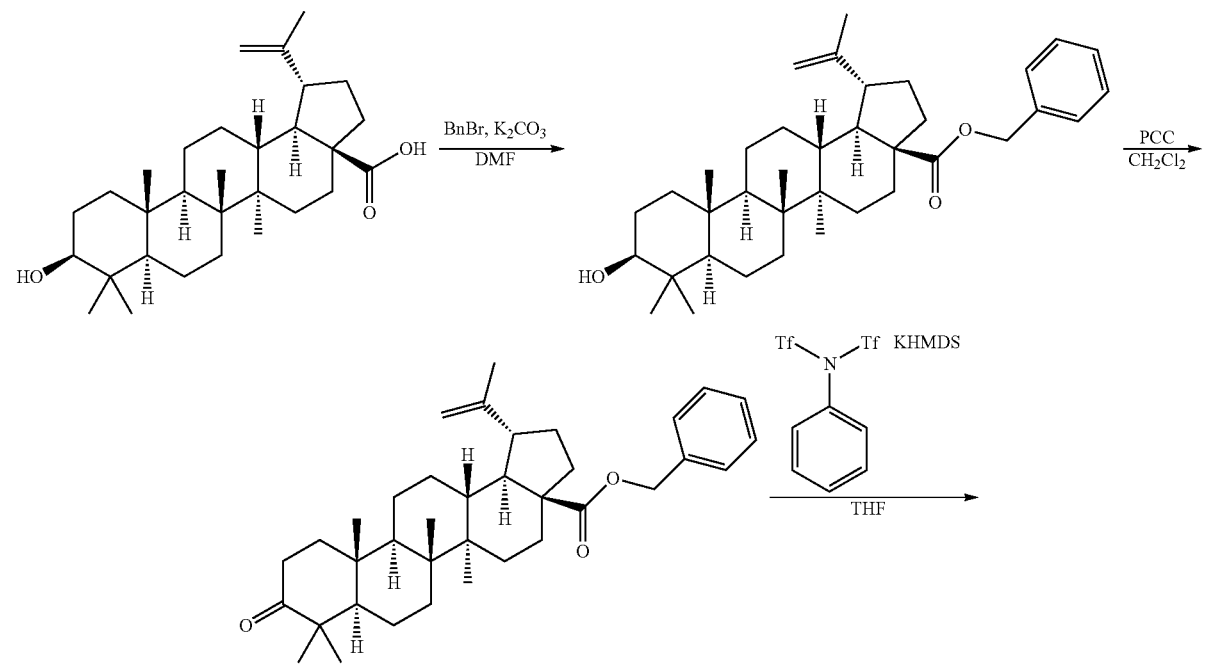

-continued
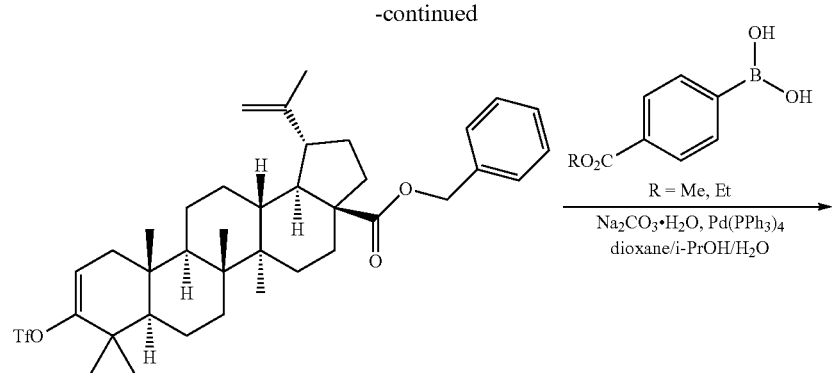
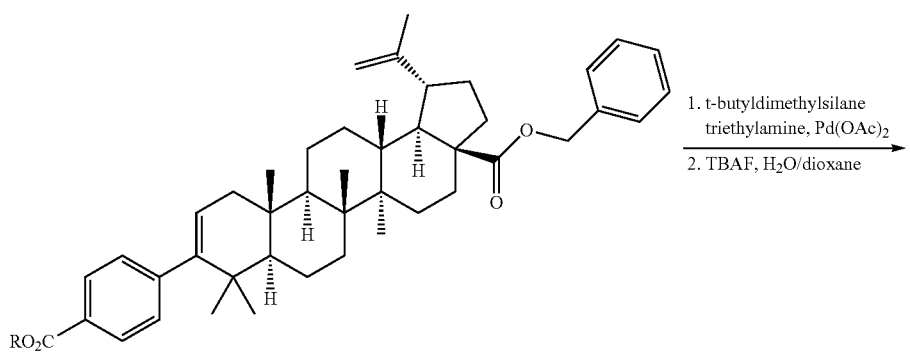
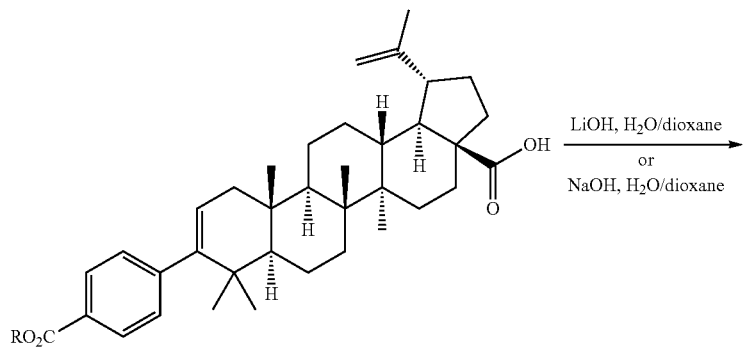
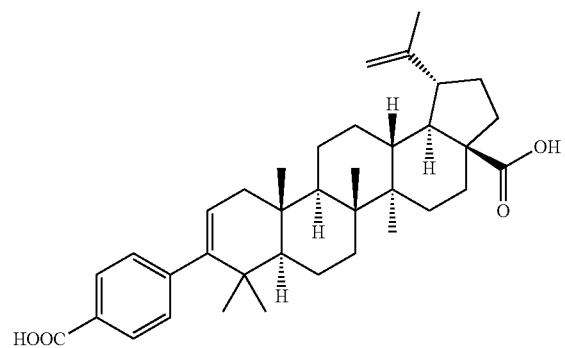

Preparation of (1R,3aS,5aR,5bR,7aR,9S,11aR,11bR, 13aR,13bR)-benzyl 9-hydroxy-5a,5b,8,8,11a-pentamethyl-1-(prop-1-en-2-yl)icosahydro-1H-cyclopenta[a]chrysene-3a-carboxylate. Intermediate 1

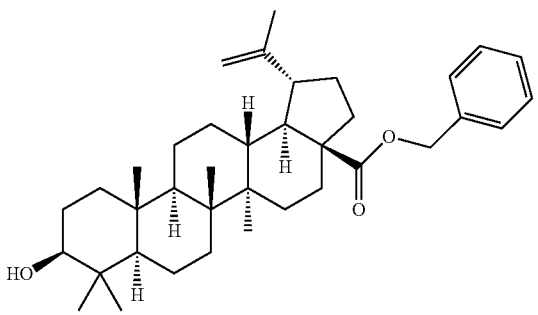

To a suspension of betulinic acid (12 g, 26.3 mmol) and potassium carbonate (7.26 g, 52.6 mmol) in DMF (150 mL) was added benzyl bromide (3.28 mL, 27.6 mmol). The mixture was heated to 60° C. for 3.5 h, and was cooled to rt. Solids started to precipitate upon cooling. The mixture was diluted with 200 mL of water and the solids that formed were collected by filtration to give (1R,3aS,5aR,5bR,7aR,9S,11aR, 11bR,13aR,13bR)-benzyl 9-hydroxy-5a,5b,8,8,11a-pentamethyl-1-(prop-1-en-2-yl)icosahydro-1H-cyclopenta[a] chrysene-3a-carboxylate (13.92 g, 25.5 mmol, 97% yield) as a white solid. $^1$H NMR (500 MHz, CHLOROFORM-d) δ ppm 7.39-7.28 (m, 5H), 5.16-5.06 (m, 2H), 4.71 (d, J=1.83 Hz, 1H), 4.59 (s, 1H), 3.17 (ddd, J=11.44, 5.65, 5.49 Hz, 1H), 3.01 (td, J=10.99, 4.88 Hz, 1H), 2.27 (ddd, J=12.36, 3.20, 3.05 Hz, 1H), 2.21-2.13 (m, 1H), 1.93-1.81 (m, 2H), 1.67 (s, 3H), 0.95 (s, 3H), 0.93 (s, 3H), 1.71-0.82 (m, 20H), 0.79 (s, 3H), 0.75 (s, 3H), 0.74 (s, 3H).

Preparation of (1R,3aS,5aR,5bR,7aR,11aR,11bR, 13aR,13bR)-benzyl 5a,5b,8,8,11a-pentamethyl-9-oxo-1-(prop-1-en-2-yl)icosahydro-1H-cyclopenta[a] chrysene-3a-carboxylate. Intermediate 2

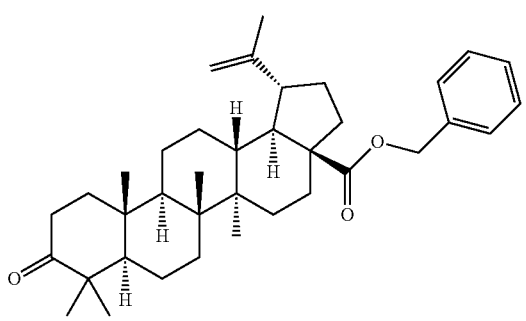

To a solution of (1R,3aS,5aR,5bR,7aR,9S,11aR,11bR, 13aR,13bR)-benzyl 9-hydroxy-5a,5b,8,8,11a-pentamethyl-1-(prop-1-en-2-yl)icosahydro-1H-cyclopenta[a]chrysene-3a-carboxylate (7.1 g, 12.98 mmol) in dichloromethane (100 mL) was added PCC (4.20 g, 19.48 mmol). After stirring for five minutes, the mixture turned a deep crimson color. The mixture was further stirred for 5.5 h. The mixture was filtered through a pad of celite and silica gel which was washed with dichloromethane and then a 1:1 mixture of ethyl acetate: hexanes. The filtrate was concentrated under reduced pressure to give (1R,3aS,5aR,5bR,7aR,11aR,11bR,13aR,13bR)-benzyl 5a,5b,8,8,11a-pentamethyl-9-oxo-1-(prop-1-en-2-yl) icosahydro-1H-cyclopenta[a]chrysene-3a-carboxylate (6.92 g, 12.7 mmol, 98% yield) as a white foam. $^1$H NMR (500 MHz, CHLOROFORM-d) δ ppm 7.38-7.28 (m, 5H), 5.17-5.06 (m, 2H), 4.72 (d, J=1.83 Hz, 1H), 4.59 (s, 1H), 3.01 (td, J=10.99, 4.88 Hz, 1H), 2.51-2.43 (m, 1H), 2.42-2.34 (m, 1H), 2.28 (dt, J=12.59, 3.17 Hz, 1H), 2.21 (td, J=12.28, 3.51 Hz, 1H), 1.94-1.82 (m, 3H), 1.67 (s, 3H), 1.05 (s, 3H), 1.01 (s, 3H), 1.73-0.95 (m, 17H), 0.94 (s, 3H), 0.89 (s, 3H), 0.78 (s, 3H).

Preparation of (1R,3aS,5aR,5bR,7aR,11aR,11bR, 13aR,13bR)-benzyl 5a,5b,8,8,11a-pentamethyl-1-(prop-1-en-2-yl)-9-(trifluoromethylsulfonyloxy)-2,3, 3a,4,5,5a,5b,6,7,7a,8,11,11a,11b,12,13,13a,13b-octadecahydro-1H-cyclopenta[a]chrysene-3a-carboxylate. Intermediate 3

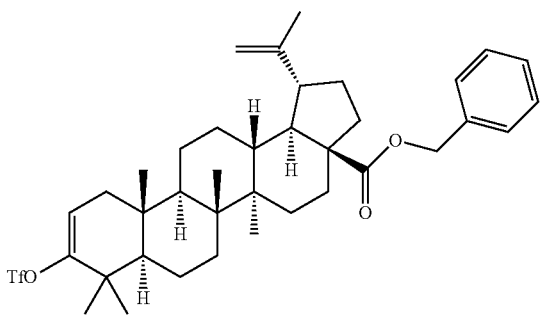

To a solution of (1R,3aS,5aR,5bR,7aR,11aR,13aR,13bR)-benzyl 5a,5b,8,8,11a-pentamethyl-9-oxo-1-(prop-1-en-2-yl) icosahydro-1H-cyclopenta[a]chrysene-3a-carboxylate (6.9 g, 12.67 mmol) and 1,1,1-trifluoro-N-phenyl-N-(trifluoromethylsulfonyl)methanesulfonamide (9.05 g, 25.3 mmol) in THF (200 mL) at −78° C. was added KHMDS (50.7 mL, 25.3 mmol) slowly. The reaction mixture was stirred for 1 hour at −78° C. TLC indicated starting material was consumed and desired product was formed. The reaction mixture was quenched with brine, extracted with diethyl ether. The extracts were dried over Na$_2$SO$_4$, filtered and concentrated under reduced pressure. The residue was dissolved in toluene and purified by biotage 2-10% toluene/hexanes and 5-10% ethyl acetate/hexanes to provide the title compound as a white solid (5.0 g, 58%). $^1$H NMR (500 MHz, CHLOROFORM-d) δ ppm 0.77 (s, 3H), 0.88 (s, 3H), 0.91-1.77 (m, 17H), 0.94 (s, 3H), 1.00 (s, 3H), 1.10 (s, 3H), 1.67 (s, 3H), 1.81-1.96 (m, 2H), 2.14 (dd, J=17.09, 6.71 Hz, 1H), 2.22 (td, J=12.21, 3.36 Hz, 1H), 2.25-2.31 (m, 1H), 3.02 (td, J=10.99, 4.58 Hz, 1H), 4.59 (s, 1H), 4.72 (d, J=1.53 Hz, 1H), 5.05-5.12 (m, 1H), 5.13-5.18 (m, 1H), 5.54 (dd, J=6.71, 1.53 Hz, 1H), 7.29-7.41 (m, 5H).

Procedure for the Suzuki Coupling.

Preparation of (1R,3aS,5aR,5bR,7aR,11aS,11bR,13aR,13bR)-benzyl 9-(4-(methoxycarbonyl)phenyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysene-3a-carboxylate. Intermediate 4

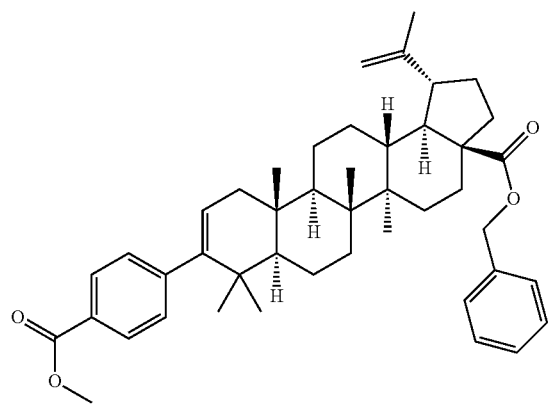

To a rb flask containing a solution of (1R,3aS,5aR,5bR,7aR,11aR,11bR,13bR)-benzyl 5a,5b,8,8,11a-pentamethyl-1-(prop-1-en-2-yl)-9-(trifluoromethylsulfonyloxy)-2,3,3a,4,5,5a,5b,6,7,7a,8,11,11a,11b,12,13,13a,13b-octadecahydro-1H-cyclopenta[a]chrysene-3a-carboxylate (6.21 g, 9.18 mmol) in dioxane (25 mL) was added 2-propanol (25 mL) and water (15 mL) followed by sodium carbonate monohydrate (3.42 g, 27.5 mmol), 4-methoxycarbonylphenylboronic acid (2.478 g, 13.77 mmol), and tetrakis(triphenylphosphine)palladium(0) (0.318 g, 0.275 mmol). The flask was attached to a reflux condenser, was flushed with $N_2$, and was heated to reflux overnight. After heating the mixture for 14.5 h, it was cooled to rt and was diluted with water (75 mL). The mixture was extracted with ethyl acetate (3×75 mL) and washed with brine. The combined organic layers were dried with $MgSO_4$, filtered, and concentrated under reduced pressure. The residue was adsorbed to silica gel and was purified by Biotage flash chromatography using a 0-20% ethyl acetate in hexanes gradient. The fractions containing the expected product was combined and concentrated under reduced pressure to give the expected product, (1R,3aS,5aR,5bR,7aR,11aS,11bR,13aR 13bR)-benzyl 9-(4-(methoxycarbonyl)phenyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysene-3a-carboxylate (4.16 g, 6.28 mmol, 68.4% yield), as a white foam. $^1$H NMR (500 MHz, CHLOROFORM-d) δ ppm 7.92 (d, J=8.24 Hz, 2H), 7.40-7.29 (m, 5H), 7.19 (d, J=8.24 Hz, 2H), 5.28 (dd, J=6.10, 1.83 Hz, 1H), 5.19-5.07 (m, 2H), 4.73 (d, J=1.83 Hz, 1H), 4.60 (s, 1H), 3.90 (s, 3H), 3.04 (td, J=10.91, 4.73 Hz, 1H), 2.20-2.32 (m, 2H), 2.09 (dd, J=17.24, 6.26 Hz, 1H), 1.95-1.82 (m, 2H), 1.69 (s, 3H), 0.97 (s, 3H), 0.95 (s, 3H), 0.92 (s, 3H), 0.91 (s, 3H), 1.75-0.87 (m, 17H), 0.82 (s, 3H).

(1R,3aS,5aR,5bR,7aR,11aS,11bR,13aR,13bR)-tert-butyldimethylsilyl 9-(4-(methoxycarbonyl)phenyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysene-3a-carboxylate. Intermediate 5

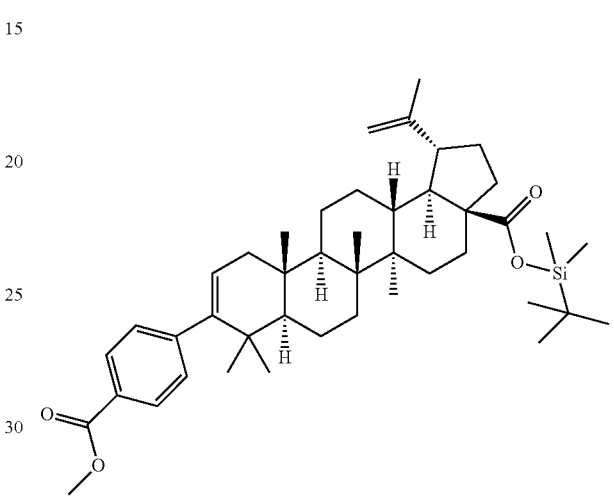

To a solution of (1R,3aS,5aR,5bR,7aR,11aS,11bR,13aR,13bR)-benzyl 9-(4-(methoxycarbonyl)phenyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysene-3a-carboxylate (3.82 g, 5.76 mmol) in dichloroethane (100 mL) was added triethylamine (1.285 mL, 9.22 mmol), tert-butyldimethylsilane (1.912 mL, 11.52 mmol), and palladium(II) acetate (0.647 g, 2.88 mmol). The mixture was flushed with $N_2$ and was heated to 60° C. After 2 h, the reaction was cooled to rt, was filtered through a pad of celite and silica gel to remove the solids which were washed with 25% EtOAc in hexanes. The filtrate was concentrated under reduced pressure and was treated with 20 mL of acetic acid, 10 mL of THF and 3 mL of water. After stirring for 1 h the solids that formed were collected by filtration and were washed with water to give (1R,3aS,5aR,5bR,7aR,11aS,11bR,13aR,13bR)-tert-butyldimethylsilyl 9-(4-(methoxycarbonyl)phenyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysene-3a-carboxylate (3.62 g, 5.27 mmol, 91% yield) as a white solid. $^1$H NMR (400 MHz, CHLOROFORM-d) δ ppm 7.94 (d, J=8.28 Hz, 2H), 7.21 (d, J=8.28 Hz, 2H), 5.30 (dd, J=6.15, 1.63 Hz, 1H), 4.75 (d, J=1.76 Hz, 1H), 4.62 (s, 1H), 3.92 (s, 4H), 3.08 (td, J=10.92, 4.27 Hz, 1H), 2.35-2.22 (m, 2H), 2.17-2.06 (m, 1H), 2.02-1.84 (m, 2H), 1.71 (s, 3H), 1.01 (s, 6H), 0.99 (br. s., 3H), 0.98 (s, 9H), 0.94 (s, 6H), 1.78-0.90 (m, 16H), 0.32-0.28 (m, 6H).

Preparation of (1R,3aS,5aR,5bR,7aR,11aS,11bR, 13aR,13bR)-9-(4-(methoxycarbonyl)phenyl)-5a,5b, 8,8,11a-pentamethyl-1-(prop-1-en-2-yl)-2,3,3a,4,5, 5a,5b,6,7,7a,8,11,11a,11b,12,13,13a,13b-octadecahydro-1H-cyclopenta[a]chrysene-3a-carboxylic acid. Intermediate 6

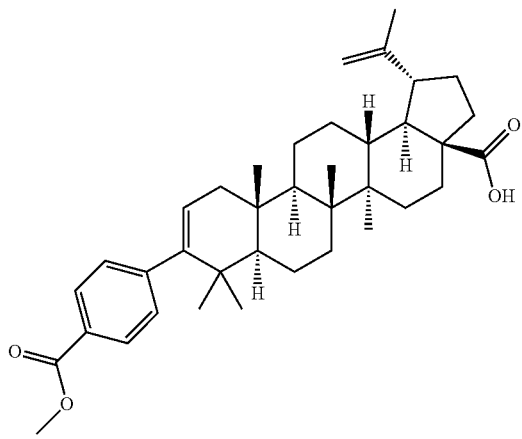

To solution of (1R,3aS,5aR,5bR,7aR,11aS,11bR,13aR, 13bR)-tert-butyldimethylsilyl 9-(4-(methoxycarbonyl)phenyl)-5a,5b,8,8,11a-pentamethyl-1-(prop-1-en-2-yl)-2,3,3a, 4,5,5a,5b,6,7,7a,8,11,11a,11b,12,13,13a,13b-octadecahydro-1H-cyclopenta[a]chrysene-3a-carboxylate (3.12 g, 4.54 mmol) in Dioxane (25 mL) was added TBAF (75% wt in water) (2.375 g, 6.81 mmol). The mixture was stirred at rt for 4 h then was diluted with 1N HCl (25 mL) and water (5 mL) and extracted with dichloromethane (3×100 mL). The combined organic layers were dried with $Na_2SO_4$, filtered, and partially concentrated under reduced pressure to about 10 mL volume. To the partially concentrated mixture was added 1N HCl (50 mL). The solids that formed were collected by filtration and were washed with water. The expected product, (1R,3aS,5aR,5bR,7aR,11aS,11bR,13aR, 13bR)-9-(4-(methoxycarbonyl)phenyl)-5a,5b,8,8,11a-pentamethyl-1-(prop-1-en-2-yl)-2,3,3a,4,5,5a,5b,6,7,7a,8,11, 11a,11b,12,13,13a,13b-octadecahydro-1H-cyclopenta[a] chrysene-3a-carboxylic acid (2.58 g, 4.50 mmol, 99% yield), was isolated as a white solid. LCMS: m/e 571.47 (M−H)$^-$, 3.60 min (method 1). $^1$H NMR (500 MHz, CHLOROFORM-d) δ ppm 9.80 (br. s., 1H), 7.92 (d, J=8.24 Hz, 2H), 7.18 (d, J=8.24 Hz, 2H), 5.32-5.26 (m, 1H), 4.75 (s, 1H), 4.62 (br. s., 1H), 3.90 (s, 3H), 3.07-2.99 (m, 1H), 2.33-2.21 (m, 2H), 2.10 (dd, J=17.09, 6.10 Hz, 1H), 2.06-1.94 (m, 2H), 1.70 (s, 3H), 1.01 (br. s., 3H), 1.00 (br. s., 3H), 0.98 (s, 3H), 0.91 (s, 6H), 1.79-0.89 (m, 17H).

General Procedure for C-28 Amide Formation

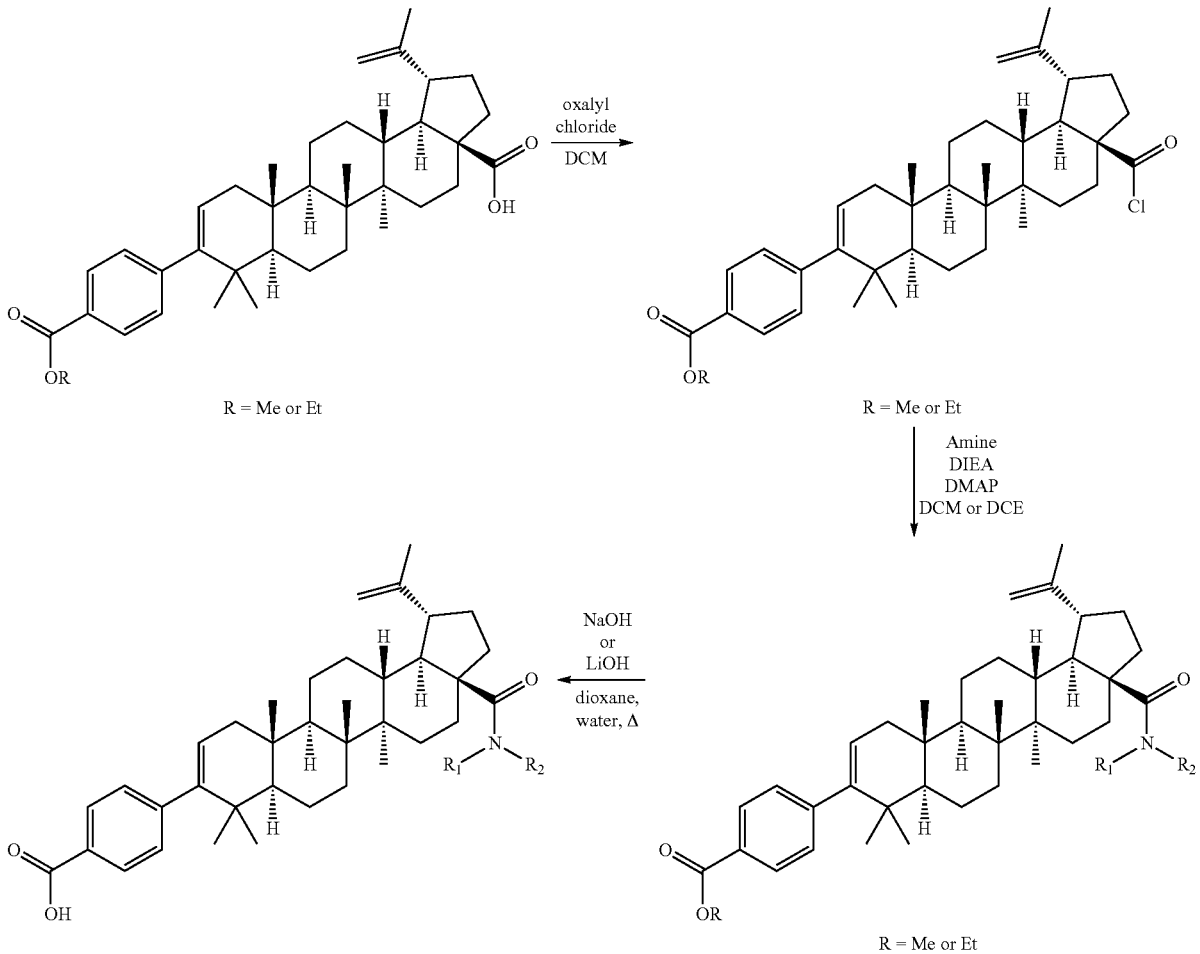

Step 1

Preparation of methyl 4-((1R,3aS,5aR,5bR,7aR, 11aS,11bR,13aR,13bR)-3a-(chlorocarbonyl)-5a,5b, 8,8,11a-pentamethyl-1-(prop-1-en-2-yl)-2,3,3a,4,5, 5a,5b,6,7,7a,8,11,11a,11b,12,13,13a,13b-octadecahydro-1H-cyclopenta[a]chrysen-9-yl) benzoate. Intermediate 7

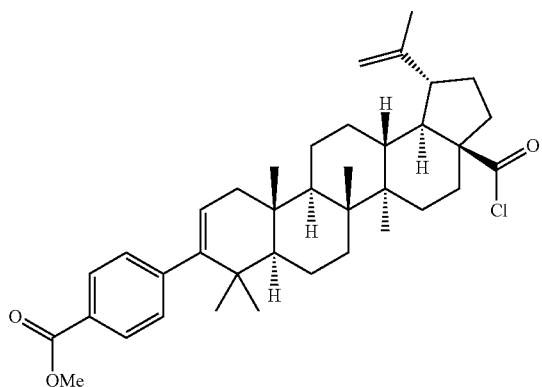

To a flask containing (1R,3aS,5aR,5bR,7aR,11aS,11bR, 13bR)-9-(4-(methoxycarbonyl)phenyl)-5a,5b,8,8,11a-pentamethyl-1-(prop-1-en-2-yl)-2,3,3a,4,5,5a,5b,6,7,7a,8,11, 11a,11b,12,13,13a,13b-octadecahydro-1H-cyclopenta[a]chrysene-3a-carboxylic acid (0.1-4.2 mmol scale) was added oxalyl chloride (2M in dichloromethane) (10-50 equiv.). The solution was stirred at rt for 2-5 h and was stripped of solvent. The residue was dissolved in dichloromethane and concentrated two additional times, then was used with no additional purification in the next step. $^1$H NMR (500 MHz, CHLOROFORM-d) δ ppm 7.92 (d, J=8.55 Hz, 2H), 7.19 (d, J=8.24 Hz, 2H), 5.26-5.30 (m, 1H), 4.73 (d, J=1.53 Hz, 1H), 4.62-4.64 (m, 1H), 3.90 (s, 3H), 2.81 (td, J=11.14, 4.58 Hz, 1H), 2.47 (ddd, J=13.58, 3.20, 3.05 Hz, 1H), 2.19-2.28 (m, 2H), 2.10 (dd, J=17.09, 6.41 Hz, 1H), 1.85-1.99 (m, 1H), 1.68 (s, 3H), 1.00 (s, 6H), 0.98 (s, 3H), 0.92 (s, 3H), 0.92 (s, 3H), 0.84-1.83 (m, 17H). $^{13}$C NMR (126 MHz, CHLOROFORM-d) δ ppm 177.49, 167.35, 149.46, 148.81, 146.39, 130.17 (s, 2C), 128.61 (s, 2C), 128.03, 124.12, 110.40, 68.00, 52.99, 52.11, 49.78, 49.67, 46.11, 42.54, 41.86, 40.70, 38.00, 37.60, 36.39, 36.31, 33.64, 32.3, 29.98, 29.72, 29.54, 25.60, 21.37, 21.13, 19.86, 19.48, 16.59, 15.71, 14.89.

Step 2

To a solution of the acid chloride in dichloroethane or dichloromethane (0.02-0.15 M) was added Hunig's Base (3-5 equiv.), the amine (1.1-2.6 equiv.), and DMAP (0.03-0.1 equiv.). The mixture was stirred at rt for 2-72 h. The reaction mixture was diluted with 1N HCl or water and was extracted with dichloromethane. The organic layer was dried with Na$_2$SO$_4$, the drying agent was removed by filtration, and the filtrate was concentrated under reduced pressure. The residue was purified by Biotage flash chromatography or was directly used in the next step with no additional purification.
Note: The same reaction conditions can be used without DMAP to successfully form the corresponding amides.
General Procedures for Hydrolysis of the Benzoic Ester Using NaOH or LiOH.H$_2$O
The C-28 amide formed above was dissolved in 1,4-dioxane and either aq. 1N or 10 N NaOH was added to the mixture and it was heated to 50-85° C. After heating for 2-24 h, the mixture was cooled to rt. The crude mixture was either purified by prep HPLC or was made acidic by dropwise addition of 1N HCL and the final product was crystallized from dioxane/water or dioxane/methanol/water.

Alternative, the deprotection can be carried out as follows: The C-28 amide formed above was dissolved in 1,4-dioxane. To the solution was added water (4:1 dioxane:water or 5:1 dioxane:water) followed by LiOH.H$_2$O (5-12 equiv.). The mixture was heated to 50-85° C. After heating for 2-24 h, the mixture was cooled to rt. The crude mixture was either purified by prep HPLC or was made acidic by dropwise addition of 1N HCL and the final product was crystallized from dioxane/water or dioxane/methanol/water.

Preparation of methyl 4-((1R,3aS,5aR,5bR,7aR, 11aS,11bR,13aR,13bR)-3a-(chlorocarbonyl)-5a,5b, 8,8,11a-pentamethyl-1-(prop-1-en-2-yl)-2,3,3a,4,5, 5a,5b,6,7,7a,8,11,11a,11b,12,13,13a,13b-octadecahydro-1H-cyclopenta[a]chrysen-9-yl)-2-fluorobenzoate. Intermediate 7a

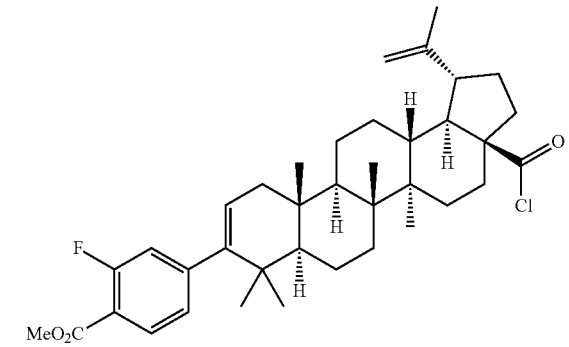

The title compound was prepared from (1R,3aS,5aR,5bR, 7aR,11aR,11bR,13aR,13bR)-benzyl 5a,5b,8,8,11a-pentamethyl-1-(prop-1-en-2-yl)-9-(trifluoromethylsulfonyloxy)-2, 3,3a,4,5,5a,5b,6,7,7a,8,11,11a,11b,12,13,13a,13b-octadecahydro-1H-cyclopenta[a]chrysene-3a-carboxylate (Intermediate 3) following the above described procedures for the Suzuki coupling (as described for intermediate 4, but using 3-fluoro-4-(methoxycarbonyl)phenylboronic acid as the reactant); deprotection of the C-28 acid (as described for intermediate 5 and 6) and conversion into acid chloride (as described for intermediate 7). The crude material was taken to the next step without further purification. LCMS: m/e 605.39 (M−Cl+OMe+H)$^+$, 4.12 min (method 1).

Example 1

Preparation of 4-((1R,3aS,5aR,5bR,7aR,11aS,11bR, 13aR,13bR)-5a,5b,8,8,11a-pentamethyl-1-(prop-1-en-2-yl)-3a-(2-(pyridin-2-yl)ethylcarbamoyl)-2,3,3a, 4,5,5a,5b,6,7,7a,8,11,11a,11b,12,13,13a,13b-octadecahydro-1H-cyclopenta[a]chrysen-9-yl) benzoic acid

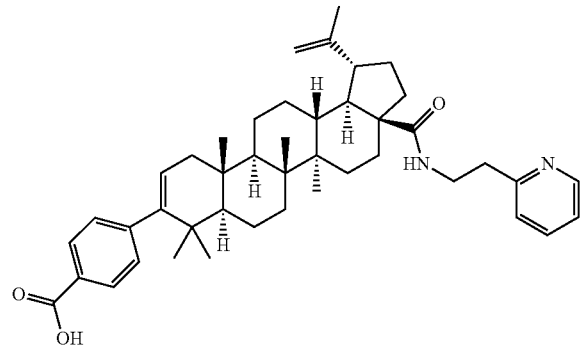

The title compound was prepared following the general procedures described above for the C-28 amide formation and hydrolysis using 2-(2-Aminoethyl)pyridine as the reactant amine. The product was isolated as a white solid (13 mg, 14%). LCMS: m/e 661.7 (M−H)⁻, 2.16 min (method 1). ¹H NMR (500 MHz, CHLOROFORM-d) δ ppm 8.59-8.50 (m, 1H), 8.02-7.95 (m, 2H), 7.69-7.64 (m, 1H), 7.24-7.17 (m, 3H), 6.77-6.71 (m, 1H), 5.28 (d, J=6.10 Hz, 1H), 4.73 (br. s., 1H), 4.58 (br. s., 1H), 3.73-3.66 (m, 2H), 3.12-3.03 (m, 3H), 2.42 (t, J=12.21 Hz, 1H), 2.08 (dd, J=16.94, 5.65 Hz, 1H), 1.97 (d, J=13.73 Hz, 1H), 1.89-1.78 (m, 1H), 1.67 (s, 3H), 1.73-0.95 (m, 19H), 0.95 (s, 3H), 0.93 (s, 3H), 0.92 (br. s., 6H), 0.89 (s, 3H).

Example 2

Preparation of 4-((1R,3aS,5aR,5bR,7aR,11aS,11bR, 13aR,13bR)-5a,5b,8,8,11a-pentamethyl-1-(prop-1-en-2-yl)-3a-(pyridin-2-ylmethylcarbamoyl)-2,3,3a,4, 5,5a,5b,6,7,7a,8,11,11a,11b,12,13,13a,13b-octadecahydro-1H-cyclopenta[a]chrysen-9-yl) benzoic acid

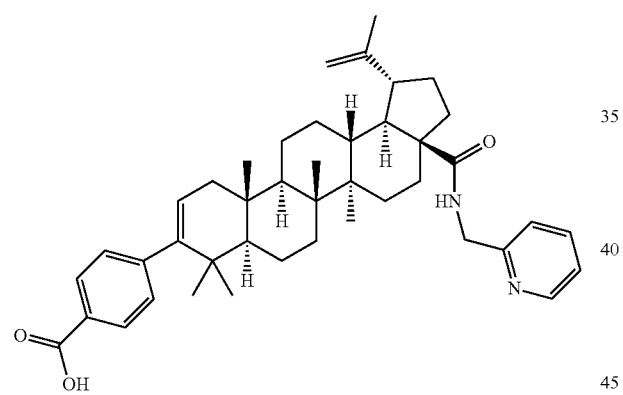

The title compound was prepared following the general procedures described above for the C-28 amide formation and hydrolysis using 2-(Aminomethyl)pyridine as the reactant amine. The product was isolated as an off-white solid (38 mg, 41%). LCMS: m/e 647.6 (M−H)⁻, 2.13 min (method 1). ¹H NMR (500 MHz, CHLOROFORM-d) δ ppm 8.54 (d, J=4.88 Hz, 1H), 7.99 (d, J=7.93 Hz, 2H), 7.69 (td, J=7.63, 1.53 Hz, 1H), 7.38 (d, J=7.93 Hz, 1H), 7.24-7.20 (m, 3H), 7.09-7.03 (m, 1H), 5.29 (d, J=5.49 Hz, 1H), 4.74 (s, 1H), 4.62-4.54 (m, 2H), 4.54-4.47 (m, 1H), 3.16 (td, J=10.99, 4.58 Hz, 1H), 2.49-2.42 (m, 1H), 2.13-2.05 (m, 2H), 2.00-1.80 (m, 3H), 1.69 (s, 3H), 0.98 (s, 3H), 1.75-0.95 (m, 16H), 0.94 (s, 3H), 0.92 (s, 3H), 0.92 (s, 3H), 0.82 (s, 3H).

Example 3

Preparation of 4-((1R,3aS,5aR,5bR,7aR,11aS,11bR, 13aR,13bR)-5a,5b,8,8,11a-pentamethyl-1-(prop-1-en-2-yl)-3a-(2-(pyridin-3-yl)ethylcarbamoyl)-2,3,3a, 4,5,5a,5b,6,7,7a,8,11,11a,11b,12,13,13a,13b-octadecahydro-1H-cyclopenta[a]chrysen-9-yl) benzoic acid

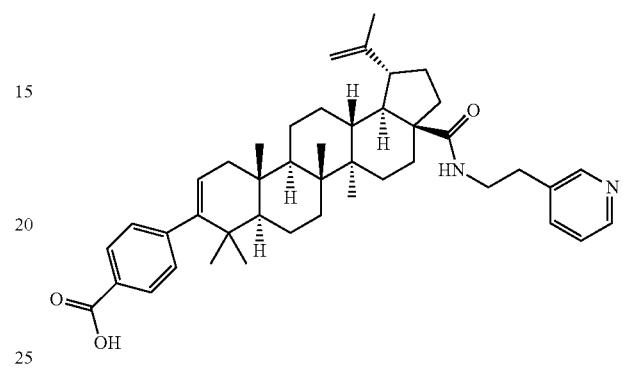

The title compound was prepared following the general procedures described above for the C-28 amide formation and hydrolysis using 3-(2-aminoethyl)pyridine as the reactant amine. The product was isolated as an off-white solid (70 mg, 74%). LCMS: m/e 661.7 (M−H)⁻, 2.12 min (method 1). ¹H NMR (500 MHz, MeOD) δ ppm 8.45 (br. s., 1H), 8.41 (d, J=4.27 Hz, 1H), 7.93 (d, J=8.24 Hz, 2H), 7.80 (d, J=7.93 Hz, 1H), 7.41 (dd, J=7.48, 5.04 Hz, 1H), 7.23 (d, J=8.24 Hz, 2H), 5.33-5.29 (m, 1H), 4.72 (d, J=2.14 Hz, 1H), 4.60 (br. s., 1H), 3.57-3.40 (m, 2H), 3.10-3.02 (m, 1H), 2.94-2.84 (m, 2H), 2.68-2.58 (m, 1H), 2.17 (dd, J=17.24, 6.56 Hz, 1H), 2.06 (d, J=13.43 Hz, 1H), 1.70 (s, 3H), 1.04 (s, 3H), 1.80-0.95 (m, 19H), 1.03 (s, 3H), 0.98 (s, 3H), 0.97 (s, 3H), 0.96 (s, 3H).

Example 4

Preparation of 4-((1R,3aS,5aR,5bR,7aR,11aS,11bR, 13aR,13bR)-3a-(4-methoxyphenethylcarbamoyl)-5a, 5b,8,8,11a-pentamethyl-1-(prop-1-en-2-yl)-2,3,3a,4, 5,5a,5b,6,7,7a,8,11,11a,11b,12,13,13a,13b-octadecahydro-1H-cyclopenta[a]chrysen-9-yl) benzoic acid

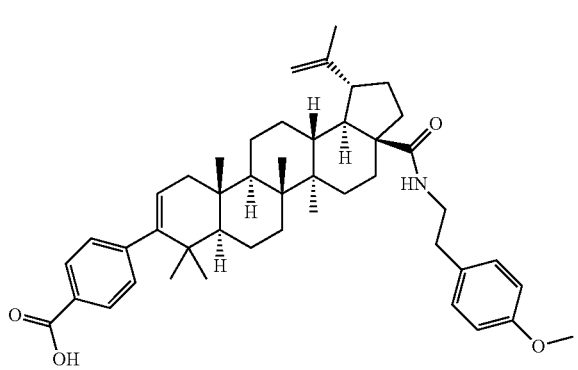

The title compound was prepared following the general procedures described above for the C-28 amide formation and hydrolysis using 2-(4-methoxyphenyl)ethylamine as the reactant amine. The product was isolated as a white solid (36 mg, 49%). LCMS: m/e 690.7 (M–H)⁻, 2.19 min (method 1). ¹H NMR (400 MHz, CHLOROFORM-d) δ ppm 8.01 (d, J=8.28 Hz, 2H), 7.24 (d, J=8.28 Hz, 2H), 7.15 (d, J=8.78 Hz, 2H), 6.89-6.84 (m, 2H), 5.58 (t, J=5.65 Hz, 1H), 5.34-5.29 (m, 1H), 4.75 (d, J=1.76 Hz, 1H), 4.61 (s, 1H), 3.81 (s, 3H), 3.63-3.42 (m, 2H), 3.07 (td, J=11.04, 3.51 Hz, 1H), 2.85-2.71 (m, 2H), 2.46 (td, J=12.17, 3.26 Hz, 1H), 2.17-2.08 (m, 1H), 2.01-1.82 (m, 2H), 1.70 (s, 3H), 1.75-0.98 (m, 18H), 0.99 (s, 6H), 0.98 (s, 3H), 0.95 (s, 3H), 0.95 (s, 3H).

Example 5

Preparation of 4-((1R,3aS,5aR,5bR,7aR,11aS,11bR, 13aR,13bR)-5a,5b,8,8,11a-pentamethyl-1-(prop-1-en-2-yl)-3a-(1-(pyridin-2-yl)cyclopropylcarbamoyl)-2,3,3a,4,5,5a,5b,6,7,7a,8,11,11a,11b,12,13,13a,13b-octadecahydro-1H-cyclopenta[a]chrysen-9-yl)benzoic acid

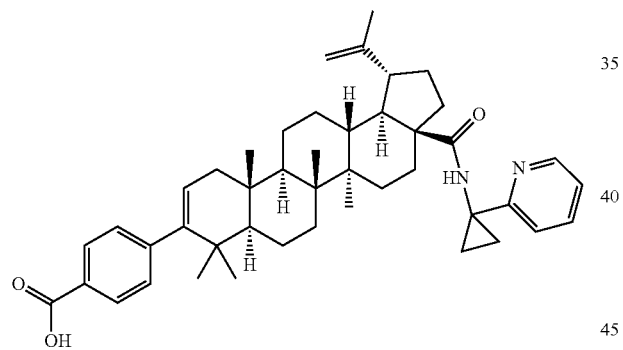

The title compound was prepared following the general procedures described above for the C-28 amide formation and hydrolysis using 1-(pyridin-2-yl)cyclopropanamine, 2 HCl as the reactant amine. The product was isolated as a white film (10 mg, 12%). LCMS: m/e 673.7 (M–H)⁻, 2.11 min (method 1). ¹H NMR (500 MHz, CHLOROFORM-d) δ ppm 8.47 (d, J=4.88 Hz, 1H), 7.99 (d, J=7.93 Hz, 2H), 7.66-7.59 (m, 1H), 7.43 (d, J=7.93 Hz, 1H), 7.22 (d, J=7.93 Hz, 2H), 7.11 (dd, J=7.32, 4.88 Hz, 1H), 6.83 (s, 1H), 5.28 (br. s., 1H), 4.71 (s, 1H), 4.58 (s, 1H), 3.16 (td, J=10.83, 3.97 Hz, 1H), 2.49 (t, J=12.05 Hz, 1H), 2.13-1.98 (m, 2H), 1.97-1.85 (m, 1H), 1.82 (dd, J=11.75, 7.78 Hz, 1H), 1.67 (s, 3H), 0.99 (s, 3H), 1.74-0.87 (m, 21H), 0.95 (s, 3H), 0.93 (s, 3H), 0.92 (s, 3H), 0.91 (s, 3H).

Example 6

Preparation of 4-((1R,3aS,5aR,5bR,7aR,11aS,11bR, 13aR,13bR)-3a-(cyclopropylsulfonylcarbamoyl)-5a, 5b,8,8,11a-pentamethyl-1-(prop-1-en-2-yl)-2,3,3a,4, 5,5a,5b,6,7,7a,8,11,11a,11b,12,13,13a,13b-octadecahydro-1H-cyclopenta[a]chrysen-9-yl)benzoic acid

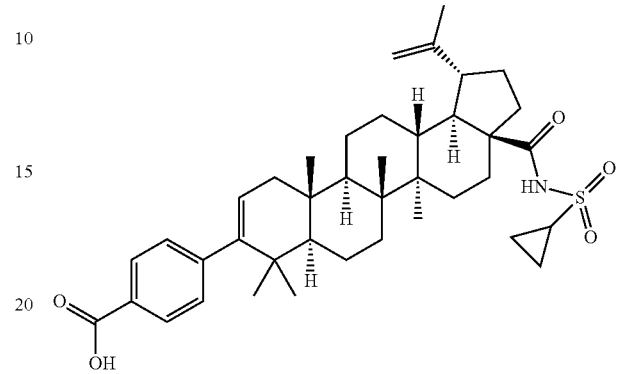

The title compound was prepared following the general procedures described above for the C-28 amide formation and hydrolysis using cyclopropanesulfonamide as the reactant amine. The product was isolated as a white solid (25 mg, 21%). LCMS: m/e 660.6 (M–H)⁻, 2.04 min (method 1). ¹H NMR (400 MHz, CHLOROFORM-d) δ ppm 7.99 (d, J=7.53 Hz, 2H), 7.22 (d, J=8.03 Hz, 2H), 7.01 (br. s., 1H), 5.31 (s, 1H), 4.76 (s, 1H), 4.64 (s, 1H), 3.18-3.00 (m, 2H), 2.51 (t, J=10.92 Hz, 1H), 2.18-2.06 (m, 2H), 2.04-1.82 (m, 3H), 1.70 (s, 3H), 1.03 (s, 3H), 1.02 (s, 3H), 0.99 (s, 3H), 0.94 (s, 6H), 1.80-0.87 (m, 20H).

Example 7

Preparation of 4-((1R,3aS,5aR,5bR,7aR,11aS,11bR, 13aR,13bR)-3a-(N,N-dimethylsulfamoylcarbamoyl)-5a,5b,8,8,11a-pentamethyl-1-(prop-1-en-2-yl)-2,3, 3a,4,5,5a,5b,6,7,7a,8,11,11a,11b,12,13,13a,13b-octadecahydro-1H-cyclopenta[a]chrysen-9-yl)benzoic acid

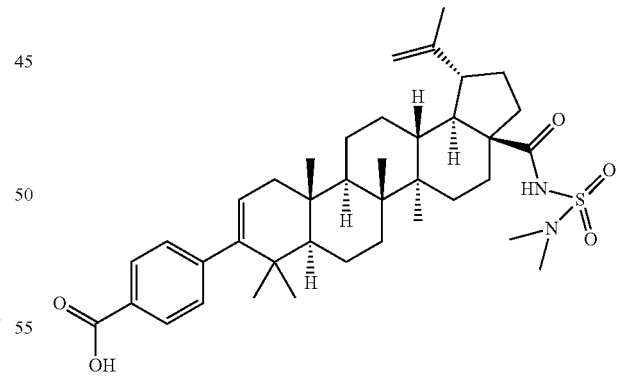

The title compound was prepared following the general procedures described above for the C-28 amide formation and hydrolysis using N,N-Dimethylsulfamide as the reactant amine. The product was isolated as a white solid (12 mg, 10%). LCMS: m/e 663.5 (M–H)⁻, 2.08 min (method 1). ¹H NMR (500 MHz, CHLOROFORM-d) δ ppm 7.99 (d, J=8.24 Hz, 2H), 7.22 (d, J=8.24 Hz, 2H), 5.30 (d, J=4.27 Hz, 1H), 4.74 (s, 1H), 4.62 (s, 1H), 3.05 (td, J=10.99, 4.27 Hz, 1H), 2.98 (s, 6H), 2.48 (td, J=12.13, 3.20 Hz, 1H), 2.11 (dd, J=17.24, 6.26 Hz, 1H), 2.00-1.90 (m, 2H), 1.84 (dd, J=12.21, 7.63 Hz, 1H), 1.68 (s, 3H), 1.76-0.95 (m, 18H), 1.03 (s, 3H), 1.00 (s, 3H), 0.98 (s, 3H), 0.93 (s, 6H).

Example 8

Preparation of 4-((1R,3aS,5aR,5bR,7aR,11aS,11bR, 13aR,13bR)-5a,5b,8,8,11a-pentamethyl-3a-(methyl-sulfonylcarbamoyl)-1-(prop-1-en-2-yl)-2,3,3a,4,5,5a, 5b,6,7,7a,8,11,11a,11b,12,13,13a,13b-octadecahydro-1H-cyclopenta[a]chrysen-9-yl) benzoic acid

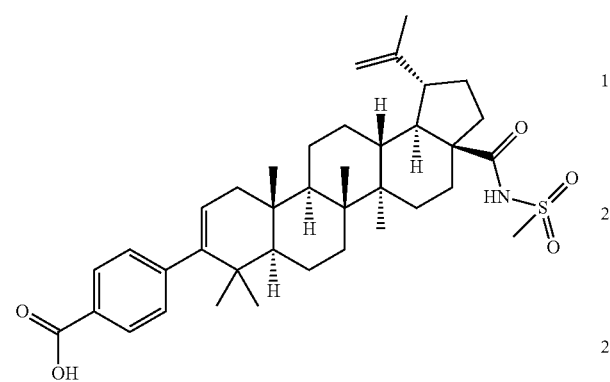

The title compound was prepared following the general procedures described above for the C-28 amide formation and hydrolysis using methanesulfonamide as the reactant amine. The product was isolated as a white solid (22 mg, 19%). LCMS: m/e 634.4 (M−H)⁻, 2.01 min (method 1). $^1$H NMR (500 MHz, CHLOROFORM-d) δ ppm 7.97 (d, J=8.24 Hz, 2H), 7.21 (d, J=8.55 Hz, 2H), 5.31-5.27 (m, 1H), 4.74 (s, 1H), 4.62 (s, 1H), 3.32 (s, 3H), 3.07 (td, J=10.99, 4.58 Hz, 1H), 2.45 (td, J=12.44, 3.20 Hz, 1H), 1.99-1.87 (m, 2H), 1.83 (dd, J=12.51, 7.63 Hz, 1H), 1.68 (s, 3H), 1.75-0.95 (m, 18H), 1.01 (s, 6H), 0.97 (s, 3H), 0.93 (s, 3H), 0.92 (s, 3H).

Example 9

Preparation of 4-((1R,3aS,5aR,5bR,7aR,11aS,11bR, 13aR,13bR)-3a-((R)-2-(hydroxymethyl)pyrrolidine-1-carbonyl)-5a,5b,8,8,11a-pentamethyl-1-(prop-1-en-2-yl)-2,3,3a,4,5,5a,5b,6,7,7a,8,11,11a,11b,12,13, 13a,13b-octadecahydro-1H-cyclopenta[a]chrysen-9-yl)benzoic acid

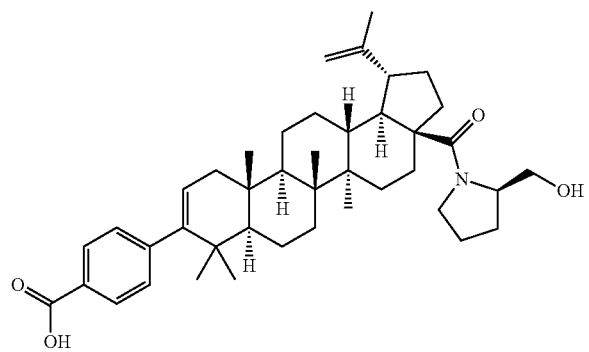

The title compound was prepared following the general procedures described above for the C-28 amide formation and hydrolysis using D(−)Prolinol as the reactant amine. The product was isolated as a white solid (22 mg, 27%). LCMS: m/e 640.6 (M−H)⁻, 2.18 min (method 1). $^1$H NMR (400 MHz, CHLOROFORM-d) δ ppm 7.99 (d, J=8.53 Hz, 2H),7.24 (d, J=8.53 Hz, 2H), 5.34-5.30 (m, 1H), 4.75 (d, J=2.01 Hz, 1H), 4.61 (s, 1H), 4.40-4.33 (m, 1H), 3.89-3.81 (m, 1H), 3.69-3.63 (m, 1H), 3.60-3.54 (m, 1H), 3.35 (ddd, J=10.73, 8.34, 6.27 Hz, 1H), 3.06-2.93 (m, 2H), 1.71 (s, 3H), 2.14-0.95 (m, 25H), 1.03 (s, 3H), 1.01 (s, 6H), 0.95 (s, 3H), 0.94 (s, 3H).

Example 10

Preparation of 4-((1R,3aS,5aR,5bR,7aR,11aS,11bR, 13aR,13bR)-5a,5b,8,8,11a-pentamethyl-3a-(4-methylpiperazine-1-carbonyl)-1-(prop-1-en-2-yl)-2,3,3a, 4,5,5a,5b,6,7,7a,8,11,11a,11b,12,13,13a,13b-octadecahydro-1H-cyclopenta[a]chrysen-9-yl) benzoic acid

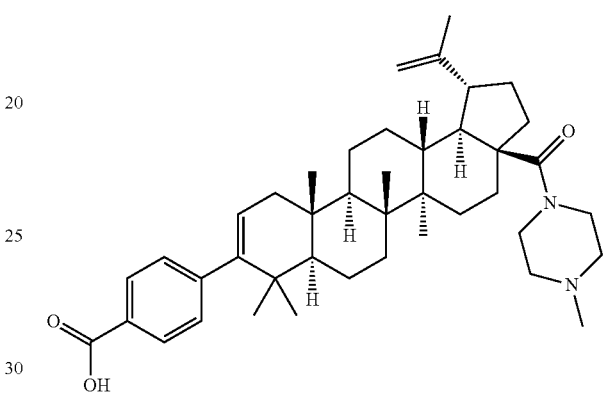

The title compound was prepared following the general procedures described above for the C-28 amide formation and hydrolysis using 1-methyl piperazine as the reactant amine. The product was isolated as a white film (8 mg, 10%). LCMS: m/e 639.7 (M−H)⁻, 2.22 min (method 1). $^1$H NMR (500 MHz, CHLOROFORM-d) δ ppm 7.98 (d, J=8.24 Hz, 2H), 7.22 (d, J=8.24 Hz, 2H), 5.29 (d, J=4.58 Hz, 1H), 4.73 (s, 1H), 4.60 (s, 1H), 4.52 (br. s., 4H), 3.68-3.58 (m, 2H), 3.38 (br. s., 4H), 2.99-2.90 (m, 1H), 2.85 (s, 3H), 2.86-2.78 (m, 1H), 2.73-2.57 (m, 2H), 2.11 (dd, J=17.09, 6.41 Hz, 1H), 1.98 (d, J=13.43 Hz, 1H), 1.69 (s, 3H), 1.88-0.95 (m, 15H), 0.99 (s, 3H), 0.97 (s, 6H), 0.93 (s, 3H), 0.92 (br. s., 3H). Note: piperazine peaks are broadened into baseline

Example 11

Preparation of 4-((1R,3aS,5aR,5bR,7aR,11aS,11bR, 13aR,13bR)-3a-(3-(diethylcarbamoyl)piperidine-1-carbonyl)-5a,5b,8,8,11a-pentamethyl-1-(prop-1-en-2-yl)-2,3,3a,4,5,5a,5b,6,7,7a,8,11,11a,11b,12,13,13a, 13b-octadecahydro-1H-cyclopenta[a]chrysen-9-yl) benzoic acid

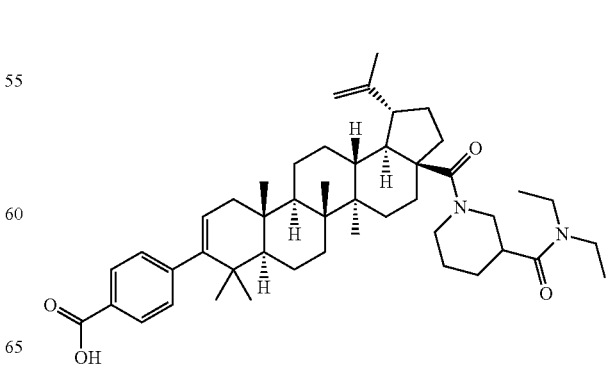

The title compound was prepared following the general procedures described above for the C-28 amide formation and hydrolysis using N,N-diethylnipecotamide as the reactant amine. The product was isolated as a white solid (42 mg, 46%). LCMS: m/e 723.7 (M–H)⁻, 2.21 min (method 1). $^1$H NMR (500 MHz, CHLOROFORM-d) δ ppm 8.01-7.95 (m, 2H), 7.24-7.24 (m, 2H), 5.30 (d, J=4.27 Hz, 1H), 4.58 (s, 1H), 4.76-4.71 (m, 1H), 1.72-1.66 (m, 3H), 3.59-0.95 (m, 42H), 1.02-0.99 (m, 3H), 0.99-0.95 (m, 6H), 0.95-0.90 (m, 6H).

Example 12

Preparation of 4-((1R,3aS,5aR,5bR,7aR,11aS,11bR,13aR,13bR)-5a,5b,8,8,11a-pentamethyl-3a-(2-morpholinoethylcarbamoyl)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

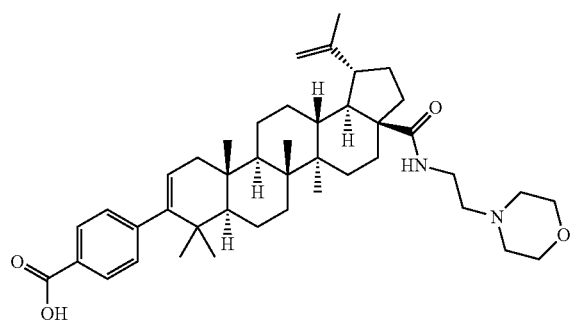

The title compound was prepared following the general procedures described above for the C-28 amide formation and hydrolysis using N-(2-aminoethyl)morpholine as the reactant amine. The product was isolated as a white solid (13.7 mg, 16%). LCMS: m/e 669.7 (M–H)⁻, 2.14 min (method 1). $^1$H NMR (500 MHz, CHLOROFORM-d) δ ppm 12.70 (br. s., 1H), 7.97 (d, J=8.24 Hz, 2H), 7.24-7.18 (m, 3H), 5.29 (d, J=4.88 Hz, 1H), 4.73 (s, 1H), 4.59 (s, 1H), 3.99 (br. s., 4H), 3.80-3.72 (m, 1H), 3.70-3.61 (m, 1H), 3.56 (t, J=11.44 Hz, 2H), 3.23 (t, J=5.19 Hz, 2H), 3.08 (td, J=10.76, 4.12 Hz, 1H), 2.96-2.87 (m, 2H), 2.48-2.39 (m, 1H), 2.09 (dd, J=17.24, 6.26 Hz, 1H), 2.01 (d, J=13.73 Hz, 1H), 0.98 (s, 3H), 1.68 (s, 3H), 1.89-0.95 (m, 19H), 0.95 (s, 6H), 0.92 (s, 6H).

Example 13

Preparation of 4-((1R,3aS,5aR,5bR,7aR,11aS,11bR,13aR,13bR)-3a-(4-(2-hydroxyethyl)piperazine-1-carbonyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid, TFA

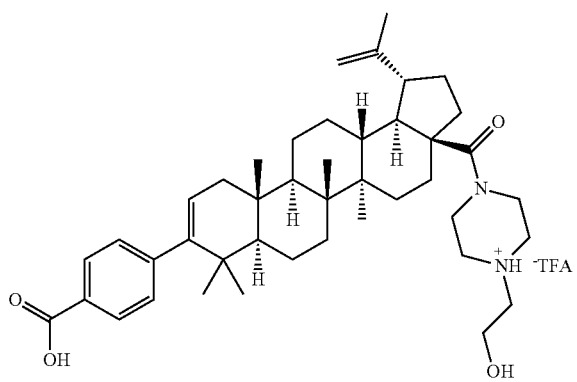

The title compound was prepared following the general procedures described above for the C-28 amide formation and hydrolysis using 1-(2-hydroxyethyl)piperazine as the reactant amine. The product was isolated as a white film (2.6 mg, 2.6%). LCMS: m/e 669.6 (M–H)⁻, 2.13 min (method 1). $^1$H NMR (400 MHz, MeOD) δ ppm 7.93 (d, J=8.28 Hz, 2H), 7.23 (d, J=8.28 Hz, 2H), 5.31 (d, J=6.27 Hz, 1H), 4.72 (s, 1H), 4.62 (s, 1H), 3.92-3.87 (m, 1H), 3.52-3.10 (m, 10H), 3.01-2.83 (m, 2H), 2.23-2.11 (m, 1H), 2.07-1.97 (m, 1H), 1.72 (s, 3H), 1.06 (s, 3H), 1.04 (s, 3H), 1.91-0.95 (m, 20H), 1.03 (s, 3H), 0.97 (s, 3H), 0.95 (s, 3H).

Example 14

Preparation of 4-((1R,3aS,5aR,5bR,7aR,11aS,11bR,13aR,13bR)-3a-(4-methoxyphenylcarbamoyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

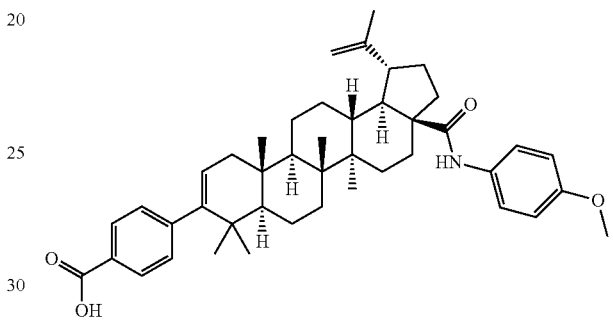

The title compound was prepared following the general procedures described above for the C-28 amide formation and hydrolysis using p-anisidine as the reactant amine. The product was isolated as a tan solid (40 mg, 47%). LCMS: m/e 662.6 (M–H)⁻, 2.15 min (method 1). $^1$H NMR (500 MHz, CHLOROFORM-d) δ ppm 7.98 (d, J=8.55 Hz, 2H), 7.40-7.34 (m, 2H), 7.22 (d, J=8.24 Hz, 2H), 7.15 (s, 1H), 6.90-6.84 (m, 2H), 5.31-5.28 (m, 1H), 4.76 (d, J=1.83 Hz, 1H), 4.61 (s, 1H), 3.79 (s, 3H), 3.21 (td, J=11.06, 4.43 Hz, 1H), 2.67-2.58 (m, 1H), 2.16-1.97 (m, 3H), 1.89 (dd, 1H), 1.76 (d, J=10.99 Hz, 1H), 1.71 (s, 3H), 1.03 (s, 3H), 1.01 (s, 3H), 1.72-0.95 (m, 16H), 0.97 (s, 3H), 0.92 (s, 6H).

Example 15

Preparation of 4-((1R,3aS,5aR,5bR,7aR,11aS,11bR,13aR,13bR)-3a-(4-methoxybenzylcarbamoyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

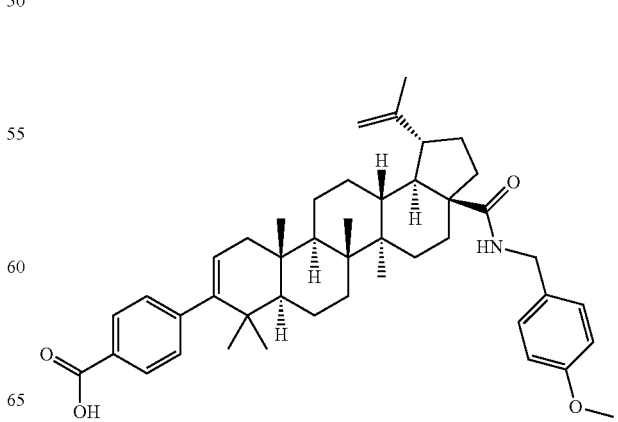

The title compound was prepared following the general procedures described above for the C-28 amide formation and hydrolysis using 4-aminomethyl-anisole as the reactant amine. The product was isolated as an off-white solid (31 mg, 36%). LCMS: m/e 676.6 (M−H)⁻, 2.16 min (method 1). $^1$H NMR (500 MHz, CHLOROFORM-d) δ ppm 7.99 (d, J=8.24 Hz, 2H), 7.24-7.19 (m, 4H), 6.86 (d, J=8.55 Hz, 2H), 5.80 (t, J=5.65 Hz, 1H), 5.30 (d, J=4.58 Hz, 1H), 4.75 (s, 1H), 4.60 (s, 1H), 4.44 (dd, J=14.34, 5.80 Hz, 1H), 4.30 (dd, J=14.34, 5.49 Hz, 1H), 3.80 (s, 3H), 3.20 (td, J=10.99, 4.27 Hz, 1H), 2.59-2.51 (m, 1H), 2.11 (dd, J=17.24, 6.26 Hz, 1H), 2.04-1.94 (m, 1H), 1.90 (d, J=13.12 Hz, 1H), 1.78-1.72 (m, 2H), 1.69 (s, 3H), 0.99 (s, 3H), 1.71-0.95 (m, 16H), 0.98 (s, 6H), 0.94 (s, 3H), 0.92 (s, 3H).

Example 16

Preparation of 4-((1R,3aS,5aR,5bR,7aR,11aS,11bR,13aR,13bR)-3a-(2-(dimethylamino)ethylcarbamoyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

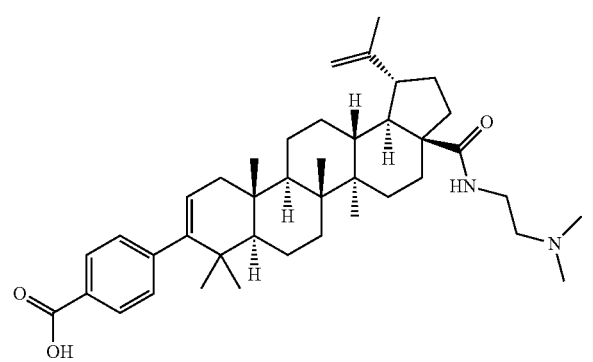

The title compound was prepared following the method described above for the general procedure for C-28 amide formation and hydrolysis using N,N-dimethylethylenediamine as the reactant amine. The product was isolated as a white solid (200 mg, 66%). LCMS: m/e 627.6 (M−H)⁻, 2.20 min (method 1). $^1$H NMR (400 MHz, CHLOROFORM-d) δ ppm 12.52 (br. s., 1H), 8.00 (d, J=8.03 Hz, 2H), 7.40 (t, J=4.64 Hz, 1H), 7.23 (d, J=8.28 Hz, 2H), 5.31 (d, J=4.52 Hz, 1H), 4.75 (d, J=1.51 Hz, 1H), 4.61 (s, 1H), 3.79-3.61 (m, 2H), 3.30-3.20 (m, 2H), 3.12 (td, J=10.79, 4.02 Hz, 1H), 2.88 (s, 6H), 2.51-2.42 (m, 1H), 2.16-2.03 (m, 2H), 1.00 (s, 3H), 1.70 (s, 3H), 0.99 (s, 3H), 1.95-0.95 (m, 19H), 0.98 (s, 3H), 0.94 (s, 6H).

Example 17

Preparation of 4-((1R,3aS,5aR,5bR,7aR,11aS,11bR,13aR,13bR)-3a-(2-hydroxyethylcarbamoyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

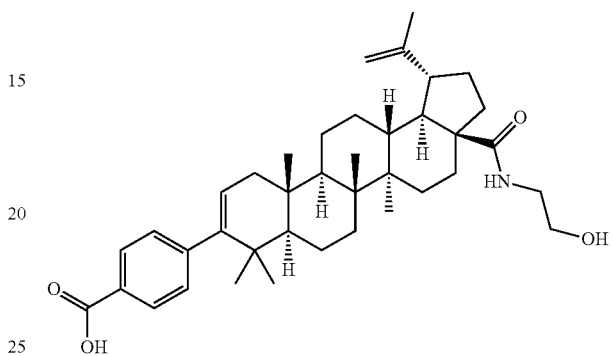

The title compound was prepared following the general procedures described above for the C-28 amide formation and hydrolysis using ethanolamine as the reactant amine. The product was isolated as a white solid (12 mg, 16%). LCMS: m/e 600.6 (M−H)⁻, 2.06 min (method 1). $^1$H NMR (500 MHz, CHLOROFORM-d) δ ppm 7.99 (d, J=8.24 Hz, 2H), 7.22 (d, J=8.24 Hz, 2H), 6.07 (t, J=5.65 Hz, 1H), 5.33-5.25 (m, 1H), 4.75 (s, 1H), 4.60 (s, 1H), 3.74 (t, J=4.88 Hz, 2H), 3.55-3.46 (m, 1H), 3.43-3.35 (m, 1H), 3.12 (td, J=10.99, 3.97 Hz, 1H), 2.52-2.45 (m, 1H), 2.10 (dd, J=17.24, 6.26 Hz, 1H), 2.03-1.92 (m, 2H), 1.69 (s, 3H), 1.00 (s, 6H), 1.82-0.95 (m, 18H), 0.97 (s, 3H), 0.92 (s, 6H).

Example 18

Preparation of 4-((1R,3aS,5aR,5bR,7aR,11aS,11bR,13aR,13bR)-3a-(benzyl(methyl)carbamoyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

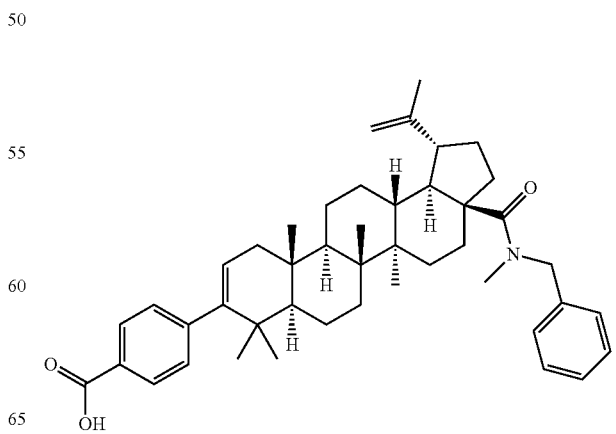

The title compound was prepared following the general procedures described above for the C-28 amide formation and hydrolysis using N-methylbenzylamine as the reactant amine. The product was isolated as a white film (15 mg, 18%). LCMS: m/e 660.6 (M–H)⁻, 2.28 min (method 1). ¹H NMR (500 MHz, CHLOROFORM-d) δ ppm 7.99 (d, J=8.55 Hz, 2H). 7.33 (t, J=7.32 Hz, 2H), 7.29-7.20 (m, 5H), 5.32-5.28 (m, 1H), 4.76 (d, J=2.14 Hz, 1H), 4.72 (d, J=14.34 Hz, 1H), 4.60 (s, 1H), 4.47 (br. s., 1H), 3.09 (td, J=11.06, 3.51 Hz, 1H), 3.05-2.88 (m, 3H), 2.32-2.18 (m, 1H), 2.16-2.03 (m, 2H), 1.71 (s, 3H), 1.04 (s, 3H), 0.99 (s, 6H), 1.82-0.95 (m, 19H), 0.94 (s, 3H), 0.93 (s, 3H).

Example 19

Preparation of 4-((1R,3aS,5aR,5bR,7aR,11aS,11bR, 13aR,13bR)-5a,5b,8,8,11a-pentamethyl-3a-(piperidine-1-carbonyl)-1-(prop-1-en-2-yl)-2,3,3a,4,5,5a, 5b,6,7,7a,8,11,11a,11b,12,13,13a,13b-octadecahydro-1H-cyclopenta[a]chrysen-9-yl) benzoic acid

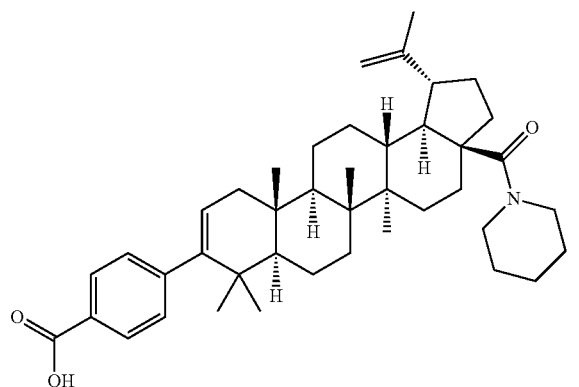

The title compound was prepared following the general procedures described above for the C-28 amide formation and hydrolysis using piperidine as the reactant amine. The product was isolated as a white solid (23 mg, 29%). ¹H NMR (400 MHz, CHLOROFORM-d) δ ppm 7.99 (d, J=8.03 Hz, 2H), 7.24 (d, J=8.03 Hz, 2H), 5.32 (d, J=3.01 Hz, 1H), 4.75 (s, 1H), 4.60 (s, 1H), 3.66-3.46 (m, 4H), 3.09-2.93 (m, 2H), 1.71 (s, 3H), 2.20-0.95 (m, 27H), 1.03 (s, 3H), 1.01 (s, 3H), 0.99 (s, 3H), 0.95 (s, 3H), 0.94 (s, 3H).

Example 20

Preparation of methyl 4-((1R,3aS,5aR,5bR,7aR, 11aS,11bR,13aR,13bR)-5a,5b,8,8,11a-pentamethyl-1-(prop-1-en-2-yl)-3a-(2-(pyridin-2-yl)ethylcarbamoyl)-2,3,3a,4,5,5a,5b,6,7,7a,8,11,11a,11b,12,13,13a, 13b-octadecahydro-1H-cyclopenta[a]chrysen-9-yl) benzoate The title compound was prepared following the general procedures described above for the C-28 amide formation using 2-(2-aminoethyl)pyridine as the reactant amine. The product was isolated as a white solid (44 mg, 25%). LCMS: m/e 677.63 (M+H)⁺, 2.71 min (method 1). ¹H NMR (500 MHz, CHLOROFORM-d) δ ppm 8.52 (d, J=3.97 Hz, 1H), 7.91 (d, J=8.24 Hz, 2H), 7.62 (td, J=7.63, 1.83 Hz, 1H), 7.21-7.12 (m, 5H), 6.73 (t, J=5.34 Hz, 1H), 5.26 (dd, J=6.26, 1.68 Hz, 1H), 4.73 (d, J=1.83 Hz, 1H), 4.58 (s, 1H), 3.89 (s, 3H), 3.67 (q, J=6.00 Hz, 2H), 3.10 (td, J=11.14, 3.97 Hz, 1H), 3.03-2.97 (m, 2H), 2.41 (td, J=12.21, 3.36 Hz, 1H), 2.07 (dd, J=17.40, 6.41 Hz, 1H), 2.00-1.94 (m, 1H), 1.94-1.84 (m, 1H), 1.67 (s, 3H), 0.95 (s, 3H), 1.74-0.92 (m, 17H), 0.92 (s, 3H), 0.89 (s, 6H), 0.88 (s, 3H).

Example 21

Preparation of methyl 4-((1R,3aS,5aR,5bR,7aR, 11aS,11bR,13aR,13bR)-3a-(4-hydroxypiperidine-1-carbonyl)-5a,5b,8,8,11a-pentamethyl-1-(prop-1-en-2-yl)-2,3,3a,4,5,5a,5b,6,7,7a,8,11,11a,11b,12,13,13a, 13b-octadecahydro-1H-cyclopenta[a]chrysen-9-yl) benzoate

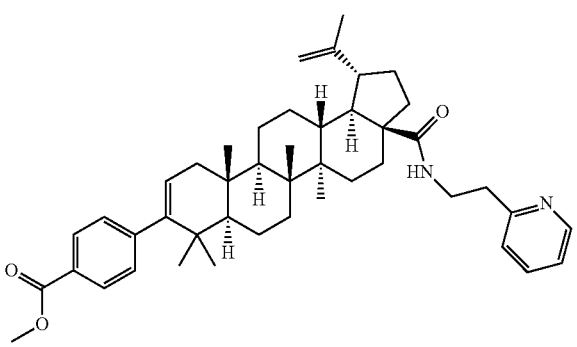

The title compound was prepared following the general procedures described above for the C-28 amide formation and hydrolysis using 4-hydroxypiperidine as the reactant amine. LCMS: m/e 656.6 (M+H)⁺, 3.10 min (method 2). ¹H NMR (500 MHz, CHLOROFORM-d) δ ppm 7.92 (d, J=8.55 Hz, 2H), 7.19 (d, J=8.55 Hz, 2H), 5.28 (dd, J=6.26, 1.68 Hz, 1H), 4.73 (d, J=2.14 Hz, 1H), 4.58 (s, 1H), 3.90 (s, 3H), 4.19-3.88 (m, 2H), 3.22-3.01 (m, 2H), 3.01 (td, J=10.99, 3.36 Hz, 1H), 2.97-2.90 (m, 1H), 2.15-2.06 (m, 2H), 1.69 (s, 3H), 2.01-0.95 (m, 25H), 0.99 (s, 3H), 0.99 (s, 3H), 0.97 (s, 3H), 0.92 (s, 3H), 0.91 (s, 3H).

Example 22

Preparation of 4-((1R,3aS,5aR,5bR,7aR,11aS,11bR,13aR,13bR)-3a-(4-hydroxypiperidine-1-carbonyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

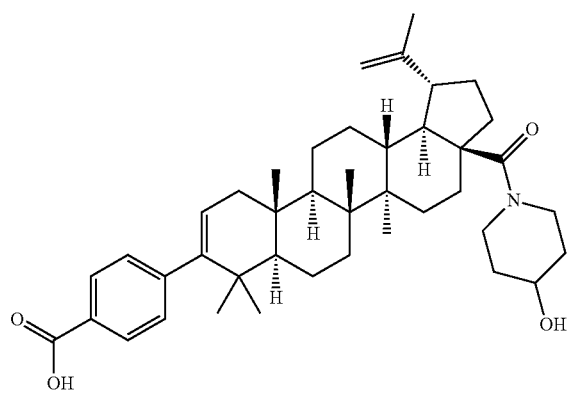

The title compound was prepared following the general procedures described above for the C-28 amide formation and hydrolysis using 4-hydroxypiperidine as the reactant amine. The product was isolated as a white solid (7.7 mg, 9.4%). LCMS: m/e 642.6 (M+H)$^+$, 2.46 min (method 2). $^1$H NMR (400 MHz, CHLOROFORM-d) δ ppm 8.00 (d, J=8.28 Hz, 2H), 7.24 (d, J=8.28 Hz, 2H), 5.32 (d, J=4.77 Hz, 1H), 4.75 (d, J=1.51 Hz, 1H), 4.60 (s, 1H), 4.21-3.89 (m, 3H), 3.25-2.90 (m, 4H), 1.71 (s, 3H), 2.17-0.95 (m, 26H), 1.02 (s, 3H), 1.01 (s, 3H), 1.00 (s, 3H), 0.95 (s, 3H), 0.95 (s, 3H).

Example 23

Preparation of 4-((1R,3aS,5aR,5bR,7aR,11aS,11bR,13aR,13bR)-3a-((2-hydroxyethyl)(methyl)carbamoyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

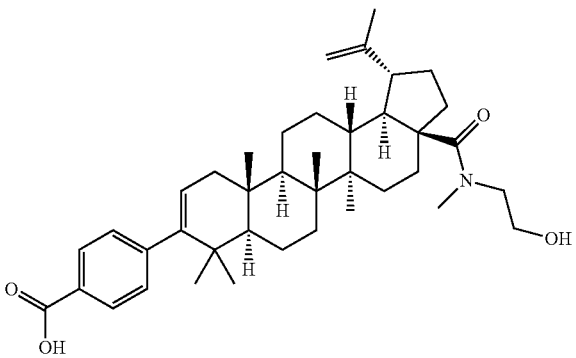

The title compound was prepared following the general procedures described above for the C-28 amide formation and hydrolysis using 2-methylaminoethanol as the reactant amine. The product was isolated as a white film (6.1 mg, 7.8%). LCMS: m/e 616.6 (M+H)$^+$, 2.50 min (method 2). $^1$H NMR (500 MHz, CHLOROFORM-d) δ ppm 7.98 (d, J=7.63 Hz, 2H), 7.21 (d, J=7.93 Hz, 2H), 5.31-5.27 (m, 1H), 4.73 (s, 1H), 4.59 (s, 1H), 3.81 (t, J=4.73 Hz, 2H), 3.58-3.53 (m, 2H), 3.15 (s, 3H), 3.01-2.93 (m, 1H), 2.88 (t, J=10.83 Hz, 1H), 2.29 (d, J=13.43 Hz, 1H), 2.16-2.03 (m, 3H), 1.94-1.81 (m, 1H), 1.69 (s, 3H), 1.78-0.95 (m, 16H), 1.00 (s, 6H), 0.97 (s, 3H), 0.92 (s, 6H).

Example 24

Preparation of 4-((1R,3aS,5aR,5bR,7aR,11aS,11bR,13aR,13bR)-5a,5b,8,8,11a-pentamethyl-3a-(methyl(2-(pyridin-2-yl)ethyl)carbamoyl)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

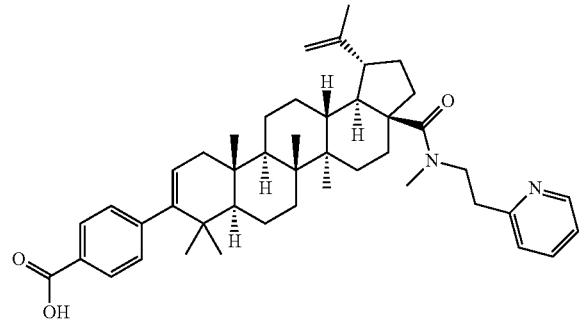

The title compound was prepared following the general procedures described above for the C-28 amide formation and hydrolysis using 2-(2-methylaminoethyl)pyridine as the reactant amine. The product was isolated as a white solid (22 mg, 25%). LCMS: m/e 675.7 (M−H)$^−$, 2.23 min (method 1). $^1$H NMR (500 MHz, DMSO-d$_6$) δ ppm 8.49 (d, J=4.58 Hz, 1H), 7.83 (d, J=8.24 Hz, 2H), 7.71 (td, J=7.63, 1.53 Hz, 1H), 7.27 (d, J=7.93 Hz, 1H), 7.22 (dd, J=7.02, 5.19 Hz, 1H), 7.15 (d, J=7.93 Hz, 2H), 5.23 (d, J=4.88 Hz, 1H), 4.67 (s, 1H), 4.55 (s, 1H), 3.69-3.60 (m, 1H), 3.02-2.84 (m, 7H), 2.19 (d, J=12.82 Hz, 1H), 2.07 (dd, J=17.55, 6.56 Hz, 1H), 2.01-1.93 (m, 1H), 1.65 (s, 3H), 1.72-0.95 (m, 19H), 0.95 (s, 6H), 0.92 (s, 3H), 0.88 (s, 6H).

Example 25

Preparation of 4-((1R,3aS,5aR,5bR,7aR,11aS,11bR,13aR,13bR)-3a-(2-carboxyethylcarbamoyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

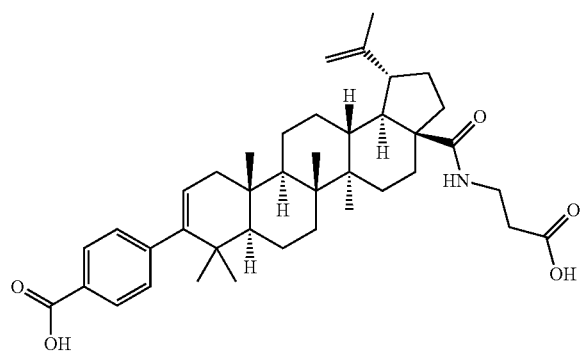

The title compound was prepared following the general procedures described above for the C-28 amide formation and hydrolysis using beta-alanine, ethyl ester hydrochloride as the reactant amine. The product was isolated as a white solid (102 mg, 73%). LCMS: m/e 628.6 (M−H)−, 1.96 min (method 1). $^1$H NMR (500 MHz, CHLOROFORM-d) δ ppm 7.97 (d, J=8.24 Hz, 2H), 7.20 (d, J=8.24 Hz, 2H), 6.27 (t, J=6.10 Hz, 1H), 5.24 (d, J=4.58 Hz, 1H), 4.75 (d, J=1.53 Hz, 1H), 4.60 (s, 1H), 3.63-3.47 (m, 2H), 3.08 (td, 1H), 2.71-2.59 (m, 2H), 2.39 (td, J=12.21, 3.36 Hz, 1H), 2.06-1.90 (m, 3H), 1.69 (s, 3H), 0.98 (s, 3H), 1.79-0.95 (m, 18H), 0.95 (s, 3H), 0.88 (br. s., 9H).

Example 26

Preparation of 4-((1R,3aS,5aR,5bR,7aR,11aS,11bR, 13aR,13bR)-5a,5b,8,8,11a-pentamethyl-3a-(methylcarbamoyl)-1-(prop-1-en-2-yl)-2,3,3a,4,5,5a,5b,6,7, 7a,8,11,11a,11b,12,13,13a,13b-octadecahydro-1H-cyclopenta[a]chrysen-9-yl)benzoic acid

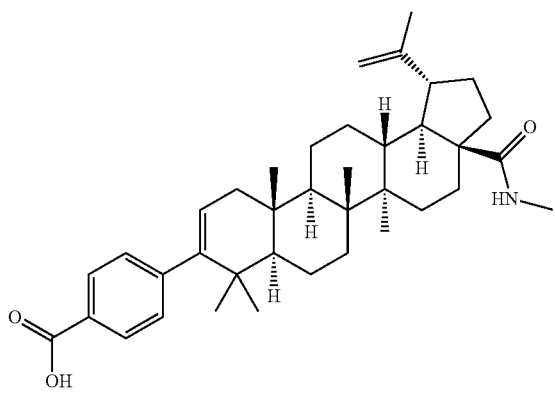

The title compound was prepared following the general procedures described above for the C-28 amide formation and hydrolysis using methylamine (2M in THF, 10 equiv. used) as the reactant amine. The product was isolated as a white solid (92 mg, 77%). LCMS: m/e 570.6 (M−H)−, 2.22 min (method 3). $^1$H NMR (500 MHz, DMSO-d$_6$) δ ppm 12.88 (br. s., 1H), 7.86 (d, J=8.24 Hz, 2H), 7.49 (q, J=4.27 Hz, 1H), 7.21 (d, J=8.24 Hz, 2H), 5.24 (d, J=4.58 Hz, 1H), 4.67 (d, J=2.14 Hz, 1H), 4.55 (s, 1H), 3.04 (td, J=10.76, 4.43 Hz, 1H), 2.66-2.59 (m, 1H), 2.56 (d, J=4.58 Hz, 3H), 2.13-2.04 (m, 2H), 1.64 (s, 3H), 0.95 (s, 3H), 0.94 (s, 3H), 1.80-0.93 (m, 19H), 0.91 (s, 3H), 0.88 (s, 6H).

Example 27

Preparation of 4-((1R,3aS,5aR,5bR,7aR,11aS,11bR, 13aR,13bR)-3a-(3-(dimethylamino)propylcarbamoyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl) benzoic acid

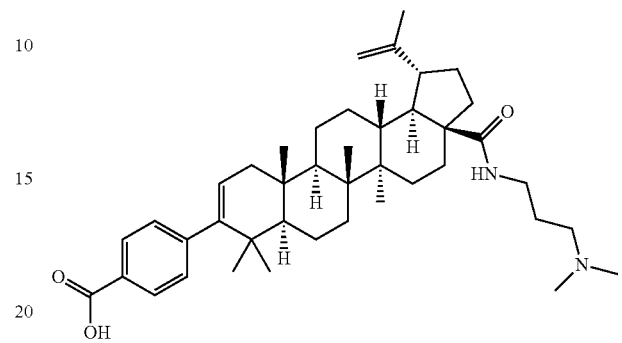

The title compound was prepared following the general procedures described above for the C-28 amide formation and hydrolysis using 3-(Dimethylamino)propylamine as the reactant amine. The product was isolated as a white solid (65 mg, 51%). LCMS: m/e 641.7 (M−H)−, 2.22 min (method 3). $^1$H NMR (500 MHz, DMSO-d$_6$) δ ppm 7.86 (d, J=8.24 Hz, 2H), 7.80 (t, J=5.80 Hz, 1H), 7.21 (d, J=7.93 Hz, 2H), 5.24 (d, J=4.88 Hz, 1H), 4.67 (d, J=1.83 Hz, 1H), 4.56 (s, 1H), 3.14-3.07 (m, 2H), 3.03 (td, J=10.76, 4.43 Hz, 1H), 2.95 (t, J=7.48 Hz, 2H), 2.72 (s, 6H), 2.66-2.57 (m, 1H), 2.13 (d, J=13.12 Hz, 1H), 2.07 (dd, J=17.55, 6.56 Hz, 1H), 1.65 (s, 3H), 1.83-0.95 (m, 21H), 0.96 (s, 3H), 0.94 (s, 3H), 0.92 (s, 3H), 0.88 (s, 6H).

Example 28

Preparation of 4-((1R,3aS,5aR,5bR,7aR,11aS,11bR, 13aR,13bR)-5a,5b,8,8,11a-pentamethyl-1-(prop-1-en-2-yl)-3a-(pyridin-4-ylmethylcarbamoyl)-2,3,3a,4, 5,5a,5b,6,7,7a,8,11,11a,11b,12,13,13a,13b-octadecahydro-1H-cyclopenta[a]chrysen-9-yl) benzoic acid

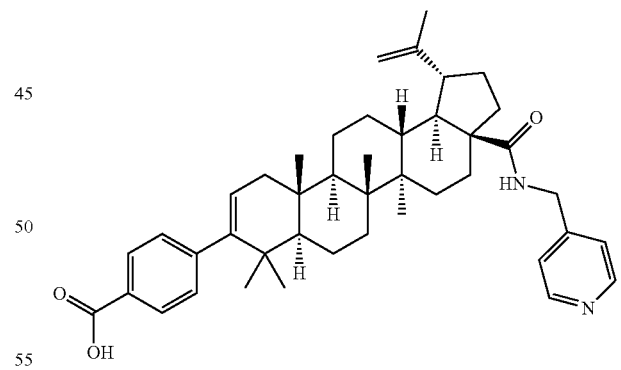

The title compound was prepared following the general procedures described above for the C-28 amide formation and hydrolysis using 4-picolylamine as the reactant amine. The product was isolated as a white solid (14 mg, 11%). LCMS: m/e 647.7 (M−H)−, 2.21 min (method 3). $^1$H NMR (500 MHz, DMSO-d$_6$) δ ppm 8.49 (d, J=5.80 Hz, 2H), 8.30 (t, J=5.95 Hz, 1H), 7.84 (d, J=8.24 Hz, 2H), 7.23 (d, J=5.80 Hz, 2H), 7.17 (d, J=7.93 Hz, 2H), 5.23 (d, J=4.58 Hz, 1H), 4.66 (d, J=1.83 Hz, 1H), 4.55 (s, 1H), 4.31-4.25 (m, 1H), 4.23-4.18 (m, 1H), 3.01 (td, J=10.99, 4.58 Hz, 1H), 2.60-2.53 (m, 1H), 2.22 (d, J=13.73 Hz, 1H), 2.06 (dd, J=17.24, 6.26 Hz, 1H), 1.87 (dd, J=12.05, 7.78 Hz, 1H), 1.65 (s, 3H), 1.77-0.95 (m, 18H), 0.96 (s, 3H), 0.93 (s, 3H), 0.88 (s, 6H), 0.83 (s, 3H).

Example 29

Preparation of 4-((1R,3aS,5aR,5bR,7aR,11aS,11bR, 13aR,13bR)-5a,5b,8,8,11a-pentamethyl-1-(prop-1-en-2-yl)-3a-(pyridin-3-ylmethylcarbamoyl)-2,3,3a,4, 5,5a,5b,6,7,7a,8,11,11a,11b,12,13,13a,13b-octadecahydro-1H-cyclopenta[a]chrysen-9-yl) benzoic acid

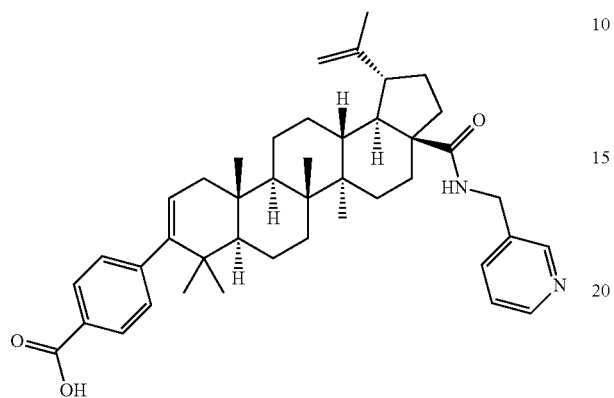

The title compound was prepared following the general procedures described above for the C-28 amide formation and hydrolysis using 3-(aminomethyl)pyridine as the reactant amine. The product was isolated as an off-white solid (25 mg, 18%). LCMS: m/e 647.6 (M−H)−, 2.21 min (method 3). $^1$H NMR (500 MHz, DMSO-d$_6$) δ ppm 8.48 (d, J=1.83 Hz, 1H), 8.43 (dd, J=4.58, 1.53 Hz, 1H), 8.26 (t, J=5.95 Hz, 1H), 7.84 (d, J=8.24 Hz, 2H), 7.64 (d, J=7.93 Hz, 1H), 7.34 (dd, J=7.78, 4.73 Hz, 1H), 7.18 (d, J=8.24 Hz, 2H), 5.23 (d, J=4.58 Hz, 1H), 4.67 (d, J=1.83 Hz, 1H), 4.55 (s, 1H), 4.31 (dd, J=15.11, 5.95 Hz, 1H), 4.18 (dd, J=14.95, 5.80 Hz, 1H), 3.03 (td, J=10.91, 4.12 Hz, 1H), 2.60-2.53 (m, 1H), 2.18 (d, J=13.43 Hz, 1H), 2.06 (dd, J=17.24, 6.56 Hz, 1H), 1.81 (dd, J=11.90, 7.63 Hz, 1H), 1.64 (s, 3H), 1.74-0.95 (m, 18H), 0.95 (s, 3H), 0.93 (s, 3H), 0.88 (s, 6H), 0.79 (s, 3H).

Example 30

Preparation of 4-((1R,3aS,5aR,5bR,7aR,11aS,11bR, 13aR,13bR)-3a-(2-acetamidoethylcarbamoyl)-5a,5b, 8,8,11a-pentamethyl-1-(prop-1-en-2-yl)-2,3,3a,4,5, 5a,5b,6,7,7a,8,11,11a,11b,12,13,13a,13b-octadecahydro-1H-cyclopenta[a]chrysen-9-yl) benzoic acid

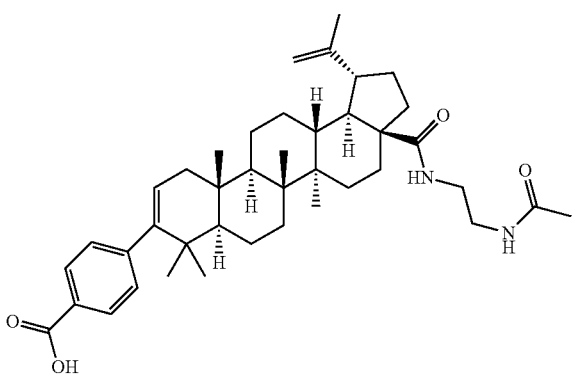

The title compound was prepared following the general procedures described above for the C-28 amide formation and hydrolysis using N-acetylethylene diamine as the reactant amine. The product was isolated as a white solid (43 mg, 34%). LCMS: m/e 641.7 (M−H)−, 2.19 min (method 3). $^1$H NMR (500 MHz, CHLOROFORM-d) δ ppm 7.84 (d, J=8.24 Hz, 2H), 7.60 (br. s., 1H), 7.19 (d, J=8.24 Hz, 2H), 5.23 (d, J=5.19 Hz, 1H), 4.66 (s, 1H), 4.54 (s, 1H), 3.16-2.97 (m, 5H), 2.65-2.55 (m, 1H), 2.13-2.03 (m, 2H), 1.79 (s, 3H), 1.64 (s, 3H), 1.82-0.95 (m, 19H), 0.95 (s, 3H), 0.94 (s, 3H), 0.91 (s, 3H), 0.88 (s, 6H).

Example 31

Preparation of 4-((1R,3aS,5aR,5bR,7aR,11aS,11bR, 13aR,13bR)-3a-((2-(dimethylamino)ethyl)(methyl) carbamoyl)-5a,5b,8,8,11a-pentamethyl-1-(prop-1-en-2-yl)-2,3,3a,4,5,5a,5b,6,7,7a,8,11,11a,11b,12,13,13a, 13b-octadecahydro-1H-cyclopenta[a]chrysen-9-yl) benzoic acid

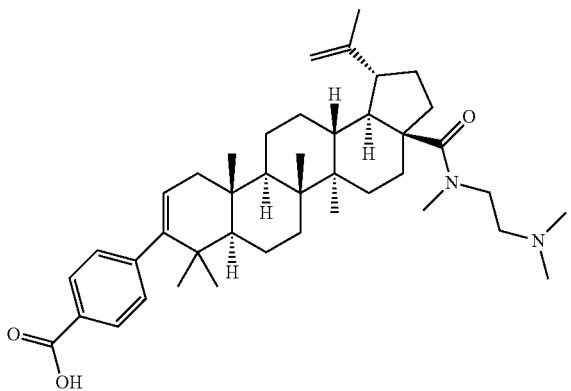

The title compound was prepared following the general procedures described above for the C-28 amide formation and hydrolysis using N,N,N'-trimethylethylenediamine as the reactant amine. The product was isolated as a white solid (58 mg, 48%). LCMS: m/e 641.7 (M−H)−, 2.31 min (method 3). $^1$H NMR (500 MHz, DMSO-d$_6$) δ ppm 7.86 (d, J=8.24 Hz, 2H), 7.22 (d, J=8.55 Hz, 2H), 5.24 (d, J=4.58 Hz, 1H), 4.67 (d, J=1.83 Hz, 1H), 4.56 (s, 1H), 3.68-3.45 (m, 2H), 2.94-2.81 (m, 2H), 3.08 (br. s., 5H), 2.73 (br. s., 6H), 2.23 (br. s., 1H), 2.13-1.98 (m, 2H), 1.66 (s, 3H), 1.73-0.95 (m, 18H), 0.97 (s, 3H), 0.95 (s, 3H), 0.93 (s, 3H), 0.88 (s, 6H).

Example 32

Preparation of 4-((1R,3aS,5aR,5bR,7aR,11aS,11bR, 13aR,13bR)-5a,5b,8,8,11a-pentamethyl-3a-(3-morpholinopropylcarbamoyl)-1-(prop-1-en-2-yl)-2,3,3a, 4,5,5a,5b,6,7,7a,8,11,11a,11b,12,13,13a,13b-octadecahydro-1H-cyclopenta[a]chrysen-9-yl) benzoic acid

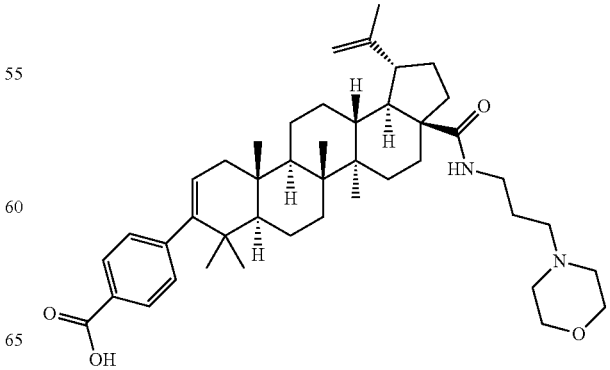

The title compound was prepared following the general procedures described above for the C-28 amide formation and hydrolysis using N-(3-aminopropyl)morpholine as the reactant amine. The product was isolated as a white solid (94 mg, 93%). LCMS: m/e 683.8 (M−H)⁻, 2.25 min (method 3). $^1$H NMR (500 MHz, DMSO-$d_6$) δ ppm 12.86 (br. s., 1H). 7.86 (d, J=8.24 Hz, 2H), 7.79 (br. s., 1H), 7.22 (d, J=8.24 Hz, 2H), 5.24 (d, J=4.58 Hz, 1H), 4.67 (d, J=1.83 Hz, 1H), 4.55 (s, 1H), 4.05-3.92 (m, 2H), 3.78-3.67 (m, 2H), 3.62 (br. s., 1H), 3.17-2.95 (m, 6H), 2.68-2.58 (m, 1H), 2.31 (br. s., 1H), 2.19-2.02 (m, 2H), 1.65 (s, 3H), 0.96 (s, 3H), 0.95 (s, 3H), 1.86-0.95 (m, 22H), 0.92 (s, 3H), 0.89 (s, 6H).

Example 33

Preparation of 4-((1R,3aS,5aR,5bR,7aR,11aS,11bR, 13aR,13bR)-5a,5b,8,8,11a-pentamethyl-3a-(2-(piperidin-1-yl)ethylcarbamoyl)-1-(prop-1-en-2-yl)-2,3, 3a,4,5,5a,5b,6,7,7a,8,11,11a,11b,12,13,13a,13b-octadecahydro-1H-cyclopenta[a]chrysen-9-yl) benzoic acid

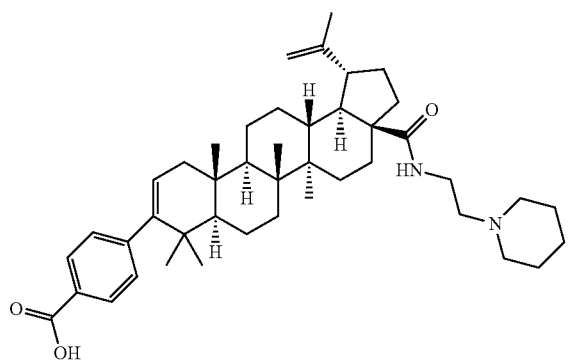

The title compound was prepared following the general procedures described above for the C-28 amide formation and hydrolysis using N-(2-aminoethyl)piperidine as the reactant amine. The product was isolated as a white solid (100 mg, 75%). LCMS: m/e 667.7 (M−H)⁻, 2.29 min (method 3). $^1$H NMR (500 MHz, Pyr) δ ppm 8.47 (d, J=8.24 Hz, 2H), 7.81 (br. s., 1H), 7.41 (d, J=8.24 Hz, 2H), 5.40 (d, J=4.58 Hz, 1H), 4.98 (d, J=2.44 Hz, 1H), 4.81 (br. s., 1H), 3.73-3.56 (m, 3H), 3.13-3.05 (m, 1H), 2.58 (t, J=6.26 Hz, 2H), 2.48-2.35 (m, 4H), 2.25 (t, J=8.39 Hz, 1H), 2.17-2.06 (m, 2H), 2.03-1.95 (m, 1H), 1.82 (s, 3H), 1.20 (s, 3H), 1.85-0.95 (m, 23H), 1.10 (s, 3H), 1.02 (s, 3H), 1.00 (s, 3H), 0.99 (s, 3H).

Example 34

Preparation of 4-((1R,3aS,5aR,5bR,7aR,11aS,11bR, 13aR,13bR)-3a-(2-amino-2-oxoethylcarbamoyl)-5a, 5b,8,8,11a-pentamethyl-1-(prop-1-en-2-yl)-2,3,3a,4, 5,5a,5b,6,7,7a,8,11,11a,11b,12,13,13a,13b-octadecahydro-1H-cyclopenta[a]chrysen-9-yl) benzoic acid

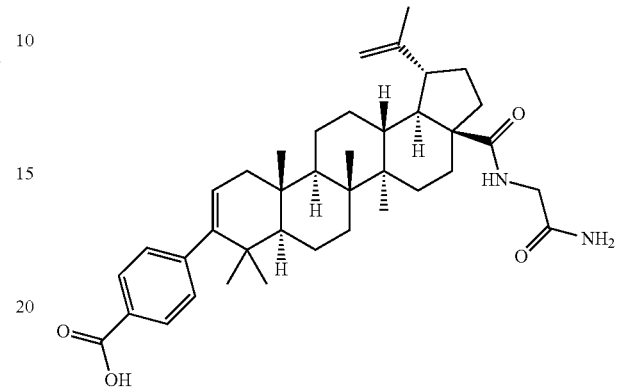

The title compound was prepared following the general procedures described above for the C-28 amide formation and hydrolysis using glycinamide hydrochloride as the reactant amine. The product was isolated as a white solid (29 mg, 33%). LCMS: m/e 613.6 (M−H)⁻, 2.16 min (method 3). $^1$H NMR (500 MHz, CHLOROFORM-d) δ ppm 7.97 (d, J=8.24 Hz, 2H), 7.21 (d, J=8.24 Hz, 2H), 6.31 (t, J=5.34 Hz, 1H), 6.11 (br. s., 1H), 5.64 (br. s., 1H), 5.31-5.27 (m, 1H), 4.75 (d, J=1.83 Hz, 1H), 4.61 (s, 1H), 4.00 (dd, J=16.17, 5.19 Hz, 1H), 3.89 (dd, J=16.17, 5.19 Hz, 1H), 3.11 (td, J=11.06, 4.73 Hz, 1H), 2.46 (td, J=12.13, 3.51 Hz, 1H), 2.10 (dd, J=17.24, 6.56 Hz, 1H), 2.04-1.87 (m, 2H), 1.81 (dd, J=12.05, 7.78 Hz, 1H), 1.69 (s, 3H), 1.00 (s, 3H), 1.76-0.95 (m, 17H), 0.97 (s, 3H), 0.95 (s, 3H), 0.92 (s, 3H), 0.91 (s, 3H).

Example 35

Preparation of 4-((1R,3aS,5aR,5bR,7aR,11aS,11bR, 13aR,13bR)-3a-(2-(dimethylamino)-2-(pyridin-3-yl) ethylcarbamoyl)-5a,5b,8,8,11a-pentamethyl-1-(prop-1-en-2-yl)-2,3,3a,4,5,5a,5b,6,7,7a,8,11,11a,11b,12, 13,13a,13b-octadecahydro-1H-cyclopenta[a] chrysen-9-yl)benzoic acid

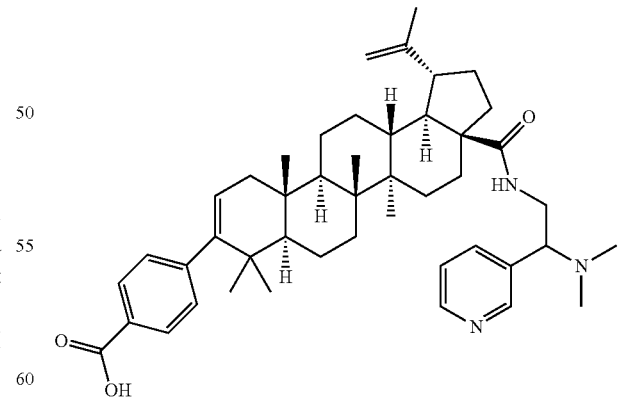

The title compound was prepared following the general procedures described above for the C-28 amide formation and hydrolysis using (2-Amino-1-(3-pyridyl)ethyl)dimethylamine as the reactant amine. The product was isolated as a white solid (80 mg, 78%). LCMS: m/e 704.7 (M−H)⁻, 2.23 min (method 3).

Example 36

Preparation of 4-((1R,3aS,5aR,5bR,7aR,11aS,11bR, 13aR,13bR)-5a,5b,8,8,11a-pentamethyl-3a-(2-(4-methylpiperazin-1-yl)ethylcarbamoyl)-1-(prop-1-en-2-yl)-2,3,3a,4,5,5a,5b,6,7,7a,8,11,11a,11b,12,13,13a, 13b-octadecahydro-1H-cyclopenta[a]chrysen-9-yl) benzoic acid

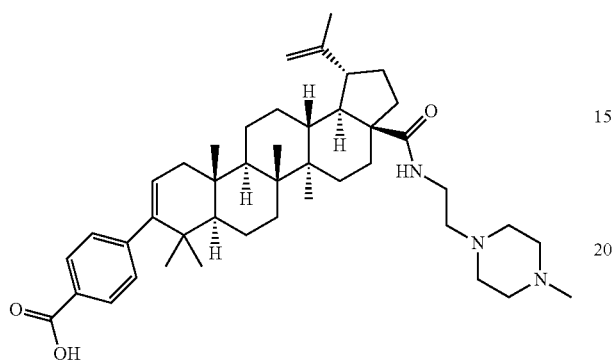

The title compound was prepared following the general procedures described above for the C-28 amide formation and hydrolysis using 2-(4-methyl-piperazin-1-yl)-ethylamine as the reactant amine. The product was isolated as a white solid (56 mg, 56%). LCMS: m/e 682.7 (M−H)⁻, 2.25 min (method 3). $^1$H NMR (500 MHz, DMSO-d$_6$) δ ppm 7.88 (br. s., 1H), 7.86 (d, J=8.24 Hz, 2H), 7.22 (d, J=7.93 Hz, 2H), 5.24 (d, J=4.88 Hz, 1H), 4.68 (d, J=1.53 Hz, 1H), 4.56 (s, 1H), 4.02-2.32 (m, 17H), 2.15 (d, J=12.51 Hz, 1H), 2.08 (dd, J=17.09, 6.10 Hz, 1H), 1.65 (s, 3H), 0.96 (s, 3H), 0.95 (s, 3H), 1.88-0.94 (m, 19H), 0.92 (s, 3H), 0.89 (s, 6H).

Example 37

Preparation of 4-((1R,3aS,5aR,5bR,7aR,11aS,11bR, 13aR,13bR)-3a-(2-(4-(tert-butoxycarbonyl)piperazin-1-yl)ethylcarbamoyl)-5a,5b,8,8,11a-pentamethyl-1-(prop-1-en-2-yl)-2,3,3a,4,5,5a,5b,6,7,7a,8, 11,11a,11b,12,13,13a,13b-octadecahydro-1H-cyclopenta[a]chrysen-9-yl)benzoic acid

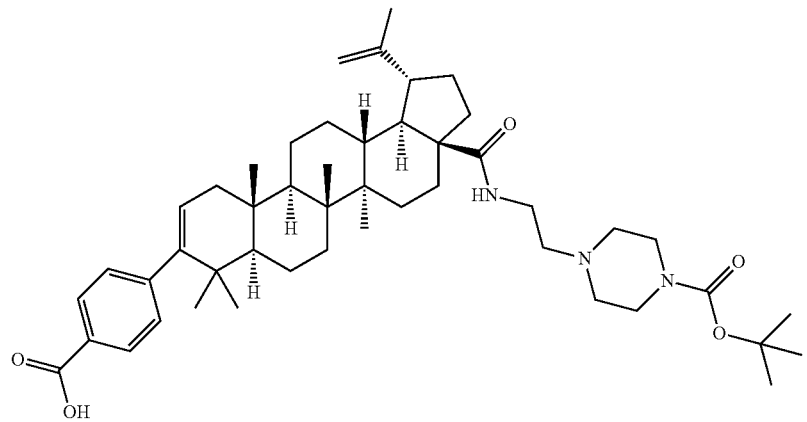

The title compound was prepared following the general procedures described above for the C-28 amide formation and hydrolysis using 4-N-(2-aminoethyl)-1-N-Boc-piperazine as the reactant amine. The product was isolated as a white solid (69 mg, 56%). LCMS: m/e 768.8 (M−H)⁻, 2.32 min (method 3). $^1$H NMR (500 MHz, DMSO-d$_6$) δ ppm 12.86 (br. s., 1H), 7.96 (br. s., 1H), 7.86 (d, J=8.24 Hz, 2H), 7.22 (d, J=8.24 Hz, 2H), 5.24 (d, J=4.58 Hz, 1H), 4.67 (s, 1H), 4.56 (s, 1H), 4.00 (br. s., 2H), 3.53-3.40 (m, 4H), 3.32-2.96 (m, 6H), 2.67-2.53 (m, 1H), 2.18-2.03 (m, 2H), 1.65 (s, 3H), 1.42 (s, 9H), 0.96 (s, 3H), 1.84-0.95 (m, 20H), 0.95 (s, 3H), 0.92 (s, 3H), 0.88 (s, 6H).

Example 38

Preparation of 4-((1R,3aS,5aR,5bR,7aR,11aS,11bR, 13aR,13bR)-3a-(2-amino-2-methylpropylcarbamoyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl) benzoic acid

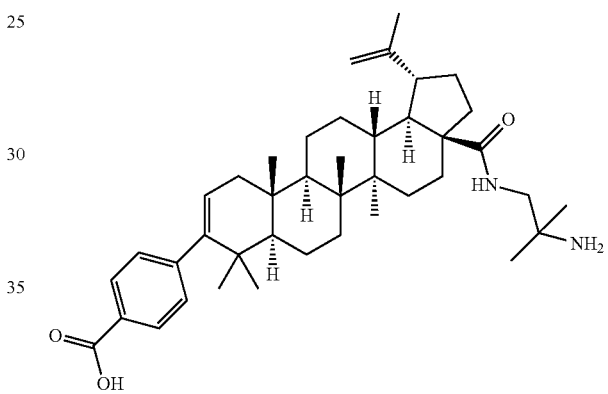

The title compound was prepared following the general procedures described above for the C-28 amide formation and hydrolysis using 1,2-diamino-2-methylpropane as the reactant amine. The product was isolated as a white solid (66 mg, 68%). LCMS: m/e 627.7 (M−H)⁻, 2.19 min (method 3). $^1$H NMR (500 MHz, Acetic Acid-d$_4$) δ ppm 8.03 (d, J=8.24 Hz, 2H), 7.76 (t, J=6.41 Hz, 1H), 7.30 (d, J=8.24 Hz, 2H), 5.37 (d, J=4.58 Hz, 1H), 4.78 (d, J=1.83 Hz, 1H), 4.65 (s, 1H), 3.66 (dd, J=14.95, 6.10 Hz, 1H), 3.58 (dd, J=14.65, 5.49 Hz, 1H), 3.15 (td, J=10.91, 4.12 Hz, 1H), 2.63 (td, J=12.36, 3.36 Hz, 1H), 2.29 (d, J=13.73 Hz, 1H), 1.74 (s, 3H), 1.44 (s, 3H), 1.42 (s, 3H), 1.09 (s, 3H), 2.23-0.95 (m, 20H), 1.07 (s, 3H), 1.05 (s, 3H), 1.01 (s, 3H), 0.99 (s, 3H).

Example 39

Preparation of 4-((1R,3aS,5aR,5bR,7aR,11aS,11bR, 13aR,13bR)-3a-((1-ethylpyrrolidin-2-yl)methylcarbamoyl)-5a,5b,8,8,11a-pentamethyl-1-(prop-1-en-2-yl)-2,3,3a,4,5,5a,5b,6,7,7a,8,11,11a,11b,12,13,13a, 13b-octadecahydro-1H-cyclopenta[a]chrysen-9-yl)benzoic acid

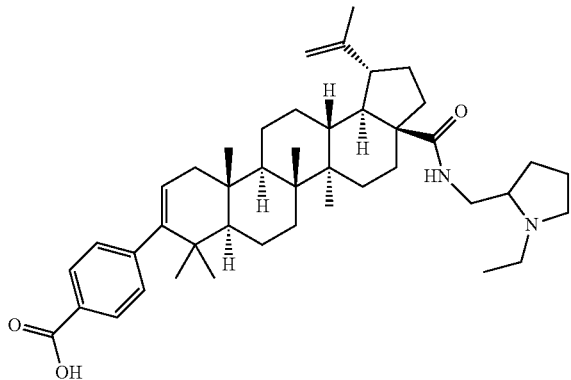

The title compound was prepared following the general procedures described above for the C-28 amide formation and hydrolysis using 1-ethyl-2-amino methylene pyrrolidine as the reactant amine. The product was isolated as a white solid (35 mg, 34%). LCMS: m/e 667.7 (M–H)⁻, 2.27 min (method 3). ¹H NMR (500 MHz, Acetic Acid-d₄) δ ppm 8.18 (br. s., 1H), 8.06 (d, J=8.24 Hz, 2H), 7.33 (d, J=8.24 Hz, 2H), 5.40 (d, J=4.58 Hz, 1H), 4.81 (s, 1H), 4.68 (s, 1H), 4.06-3.67 (m, 4H), 3.58-3.43 (m, 1H), 3.26-3.12 (m, 3H), 2.65-2.55 (m, 1H), 2.41 (d, J=13.12 Hz, 1H), 1.77 (s, 3H), 1.12 (s, 3H), 1.09 (s, 3H), 1.08 (s, 3H), 2.34-0.95 (m, 27H), 1.03 (s, 3H), 1.02 (s, 3H).

Example 40

Preparation of 4-((1R,3aS,5aR,5bR,7aR,11aS,11bR, 13aR,13bR)-3a-((1H-benzo[d]imidazol-2-yl)methylcarbamoyl)-5a,5b,8,8,11a-pentamethyl-1-(prop-1-en-2-yl)-2,3,3a,4,5,5a,5b,6,7,7a,8,11,11a,11b,12,13,13a, 13b-octadecahydro-1H-cyclopenta[a]chrysen-9-yl)benzoic acid

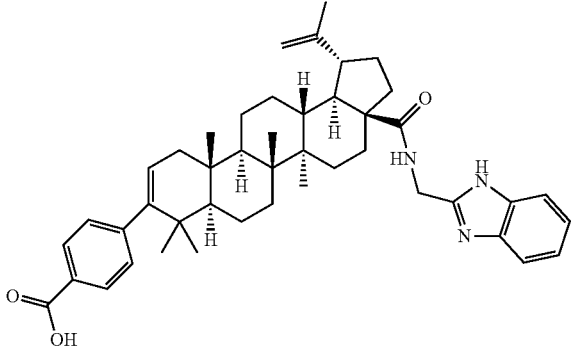

The title compound was prepared following the method described above for the general procedure for C-28 amide formation and hydrolysis using 2-aminomethylbenzimidazole, HCl as the reactant amine. The product was isolated as a tan solid (32 mg, 46%). LCMS: m/e 686.7 (M–H)⁻, 2.27 min (method 3). ¹H NMR (400 MHz, DMSO-d₆) δ ppm 12.83 (br. s., 1H), 8.49 (t, J=4.52 Hz, 1H), 7.87 (d, J=8.28 Hz, 2H), 7.72-7.65 (m, 2H), 7.42-7.35 (m, 2H), 7.22 (ddd, 2H), 5.24 (d, J=4.77 Hz, 1H), 4.65 (d, J=2.01 Hz, 1H), 4.55 (br. s., 2H), 4.53 (s, 1H), 3.00 (td, J=10.79, 4.27 Hz, 1H), 2.51-2.43 (m, 1H), 2.26 (d, J=12.80 Hz, 1H), 2.06 (dd, J=16.81, 6.27 Hz, 1H), 1.95 (dd, J=11.42, 7.91 Hz, 1H), 1.65 (s, 3H), 0.96 (s, 3H), 0.88 (s, 9H), 1.81-0.83 (m, 18H), 0.68 (s, 3H).

Example 41

Preparation of 4-((1R,3aS,5aR,5bR,7aR,11aS,11bR, 13aR,13bR)-5a,5b,8,8,11a-pentamethyl-1-(prop-1-en-2-yl)-3a-(thiazol-2-ylmethylcarbamoyl)-2,3,3a,4, 5,5a,5b,6,7,7a,8,11,11a,11b,12,13,13a,13b-octadecahydro-1H-cyclopenta[a]chrysen-9-yl)benzoic acid

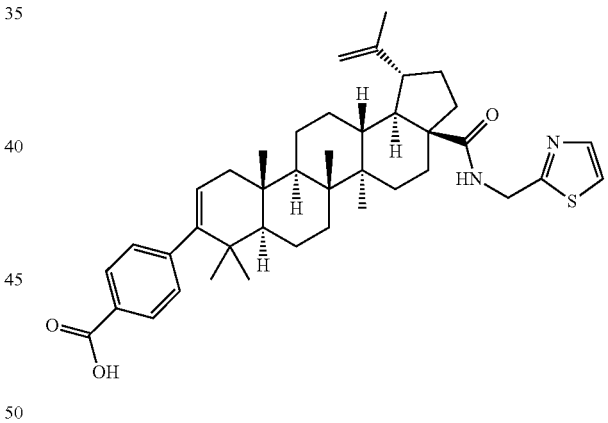

The title compound was prepared following the general procedures described above for the C-28 amide formation and hydrolysis using 2-aminomethylthiazole hydrochloride as the reactant amine. The product was isolated as a white solid (55 mg, 85%). LCMS: m/e 653.6 (M–H)⁻, 2.23 min (method 3). ¹H NMR (400 MHz, DMSO-d₆) δ ppm 8.53 (t, J=5.90 Hz, 1H), 7.87 (d, J=8.28 Hz, 2H), 7.71 (d, J=3.26 Hz, 1H), 7.62 (d, J=3.26 Hz, 1H), 7.23 (d, J=8.28 Hz, 2H), 5.26 (d, J=4.52 Hz, 1H), 4.70 (d, J=2.26 Hz, 1H), 4.63-4.45 (m, 3H), 3.00-3.09 (m, 1H), 2.70-2.59 (m, 1H), 2.21 (d, J=12.80 Hz, 1H), 2.09 (dd, J=17.44, 6.15 Hz, 1H), 1.67 (s, 3H), 0.98 (s, 3H), 1.94-0.95 (m, 20H), 0.96 (s, 3H), 0.92 (s, 3H), 0.90 (s, 6H).

Example 42

Preparation of 4-((1R,3aS,5aR,5bR,7aR,11aS,11bR, 13aR,13bR)-5a,5b,8,8,11a-pentamethyl-1-(prop-1-en-2-yl)-3a-(thiophen-2-ylmethylcarbamoyl)-2,3,3a, 4,5,5a,5b,6,7,7a,8,11,11a,11b,12,13,13a,13b-octadecahydro-1H-cyclopenta[a]chrysen-9-yl) benzoic acid

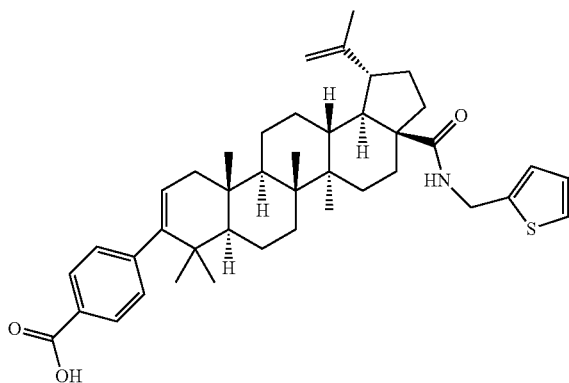

The title compound was prepared following the general procedures described above for the C-28 amide formation and hydrolysis using 2-Thiophenemethylamine as the reactant amine. The product was isolated as a white solid (44 mg, 66%). LCMS: m/e 652.7 (M−H)⁻, 2.24 min (method 3). $^1$H NMR (400 MHz, DMSO-$d_6$) δ ppm 12.81 (br. s., 1H), 8.25 (t, J=5.90 Hz, 1H), 7.87 (d, J=8.28 Hz, 2H), 7.37 (dd, J=4.39, 1.88 Hz, 1H), 7.23 (d, J=8.28 Hz, 2H), 6.97-6.92 (m, 2H), 5.26 (d, J=4.52 Hz, 1H), 4.69 (d, J=2.26 Hz, 1H), 4.57 (s, 1H), 4.48 (dd, J=15.31, 5.77 Hz, 1H), 4.37 (dd, J=15.06, 6.02 Hz, 1H), 3.11-3.01 (m, 1H), 2.71-2.61 (m, 1H), 2.16 (d, J=12.80 Hz, 1H), 2.09 (dd, J=17.19, 6.15 Hz, 1H), 1.67 (s, 3H), 1.88-0.94 (m, 19H), 0.97 (s, 6H), 0.91 (s, 3H), 0.90 (s, 6H).

Example 43

Preparation of 4-((1R,3aS,5aR,5bR,7aR,11aS,11bR, 13aR,13bR)-3a#1H-imidazol-2-yl)methylcarbamoyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl) benzoic acid

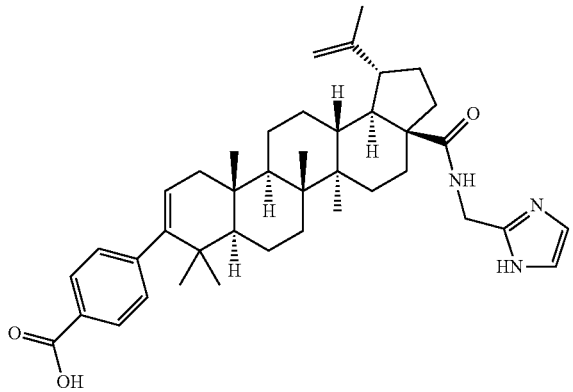

The title compound was prepared following the general procedures described above for the C-28 amide formation and hydrolysis using 2-aminomethyl-1H-imidazole dihydrochloride as the reactant amine. The product was isolated as a white solid (35 mg, 52%). LCMS: m/e 636.7 (M−H)⁻, 2.23 min (method 3). $^1$H NMR (400 MHz, DMSO-$d_6$) δ ppm 8.33 (t, J=5.14 Hz, 1H), 7.87 (d, J=8.28 Hz, 2H), 7.37 (s, 2H), 7.23 (d, J=8.28 Hz, 2H), 5.25 (d, J=4.52 Hz, 1H), 4.67 (d, J=2.26 Hz, 1H), 4.57 (s, 1H), 4.41-4.30 (m, 2H), 3.01 (td, J=10.98, 5.14 Hz, 1H), 2.54-2.44 (m, 1H), 2.23-2.16 (m, 1H), 2.08 (dd, J=17.94, 6.65 Hz, 1H), 1.91-1.83 (m, 1H), 1.65 (s, 3H), 1.77-0.95 (m, 19H), 0.96 (s, 3H), 0.94 (s, 3H), 0.90 (s, 6H), 0.77 (s, 3H).

Example 44

Preparation of 4-((1R,3aS,5aR,5bR,7aR,11aS,11bR, 13aR,13bR)-5a,5b,8,8,11a-pentamethyl-3a-(1-(5-methyl-4H-1,2,4-triazol-3-yl)ethylcarbamoyl)-1-(prop-1-en-2-yl)-2,3,3a,4,5,5a,5b,6,7,7a,8,11,11a, 11b,12,13,13a,13b-octadecahydro-1H-cyclopenta[a]chrysen-9-yl)benzoic acid

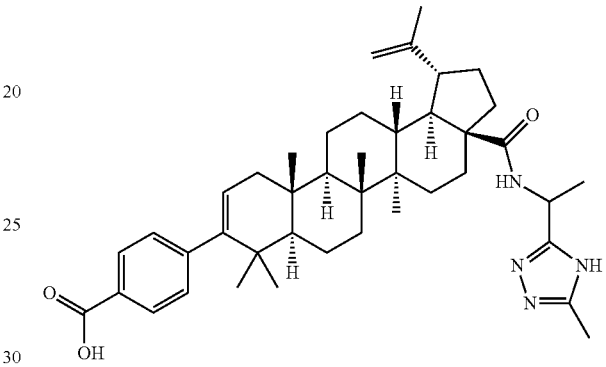

The title compound was prepared following the general procedures described above for the C-28 amide formation and hydrolysis using 1-(5-methyl-4H-1,2,4-triazol-3-yl)ethanamine, 2 HCl as the reactant amine. The product was isolated as a white solid (24 mg, 35%). LCMS: m/e 665.7 (M−H)⁻, 2.20 min (method 3). $^1$H NMR (500 MHz, DMSO-$d_6$) δ ppm 13.29 (br. s., 1H), 12.85 (br. s., 1H), 7.86 (d, J=8.24 Hz, 2H), 7.63 (br. s., 1H), 7.22 (d, J=8.24 Hz, 2H), 5.24 (d, J=4.58 Hz, 1H), 4.98 (br. s., 1H), 4.66 (d, J=2.14 Hz, 1H), 4.54 (s, 1H), 3.00 (td, J=10.83, 4.58 Hz, 1H), 2.67-2.67 (m, 1H), 2.34-2.20 (m, 4H), 2.08 (dd, J=17.24, 6.26 Hz, 1H), 1.91 (dd, J=11.29, 7.93 Hz, 1H), 1.64 (s, 3H), 0.96 (s, 3H), 0.95 (s, 3H), 1.80-0.93 (m, 21H), 0.93 (s, 3H), 0.89 (s, 6H).

Example 45

Preparation of 4-((1R,3aS,5aR,5bR,7aR,11aS,11bR, 13aR,13bR)-3a-(benzo[d]thiazol-2-ylmethylcarbamoyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl) benzoic acid

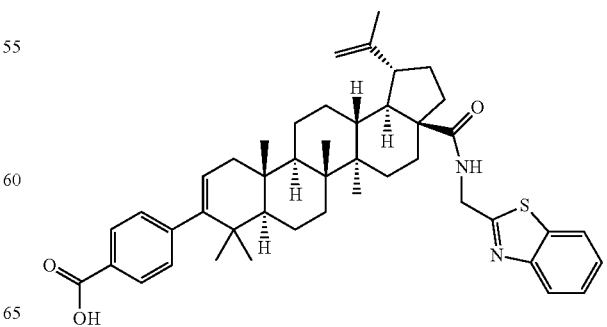

The title compound was prepared following the general procedures described above for the C-28 amide formation and hydrolysis using 1,3-Benzothiazol-2-ylmethylamine hydrochloride as the reactant amine. The product was isolated as a white solid (55 mg, 85%). LCMS: m/e 703.7 (M−H)⁻, 2.28 min (method 3). $^1$H NMR (400 MHz, DMSO-d$_6$) δ ppm 12.83 (br. s., 1H), 8.64 (t, J=5.90 Hz, 1H), 8.09 (d, J=7.53 Hz, 1H), 7.95 (d, J=7.53 Hz, 1H), 7.87 (d, J=8.28 Hz, 2H), 7.54-7.49 (m, 1H), 7.46-7.40 (m, 1H), 7.23 (d, J=8.28 Hz, 2H), 5.26 (d, J=4.77 Hz, 1H), 4.69 (d, J=2.01 Hz, 1H), 4.66 (d, J=6.02 Hz, 2H), 4.57 (s, 1H), 3.04 (td, J=10.98, 4.14 Hz, 1H), 2.69-2.59 (m, 1H), 2.30-2.22 (m, 1H), 2.09 (dd, J=17.19, 6.40 Hz, 1H), 2.00-1.91 (m, 1H), 1.91-1.78 (m, 1H), 1.68 (s, 3H), 0.99 (s, 3H), 1.74-0.95 (m, 17H), 0.94 (s, 3H), 0.92 (s, 3H), 0.90 (s, 6H).

Example 46

Preparation of 4-((1R,3aS,5aR,5bR,7aR,11aS,11bR,13aR,13bR)-5a,5b,8,8,11a-pentamethyl-3a-(2-(2-oxopyrrolidin-1-yl)ethylcarbamoyl)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

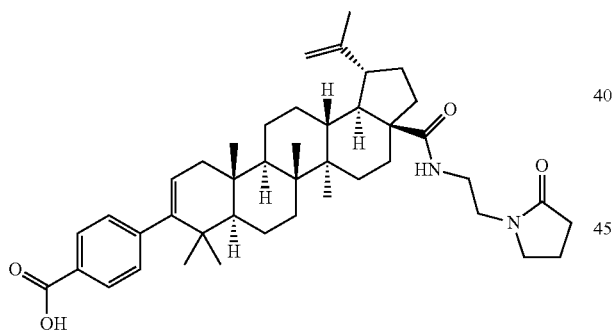

The title compound was prepared following the general procedures described above for the C-28 amide formation and hydrolysis using 1-(2-aminoethyl)pyrrolidin-2-one as the reactant amine. The product was isolated as a white solid (52 mg, 45%). LCMS: m/e 667.5 (M−H)⁻, 2.19 min (method 3). $^1$H NMR (500 MHz, CHLOROFORM-d) δ ppm 7.98 (d, J=8.24 Hz, 2H), 7.22 (d, J=8.24 Hz, 2H), 6.30-6.26 (m, 1H), 5.29 (d, J=4.58 Hz, 1H), 4.74 (d, J=1.83 Hz, 1H), 4.59 (s, 1H), 3.54-3.41 (m, 6H), 3.14 (td, J=11.06, 4.12 Hz, 1H), 2.51-2.43 (m, 1H), 2.41 (t, J=8.09 Hz, 2H), 2.02-2.14 (m, 3H), 1.99-1.85 (m, 2H), 1.68 (s, 3H), 1.77-0.95 (m, 18H), 0.98 (s, 6H), 0.96 (s, 3H), 0.92 (s, 6H).

Example 47

Preparation of 2-((1R,3aS,5aR,5bR,7aR,11aS,11bR,13aR,13bR)-9-(4-carboxyphenyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysene-3a-carboxamido)-5-methylthiazole-4-carboxylic acid

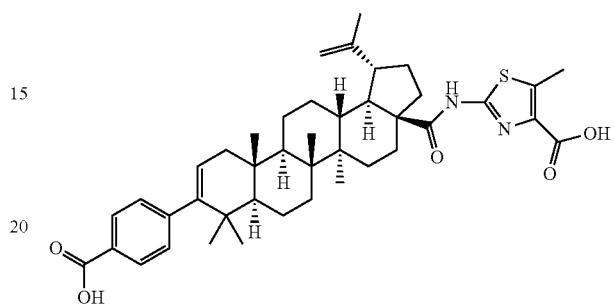

The title compound was prepared following the general procedures described above for the C-28 amide formation and hydrolysis using 2-amino-4-methyl-thiazole-5-carboxylic acid ethyl ester as the reactant amine. The product was isolated as a white solid (14 mg, 16%). LCMS: m/e 697.4 (M−H)⁻, 2.41 min (method 4). $^1$H NMR (500 MHz, Acetic Acid-d$_4$) δ ppm 8.03 (d, J=8.24 Hz, 2H), 7.29 (d, J=8.24 Hz, 2H), 5.37 (d, J=4.88 Hz, 1H), 4.84 (s, 1H), 4.68 (s, 1H), 3.11-3.19 (m, 1H), 2.78-2.86 (m, 1H), 2.60 (s, 3H), 2.41 (d, J=13.73 Hz, 1H), 1.77 (s, 3H), 1.11 (s, 3H), 1.07 (s, 3H), 1.04 (s, 3H), 1.00 (s, 3H), 0.98 (s, 3H), 0.86-2.28 (m, 20H).

Example 48

Preparation of 4-((1R,3aS,5aR,5bR,7aR,11aS,11bR,13aR,13bR)-5a,5b,8,8,11a-pentamethyl-3a-(5-methylthiazol-2-ylcarbamoyl)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

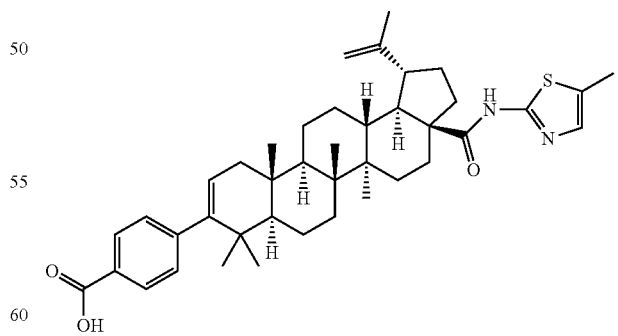

The title compound was prepared following the general procedures described above for the C-28 amide formation and hydrolysis using 2-amino-4-methyl-thiazole-5-carboxylic acid ethyl ester as the reactant amine. Upon hydrolysis of the thiazole carboxylate, decarboxylation occurred as a minor side product. The product was isolated as a white solid (4.3 mg, 4.7%). LCMS: m/e 653.4 (M−H)⁻, 2.68 min (method 4). ¹H NMR (500 MHz, CHLOROFORM-d) δ ppm 7.99 (d, J=8.24 Hz, 2H), 7.21 (d, J=8.24 Hz, 2H), 6.52 (s, 1H), 5.30 (d, J=4.58 Hz, 1H), 4.78 (s, 1H), 4.62 (s, 1H), 3.10-3.18 (m, 1H), 2.58-2.69 (m, 1H), 2.45 (d, J=13.73 Hz, 1H), 2.39 (s, 3H), 1.71 (s, 3H), 1.02 (s, 3H), 0.97 (s, 3H), 0.95 (s, 3H), 0.92 (s, 3H), 0.90 (s, 3H), 0.80-2.17 (m, 20H).
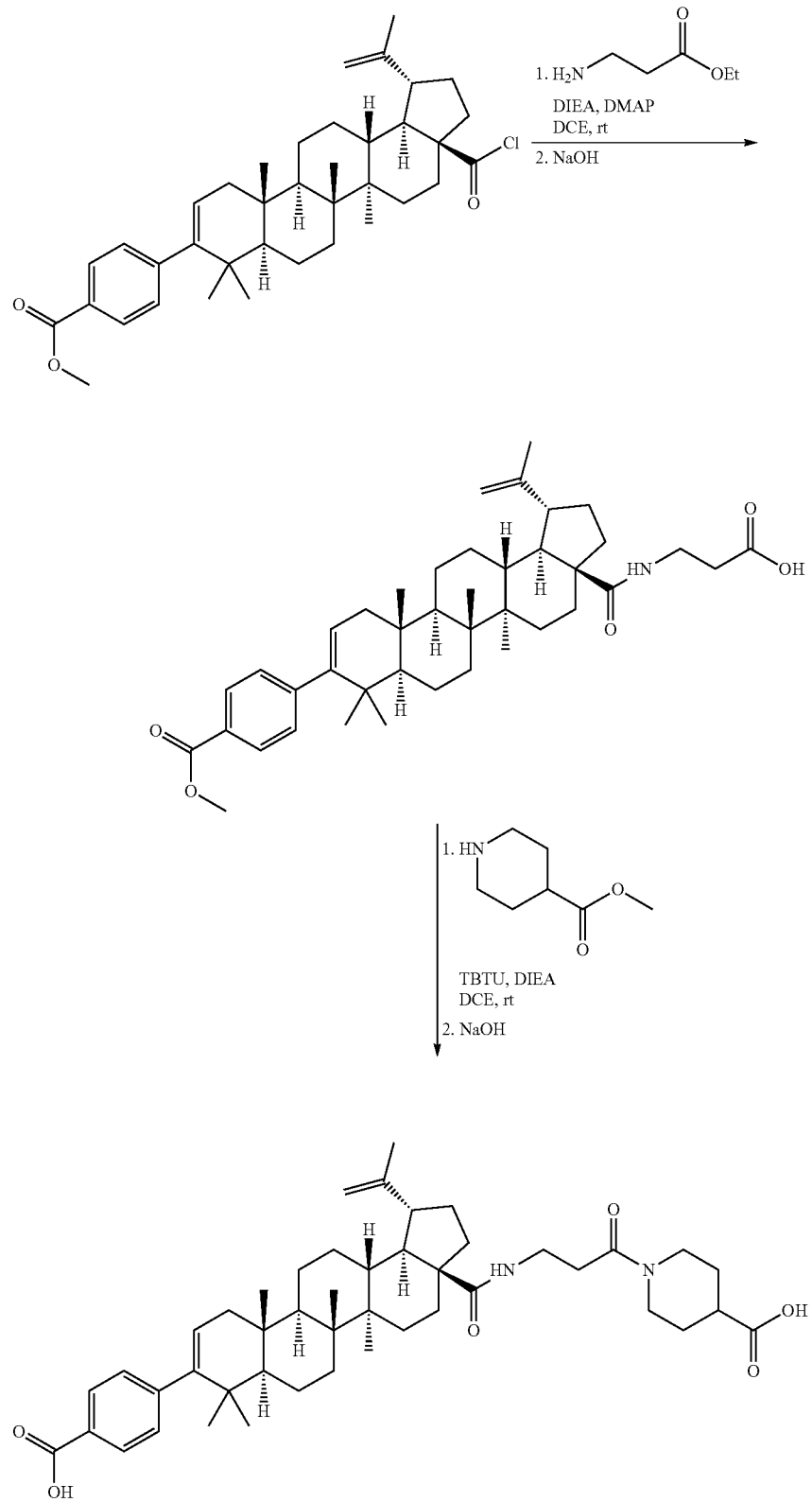

Preparation of 3-((1R,3aS,5aR,5bR,7aR,11aS,11bR, 13aR,13bR)-9-(4-(methoxycarbonyl)phenyl)-5a,5b, 8,8,11a-pentamethyl-1-(prop-1-en-2-yl)-2,3,3a,4,5, 5a,5b,6,7,7a,8,11,11a,11b,12,13,13a,13b-octadecahydro-1H-cyclopenta[a]chrysene-3a-carboxamido)propanoic acid. Intermediate 8

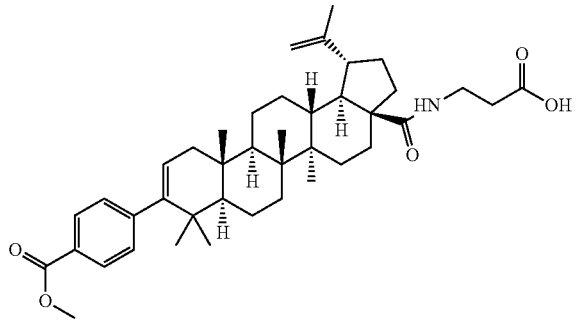

The title compound was prepared following the method described above for the general procedure for C-28 amide formation using beta-alanine, ethyl ester hydrochloride as the reactant amine. The resulting ethyl ester was hydrolyzed using 4 equiv. of 1N NaOH and 1,4-dioxane as the solvent at rt. After 1.5 h the mixture was acidified with 1N HCl and was extracted with dichloromethane (3×20 mL). The organic layers were combined, dried with $Na_2SO_4$, filtered, and concentrated under reduced pressure. The residue was purified by Biotage flash chromatography (0-50% ethyl acetate in hexanes with 0.1% acetic acid added) to give the title product as a white solid (330 mg, 61%). LCMS: m/e 642.4 (M−H)$^−$, 2.89 min (method 4). $^1$H NMR (500 MHz, CHLOROFORM-d) δ ppm 7.92 (d, J=8.24 Hz, 2H), 7.18 (d, J=8.24 Hz, 2H), 6.18 (t, J=5.80 Hz, 1H), 5.26-5.29 (m, 1H), 4.74 (d, J=1.83 Hz, 1H), 4.60 (s, 1H), 3.90 (s, 3H), 3.53-3.61 (m, 1H), 3.44-3.52 (m, 1H), 3.11 (td, J=11.06, 4.12 Hz, 1H), 2.64 (t, J=5.49 Hz, 2H), 2.43-2.50 (m, 1H), 2.09 (dd, J=17.40, 6.10 Hz, 1H), 1.88-1.98 (m, 2H), 1.69 (s, 3H), 0.99 (s, 3H), 0.98 (s, 3H), 0.97-1.77 (m, 18H), 0.96 (s, 3H), 0.91 (s, 6H).

Example 49

Preparation of 1-(3-((1R,3aS,5aR,5bR,7aR,11aS, 11bR,13aR,13bR)-9-(4-carboxyphenyl)-5a,5b,8,8, 11a-pentamethyl-1-(prop-1-en-2-yl)-2,3,3a,4,5,5a, 5b,6,7,7a,8,11,11a,11b,12,13,13a,13b-octadecahydro-1H-cyclopenta[a]chrysene-3a-carboxamido)propanoyl)piperidine-4-carboxylic acid To a solution of 3-((1R,3aS,5aR,5bR,7aR,11aS,11bR, 13aR,13bR)-9-(4-(methoxycarbonyl)phenyl)-5a,5b,8,8,11a-pentamethyl-1-(prop-1-en-2-yl)-2,3,3a,4,5,5a,5b,6,7,7a,8, 11,11a,11b,12,13,13a,13b-octadecahydro-1H-cyclopenta[a] chrysene-3a-carboxamido)propanoic acid (0.06 g, 0.093 mmol) in DCE (2 mL) was added DIEA (0.049 mL, 0.280 mmol), O-benzotriazol-1-yl-N,N,N',N'-tetra-methyluronium tetrafluoroborate (0.048 g, 0.149 mmol), and methyl isonipecotate (0.019 mL, 0.140 mmol). The mixture was stirred at rt for 15.75 h, then was diluted with 7 mL of water and was extracted with dichloromethane (3×7 mL). The combined organic layers were dried with $Na_2SO_4$, the drying agent was removed by filtration and the filtrate was concentrated under reduced pressure. The residue was purified by Biotage flash chromatography using a 0-75% ethyl acetate in hexanes gradient. The fractions containing the expected product were combined and were concentrated under reduced pressure. The expected product, methyl 1-(3-((1R,3aS,5aR,5bR,7aR, 11aS,11bR,13aR,13bR)-9-(4-(methoxycarbonyl)phenyl)-5a,5b,8,8,11a-pentamethyl-1-(prop-1-en-2-yl)-2,3,3a,4,5, 5a,5b,6,7,7a,8,11,11a,11b,12,13,13a,13b-octadecahydro-1H-cyclopenta[a]chrysene-3a-carboxamido)propanoyl) piperidine-4-carboxylate (0.058 g, 0.075 mmol, 81% yield), was isolated as a white foam. LCMS: m/e 767.5 (M−H)$^−$, 3.46 min (method 4).

To a solution of methyl 1-(3-((1R,3aS,5aR,5bR,7aR,11aS, 11bR,13aR,13bR)-9-(4-(methoxycarbonyl)phenyl)-5a,5b,8, 8,11a-pentamethyl-1-(prop-1-en-2-yl)-2,3,3a,4,5,5a,5b,6,7, 7a,8,11,11a,11b,12,13,13a,13b-octadecahydro-1H-cyclopenta[a]chrysene-3a-carboxamido)propanoyl) piperidine-4-carboxylate (0.058 g, 0.075 mmol) in 1,4-dioxane (2 mL) was added NaOH (1N) (0.377 mL, 0.377 mmol). The mixture was heated to 85° C. for 15 h then was cooled to rt. The mixture was diluted with 5 mL of 1N HCl and was extracted with dichloromethane (4×5 mL). The combined organic layers were dried with $Na_2SO_4$, the drying agent was removed by filtration and the filtrate was concentrated under reduced pressure. The residue was purified by Biotage flash chromatography using a 0-10% MeOH in dichloromethane gradient with 0.1% HOAc added to the mixture. The compound was further purified by prep HPLC. The fractions containing the expected product were combined and concentrated under reduced pressure to give the title compound (41.5 mg, 0.056 mmol, 74.3% yield) as a white solid. LCMS: m/e 739.4 (M−H)$^−$, 2.37 min (method 4). $^1$H NMR (500 MHz, Acetic Acid-d$_4$) δ ppm 8.03 (d, J=8.24 Hz, 2H), 7.30 (d, J=8.24 Hz, 2H), 5.37 (d, J=6.10 Hz, 1H), 4.79 (s, 1H), 4.64 (s, 1H), 4.43-4.53 (m, 1H), 3.95-4.02 (m, 1H), 3.46-3.70 (m, 2H), 3.18-3.27 (m, 1H), 3.13 (qd, J=11.04, 4.12 Hz, 1H),

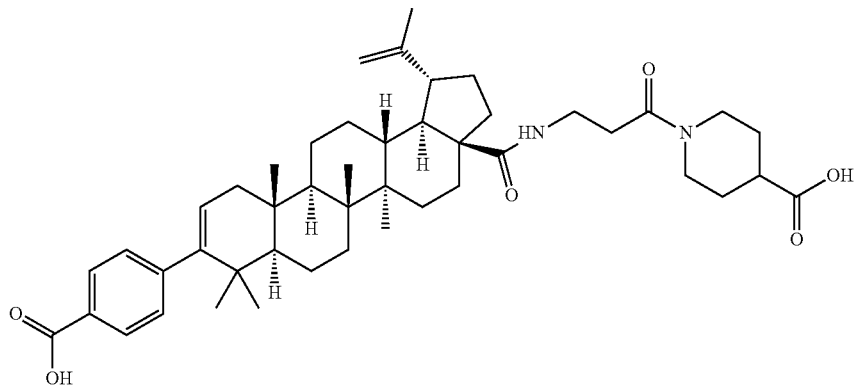

2.65-2.97 (m, 4H), 2.47-2.57 (m, 1H), 1.74 (s, 3H), 1.07 (s, 3H), 1.06 (s, 3H), 1.05 (s, 3H), 1.03-2.24 (m, 25H), 1.00 (s, 3H), 0.99 (s, 3H).

Example 50

Preparation of 2-((1R,3aS,5aR,5bR,7aR,11aS,11bR, 13aR,13bR)-9-(4-carboxyphenyl)-5a,5b,8,8,11a-pentamethyl-1-(prop-1-en-2-yl)-2,3,3a,4,5,5a,5b,6,7, 7a,8,11,11a,11b,12,13,13a,13b-octadecahydro-1H-cyclopenta[a]chrysene-3a-carboxamido)thiazole-5-carboxylic acid

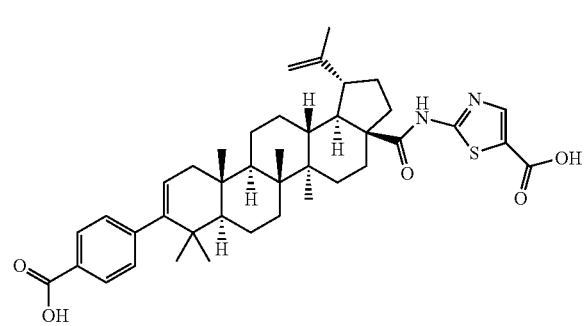

The title compound was prepared following the general procedures described above for the C-28 amide formation and hydrolysis using methyl 2-aminothiazole-5-carboxylate as the reactant amine. The product was isolated as a white solid (14 mg, 10.7%). LCMS: m/e 683.3 (M−H)⁻, 2.36 min (method 4). ¹H NMR (500 MHz, Acetic Acid-d₄) δ ppm 8.18 (s, 1H), 8.03 (d, J=8.24 Hz, 2H), 7.30 (d, J=8.24 Hz, 2H), 5.37 (d, J=4.58 Hz, 1H), 4.84 (s, 1H), 4.69 (s, 1H), 3.16 (td, J=10.99, 4.58 Hz, 1H), 2.79-2.86 (m, 1H), 2.39-2.45 (m, 1H), 1.77 (s, 3H), 1.11 (s, 3H), 1.07 (s, 3H), 1.04 (s, 3H), 1.02-2.25 (m, 20H), 1.00 (s, 3H), 0.98 (s, 3H).

Example 51

Preparation of 4-((1R,3aS,5aR,5bR,7aR,11aS,11bR, 13aR,13bR)-3a-(1,3,4-thiadiazol-2-ylcarbamoyl)-5a, 5b,8,8,11a-pentamethyl-1-(prop-1-en-2-yl)-2,3,3a,4, 5,5a,5b,6,7,7a,8,11,11a,11b,12,13,13a,13b-octadecahydro-1H-cyclopenta[a]chrysen-9-yl)benzoic acid

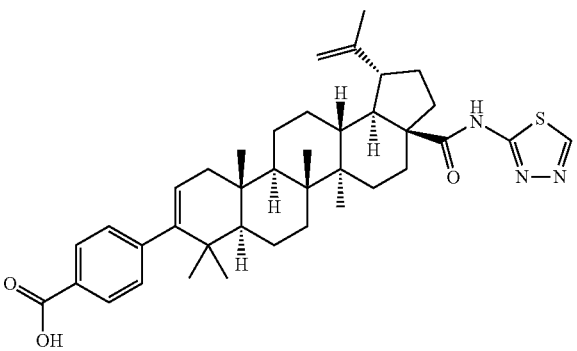

The title compound was prepared following the general procedures described above for the C-28 amide formation and hydrolysis using 5-amino-1,3,4-thiadiazole-2-carboxylic acid ethyl ester as the reactant amine. Upon hydrolysis of the thiadiazole carboxylate, decarboxylation occurred as a minor side product. The product was isolated as a white solid (9 mg, 9.9%). LCMS: m/e 640.3 (M−H)⁻, 2.53 min (method 4). ¹H NMR (500 MHz, CHLOROFORM-d) δ ppm 11.84 (br. s., 1H), 8.81 (s, 1H), 8.00 (d, J=8.24 Hz, 2H), 7.21 (d, J=7.93 Hz, 2H), 5.30 (d, J=4.58 Hz, 1H), 4.79 (s, 1H), 4.64 (s, 1H), 3.07-3.15 (m, 1H), 2.57-2.65 (m, 1H), 2.46 (d, J=13.73 Hz, 1H), 2.07-2.16 (m, 2H), 1.72 (s, 3H), 1.03 (s, 3H), 0.97 (s, 3H), 0.95-1.93 (m, 18H), 0.94 (s, 3H), 0.92 (s, 3H), 0.90 (s, 3H).

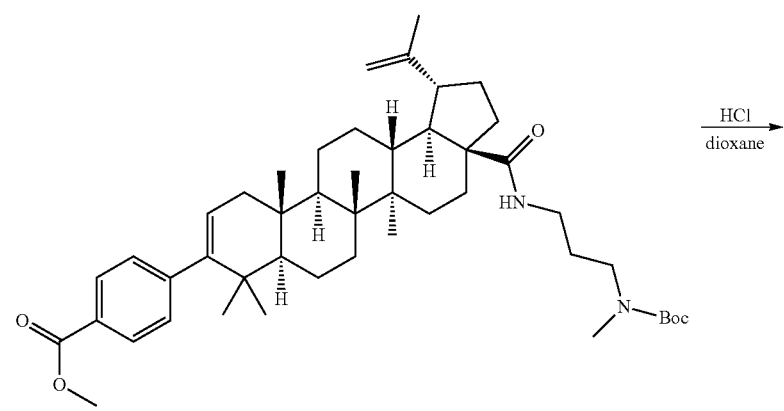

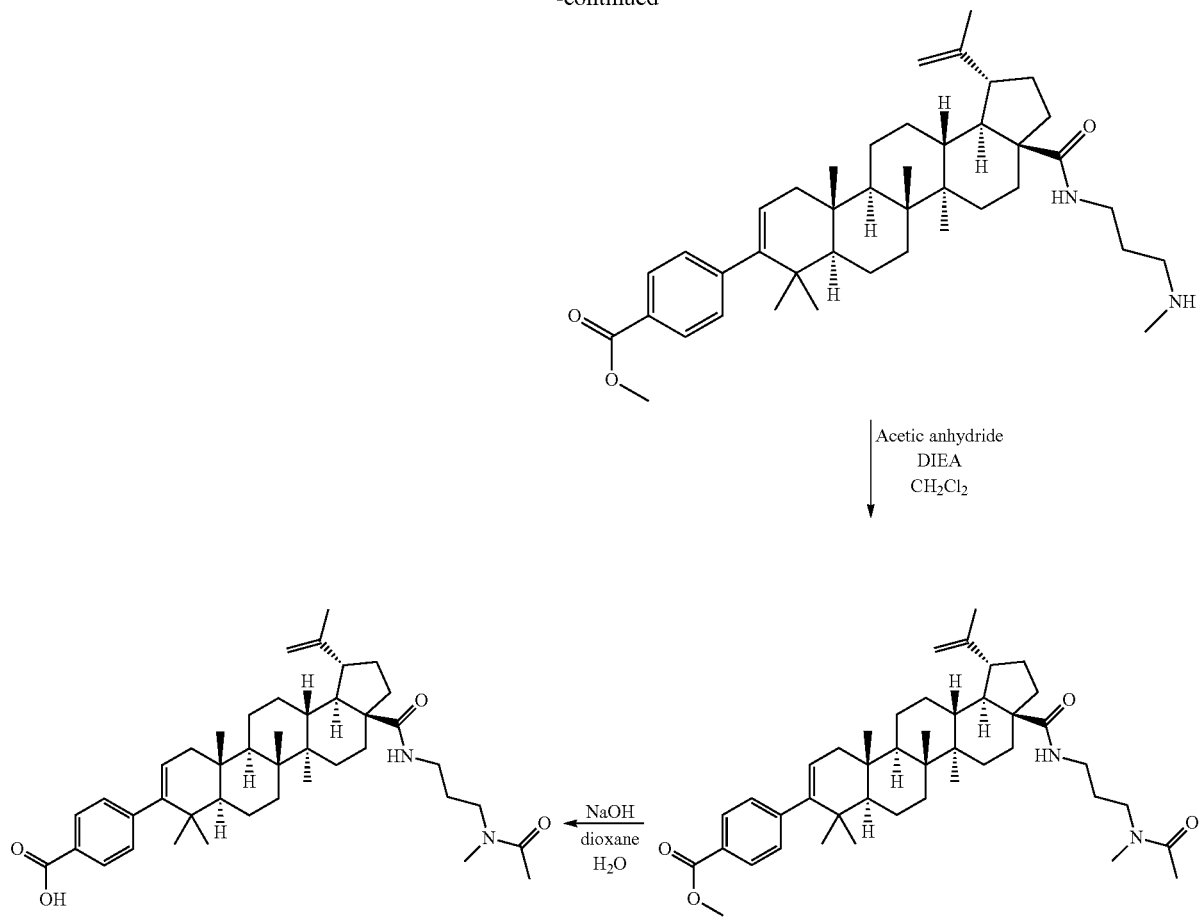

Preparation of methyl 4-((1R,3aS,5aR,5bR,7aR,11aS,11bR,13aR,13bR)-3a-(3-(tert-butoxycarbonyl(methyl)amino)propylcarbamoyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate. Intermediate 9

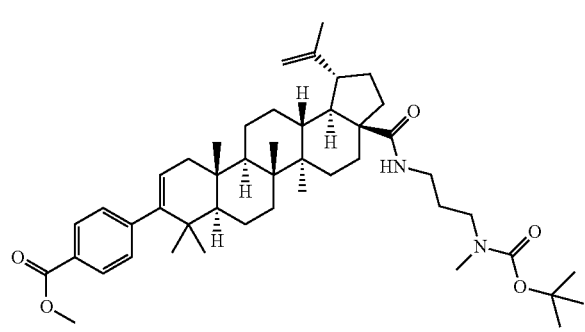

To a flask containing (1R,3aS,5aR,5bR,7aR,11aS,11bR,13aR,13bR)-9-(4-(methoxycarbonyl)phenyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysene-3a-carboxylic acid (0.1 g, 0.175 mmol) was added oxalyl chloride (2M in DCM) (3 mL, 6.00 mmol). The mixture bubbled vigorously for several minutes, then bubbling ceased and the clear solution was stirred at rt for 3 h. The mixture was concentrated under reduced pressure. The residue was dissolved in dichloromethane and concentrated two additional times. The crude product was diluted with DCE (2 mL) and Hunig'sBase (0.152 mL, 0.873 mmol) and N-(3-aminopropyl)-N-methylcarbamic acid tert-butyl ester (0.061 g, 0.324 mmol) were added to the mixture. After stirring the mixture for 19 h at rt, the mixture was diluted with 10 mL of water and was extracted with dichloromethane (3×10 mL). The combined organic layers were dried with $Na_2SO_4$. The drying agent was removed by filtration and the filtrate was concentrated under reduced pressure. The residue was purified by Biotage flash chromatography using a 0-5% MeOH in DCM gradient. The fractions containing the expected product were combined and concentrated under reduced pressure to give methyl 4-((1R,3aS,5aR,5bR,7aR,11aS,11bR,13aR,13bR)-3a-(3-(tert-butoxycarbonyl(methyl)amino)propylcarbamoyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate (122 mg, 0.164 mmol, 94% yield) as a white foam. LCMS: m/e 741.6 (M−H)⁻, 3.41 min (method 3). $^1$H NMR (500 MHz, CHLOROFORM-d) δ ppm 7.90 (d, J=8.24 Hz, 2H), 7.17 (d, J=8.24 Hz, 2H), 6.89 (br. s., 1H), 5.26 (d, J=4.58 Hz, 1H), 4.74 (d, J=1.83 Hz, 1H), 4.57 (s, 1H), 3.88 (s, 3H), 3.40-3.04 (m, 5H), 2.81 (s, 3H), 2.51 (t, J=10.83 Hz, 1H), 2.19-2.04 (m, 2H), 1.99-1.87 (m, 1H), 1.68 (s, 3H), 1.45 (s, 9H), 0.98 (s, 3H), 1.52-0.95 (m, 20H), 0.97 (s, 3H), 0.94 (s, 3H), 0.90 (s, 6H).

Preparation of methyl 4-((1R,3aS,5aR,5bR,7aR, 11aS,11bR,13aR,13bR)-5a,5b,8,8,11a-pentamethyl-3a-(3-(methylamino)propylcarbamoyl)-1-(prop-1-en-2-yl)-2,3,3a,4,5,5a,5b,6,7,7a,8,11,11a,11b,12,13,13a, 13b-octadecahydro-1H-cyclopenta[a]chrysen-9-yl) benzoate. Intermediate 10

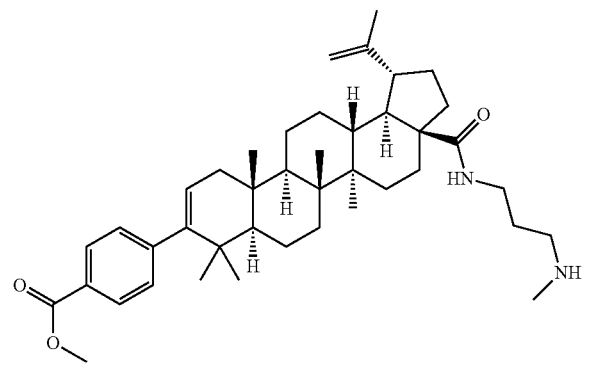

A vial containing methyl 4-((1R,3aS,5aR,5bR,7aR,11aS, 11bR,13aR,13bR)-3a-(3-(tert-butoxycarbonyl(methyl) amino)propylcarbamoyl)-5a,5b,8,8,11a-pentamethyl-1-(prop-1-en-2-yl)-2,3,3a,4,5,5a,5b,6,7,7a,8,11,11a,11b,12, 13,13a,13b-octadecahydro-1H-cyclopenta[a]chrysen-9-yl) benzoate (122 mg, 0.164 mmol) was diluted with HCl (4M in dioxane) (3 mL, 12.00 mmol). The mixture was stirred at rt. After 1.5 h of stirring at rt, LC/MS indicated the reaction was complete. The mixture was concentrated under reduced pressure. The crude product was carried forward to the next step with no additional purification. LCMS: m/e 641.5 (M–H)⁻, 2.73 min (method 3).

Preparation of methyl 4-((1R,3aS,5aR,5bR,7aR, 11aS,11bR,13aR,13bR)-5a,5b,8,8,11a-pentamethyl-3a-(3-(N-methylacetamido)propylcarbamoyl)-1-(prop-1-en-2-yl)-2,3,3a,4,5,5a,5b,6,7,7a,8,11,11a, 11b,12,13,13a,13b-octadecahydro-1H-cyclopenta[a] chrysen-9-yl)benzoate. Intermediate 11

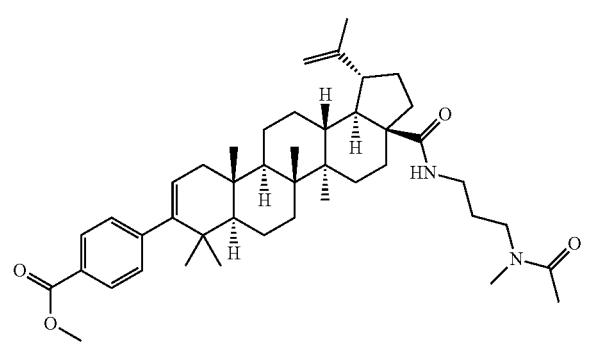

To a solution of methyl 4-((1R,3aS,5aR,5bR,7aR,11aS, 11bR,13aR,13bR)-5a,5b,8,8,11a-pentamethyl-3a-(3-(methylamino)propylcarbamoyl)-1-(prop-1-en-2-yl)-2,3,3a,4,5, 5a,5b,6,7,7a,8,11,11a,11b,12,13,13a,13b-octadecahydro-1H-cyclopenta[a]chrysen-9-yl)benzoate, HCl (111 mg, 0.164 mmol) in dichloromethane (2 mL) was added Hunig's Base (0.058 mL, 0.330 mmol) and acetic anhydride (0.023 mL, 0.247 mmol). The mixture was stirred at rt for 3 h then was diluted with 7 mL of water and was extracted with dichloromethane (3×7 mL). The combined organic layers were dried with Na₂SO₄. The drying agent was removed by filtration and the filtrate was concentrated under reduced pressure to give the crude product as a light-yellow foam. The crude product was used in the next step with no additional purification. LCMS: m/e 683.5 (M–H)⁻, 2.87 min (method 3).

Example 52

Preparation of 4-((1R,3aS,5aR,5bR,7aR,11aS,11bR, 13aR,13bR)-5a,5b,8,8,11a-pentamethyl-3a-(3-(N-methylacetamido)propylcarbamoyl)-1-(prop-1-en-2-yl)-2,3,3a,4,5,5a,5b,6,7,7a,8,11,11a,11b,12,13,13a, 13b-octadecahydro-1H-cyclopenta[a]chrysen-9-yl) benzoic acid

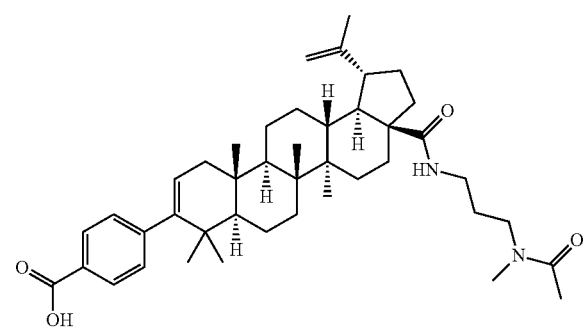

The title compound was prepared following the method described above for the general procedure for hydrolysis of the benzoic ester using NaOH. The product was isolated as a white solid (62 mg, 56%). LCMS: m/e 669.4 (M–H)⁻, 2.24 min (method 3). ¹H NMR (500 MHz, CHLOROFORM-d) δ ppm 7.98 (d, J=8.24 Hz, 2H), 7.22 (d, J=8.55 Hz, 2H), 6.93 (t, J=6.26 Hz, 1H), 5.29 (d, J=4.58 Hz, 1H), 4.74 (d, J=2.14 Hz, 1H), 4.58 (s, 1H), 3.64-3.56 (m, 1H), 3.36-3.25 (m, 2H), 3.20 (td, J=11.06, 4.43 Hz, 1H), 2.99 (s, 3H), 3.05-2.96 (m, 1H), 2.58-2.50 (m, 1H), 2.13 (s, 3H), 1.69 (s, 3H), 0.99 (s, 3H), 0.98 (s, 3H), 2.16-0.95 (m, 23H), 0.96 (s, 3H), 0.92 (s, 6H).

Preparation of N-(3-aminopropyl)acetamide, TFA

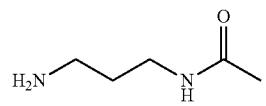

To a solution of tert-butyl 3-aminopropylcarbamate (0.1 g, 0.574 mmol) in dichloromethane (5 mL) was added acetic anhydride (0.060 mL, 0.631 mmol). The mixture was stirred at rt for 1.5 h and was concentrated under reduced pressure to give the acylated product as a clear, colorless film. The film was dissolved in dichloromethane (5 mL) and TFA (0.2 mL, 2.60 mmol) was added. The mixture was stirred at rt for 2 h and an additional 0.5 mL of TFA was added. The mixture was stirred for 3 h then was concentrated under reduced pressure to give the title product (0.132 g, 100%). The crude product was used in the next step with no additional purification. ¹H NMR (500 MHz, MeOD) δ ppm 3.29 (t, J=6.71 Hz, 2H), 2.96 (t, J=7.17 Hz, 2H), 1.99 (s, 3H), 1.85 (quin, 2H).

Example 53

Preparation of 4-((1R,3aS,5aR,5bR,7aR,11aS,11bR,13aR,13bR)-3a-(3-acetamidopropylcarbamoyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

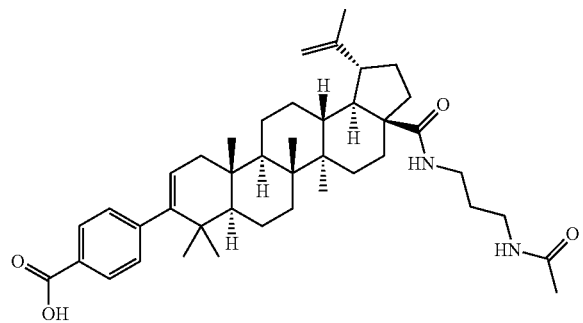

The title compound was prepared following the general procedures described above for the C-28 amide formation and hydrolysis using N-(3-aminopropyl)acetamide, TFA as the reactant amine (4.08 equiv. of amine used, 8.2 equiv. of Hunig's Base used). The product was isolated as a white solid (77 mg, 90%). LCMS: m/e 655.6 (M−H)⁻, 2.24 min (method 3). $^1$H NMR (500 MHz, CHLOROFORM-d) δ ppm 7.98 (d, J=7.93 Hz, 2H), 7.22 (d, J=7.93 Hz, 2H), 6.30 (t, J=6.26 Hz, 1H), 6.24 (t, J=6.41 Hz, 1H), 5.29 (d, J=5.80 Hz, 1H), 4.75 (s, 1H), 4.60 (s, 1H), 3.44-3.33 (m, 2H), 3.25-3.10 (m, 3H), 2.58-2.50 (m, 1H), 2.11 (dd, J=17.40, 6.41 Hz, 1H), 2.04 (s, 3H), 1.69 (s, 3H), 1.00 (s, 3H), 0.98 (s, 3H), 2.06-0.95 (m, 22H), 0.97 (s, 3H), 0.92 (s, 6H).

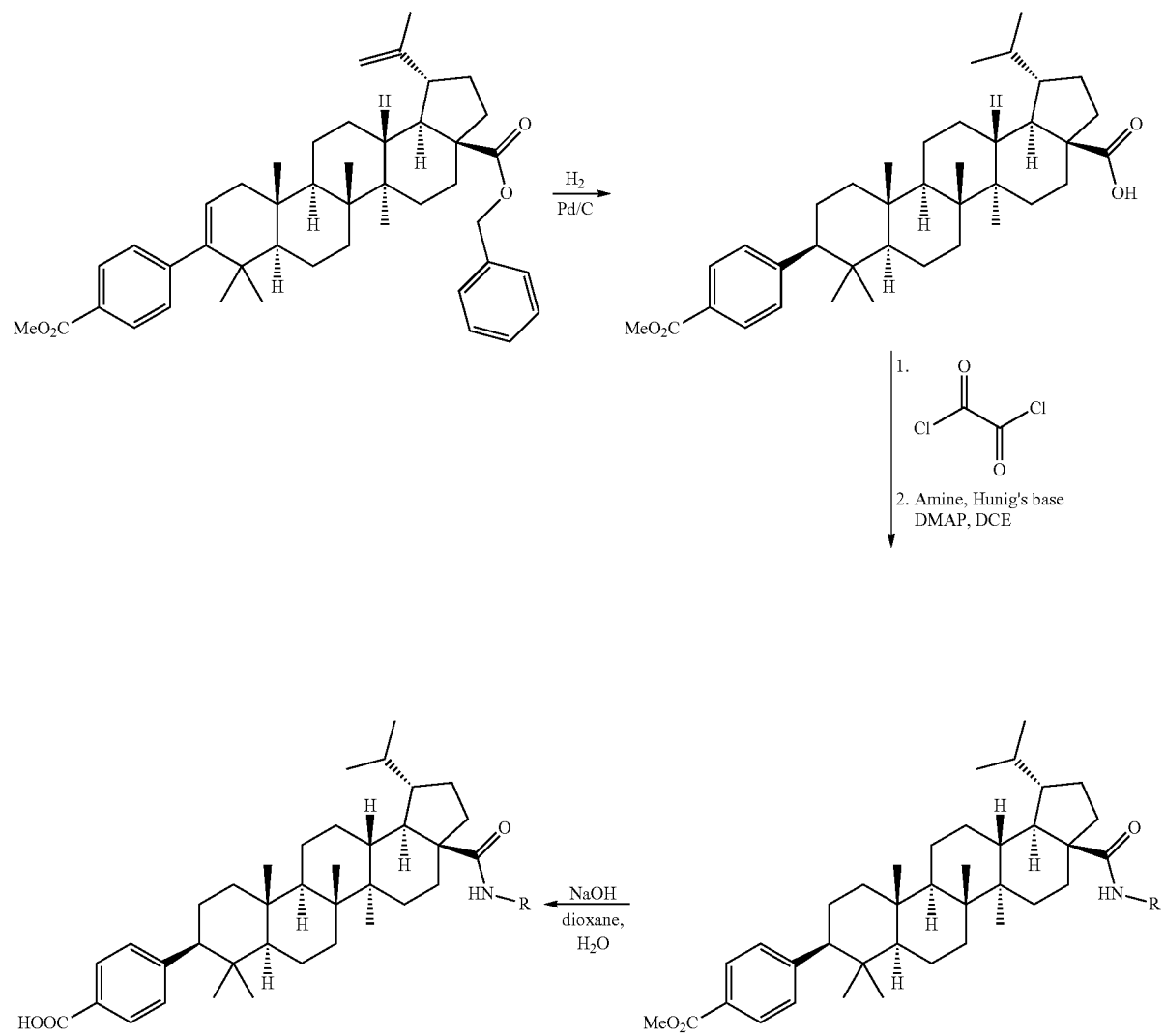

Preparation of (1S,3aS,5aR,5bR,7aS,9S,11aS,11bR, 13aR,13bR)-1-isopropyl-9-(4-(methoxycarbonyl) phenyl)-5a,5b,8,8,11a-pentamethylicosahydro-1H-cyclopenta[a]chrysene-3a-carboxylic acid. Intermediate 12

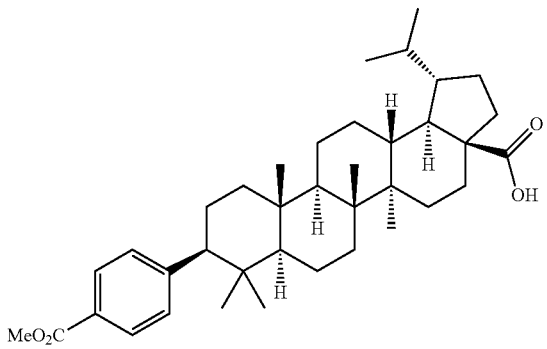

To a solution of (1R,3aS,5aR,5bR,7aR,11aS,11bR,13aR, 13bR)-benzyl 9-(4-(methoxycarbonyl)phenyl)-5a,5b,8,8, 11a-pentamethyl-1-(prop-1-en-2-yl)-2,3,3a,4,5,5a,5b,6,7, 7a,8,11,11a,11b,12,13,13a,13b-octadecahydro-1H-cyclopenta[a]chrysene-3a-carboxylate (0.2 g, 0.302 mmol) in ethanol (5 mL), 1,4-dioxane (7 mL), and acetic acid (0.5 mL, 8.73 mmol) was added Pd/C (10% by wt.) (0.1 g, 0.094 mmol). The mixture was flushed with $N_2$ and was put on the Parr shaker under 30 psi $H_2$. After 2 h, the reaction was checked by $^1$H NMR. The benzyl group had been removed, but the alkene still remained. The mixture was again flushed with $N_2$. An additional 50 mg of 10% Pd/C was added and the mixture was pressurized to 40 psi $H_2$. After stirring the mixture overnight, it reaction was removed from the Parr shaker and the palladium catalyst was removed by filtration. The filtrate was concentrated under reduced pressure to give the expected product, (1S,3aS,5aR,5bR,7aS,9S,11aS,11bR, 13aR,13bR)-1-isopropyl-9-(4-(methoxycarbonyl)phenyl)-5a,5b,8,8,11a-pentamethylicosahydro-1H-cyclopenta[a]chrysene-3a-carboxylic acid (0.174 g, 100% yield), as a white solid. $^1$H NMR (500 MHz, CHLOROFORM-d) δ ppm 7.91 (d, J=8.24 Hz, 2H), 7.22 (d, J=8.55 Hz, 2H), 3.89 (s, 3H), 2.39 (dd, J=13.12, 3.05 Hz, 1H), 2.19-2.29 (m, 3H), 2.01-2.13 (m, 1H), 0.99 (s, 3H), 0.96 (s, 3H), 0.95 (s, 3H), 0.86 (d, J=6.71 Hz, 3H), 0.79-1.92 (m, 22H), 0.76 (d, J=6.71 Hz, 3H), 0.75 (s, 3H), 0.68 (s, 3H).

Preparation of methyl 4-((1S,3aS,5aR,5bR,7aS,9S, 11aS,11bR,13aR,13bR)-3a-(chlorocarbonyl)-1-isopropyl-5a,5b,8,8,11a-pentamethylicosahydro-1H-cyclopenta[a]chrysen-9-yl)benzoate. Intermediate 13

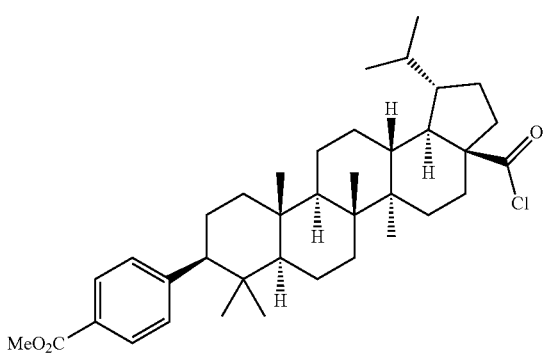

To a flask containing (1S,3aS,5aR,5bR,7aS,9S,11aS, 11bR,13aR,13bR)-1-isopropyl-9-(4-(methoxycarbonyl)phenyl)-5a,5b,8,8,11a-pentamethylicosahydro-1H-cyclopenta[a]chrysene-3a-carboxylic acid (0.154 g, 0.267 mmol) was added oxalyl chloride (2M in dichloromethane) (5 mL, 10.00 mmol). The solution was stirred at rt for 3 h. The mixture was concentrated under reduced pressure and was dissolved in dichloromethane and concentrated two additional times. The crude product was used in the next step with no additional purification.

Preparation of methyl 4-((1S,3aS,5aR,5bR,7aS,9S, 11aS,11bR,13aR,13bR)-1-isopropyl-5a,5b,8,8,11a-pentamethyl-3a-(2-(pyridin-2-yl)ethylcarbamoyl) icosahydro-1H-cyclopenta[a]chrysen-9-yl)benzoate. Intermediate 14

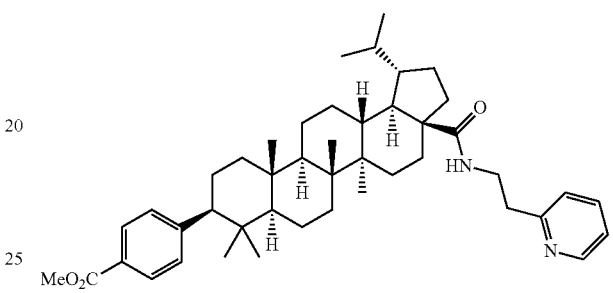

To a flask containing methyl 4-((1S,3aS,5aR,5bR,7aS,9S, 11aS,11bR,13aR,13bR)-3a-(chlorocarbonyl)-1-isopropyl-5a,5b,8,8,11a-pentamethylicosahydro-1H-cyclopenta[a] chrysen-9-yl)benzoate (77 mg, 0.13 mmol) in DCE (2 mL) was added Hunig'sBase (0.068 mL, 0.390 mmol), DMAP (1 mg, 8.19 μmol), and 2-(2-Aminoethyl)pyridine (0.031 mL, 0.260 mmol). The mixture was stirred for 2.5 hours at rt. The reaction was diluted with 5 mL of water and was extracted with dichloromethane (3×5 mL). The combined organic layers were dried with $Na_2SO_4$. The drying agent was removed by filtration and the filtrate was concentrated under reduced pressure. The residue was purified by Biotage flash chromatography using a 0-75% ethyl acetate in hexanes gradient. The fractions containing the expected product were combined and concentrated. The expected product, methyl 4-((1S,3aS,5aR, 5bR,7aS,9S,11aS,11bR,13aR,13bR)-1-isopropyl-5a,5b,8,8, 11a-pentamethyl-3a-(2-(pyridin-2-yl)ethylcarbamoyl) icosahydro-1H-cyclopenta[a]chrysen-9-yl)benzoate (0.062 g, 0.091 mmol, 70.0% yield), was isolated as a white foam. LCMS: m/e 679.7 (M−H)⁻, 3.09 min (method 3).

Example 54

Preparation of 4-((1S,3aS,5aR,5bR,7aS,9S,11aS, 11bR,13aR,13bR)-1-isopropyl-5a,5b,8,8,11a-pentamethyl-3a-(2-(pyridin-2-yl)ethylcarbamoyl) icosahydro-1H-cyclopenta[a]chrysen-9-yl)benzoic acid

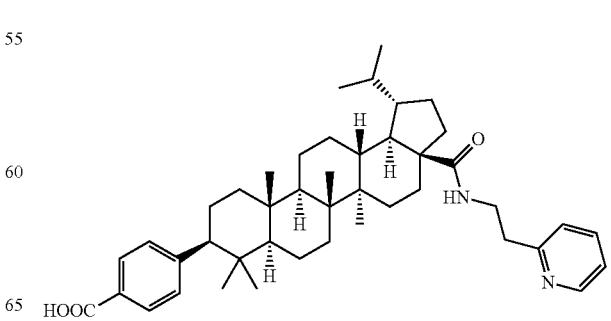

The title compound was prepared following the method described above for the general procedure for the benzoic acid hydrolysis using sodium hydroxide. The product was isolated as a light-yellow (48 mg, 73%). LCMS: m/e 667.6 (M−H)⁻, 2.32 min (method 3). ¹H NMR (500 MHz, DMSO-d₆) δ ppm 12.77 (br. s., 1H), 8.78 (br. s., 1H), 8.33 (br. s., 1H), 7.82 (d, J=7.93 Hz, 2H), 7.66-7.81 (m, 3H), 7.31 (d, J=7.93 Hz, 2H), 3.47-3.56 (m, 2H), 3.05-3.20 (m, 2H), 2.37-2.46 (m, 1H), 1.98-2.23 (m, 3H), 1.64-1.79 (m, 2H), 0.57-1.63 (m, 42H).

Preparation of methyl 4-((1S,3aS,5aR,5bR,7aS,9S,11aS,11bR,13aR,13bR)-3a-(2-(dimethylamino)ethylcarbamoyl)-1-isopropyl-5a,5b,8,8,11a-pentamethylicosahydro-1H-cyclopenta[a]chrysen-9-yl) benzoate. Intermediate 15

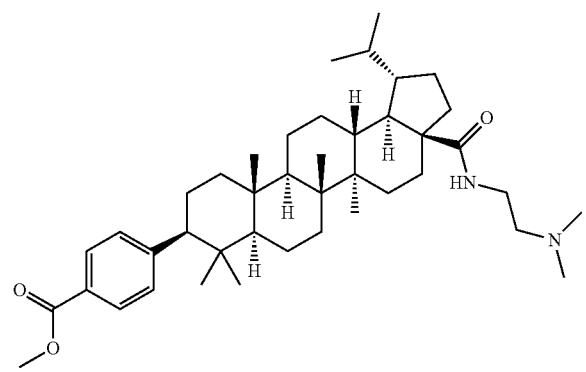

To a flask containing methyl 4-((1R,3aS,5aR,5bR,7aR,11aS,11bR,13aR,13bR)-3a-(chlorocarbonyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate (77 mg, 0.13 mmol) in DCE (2 mL) was added Hunig's base (0.068 mL, 0.390 mmol), DMAP (1 mg, 8.19 mmol), and N,N-dimethylethylenediamine (0.029 mL, 0.260 mmol). The mixture was stirred for two hours at rt. The reaction was quenched with 5 mL of water and was extracted with dichloromethane (3×5 mL). The combined organic layers were dried with Na₂SO₄. The drying agent was removed by filtration and the filtrate was concentrated under reduced pressure and was purified by Biotage flash chromatography using a 0-10% MeOH in dichloromethane gradient. The fractions containing the expected product were combined and concentrated under reduced pressure to give methyl 4-((1S,3aS,5aR,5bR,7aS,9S,11aS,11bR,13aR,13bR)-3a-(2-(dimethylamino)ethylcarbamoyl)-1-isopropyl-5a,5b,8,8,11a-pentamethylicosahydro-1H-cyclopenta[a]chrysen-9-yl) benzoate as a white foam (37 mg, 44% yield). LCMS: m/e 647.7 (M+H)⁺, 3.09 min (method 3).

Example 55

Preparation of 4-((1S,3aS,5aR,5bR,7aS,9S,11aS,11bR,13aR,13bR)-3a-(2-(dimethylamino)ethylcarbamoyl)-1-isopropyl-5a,5b,8,8,11a-pentamethylicosahydro-1H-cyclopenta[a]chrysen-9-yl)benzoic acid

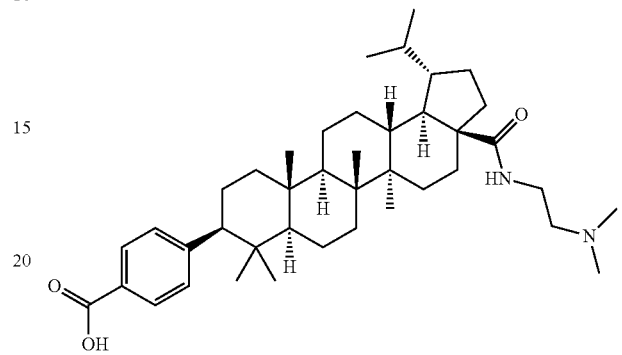

The title compound was prepared following the method described above for the general procedure for the benzoic acid ester hydrolysis using sodium hydroxide. The product was isolated as a white film (3 mg, 8%). LCMS: m/e 631.7 (M−H)⁻, 2.31 min (method 3). ¹H NMR (500 MHz, CHLOROFORM-d) δ ppm 7.94 (d, J=7.94 Hz, 2H), 7.21 (d, J=7.93 Hz, 2H), 7.02 (br. s., 1H), 3.40-3.62 (m, 2H), 2.73-2.85 (m, 2H), 2.54 (s, 6H), 0.65-2.73 (m, 48H).

Example 56

Preparation of 4-((1R,3aS,5aR,5bR,7aR,11aS,11bR,13aR,13bR)-3a-((S)-carboxy(phenyl)methylcarbamoyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl) benzoic acid

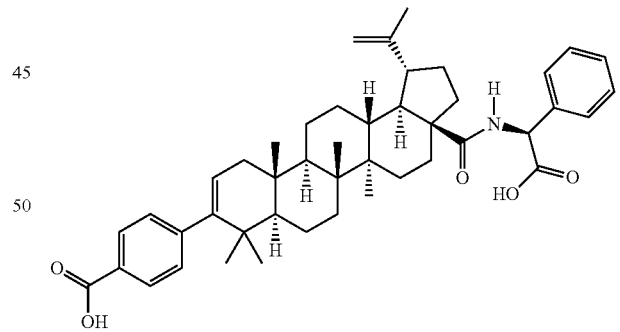

The title compound was prepared following the general procedures described above for the C-28 amide formation and hydrolysis using (S)-methyl 2-amino-2-phenylacetate as the reactant amine. The product was isolated as a white solid (23 mg, 40%). LCMS: m/e 692.60 (M+H)⁺, 2.06 min (method 1). ¹H NMR (500 MHz, DMSO-d₆) δ ppm 7.78 (d, J=7.93 Hz, 2H), 7.59 (d, J=5.19 Hz, 1H), 7.29 (d, J=7.32 Hz, 2H), 7.20 (t, J=7.48 Hz, 2H), 7.15-7.04 (m, 3H), 5.19 (d, J=4.88 Hz, 1H), 4.65 (s, 1H), 4.63 (d, J=5.19 Hz, 1H), 4.54 (s, 1H), 3.13-3.02 (m, 1H), 2.31 (d, J=12.82 Hz, 1H), 2.18-1.98 (m, 2H), 1.64 (s, 3H), 1.86-1.01 (m, 19H), 0.95 (s, 3H), 0.88 (s, 3H), 0.87 (s, 6H), 0.66 (s, 3H).

Example 57

Preparation of 4-((1R,3aS,5aR,5bR,7aR,11aS,11bR, 13aR,13bR)-3a-((S)-1-carboxyethylcarbamoyl)-5a, 5b,8,8,11a-pentamethyl-1-(prop-1-en-2-yl)-2,3,3a,4, 5,5a,5b,6,7,7a,8,11,11a,11b,12,13,13a,13b-octadecahydro-1H-cyclopenta[a]chrysen-9-yl) benzoic acid

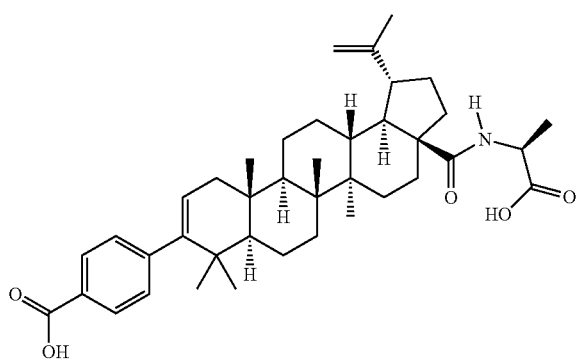

The title compound was prepared following the general procedures described above for the C-28 amide formation and hydrolysis using (S)-methyl 2-aminopropanoate as the reactant amine. The product was isolated as a white solid (33 mg, 55%). LCMS: m/e 630.50 (M+H)$^+$, 2.01 min (method 1). $^1$H NMR (500 MHz, DMSO-d$_6$) δ ppm 7.82 (d, J=8.24 Hz, 2H), 7.45 (d, J=6.10 Hz, 1H), 7.14 (d, J=8.24 Hz, 2H), 5.22 (d, J=4.58 Hz, 1H), 4.67 (d, J=1.83 Hz, 1H), 4.55 (s, 1H), 3.80-3.76 (m, 1H), 3.08-2.94 (m, 1H), 2.59-2.49 (m, 1H), 2.19-1.99 (m, 2H), 1.65 (s, 3H), 1.18 (d, J=7.02 Hz, 3H), 1.81-0.96 (m, 19H), 0.95 (s, 3H), 0.94 (s, 3H), 0.90 (s, 3H), 0.88 (s, 6H).

Example 58

Preparation of 4-((1R,3aS,5aR,5bR,7aR,11aS,11bR, 13aR,13bR)-3a-((S)-1-carboxy-2-phenylethylcarbamoyl)-5a,5b,8,8,11a-pentamethyl-1-(prop-1-en-2-yl)-2,3,3a,4,5,5a,5b,6,7,7a,8,11,11a,11b,12,13,13a, 13b-octadecahydro-1H-cyclopenta[a]chrysen-9-yl) benzoic acid

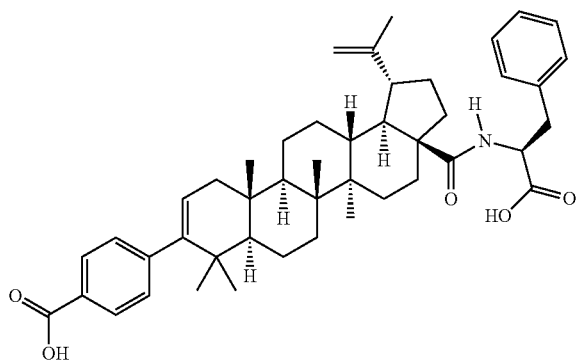

The title compound was prepared following the general procedures described above for the C-28 amide formation and hydrolysis using (S)-methyl 2-amino-3-phenylpropanoate as the reactant amine. The product was isolated as a white solid (28 mg, 46%). LCMS: m/e 706.60 (M+H)$^+$, 2.13 min (method 1). $^1$H NMR (500 MHz, DMSO-d$_6$) δ ppm 7.82 (d, J=8.24 Hz, 2H), 7.28-7.08 (m, 8H), 5.22 (d, J=4.58 Hz, 1H), 4.64 (d, J=2.14 Hz, 1H), 4.52 (s, 1H), 4.21-4.08 (m, 2H), 3.09 (dd, J=13.12, 4.88 Hz, 1H), 2.98 (dd, J=13.12, 7.02 Hz, 1H), 2.57-2.52 (m, 1H), 2.13-1.97 (m, 2H), 1.61 (s, 3H), 1.72-0.96 (m, 19H), 0.93 (s, 6H), 0.88 (s, 3H), 0.88 (s, 6H).

Example 59

Preparation of 4-((1R,3aS,5aR,5bR,7aR,11aS,11bR, 13aR,13bR)-3a-((S)-1-carboxy-3-methylbutylcarbamoyl)-5a,5b,8,8,11a-pentamethyl-1-(prop-1-en-2-yl)-2,3,3a,4,5,5a,5b,6,7,7a,8,11,11a,11b,12,13,13a, 13b-octadecahydro-1H-cyclopenta[a]chrysen-9-yl) benzoic acid

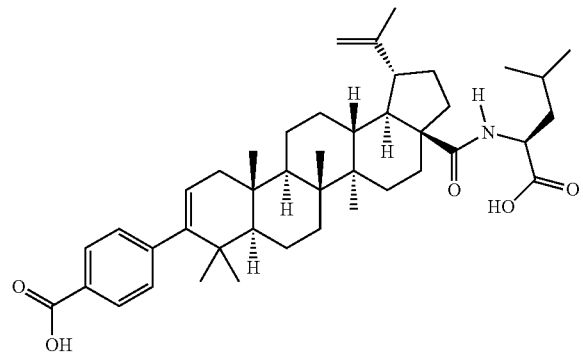

The title compound was prepared following the general procedures described above for the C-28 amide formation and hydrolysis using (S)-methyl 2-amino-4-methylpentanoate as the reactant amine. The product was isolated as a white solid (24 mg, 40%). LCMS: m/e 672.58 (M+H)$^+$, 2.08 min (method 1). $^1$H NMR (500 MHz, DMSO-d$_6$) δ ppm 7.82 (d, J=7.93 Hz, 2H), 7.49 (d, J=7.32 Hz, 1H), 7.15 (d, J=8.24 Hz, 2H), 5.23 (d, J=4.58 Hz, 1H), 4.67 (d, J=2.44 Hz, 1H), 4.55 (s, 1H), 4.19-4.04 (m, 1H), 3.03-2.96 (m, 1H), 2.63-2.53 (m, 1H), 2.23 (d, J=12.82 Hz, 1H), 2.06 (dd, J=17.40, 6.71 Hz, 1H), 1.65 (s, 3H), 1.86-0.96 (m, 22H), 0.95 (s, 3H), 0.93 (s, 3H), 0.90 (s, 3H), 0.88 (s, 6H), 0.86 (d, J=6.41 Hz, 3H), 0.84 (d, J=6.41 Hz, 3H).

Example 60

Preparation of 4-((1R,3aS,5aR,5bR,7aR,11aS,11bR, 13aR,13bR)-3a-(4-chlorobenzylcarbamoyl)-5a,5b,8, 8,11a-pentamethyl-1-(prop-1-en-2-yl)-2,3,3a,4,5,5a, 5b,6,7,7a,8,11,11a,11b,12,13,13a,13b-octadecahydro-1H-cyclopenta[a]chrysen-9-yl) benzoic acid

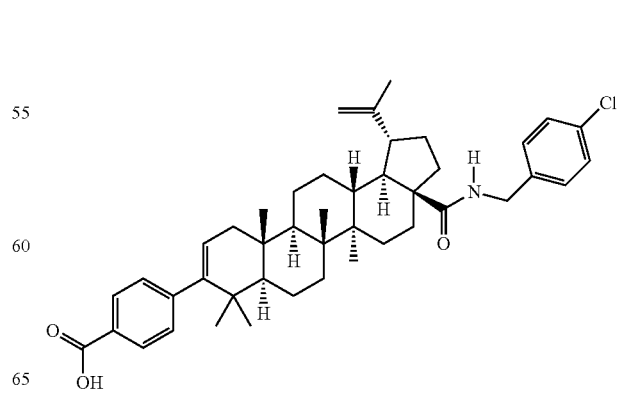

The title compound was prepared following the general procedures described above for the C-28 amide formation and hydrolysis using (4-chlorophenyl)methanamine as the reactant amine. The product was isolated as a white solid (44 mg, 71%). LCMS: m/e 682.53 (M+H)$^+$, 2.22 min (method 1). $^1$H NMR (500 MHz, DMSO-d$_6$) δ ppm 8.22 (t, J=6.26 Hz, 1H), 7.85 (d, J=8.24 Hz, 2H), 7.42-7.33 (m, 2H), 7.27 (d, J=8.55 Hz, 2H), 7.20 (d, J=7.93 Hz, 2H), 5.24 (d, J=4.58 Hz, 1H), 4.67 (d, J=1.83 Hz, 1H), 4.55 (s, 1H), 4.32-4.23 (m, 1H), 4.21-4.13 (m, 1H), 3.03 (td, J=10.99, 3.97 Hz, 1H), 2.56 (d, J=19.84 Hz, 1H), 2.24-2.15 (m, 1H), 2.07 (dd, J=17.85, 6.87 Hz, 1H), 1.64 (s, 3H), 1.88-0.97 (m, 19H), 0.95 (s, 3H), 0.94 (s, 3H), 0.89 (s, 6H), 0.83 (s, 3H).

Example 61

Preparation of 4-((1R,3aS,5aR,5bR,7aR,11aS,11bR, 13aR,13bR)-3a-((S)-1-carboxy-2-methylpropylcarbamoyl)-5a,5b,8,8,11a-pentamethyl-1-(prop-1-en-2-yl)-2,3,3a,4,5,5a,5b,6,7,7a,8,11,11a,11b,12,13,13a, 13b-octadecahydro-1H-cyclopenta[a]chrysen-9-yl) benzoic acid

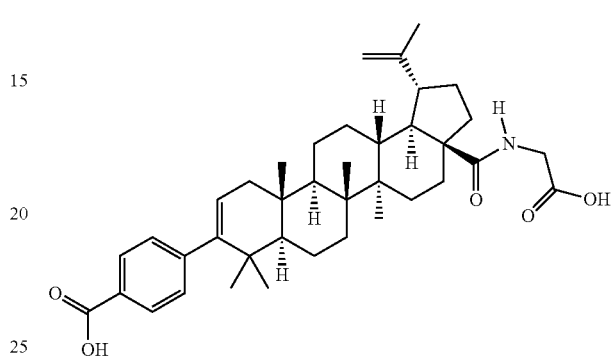

The title compound was prepared following the method described above for the general procedure for C-28 amide formation and hydrolysis using (S)-methyl 2-amino-3-methylbutanoate as the reactant amine. The product was isolated as a white solid (30 mg, 50%). LCMS: m/e 658.56 (M+H)$^+$, 2.04 min (method 1). $^1$H NMR (500 MHz, DMSO-d$_6$) δ ppm 7.85 (d, J=8.24 Hz, 2H), 7.41 (d, J=8.24 Hz, 1H), 7.21 (d, J=8.24 Hz, 2H), 5.24 (d, J=4.58 Hz, 1H), 4.66 (d, J=2.14 Hz, 1H), 4.54 (s, 1H), 4.06 (t, J=7.17 Hz, 1H), 3.06-2.94 (m, 1H), 2.69-2.56 (m, 1H), 2.27 (br. s., 1H), 2.17-2.02 (m, 2H), 1.98-1.89 (m, 1H), 1.65 (s, 3H), 1.77-1.59 (m, 3H), 1.50 (t, J=11.14 Hz, 10H), 1.30-0.97 (m, 5H), 0.96 (s, 3H), 0.94 (s, 3H), 0.92-0.85 (m, 15H).

Example 62

Preparation of 4-((1R,3aS,5aR,5bR,7aR,11aS,11bR, 13aR,13bR)-3a-(carboxymethylcarbamoyl)-5a,5b,8, 8,11a-pentamethyl-1-(prop-1-en-2-yl)-2,3,3a,4,5,5a, 5b,6,7,7a,8,11,11a,11b,12,13,13a,13b-octadecahydro-1H-cyclopenta[a]chrysen-9-yl) benzoic acid

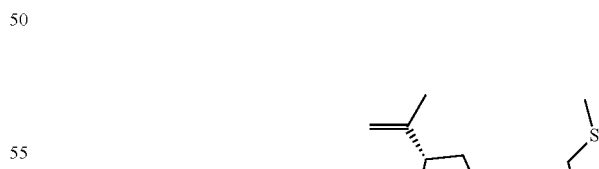

The title compound was prepared following the general procedures described above for the C-28 amide formation and hydrolysis using methyl 2-aminoacetate as the reactant amine. The product was isolated as a white solid (10 mg, 17%). LCMS: m/e 616.48 (M+H)$^+$, 2.01 min (method 1). $^1$H NMR (500 MHz, DMSO-d$_6$) δ ppm 7.78 (d, J=7.93 Hz, 2H), 7.17 (br. s., 1H), 7.08 (d, J=7.32 Hz, 2H), 5.21 (d, J=4.58 Hz, 1H), 4.67 (s, 1H), 4.55 (s, 1H), 3.49-3.40 (m, 2H), 3.05 (t, J=10.38 Hz, 1H), 2.58-2.53 (m, 1H), 2.16-1.98 (m, 2H), 1.64 (s, 3H), 1.84-0.97 (m, 19H), 0.96 (s, 3H), 0.94 (s, 3H), 0.91 (s, 3H), 0.88 (d, J=2.75 Hz, 6H).

Example 63

Preparation of 4-((1R,3aS,5aR,5bR,7aR,11aS,11bR, 13aR,13bR)-3a-((S)-1-carboxy-3-(methylthio)propylcarbamoyl)-5a,5b,8,8,11a-pentamethyl-1-(prop-1-en-2-yl)-2,3,3a,4,5,5a,5b,6,7,7a,8,11,11a,11b,12,13, 13a,13b-octadecahydro-1H-cyclopenta[a]chrysen-9-yl)benzoic acid

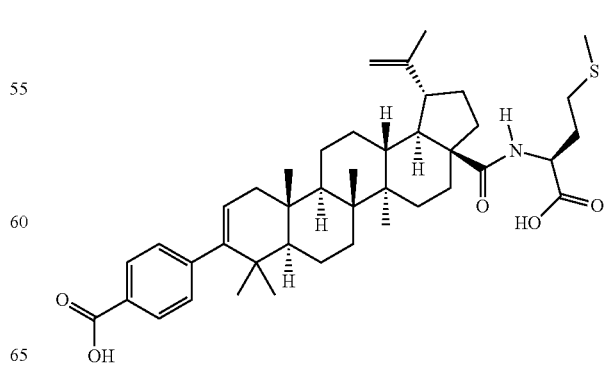

The title compound was prepared following the general procedures described above for the C-28 amide formation and hydrolysis using (S)-methyl 2-amino-4-(methylthio)butanoate as the reactant amine. The product was isolated as a white solid (33 mg, 54%). LCMS: m/e 690.56 (M+H)$^+$, 2.04 min (method 1). $^1$H NMR (500 MHz, DMSO-d$_6$) δ ppm 7.82 (d, J=8.24 Hz, 2H), 7.33 (d, J=5.80 Hz, 1H), 7.15 (d, J=8.24 Hz, 2H), 5.22 (d, J=4.58 Hz, 1H), 4.67 (d, J=1.83 Hz, 1H), 4.55 (s, 1H), 3.92 (d, J=5.49 Hz, 1H), 3.11-2.98 (m, 1H), 2.61-2.53 (m, 1H), 2.42 (t, J=7.78 Hz, 2H), 2.13-2.04 (m, 2H), 2.01 (s, 3H), 1.65 (s, 3H), 2.00-0.98 (m, 21H), 0.96 (s, 3H), 0.94 (s, 3H), 0.92 (s, 3H), 0.88 (s, 6H).

Example 64

Preparation of 4-((1R,3aS,5aR,5bR,7aR,11aS,11bR, 13aR,13bR)-3a-(3-amino-2-hydroxypropylcarbamoyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl) benzoic acid

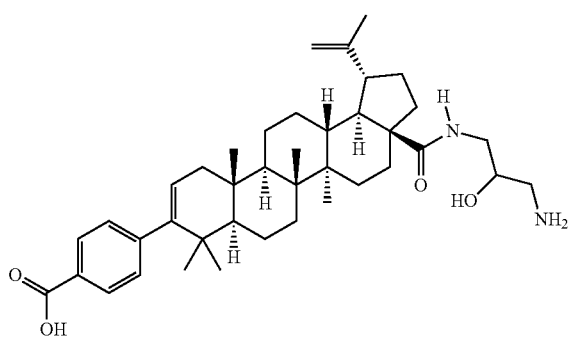

The title compound was prepared following the general procedures described above for the C-28 amide formation and hydrolysis using 1,3-diaminopropan-2-ol as the reactant amine. The product was isolated as a white solid (31 mg, 50%). LCMS: m/e 631.56 (M+H)$^+$, 2.11 min (method 1). $^1$H NMR (500 MHz, DMSO-d$_6$) δ ppm 7.72 (d, J=7.93 Hz, 2H), 7.60 (d, J=5.19 Hz, 1H), 6.95 (d, J=7.94 Hz, 2H), 5.18 (d, J=5.19 Hz, 1H), 4.67 (br. s., 1H), 4.55 (br. s., 1H), 3.44-3.38 (m, 1H), 3.21-2.88 (m, 4H), 2.69-2.58 (m, 1H), 2.45-2.35 (m, 1H), 2.14 (d, J=13.73 Hz, 1H), 2.05 (dd, J=16.48, 6.10 Hz, 1H), 1.64 (s, 3H), 1.85-0.98 (m, 19H), 0.95 (s, 6H), 0.92 (d, J=4.88 Hz, 3H), 0.88 (s, 3H), 0.87 (s, 3H).

Example 65

Preparation of 4-((1R,3aS,5aR,5bR,7aR,11aS,11bR, 13aR,13bR)-3a-((S)-1-carboxy-2-(dimethylamino) ethylcarbamoyl)-5a,5b,8,8,11a-pentamethyl-1-(prop-1-en-2-yl)-2,3,3a,4,5,5a,5b,6,7,7a,8,11,11a,11b,12, 13,13a,13b-octadecahydro-1H-cyclopenta[a] chrysen-9-yl)benzoic acid

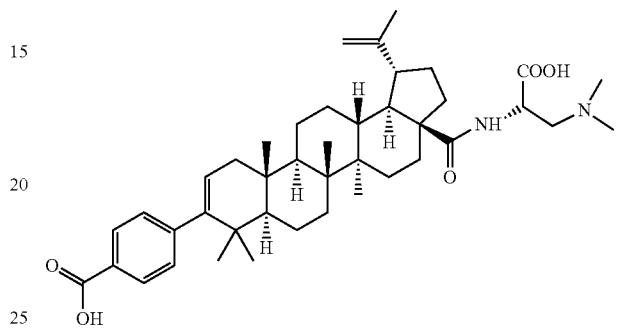

The title compound was prepared following the general procedures described above for the C-28 amide formation and hydrolysis using (S)-2-amino-3-(dimethylamino)propanoic acid as the reactant amine. The product was isolated as a white solid (15 mg, 24%). LCMS: m/e 673.60 (M+H)$^+$, 2.04 min (method 1). $^1$H NMR (500 MHz, DMSO-d$_6$) δ ppm 7.83 (d, J=8.24 Hz, 2H), 7.41-7.28 (m, 1H), 7.18 (d, J=8.24 Hz, 2H), 5.23 (d, J=4.88 Hz, 1H), 4.67 (s, 1H), 4.55 (s, 1H), 4.21-4.11 (m, 1H), 3.10-2.99 (m, 1H), 2.89-2.69 (m, 2H), 2.55-2.52 (m, 1H), 2.44 (s, 6H), 2.15-2.03 (m, 2H), 1.65 (s, 3H), 1.90-1.02 (m, 19H), 0.96 (s, 3H), 0.94 (s, 3H), 0.93 (s, 3H), 0.88 (s, 6H).

Example 66

Procedures for the Preparation of 5-((1R,3aS,5aR, 5bR,7aR,11aS,11bR,13aR,13bR)-3a-(2-(dimethylamino)ethylcarbamoyl)-5a,5b,8,8,11a-pentamethyl-1-(prop-1-en-2-yl)-2,3,3a,4,5,5a,5b,6,7,7a,8,11,11a, 11b,12,13,13a,13b-octadecahydro-1H-cyclopenta[a] chrysen-9-yl)thiophene-2-carboxylic acid

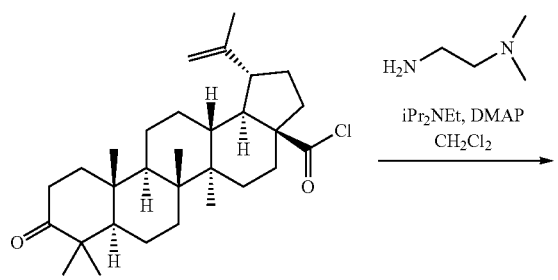

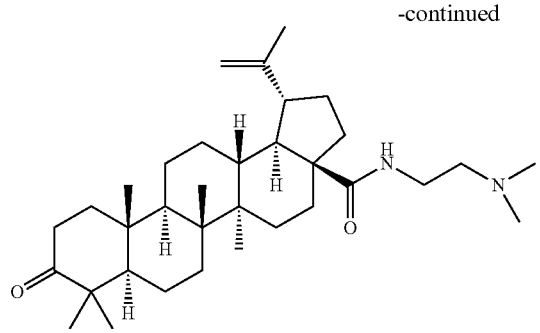 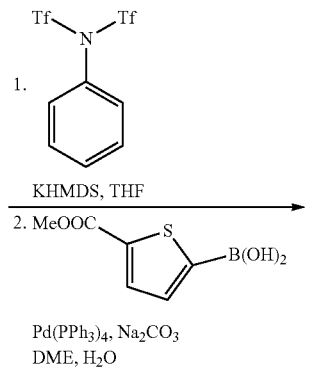

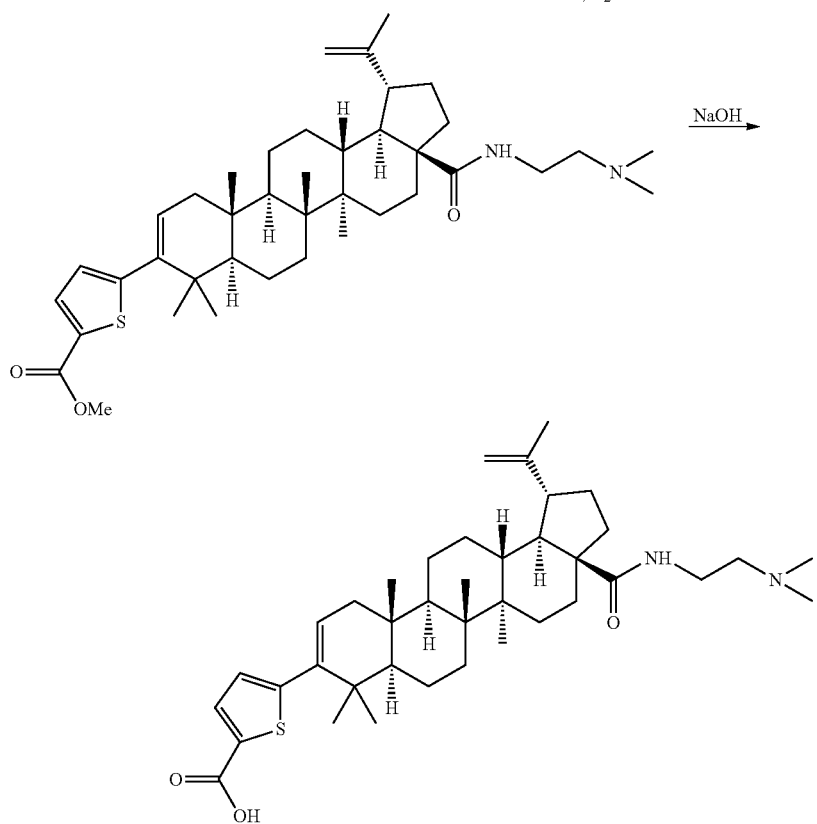

Preparation of (1R,3aS,5aR,5bR,7aR,11aR,11bR, 13aR,13bR)—N-(2-(dimethylamino)ethyl)-5a,5b,8, 8,11a-pentamethyl-9-oxo-1-(prop-1-en-2-yl)icosahy- dro-1H-cyclopenta[a]chrysene-3a-carboxamide. Intermediate 16

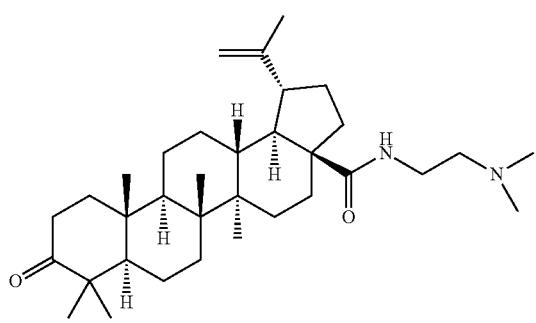

To a mixture of N1,N1-dimethylethane-1,2-diamine (74.5 mg, 0.845 mmol), Hunig'sBase (0.369 mL, 2.114 mmol) and DMAP (5.16 mg, 0.042 mmol) in dichloromethane (2 mL) was added (1R,3aS,5aR,5bR,7aR,11aR,11bR,13aR,13bR)-5a,5b,8,8,11a-pentamethyl-9-oxo-1-(prop-1-en-2-yl) icosahydro-1H-cyclopenta[a]chrysene-3a-carbonyl chloride (200 mg, 0.423 mmol). The reaction mixture was stirred for 16 h. LCMS indicated the formation of desired product. The reaction mixture was concentrated under reduced pressure. The residue was dissolved in methanol and the clear solution was purified by prep HPLC to provide the title compound as a colorless oil (150 mg, 68%). LCMS: m/e 525.56 (M+H)$^+$, 2.27 min (method 1). $^1$H NMR (500 MHz, CHLOROFORM-d) δ ppm 6.89 (t, J=5.04 Hz, 1H), 4.72 (d, J=2.14 Hz, 1H), 4.58 (s, 1H), 3.59-3.34 (m, 2H), 3.12 (td, J=11.06, 4.12 Hz, 1H), 2.67 (t, J=5.80 Hz, 2H), 2.53-2.43 (m, 2H), 2.41 (s, 6H), 2.40-2.32 (m, 1H), 2.07-2.03 (m, 1H), 1.97-1.84 (m, 2H), 1.78 (dd, J=11.60, 7.93 Hz, 1H), 1.71 (dd, J=13.12, 2.44 Hz, 1H), 1.67 (s, 3H), 1.62-1.22 (m, 14H), 1.21-1.11 (m, 1H), 1.06 (s, 3H), 1.01 (s, 3H), 1.04-0.97 (m, 1H), 0.97 (s, 6H), 0.91 (s, 3H).

Preparation of methyl 5-((1R,3aS,5aR,5bR,7aR, 11aS,11bR,13aR,13bR)-3a-(2-(dimethylamino)ethylcarbamoyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)thiophene-2-carboxylate. Intermediate 17

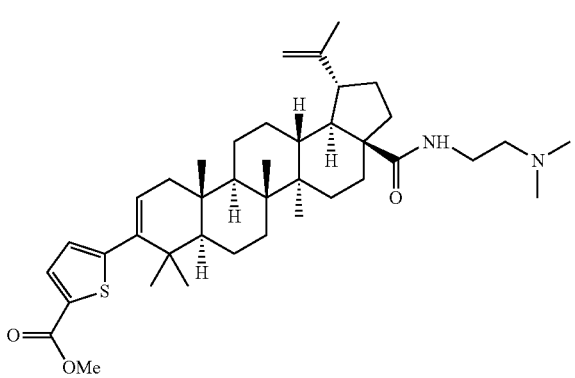

To (1R,3aS,5aR,5bR,7aR,11aR,13aR,13bR)—N-(2-(dimethylamino)ethyl)-5a,5b,8,8,11a-pentamethyl-9-oxo-1-(prop-1-en-2-yl)icosahydro-1H-cyclopenta[a]chrysene-3a-carboxamide (150 mg, 0.286 mmol) in THF (5 mL) at −78° C. was added KHMDS (1.143 mL, 0.572 mmol), the reaction mixture was stirred for 15 minutes at −78° C. then 1,1,1-trifluoro-N-phenyl-N-(trifluoromethylsulfonyl)methanesulfonamide (112 mg, 0.314 mmol) in THF (15 ml) and toluene (5 ml) was added slowly through 20 minutes at −78° C. The reaction mixture was stirred for 2 hours at −78° C. TLC indicated formation of desired product. The reaction mixture was quenched with water, extracted with ethyl acetate (3×5 mL), the extracts was combined, dried over sodium sulfate, filtered and concentrated under reduced pressure to provide the crude (1R,3aS,5aR,5bR,7aR,11aR,13aR,13bR)-3a-(2-(dimethylamino)ethylcarbamoyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl trifluoromethanesulfonate 100 mg as pale red oil.

A mixture of (1R,3aS,5aR,5bR,7aR,11aR,13aR,13bR)-3a-(2-(dimethylamino)ethylcarbamoyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl trifluoromethanesulfonate (100 mg, 0.152 mmol), 5-(methoxycarbonyl)thiophen-2-ylboronic acid (36 mg, 0.228 mmol), tetrakis(triphenylphosphine)palladium(0) (5.2 mg, 0.0045 mmol) and sodium carbonate (48 mg, 0.456 mmol) in water (1 mL) and DME (1 mL) was heated up at 90° C. for 2 hours. The reaction mixture was quenched with distilled water, extracted with ethyl acetate (3×5 mL), the extracts were combined, dried over sodium sulfate, filtered and concentrated under reduced pressure to provide the desired product as a brown oil (60 mg, 32%). LCMS: m/e 647.63 (M−H)⁻, 2.67 min (method 1).

Preparation of 5-((1R,3aS,5aR,5bR,7aR,11aS,11bR, 13aR,13bR)-3a-(2-(dimethylamino)ethylcarbamoyl)-5a,5b,8,8,11a-pentamethyl-1-(prop-1-en-2-yl)-2,3, 3a,4,5,5a,5b,6,7,7a,8,11,11a,11b,12,13,13a,13b-octadecahydro-1H-cyclopenta[a]chrysen-9-yl)thiophene-2-carboxylic acid

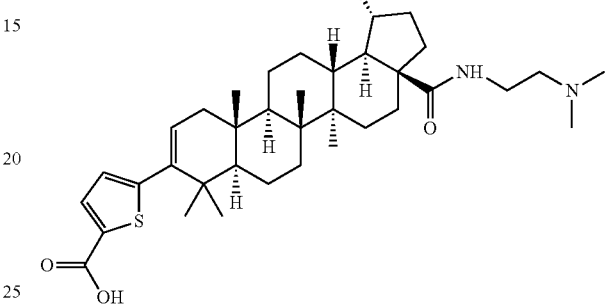

A mixture of methyl 5-((1R,3aS,5aR,5bR,7aR,11aS, 11bR,13aR,13bR)-3a-(2-(dimethylamino)ethylcarbamoyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)thiophene-2-carboxylate (60 mg, 0.092 mmol) and sodium hydroxide (0.028 mL, 0.277 mmol) in dioxane (2 mL) was heated up at 70° C. for 3 hours. LCMS indicated the formation of desired product. The reaction mixture was filtered and purified by prep HPLC to give the title compound as a white solid (6.4 mg, 10%). LCMS: m/e 635.35 (M+H)⁺, 2.18 min (method 1). ¹H NMR (500 MHz, DMSO-d₆) δ ppm 7.49 (t, J=5.65 Hz, 1H), 7.37 (br. s., 1H), 6.86 (d, J=3.66 Hz, 1H), 5.72 (d, J=4.88 Hz, 1H), 4.67 (d, J=2.44 Hz, 1H), 4.55 (s, 1H), 3.21 (td, J=13.20, 6.56 Hz, 1H), 3.08-2.98 (m, 2H), 2.61-2.53 (m, 1H), 2.26 (td, J=6.79, 2.29 Hz, 2H), 2.15 (s, 6H), 2.15-2.06 (m, 2H), 1.64 (s, 3H), 1.82-1.04 (m, 19H), 1.03 (s, 3H), 1.01 (s, 3H), 0.94 (s, 3H), 0.91 (s, 3H), 0.87 (s, 3H).

Preparation of (1R,3aS,5aR,5bR,7aR,11aR,13aR, 13bR)-5a,5b,8,8,11a-pentamethyl-9-oxo-1-(prop-1-en-2-yl)-N-(2-(pyridin-2-yl)ethyl)icosahydro-1H-cyclopenta[a]chrysene-3a-carboxamide. Intermediate 18

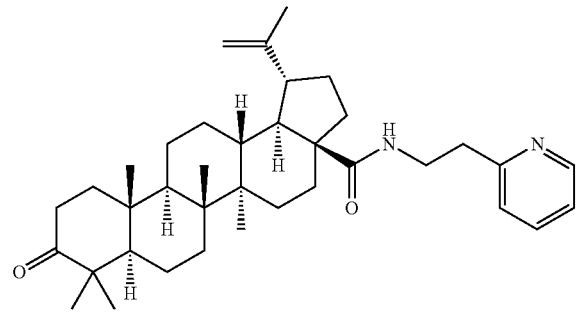

The title compound was prepared following the method described above for (1R,3aS,5aR,5bR,7aR,11aR,11bR, 13aR,13bR)—N-(2-(dimethylamino)ethyl)-5a,5b,8,8,11a-pentamethyl-9-oxo-1-(prop-1-en-2-yl)icosahydro-1H-cyclopenta[a]chrysene-3a-carboxamide using N1,N1-diisopropylethane-1,2-diamine as the reactant amine. The product was isolated as a white solid (150 mg, 64%). LCMS: m/e 559.25 (M+H)$^+$, 2.25 min (method 1). $^1$H NMR (500 MHz, CHLOROFORM-d) δ ppm 8.51 (d, J=3.97 Hz, 1H), 7.62 (td, J=7.63, 1.83 Hz, 1H), 7.22-7.10 (m, 2H), 6.71 (t, J=5.34 Hz, 1H), 4.72 (d, J=2.14 Hz, 1H), 4.58 (s, 1H), 3.80-3.58 (m, 2H), 3.08 (td, J=11.14, 3.97 Hz, 1H), 3.03-2.92 (m, 2H), 2.58-2.29 (m, 4H), 1.96 (dt, J=13.35, 3.09 Hz, 1H), 1.92-1.82 (m, 2H), 1.70-1.65 (m, 2H), 1.66 (s, 3H), 1.56 (t, J=11.44 Hz, 1H), 1.50-1.14 (m, 13H), 1.05 (s, 3H), 1.00 (s, 3H), 1.04-0.95 (m, 1H), 0.93 (s, 3H), 0.88 (s, 3H), 0.86 (s, 3H).

Example 67

Preparation of 4-((1R,3aS,5aR,5bR,7aR,11aS,11bR, 13aR,13bR)-3a-(2-(diisopropylamino)ethylcarbamoyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

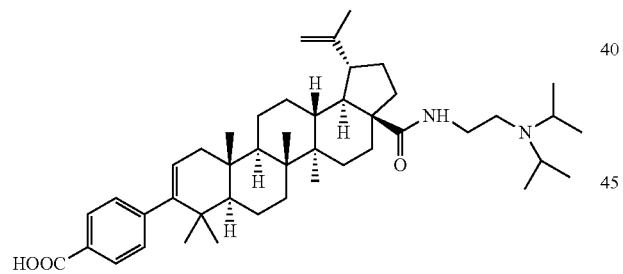

The title compound was prepared following the general procedures described above for the C-28 amide formation and hydrolysis using N1,N1-diisopropylethane-1,2-diamine as the reactant amine. The product was isolated as a white solid (19 mg, 31%). LCMS: m/e 685.39 (M+H)$^+$, 2.22 min (method 1). $^1$H NMR (500 MHz, CHLOROFORM-d) δ ppm 7.95 (d, J=8.24 Hz, 2H), 7.63 (br. s., 1H), 7.16 (d, J=8.24 Hz, 2H), 5.28 (d, J=4.58 Hz, 1H), 4.74 (s, 1H), 4.58 (s, 1H), 3.65-3.43 (m, 2H), 3.43-3.32 (m, 2H), 3.21-3.08 (m, 1H), 3.01-2.78 (m, 2H), 2.48 (td, J=12.13, 3.51 Hz, 1H), 1.25 (t, J=5.95 Hz, 12H), 2.30-0.99 (m, 21H), 0.98 (s, 3H), 0.97 (s, 3H), 0.96 (s, 3H), 0.91 (s, 6H).

Example 68

Preparation of 4-((1R,3aS,5aR,5bR,7aR,11aS,11bR, 13aR,13bR)-3a-((S)-1-(dimethylamino)propan-2-ylcarbamoyl)-5a,5b,8,8,11a-pentamethyl-1-(prop-1-en-2-yl)-2,3,3a,4,5,5a,5b,6,7,7a,8,11,11a,11b,12,13, 13a,13b-octadecahydro-1H-cyclopenta[a]chrysen-9-yl)benzoic acid

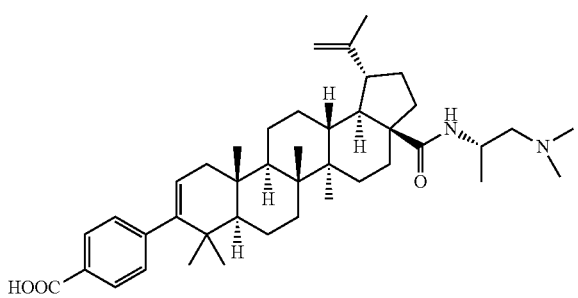

The title compound was prepared following the general procedures described above for the C-28 amide formation and hydrolysis using (S)—N1,N1-dimethylpropane-1,2-diamine as the reactant amine. The product was isolated as a white solid (39 mg, 76%). LCMS: m/e 643.58 (M+H)$^+$, 2.25 min (method 1). $^1$H NMR (500 MHz, CHLOROFORM-d) δ ppm 7.93 (d, J=7.94 Hz, 2H), 7.18 (d, J=8.24 Hz, 2H), 5.29 (d, J=5.19 Hz, 1H), 4.72 (d, J=10.07 Hz, 1H), 4.56 (br. s., 1H), 4.38-4.04 (m, 1H), 3.30-3.02 (m, 1H), 2.77-2.30 (m, 8H), 1.65 (s, 3H), 2.23-1.03 (m, 25H), 0.99 (d, J=3.97 Hz, 3H), 0.96 (s, 3H), 0.94 (d, J=3.97 Hz 3H), 0.92 (s, 6H).

Example 69

Preparation of 4-((1R,3aS,5aR,5bR,7aR,11aS,11bR, 13aR,13bR)-3a-(2-methoxyethylcarbamoyl)-5a,5b,8, 8,11a-pentamethyl-1-(prop-1-en-2-yl)-2,3,3a,4,5,5a, 5b,6,7,7a,8,11,11a,11b,12,13,13a,13b-octadecahydro-1H-cyclopenta[a]chrysen-9-yl)benzoic acid

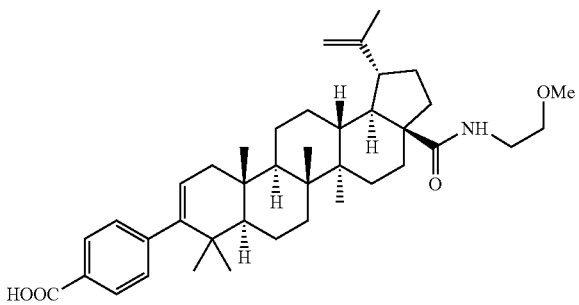

The title compound was prepared following the general procedures described above for the C-28 amide formation and hydrolysis using 2-methoxyethanamine as the reactant amine. The product was isolated as a white solid (31 mg, 50%). LCMS: m/e 616.47 (M+H)$^+$, 2.18 min (method 1). $^1$H NMR (500 MHz, CHLOROFORM-d) δ ppm 7.98 (d, J=7.93 Hz, 2H), 7.22 (d, J=8.24 Hz, 2H), 5.98 (t, J=5.49 Hz, 1H), 5.29 (d, J=4.58 Hz, 1H), 4.75 (d, J=1.83 Hz, 1H), 4.59 (s, 1H), 3.57-3.37 (m, 4H), 3.36 (s, 3H), 3.14 (td, J=11.06, 4.12 Hz, 1H), 2.56-2.41 (m, 1H), 2.10 (dd, J=17.24, 6.56 Hz, 1H), 1.96 (d, J=10.38 Hz, 1H), 1.68 (s, 3H), 1.82-1.01 (m, 19H), 1.00 (s, 6H), 0.97 (s, 3H), 0.92 (d, J=1.83 Hz, 6H).

Example 70

Preparation of 4-((1R,3aS,5aR,5bR,7aR,11aS,11bR,13aR,13bR)-3a-(2-(diethylamino)ethylcarbamoyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

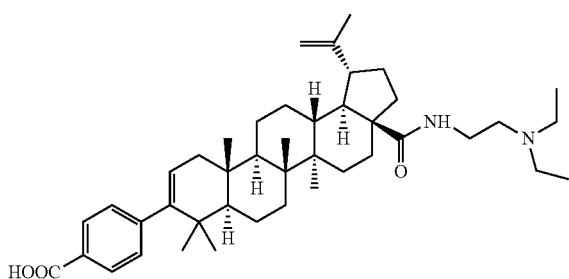

The title compound was prepared following the general procedures described above for the C-28 amide formation and hydrolysis using N1,N1-diethylethane-1,2-diamine as the reactant amine. The product was isolated as a white solid (30 mg, 49%). LCMS: m/e 657.51 (M+H)+, 2.27 min (method 1). ¹H NMR (500 MHz, CHLOROFORM-d) δ ppm 7.93 (d, J=8.24 Hz, 2H), 7.48 (br. s., 1H), 7.15 (d, J=8.24 Hz, 2H), 5.29 (d, J=5.19 Hz, 1H), 4.73 (s, 1H), 4.58 (s, 1H), 3.69-3.48 (m, 2H), 3.19-3.08 (m, 1H), 3.02-2.89 (m, 6H), 2.52-2.40 (m, 1H), 1.67 (s, 3H), 1.28-1.22 (m, 6H), 2.18-0.99 (m, 21H), 0.97 (s, 3H), 0.95 (s, 6H), 0.91 (s, 6H).

Example 71

Preparation of 4-((1R,3aS,5aR,5bR,7aR,11aS,11bR,13aR,13bR)-3a-(2,3-dihydroxypropylcarbamoyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

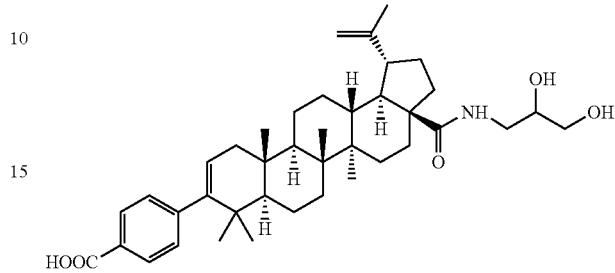

The title compound was prepared following the general procedures described above for the C-28 amide formation and hydrolysis using 3-aminopropane-1,2-diol as the reactant amine. The product was isolated as a white solid (33 mg, 55%). LCMS: m/e 632.44 (M+H)+, 2.08 min (method 1). ¹H NMR (500 MHz, CHLOROFORM-d) δ ppm 7.97 (d, J=7.94 Hz, 2H), 7.22 (d, J=8.24 Hz, 2H), 6.03 (t, J=5.95 Hz, 1H), 5.29 (d, J=5.49 Hz, 1H), 4.75 (s, 1H), 4.61 (s, 1H), 3.81-3.73 (m, 1H), 3.62-3.51 (m, 2H), 3.52-3.35 (m, 2H), 3.19-3.03 (m, 1H), 2.58-2.40 (m, 1H), 2.11 (dd, J=17.09, 6.71 Hz, 1H), 2.02-1.89 (m, 1H), 1.69 (s, 3H), 1.82-1.02 (m, 19H), 1.01 (s, 3H), 1.00 (s, 3H), 0.98 (s, 3H), 0.92 (s, 6H).

Example 72

Preparation of 4-((1R,3aS,5aR,5bR,7aR,11aS,11bR,13aR,13bR)-3a-(2-(ethyl(2-hydroxyethyl)amino)ethylcarbamoyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

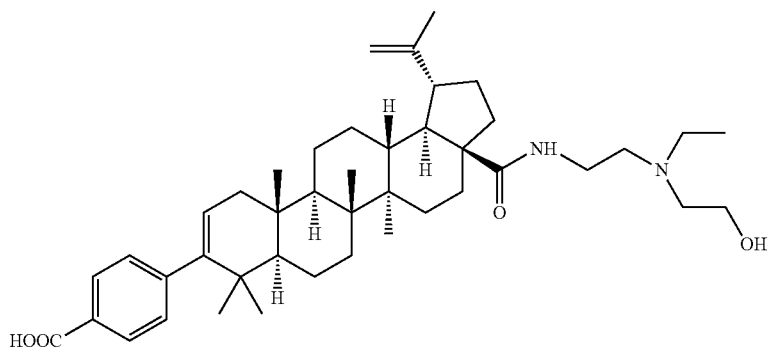

The title compound was prepared following the general procedures described above for the C-28 amide formation and hydrolysis using 2-((2-aminoethyl)(ethyl)amino)ethanol as the reactant amine. The product was isolated as a white solid (37 mg, 72%). LCMS: m/e 673.56 (M+H)+, 2.15 min (method 1). ¹H NMR (500 MHz, Acetic Acid-d₄) δ ppm 8.03 (d, J=8.24 Hz, 2H), 7.30 (d, J=8.55 Hz, 2H), 5.37 (d, J=4.58 Hz, 1H), 4.78 (d, J=1.83 Hz, 1H), 4.65 (s, 1H), 4.06 (t, J=5.04 Hz, 2H), 3.88-3.64 (m, 2H), 3.55-3.35 (m, 6H), 3.14 (t, J=11.29 Hz, 1H), 2.62-2.47 (m, 1H), 2.29-2.14 (m, 2H), 1.39 (t, J=7.17 Hz, 3H), 2.13-1.09 (m, 19H), 1.08 (s, 3H), 1.06 (s, 3H), 1.06 (s, 3H), 1.01 (s, 3H), 0.99 (s, 3H).

Example 73

Preparation of 4-((1R,3aS,5aR,5bR,7aR,11aS,11bR,13aR,13bR)-3a-(2-((2-hydroxyethyl)(methyl)amino)ethylcarbamoyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

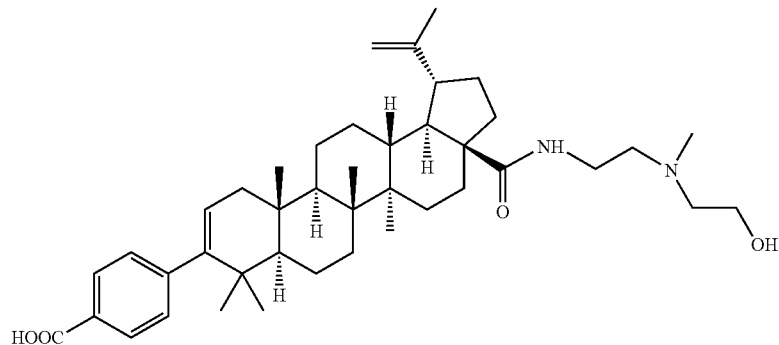

The title compound was prepared following the general procedures described above for the C-28 amide formation and hydrolysis using 2-((2-aminoethyl)(methyl)amino)ethanol as the reactant amine. The product was isolated as a white solid (30 mg, 56%). LCMS: m/e 659.48 (M+H)$^+$, 2.15 min (method 1). $^1$H NMR (500 MHz, Acetic Acid-d$_4$) δ ppm 8.03 (d, J=8.24 Hz, 2H), 7.30 (d, J=8.24 Hz, 2H), 5.37 (d, J=4.27 Hz, 1H), 4.78 (d, J=1.22 Hz, 1H), 4.65 (s, 1H), 4.05 (t, J=5.04 Hz, 2H), 3.89-3.68 (m, 2H), 3.60-3.38 (m, 4H), 3.22-3.10 (m, 1H), 3.04 (s, 3H), 2.54 (td, J=12.21, 3.36 Hz, 1H), 2.28-2.20 (m, 2H), 1.74 (s, 3H), 2.11-1.09 (m, 19H), 1.08 (s, 3H), 1.06 (s, 3H), 1.05 (s, 3H), 1.01 (s, 3H), 0.99 (s, 3H).

Example 74

Preparation of 4-((1R,3aS,5aR,5bR,7aR,11aS,11bR,13aR,13bR)-3a-(2-(2-hydroxyethylamino)ethylcarbamoyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

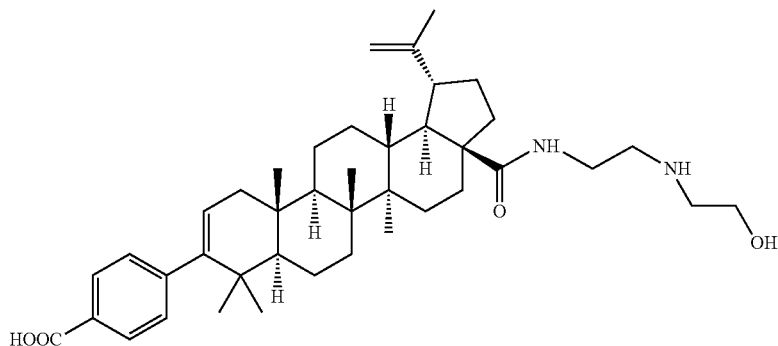

The title compound was prepared following the general procedures described above for the C-28 amide formation and hydrolysis using 2-(2-aminoethylamino)ethanol as the reactant amine. The product was isolated as a white solid (32 mg, 56%). LCMS: m/e 645.54 (M+H)$^+$, 2.13 min (method 1). $^1$H NMR (500 MHz, Acetic Acid-d$_4$) δ ppm 8.03 (d, J=8.54 Hz, 2H), 7.30 (d, J=8.24 Hz, 2H), 5.37 (d, J=4.58 Hz, 1H), 4.78 (s, 1H), 4.65 (s, 1H), 4.10-3.92 (m, 2H), 3.84-3.60 (m, 2H), 3.46-3.28 (m, 4H), 3.24-2.95 (m, 1H), 2.56 (td, J=12.13, 3.20 Hz, 1H), 1.74 (s, 3H), 2.28-1.19 (m, 21H), 1.08 (s, 3H), 1.06 (s, 3H), 1.05 (s, 3H), 1.01 (s, 3H), 0.99 (s, 3H).

Example 75
Procedures for the Preparation of 4-((1R,3aS,5aR,5bR,7aR,11aS,11bR,13aR,13bR)-5a,5b,8,8,11a-pentamethyl-3a-(2-(N-methylacetamido)ethylcarbamoyl)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid
5
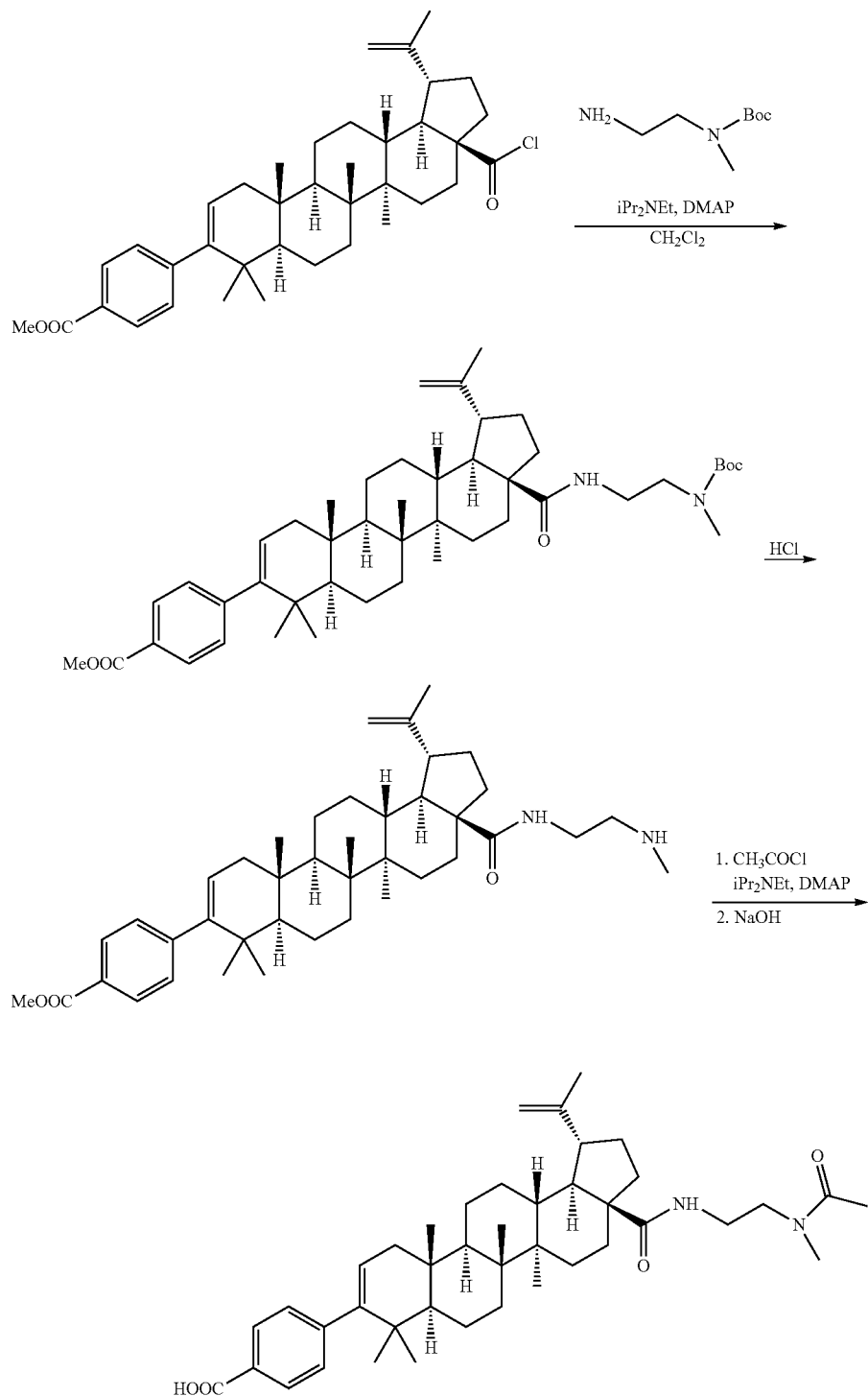

Preparation of methyl 4-((1R,3aS,5aR,5bR,7aR, 11aS,11bR,13aR,13bR)-3a-(2-(tert-butoxycarbonyl (methyl)amino)ethylcarbamoyl)-5a,5b,8,8,11a-pentamethyl-1-(prop-1-en-2-yl)-2,3,3a,4,5,5a,5b,6,7,7a, 8,11,11a,11b,12,13,13a,13b-octadecahydro-1H-cyclopenta[a]chrysen-9-yl)benzoate. Intermediate 19

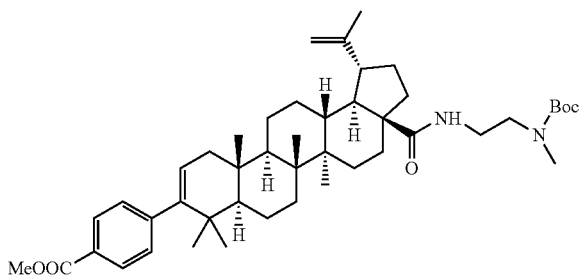

To a mixture of tert-butyl 2-aminoethyl(methyl)carbamate (17.68 mg, 0.101 mmol), Hunig'sBase (0.053 mL, 0.304 mmol) and DMAP (1.240 mg, 10.15 µmol) in DCM (1 mL) was added methyl 4-((1R,3aS,5aR,5bR,7aR,11aS,11bR, 13aR,13bR)-3a-(chlorocarbonyl)-5a,5b,8,8,11a-pentamethyl-1-(prop-1-en-2-yl)-2,3,3a,4,5,5a,5b,6,7,7a,8,11,11a, 11b,12,13,13a,13b-octadecahydro-1H-cyclopenta[a] chrysen-9-yl)benzoate (60 mg, 0.101 mmol) in DCM (1 mL). The reaction mixture was stirred for 1 hour. LCMS indicated the formation of desired product. The reaction mixture was quenched with distilled water, extracted with DCM (3×3 mL). All the extracts were combined, dried over sodium sulfate, filtered and concentrated under reduced pressure to provide the desired product as white solid (65 mg, 88%). LCMS: m/e 729.61 (M+H)+, 2.72 min (method 1).

Preparation of methyl 4-((1R,3aS,5aR,5bR,7aR, 11aS,11bR,13aR,13bR)-5a,5b,8,8,11a-pentamethyl-3a-(2-(methylamino)ethylcarbamoyl)-1-(prop-1-en-2-yl)-2,3,3a,4,5,5a,5b,6,7,7a,8,11,11a,11b,12,13,13a, 13b-octadecahydro-1H-cyclopenta[a]chrysen-9-yl) benzoate. Intermediate 20

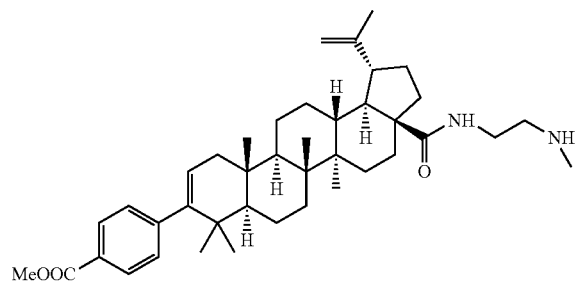

A mixture of methyl 4-((1R,3aS,5aR,5bR,7aR,11aS, 11bR,13aR,13bR)-3a-(2-(tert-butoxycarbonylmethyl) amino)ethylcarbamoyl)-5a,5b,8,8,11a-pentamethyl-1-(prop-1-en-2-yl)-2,3,3a,4,5,5a,5b,6,7,7a,8,11,11a,11b,12, 13,13a,13b-octadecahydro-1H-cyclopenta[a]chrysen-9-yl) benzoate (65 mg, 0.089 mmol) and 4N HCl (0.111 mL, 0.446 mmol) in DCM (1 mL) was stirred for 16 hours at room temperature. LCMS indicated the formation of desired product. The reaction mixture was concentrated under reduced pressure to provide the desired product as white solid (45 mg, 80%). LCMS: m/e 629.52 (M+H)+, 2.65 min (method 1).

Preparation of 4-((1R,3aS,5aR,5bR,7aR,11aS,11bR, 13aR,13bR)-5a,5b,8,8,11a-pentamethyl-3a-(2-(N-methylacetamido)ethylcarbamoyl)-1-(prop-1-en-2-yl)-2,3,3a,4,5,5a,5b,6,7,7a,8,11,11a,11b,12,13,13a, 13b-octadecahydro-1H-cyclopenta[a]chrysen-9-yl) benzoic acid

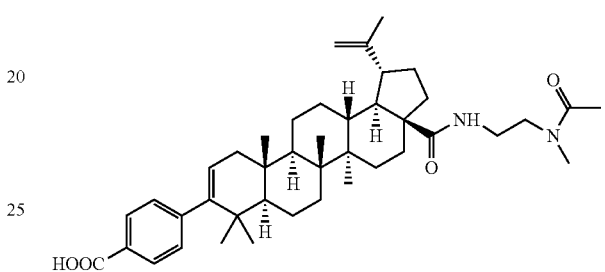

The title compound was prepared following the general procedures described above for the C-28 amide formation and hydrolysis using methyl 4-((1R,3aS,5aR,5bR,7aR,11aS, 11bR,13aR,13bR)-5a,5b,8,8,11a-pentamethyl-3a-(2-(methylamino)ethylcarbamoyl)-1-(prop-1-en-2-yl)-2,3,3a,4,5, 5a,5b,6,7,7a,8,11,11a,11b,12,13,13a,13b-octadecahydro-1H-cyclopenta[a]chrysen-9-yl)benzoate as the reactant amine and acetyl chloride as the reactant acid chloride. The product was isolated as a white solid (35 mg, 75%). LCMS: m/e 657.53 (M+H)+, 2.13 min (method 1). $^1$H NMR (500 MHz, Acetic Acid-d$_4$) δ ppm 8.03 (d, J=8.24 Hz, 2H), 7.30 (d, J=8.24 Hz, 2H), 5.37 (d, J=4.27 Hz, 1H), 4.78 (s, 1H), 4.64 (br. s., 1H), 3.72-3.41 (m, 4H), 3.20-3.15 (m, 1H), 3.14 (s, 3H), 2.68-2.48 (m, 1H), 2.18 (s, 3H), 1.73 (s, 3H), 2.26-1.17 (m, 21H), 1.07 (s, 3H), 1.06 (s, 3H), 1.06 (s, 3H), 1.01 (s, 3H), 0.99 (s, 3H).

Example 76

Preparation of 4-((1R,3aS,5aR,5bR,7aR,11aS,11bR, 13aR,13bR)-3a-(2-(bis(2-hydroxyethyl)amino)ethylcarbamoyl)-5a,5b,8,8,11a-pentamethyl-1-(prop-1-en-2-yl)-2,3,3a,4,5,5a,5b,6,7,7a,8,11,11a,11b,12,13,13a, 13b-octadecahydro-1H-cyclopenta[a]chrysen-9-yl) benzoic acid

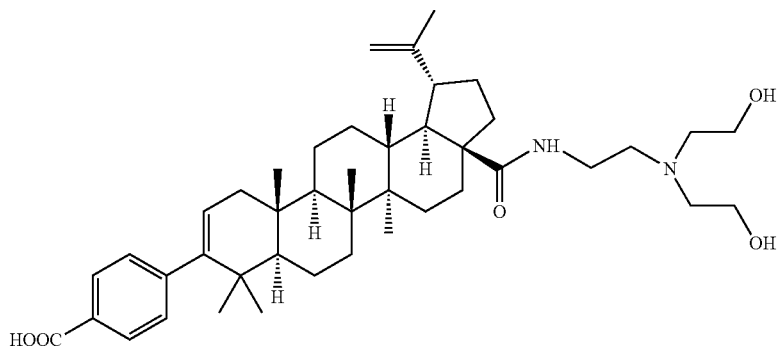

The title compound was prepared following the general procedures described above for the C-28 amide formation and hydrolysis using 2,2'-(2-aminoethylazanediyl)diethanol as the reactant amine. The product was isolated as a white solid (14 mg, 28%). LCMS: m/e 689.56 (M+H)$^+$, 2.11 min (method 1). $^1$H NMR (500 MHz, Acetic Acid-d$_4$) δ ppm 8.03 (d, J=8.24 Hz, 2H), 7.30 (d, J=8.24 Hz, 2H), 5.50-5.29 (m, 1H), 4.78 (s, 1H), 4.65 (s, 1H), 4.11 (t, J=4.58 Hz, 4H), 3.95-3.72 (m, 2H), 3.62 (d, J=4.58 Hz, 6H), 3.25-3.06 (m, 1H), 2.54 (td, J=12.59, 2.90 Hz, 1H), 1.74 (s, 3H), 2.34-1.21 (m, 21H), 1.08 (s, 3H), 1.06 (s, 3H), 1.06 (s, 3H), 1.01 (s, 3H), 0.99 (s, 3H).

Example 77

Procedures for the Preparation of 4-((1R,3aS,5aR, 5bR,7aR,11aS,11bR,13aR,13bR)-3a-((2-(dimethylamino)ethyl)(2-hydroxyethyl)carbamoyl)-5a,5b,8,8, 11a-pentamethyl-1-(prop-1-en-2-yl)-2,3,3a,4,5,5a, 5b,6,7,7a,8,11,11a,11b,12,13,13a,13b-octadecahydro-1H-cyclopenta[a]chrysen-9-yl) benzoic acid

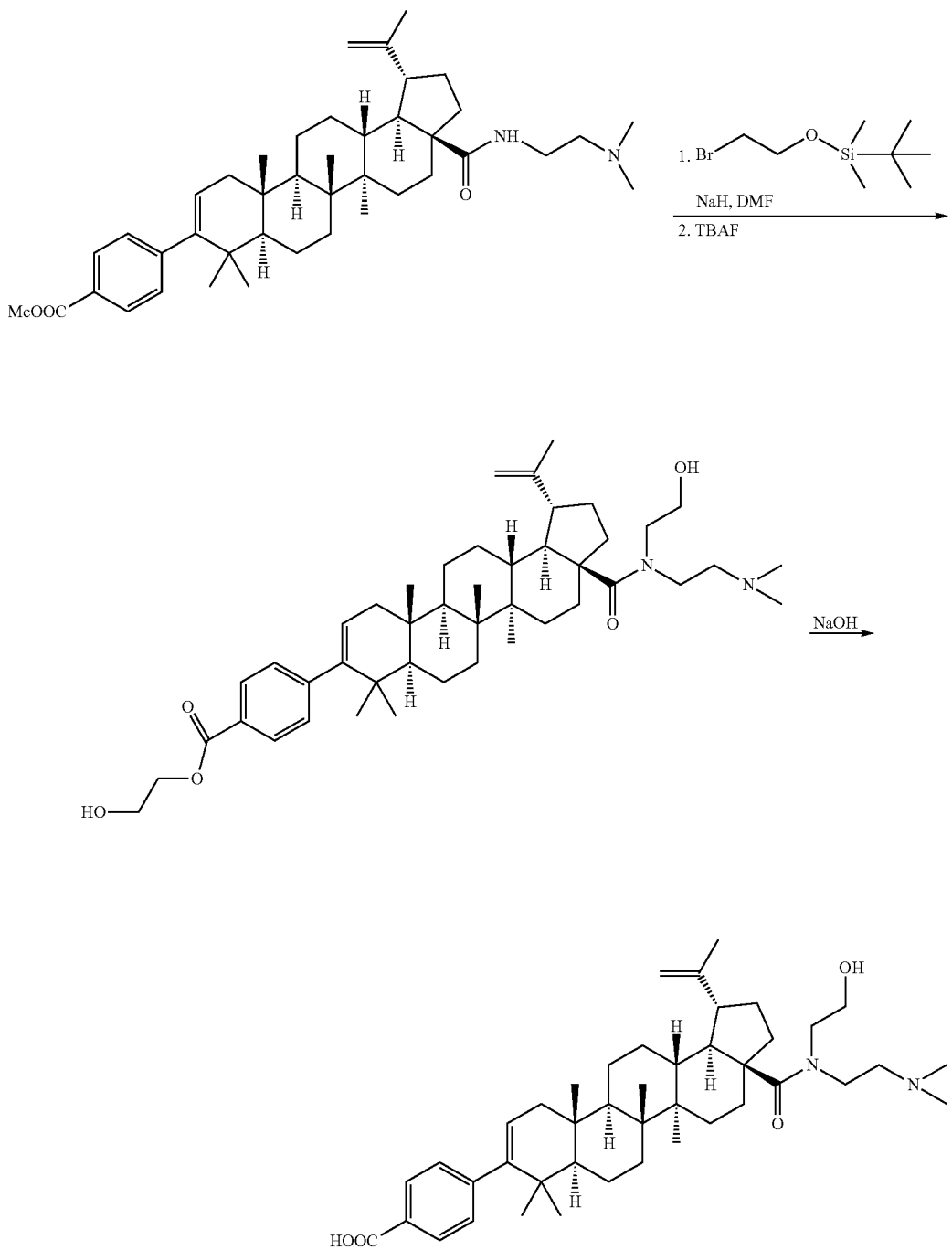

Preparation of 2-hydroxyethyl 4-((1R,3aS,5aR,5bR,7aR,11aS,11bR,13aR,13bR)-3a-((2-(dimethylamino)ethyl)(2-hydroxyethyl)carbamoyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate. Intermediate 21

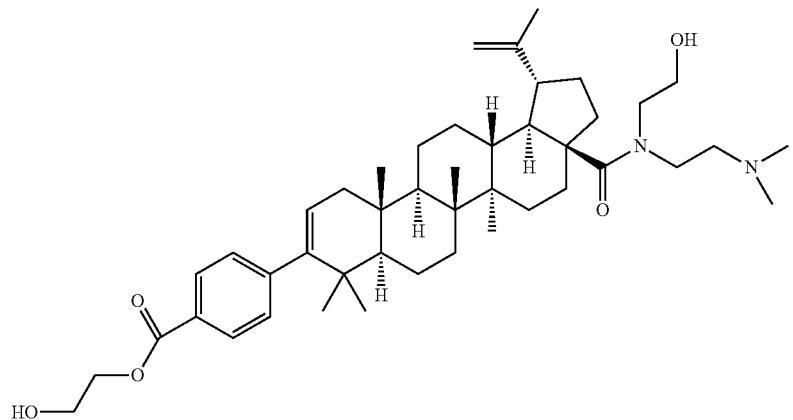

To a mixture of methyl 4-((1R,3aS,5aR,5bR,7aR,11aS,11bR,13aR,13bR)-3a-(2-(dimethylamino)ethylcarbamoyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate (30 mg, 0.047 mmol) in DMF (1 mL) was added 60% sodium hydride (3.73 mg, 0.093 mmol) under nitrogen atmosphere. The reaction mixture was stirred for 20 minutes at room temperature. (2-bromoethoxy)(tert-butyl)dimethylsilane (13.39 mg, 0.056 mmol) was added under nitrogen atmosphere at room temperature. The reaction mixture was heated up at 78° C. for 18 hours. The reaction mixture was quenched with water, extracted with DCM (3×4 mL), the extracts was combined, dried over sodium sulfate, filtered and concentrated under reduced to provide the desired intermediate as colourless oil. To this intermediate in DCM (1 mL) was added TBAF (16.46 mg, 0.047 mmol). The reaction mixture was stirred for 20 minutes. LCMS indicated the formation of desired product. The reaction mixture was concentrated under reduced pressure to provide the title compound as white solid (6 mg, 33%). LCMS: m/e 717.64 (M+H)⁺, 2.27 min (method 1).

Preparation of 4-((1R,3aS,5aR,5bR,7aR,11aS,11bR,13aR,13bR)-3a-((2-(dimethylamino)ethyl)(2-hydroxyethyl)carbamoyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

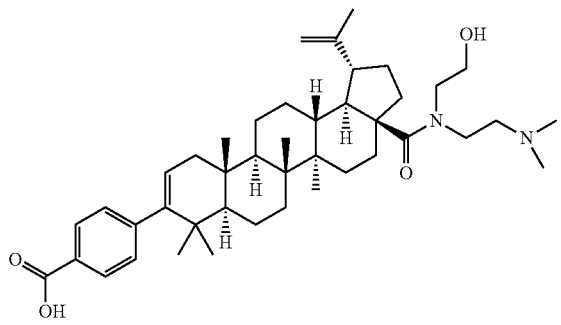

A mixture of 2-hydroxyethyl 4-((1R,3aS,5aR,5bR,7aR,11aS,11bR,13aR,13bR)-3a-((2-(dimethylamino)ethyl)(2-hydroxyethyl)carbamoyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate (6 mg, 8.37 μmol) and sodium hydroxide (0.042 mL, 0.042 mmol) in dioxane (1 mL) was heated up at 78° C. for 3 hours. The solution was diluted with water and filtered. The clear solution was purified by prep HPLC to provide the title compound as a white solid (5 mg, 84%). LCMS: m/e 673.58 (M+H)⁺, 2.08 min (method 1). ¹H NMR (500 MHz, Acetic Acid-d₄) δ ppm 8.03 (d, J=8.24 Hz, 2H), 7.30 (d, J=8.55 Hz, 2H), 5.43-5.31 (m, 1H), 4.78 (d, J=1.53 Hz, 1H), 4.66 (s, 1H), 4.26-4.13 (m, 2H), 3.90-3.78 (m, 2H), 3.75-3.63 (m, 4H), 3.30 (s, 6H), 3.20-3.07 (m, 1H), 2.60-2.45 (m, 1H), 1.74 (s, 3H), 2.26-1.22 (m, 21H), 1.08 (s, 3H), 1.07 (s, 3H), 1.05 (s, 3H), 1.01 (s, 3H), 0.99 (s, 3H).

Example 78

Procedures for the Preparation of 4-((1S,3aS,5aR,5bR,7aR,11aS,11bR,13aR,13bR)-3a-(2-(dimethylamino)ethylcarbamoyl)-1-isopropyl-5a,5b,8,8,11a-pentamethyl-2,3,3a,4,5,5a,5b,6,7,7a,8,11,11a,11b,12,13,13a,13b-octadecahydro-1H-cyclopenta[a]chrysen-9-yl)benzoic acid

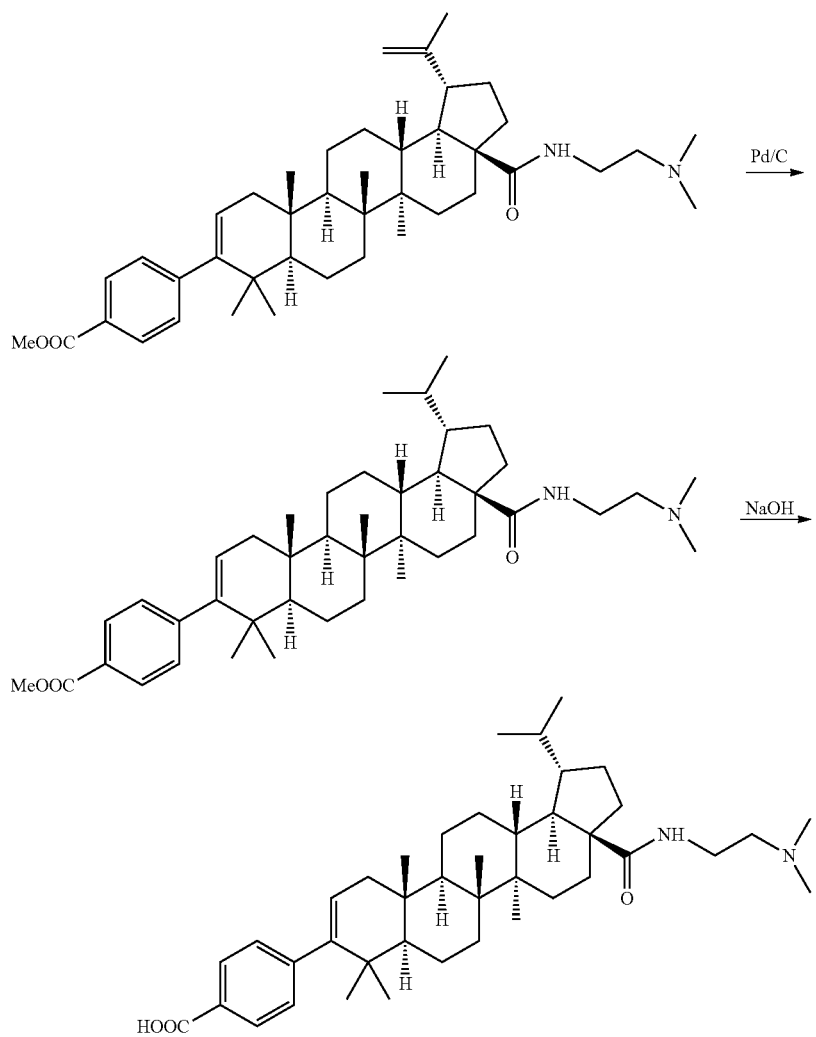

Preparation of methyl 4-((1S,3aS,5aR,5bR,7aR,11aS,11bR,13aR,13bR)-3a-(2-(dimethylamino)ethylcarbamoyl)-1-isopropyl-5a,5b,8,8,11a-pentamethyl-2,3,3a,4,5,5a,5b,6,7,7a,8,11,11a,11b,12,13,13a,13b-octadecahydro-1H-cyclopenta[a]chrysen-9-yl)benzoate. Intermediate 22

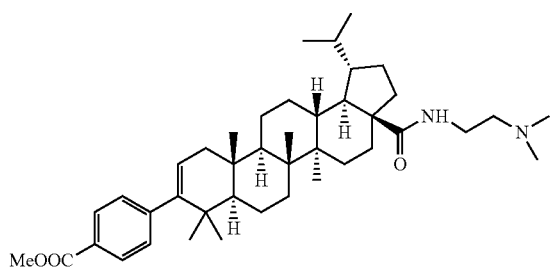

A mixture of methyl 4-((1R,3aS,5aR,5bR,7aR,11aS,11bR,13aR,13bR)-3a-(2-(dimethylamino)ethylcarbamoyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate (27 mg, 0.042 mmol) and Pd/C (14.30 mg, 0.013 mmol) in acetic acid (4 mL) and MeOH (4 mL) was reacted in Parr shaker for 18 hours under 40 psi. The reaction mixture was filtered through celite to remove Pd/C. The filtrates were concentrated under reduced pressure. The residue was dissolved in methanol and then purified by prep HPLC to provide the title compound as a white solid (6 mg, 22%). LCMS: m/e 645.62 (M+H)+, 2.87 min (method 1). $^1$H NMR (500 MHz, Acetic Acid-$d_4$) δ ppm 7.98 (d, J=8.24 Hz, 2H), 7.27 (d, J=8.24 Hz, 2H), 5.37 (d, J=4.88 Hz, 1H), 3.94 (s, 3H), 3.74 (t, J=5.95 Hz, 2H), 3.43-3.32 (m, 2H), 2.95 (s, 6H), 2.59-2.48 (m, 1H), 2.42-2.31 (m, 1H), 2.28-1.10 (m, 22H), 1.07 (d, J=3.97 Hz, 6H), 1.05 (s, 3H), 1.00 (s, 3H), 0.99 (s, 3H), 0.91 (d, J=6.71 Hz, 3H), 0.82 (d, J=6.71 Hz, 3H).

Preparation of 4-((1S,3aS,5aR,5bR,7aR,11aS,11bR, 13aR,13bR)-3a-(2-(dimethylamino)ethylcarbamoyl)-1-isopropyl-5a,5b,8,8,11a-pentamethyl-2,3,3a,4,5,5a, 5b,6,7,7a,8,11,11a,11b,12,13,13a,13b-octadecahydro-1H-cyclopenta[a]chrysen-9-yl) benzoic acid

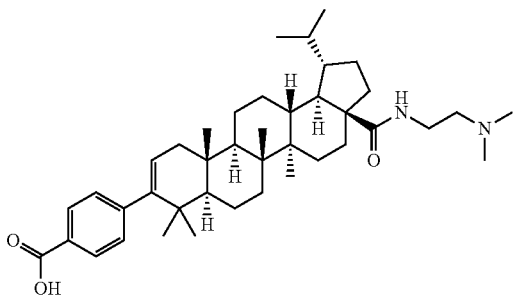

A mixture of methyl 4-((1S,3aS,5aR,5bR,7aR,11aS,11bR, 13aR,13bR)-3a-(2-(dimethylamino)ethylcarbamoyl)-1-isopropyl-5a,5b,8,8,11a-pentamethyl-2,3,3a,4,5,5a,5b,6,7,7a, 8,11,11a,11b,12,13,13a,13b-octadecahydro-1H-cyclopenta[a]chrysen-9-yl)benzoate (6 mg, 9.30 mmol) and sodium hydroxide (0.037 mL, 0.037 mmol) in dioxane (1 mL) was heated for 3 hours at 78° C. The reaction mixture was filtered and purified by prep HPLC to provide the title compound as a white solid (2.2 mg, 36%). LCMS: m/e 631.59 (M+H)$^+$, 2.29 min (method 1). $^1$H NMR (500 MHz, Acetic Acid-d$_4$) δ ppm 8.03 (d, J=8.24 Hz, 2H), 7.30 (d, J=8.24 Hz, 2H), 5.38 (d, J=4.58 Hz, 1H), 3.74 (t, J=6.10 Hz, 2H), 3.46-3.33 (m, 2H), 2.96 (s, 6H), 2.63-2.47 (m, 1H), 2.44-2.27 (m, 1H), 2.25-1.15 (m, 22H), 1.08 (s, 3H), 1.06 (s, 3H), 1.05 (s, 3H), 1.01 (s, 3H), 1.00 (s, 3H), 0.91 (d, J=6.71 Hz, 3H), 0.82 (d, J=6.71 Hz, 3H).

Example 79

Preparation of 4-((1R,3aS,5aR,5bR,7aR,11aS,11bR, 13aR,13bR)-3a-(2-carboxy-2-hydroxyethylcarbamoyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl) benzoic acid

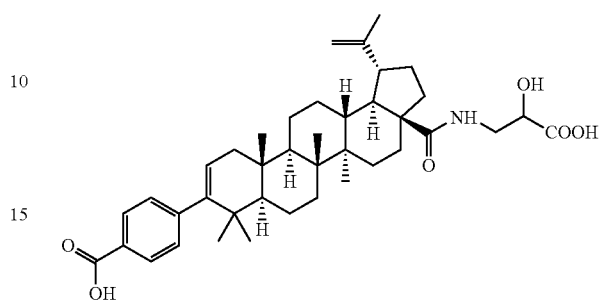

The title compound was prepared following the general procedures described above for the C-28 amide formation and hydrolysis using methyl 3-amino-2-hydroxypropanoate as the reactant amine. The product was isolated as a white solid (22 mg, 40%). LCMS: m/e 646.34 (M+H)$^+$, 2.04 min (method 1). $^1$H NMR (500 MHz, Acetic Acid-d$_4$) δ ppm 8.03 (d, J=8.24 Hz, 2H), 7.30 (d, J=8.24 Hz, 2H), 5.37 (d, J=4.88 Hz, 1H), 4.78 (s, 1H), 4.64 (s, 1H), 4.55-4.45 (m, 1H), 3.81-3.68 (m, 2H), 3.22-3.06 (m, 1H), 2.71-2.53 (m, 1H), 2.26-2.13 (m, 2H), 1.74 (s, 3H), 2.03-1.18 (m, 19H), 1.07 (s, 3H), 1.07 (s, 3H), 1.06 (s, 3H), 1.01 (s, 3H), 0.99 (s, 3H).

Example 80

Preparation of 4-((1R,3aS,5aR,5bR,7aR,11aS,11bR, 13aR,13bR)-3a-(2-((carboxymethyl)(methyl)amino) ethylcarbamoyl)-5a,5b,8,8,11a-pentamethyl-1-(prop-1-en-2-yl)-2,3,3a,4,5,5a,5b,6,7,7a,8,11,11a,11b,12, 13, 13a,13b-octadecahydro-1H-cyclopenta[a] chrysen-9-yl)benzoic acid

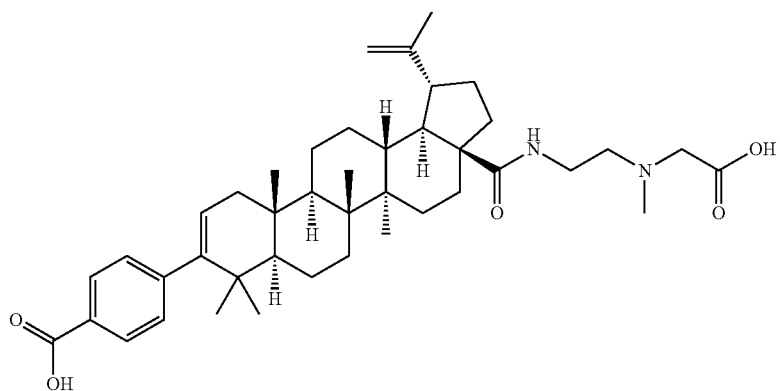

The title compound was prepared following the general procedures described above for the C-28 amide formation and hydrolysis using ethyl 2-((2-aminoethyl)(methyl)amino)acetate as the reactant amine. The product was isolated as a white solid (40 mg, 83%). LCMS: m/e 673.38 (M+H)$^+$, 2.08 min (method 1). $^1$H NMR (500 MHz, Acetic Acid-d$_4$) δ ppm 8.03 (d, J=8.24 Hz, 2H), 7.30 (d, J=8.55 Hz, 2H), 5.37 (d, J=4.88 Hz, 1H), 4.78 (s, 1H), 4.65 (s, 1H), 4.03 (s, 2H), 3.88-3.65 (m, 2H), 3.49 (t, J=5.80 Hz, 2H), 3.19-3.12 (m, 1H), 3.11 (s, 3H), 2.63-2.48 (m, 1H), 1.74 (s, 3H), 2.29-1.18 (m, 21H), 1.08 (s, 3H), 1.06 (s, 3H), 1.05 (s, 3H), 1.01 (s, 3H), 0.99 (s, 3H).

Example 81

Preparation of 4-((1R,3aS,5aR,5bR,7aR,11aS,11bR, 13aR,13bR)-3a-(2-(carboxymethylamino)ethylcarbamoyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

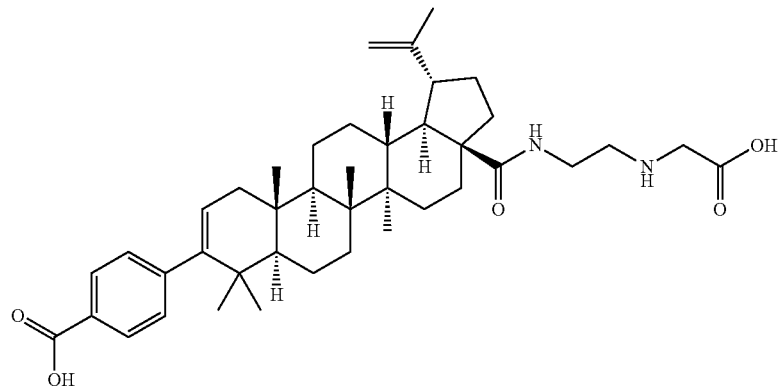

The title compound was prepared following the general procedures described above for the C-28 amide formation and hydrolysis using methyl 2-(2-aminoethylamino)acetate as the reactant amine. The product was isolated as a white solid (26 mg, 64%). LCMS: m/e 659.38 (M+H)$^+$, 2.08 min (method 1). $^1$H NMR (500 MHz, Acetic Acid-d$_4$) δ ppm 8.03 (d, J=8.24 Hz, 2H), 7.30 (d, J=8.24 Hz, 2H), 5.37 (d, J=4.58 Hz, 1H), 4.78 (s, 1H), 4.65 (s, 1H), 3.98 (d, J=2.75 Hz, 2H), 3.84-3.72 (m, 1H), 3.66 (ddd, J=14.80, 5.49, 5.34 Hz, 1H), 3.40 (t, J=5.65 Hz, 2H), 3.13 (td, J=10.99, 3.97 Hz, 1H), 2.70-2.47 (m, 1H), 2.25-2.13 (m, 2H), 1.75 (s, 3H), 2.02-1.17 (m, 19H), 1.09 (s, 3H), 1.07 (s, 3H), 1.06 (s, 3H), 1.01 (s, 3H), 0.99 (s, 3H).

Example 82

Preparation of sodium 4-((1R,3aS,5aR,5bR,7aR, 11aS,11bR,13aR,13bR)-5a,5b,8,8,11a-pentamethyl-1-(prop-1-en-2-yl)-3a-(2-sulfonatoethylcarbamoyl)-2,3,3a,4,5,5a,5b,6,7,7a,8,11,11a,11b,12,13,13a,13b-octadecahydro-1H-cyclopenta[a]chrysen-9-yl)benzoate

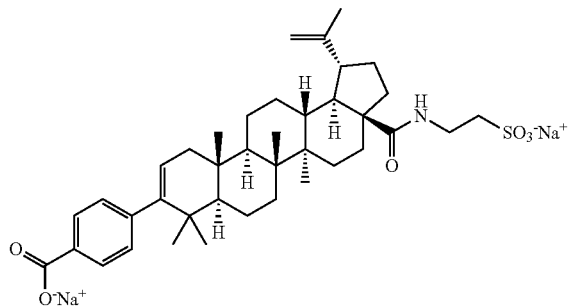

To a solution of 2-aminoethanesulfonic acid (19.05 mg, 0.152 mmol) and triethylamine (0.141 mL, 1.015 mmol) in water (1 mL) was added methyl 4-((1R,3aS,5aR,5bR,7aR, 11aS,11bR,13aR,13bR)-3a-(chlorocarbonyl)-5a,5b,8,8,11a-pentamethyl-1-(prop-1-en-2-yl)-2,3,3a,4,5,5a,5b,6,7,7a,8, 11,11a,11b,12,13,13a,13b-octadecahydro-1H-cyclopenta[a]chrysen-9-yl)benzoate(80492-081) (30 mg, 0.051 mmol) and triethylamine (0.141 mL, 1.015 mmol) in dioxane (1 mL). The reaction mixture was stirred for 1 hour at room temperature. LCMS indicated the formation of desired intermediate. To the reaction mixture was then added 1N sodium hydroxide (0.099 mL, 0.099 mmol) and heated up at 78° C. for 3 hours until LCMS indicated the consumption of starting material. The reaction mixture was filtered and the clear solution was purified by prep HPLC to provide the title compound as a white solid (15 mg, 49%). LCMS: m/e 666.32 (M+H)$^+$, 2.04 min (method 1). $^1$H NMR (500 MHz, MeOD) δ ppm 7.90 (d, J=7.93 Hz, 2H), 7.69 (t, J=5.34 Hz, 1H), 7.18 (d, J=8.24 Hz, 2H), 5.30 (d, J=5.19 Hz, 1H), 4.75 (s, 1H), 4.61 (s, 1H), 3.79-3.55 (m, 2H), 3.19-3.08 (m, 1H), 3.05-2.91 (m, 2H), 2.59 (t, J=13.73 Hz, 1H), 2.22-2.09 (m, 2H), 1.72 (s, 3H), 1.96-1.15 (m, 19H), 1.06 (s, 6H), 1.05 (s, 3H), 0.98 (s, 3H), 0.96 (s, 3H).

Example 83
Procedures for the Preparation of 4-((1R,3aS,5aR,5bR,7aR,11aS,11bR,13aR,13bR)-3a-(2-((carboxymethyl)(ethyl)amino)ethylcarbamoyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid
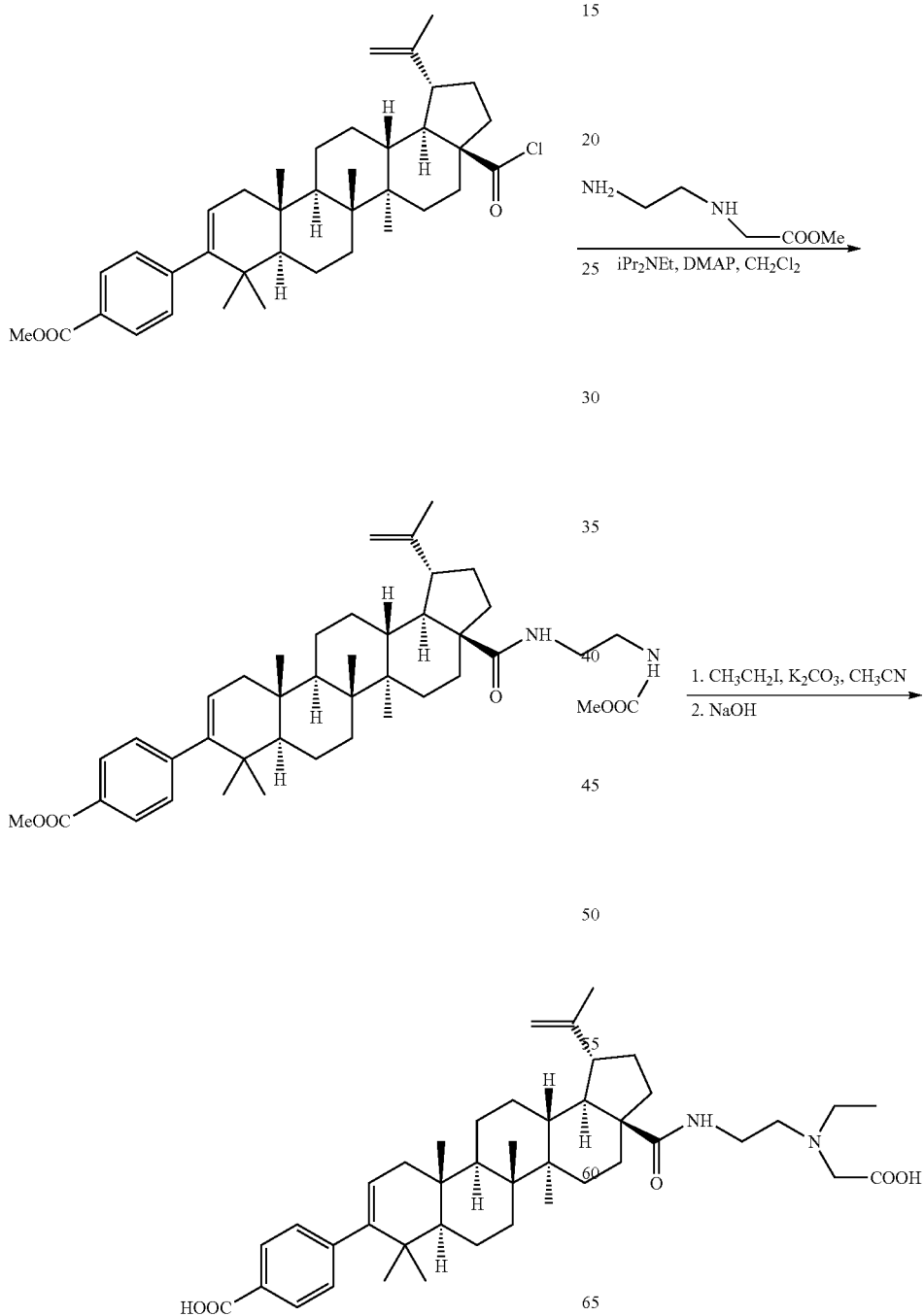

Preparation of methyl 4-((1R,3aS,5aR,5bR,7aR, 11aS,11bR,13aR,13bR)-3a-(2-(2-methoxy-2-oxoethylamino)ethylcarbamoyl)-5a,5b,8,8,11a-pentamethyl-1-(prop-1-en-2-yl)-2,3,3a,4,5,5a,5b,6,7,7a,8, 11,11a,11b,12,13,13a,13b-octadecahydro-1H-cyclopenta[a]chrysen-9-yl)benzoate. Intermediate 23

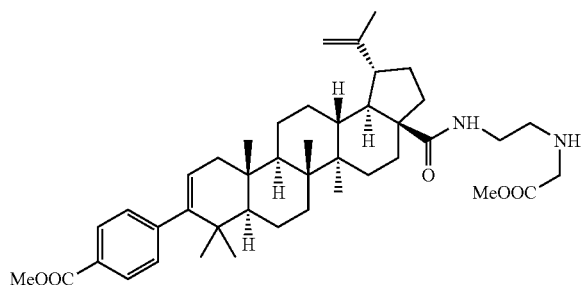

To a solution of methyl 2-(2-aminoethylamino)acetate (33.5 mg, 0.254 mmol), Hunig'sBase (0.089 mL, 0.507 mmol) and DMAP (20.66 mg, 0.169 mmol) in DCM (1.5 mL) was added methyl 4-((1R,3aS,5aR,5bR,7aR,11aS,11bR, 13aR,13bR)-3a-(chlorocarbonyl)-5a,5b,8,8,11a-pentamethyl-1-(prop-1-en-2-yl)-2,3,3a,4,5,5a,5b,6,7,7a,8,11,11a, 11b,12,13,13a,13b-octadecahydro-1H-cyclopenta[a]chrysen-9-yl)benzoate (100 mg, 0.169 mmol) in DCM (1.5 mL). The reaction mixture was stirred at 20° C. for three hours. LCMS indicated the formation of desired product. The reaction mixture was quenched with distilled water, extracted with DCM (3×4 mL). All the extracts were combined, dried over sodium sulfate, filtered and concentrated under reduced pressure to provide the title compound as a white solid (90 mg, 76%). LCMS: m/e 713.45 (M−H)⁻, 2.75 min (method 1).

Preparation of 4-((1R,3aS,5aR,5bR,7aR,11aS,11bR, 13aR,13bR)-3a-(2-((carboxymethyl)(ethyl)amino)ethylcarbamoyl)-5a,5b,8,8,11a-pentamethyl-1-(prop-1-en-2-yl)-2,3,3a,4,5,5a,5b,6,7,7a,8,11,11a,11b,12, 13,13a,13b-octadecahydro-1H-cyclopenta[a]chrysen-9-yl)benzoic acid

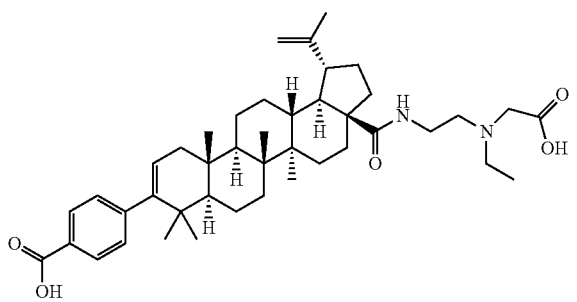

A mixture of methyl 4-((1R,3aS,5aR,5bR,7aR,11aS, 11bR,13aR,13bR)-3a-(2-(2-methoxy-2-oxoethylamino)ethylcarbamoyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate (50 mg, 0.071 mmol), iodoethane (0.047 mL, 0.571 mmol) and potassium carbonate (19.72 mg, 0.143 mmol) in acetonitrile (2.0 mL) and dioxane (2.0 mL) was heated up for 8 hours. LCMS indicated the formation of desired product and consumption of starting material. The reaction mixture was quenched with distilled water, extracted with DCM (3×3 mL). All the extracts were combined, dried over sodium sulfate, filtered and concentrated under reduced pressure to provide the crude intermediate methyl 4-((1R,3aS,5aR,5bR,7aR, 11aS,11bR,13aR,13bR)-3a-(2-(ethyl(2-methoxy-2-oxoethyl)amino)ethylcarbamoyl)-5a,5b,8,8,11a-pentamethyl-1-(prop-1-en-2-yl)-2,3,3a,4,5,5a,5b,6,7,7a,8, 11,11a,11b,12,13,13a,13b-octadecahydro-1H-cyclopenta[a]chrysen-9-yl)benzoate. To this intermediate in dioxane (1 mL) was added 1N sodium hydroxide (0.224 mL, 0.224 mmol). The reaction mixture was heated up at 78° C. for 3 hours until LCMS indicated the consumption of starting material. The reaction mixture was filtered and the clear solution was purified by prep HPLC to provide the title compound as a white solid (29 mg, 59%). LCMS: m/e 687.40 (M+H)⁺, 2.11 min (method 1). ¹H NMR (500 MHz, Acetic Acid-d₄) δ ppm 8.03 (d, J=8.24 Hz, 2H), 7.30 (d, J=8.24 Hz, 2H), 5.37 (d, J=4.58 Hz, 1H), 4.78 (s, 1H), 4.65 (s, 1H), 4.02 (s, 2H), 3.85-3.63 (m, 2H), 3.58-3.37 (m, 4H), 3.22-3.01 (m, 1H), 2.69-2.43 (m, 1H), 1.73 (s, 3H), 2.30-1.20 (m, 24H), 1.08 (s, 3H), 1.07 (s., 3H), 1.06 (s., 3H), 1.01 (s, 3H), 0.99 (s, 3H).

Example 84

Preparation of 4-((1R,3aS,5aR,5bR,7aR,11aS,11bR, 13aR,13bR)-5a,5b,8,8,11a-pentamethyl-1-(prop-1-en-2-yl)-3a-(vinylcarbamoyl)-2,3,3a,4,5,5a,5b,6,7, 7a,8,11,11a,11b,12,13,13a,13b-octadecahydro-1H-cyclopenta[a]chrysen-9-yl)benzoic acid

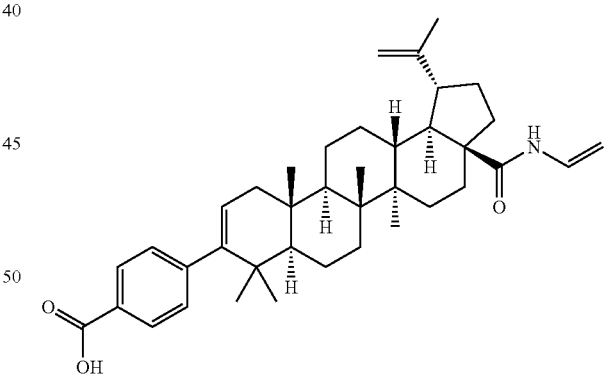

The title compound was prepared following the general procedures described above for the C-28 amide formation and hydrolysis using 2-chloroethanaminium chloride as the reactant amine. The product was isolated as a white solid (9 mg, 58%). LCMS: m/e 584.30 (M+H)⁺, 2.37 min (method 1). ¹H NMR (400 MHz, CHLOROFORM-d) δ ppm 7.98 (br. s., 2H), 7.26-7.20 (m, 2H), 5.31 (d, J=4.52 Hz, 1H), 4.78 (br. s., 1H), 4.62 (br. s., 1H), 4.18 (t, J=10.67 Hz, 1H), 3.91 (t, J=9.16 Hz, 2H), 3.18-2.98 (m, 1H), 2.61-1.10 (m, 25H), 1.01 (s., 3H), 1.00 (s., 3H), 0.98 (s., 3H), 0.94 (s., 6H).

Example 85

Preparation of 4-((1R,3aS,5aR,5bR,7aR,11aS,11bR, 13aR,13bR)-3a-((3-(1,1-dioxido-4-thiomorpholinyl) propyl)carbamoyl)-1-isopropenyl-5a,5b,8,8,11a-pentamethyl-2,3,3a,4,5,5a,5b,6,7,7a,8,11,11a,11b,12, 13,13a,13b-octadecahydro-1H-cyclopenta[a] chrysen-9-yl)benzoic acid

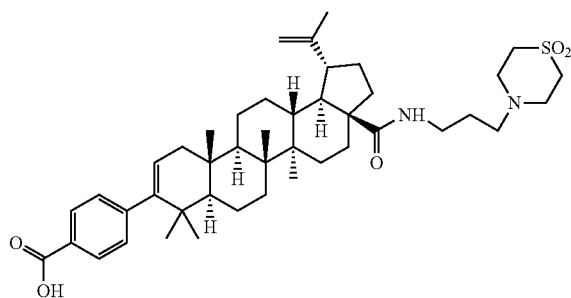

The title compound was prepared following the general procedures described above for the C-28 amide formation and hydrolysis using 4-(3-aminopropyl)thiomorpholine 1,1-dioxide as the reactant amine. The product was isolated as a white solid (27 mg, 65%). LCMS: m/e 733.44 (M+H)$^+$, 2.11 min (method 1). $^1$H NMR (500 MHz, Acetic Acid-d$_4$) δ ppm 8.03 (d, J=8.24 Hz, 2H), 7.30 (d, J=8.24 Hz, 2H), 5.37 (d, J=4.58 Hz, 1H), 4.78 (s, 1H), 4.65 (s, 1H), 3.85 (br. s., 4H), 3.60 (br. s., 4H), 3.49-3.33 (m, 2H), 3.33-3.25 (m, 2H), 3.15 (td, J=11.06, 4.73 Hz, 1H), 2.66-2.54 (m, 1H), 2.26-2.13 (m, 2H), 1.74 (s, 3H), 2.03-1.09 (m, 21H), 1.08 (s, 3H), 1.07 (s, 3H), 1.06 (s, 3H), 1.01 (s, 3H), 0.99 (s, 3H).

Example 86

Preparation of 4-((1R,3aS,5aR,5bR,7aR,11aS,11bR, 13aR,13bR)-3a-(3-(1H-imidazol-1-yl)propylcarbamoyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl) benzoic acid

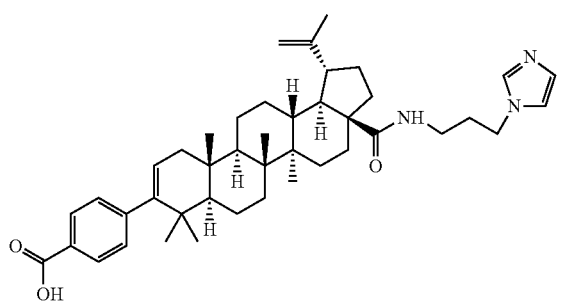

The title compound was prepared following the general procedures described above for the C-28 amide formation and hydrolysis using 3-(1H-imidazol-1-yl)propan-1-amine as the reactant amine. The product was isolated as a white solid (7 mg, 23%). LCMS: m/e 666.39 (M+H)$^+$, 2.15 min (method 1). $^1$H NMR (500 MHz, Acetic Acid-d$_4$) δ ppm 9.05-8.94 (m, 1H), 8.03 (d, J=8.24 Hz, 2H), 7.59 (d, J=14.65 Hz, 2H), 7.30 (d, J=8.24 Hz, 2H), 5.37 (d, J=4.88 Hz, 1H), 4.78 (s, 1H), 4.65 (s, 1H), 4.36 (t, J=6.87 Hz, 2H), 3.47-3.31 (m, 2H), 3.17 (td, J=11.06, 4.12 Hz, 1H), 2.69-2.54 (m, 1H), 2.30-2.13 (m, 4H), 1.75 (s, 3H), 2.03-1.07 (m, 19H), 1.08 (s, 3H), 1.06 (s, 3H), 1.05 (s, 3H), 1.00 (s, 3H), 0.99 (s, 3H).

Example 87

Preparation of 4-((1R,3aS,5aR,5bR,7aR,11aS,11bR, 13aR,13bR)-5a,5b,8,8,11a-pentamethyl-3a-(3-(2-oxopyrrolidin-1-yl)propylcarbamoyl)-1-(prop-1-en-2-yl)-2,3,3a,4,5,5a,5b,6,7,7a,8,11,11a,11b,12,13,13a, 13b-octadecahydro-1H-cyclopenta[a]chrysen-9-yl) benzoic acid The title compound was prepared following the general procedures described above for the C-28 amide formation and hydrolysis using 1-(3-aminopropyl)pyrrolidin-2-one as the reactant amine. The product was isolated as a white solid (17 mg, 47%). LCMS: m/e 683.42 (M+H)$^+$, 2.18 min (method 1). $^1$H NMR (500 MHz, Acetic Acid-d$_4$) δ ppm 8.03 (d, J=8.24 Hz, 2H), 7.30 (d, J=8.24 Hz, 2H), 5.37 (d, J=4.58 Hz, 1H), 4.78 (s, 1H), 4.64 (s, 1H), 3.62-3.42 (m, 3H), 3.42-3.29 (m, 2H), 3.27-3.13 (m, 2H), 2.66-2.58 (m, 1H), 2.56 (t, J=8.09 Hz, 2H), 2.26-2.15 (m, 2H), 1.74 (s, 3H), 2.15-1.09 (m, 23H), 1.09 (s, 3H), 1.06 (s, 3H), 1.06 (s, 3H), 1.01 (s, 3H), 0.99 (s, 3H).

Example 88

Procedures for the preparation of 2,2'-(2-((1R,3aS,5aR,5bR,7aR,11aS,11bR,13aR,13bR)-9-(4-carboxyphenyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysene-3a-carboxamido)ethylazanediyl)diacetic acid

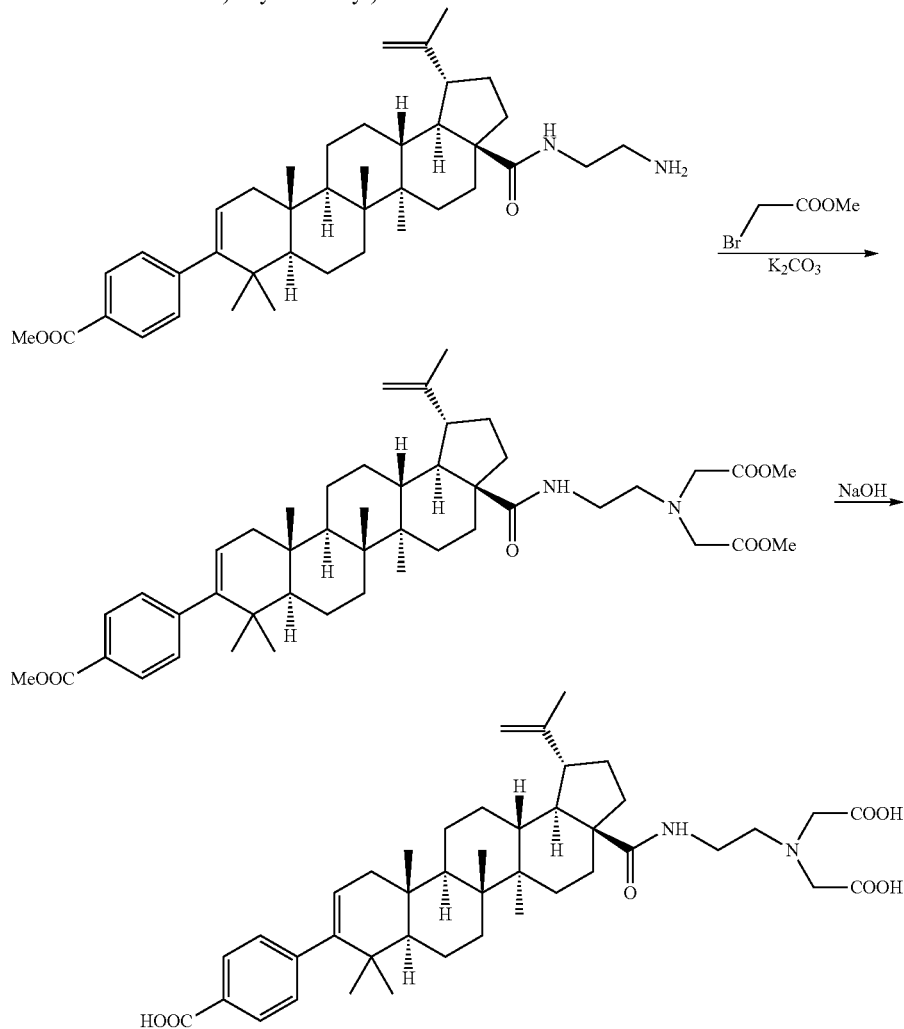

Preparation of dimethyl 2,2'-(2-((1R,3aS,5aR,5bR,7aR,11aS,11bR,13aR,13bR)-9-(4-(methoxycarbonyl)phenyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysene-3a-carboxamido)ethylazanediyl)diacetate.
Intermediate 24

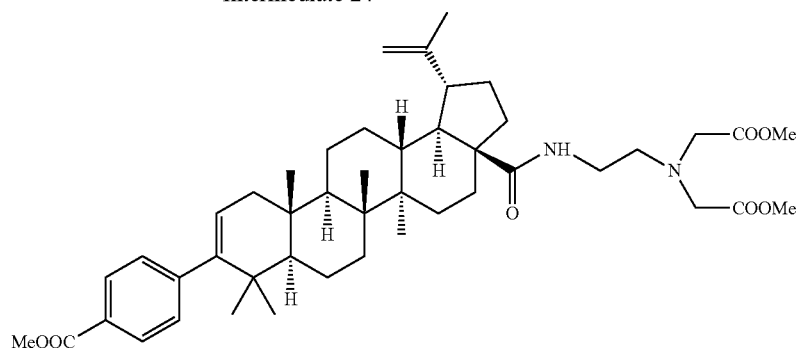

To a solution of methyl 4-((1R,3aS,5aR,5bR,7aR,11aS,11bR,13aR,13bR)-3a-(2-aminoethylcarbamoyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate (20 mg, 0.033 mmol) in acetonitrile (1 mL) and dioxane (1 mL) was added methyl 2-bromoacetate (14.93 mg, 0.098 mmol) and potassium carbonate (22.48 mg, 0.163 mmol). The reaction mixture was heated up at 78° C. for 3 hours. LCMS indicated the formation of desired product and consumption of starting material. The reaction mixture was quenched with distilled water, extracted with DCM (3×3 mL). All the extracts were combined, dried over sodium sulfate, filtered and concentrated under reduced pressure to provide the desired product (17 mg, 69%) as white solid. LCMS: m/e 759.7 (M+H)$^+$, 2.88 min (method 1).

Preparation of 2,2'-(2-((1R,3aS,5aR,5bR,7aR,11aS,11bR,13aR,13bR)-9-(4-carboxyphenyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysene-3a-carboxamido)ethylazanediyl)diacetic acid

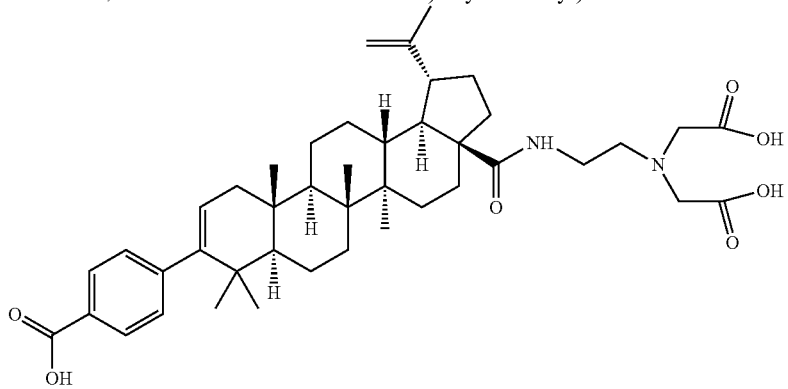

A mixture of dimethyl 2,2'-(2-((1R,3aS,5aR,5bR,7aR,11aS,11bR,13aR,13bR)-9-(4-(methoxycarbonyl)phenyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysene-3a-carboxamido)ethylazanediyl)diacetate (17 mg, 0.022 mmol) and 1 N sodium hydroxide (0.112 mL, 0.112 mmol) in dioxane (0.5 mL) was heated up at 78° C. for 3 hours. LCMS indicated the formation of desired product. The reaction mixture was filtered and the clear solution was purified by prep HPLC to provide the title compound (10 mg, 59%) as white solid. LCMS: m/e 717.35 (M+H)$^+$, 1.97 min (method 1). $^1$H NMR (500 MHz, Acetic Acid-d$_4$) δ ppm 8.03 (d, J=7.93 Hz, 2H), 7.30 (d, J=8.24 Hz, 2H), 5.37 (d, J=4.88 Hz, 1H), 4.78 (s, 1H), 4.64 (s, 1H), 4.35-4.14 (m, 4H), 3.94-3.81 (m, 1H), 3.71-3.61 (m, 1H), 3.60-3.49 (m, 2H), 3.18-3.06 (m, 1H), 2.53 (td, J=12.13, 3.51 Hz, 1H), 2.24-2.13 (m, 2H), 1.75 (s, 3H), 2.10-1.09 (m, 19H), 1.08 (s, 3H), 1.06 (s, 3H), 1.05 (s, 3H), 1.01 (s, 3H), 0.99 (s, 3H).

Example 89

Procedures for Preparation of 4-((1R,3aS,5aR,5bR,7aR,11aS,11bR,13aR,13bR)-3a-(2-((2-carboxyethyl)(ethyl)amino)ethylcarbamoyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

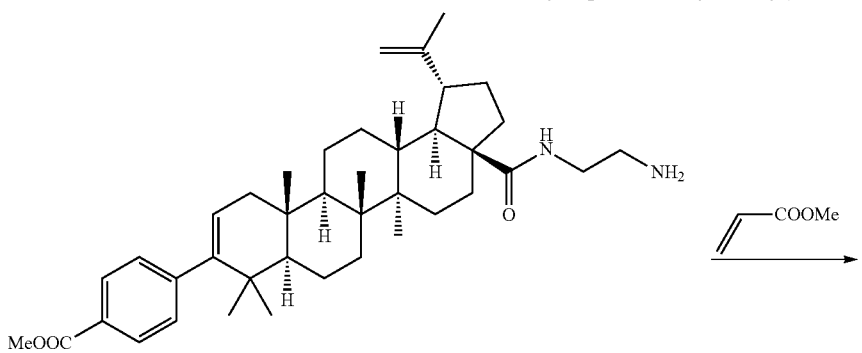

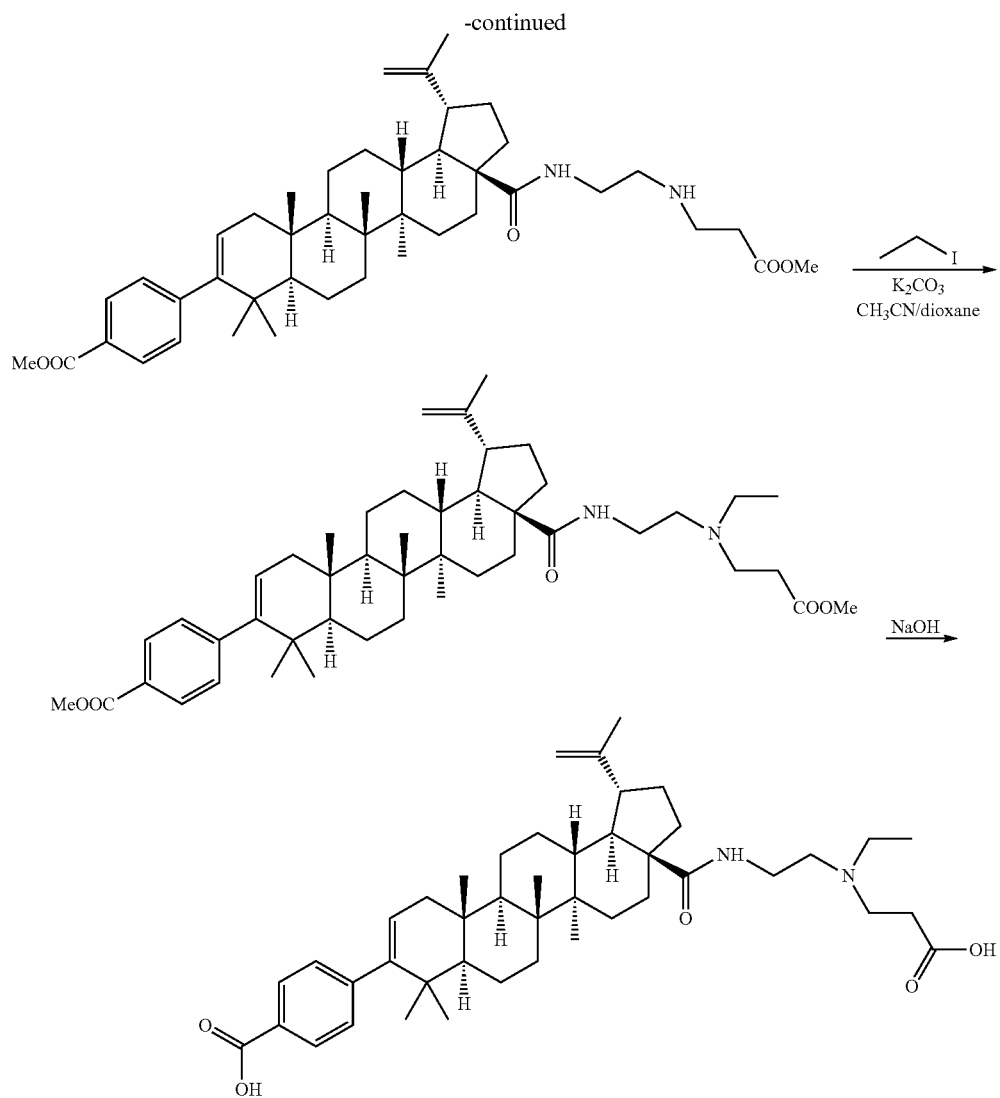
Preparation of methyl 4-((1R,3aS,5aR,5bR,7aR,11aS,11bR,13aR,13bR)-3a-(2-(3-methoxy-3-oxopropylamino)ethylcarbamoyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate. Intermediate 25
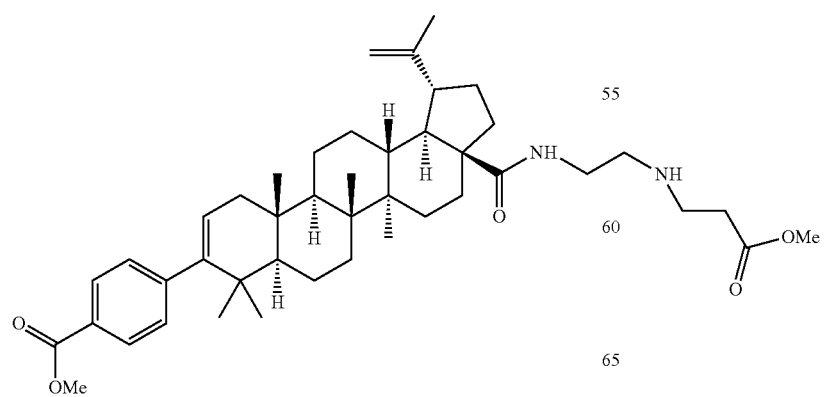

To a solution of methyl 4-((1R,3aS,5aR,5bR,7aR,11aS,11bR,13aR,13bR)-3a-(2-aminoethylcarbamoyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate (60 mg, 0.098 mmol) in methanol (1 mL) was added methyl acrylate (25.2 mg, 0.293 mmol), the reaction mixture was stirred at 20° C. for 3 hours. LCMS indicated the formation of desired product. The reaction mixture was quenched with distilled water, extracted with DCM (3×3 mL). All the extracts were combined, dried over sodium sulfate, filtered and concentrated under reduced pressure to provide the desired product as white solid (60 mg, 88%). LCMS: m/e 701.46 (M+H)$^+$, 2.58 min (method 1).

Preparation of methyl 4-((1R,3aS,5aR,5bR,7aR,11aS,11bR,13aR,13bR)-3a-(2-(ethyl(3-methoxy-3-oxopropyl)amino)ethylcarbamoyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate. Intermediate 26

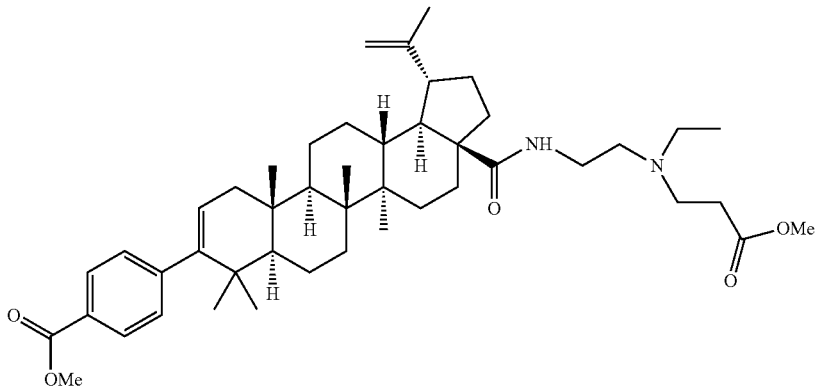

A mixture of methyl 4-((1R,3aS,5aR,5bR,7aR,11aS,11bR,13aR,13bR)-3a-(2-(3-methoxy-3-oxopropylamino)ethylcarbamoyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate (20 mg, 0.029 mmol), iodoethane (0.019 mL, 0.228 mmol) and potassium carbonate (7.89 mg, 0.057 mmol) in acetonitrile (2 mL) and dioxane (2 mL) was refluxed for 8 hours. LCMS indicated the formation of desired product and consumption of starting material. The reaction mixture was quenched with distilled water, extracted with DCM (3×3 mL). All the extracts were combined, dried over sodium sulfate, filtered and concentrated under reduced pressure to provide the title compound as white solid (16 mg, 77%). LCMS: m/e 729.45 (M+H)$^+$, 2.76 min (method 1).

Preparation of 4-((1R,3aS,5aR,5bR,7aR,11aS,11bR,13aR,13bR)-3a-(2-((2-carboxyethyl)(ethyl)amino)ethylcarbamoyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

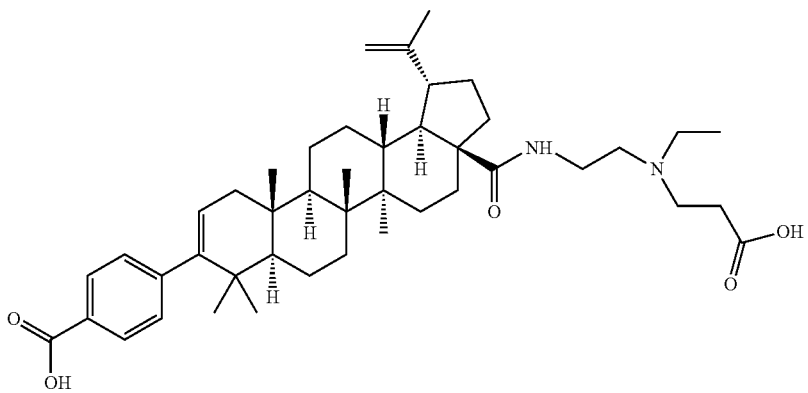

The title compound was prepared following the method described above for 2,2'-(2-((1R,3aS,5aR,5bR,7aR,11aS,11bR,13aR,13bR)-9-(4-carboxyphenyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysene-3a-carboxamido)ethylazanediyl)diacetic acid (example 88). The product was isolated as a white solid (8.7 mg, 54%). LCMS: m/e 701.41 (M+H)+, 2.06 min (method 1). 1H NMR (500 MHz, Acetic Acid-d4) δ ppm 8.03 (d, J=8.24 Hz, 2H), 7.30 (d, J=8.55 Hz, 2H), 5.37 (d, J=4.58 Hz, 1H), 4.78 (d, J=1.22 Hz, 1H), 4.65 (s, 1H), 3.90-3.69 (m, 2H), 3.53 (t, J=7.02 Hz, 2H), 3.49-3.31 (m, 4H), 3.13 (td, J=10.76, 4.43 Hz, 1H), 2.96 (t, J=6.87 Hz, 2H), 2.64-2.48 (m, 1H), 2.24-2.14 (m, 2H), 1.75 (s, 3H), 1.40 (t, J=7.17 Hz, 3H), 2.05-1.09 (m, 19H), 1.08 (s, 3H), 1.06 (s, 3H), 1.06 (s, 3H), 1.01 (s, 3H), 0.99 (s, 3H).

Example 90

Procedures for Preparation of 3,3'-(2-((1R,3aS,5aR,5bR,7aR,11aS,11bR,13aR,13bR)-9-(4-carboxyphenyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysene-3a-carboxamido)ethylazanediyl)dipropanoic acid

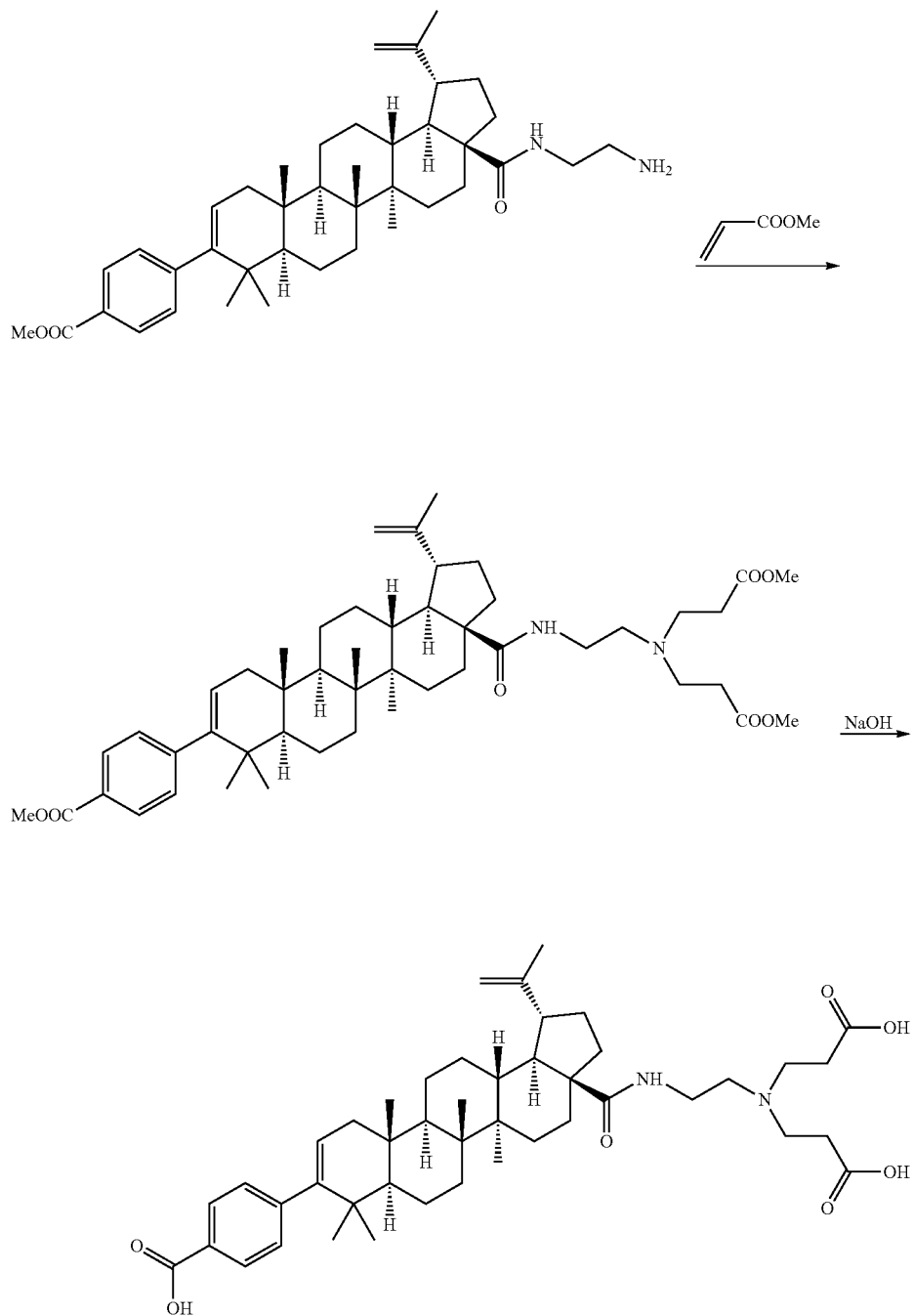

Preparation of dimethyl 3,3'-(2-((1R,3aS,5aR,5bR,7aR,11aS,11bR,13aR,13bR)-9-(4-(methoxycarbonyl)phenyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysene-3a-carboxamido)ethylazanediyl)dipropanoate.
Intermediate 27

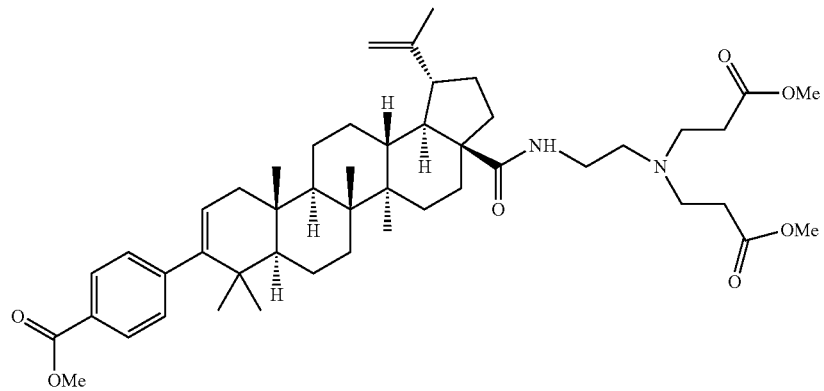

A mixture of methyl 4-((1R,3aS,5aR,5bR,7aR,11aS,11bR,13aR,13bR)-3a-(2-aminoethylcarbamoyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate (20 mg, 0.033 mmol) and methyl acrylate (8.40 mg, 0.098 mmol) in methanol (1 mL) was stirred at 20° C. for 3 hours. LCMS indicated the mono-substitution. Methyl acrylate (8.40 mg, 0.098 mmol) was added to the reaction mixture again. The reaction mixture was stirred for 16 hours. The reaction mixture was quenched with distilled water, extracted with DCM (3×3 mL). All the extracts were combined, dried over sodium sulfate, filtered and concentrated under reduced pressure to provide the title compound as a white solid (25 mg, 98%). LCMS: m/e 787.48 (M+H)$^+$, 2.67 min (method 1).

Preparation of 3,3'-(2-((1R,3aS,5aR,5bR,7aR,11aS,11bR,13aR,13bR)-9-(4-carboxyphenyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysene-3a-carboxamido)ethylazanediyl)dipropanoic acid The title compound was prepared following the method described above for 2,2'-(2-((1R,3aS,5aR,5bR,7aR,11aS,11bR,13aR,13bR)-9-(4-carboxyphenyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysene-3a-carboxamido)ethylazanediyl)diacetic acid (example 88). The product was isolated as a white solid (16 mg, 64%). LCMS: m/e 745.39 (M+H)$^+$, 1.97 min (method 1). $^1$H NMR (500 MHz, Acetic Acid-d$_4$) δ ppm 8.03 (d, J=8.24 Hz, 2H), 7.30 (d, J=8.24 Hz, 2H), 5.37 (d, J=4.58 Hz, 1H), 4.78 (s, 1H), 4.65 (s, 1H), 3.89-3.75 (m, 2H), 3.59 (t, J=6.56 Hz, 4H), 3.54-3.41 (m, 2H), 3.19-3.07 (m, 1H), 3.00 (t, J=6.56 Hz, 4H), 2.62-2.49 (m, 1H), 2.24-2.14 (m, 2H), 1.74 (s, 3H), 2.03-1.09 (m, 19H), 1.08 (s, 3H), 1.06 (s, 3H), 1.06 (s, 3H), 1.01 (s, 3H), 0.99 (s, 3H).

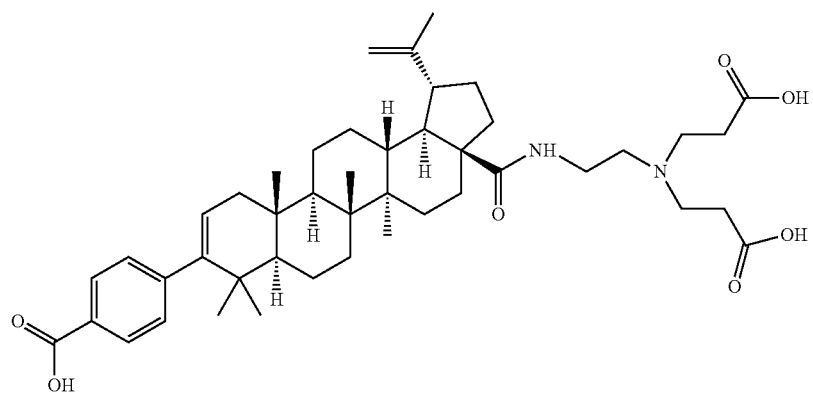

Example 91

Preparation of 4-((1R,3aS,5aR,5bR,7aR,11aS,11bR,13aR,13bR)-3a-(2-(2-carboxyethylamino)ethylcarbamoyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

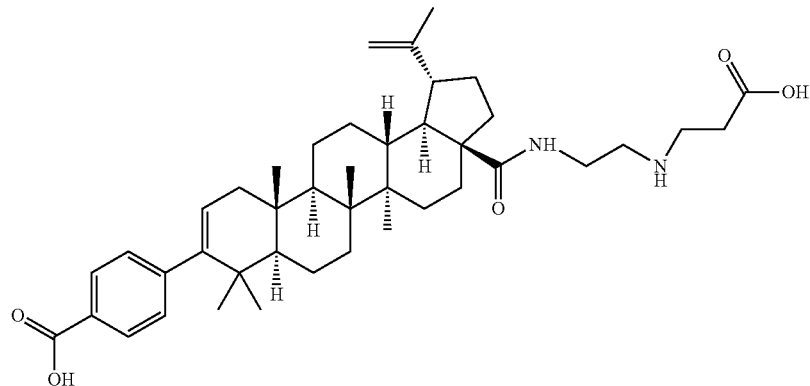

The title compound was prepared following the method described above for 2,2'-(2-((1R,3aS,5aR,5bR,7aR,11aS,11bR,13aR,13bR)-9-(4-carboxyphenyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysene-3a-carboxamido)ethylazanediyl)diacetic acid (example 88). The product was isolated as a white solid (5.5 mg, 54%). LCMS: m/e 673.38 (M+H)$^+$, 2.08 min (method 1). $^1$H NMR (500 MHz, Acetic Acid-d$_4$) δ ppm 8.03 (d, J=8.24 Hz, 2H), 7.30 (d, J=8.24 Hz, 2H), 5.37 (d, J=4.58 Hz, 1H), 4.78 (s, 1H), 4.65 (s, 1H), 3.83-3.59 (m, 2H), 3.44 (t, J=6.41 Hz, 2H), 3.37 (t, J=5.80 Hz, 2H), 3.14 (td, J=10.83, 4.27 Hz, 1H), 2.93 (t, J=6.41 Hz, 2H), 2.56 (td, J=12.51, 2.75 Hz, 1H), 2.26-2.14 (m, 2H), 1.74 (s, 3H), 2.06-1.09 (m, 19H), 1.08 (s, 3H), 1.06 (s, 3H), 1.05 (s, 3H), 1.01 (s, 3H), 0.99 (s, 3H).

Example 92

Preparation of 4-((1R,3aS,5aR,5bR,7aR,11aS,11bR,13aR,13bR)-5a,5b,8,8,11a-pentamethyl-1-(prop-1-en-2-yl)-3a-(2-(2-sulfoethylamino)ethylcarbamoyl)-2,3,3a,4,5,5a,5b,6,7,7a,8,11,11a,11b,12,13,13a,13b-octadecahydro-1H-cyclopenta[a]chrysen-9-yl)benzoic acid The title compound was prepared following the method described above for 2,2'-(2-((1R,3aS,5aR,5bR,7aR,11aS,11bR,13aR,13bR)-9-(4-carboxyphenyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysene-3a-carboxamido)ethylazanediyl)diacetic acid (example 88). using 2-bromoethanesulfonic acid as alkylating reagent. The product was isolated as a white solid (3 mg, 39%). LCMS: m/e 709.37 (M+H)$^+$, 2.04 min (method 1). $^1$H NMR (500 MHz, Acetic Acid-d$_4$) δ ppm 8.03 (d, J=8.54 Hz, 2H), 7.30 (d, J=8.24 Hz, 2H), 5.37 (d, J=6.10 Hz, 1H), 4.79 (s, 1H), 4.66 (s, 1H), 3.93-3.75 (m, 2H), 3.74-3.62 (m, 2H), 3.50-3.44 (m, 2H), 3.42 (t, J=5.80 Hz, 2H), 3.20-3.06 (m, 1H), 2.66-2.47 (m, 1H), 1.75 (s, 3H), 2.31-1.10 (m, 21H), 1.09 (s, 3H), 1.06 (s, 3H), 1.06 (s, 3H), 1.01 (s, 3H), 0.99 (s, 3H).

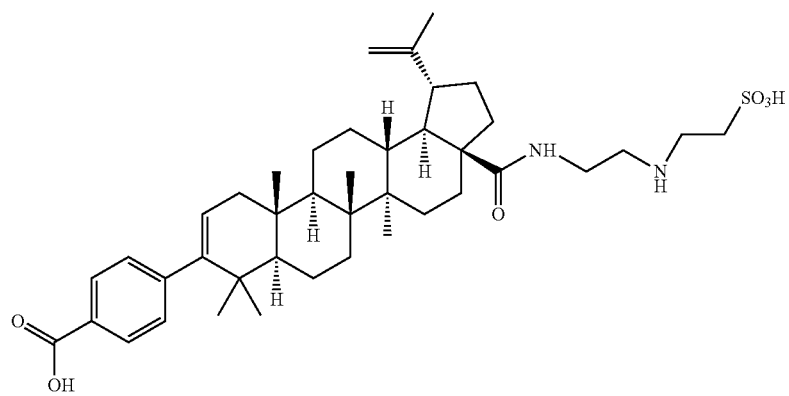

Example 93

Preparation of 4-((1R,3aS,5aR,5bR,7aR,11aS,11bR,13aR,13bR)-3a-(2-((2-carboxyethyl)(propyl)amino)ethylcarbamoyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

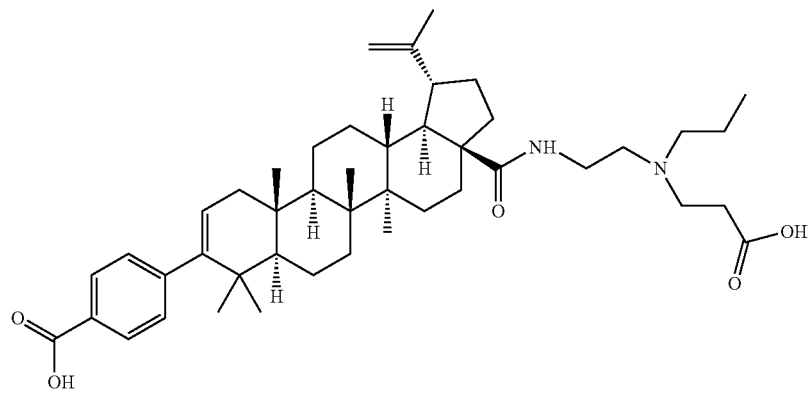

The title compound was prepared following the method described above for the preparation of 4-((1R,3aS,5aR,5bR,7aR,11aS,11bR,13aR,13bR)-3a-(2-((2-carboxyethyl)(ethyl)amino)ethylcarbamoyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl) benzoic acid (example 89). using 1-iodopropane as alkylating reagent. The product was isolated as a white solid (10 mg, 49%). LCMS: m/e 715.50 (M+H)$^+$, 2.08 min (method 1). $^1$H NMR (500 MHz, Acetic Acid-d$_4$) δ ppm 8.03 (d, J=7.93 Hz, 2H), 7.30 (d, J=8.24 Hz, 2H), 5.37 (d, J=4.58 Hz, 1H), 4.78 (s, 1H), 4.65 (s, 1H), 3.88-3.72 (m, 2H), 3.55 (t, J=7.02 Hz, 2H), 3.44 (q, J=6.51 Hz, 2H), 3.32-3.21 (m, 2H), 3.13 (td, J=11.22, 3.51 Hz, 1H), 2.97 (t, J=6.71 Hz, 2H), 2.55 (td, J=12.13, 3.81 Hz, 1H), 2.25-2.13 (m, 2H), 1.75 (s, 3H), 2.04-1.10 (m, 21H), 1.08 (s, 3H), 1.07 (s, 3H), 1.06 (s, 3H), 1.03 (t, J=5 Hz, 2H), 1.01 (s, 3H), 0.99 (s, 3H).

Example 94

Procedures for the preparation of 4-((1R,3aS,5aR,5bR,7aR,11aS,11bR,13aR,13bR)-3a-(2-((carboxymethyl)(propyl)amino)ethylcarbamoyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

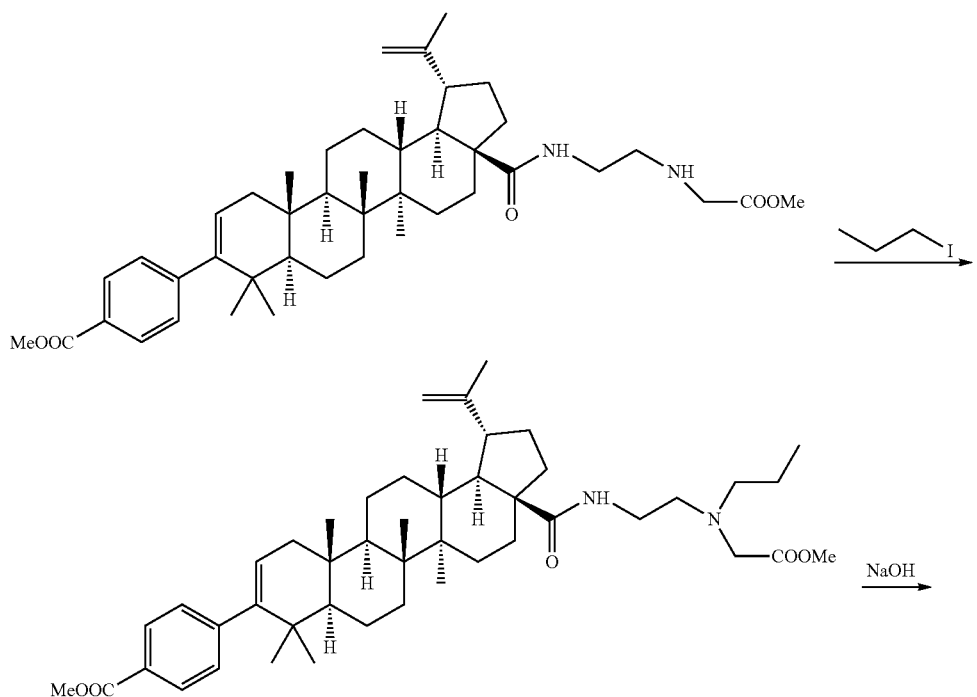

-continued

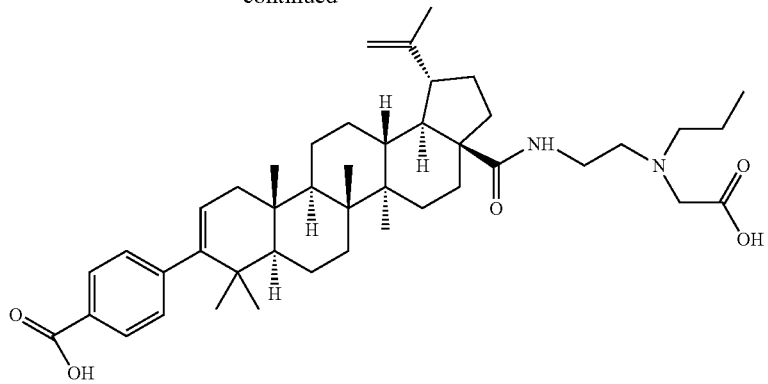

Preparation of methyl 4-((1R,3aS,5aR,5bR,7aR,
11aS,11bR,13aR,13bR)-3a-(2-((2-methoxy-2-oxoethyl)(propyl)amino)ethylcarbamoyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate. Intermediate 28

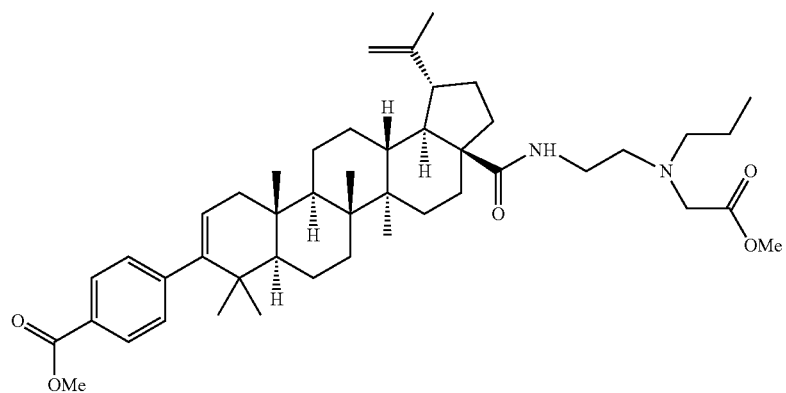

A mixture of methyl 4-((1R,3aS,5aR,5bR,7aR,11aS,11bR,13aR,13bR)-3a-(2-(2-methoxy-2-oxoethylamino)ethylcarbamoyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate (28 mg, 0.041 mmol), 1-iodopropane (55.4 mg, 0.326 mmol) and potassium carbonate (11.27 mg, 0.082 mmol) in acetonitrile (2 mL) and dioxane (2.000 mL) was heated up for 8 hours. LCMS indicated the formation of desired product and consumption of starting material. The reaction mixture was quenched with distilled water, extracted with DCM (3×3 mL). All the extracts were combined, dried over sodium sulfate, filtered and concentrated under reduced pressure to provide the desired product as a white solid (20 mg, 67%). LCMS: m/e 729.47 (M+H)+, 2.96 min (method 1).

Preparation of 4-((1R,3aS,5aR,5bR,7aR,11aS,11bR,13aR,13bR)-3a-(2-((carboxymethyl)(propyl)amino)ethylcarbamoyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

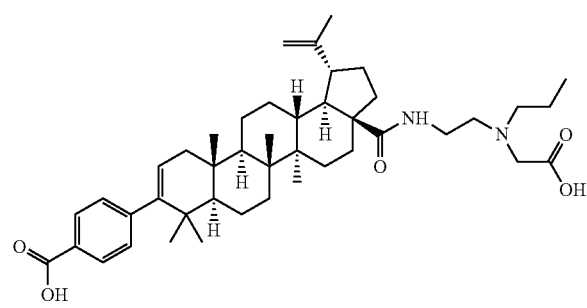

The title compound was prepared following the method described above for 2,2'-(2-(((1R,3aS,5aR,5bR,7aR,11aS,11bR,13aR,13bR)-9-(4-carboxyphenyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysene-3a-carboxamido)ethylazanediyl)diacetic acid (example 88). The product was isolated as a white solid (14 mg, 68%). LCMS: m/e 701.50 (M+H)$^+$, 2.08 min (method 1). $^1$H NMR (500 MHz, Acetic Acid-d$_4$) δ ppm 8.03 (d, J=8.24 Hz, 2H), 7.30 (d, J=8.24 Hz, 2H), 5.37 (d, J=5.49 Hz, 1H), 4.78 (s, 1H), 4.65 (s, 1H), 4.04 (s, 2H), 3.86-3.64 (m, 2H), 3.58-3.46 (m, 2H), 3.34 (dd, J=10.68, 6.71 Hz, 2H), 3.22-3.04 (m, 1H), 2.67-2.45 (m, 1H), 2.26-2.13 (m, 2H), 1.75 (s, 3H), 2.03-1.11 (m, 21H), 1.08 (s, 3H), 1.07 (s, 3H), 1.06 (s, 3H), 1.04 (t, J=5 Hz, 3H), 1.01 (s, 3H), 0.99 (s, 3H).

(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid (example 94) using 2-iodopropane as alkylating reagent. The product was isolated as a white solid (16 mg, 65%). LCMS: m/e 701.63 (M+H)$^+$, 2.06 min (method 1). 1H NMR (500 MHz, Acetic Acid-d$_4$) δ ppm 8.03 (d, J=7.93 Hz, 2H), 7.30 (d, J=7.93 Hz, 2H), 5.37 (d, J=4.88 Hz, 1H), 4.78 (s, 1H), 4.65 (s, 1H), 4.06-3.85 (m, 3H), 3.82-3.62 (m, 2H), 3.56-3.33 (m, 2H), 3.13 (td, J=10.91, 4.12 Hz, 1H), 2.66-2.48 (m, 1H), 2.25-2.13 (m, 2H), 1.74 (s, 3H), 1.41 (d, J=6.41 Hz, 6H), 2.04-1.10 (m, 19H), 1.08 (s, 3H), 1.06 (s, 3H), 1.06 (s, 3H), 1.01 (s, 3H), 0.99 (s, 3H).

Example 96

Preparation of 4-((1R,3aS,5aR,5bR,7aR,11aS,11bR,13aR,13bR)-3a-(2-((2-carboxyethyl)(isopropyl)amino)ethylcarbamoyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

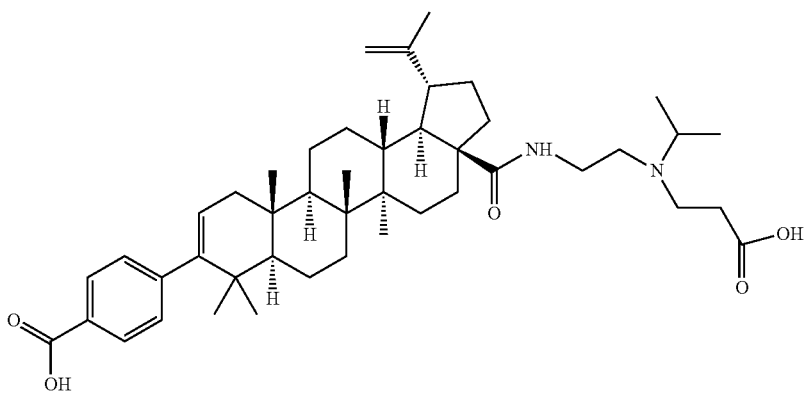

Example 95

Preparation of 4-((1R,3aS,5aR,5bR,7aR,11aS,11bR,13aR,13bR)-3a-(2-((carboxymethyl)(isopropyl)amino)ethylcarbamoyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

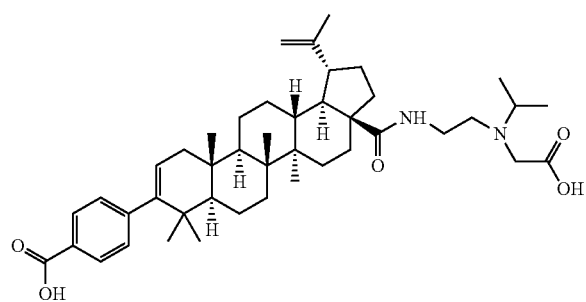

The title compound was prepared following the method described above for the preparation of 4-((1R,3aS,5aR,5bR,7aR,11aS,11bR,13aR,13bR)-3a-(2-((carboxymethyl)(propyl)amino)ethylcarbamoyl)-5a,5b,8,8,11a-pentamethyl-1-

The title compound was prepared following the method described above for the preparation of 4-((1R,3aS,5aR,5bR,7aR,11aS,11bR,13aR,13bR)-3a-(2-((2-carboxyethyl)(ethyl)amino)ethylcarbamoyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid (example 89) using 2-iodopropane as alkylating reagent. The product was isolated as a white solid (12 mg, 66%). LCMS: m/e 715.62 (M+H)$^+$, 2.08 min (method 1). $^1$H NMR (500 MHz, Acetic Acid-d$_4$) δ ppm 8.03 (d, J=7.93 Hz, 2H), 7.30 (d, J=8.24 Hz, 2H), 5.37 (d, J=4.88 Hz, 1H), 4.78 (s, 1H), 4.65 (s, 1H), 4.00-3.85 (m, 1H), 3.85-3.65 (m, 2H), 3.55-3.32 (m, 4H), 3.23-3.08 (m, 1H), 3.01-2.87 (m, 2H), 2.64-2.47 (m, 1H), 2.27-2.14 (m, 2H), 1.75 (s, 3H), 1.41 (d, J=4.88 Hz, 6H), 2.04-1.10 (m, 19H), 1.08 (s, 3H), 1.06 (s, 3H), 1.06 (s, 3H), 1.01 (s, 3H), 0.99 (s, 3H).

Example 97
Procedures for the preparation of 2-((1S,3aS,5aR, 5bR,7aR,11aS,11bR,13aR,13bR)-9-(4-carboxyphenyl)-1-isopropyl-5a,5b,8,8,11a-pentamethyl-2,3,3a,4, 5,5a,5b,6,7,7a,8,11,11a,11b,12,13,13a,13b-octadecahydro-1H-cyclopenta[a]chrysene-3a-carboxamido)-N,N-dimethylethanamine oxide
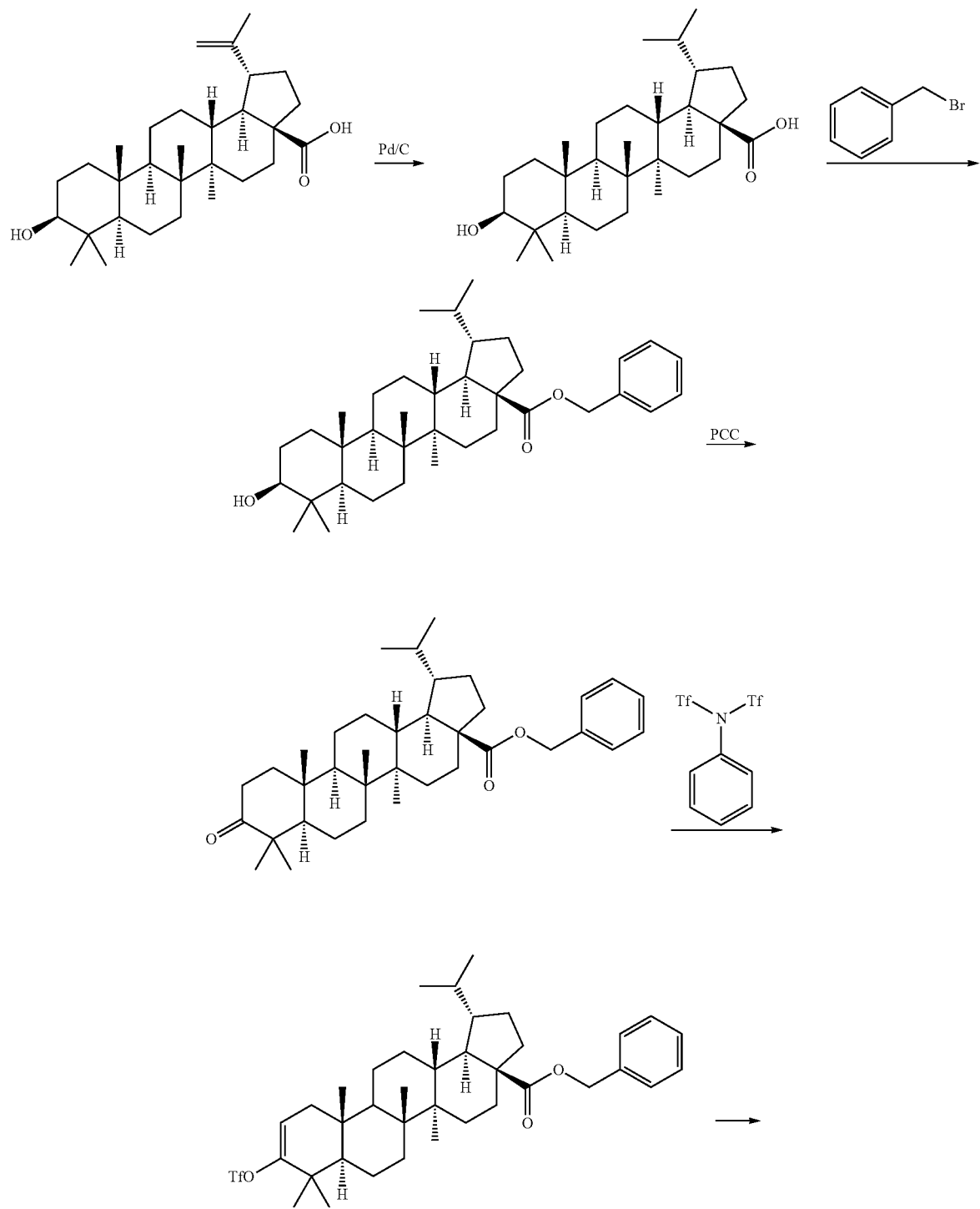

-continued
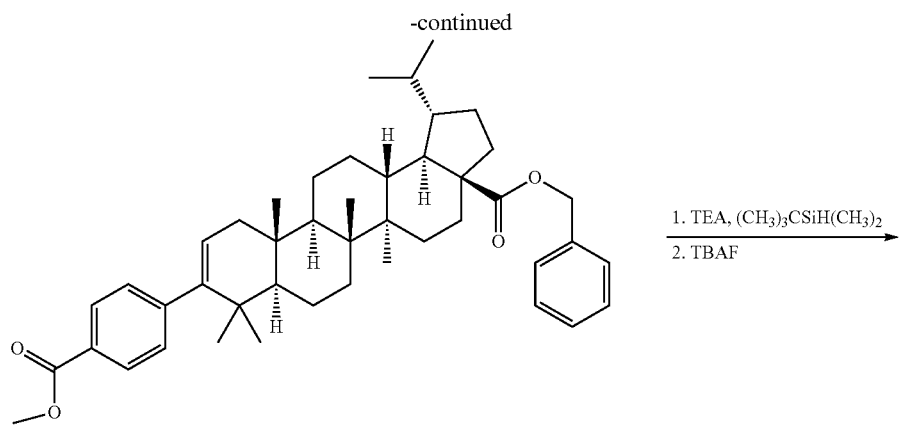
1. TEA, (CH₃)₃CSiH(CH₃)₂
2. TBAF
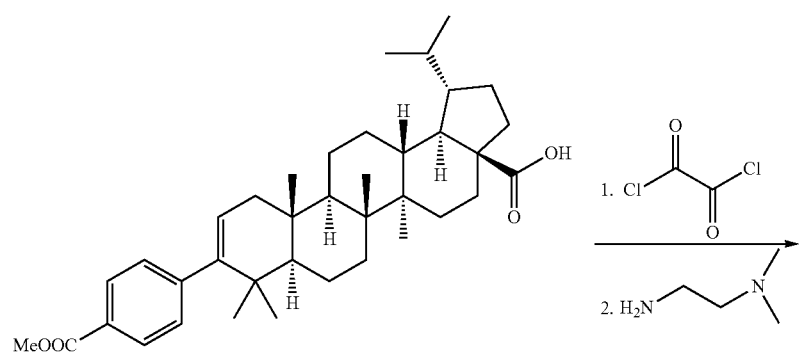
1. <img chem>ClC(O)C(O)Cl</img>
2. H₂N-CH₂CH₂-N(CH₃)₂
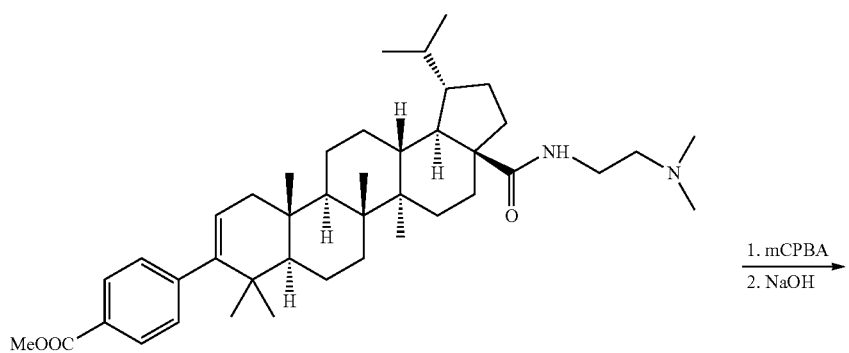
1. mCPBA
2. NaOH
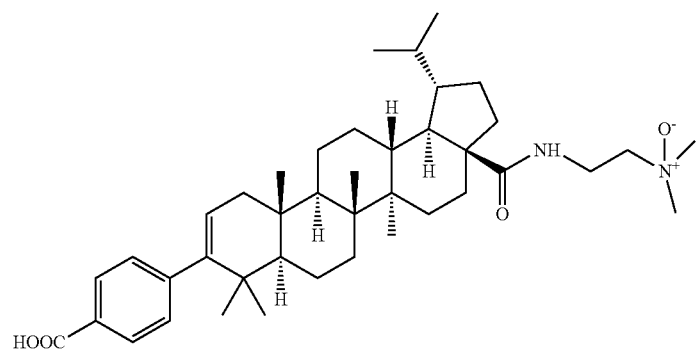

Preparation of (1S,3aS,5aR,5bR,7aR,9S,11aR,11bR, 13aR,13bR)-9-hydroxy-1-isopropyl-5a,5b,8,8,11a-pentamethylicosahydro-1H-cyclopenta[a]chrysene-3a-carboxylic acid. Intermediate 29

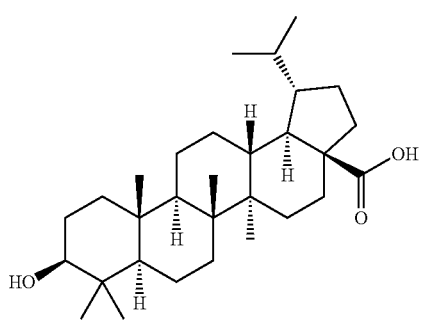

A mixture of (1R,3aS,5aR,5bR,7aR,9S,11aR,11bR,13aR, 13bR)-9-hydroxy-5a,5b,8,8,11a-pentamethyl-1-(prop-1-en-2-yl)icosahydro-1H-cyclopenta[a]chrysene-3a-carboxylic acid (4 g, 8.76 mmol) and 10% Pd/C (1.398 g, 1.314 mmol) in ethyl acetate (80 mL) and MeOH (30 mL) was connected to Parr Shaker and shaked for 18 h under 45 psi at room temperature. LCMS indicated the formation of desired product. The reaction mixture was filtered through celite and the filtrates were concentrated under reduced pressure to give the title compound as white solid (3 g, 75%). LCMS: m/e 457.27 (M−H)⁻, 2.40 min (method 1).

Preparation of (1S,3aS,5aR,5bR,7aR,9S,11aR,11bR, 13aR,13bR)-benzyl 9-hydroxy-1-isopropyl-5a,5b,8, 8,11a-pentamethylicosahydro-1H-cyclopenta[a]chrysene-3a-carboxylate. Intermediate 30

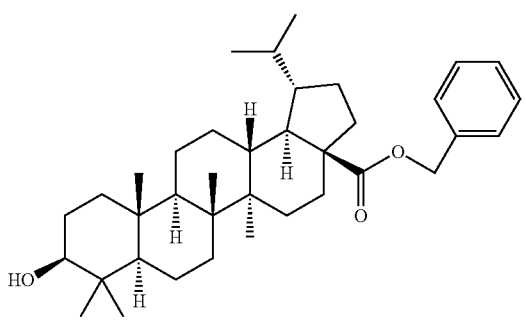

To a solution of (1S,3aS,5aR,5bR,7aR,9S,11aR,11bR, 13aR,13bR)-9-hydroxy-1-isopropyl-5a,5b,8,8,11a-pentamethylicosahydro-1H-cyclopenta[a]chrysene-3a-carboxylic acid (3 g, 6.54 mmol) and potassium carbonate (1.808 g, 13.08 mmol) in DMF (60 mL) was added (bromomethyl) benzene (0.816 mL, 6.87 mmol). The reaction mixture was heated up to 60° C. for 3 h. LCMS indicated the starting material was consumed. The reaction mixture was quenched with 60 ml water, a white precipitate was observed. The white solid was collected through filtration and washed with distilled water. The solid was dried in the air to provide the title compound as white solid (3.3 g, 92%). ¹H NMR (500 MHz, CHLOROFORM-d) δ ppm 7.42-7.28 (m, 5H), 5.27-5.01 (m, 2H), 3.18 (dt, J=11.22, 5.53 Hz, 1H), 2.40-2.09 (m, 3H), 1.91-1.73 (m, 2H), 1.72-0.78 (m, 21H), 0.95 (s, 3H), 0.91 (s, 3H), 0.84 (d, J=7.02 Hz, 3H), 0.80 (s, 3H), 0.75 (s, 3H), 0.73 (s, 3H), 0.73 (d, J=6.71 Hz, 3H).

Preparation of (1S,3aS,5aR,5bR,7aR,11aR,11bR, 13aR,13bR)-benzyl 1-isopropyl-5a,5b,8,8,11a-pentamethyl-9-oxoicosahydro-1H-cyclopenta[a]chrysene-3a-carboxylate. Intermediate 31

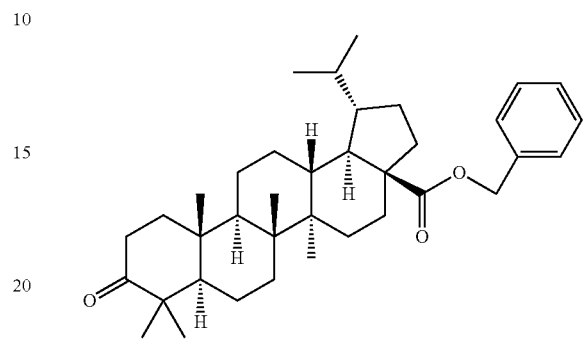

To a solution of (1S,3aS,5aR,5bR,7aR,9S,11aR,11bR, 13aR,13bR)-benzyl 9-hydroxy-1-isopropyl-5a,5b,8,8,11a-pentamethylicosahydro-1H-cyclopenta[a]chrysene-3a-carboxylate (3.3 g, 6.01 mmol) in DCM (50 mL) was added PCC (3.89 g, 18.04 mmol). The reaction mixture was stirred for 4 hours. TLC indicated sm was consumed and desired product was formed. The reaction mixture was concentrated under reduced pressure. The residue was purified by biotage with 0-10% ethyl acetate/hexane to provide the title compound as white solid (3.05, 93%). LCMS: m/e 547.25 (M+H)⁺, 2.77 min (method 1). 1H NMR (500 MHz, CHLOROFORM-d) δ ppm 7.41-7.28 (m, 5H), 5.10 (q, J=12.41 Hz, 2H), 2.57-2.34 (m, 2H), 2.31-2.16 (m, 3H), 1.98-1.86 (m, 1H), 1.85-1.73 (m, 2H), 1.73-1.61 (m, 1H), 1.54-1.07 (m, 17H), 1.06 (s, 3H), 1.01 (s, 3H), 0.92 (s, 3H), 0.90 (s, 3H), 0.84 (d, J=7.02 Hz, 3H), 0.76 (s, 3H), 0.73 (d, 3H).

Preparation of (1S,3aS,5aR,5bR,7aR,11aR,13aR, 13bR)-benzyl 1-isopropyl-5a,5b,8,8,11a-pentamethyl-9-(trifluoromethylsulfonyloxy)-2,3,3a,4,5,5a, 5b,6,7,7a,8,11,11a,11b,12,13,13a,13b-octadecahydro-1H-cyclopenta[a]chrysene-3a-carboxylate. Intermediate 32

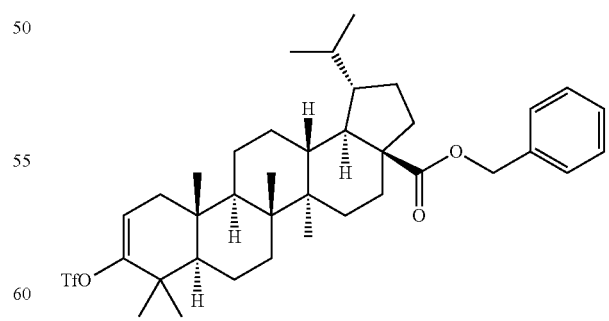

To (1S,3aS,5aR,5bR,7aR,11aR,13aR,13bR)-benzyl 1-isopropyl-5a,5b,8,8,11a-pentamethyl-9-oxoicosahydro-1H-cyclopenta[a]chrysene-3a-carboxylate (3.05 g, 5.58 mmol) in THF (100 mL) at −78° C. was added KHMDS (22.31 mL, 11.16 mmol), the reaction mixture was stirred for 15 minutes at −78° C. then 1,1,1-trifluoro-N-phenyl-N-(trifluoromethyl-sulfonyl)methanesulfonamide (2.192 g, 6.14 mmol) in THF (15 mL) and toluene (5 mL) was added slowly through 20 minutes at −78° C. The reaction mixture was stirred for 2 hours at that temperature. TLC indicated the formation of desired product. The reaction mixture was quenched with water (100 mL), extracted with ethyl acetate (3×50 mL). The extracts were dried over sodium sulfate, filtered and concentrated under reduced pressure. The residue was purified by biotage with 0-6% ethyl acetate/hexanes to provide the title compound as a white solid (3.5 g, 92%). ¹H NMR (500 MHz, CHLOROFORM-d) δ ppm 7.42-7.28 (m, 5H), 5.55 (dd, J=6.71, 2.14 Hz, 1H), 5.19-5.03 (m, 2H), 2.32-2.11 (m, 4H), 1.87-1.62 (m, 4H), 1.11 (s, 3H), 1.53-1.06 (m, 16H), 1.00 (s, 3H), 0.92 (s, 3H), 0.88 (s, 3H), 0.84 (d, J=6.71 Hz, 3H), 0.75 (s, 3H), 0.74 (d, J=6.71 Hz, 3H).

Preparation of (1S,3aS,5aR,5bR,7aR,11aS,11bR, 13aR,13bR)-benzyl 1-isopropyl-9-(4-(methoxycarbonyl)phenyl)-5a,5b,8,8,11a-pentamethyl-2,3,3a,4,5, 5a,5b,6,7,7a,8,11,11a,11b,12,13,13a,13b-octadecahydro-1H-cyclopenta[a]chrysene-3a-carboxylate. Intermediate 33

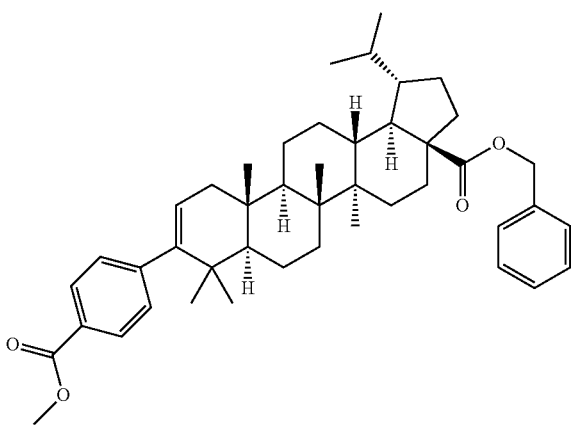

A mixture of (1S,3aS,5aR,5bR,7aR,11aR,11bR,13aR, 13bR)-benzyl 1-isopropyl-5a,5b,8,8,11a-pentamethyl-9-(trifluoromethylsulfonyloxy)-2,3,3a,4,5,5a,5b,6,7,7a,8,11,11a, 11b,12,13,13a,13b-octadecahydro-1H-cyclopenta[a] chrysene-3a-carboxylate (3.5 g, 5.16 mmol), 4-(methoxycarbonyl)phenylboronic acid (1.206 g, 6.70 mmol), Pd(Ph₃P)₄ (0.179 g, 0.155 mmol) and sodium carbonate (1.639 g, 15.47 mmol) in dioxane (20 mL) and water (20 mL) was heated up at 90° C. for 2 h. TLC indicated starting material was consumed and a new spot was present. The reaction mixture was purified by biotage with 0-10% ethyl acetate/hexanes to provide the title compound as white solid (3.05 g, 89%). ¹H NMR (500 MHz, CHLOROFORM-d) δ ppm 7.92 (d, J=8.24 Hz, 2H), 7.48-7.28 (m, 5H), 7.19 (d, J=7.93 Hz, 2H), 5.28 (dd, J=6.26, 1.68 Hz, 1H), 5.19-5.00 (m, 2H), 3.90 (s, 3H), 2.38-2.20 (m, 3H), 2.11 (dd, J=17.09, 6.41 Hz, 1H), 1.89-1.75 (m, 2H), 1.72-1.61 (m, 2H), 1.53-1.07 (m, 16H), 0.95 (s, 6H), 0.92 (s, 3H), 0.90 (s, 3H), 0.85 (d, J=6.71 Hz, 3H), 0.80 (s, 3H), 0.75 (d, 3H).

Preparation of (1S,3aS,5aR,5bR,7aR,11aS,11bR, 13aR,13bR)-1-isopropyl-9-(4-(methoxycarbonyl) phenyl)-5a,5b,8,8,11a-pentamethyl-2,3,3a,4,5,5a,5b, 6,7,7a,8,11,11a,11b,12,13,13a,13b-octadecahydro-1H-cyclopenta[a]chrysene-3a-carboxylic acid. Intermediate 34

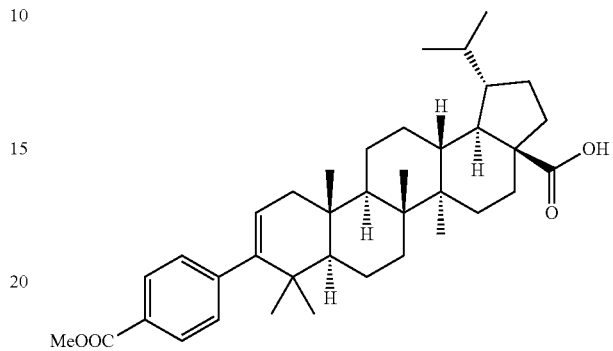

A mixture of (1S,3aS,5aR,5bR,7aR,11aS,11bR,13aR, 13bR)-benzyl 1-isopropyl-9-(4-(methoxycarbonyl)phenyl)-5a,5b,8,8,11a-pentamethyl-2,3,3a,4,5,5a,5b,6,7,7a,8,11, 11a,11b,12,13,13a,13b-octadecahydro-1H-cyclopenta[a] chrysene-3a-carboxylate (220 mg, 0.331 mmol), tert-butyldimethylsilane (77 mg, 0.662 mmol), TEA (0.074 mL, 0.529 mmol) and palladium (II) acetate (18.57 mg, 0.083 mmol) in DCM (2 mL) was heated up at 60° C. for 3 h, TLC indicated the starting material was consumed. The reaction mixture was filtered a pad of celite. The filtrates were concentrated under reduced pressure to provide the intermediate. To this intermediate in dioxane (2 mL) was added TBAF (346 mg, 0.993 mmol), the reaction mixture was stirred for 2 h at room temperature. LCMS indicated the formation of desired product. The reaction mixture was quenched with distilled water (5 mL), extracted with DCM (3×8 mL). All the extracts were combined, dried over sodium sulfate, filtered and concentrated under reduced pressure to provide the desired product as a pale yellow solid (150 mg, 79%). LCMS: m/e 575.35 (M+H)⁺, 2.84 min (method 1).

Preparation of methyl 4-((1S,3aS,5aR,5bR,7aR, 11aS,11bR,13aR,13bR)-3a-(2-(dimethylamino)ethylcarbamoyl)-1-isopropyl-5a,5b,8,8,11a-pentamethyl-2,3,3a,4,5,5a,5b,6,7,7a,8,11,11a,11b,12,13,13a, 13b-octadecahydro-1H-cyclopenta[a]chrysen-9-yl) benzoate. Intermediate 35

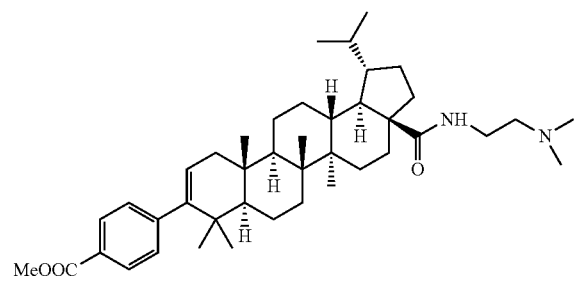

A mixture of (1S,3aS,5aR,5bR,7aR,11aS,11bR,13aR,13bR)-1-isopropyl-9-(4-(methoxycarbonyl)phenyl)-5a,5b,8,8,11a-pentamethyl-2,3,3a,4,5,5a,5b,6,7,7a,8,11,11a,11b,12,13,13a,13b-octadecahydro-1H-cyclopenta[a]chrysene-3a-carboxylic acid (150 mg, 0.261 mmol) and oxalyl dichloride (0.783 mL, 1.566 mmol) in DCM (4 mL) was stirred for 2 h at room temperature. LCMS indicated the formation of desired product. The reaction mixture was concentrated under reduced pressure to provide the intermediate acid chloride as a yellow solid. To a mixture of N1N1-dimethylethane-1,2-diamine (46.0 mg, 0.522 mmol) and Hunig'sBase (0.228 mL, 1.305 mmol) in DCM (4 mL) was added the acid chloride in DCM (4 mL), the reaction mixture was stirred for 2 h at 20° C. LCMS indicated the formation of desired product. The reaction mixture was quenched with distilled water (3 mL), extracted with DCM (3×3 mL). All the extracts were combined, dried over sodium sulfate, filtered and concentrated under reduced pressure to provide the title compound as a pale yellow solid (140 mg, 83%). LCMS: m/e 645.51 (M+H)$^+$, 3.00 min (method 1).

Preparation of 2-((1S,3aS,5aR,5bR,7aR,11aS,11bR,13aR,13bR)-9-(4-carboxyphenyl)-1-isopropyl-5a,5b,8,8,11a-pentamethyl-2,3,3a,4,5,5a,5b,6,7,7a,8,11,11a,11b,12,13,13a,13b-octadecahydro-1H-cyclopenta[a]chrysene-3a-carboxamido)-N,N-dimethylethanamine oxide. Intermediate 36

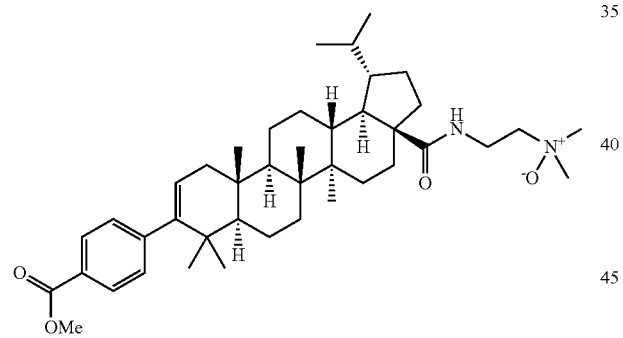

To a mixture of methyl 4-((1S,3aS,5aR,5bR,7aR,11aS,11bR,13aR,13bR)-3a-(2-(dimethylamino)ethylcarbamoyl)-1-isopropyl-5a,5b,8,8,11a-pentamethyl-2,3,3a,4,5,5a,5b,6,7,7a,8,11,11a,11b,12,13,13a,13b-octadecahydro-1H-cyclopenta[a]chrysen-9-yl)benzoate (20 mg, 0.031 mmol) in DCM (2 mL) was added 3-chlorobenzoperoxoic acid (13.90 mg, 0.062 mmol) at −78° C. The reaction mixture was stirred for 3 hours. LCMS indicated the formation of desired product and consumption of the starting material. The reaction mixture was quenched with distilled water, extracted with DCM (3×2 mL). All the extracts were combined, dried over sodium sulfate, filtered and concentrated under reduced pressure to provide the title compound as an yellow oil (10 mg, 49%). LCMS: m/e 661.49 (M+H)$^+$, 2.79 min (method 1).

Preparation of 2-((1S,3aS,5aR,5bR,7aR,11aS,11bR,13aR,13bR)-9-(4-carboxyphenyl)-1-isopropyl-5a,5b,8,8,11a-pentamethyl-2,3,3a,4,5,5a,5b,6,7,7a,8,11,11a,11b,12,13,13a,13b-octadecahydro-1H-cyclopenta[a]chrysene-3a-carboxamido)-N,N-dimethylethanamine oxide

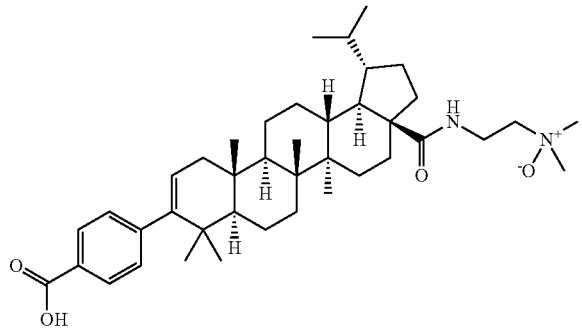

The title compound was prepared following the method described above for 2,2'-(2-((1R,3aS,5aR,5bR,7aR,11aS,11bR,13aR,13bR)-9-(4-carboxyphenyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysene-3a-carboxamido)ethylazanediyl)diacetic acid (example 88). The product was isolated as a white solid (7 mg, 68%). LCMS: m/e 647.45 (M+H)$^+$, 2.22 min (method 1). $^1$H NMR (500 MHz, Acetic Acid-d$_4$) δ ppm 8.03 (d, J=8.24 Hz, 2H), 7.30 (d, J=8.24 Hz, 2H), 5.38 (d, J=4.58 Hz, 1H), 4.08-3.83 (m, 4H), 3.59 (s, 6H), 2.61-2.47 (m, 1H), 2.41-2.30 (m, 1H), 2.27-2.16 (m, 2H), 1.90-1.67 (m, 4H), 1.67-1.38 (m, 12H), 1.36-1.17 (m, 4H), 1.08 (s, 3H), 1.07 (s, 3H), 1.05 (s, 3H), 1.01 (s, 3H), 1.00 (s, 3H), 0.91 (d, J=6.71 Hz, 3H), 0.82 (d, J=6.71 Hz, 3H).

Example 98

Preparation of 4-((1R,3aS,5aR,5bR,7aR,11aS,11bR,13aR,13bR)-3a-(3-aminopropylcarbamoyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

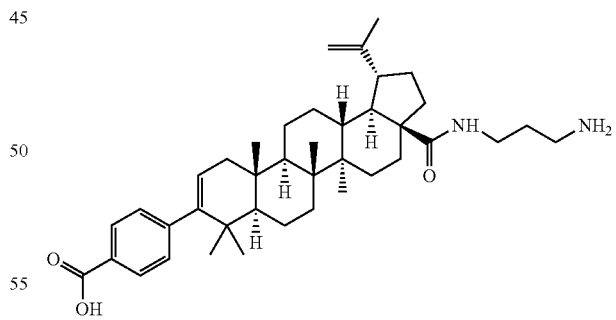

The title compound was prepared following the general procedures described above for the C-28 amide formation and hydrolysis using propane-1,3-diamine as the reactant amine. The product was isolated as a white solid (1.2 mg, 15%). LCMS: m/e 615.42 (M+H)$^+$, 2.15 min (method 1). $^1$H NMR (500 MHz, Acetic Acid-d$_4$) δ ppm 8.03 (d, J=8.24 Hz, 2H), 7.30 (d, J=8.55 Hz, 2H), 5.37 (d, J=4.58 Hz, 1H), 4.79 (d, J=1.83 Hz, 1H), 4.65 (s, 1H), 3.58-3.33 (m, 2H), 3.25-3.03 (m, 3H), 2.72-2.50 (m, 1H), 2.25-2.13 (m, 2H), 1.75 (s, 3H), 2.04-1.09 (m, 21H), 1.08 (s, 3H), 1.07 (s, 3H), 1.06 (s, 3H), 1.01 (s, 3H), 0.99 (s, 3H).

Example 99

Preparation of 4-((1R,3aS,5aR,5bR,7aR,11aS,11bR,13aR,13bR)-3a-(3-((2-carboxyethyl)(ethyl)amino)propylcarbamoyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

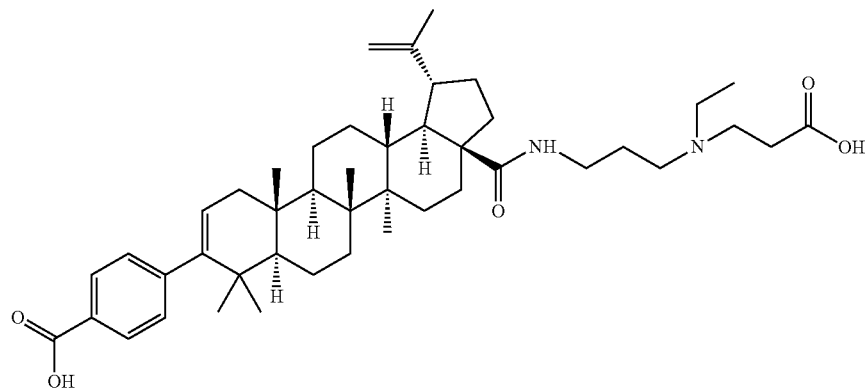

The title compound was prepared following the method described above for the preparation of 4-((1R,3aS,5aR,5bR,7aR,11aS,11bR,13aR,13bR)-3a-(2-((2-carboxyethyl)(ethyl)amino)ethylcarbamoyl)-5a,5b,8,8,11a-pentamethyl-1-(prop-1-en-2-yl)-2,3,3a,4,5,5a,5b,6,7,7a,8,11,11a,11b,12,13,13a,13b- octadecahydro-1H-cyclopenta[a]chrysen-9-yl) benzoic acid (example 89) using methyl 4-((1R,3aS,5aR,5bR,7aR,11aS,11bR,13aR,13bR)-3a-(3-(3-methoxy-3-oxopropylamino)propylcarbamoyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl) benzoate as amine and iodoethane as alkylating reagent. The product was isolated as a white solid (3 mg, 30%). LCMS: m/e 715.49 (M+H)$^+$, 2.11 min (method 1). $^1$H NMR (500 MHz, Acetic Acid-d$_4$) δ ppm 8.03 (d, J=8.24 Hz, 2H), 7.30 (d, J=8.24 Hz, 2H), 5.37 (d, J=5.19 Hz, 1H), 4.78 (s, 1H), 4.65 (s, 1H), 3.50 (t, J=7.17 Hz, 2H), 3.46-3.40 (m, 2H), 3.39-3.31 (m, 2H), 3.27 (t, J=7.63 Hz, 2H), 3.21-3.08 (m, 1H), 2.97 (t, J=7.02 Hz, 2H), 2.67-2.54 (m, 1H), 2.25-2.17 (m, 2H), 1.74 (s, 3H), 1.39 (t, J=7.17 Hz, 3H), 2.05-1.10 (m, 21H), 1.08 (s, 3H), 1.06 (s, 6H), 1.01 (s, 3H), 0.99 (s, 3H).

Example 100

Preparation of 3,3'-(3-((1R,3aS,5aR,5bR,7aR,11aS,11bR,13aR,13bR)-9-(4-carboxyphenyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysene-3a-carboxamido)propylazanediyl)dipropanoic acid

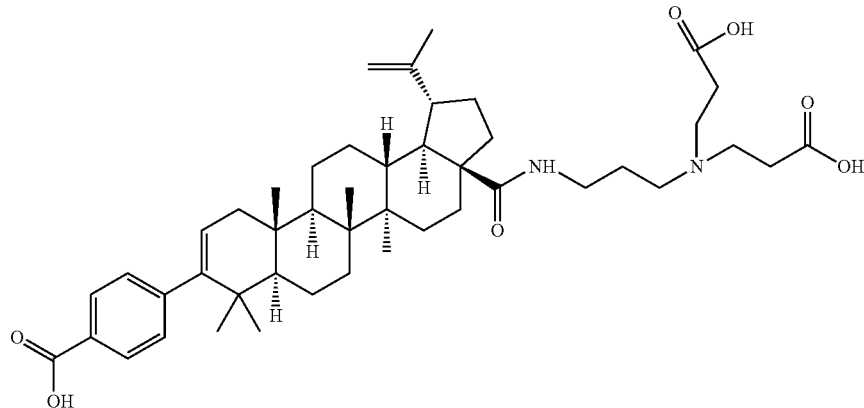

The title compound was prepared following the method described above for 3,3'-(2-((1R,3aS,5aR,5bR,7aR,11aS,11bR,13aR,13bR)-9-(4-carboxyphenyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysene-3a-carboxamido)ethylazanediyl)dipropanoic acid (example 90) using methyl 4-((1R,3aS,5aR,5bR,7aR,11aS,11bR,13aR,13bR)-3a-(3-(3-methoxy-3-oxopropylamino)propylcarbamoyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate as amine. The product was isolated as a white solid (4 mg, 40%). LCMS: m/e 759.62 (M+H)$^+$, 2.01 min (method 1). $^1$H NMR (500 MHz, Acetic Acid-d$_4$) δ ppm 8.03 (d, J=8.24 Hz, 2H), 7.30 (d, J=8.24 Hz, 2H), 5.31-5.43 (m, 1H), 4.78 (d, J=1.53 Hz, 1H), 4.65 (s, 1H), 3.55 (t, J=6.71 Hz, 4H), 3.48-3.39 (m, 2H), 3.34 (t, J=7.93 Hz, 2H), 3.15 (td, J=10.83, 4.58 Hz, 1H), 3.00 (t, J=6.71 Hz, 4H), 2.59 (td, J=11.90, 3.66 Hz, 1H), 1.74 (s, 3H), 2.23-1.09 (m, 23H), 1.08 (s, 3H), 1.06 (s, 6H), 1.01 (s, 3H), 0.99 (s, 3H).

Example 101
Procedure for the preparation of 4-(((1R,3aS,5aR,5bR,7aR,11aS,11bR,13aR,13bR)-3a-(3-((3-carboxypropyl)(ethyl)amino)propylcarbamoyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl) benzoic acid
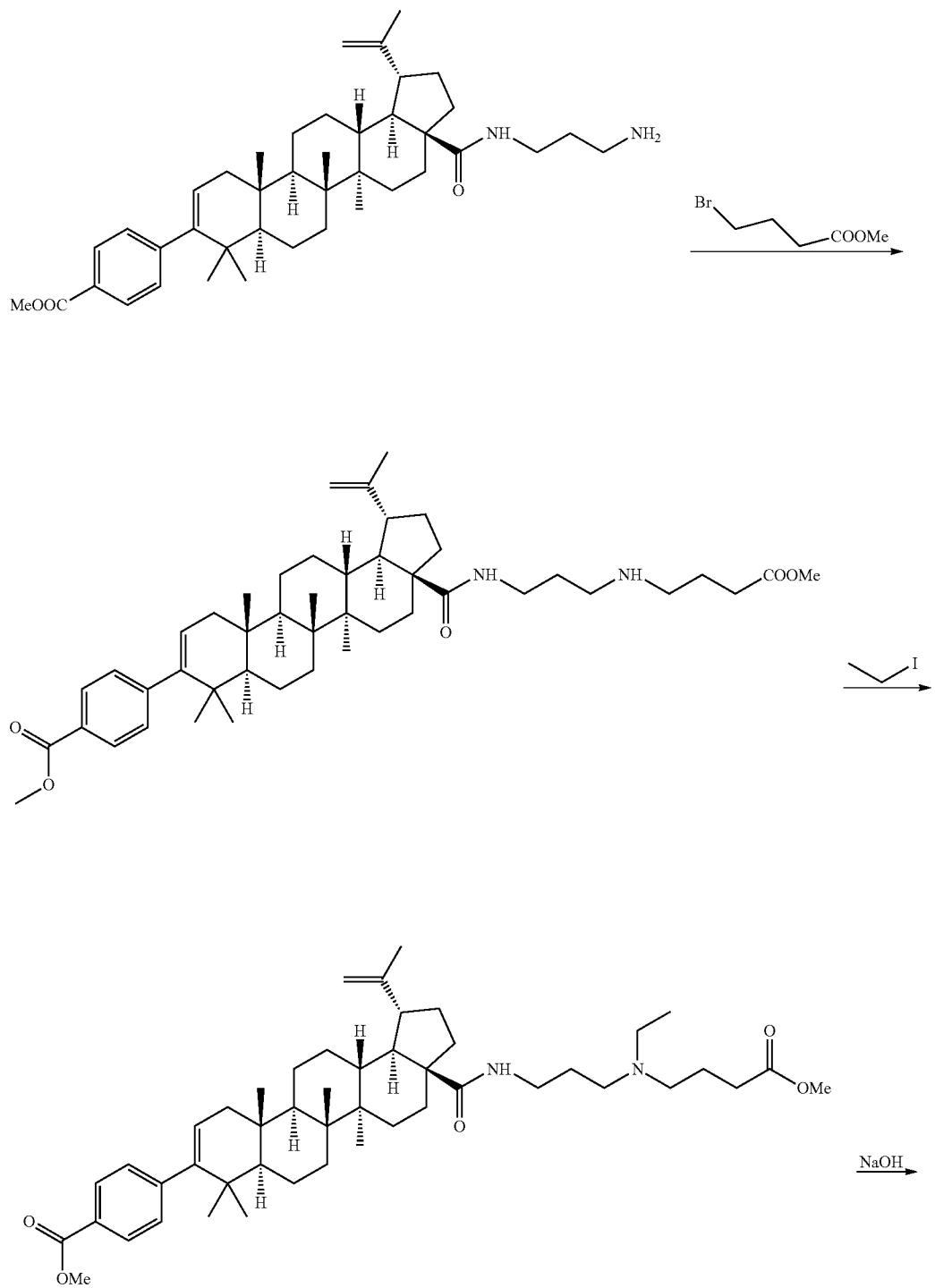

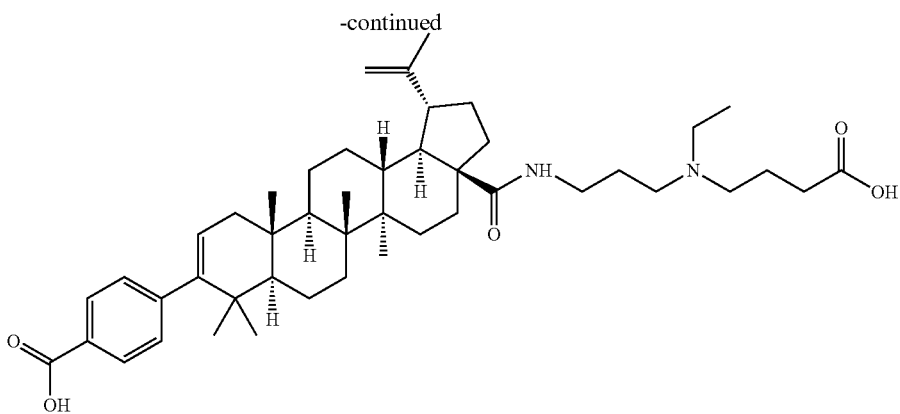

Preparation of methyl 4-((1R,3aS,5aR,5bR,7aR, 11aS,11bR,13aR,13bR)-3a-(3-(4-methoxy-4-oxobutylamino)propylcarbamoyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate. Intermediate 37

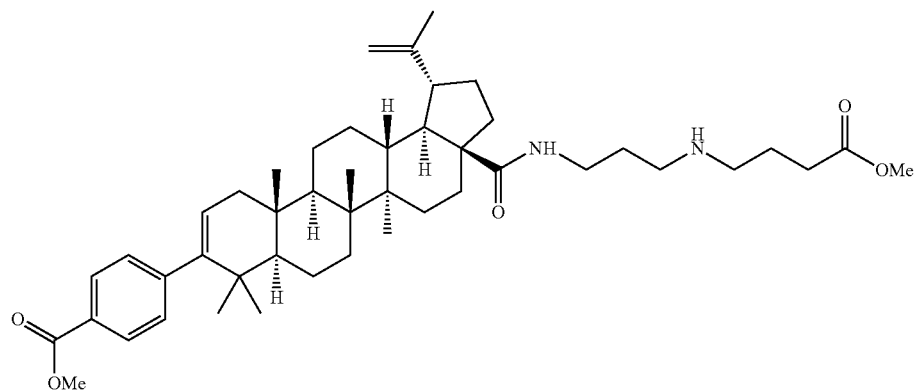

A mixture of methyl 4-((1R,3aS,5aR,5bR,7aR,11aS,11bR,13aR,13bR)-3a-(3-aminopropylcarbamoyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate (30 mg, 0.048 mmol), methyl 4-bromobutanoate (25.9 mg, 0.143 mmol) and potassium carbonate (19.78 mg, 0.143 mmol) in dioxane (1 mL) and Acetonitrile (1 mL) was heated up at 78° C. for 3 hours. LCMS indicated the formation of desired product, the reaction mixture was filtered and the clear solution was purified by prep HPLC to give the title compound as a white solid (10 mg, 29%). LCMS: m/e 729.48 (M+H)$^+$, 2.62 min (method 1).

Preparation of methyl 4-((1R,3aS,5aR,5bR,7aR, 11aS,11bR,13aR,13bR)-3a-(3-(ethyl(4-methoxy-4-oxobutyl)amino)propylcarbamoyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate. Intermediate 38

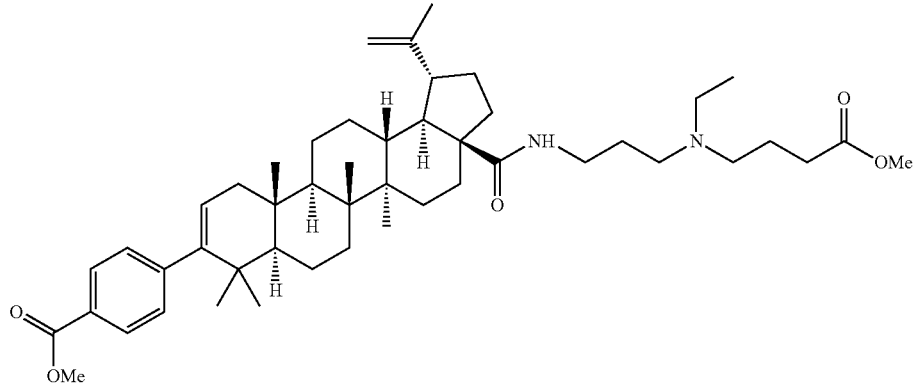

A mixture of methyl 4-((1R,3aS,5aR,5bR,7aR,11aS,11bR,13aR,13bR)-3a-(3-(4-methoxy-4-oxobutylamino)propylcarbamoyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate (10 mg, 0.014 mmol) and potassium carbonate (5.69 mg, 0.041 mmol) in dioxane (1 mL) and acetonitrile (1.000 mL) was heated up at 78° C. for 3 hours, LCMS indicated the formation of desired product. The reaction mixture was quenched with distilled water (2 mL), extracted with DCM (3×2 mL). All the extracts were combined, dried over sodium sulfate, filtered and concentrated under reduced pressure to provide the title compound as a colorless oil (10 mg, 96%). LCMS: m/e 757.50 (M+H)$^+$, 2.73 min (method 1).

Preparation of 4-((1R,3aS,5aR,5bR,7aR,11aS,11bR,13aR,13bR)-3a-(3-((3-carboxypropyl)(ethyl)amino)propylcarbamoyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

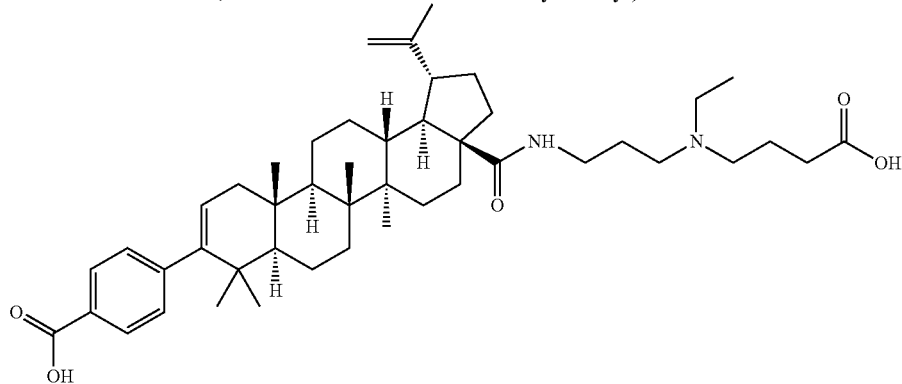

The title compound was prepared following the method described above for 2,2'-(2-((1R,3aS,5aR,5bR,7aR,11aS,11bR,13aR,13bR)-9-(4-carboxyphenyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysene-3a-carboxamido)ethylazanediyl)diacetic acid (example 88). The product was isolated as a white solid (3 mg, 30%). LCMS: m/e 730.31 (M+H)$^+$, 2.08 min (method 1). $^1$H NMR (500 MHz, Acetic Acid-d$_4$) δ ppm 8.03 (d, J=8.24 Hz, 2H), 7.30 (d, J=7.93 Hz, 2H), 5.37 (d, J=4.88 Hz, 1H), 4.78 (s, 1H), 4.65 (s, 1H), 3.56-3.37 (m, 4H), 3.36-3.31 (m, 1H), 3.29-3.21 (m, 2H), 3.20-3.07 (m, 2H), 2.74-2.48 (m, 3H), 1.74 (s, 3H), 2.33-1.10 (m, 28H), 1.09 (s, 3H), 1.06 (s, 6H), 1.01 (s, 3H), 0.99 (s, 3H).

Example 102

Preparation of 4-((1R,3aS,5aR,5bR,7aR,11aS,11bR,13aR,13bR)-3a-(3-((carboxymethyl)(ethyl)amino)propylcarbamoyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

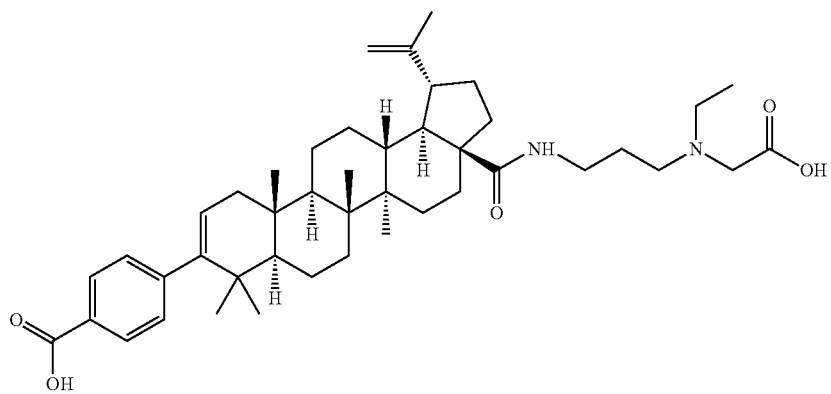

The title compound was prepared following the method described above for the preparation of 4-((1R,3aS,5aR,5bR,7aR,11aS,11bR,13aR,13bR)-3a-(2-((carboxymethyl)(propyl)amino)ethylcarbamoyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid (example 94) using methyl 4-((1R,3aS,5aR,5bR,7aR,11aS,11bR,13aR,13bR)-3a-(3-(2-methoxy-2-oxoethylamino)propylcarbamoyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate as starting material. The product was isolated as a white solid (11 mg, 39%). LCMS: m/e 701.04 (M+H)+, 2.04 min (method 1). $^1$H NMR (500 MHz, Acetic Acid-$d_4$) δ ppm 8.03 (d, J=8.24 Hz, 2H), 7.30 (d, J=8.24 Hz, 2H), 5.37 (d, J=4.88 Hz, 1H), 4.78 (br. s., 1H), 4.65 (br. s., 1H), 4.05-3.92 (m, 2H), 3.45 (s, 2H), 3.42-3.35 (m, 2H), 3.35-3.21 (m, 2H), 3.16 (td, J=10.99, 3.97 Hz, 1H), 2.67-2.55 (m, 1H), 2.25-2.13 (m, 2H), 1.74 (s, 3H), 1.39 (t, J=7.32 Hz, 3H), 2.05-1.13 (m, 22H), 1.08 (s, 3H), 1.07 (s, 3H), 1.06 (s, 3H), 1.01 (s, 3H), 0.99 (s, 3H).

Example 103

Preparation of 4-((1R,3aS,5aR,5bR,7aR,11aS,11bR,13aR,13bR)-3a-(2-((3-carboxypropyl)(ethyl)amino)ethylcarbamoyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

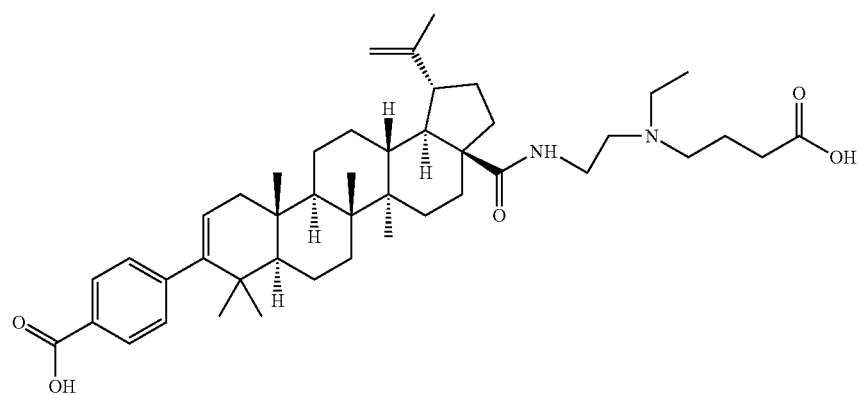

The title compound was prepared following the method described above for 4-((1R,3aS,5aR,5bR,7aR,11aS,11bR,13aR,13bR)-3a-(2-((3-carboxypropyl)(ethyl)amino)propylcarbamoyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid (example 101) using methyl 4-((1R,3aS,5aR,5bR,7aR,11aS,11bR,13aR,13bR)-3a-(2-aminoethylcarbamoyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate as amine. The product was isolated as a white solid (3 mg, 25%). LCMS: m/e 715.45 (M+H)+, 2.06 min (method 1). $^1$H NMR (500 MHz, Acetic Acid-$d_4$) δ ppm 8.03 (d, J=8.24 Hz, 2H), 7.30 (d, J=8.24 Hz, 2H), 5.37 (d, J=4.88 Hz, 1H), 4.78 (s, 1H), 4.65 (s, 1H), 3.88-3.68 (m, 2H), 3.49-3.34 (m, 4H), 3.34-3.27 (m, 2H), 3.19-3.06 (m, 1H), 2.67-2.49 (m, 3H), 2.23-2.15 (m, 2H), 1.74 (s, 3H), 1.38 (t, J=7.17 Hz, 3H), 2.04-1.09 (m, 21H), 1.08 (s, 3H), 1.06 (s, 3H), 1.05 (s, 3H), 1.01 (s, 3H), 0.99 (s, 3H).

Example 104

Preparation of 4-((1R,3aS,5aR,5bR,7aR,11aS,11bR,13aR,13bR)-3a-(2-(dimethylamino)ethylcarbamoyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-2-fluorobenzoic acid

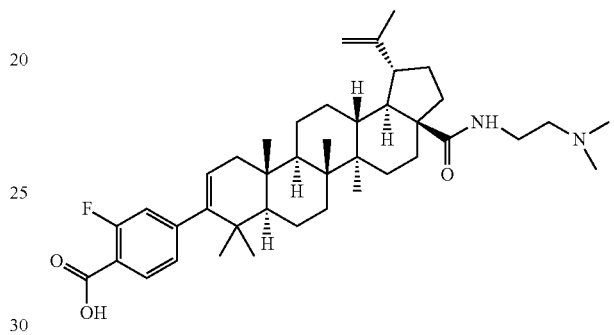

The title compound was prepared following the general procedures described above for the Suzuki coupling using 3-fluoro-4-(methoxycarbonyl)phenylboronic acid as boronic acid, the C-28 amide formation and hydrolysis using N1,N1-dimethylethane-1,2-diamine as the reactant amine. The product was isolated as a white solid (30 mg, 71%). LCMS: m/e 647.54 (M+H)+, 2.26 min (method 1). $^1$H NMR (500 MHz, Acetic Acid-$d_4$) δ ppm 7.96 (t, J=7.93 Hz, 1H), 7.08 (d, J=8.24 Hz, 1H), 7.02 (d, J=11.90 Hz, 1H), 5.42 (d, J=4.88 Hz, 1H), 4.78 (d, J=1.53 Hz, 1H), 4.65 (s, 1H), 3.75 (t, J=5.95 Hz, 2H), 3.44-3.33 (m, 2H), 3.14 (td, J=10.91, 4.12 Hz, 1H), 2.95 (s, 6H), 2.54 (td, J=12.28, 2.90 Hz, 1H), 2.25-2.15 (m, 2H), 1.73 (s, 3H), 2.01-1.09 (m, 19H), 1.08 (s, 3H), 1.04 (s, 6H), 1.02 (s, 3H), 1.00 (s, 3H).

Example 105

Preparation of 4-((1R,3aS,5aR,5bR,7aR,11aS,11bR, 13aR,13bR)-3a-((3-(1,1-dioxido-4-thiomorpholinyl) propyl)carbamoyl)-1-isopropenyl-5a,5b,8,8,11a-pentamethyl-2,3,3a,4,5,5a,5b,6,7,7a,8,11,11a,11b,12, 13,13a,13b-octadecahydro-1H-cyclopenta[a] chrysen-9-yl)-2-fluorobenzoic acid

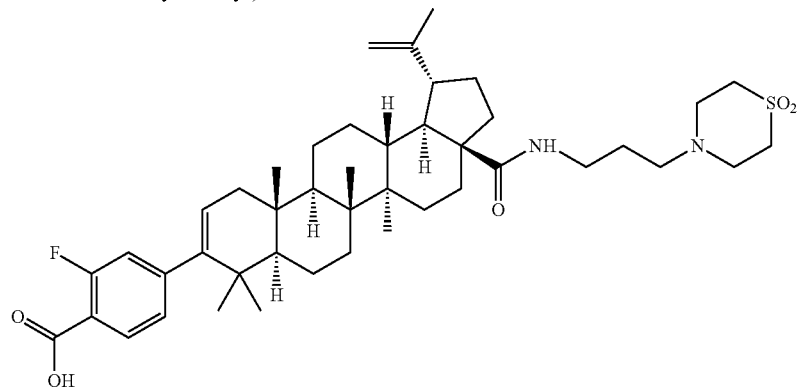

The title compound was prepared following the general procedures described above for the Suzuki coupling using 3-fluoro-4-(methoxycarbonyl)phenylboronic acid as boronic acid, the C-28 amide formation and hydrolysis using 4-(3-aminopropyl)thiomorpholine 1,1-dioxide as the reactant amine. The product was isolated as a white solid (15 mg, 36%). LCMS: m/e 751.46 (M+H)$^+$, 2.27 min (method 1). $^1$H NMR (500 MHz, Acetic Acid-d$_4$) δ ppm 7.96 (t, J=7.93 Hz, 1H), 7.08 (dd, J=8.09, 1.37 Hz, 1H), 7.03 (d, J=11.60 Hz, 1H), 5.42 (d, J=4.58 Hz, 1H), 4.78 (d, J=1.53 Hz, 1H), 4.65 (s, 1H), 3.85 (br. s., 4H), 3.59 (br. s., 4H), 3.50-3.32 (m, 2H), 3.32-3.24 (m, 2H), 3.15 (td, J=10.99, 3.97 Hz, 1H), 2.60 (td, J=12.21, 3.05 Hz, 1H), 2.25-2.12 (m, 2H), 1.74 (s, 3H), 2.05-1.10 (m, 21H), 1.08 (s, 3H), 1.06 (s, 3H), 1.05 (s, 3H), 1.02 (s, 3H), 1.00 (s, 3H).

Example 106

Preparation of 4-((1R,3aS,5aR,5bR,7aR,11aS,11bR, 13aR,13bR)-3a-((2-(1,1-dioxido-4-thiomorpholinyl) ethyl)carbamoyl)-1-isopropenyl-5a,5b,8,8,11a-pentamethyl-2,3,3a,4,5,5a,5b,6,7,7a,8,11,11a,11b,12,13, 13a,13b-octadecahydro-1H-cyclopenta[a]chrysen-9-yl)benzoic acid

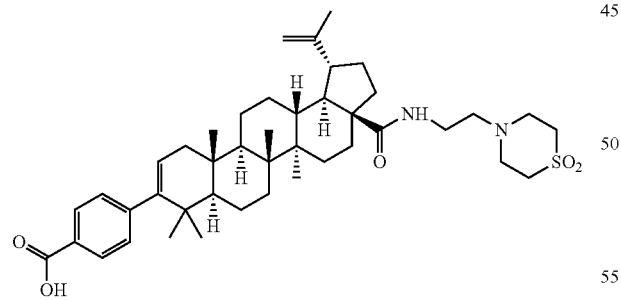

The title compound was prepared following the general procedures described above for the C-28 amide formation and hydrolysis using N-(2-aminoethyl)thiomorpholine 1,1-dioxide as the reactant amine. The product was isolated as a white solid (39 mg, 69%). LCMS: m/e 720.18 (M+H)$^+$, 2.15 min (method 1). $^1$H NMR (500 MHz, Acetic Acid-d$_4$) δ ppm 8.03 (d, J=8.24 Hz, 2H), 7.30 (d, J=8.24 Hz, 2H), 5.37 (d, J=4.58 Hz, 1H), 4.78 (s, 1H), 4.65 (s, 1H), 3.83 (br. s., 4H), 3.81-3.67 (m, 2H), 3.56 (br. s., 4H), 3.46-3.31 (m, 2H), 3.14 (td, J=10.91, 4.12 Hz, 1H), 2.60-2.48 (m, 1H), 2.26-2.11 (m, 2H), 1.74 (s, 3H), 2.03-1.09 (m, 19H), 1.08 (s, 3H), 1.06 (s, 3H), 1.04 (s, 3H), 1.01 (s, 3H), 0.99 (s, 3H).

Example 107

Procedures for the preparation of 4-((1R,3aS,5aR, 5bR,7aR,11aS,11bR,13aR,13bR)-3a-(2-(benzyl(carboxymethyl)amino)ethylcarbamoyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

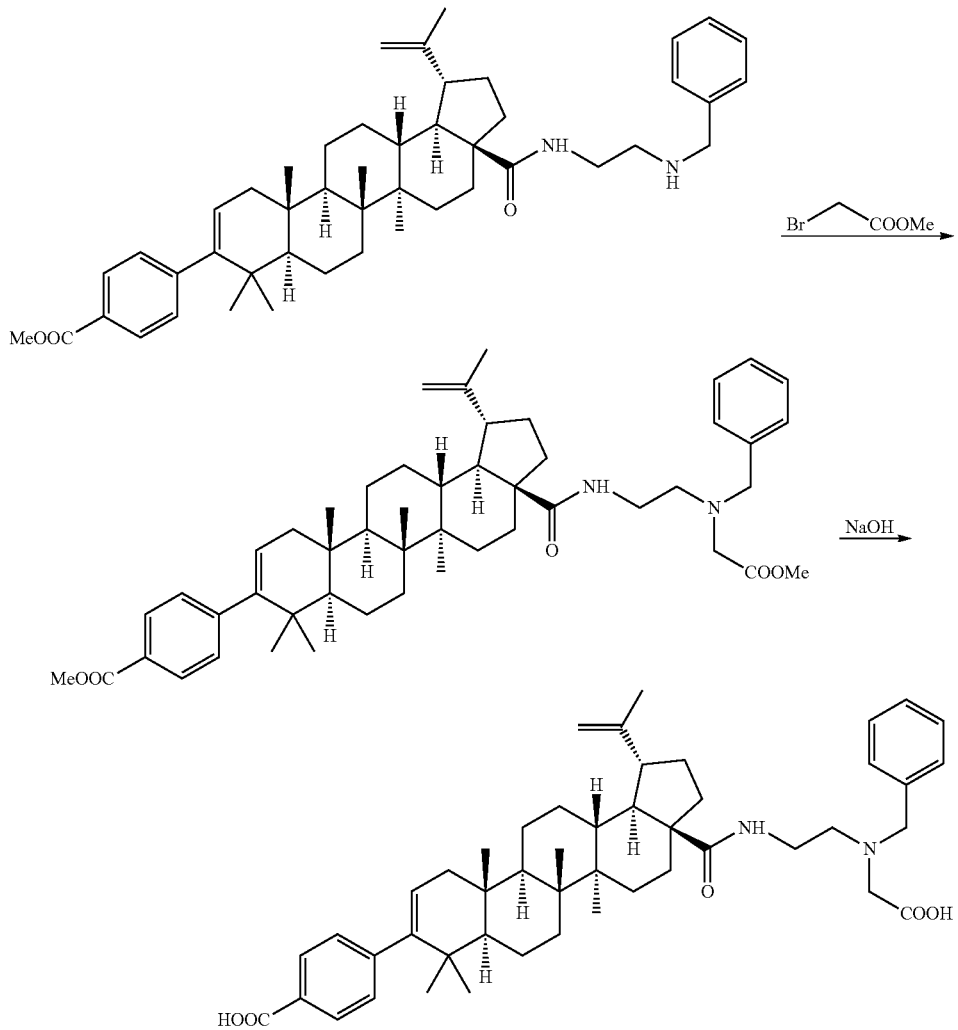

Preparation of methyl 4-((1R,3aS,5aR,5bR,7aR,11aS,11bR,13aR,13bR)-3a-(2-(benzyl(2-methoxy-2-oxoethyl)amino)ethylcarbamoyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate. Intermediate 39

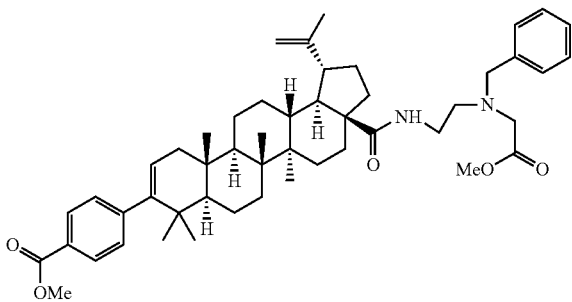

A mixture of methyl 4-((1R,3aS,5aR,5bR,7aR,11aS,11bR,13aR,13bR)-3a-(2-(benzylamino)ethylcarbamoyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate (50 mg, 0.071 mmol), methyl 2-bromoacetate (32.5 mg, 0.213 mmol) and potassium carbonate (29.4 mg, 0.213 mmol) in dioxane (1 mL) and acetonitrile (1 mL) was heated up at 78° C. for 3 hours. LCMS indicated the formation of desired product. The reaction mixture was quenched with distilled water, extracted with DCM (3×4 mL). All the extracts were combined, dried over sodium sulfate, filtered and concentrated under reduced pressure to provide the title compound as a white solid (45 mg, 82%). LCMS: m/e 777.48 (M+H)$^+$, 3.12 min (method 1).

Preparation of 4-((1R,3aS,5aR,5bR,7aR,11aS,11bR, 13aR,13bR)-3a-(2-(benzyl(carboxymethyl)amino) ethylcarbamoyl)-5a,5b,8,8,11a-pentamethyl-1-(prop-1-en-2-yl)-2,3,3a,4,5,5a,5b,6,7,7a,8,11,11a,11b,12, 13,13a,13b-octadecahydro-1H-cyclopenta[a] chrysen-9-yl)benzoic acid

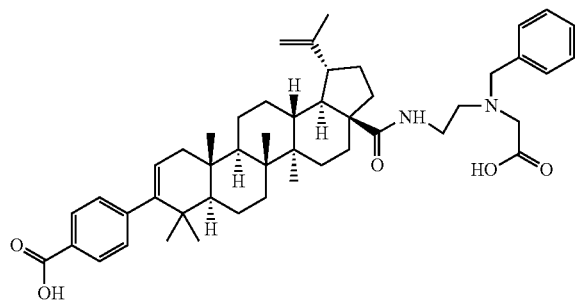

The title compound was prepared following the method described above for 2,2'-(2-((1R,3aS,5aR,5bR,7aR,11aS, 11bR,13aR,13bR)-9-(4-carboxyphenyl)-5a,5b,8,8,11a-pentamethyl-1-(prop-1-en-2-yl)-2,3,3a,4,5,5a,5b,6,7,7a,8,11, 11a,11b,12,13,13a,13b-octadecahydro-1H-cyclopenta[a] chrysene-3a-carboxamido)ethylazanediyl)diacetic acid (example 88). The product was isolated as a white solid (23 mg, 50%). LCMS: m/e 749.44 (M+H)+, 2.13 min (method 1). 1H NMR (500 MHz, Acetic Acid-d4) δ ppm 8.03 (d, J=8.24 Hz, 2H), 7.69-7.61 (m, 2H), 7.56-7.47 (m, 3H), 7.30 (d, J=8.24 Hz, 2H), 5.37 (d, J=4.58 Hz, 1H), 4.79 (d, J=1.53 Hz, 1H), 4.66 (s, 1H), 4.64-4.54 (m, 2H), 4.03 (s, 2H), 3.90-3.79 (m, 1H), 3.71 (ddd, J=14.42, 6.03, 5.80 Hz, 1H), 3.59-3.40 (m, 2H), 3.11 (td, J=10.91, 4.12 Hz, 1H), 2.61-2.47 (m, 1H), 2.25-2.12 (m, 2H), 1.74 (s, 3H), 2.03-1.08 (m, 19H), 1.07 (s, 3H), 1.07 (s, 3H), 1.01 (s, 3H), 1.01 (s, 3H), 0.99 (s, 3H).

Example 108

Preparation of 4-((1R,3aS,5aR,5bR,7aR,11aS,11bR, 13aR,13bR)-5a,5b,8,8,11a-pentamethyl-3a-(2-(3-oxopiperazin-1-yl)ethylcarbamoyl)-1-(prop-1-en-2-yl)-2,3,3a,4,5,5a,5b,6,7,7a,8,11,11a,11b,12,13,13a, 13b-octadecahydro-1H-cyclopenta[a]chrysen-9-yl) benzoic acid

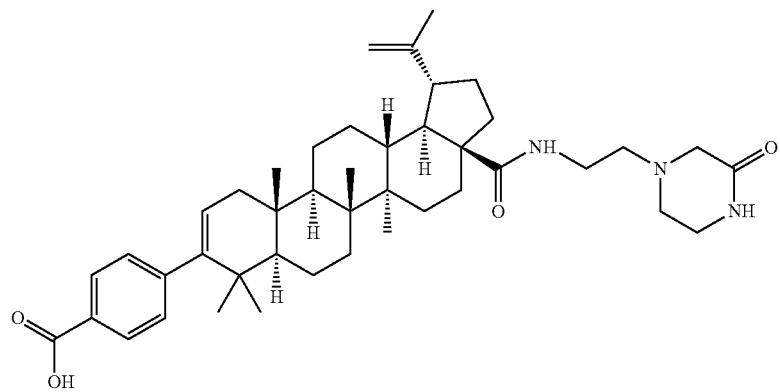

The title compound was prepared following the general procedures described above for the C-28 amide formation and hydrolysis using 4-(2-aminoethyl)piperazin-2-one as the reactant amine. The product was isolated as a white solid (18 mg, 44%). LCMS: m/e 684.54 (M+H)+, 2.13 min (method 1). 1H NMR (500 MHz, Acetic Acid-d4) δ ppm 8.03 (d, J=8.24 Hz, 2H), 7.30 (d, J=8.24 Hz, 2H), 5.37 (d, J=4.88 Hz, 1H), 4.78 (d, J=1.53 Hz, 1H), 4.65 (s, 1H), 4.06 (s, 2H), 3.87-3.76 (m, 2H), 3.73 (d, J=5.19 Hz, 2H), 3.62 (d, J=4.88 Hz, 2H), 3.46 (d, J=5.19 Hz, 2H), 3.14 (td, J=10.91, 4.12 Hz, 1H), 2.69-2.41 (m, 1H), 2.28-2.12 (m, 2H), 1.74 (s, 3H), 2.03-1.10 (m, 19H), 1.08 (s, 3H), 1.06 (s, 3H), 1.05 (s, 3H), 1.01 (s, 3H), 0.99 (s, 3H).

Example 109

Preparation of 4-((1R,3aS,5aR,5bR,7aR,11aS,11bR, 13aR,13bR)-3a-((3-(1,1-dioxido-4-thiomorpholinyl) propyl)carbamoyl)-1-isopropenyl-5a,5b,8,8,11a-pentamethyl-2,3,3a,4,5,5a,5b,6,7,7a,8,11,11a,11b,12, 13,13a,13b-octadecahydro-1H-cyclopenta[a] chrysen-9-yl)-3-fluorobenzoic acid

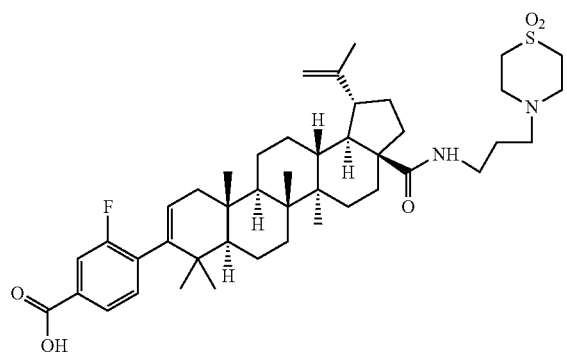

The title compound was prepared following the general procedures described above for the Suzuki coupling using 2-fluoro-4-(methoxycarbonyl)phenylboronic acid as boronic acid, the C-28 amide formation and hydrolysis using 4-(3-aminopropyl)thiomorpholine 1,1-dioxide as the reactant amine. The product was isolated as a white solid (12 mg, 33%). LCMS: m/e 751.39 (M+H)+, 2.08 min (method 1). 1H NMR (500 MHz, Acetic Acid-d4) δ ppm 7.85 (dd, J=7.93, 1.22 Hz, 1H), 7.77 (dd, J=9.61, 1.37 Hz, 1H), 7.28 (t, J=7.63

Hz, 1H), 5.43 (d, J=4.88 Hz, 1H), 4.78 (s, 1H), 4.65 (s, 1H), 3.85 (br. s., 4H), 3.59 (br. s., 4H), 3.50-3.40 (m, 1H), 3.40-3.32 (m, 1H), 3.29 (ddd, J=12.21, 3.51, 3.20 Hz, 2H), 3.15 (td, J=10.91, 4.12 Hz, 1H), 2.69-2.54 (m, 1H), 2.25-2.13 (m, 2H), 1.74 (s, 3H), 2.04-1.10 (m, 21H), 1.08 (s, 6H), 1.06 (s, 3H), 1.00 (s, 3H), 0.96 (s, 3H).

Example 110

Preparation of 4-((1R,3aS,5aR,5bR,7aR,11aS,11bR, 13aR,13bR)-5a,5b,8,8,11a-pentamethyl-3a-(2-(phenylamino)ethylcarbamoyl)-1-(prop-1-en-2-yl)-2,3, 3a,4,5,5a,5b,6,7,7a,8,11,11a,11b,12,13,13a,13b-octadecahydro-1H-cyclopenta[a]chrysen-9-yl) benzoic acid

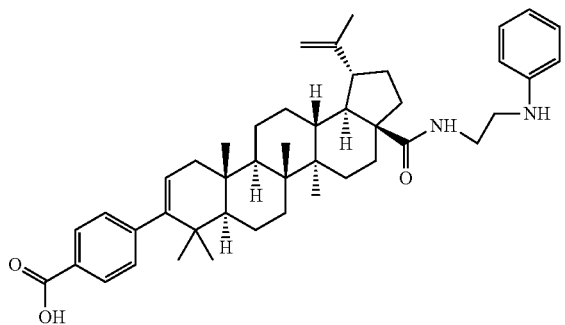

The title compound was prepared following the general procedures described above for the C-28 amide formation and hydrolysis using N1-phenylethane-1,2-diamine as the reactant amine. The product was isolated as a white solid (1.1 mg, 11%). LCMS: m/e 677.5 (M+H)+, 2.43 min (method 1). $^1$H NMR (500 MHz, Acetic Acid-$d_4$) δ ppm 8.03 (d, J=8.24 Hz, 2H), 7.45 (t, J=7.93 Hz, 2H), 7.34 (d, J=7.63 Hz, 2H), 7.32-7.24 (m, 3H), 5.36 (d, J=4.88 Hz, 1H), 4.78 (s, 1H), 4.64 (s, 1H), 3.75-3.65 (m, 2H), 3.57 (t, J=5.49 Hz, 2H), 3.23-3.10 (m, 1H), 2.56 (td, J=11.90, 3.66 Hz, 1H), 2.24-2.13 (m, 2H), 1.74 (s, 3H), 2.09-1.09 (m, 19H), 1.07 (s, 3H), 1.05 (s, 3H), 1.00 (s, 3H), 1.00 (s, 3H), 0.98 (s, 3H).

Example 111

Preparation of 4-((1R,3aS,5aR,5bR,7aR,11aS,11bR, 13aR,13bR)-3a-(2-((carboxymethyl)(phenyl)amino) ethylcarbamoyl)-5a,5b,8,8,11a-pentamethyl-1-(prop-1-en-2-yl)-2,3,3a,4,5,5a,5b,6,7,7a,8,11,11a,11b,12, 13,13a,13b-octadecahydro-1H-cyclopenta[a] chrysen-9-yl)benzoic acid

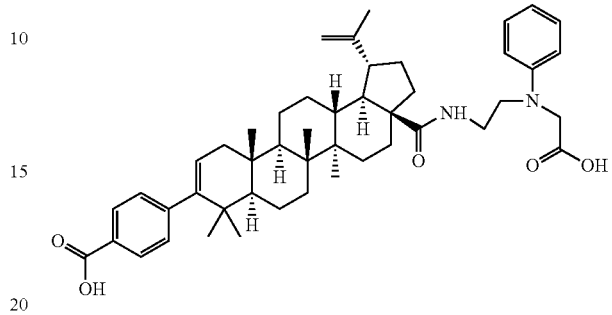

The title compound was prepared following the method described above for the preparation of 4-((1R,3aS,5aR,5bR, 7aR,11aS,11bR,13aR,13bR)-3a-(2-(benzyl(carboxymethyl) amino)ethylcarbamoyl)-5a,5b,8,8,11a-pentamethyl-1-(prop-1-en-2-yl)-2,3,3a,4,5,5a,5b,6,7,7a,8,11,11a,11b,12, 13,13a,13b-octadecahydro-1H-cyclopenta[a]chrysen-9-yl) benzoic acid (example 89) using N1-phenylethane-1,2-diamine as amine. The product was isolated as a white solid (0.9 mg, 9%). LCMS: m/e 735.5 (M+H)+, 1.80 min (method 1). $^1$H NMR (500 MHz, Acetic Acid-$d_4$) δ ppm 8.03 (d, J=8.24 Hz, 2H), 7.30 (d, J=8.24 Hz, 2H), 7.26-7.19 (m, 2H), 6.86-6.70 (m, 3H), 5.37 (d, J=4.58 Hz, 1H), 4.77 (s, 1H), 4.63 (s, 1H), 4.22 (s, 2H), 3.82-3.43 (m, 4H), 3.21-3.07 (m, 1H), 2.69-2.53 (m, 1H), 2.23-2.13 (m, 2H), 1.73 (s, 3H), 2.05-1.07 (m, 19H), 1.06 (s, 3H), 1.04 (s, 3H), 1.02 (s, 3H), 1.01 (s, 3H), 0.99 (s, 3H).

Example 112

Preparation of 4-((1R,3aS,5aR,5bR,7aR,11aS,11bR, 13aR,13bR)-3a-((3-(1,1-dioxido-4-thiomorpholinyl) propyl)carbamoyl)-1-isopropenyl-5a,5b,8,8,11a-pentamethyl-2,3,3a,4,5,5a,5b,6,7,7a,8,11,11a,11b,12, 13,13a,13b-octadecahydro-1H-cyclopenta[a] chrysen-9-yl)phthalic acid

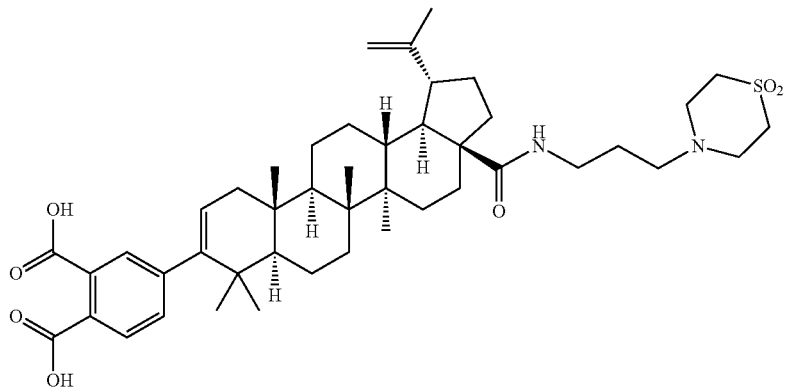

The title compound was prepared following the general procedures described above for the Suzuki coupling using 3,4-bis(methoxycarbonyl)phenylboronic acid as boronic acid, the C-28 amide formation and hydrolysis using 4-(3-aminopropyl)thiomorpholine 1,1-dioxide as the reactant amine. The product was isolated as a white solid (13 mg, 52%). LCMS: m/e 777.43 (M+H)$^+$, 2.34 min (method 1). $^1$H NMR (500 MHz, Acetic Acid-d$_4$) δ ppm 7.83 (d, J=7.93 Hz, 1H), 7.61 (d, J=1.83 Hz, 1H), 7.44 (dd, J=7.78, 1.68 Hz, 1H), 5.48-5.35 (m, 1H), 4.78 (s, 1H), 4.65 (s, 1H), 3.87 (br. s., 4H), 3.62 (br. s., 4H), 3.52-3.43 (m, 2H), 3.31 (d, J=3.97 Hz, 2H), 3.15 (td, J=10.68, 4.88 Hz, 1H), 2.70-2.49 (m, 1H), 2.23-2.13 (m, 2H), 1.74 (s, 3H), 2.03-1.10 (m, 21H), 1.08 (s, 3H), 1.06 (s, 3H), 1.06 (s, 3H), 1.02 (s, 3H), 1.00 (s, 3H).

Example 113

Preparation of 4-((1R,3aS,5aR,5bR,7aR,11aS,11bR,13aR,13bR)-3a-(2-(dimethylamino)ethylcarbamoyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)phthalic acid

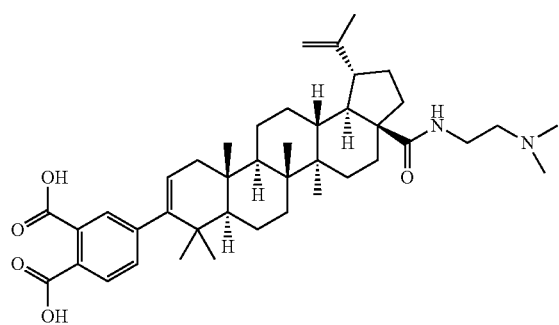

The title compound was prepared following the general procedures described above for the Suzuki coupling using 3,4-bis(methoxycarbonyl)phenylboronic acid as boronic acid, followed by the C-28 amide formation and hydrolysis using N1,N1-dimethylethane-1,2-diamine as the reactant amine. The product was isolated as a white solid (2.6 mg, 8%). LCMS: m/e 673.37 (M+H)$^+$, 2.39 min (method 1). $^1$H NMR (500 MHz, Acetic Acid-d$_4$) δ ppm 7.84 (d, J=7.93 Hz, 1H), 7.61 (d, J=1.22 Hz, 1H), 7.49-7.39 (m, 1H), 5.42 (d, J=4.88 Hz, 1H), 4.78 (s, 1H), 4.65 (s, 1H), 3.75 (t, J=5.80 Hz, 2H), 3.49-3.33 (m, 2H), 3.22-3.07 (m, 1H), 2.96 (s, 6H), 2.64-2.45 (m, 1H), 2.29-2.13 (m, 2H), 1.73 (s, 3H), 2.03-1.10 (m, 19H), 1.08 (s, 3H), 1.06 (s, 3H), 1.05 (s, 3H), 1.02 (s, 3H), 1.00 (s, 3H).

Example 114

Preparation of 4-(2-((1R,3aS,5aR,5bR,7aR,11aS,11bR,13aR,13bR)-9-(4-carboxyphenyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysene-3a-carboxamido)ethylamino)benzoic acid

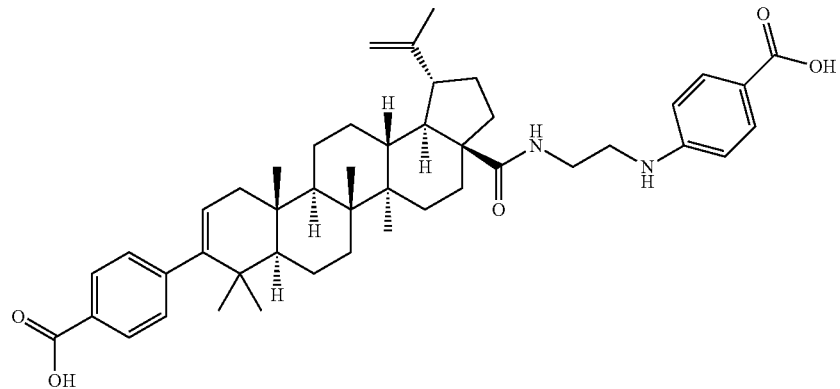

The title compound was prepared following the general procedures described above for the C-28 amide formation and hydrolysis using ethyl 4-(2-aminoethylamino)benzoate as the reactant amine. The product was isolated as a white solid (3.6 mg, 45%). LCMS: m/e 721.42 (M+H)$^+$, 2.37 min (method 1). $^1$H NMR (500 MHz, Acetic Acid-d$_4$) δ ppm 8.03 (d, J=8.24 Hz, 2H), 7.90 (d, J=8.85 Hz, 2H), 7.29 (d, J=8.24 Hz, 2H), 6.68 (d, J=8.85 Hz, 2H), 5.35 (d, J=4.58 Hz, 1H), 4.78 (d, J=1.53 Hz, 1H), 4.64 (s, 1H), 3.71 (dt, J=13.73, 6.10 Hz, 1H), 3.57-3.46 (m, 1H), 3.44-3.35 (m, 2H), 3.16 (td, J=10.91, 4.12 Hz, 1H), 2.63-2.50 (m, 1H), 2.24-2.13 (m, 2H), 1.72 (s, 3H), 2.05-1.05 (m, 19H), 1.04 (s, 3H), 1.02 (s, 3H), 0.99 (s, 3H), 0.97 (s, 3H), 0.90 (s, 3H).

Example 115
Procedures for the preparation of 4-((1R,3aS,5aR,5bR,7aR,11aS,11bR,13aR,13bR)-3a-(2-((2-(3-carboxypropanoyloxy)ethyl)(methyl)amino)ethylcarbamoyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid
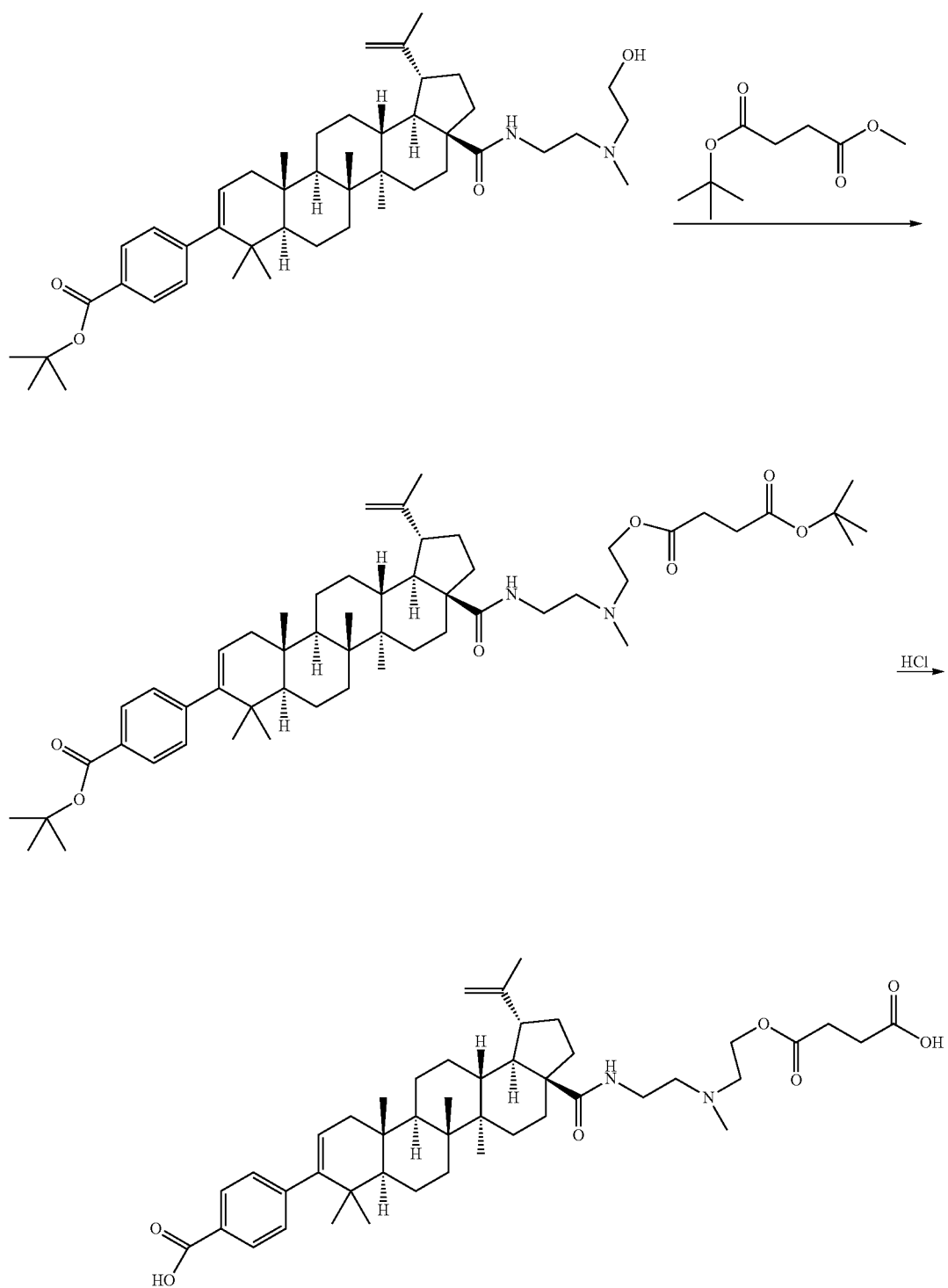

Preparation of 2-((2-((1R,3aS,5aR,5bR,7aR,11aS, 11bR,13aR,13bR)-9-(4-(tert-butoxycarbonyl)phenyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysene-3a-carboxamido)ethyl)(methyl)amino)ethyl tert-butyl succinate. Intermediate 40

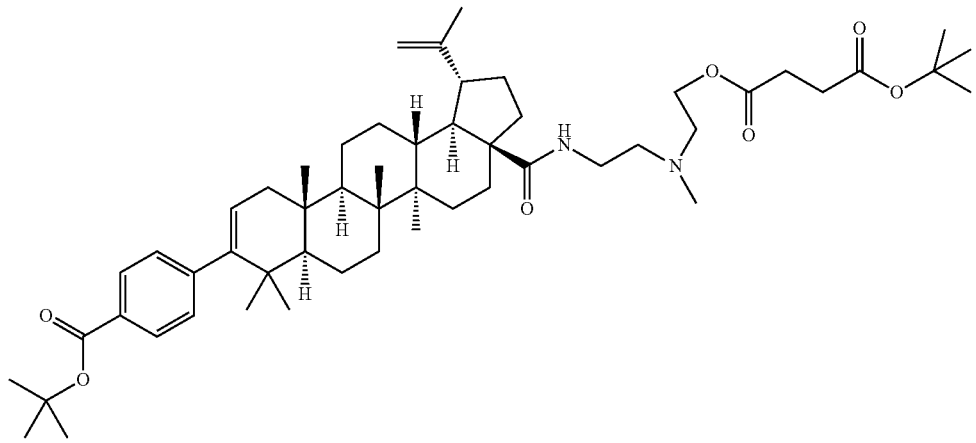

A mixture of tert-butyl 4-((1R,3aS,5aR,5bR,7aR,11aS,11bR,13aR,13bR)-3a-(2-((2-hydroxyethyl)(methyl)amino) ethylcarbamoyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate (40 mg, 0.056 mmol), tert-butyl methyl succinate (21.06 mg, 0.112 mmol), Hunig'sBase (0.049 mL, 0.280 mmol) and EDC (21.45 mg, 0.112 mmol) in dichloromethane (1 mL) was stirred at 20° C. for 12 hours. LCMS indicated the formation of desired product. The reaction mixture was quenched with distilled water, extracted with DCM (3×4 mL). All the extracts were combined, dried over sodium sulfate, filtered and concentrated under reduced pressure to provide the crude including the title compound as a white solid (40 mg, 82%). LCMS: m/e 871.43 (M+H)+, 3.93 min (method 1).

Preparation of 4-((1R,3aS,5aR,5bR,7aR,11aS,11bR, 13aR,13bR)-3a-(2-((2-(3-carboxypropanoyloxy) ethyl)(methyl)amino)ethylcarbamoyl)-5a,5b,8,8,11a-pentamethyl-1-(prop-1-en-2-yl)-2,3,3a,4,5,5a,5b,6,7, 7a,8,11,11a,11b,12,13,13a,13b-octadecahydro-1H-cyclopenta[a]chrysen-9-yl)benzoic acid To a solution of 2-((2-((1R,3aS,5aR,5bR,7aR,11aS,11bR,13aR,13bR)-9-(4-(tert-butoxycarbonyl)phenyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysene-3a-carboxamido)ethyl)(methyl) amino)ethyl tert-butyl succinate (40 mg, 0.046 mmol) in dioxane (1 mL) was added 4N HCl (0.115 mL, 0.459 mmol). The reaction mixture was stirred at 20° C. for 3 hours. LCMS indicated the formation of desired product. The reaction mixture was neutralized with 1N NaOH and then filtered. The clear solution was purified by prep HPLC to provide the desired product as colourless oil (7.2 mg, 20%). LCMS: m/e 759.34 (M+H)+, 2.37 min (method 1). $^1$H NMR (400 MHz, Acetic Acid-$d_4$) δ ppm 7.99 (d, J=8.28 Hz, 2H), 7.26 (d, J=8.53 Hz, 2H), 5.33 (d, J=4.77 Hz, 1H), 4.74 (s, 1H), 4.61 (s, 1H), 4.56-4.44 (m, 2H), 3.90-3.65 (m, 2H), 3.62-3.52 (m, 2H), 3.50-3.38 (m, 2H), 3.19-3.05 (m, 1H), 3.01 (s, 3H), 2.72 (s, 4H), 2.58-2.42 (m, 1H), 2.26-2.11 (m, 2H), 1.69 (s, 3H), 1.96-1.07 (m, 19H), 1.04 (s, 3H), 1.02 (s, 3H), 1.02 (s, 3H), 0.97 (s, 3H), 0.95 (s, 3H).

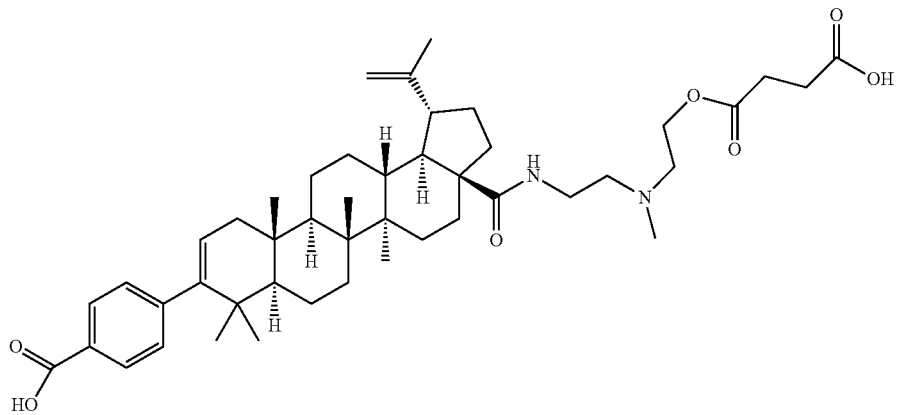

Example 116

Preparation of 4-((1R,3aS,5aR,5bR,7aR,11aS,11bR, 13aR,13bR)-3a-((2-(1,1-dioxido-4-thiomorpholinyl) ethyl)carbamoyl)-1-isopropenyl-5a,5b,8,8,11a-pentamethyl-2,3,3a,4,5,5a,5b,6,7,7a,8,11,11a,11b,12,13, 13a,13b-octadecahydro-1H-cyclopenta[a]chrysen-9-yl)-2-fluorobenzoic acid

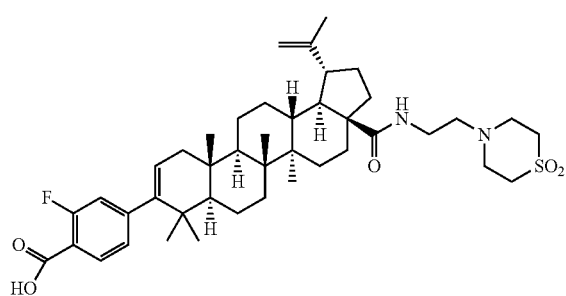

The title compound was prepared following the general procedures described above for the Suzuki coupling using 3-fluoro-4-(methoxycarbonyl)phenylboronic acid as boronic acid, the C-28 amide formation and hydrolysis using N-(2-aminoethyl)thiomorpholine 1,1-dioxide as the reactant amine. The product was isolated as a white solid (23 mg, 56%). LCMS: m/e 737.36 (M+H)$^+$, 2.37 min (method 1). $^1$H NMR (500 MHz, Acetic Acid-d$_4$) δ ppm 7.96 (t, J=7.93 Hz, 1H), 7.08 (dd, J=8.09, 1.37 Hz, 1H), 7.02 (d, J=11.90 Hz, 1H), 5.42 (d, J=4.58 Hz, 1H), 4.78 (d, J=1.53 Hz, 1H), 4.65 (s, 1H), 3.83 (br. s., 4H), 3.80-3.67 (m, 2H), 3.57 (br. s., 4H), 3.43-3.34 (m, 2H), 3.14 (td, J=10.76, 4.43 Hz, 1H), 2.62-2.46 (m, 1H), 2.26-2.12 (m, 2H), 1.74 (s, 3H), 2.02-1.09 (m, 19H), 1.08 (s, 3H), 1.05 (s, 3H), 1.04 (s, 3H), 1.02 (s, 3H), 1.00 (s, 3H).

Example 117

Preparation of 4-((1R,3aS,5aR,5bR,7aR,11aS,11bR, 13aR,13bR)-3a-(2-(4,4-difluoropiperidin-1-yl)ethylcarbamoyl)-5a,5b,8,8,11a-pentamethyl-1-(prop-1-en-2-yl)-2,3,3a,4,5,5a,5b,6,7,7a,8,11,11a,11b,12,13,13a, 13b-octadecahydro-1H-cyclopenta[a]chrysen-9-yl)-2-fluorobenzoic acid

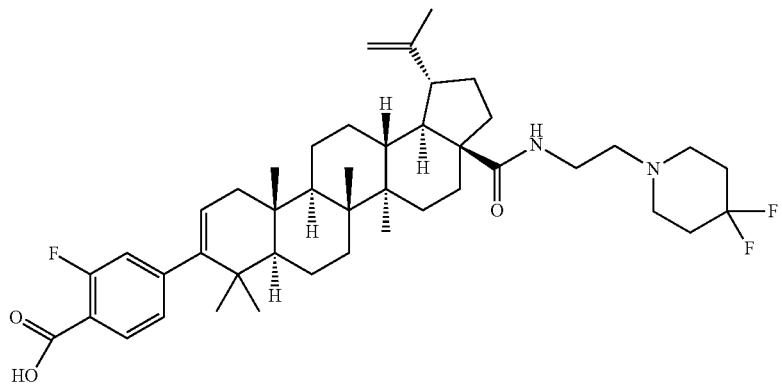

The title compound was prepared following the general procedures described above for the Suzuki coupling using 3-fluoro-4-(methoxycarbonyl)phenylboronic acid as boronic acid, followed by the C-28 amide formation and hydrolysis using 2-(4,4-difluoropiperidin-1-yl)ethanamine as the reactant amine. The product was isolated as a white solid (10 mg, 24%). LCMS: m/e 723.39 (M+H)$^+$, 2.46 min (method 1). $^1$H NMR (500 MHz, Acetic Acid-d$_4$) δ ppm 7.96 (t, J=7.78 Hz, 1H), 7.08 (dd, J=8.09, 1.37 Hz, 1H), 7.02 (d, J=11.60 Hz, 1H), 5.50-5.32 (m, 1H), 4.77 (d, J=1.83 Hz, 1H), 4.65 (s, 1H), 3.90-3.69 (m, 2H), 3.55 (br. s., 4H), 3.47-3.36 (m, 2H), 3.13 (td, J=10.91, 4.12 Hz, 1H), 2.59-2.48 (m, 1H), 2.42 (br. s., 4H), 2.25-2.13 (m, 2H), 1.73 (s, 3H), 2.05-1.08 (m, 19H), 1.07 (s, 3H), 1.05 (s, 3H), 1.04 (s, 3H), 1.02 (s, 3H), 1.00 (s, 3H).

Example 118

Preparation of 4-((1R,3aS,5aR,5bR,7aR,11aS,11bR, 13aR,13bR)-3a-(2-(4,4-difluoropiperidin-1-yl)ethylcarbamoyl)-5a,5b,8,8,11a-pentamethyl-1-(prop-1-en-2-yl)-2,3,3a,4,5,5a,5b,6,7,7a,8,11,11a,11b,12,13,13a, 13b-octadecahydro-1H-cyclopenta[a]chrysen-9-yl) benzoic acid

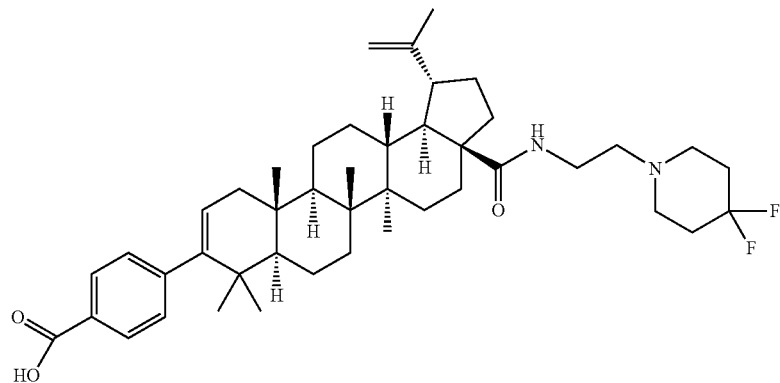

The title compound was prepared following the general procedures described above for the C-28 amide formation and hydrolysis using 2-(4,4-difluoropiperidin-1-yl)ethanamine as the reactant amine. The product was isolated as a white solid (40 mg, 78%). LCMS: m/e 705.42 (M+H)$^+$, 2.53 min (method 1). $^1$H NMR (500 MHz, Acetic Acid-d$_4$) δ ppm 8.03 (d, J=8.24 Hz, 2H), 7.30 (d, J=8.24 Hz, 2H), 5.43-5.30 (m, 1H), 4.77 (d, J=1.83 Hz, 1H), 4.65 (s, 1H), 3.78 (dt, J=16.17, 6.26 Hz, 2H), 3.55 (br. s., 4H), 3.47-3.35 (m, 2H), 3.13 (td, J=10.76, 4.12 Hz, 1H), 2.61-2.48 (m, 1H), 2.42 (br. s., 4H), 2.26-2.12 (m, 2H), 1.74 (s, 3H), 2.00-1.09 (m, 19H), 1.08 (s, 3H), 1.06 (s, 3H), 1.04 (s, 3H), 1.00 (s, 3H), 0.99 (s, 3H).

Example 119

Preparation of 4-((1R,3aS,5aR,5bR,7aR,11aS,11bR, 13aR,13bR)-3a-(2-(4,4-difluoropiperidin-1-yl)ethylcarbamoyl)-5a,5b,8,8,11a-pentamethyl-1-(prop-1-en-2-yl)-2,3,3a,4,5,5a,5b,6,7,7a,8,11,11a,11b,12,13,13a, 13b-octadecahydro-1H-cyclopenta[a]chrysen-9-yl)-3-fluorobenzoic acid The title compound was prepared following the general procedures described above for the Suzuki coupling using 2-fluoro-4-(methoxycarbonyl)phenylboronic acid as boronic acid, the C-28 amide formation using 2-(4,4-difluoropiperidin-1-yl)ethanamine as the reactant amine and hydrolysis. The product was isolated as a white solid (21 mg, 51%). LCMS: m/e 723.43 (M+H)$^+$, 2.48 min (method 1). $^1$H NMR (500 MHz, Acetic Acid-d$_4$) δ ppm 7.85 (dd, J=7.93, 1.53 Hz, 1H), 7.77 (dd, J=9.77, 1.53 Hz, 1H), 7.28 (t, J=7.48 Hz, 1H), 5.43 (d, J=4.58 Hz, 1H), 4.78 (d, J=1.53 Hz, 1H), 4.65 (s, 1H), 3.91-3.68 (m, 2H), 3.54 (br. s., 4H), 3.48-3.35 (m, 2H), 3.14 (td, J=10.91, 4.12 Hz, 1H), 2.53 (td, J=12.21, 3.05 Hz, 1H), 2.48-2.35 (m, 4H), 2.24-2.12 (m, 2H), 1.74 (s, 3H), 2.01-1.10 (m, 19H), 1.08 (s, 6H), 1.04 (s, 3H), 1.00 (s, 3H), 0.96 (s, 3H).

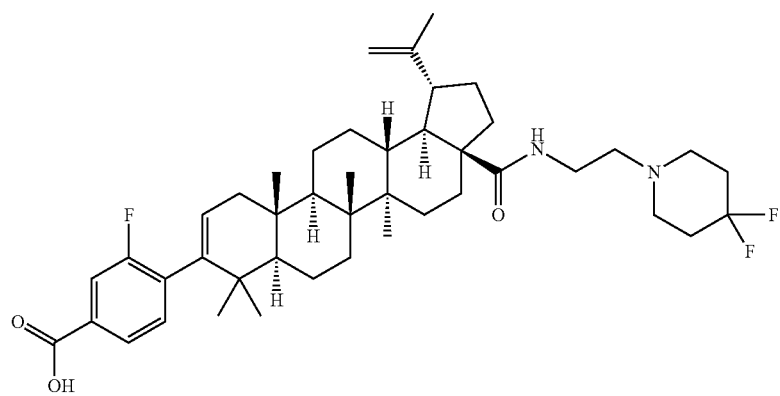

Example 120

Preparation of 4-((1R,3aS,5aR,5bR,7aR,11aS,11bR,13aR,13bR)-3a-((2-(1,1-dioxido-4-thiomorpholinyl)ethyl)carbamoyl)-1-isopropenyl-5a,5b,8,8,11a-pentamethyl-2,3,3a,4,5,5a,5b,6,7,7a,8,11,11a,11b,12,13,13a,13b-octadecahydro-1H-cyclopenta[a]chrysen-9-yl)-3-fluorobenzoic acid

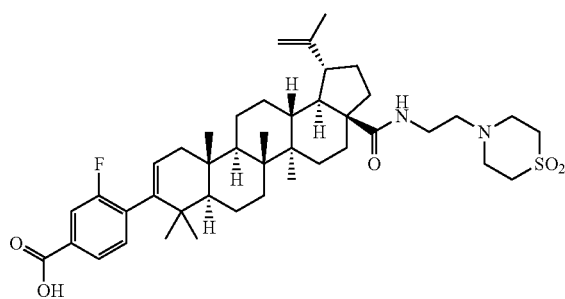

The title compound was prepared following the general procedures described above for the Suzuki coupling using 2-fluoro-4-(methoxycarbonyl)phenylboronic acid as boronic acid, the C-28 amide formation using N-(2-aminoethyl)thiomorpholine 1,1-dioxide as the reactant amine and hydrolysis. The product was isolated as a white solid (22 mg, 47%). LCMS: m/e 737.34 (M+H)$^+$, 2.37 min (method 1). $^1$H NMR (500 MHz, Acetic Acid-d$_4$) δ ppm 7.85 (dd, J=7.78, 1.37 Hz, 1H), 7.80-7.73 (m, 1H), 7.28 (t, J=7.48 Hz, 1H), 5.43 (d, J=4.58 Hz, 1H), 4.78 (s, 1H), 4.65 (s, 1H), 3.83 (br. s., 4H), 3.80-3.66 (m, 2H), 3.56 (br. s., 4H), 3.47-3.33 (m, 2H), 3.14 (td, J=10.83, 4.27 Hz, 1H), 2.63-2.48 (m, 1H), 2.30-2.13 (m, 2H), 1.74 (s, 3H), 2.03-1.11 (m, 19H), 1.08 (s, 6H), 1.04 (s, 3H), 1.00 (s, 3H), 0.96 (s, 3H).

Example 121

Preparation of 4-((1R,3aS,5aR,5bR,7aR,11aS,11bR,13aR,13bR)-3a-((2-(1,1-dioxido-4-thiomorpholinyl)ethyl)carbamoyl)-1-isopropenyl-5a,5b,8,8,11a-pentamethyl-2,3,3a,4,5,5a,5b,6,7,7a,8,11,11a,11b,12,13,13a,13b-octadecahydro-1H-cyclopenta[a]chrysen-9-yl)-2,6-difluorobenzoic acid

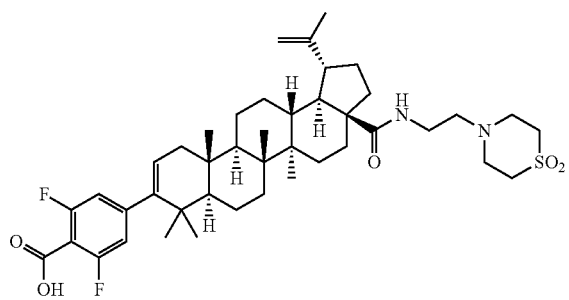

The title compound was prepared following the general procedures described above for the Suzuki coupling using 3,5-difluoro-4-(methoxycarbonyl)phenylboronic acid as boronic acid, the C-28 amide formation using N-(2-aminoethyl)thiomorpholine 1,1-dioxide as the reactant amine and hydrolysis. The product was isolated as a white solid (22 mg, 53%). LCMS: m/e 755.40 (M+H)$^+$, 2.32 min (method 1). $^1$H NMR (500 MHz, Acetic Acid-d$_4$) δ ppm 6.87 (d, J=9.16 Hz, 2H), 5.57-5.35 (m, 1H), 4.77 (s, 1H), 4.65 (s, 1H), 3.84 (br. s., 4H), 3.80-3.65 (m, 2H), 3.57 (br. s., 4H), 3.46-3.33 (m, 2H), 3.22-3.04 (m, 1H), 2.54 (td, J=12.36, 3.36 Hz, 1H), 2.25-2.11 (m, 2H), 1.73 (s, 3H), 2.00-1.10 (m, 19H), 1.07 (s, 3H), 1.04 (s, 3H), 1.03 (s, 3H), 1.03 (s, 3H), 1.00 (s, 3H).

Example 122

Preparation of 4-((1R,3aS,5aR,5bR,7aR,11aS,11bR,13aR,13bR)-3a-(2-(dimethylamino)ethylcarbamoyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-2,6-difluorobenzoic acid

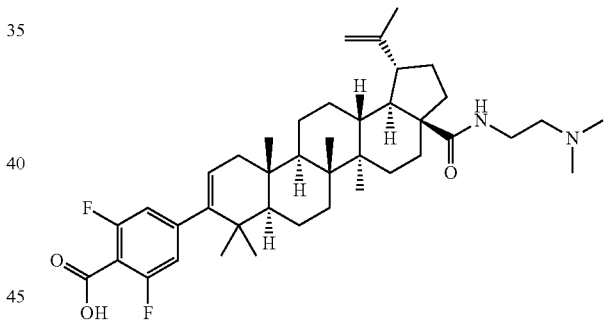

The title compound was prepared following the general procedures described above for the Suzuki coupling using 3,5-difluoro-4-(methoxycarbonyl)phenylboronic acid as boronic acid, the C-28 amide formation using N1,N1-dimethylethane-1,2-diamine as the reactant amine and hydrolysis. The product was isolated as a white solid (6 mg, 17%). LCMS: m/e 665.42 (M+H)$^+$, 2.39 min (method 1). $^1$H NMR (500 MHz, Acetic Acid-d$_4$) δ ppm 6.87 (d, J=9.46 Hz, 2H), 5.45 (d, J=4.58 Hz, 1H), 4.78 (d, J=1.83 Hz, 1H), 4.64 (s, 1H), 3.82-3.69 (m, 2H), 3.50-3.34 (m, 2H), 3.22-3.08 (m, 1H), 2.96 (s, 6H), 2.54 (td, J=12.21, 3.36 Hz, 1H), 2.26-2.15 (m, 2H), 1.73 (s, 3H), 2.02-1.09 (m, 19H), 1.07 (s, 3H), 1.04 (s, 3H), 1.03 (s, 3H), 1.03 (s, 3H), 1.00 (s, 3H).

Example 123

Preparation of 4-((1R,3aS,5aR,5bR,7aR,11aS,11bR,13aR,13bR)-3a-((3-(1,1-dioxido-4-thiomorpholinyl)propyl)carbamoyl)-1-isopropenyl-5a,5b,8,8,11a-pentamethyl-2,3,3a,4,5,5a,5b,6,7,7a,8,11,11a,11b,12,13,13a,13b-octadecahydro-1H-cyclopenta[a]chrysen-9-yl)-2,6-difluorobenzoic acid

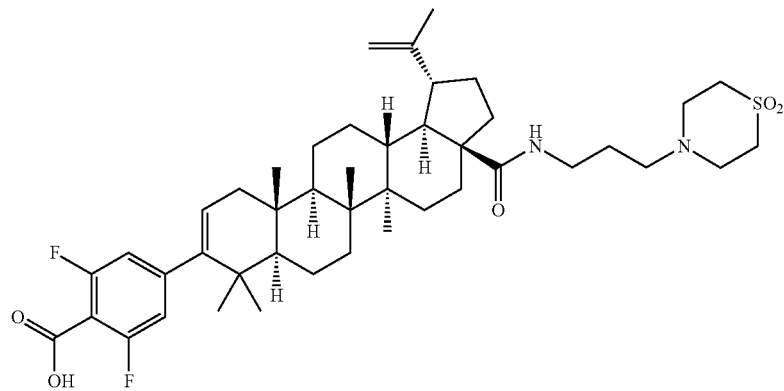

The title compound was prepared following the general procedures described above for the Suzuki coupling using 3,5-difluoro-4-(methoxycarbonyl)phenylboronic acid as boronic acid, the C-28 amide formation using 4-(3-aminopropyl)thiomorpholine 1,1-dioxide as the reactant amine and hydrolysis. The product was isolated as a white solid (13 mg, 31%). LCMS: m/e 769.46 (M+H)$^+$, 2.34 min (method 1). $^1$H NMR (500 MHz, Acetic Acid-d$_4$) δ ppm 6.87 (d, J=9.46 Hz, 2H), 5.45 (d, J=4.58 Hz, 1H), 4.78 (d, J=1.83 Hz, 1H), 4.65 (s, 1H), 3.85 (br. s., 4H), 3.57 (br. s., 4H), 3.50-3.33 (m, 2H), 3.29 (dd, J=9.00, 4.12 Hz, 2H), 3.15 (td, J=10.99, 4.27 Hz, 1H), 2.60 (td, J=12.28, 3.20 Hz, 1H), 2.29-2.12 (m, 2H), 1.74 (s, 3H), 2.04-1.09 (m, 21H), 1.07 (s, 3H), 1.05 (s, 3H), 1.04 (s, 3H), 1.03 (s, 3H), 1.00 (s, 3H).

Example 124

Preparation of 4-((1S,3aS,5aR,5bR,7aS,9S,11aS,11bR,13aR,13bR)-3a-(2-carboxyethylcarbamoyl)-1-isopropyl-5a,5b,8,8,11a-pentamethylicosahydro-1H-cyclopenta[a]chrysen-9-yl)benzoic acid

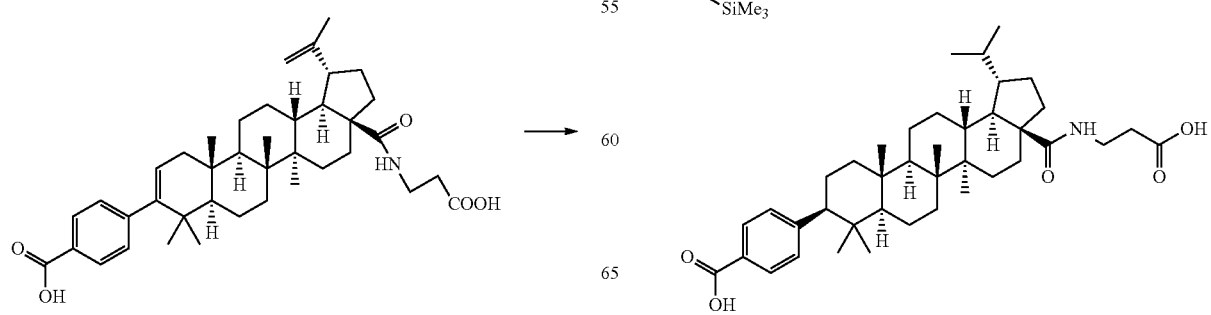

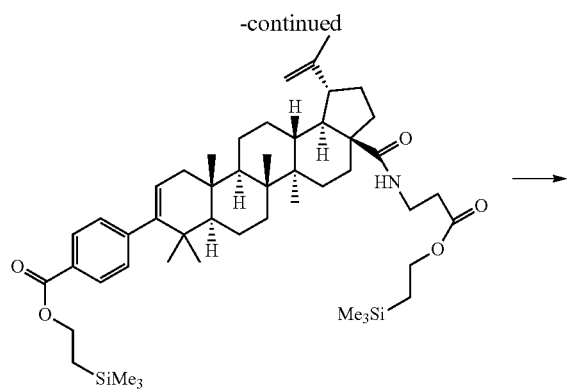

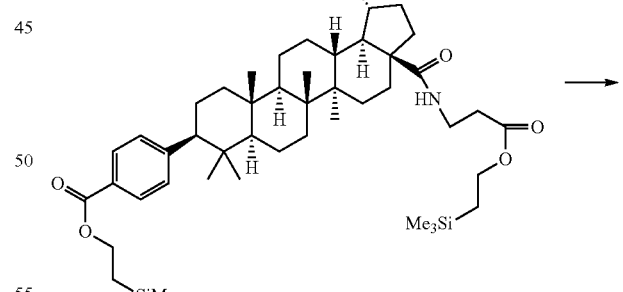

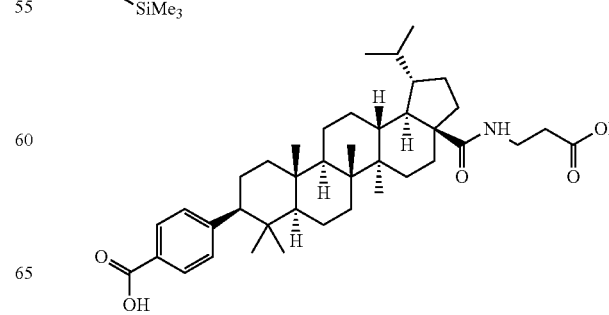

Preparation of 2-(trimethylsilyl)ethyl 4-((1R,3aS, 5aR,5bR,7aR,11aS,11bR,13aR,13bR)-5a,5b,8,8,11a-pentamethyl-3a-(3-oxo-3-(2-(trimethylsilyl)ethoxy) propylcarbamoyl)-1-(prop-1-en-2-yl)-2,3,3a,4,5,5a, 5b,6,7,7a,8,11,11a,11b,12,13,13a,13b-octadecahydro-1H-cyclopenta[a]chrysen-9-yl) benzoate. Intermediate 41

Preparation of 2-(trimethylsilyl)ethyl 4-((1S,3aS, 5aR,5bR,7aS,9S,11aS,11bR,13aR,13bR)-1-isopropyl-5a,5b,8,8,11a-pentamethyl-3a-(3-oxo-3-(2-(trimethylsilyl)ethoxy)propylcarbamoyl)icosahydro-1H-cyclopenta[a]chrysen-9-yl)benzoate. Intermediate 42

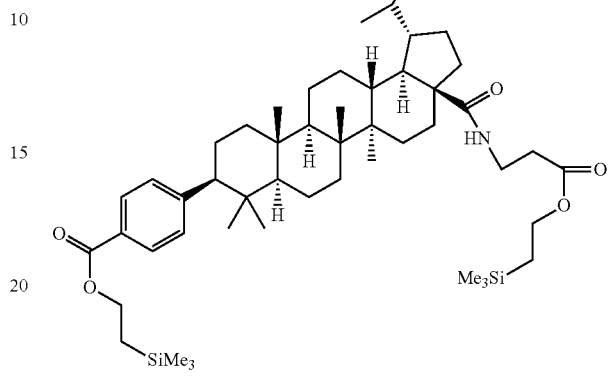

2-(trimethylsilyl)ethyl 4-((1R,3aS,5aR,5bR,7aR,11aS, 11bR,13aR,13bR)-5a,5b,8,8,11a-pentamethyl-3a-(3-oxo-3-(2-(trimethylsilyl)ethoxy)propylcarbamoyl)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate (15 mg, 0.018 mmol) was dissolved in a mixture of ethyl acetate and methanol (2 ml, 1:1) and treated with palladium (10% in carbon, 1 mg, 9.40 mmol) and a balloon with hydrogen. The mixture was stirred at rt for 3 h. The solvent was removed in vacuo and the residue was dissolved in methylene chloride and filtered through a fine pad of celite. The solvent was removed in vacuo and the crude was purified in silica gel to afford 2-(trimethylsilyl)ethyl 4-((1S,3aS,5aR,5bR,7aS,11aS, 11bR,13aR,13bR)-1-isopropyl-5a,5b,8,8,11a-pentamethyl-3a-(3-oxo-3-(2-(trimethylsilyl)ethoxy)propylcarbamoyl) icosahydro-1H-cyclopenta[a]chrysen-9-yl) (12 mg, 80%) as a clear oil. $^1$H NMR (400 MHz, CHLOROFORM-d) δ ppm 7.92 (d, J=8.28 Hz, 2H), 7.23 (d, J=8.53 Hz, 2H), 6.22 (t, J=6.15 Hz, 1H), 4.50-4.36 (m, 2H), 4.24-4.16 (m, 2H), 3.51 (td, J=11.48, 6.40 Hz, 2H), 2.59-2.49 (m, 2H), 2.40 (dd, J=12.92, 2.89 Hz, 2H), 2.35-2.24 (m, 1H), 2.18-2.04 (m, 1H), 2.03-1.95 (m, 1H), 1.89-0.91 (m, 26H), 0.99 (s, 3H), 0.96 (s, 6H), 0.88 (d, J=7.03 Hz, 3H), 0.77 (d, J=7.03 Hz, 3H), 0.76 (s, 3H), 0.70 (s, 3H), 0.09 (s, 9H), 0.06 (s, 9H).

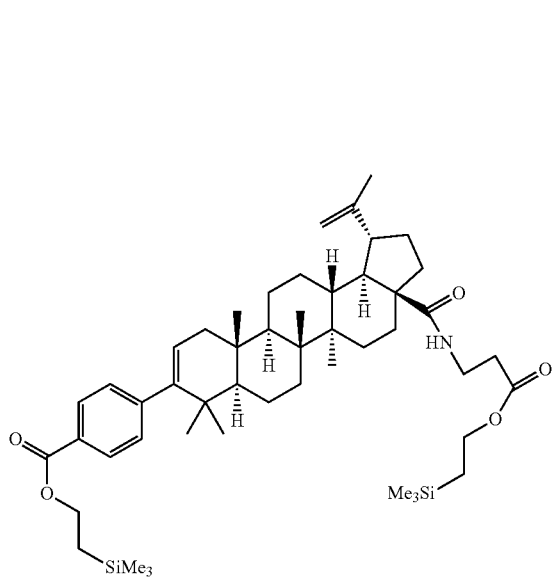

A mixture of 4-((1R,3aS,5aR,5bR,7aR,11aS,11bR,13aR, 13bR)-3a-(2-carboxyethylcarbamoyl)-5a,5b,8,8,11a-pentamethyl-1-(prop-1-en-2-yl)-2,3,3a,4,5,5a,5b,6,7,7a,8,11, 11a,11b,12,13,13a,13b-octadecahydro-1H-cyclopenta[a] chrysen-9-yl)benzoic acid (35 mg, 0.056 mmol) and (Z)-2-(trimethylsilyl)ethyl N,N'-diisopropylcarbamimidate (27.2 mg, 0.111 mmol) was refluxed in THF (1 mL) for 4 h. Then the mixture was placed at room temperature for 16 h. TLC showed no starting material and a new less polar product Rf=0.4 in 10% AcOEt/Hex. The solvent was removed in vacuo. The residue was dissolved in methylene chloride and purified in silica gel (0-10% AcOEt/Hex) to afford 2-(trimethylsilyl)ethyl 4-((1R,3aS,5aR,5bR,7aR,11aS,11bR,13aR, 13bR)-5a,5b,8,8,11a-pentamethyl-3a-(3-oxo-3-(2-(trimethylsilyl)ethoxy)propylcarbamoyl)-1-(prop-1-en-2-yl)-2,3,3a, 4,5,5a,5b,6,7,7a,8,11,11a,11b,12,13,13a,13b-octadecahydro-1H-cyclopenta[a]chrysen-9-yl)benzoate (43 mg, 0.049 mmol, 89% yield) as a white solid. $^1$H NMR (400 MHz, CHLOROFORM-d) δ ppm 7.93 (d, J=8.28 Hz, 2H), 7.20 (d, J=8.03 Hz, 2H), 6.24 (t, J=6.02 Hz, 1H), 5.30 (d, J=4.77 Hz, 1H), 4.76 (d, J=1.51 Hz, 1H), 4.61 (s, 1H), 4.49-4.37 (m, 2H), 4.28-4.17 (m, 2H), 3.65-3.52 (m, 1H), 3.52-3.39 (m, 1H), 3.15 (td, J=10.85, 3.64 Hz, 1H), 2.63-2.43 (m, 3H), 2.11 (dd, J=17.19, 6.40 Hz, 1H), 2.02-1.90 (m, 2H), 1.80-1.04 (m, 22H), 1.70 (s, 3H), 1.01 (s, 3H), 1.00 (s, 3H), 0.98 (s, 3H), 0.93 (s, 6H), 0.10 (s, 9H), 0.06 (s, 9H).

Preparation of 4-((1S,3aS,5aR,5bR,7aS,9S,11aS, 11bR,13aR,13bR)-3a-(2-carboxyethylcarbamoyl)-1-isopropyl-5a,5b,8,8,11a-pentamethylicosahydro-1H-cyclopenta[a]chrysen-9-yl)benzoic acid

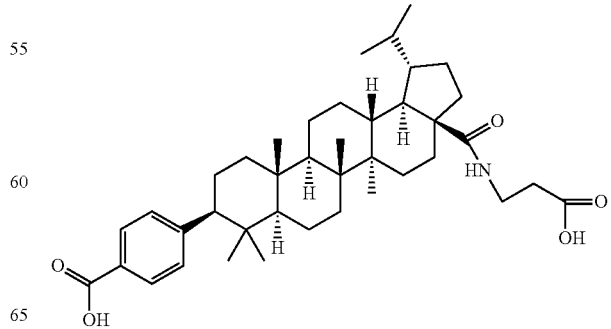

2-(trimethylsilyl)ethyl 4-((1S,3aS,5aR,5bR,7aS,11aS,11bR,13aR,13bR)-1-isopropyl-5a,5b,8,8,11a-pentamethyl-3a-(3-oxo-3-(2-(trimethylsilyl)ethoxy)propylcarbamoyl)icosahydro-1H-cyclopenta[a]chrysen-9-yl)benzoate (14 mg, 0.017 mmol) was dissolved in THF (Volume: 0.5 mL) and treated with TBAF (0.5 mL, 0.500 mmol). The mixture was stirred at rt for 1 h. The solvent was removed in vacuo and the residue was dissolved in DMF and purified using reverse phase prep HPLC to afford 4-((1S,3aS,5aR,5bR,7aS,11aS,11bR,13aR,13bR)-3a-(2-carboxyethylcarbamoyl)-1-isopropyl-5a,5b,8,8,11a-pentamethylicosahydro-1H-cyclopenta[a]chrysen-9-yl)benzoic acid (6 mg, 8.99 mmol, 53.6% yield) as a white solid. $^1$H NMR (400 MHz, DMSO-$d_6$) δ ppm 7.82 (d, J=8.28 Hz, 2H), 7.56 (t, J=5.52 Hz, 1H), 7.29 (d, J=8.28 Hz, 2H), 3.37-3.11 (m, 2H), 2.65-2.56 (m, 1H), 2.47-2.39 (m, 1H), 2.39-2.31 (m, 2H), 2.28-2.18 (m, 1H), 2.18-2.08 (m, 2H), 1.84-0.97 (m, 22H), 0.94 (s, 6H), 0.91 (s, 3H), 0.83 (d, J=6.78 Hz, 3H), 0.74 (d, J=6.78 Hz, 3H), 0.72 (s, 3H), 0.67 (s, 3H).

Example 125

Preparation of 4-((1R,3aS,5aR,5bR,7aR,11aS,11bR,13aR,13bR)-3a-(2-aminoethylcarbamoyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

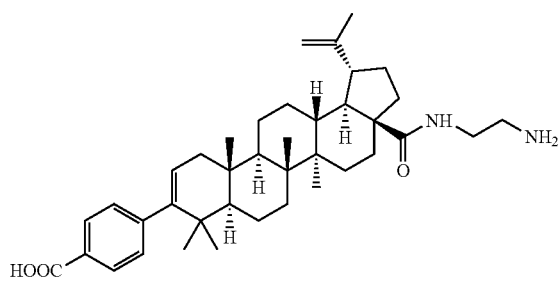

The title compound was prepared following the general procedures described above for the C-28 amide formation and hydrolysis using ethane-1,2-diamine as the reactant amine. The product was isolated as a white solid (40 mg, 63%). LCMS: m/e 601.41 (M+H)$^+$, 2.18 min (method 1). $^1$H NMR (500 MHz, Acetic Acid-$d_4$) δ ppm 8.03 (d, J=8.24 Hz, 2H), 7.30 (d, J=8.24 Hz, 2H), 5.47-5.29 (m, 1H), 4.78 (s, 1H), 4.65 (s, 1H), 3.80-3.54 (m, 2H), 3.27 (td, J=5.87, 2.29 Hz, 2H), 3.21-3.10 (m, 1H), 2.70-2.51 (m, 1H), 2.27-2.15 (m, 2H), 1.74 (s, 3H), 2.12-1.09 (m, 19H), 1.08 (s, 3H), 1.07 (s, 3H), 1.05 (s, 3H), 1.01 (s, 3H), 0.99 (s, 3H).

Example 126

Preparation of 4-((1R,3aS,5aR,5bR,7aR,11aS,11bR,13aR,13bR)-3a-(furan-3-ylmethylcarbamoyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

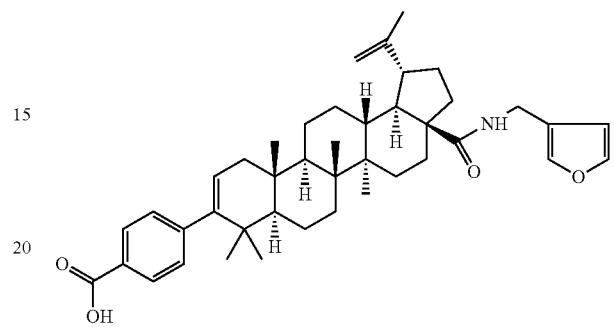

The title compound was prepared following the method described above for the general procedure for C-28 amide formation and hydrolysis using furan-3-ylmethanamine as the reactant amine. The product was isolated as a tan solid (38 mg, 67%). LCMS: m/e 636.5 (M−H)$^-$, 2.52 min (method 4). $^1$H NMR (500 MHz, CHLOROFORM-d) δ ppm 7.98 (d, J=8.24 Hz, 2H), 7.37-7.39 (m, 2H), 7.22 (d, J=8.24 Hz, 2H), 6.36 (s, 1H), 5.76 (t, J=5.65 Hz, 1H), 5.29 (d, J=4.58 Hz, 1H), 4.75 (d, J=1.83 Hz, 1H), 4.60 (s, 1H), 4.35 (dd, J=14.95, 5.80 Hz, 1H), 4.20 (dd, J=14.80, 5.34 Hz, 1H), 3.17 (td, J=11.06, 4.43 Hz, 1H), 2.49-2.56 (m, 1H), 1.69 (s, 3H), 0.99 (s, 3H), 0.97 (s, 3H), 0.96 (s, 3H), 0.95-2.14 (m, 21H), 0.93 (s, 3H), 0.92 (s, 3H).

Example 127

Preparation of 1-(3-((1R,3aS,5aR,5bR,7aR,11aS,11bR,13aR,13bR)-9-(4-carboxyphenyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysene-3a-carboxamido)propanoyl)pyrrolidine-2-carboxylic acid

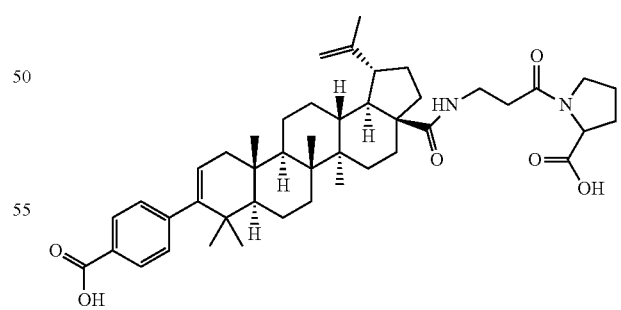

To a solution of 3-((1R,3aS,5aR,5bR,7aR,11aS,11bR,13aR,13bR)-9-(4-(methoxycarbonyl)phenyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysene-3a-carboxamido)propanoic acid (intermediate 8) (0.06 g, 0.093 mmol) in DCE (2 mL) was added DIEA (0.049 mL, 0.280 mmol), O-Benzotriazol-1-yl-N,N,N',N'-tetra-methyluronium tetrafluoroborate (0.045 g, 0.140 mmol), and methyl pyrrolidine-2-carboxylate (0.014 g, 0.112 mmol). The mixture was stirred at rt for 15.5 h, then was diluted with 7 mL of water and was extracted with dichloromethane (3×7 mL). The combined organic layers were dried with Na$_2$SO$_4$. The drying agent was removed by filtration and the filtrate was concentrated under reduced pressure. The residue was purified by Biotage flash chromatography using a 0-75% EtOAc in hexanes gradient. The fractions containing the expected product were combined and concentrated under reduced pressure to give methyl 1-(3-((1R,3aS,5aR,5bR,7aR,11aS,11bR,13aR,13bR)-9-(4-(methoxycarbonyl)phenyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysene-3a-carboxamido)propanoyl)pyrrolidine-2-carboxylate (63 mg, 0.083 mmol, 90% yield) as a white foam. LCMS: m/e 753.5 (M–H)⁻, 3.09 min (method 4).

To a solution of methyl 1-(3-((1R,3aS,5aR,5bR,7aR,11aS,11bR,13aR,13bR)-9-(4-(methoxycarbonyl)phenyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysene-3a-carboxamido)propanoyl)pyrrolidine-2-carboxylate (63 mg, 0.083 mmol) in Dioxane (2 mL) was added NaOH (1N) (0.417 mL, 0.417 mmol). The mixture was heated to 85° C. for 15 h, then cooled to rt and was diluted with 5 mL of 1N HCl and was extracted with dichloromethane (4×5 mL). The combined organic layers were dried with Na$_2$SO$_4$, the drying agent was removed by filtration, and the filtrate was concentrated under reduced pressure. The residue was purified by Biotage flash chromatography using a 0-10% MeOH in DCM gradient with 0.1% HOAc then by prep HPLC. The fractions containing the expected product were combined and concentrated under reduced pressure to give 1-(3-((1R,3aS,5aR,5bR,7aR,11aS,11bR,13aR,13bR)-9-(4-carboxyphenyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysene-3a-carboxamido)propanoyl)pyrrolidine-2-carboxylic acid (27.3 mg, 0.038 mmol, 45.0% yield) as a white solid. LCMS: m/e 726.4 (M–H)⁻, 2.36 min (method 4). $^1$H NMR (500 MHz, Acetic) δ ppm 8.03 (d, J=8.24 Hz, 2H), 7.30 (d, J=8.24 Hz, 2H), 5.37 (d, J=4.58 Hz, 1H), 4.78 (s, 1H), 4.64 (s, 1H), 4.57 (dd, J=8.70, 3.51 Hz, 1H), 3.52-3.75 (m, 4H), 3.09-3.20 (m, J=18.43, 11.08, 11.08, 4.27 Hz, 1H), 2.68-2.82 (m, 2H), 2.58 (td, J=12.36, 3.05 Hz, 1H), 1.73 (s, 3H), 1.07 (s, 6H), 1.05 (s, 3H), 1.03-2.53 (m, 25H), 1.01 (s, 3H), 0.99 (s, 3H).

Example 128

Preparation of 1-((1R,3aS,5aR,5bR,7aR,11aS,11bR,13aR,13bR)-9-(4-carboxyphenyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysene-3a-carbonyl)pyrrolidine-2-carboxylic acid

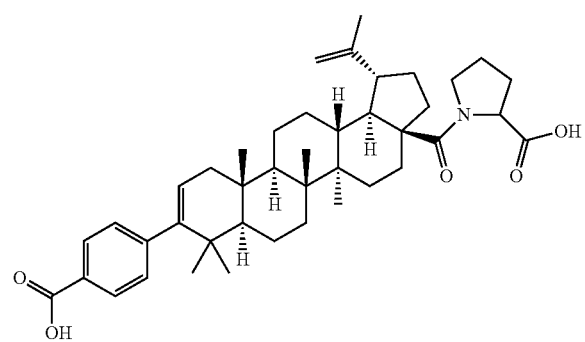

The title compound was prepared following the method described above for the general procedure for C-28 amide formation and hydrolysis using methylpyrrolidine-2-carboxylate as the reactant amine. The product was isolated as a white solid (19 mg, 23%). LCMS: m/e 654.4 (M–H)⁻, 2.47 min (method 4).

Preparation of methyl 4-((1R,3aS,5aR,5bR,7aR,11aS,11bR,13aR,13bR)-3a-(isopentylcarbamoyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoate. Intermediate 43

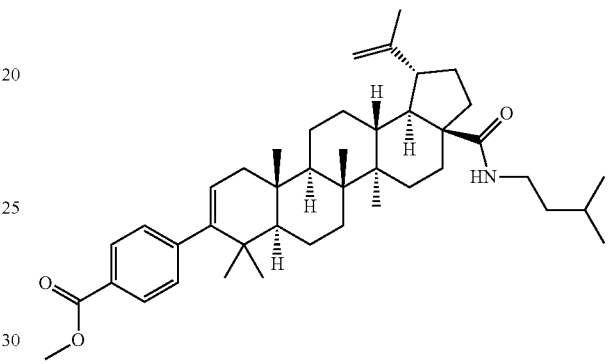

To a solution of (1R,3aS,5aR,5bR,7aR,11aS,11bR,13aR,13bR)-9-(4-(methoxycarbonyl)phenyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysene-3a-carboxylic acid (358.0 mg, 0.625 mmol) in THF (10 mL) was added N,N-diisopropylamine (0.327 mL, 1.875 mmol), isoamylamine (0.110 mL, 0.937 mmol) and HATU (356 mg, 0.937 mmol). The reaction mixture was stirred at 25° C. After 16 h, the reaction mixture was diluted with EtOAc (50 mL), washed with 1N HCl (5 mL), 5% NaHCO$_3$, brine, dried over MgSO$_4$, filtered and concentrated to a foam product. The residue was absorbed on to 4 g of silica gel, loaded on to a silica gel column (40 g cartridge) and eluted with 0% B to 50% B for 240 mL then 50% B (solvent: A=hexanes, B=5:1 hex:EtOAc) to afford the title compound as a white solid (229 mg, 0.342 mmol, 54.8% yield). LCMS: m/e 642.6 (M–H)⁺, 3.24 min (method 5); $^1$H NMR (500 MHz, CHLOROFORM-d) δ ppm 7.9 (2H, m, J=8.2 Hz), 7.2 (2H, m, J=8.5 Hz), 5.6 (1H, t, J=5.6 Hz), 5.3 (1H, dd, J=6.3, 2.0 Hz), 4.8 (1H, d, J=2.1 Hz), 4.6-4.6 (1H, m), 3.9 (3H, s), 3.3-3.4 (1H, m), 3.2-3.3 (2H, m), 2.5-2.6 (1H, m), 2.1 (1H, dd, J=17.1, 6.4 Hz), 2.0-2.1 (1H, m), 1.9-2.0 (1H, m), 1.8 (2H, dd, J=11.7, 7.5 Hz), 1.7 (3H, s), 1.6-1.7 (2H, m), 1.6 (1H, s), 1.6 (1H, dd, J=13.3, 2.6 Hz), 1.4-1.5 (11H, m), 1.2-1.3 (2H, m), 1.1 (1H, dd, J=12.5, 4.6 Hz), 1.0 (6H, s), 1.0 (3H, s), 1.0 (3H, s), 0.9 (3H, s), 0.9 (6H, d, J=2.4 Hz); $^{13}$C NMR(CHLOROFORM-d) δ ppm 14.4, 15.6, 16.2, 19.3, 19.5, 20.7, 21.1, 22.2, 22.3, 25.5, 25.7, 29.2, 30.6, 33.4, 33.6, 36.0, 37.2, 37.7, 38.2, 38.5, 40.3, 41.5, 42.2, 46.5, 49.3, 49.9, 51.7, 52.6, 55.4, 65.6, 109.0, 123.9, 127.6, 128.2, 129.8, 145.9, 148.5, 150.8, 167.0, 175.6.

Example 129

Preparation of 4-((1R,3aS,5aR,5bR,7aR,11aS,11bR, 13aR,13bR)-3a-(isopentylcarbamoyl)-5a,5b,8,8,11a-pentamethyl-1-(prop-1-en-2-yl)-2,3,3a,4,5,5a,5b,6,7, 7a,8,11,11a,11b,12,13,13a,13b-octadecahydro-1H-cyclopenta[a]chrysen-9-yl)benzoic acid

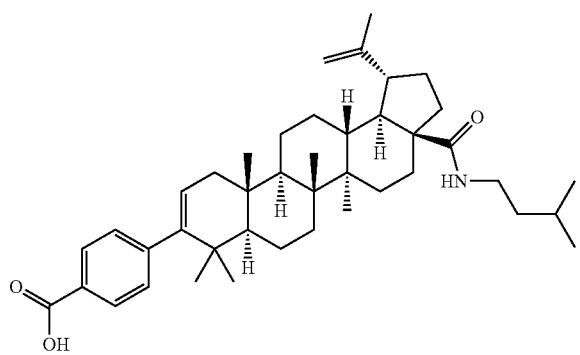

To a solution of methyl 4-((1R,3aS,5aR,5bR,7aR,11aS, 11bR,13aR,13bR)-3a-(isopentylcarbamoyl)-5a,5b,8,8,11a-pentamethyl-1-(prop-1-en-2-yl)-2,3,3a,4,5,5a,5b,6,7,7a,8, 11,11a,11b,12,13,13a,13b-octadecahydro-1H-cyclopenta[a]chrysen-9-yl)benzoate (0.204 g, 0.318 mmol) in THF (5 mL) was added a solution of lithium hydroxide monohydrate (0.040 g, 0.953 mmol) in H$_2$O (1.000 mL). The resulting white slurry was stirred at rt overnight. After 15 h, TLC showed significant starting material left thus reaction was heated to 75° C. for 3 h. Reaction was treated with 1N HCl (1 mL) and concentrated to dryness. Material was absorbed onto silica gel, loaded onto a silica gel column (12 g cartridge) and was eluted with 0% B to 100% B for 180 mL and held 100% B for 600 mL (Solvents: A=100% DCM, B=90:10 DCM:MeOH). Obtained 4-((1R,3aS,5aR,5bR,7aR,11aS, 11bR,13aR,13bR)-3a-(isopentylcarbamoyl)-5a,5b,8,8,11a-pentamethyl-1-(prop-1-en-2-yl)-2,3,3a,4,5,5a,5b,6,7,7a,8, 11,11a,11b,12,13,13a,13b-octadecahydro-1H-cyclopenta[a]chrysen-9-yl)benzoic acid (182 mg, 0.281 mmol, 88% yield) as white solid. LCMS: m/e 628.6 (M−H)$^+$, 2.45 min (method 5); $^1$H NMR (500 MHz, CHLOROFORM-d) δ ppm 8.0 (2H, d, J=8.2 Hz), 7.3 (2H, d, J=8.5 Hz), 5.6 (1H, t, J=5.6 Hz), 5.3 (1H, dd, J=6.1, 1.8 Hz), 4.8 (1H, d, J=2.1 Hz), 4.6-4.6 (1H, m), 3.3-3.4 (1H, m), 3.2-3.3 (2H, m), 2.5-2.6 (1H, m), 2.1 (1H, dd, J=17.4, 6.4 Hz), 1.9-2.1 (2H, m), 1.7-1.8 (2H, m), 1.7 (3H, s), 1.6-1.7 (3H, m), 1.3-1.6 (11H, m), 1.2-1.3 (2H, m), 1.0 (6H, s), 1.0 (3H, s), 1.0 (6H, s), 0.9-1.0 (6H, m) $^{13}$C NMR(CHLOROFORM-d) δ ppm 14.4, 15.6, 16.2, 19.3, 19.5, 20.8, 21.1, 22.2, 22.3, 25.5, 25.7, 29.2, 30.7, 33.4, 33.6, 36.0, 37.2, 37.7, 38.2, 38.5, 40.4, 41.5, 42.2, 46.5, 49.3, 49.9, 52.6, 55.4, 77.3, 109.0, 124.0, 126.7, 128.9, 129.9, 145.9, 149.4, 150.8, 171.1, 175.7.

Example 130

Preparation of (4-((1R,3aS,5aR,5bR,7aR,11aS,11bR, 13aR,13bR)-3a-((2-(1,1-dioxidothiomorpholino) ethyl)carbamoyl)-5a,5b,8,8,11a-pentamethyl-1-(prop-1-en-2-yl)-2,3,3a,4,5,5a,5b,6,7,7a,8,11,11a, 11b,12,13,13a,13b-octadecahydro-1H-cyclopenta[a] chrysen-9-yl)phenyl)boronic acid, TFA

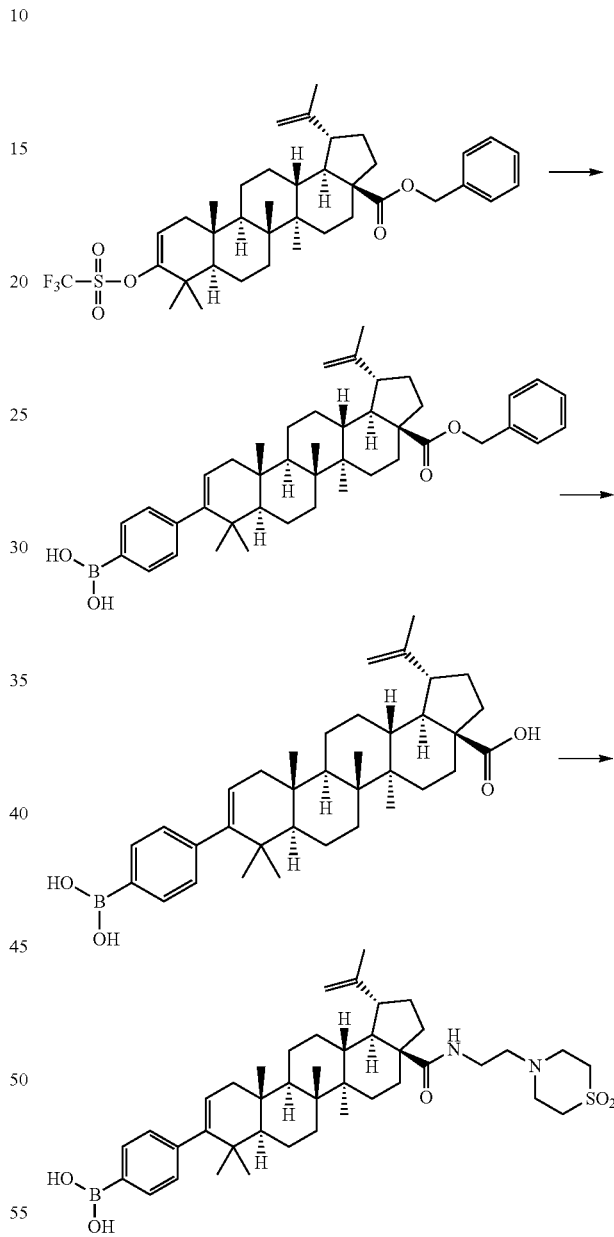

Step 1: To a solution of (1R,3aS,5aR,5bR,7aR,11aR,11bR, 13aR,13bR)-benzyl 5a,5b,8,8,11a-pentamethyl-1-(prop-1-en-2-yl)-9-(((trifluoromethyl)sulfonyl)oxy)-2,3,3a,4,5,5a, 5b,6,7,7a,8,11,11a,11b,12,13,13a,13b-octadecahydro-1H-cyclopenta[a]chrysene-3a-carboxylate (3.0 g, 4.43 mmol) in THF (100 mL) was added 1,4-benzenediboronic acid (1.469 g, 8.86 mmol) and tetrakis(triphenylphosphine)palladium(0)

(0.259 g, 0.222 mmol). The resulting yellow mixture was purged with $N_2$. Then, a solution of sodium carbonate (2.82 g, 26.6 mmol) in $H_2O$ (25.00 mL) was added and the reaction mixture was heated to reflux at 90° C. After 6 h, the reaction mixture was cooled to rt, diluted with EtOAc (50 mL) and washed with $H_2O$ (50 mL). The aqueous layer was extracted with EtOAc (2×50 mL). The combined organic layer was filtered through celite pad, washed with brine, dried over $MgSO_4$, filtered and concentrated to afford a light brown solid. The crude material was absorbed onto silica gel (20 g), loaded onto a silica gel column and eluted with 3:1 hexanes:EtOAc to give (4-((1R,3aS,5aR,5bR,7aR,11aS,11bR,13aR,13bR)-3a-((benzyloxy)carbonyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)phenyl)boronic acid (983 mg, 34.2%) as a white solid. $^1$H NMR (500 MHz, CHLOROFORM-d) δ 8.18-8.14 (m, 2H), 7.43-7.38 (m, 4H), 7.38-7.35 (m, 1H), 7.31-7.29 (m, 1H), 5.37-5.34 (m, 1H), 5.17 (t, J=1.0 Hz, 2H), 4.77 (d, J=1.5 Hz, 1H), 4.64 (s, 1H), 3.08 (td, J=10.8, 4.7 Hz, 1H), 2.35-2.30 (m, 1H), 2.30-2.25 (m, 1H), 2.15 (dd, J=17.1, 6.1 Hz, 1H), 1.98-1.89 (m, 2H), 1.73 (s, 3H), 1.69 (d, J=3.7 Hz, 1H), 1.67-1.64 (m, 1H), 1.56-1.37 (m, 10H), 1.37-1.23 (m, 3H), 1.19 (d, J=13.1 Hz, 1H), 1.07 (dd, J=13.1, 4.3 Hz, 1H), 1.02 (s, 6H), 0.99 (br. s., 3H), 0.99 (br. s., 3H), 0.96-0.93 (m, 1H), 0.87 (s, 3H). $^{13}$C NMR (126 MHz, CHLOROFORM-d) δ 175.8, 150.6, 148.41-148.39 (m, 1C), 148.3, 146.8, 136.5, 134.6, 129.7, 128.5, 128.2, 128.1, 123.7, 109.6, 65.7, 56.6, 52.9, 49.6, 49.4, 46.9, 42.4, 41.8, 40.5, 38.4, 37.5, 37.0, 36.3, 33.6, 32.1, 30.6, 29.6, 29.5, 25.7, 21.3, 21.1, 19.8, 19.4, 16.5, 15.6, 14.7.

Step 2: A −78° C. solution of (4-((1R,3aS,5aR,5bR,7aR,11aS,11bR,13aR,13bR)-3a-((benzyloxy)carbonyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)phenyl)boronic acid (0.200 g, 0.308 mmol) in DCM (3 mL) was purged with $N_2$(g). Boron tribromide (1M solution in DCM) (1.079 mL, 1.079 mmol) was added dropwise. The resulting yellow reaction mixture was stirred at −78° C. for 1 h. The cold bath was removed and $H_2O$ (5 mL) was added to quench the reaction. The resulting white paste was filtered and washed with $H_2O$. The crude material was dissolved in THF and DCM loaded onto a silica gel column and eluted with 1:1 hexanes:EtOAc to give 93 mg crude material which was further purified by reverse phase HPLC to give (1R,3aS,5aR,5bR,7aR,11aS,11bR,13aR,13bR)-9-(4-boronophenyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysene-3a-carboxylic acid (45.2 mg, 24.15%) as a white solid. $^1$H NMR (500 MHz, DMSO-$d_6$) δ 12.09 (br. s., 1H), 7.97 (br. s., 2H), 7.68 (d, J=7.9 Hz, 2H), 7.04 (d, J=7.9 Hz, 2H), 5.18 (d, J=4.6 Hz, 1H), 4.70 (s, 1H), 4.57 (s, 1H), 3.02-2.90 (m, 1H), 2.33-2.23 (m, 1H), 2.12 (d, J=6.4 Hz, 1H), 2.05 (dd, J=17.2, 6.3 Hz, 1H), 1.80 (d, J=7.3 Hz, 2H), 1.69-1.66 (m, 1H), 1.65 (s, 3H), 1.56 (t, J=11.3 Hz, 1H), 1.50 (br. s., 1H), 1.45-1.36 (m, 8H), 1.33-1.28 (m, 1H), 1.23 (br. s., 1H), 1.21-1.12 (m, 3H), 1.02-0.98 (m, 1H), 0.97 (s, 3H), 0.93 (s, 6H), 0.87 (s, 3H), 0.86 (s, 3H).

Step 3: To a solution of (1R,3aS,5aR,5bR,7aR,11aS,11bR,13aR,13bR)-9-(4-boronophenyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysene-3a-carboxylic acid (104 mg, 0.186 mmol) in THF (3 mL) was added N,N-diisopropylethylamine (0.162 mL, 0.931 mmol), 4-(2-aminoethyl)thiomorpholine 1,1-dioxide (46.5 mg, 0.261 mmol) and 2-(3H-[1,2,3]triazolo[4,5-b]pyridin-3-yl)-1,1,3,3-tetramethylisouronium hexafluorophosphate(V) (106 mg, 0.279 mmol). The resulting creamy mixture was stirred at rt. After two weeks, reaction was concentrated and purified by reverse phase HPLC to give (4-((1R,3aS,5aR,5bR,7aR,11aS,11bR,13aR,13bR)-3a-((2-(1,1-dioxidothiomorpholino)ethyl)carbamoyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)phenyl)boronic acid, TFA (33 mg, 19.15%). $^1$H NMR (500 MHz, DMSO-$d_6$) δ 7.74 (br. s., 1H), 7.68 (d, J=7.9 Hz, 2H), 7.04 (d, J=7.9 Hz, 2H), 5.18 (d, J=4.9 Hz, 1H), 4.66 (s, 1H), 4.55 (br. s., 1H), 3.62-3.57 (m, 1H), 3.39-3.23 (m, 9H), 3.02 (td, J=10.5, 4.4 Hz, 1H), 2.88 (br. s., 2H), 2.65-2.57 (m, 1H), 2.13-2.01 (m, 2H), 1.76 (dt, J=6.8, 3.2 Hz, 3H), 1.67 (br. s., 1H), 1.64 (s, 3H), 1.52-1.43 (m, 3H), 1.42-1.33 (m, 6H), 1.33-1.15 (m, 5H), 1.09 (d, J=12.8 Hz, 1H), 1.04 (s, 1H), 0.95 (s, 3H), 0.94 (s, 3H), 0.92 (s, 3H), 0.87 (br. s., 3H), 0.86 (br. s., 3H).

Preparation of Compounds of Formula III.

As previously set forth, compounds of formula III can be prepared as described for compounds of formulas I and II, using ursolic acid, oleanolic acid and moronic acid as starting material instead of betulinic acid to give the corresponding E-ring modified final products. The following scheme is a more specific version of the scheme 7 for preparation of compounds of formula III set forth above.

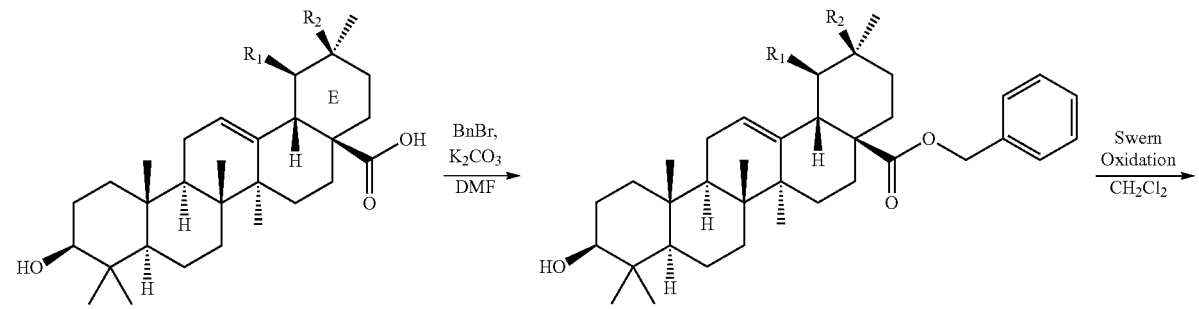

$R_1$ = Me, $R_2$ = H (Ursolic acid)
$R_1$ = H, $R_2$ = Me (Oleanolic acid)

-continued
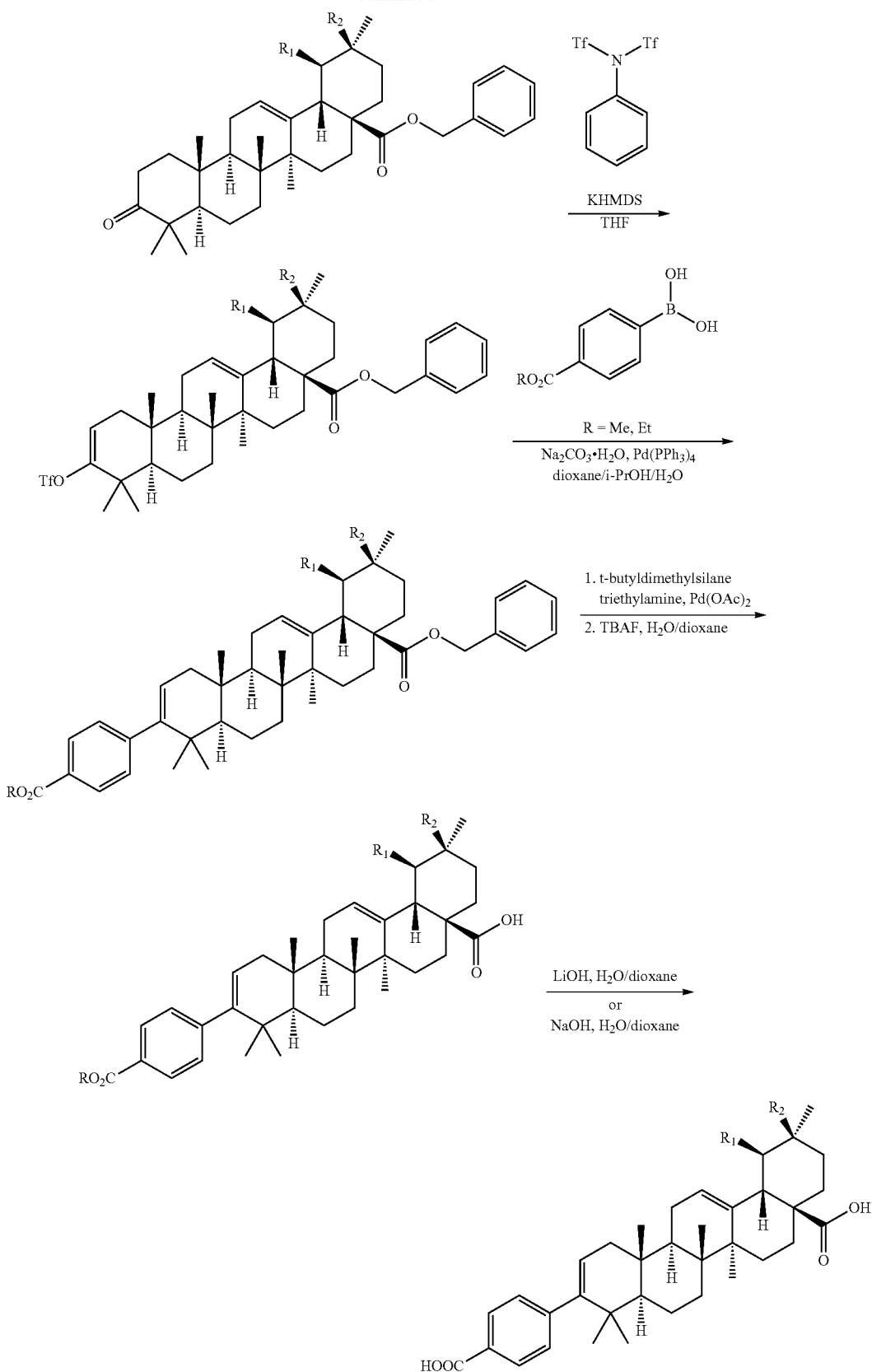

Preparation of Intermediates A1, and B1

(1S,2R,4aS,6aS,6bR,8aR,10S,12aR,12bR,14bS)-benzyl 10-hydroxy-1,2,6a,6b,9,9,12a-heptamethyl-1,2,3,4,4a,5,6,6a,6b,7,8,8a,9,10,11,12,12a,12b,13,14b-icosahydropicene-4-a-carboxylate. Intermediate A1

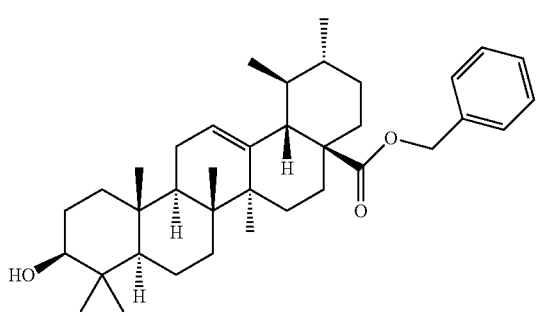

Using ursolic acid as the starting material, the title compound was prepared in accordance to the procedure described for the preparation of intermediate 1, (white solid, 98%). $^1$H NMR (400 MHz, CHLOROFORM-d) δ ppm 0.79 (s, 3H), 0.86 (d, J=6.53 Hz, 3H), 0.90 (s, 3H), 0.93-0.96 (m, 3H), 0.99 (s, 3H), 1.08 (s, 3H), 1.23-1.42 (m, 7H), 1.42-1.53 (m, 4H), 1.59-1.92 (m, 10H), 1.96-2.08 (m, 1H), 2.23-2.31 (m, 1H), 3.22 (dt, J=11.04, 5.52 Hz, 1H), 4.96-5.14 (m, 2H), 5.25 (t, J=3.64 Hz, 1H), 7.35 (s, 5H).

(4aS,6aS,6bR,8aR,10S,12aR,12bR,14bS)-benzyl 10-hydroxy-2,2,6a,6b,9,9,12a-heptamethyl-1,2,3,4,4a,5,6,6a,6b,7,8,8a,9,10,11,12,12a,12b,13,14b-icosahydropicene-4-a-carboxylate. Intermediate B1

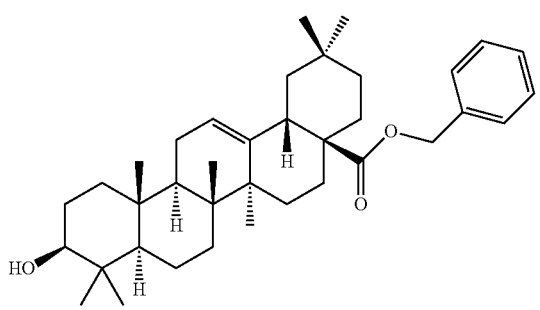

The title compound was obtained following the procedure described above for intermediate 1 using oleanoic acid as the starting material, (white solid, 94%). $^1$H NMR (400 MHz, CHLOROFORM-d) δ ppm 0.62 (s, 3H), 0.70-0.74 (m, 1H), 0.78 (s, 3H), 0.89 (s, 3H), 0.91 (s, 3H), 0.93 (s, 3H), 0.99 (s, 3H), 1.02-1.08 (m, 1H), 1.13 (s, 3H), 1.16-1.30 (m, 4H), 1.30-1.37 (m, 2H), 1.37-1.48 (m, 2H), 1.51-1.53 (m, 1H), 1.60-1.63 (m, 2H), 1.64-1.66 (m, 1H), 1.67-1.71 (m, 1H), 1.71-1.77 (m, 1H), 1.86 (dd, J=8.78, 3.51 Hz, 2H), 1.92-2.05 (m, 1H), 2.86-2.97 (m, 1H), 3.16-3.28 (m, 1H), 5.01-5.16 (m, 2H), 5.30 (t, J=3.51 Hz, 1H), 7.35 (s, 5H).

Preparation of Intermediates A2, and B2. Swern Oxidation (1S,2R,4aS,6aS,6bR,8aR,12aR,12bR,14bS)-benzyl 1,2,6a,6b,9,9,12a-heptamethyl-10-oxo-1,2,3,4,4a,5,6,6a,6b,7,8,8a,9,10,11,12,12a,12b,13,14b-icosahydropicene-4-a-carboxylate. Intermediate A2

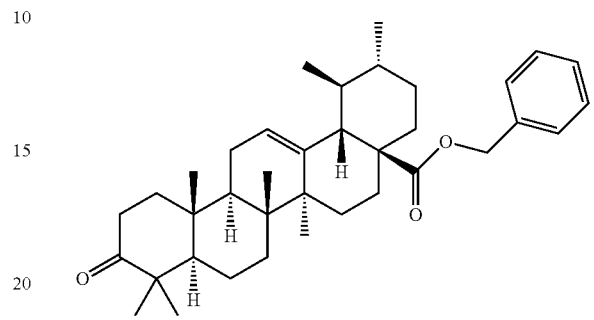

To a solution of oxalyl chloride (2.57 mL, 5.14 mmol) in methylene chloride (5 mL) at −78° C. under nitrogen was added dropwise a solution of DMSO (0.46 mL 6.4 mmol) in methylene chloride (5 mL). The mixture was allowed to warm to −50° C. To this was added a solution of the (1S,2R,4aS,6aS,6bR,8aR,10S,12aR,12bR,14bS)-benzyl 10-hydroxy-1,2,6a,6b,9,9,12a-heptamethyl-1,2,3,4,4a,5,6,6a,6b,7,8,8a,9,10,11,12,12a,12b,13,14b-icosahydropicene-4-a-carboxylate (intermediate A1) (2.34 gm, 4.28 mmol) in methylene chloride (15 mL) forming a white milky suspension. The mixture was stirred for an additional 15 minutes at −50° C. after the addition, it was then treated with triethylamine (1.79 mL, 12.84 mmol) and the reaction mixture was slowly warmed to RT. It was diluted with methylene chloride (100 mL), washed with water (2×100 mL), followed by brine (50 mL). The organic phase was separated out, dried over anhydrous sodium sulfate, and concentrated in vacuo to a syrup. This crude material was partitioned over a silica gel column, eluted with 9:1, hexanes:ethyl acetate solvent to give the title compound as a pale solid (2.22 g, 95%). $^1$H NMR (400 MHz, CHLOROFORM-d) δ ppm 0.69 (s, 3H), 0.87 (d, J=6.53 Hz, 3H), 0.93-0.97 (m, 3H), 1.03 (s, 3H), 1.05 (s, 3H), 1.09 (s, 6H), 1.26-1.40 (m, 4H), 1.40-1.54 (m, 5H), 1.59 (d, J=9.03 Hz, 2H), 1.70 (br. s., 2H), 1.93 (dd, J=9.54, 3.26 Hz, 4H), 1.97-2.08 (m, 2H), 2.29 (d, J=11.04 Hz, 1H), 2.38 (ddd, J=15.94, 6.90, 3.76 Hz, 1H), 2.49-2.61 (m, 1H), 4.97-5.03 (m, 1H), 5.10-5.15 (m, 1H), 5.27 (t, J=3.51 Hz, 1H), 7.31-7.39 (m, 5H).

(4aS,6aS,6bR,8aR,12aR,12bR,14bS)-benzyl 2,2,6a,6b,9,9,12a-heptamethyl-10-oxo-1,2,3,4,4a,5,6,6a,6b,7,8,8a,9,10,11,12,12a,12b,13,14b-icosahydropicene-4-a-carboxylate. Intermediate B2

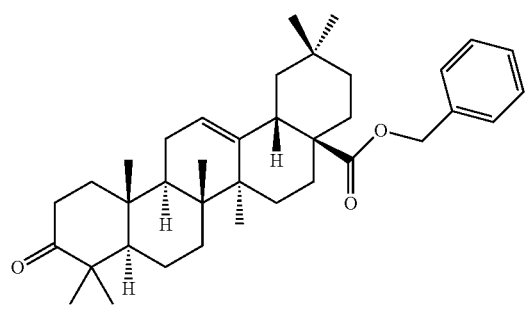

The title compound was obtained via Swern oxidation as described above using intermediate A1 as starting material, (pale solid, 94%). ¹H NMR (400 MHz, CHLOROFORM-d) δ ppm 0.66 (s, 3H), 0.91 (s, 3H), 0.93 (s, 3H), 1.03 (s, 3H), 1.05 (s, 3H), 1.09 (s, 3H), 1.14 (s, 3H), 1.17-1.24 (m, 2H), 1.25-1.50 (m, 8H), 1.57-1.78 (m, 6H), 1.84-1.94 (m, 3H), 1.95-2.05 (m, 1H), 2.37 (ddd, J=15.81, 6.78, 3.76 Hz, 1H), 2.50-2.60 (m, 1H), 2.93 (dd, J=13.93, 3.89 Hz, 1H), 5.04-5.09 (m, 1H), 5.09-5.14 (m, 1H), 5.32 (t, J=3.64 Hz, 1H), 7.35-7.37 (m, 5H).

Preparation of Intermediates A3 and B3

(1S,2R,4aS,6aS,6bR,8aR,12aR,12bR,14bS)-benzyl 1,2,6a,6b,9,9,12a-heptamethyl-10-(trifluoromethylsulfonyloxy)-1,2,3,4,4a,5,6,6a,6b,7,8,8a,9,12,12a, 12b,13,14b-octadecahydropicene-4-a-carboxylate. Intermediate A3

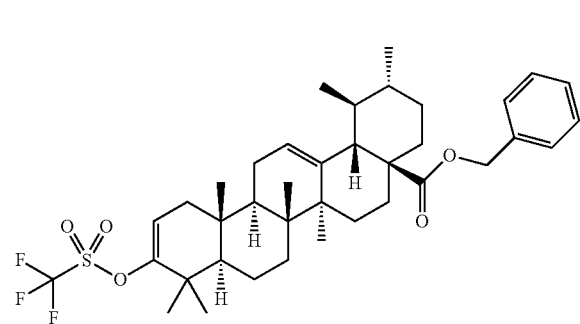

The title compound was prepared using the procedure described previously for the preparation of intermediate 3, using ketone intermediate A2 as starting material (45%). ¹H NMR (400 MHz, CHLOROFORM-d) δ ppm 0.67 (s, 3H), 0.87 (d, J=6.53 Hz, 3H), 0.93-0.97 (m, 3H), 0.99 (s, 3H), 1.04 (s, 3H), 1.08 (s, 3H), 1.14 (s, 3H), 1.17-1.21 (m, 1H), 1.21-1.47 (m, 5H), 1.50 (dd, J=13.05, 3.26 Hz, 2H), 1.56 (s, 3H), 1.58-1.78 (m, 3H), 1.78-1.97 (m, 3H), 1.97-2.07 (m, 2H), 2.15 (dd, J=17.07, 6.78 Hz, 1H), 2.30 (d, J=11.54 Hz, 1H), 4.97-5.02 (m, 1H), 5.10-5.15 (m, 1H), 5.27 (t, J=3.51 Hz, 1H), 5.59 (dd, J=6.78, 2.01 Hz, 1H), 7.35 (s, 5H); ¹⁹F NMR (376.46 MHz, CHLOROFORM-d) δ ppm −74.83.

(4aS,6aS,6bR,8aR,12aR,12bR,14bS)-benzyl 2,2,6a,6b,9,9,12a-heptamethyl-10-(trifluoromethylsulfonyloxy)-1,2,3,4,4a,5,6,6a,6b,7,8,8a,9,12,12a,12b,13, 14b-octadecahydropicene-4-a-carboxylate. Intermediate B3

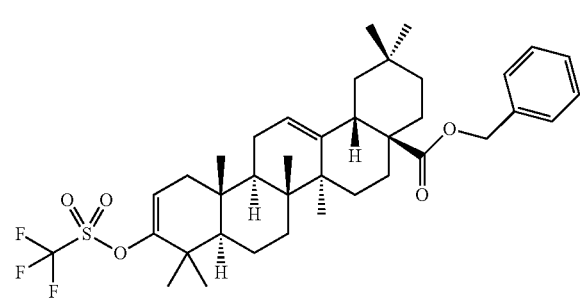

The title compound was prepared using the procedure described previously for the preparation of intermediate 3, using ketone intermediate B2 as starting material (29%). ¹H NMR (400 MHz, CHLOROFORM-d) δ ppm 0.65 (s, 3H), 0.91 (s, 3H), 0.94 (s, 3H), 0.97 (s, 3H), 1.04 (s, 3H), 1.05-1.12 (m, 1H), 1.14 (s, 6H), 1.16-1.28 (m, 3H), 1.28-1.42 (m, 2H), 1.42-1.54 (m, 2H), 1.57-1.65 (m, 2H), 1.68 (d, J=14.56 Hz, 2H), 1.73 (d, J=4.52 Hz, 1H), 1.78-1.84 (m, 2H), 1.86 (dd, J=5.90, 4.14 Hz, 1H), 1.90-1.97 (m, 1H), 1.98-2.04 (m, 1H), 2.12 (dd, J=17.07, 6.78 Hz, 1H), 2.93 (dd, J=13.93, 4.14 Hz, 1H), 5.03-5.14 (m, 3H), 5.33 (t, J=3.51 Hz, 1H), 5.58 (dd, J=6.78, 2.01 Hz, 1H), 7.34-7.38 (m, 5H); ¹⁹F NMR (376.46 MHz, CHLOROFORM-d) δ ppm −74.84.

Preparation of intermediates A4 and B4

(1S,2R,4aS,6aS,6bR,8aR,12aS,12bR,14bS)-benzyl 10-(4-(methoxycarbonyl)phenyl)-1,2,6a,6b,9,9,12a-heptamethyl-1,2,3,4,4a,5,6,6a,6b,7,8,8a,9,12,12a, 12b,13,14b-octadecahydropicene-4-a-carboxylate. Intermediate A4

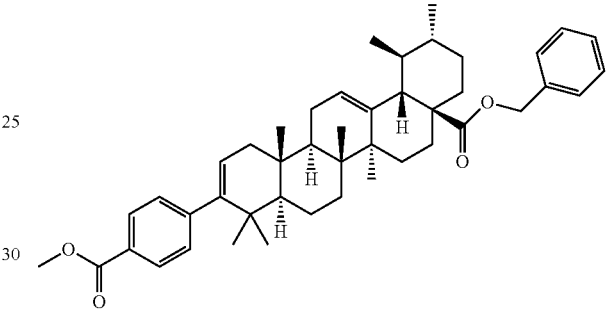

The title compound was prepared via from triflate intermediate A3 using the Suzuki coupling procedure described previously for the preparation of intermediate 4, (68%). ¹H NMR (400 MHz, CHLOROFORM-d) δ ppm 0.73 (s, 3H), 0.88 (d, J=6.53 Hz, 3H), 0.93-0.97 (m, 9H), 1.06 (s, 3H), 1.12 (s, 3H), 1.14-1.19 (m, 1H), 1.25 (d, J=12.30 Hz, 2H), 1.31-1.45 (m, 4H), 1.45-1.54 (m, 2H), 1.57-1.62 (m, 1H), 1.65 (dd, J=13.05, 4.02 Hz, 1H), 1.68-1.79 (m, 3H), 1.80-1.87 (m, 1H), 1.91-1.98 (m, 2H), 2.02 (dd, J=12.92, 4.64 Hz, 1H), 2.10 (dd, J=17.07, 6.27 Hz, 1H), 2.31 (d, J=11.04 Hz, 1H), 3.92 (s, 3H), 4.98-5.03 (m, 1H), 5.11-5.15 (m, 1H), 5.29-5.34 (m, 2H), 7.21 (d, J=8.53 Hz, 2H), 7.31-7.39 (m, 5H), 7.94 (d, J=8.28 Hz, 2H).

(4aS,6aS,6bR,8aR,12aS,12bR,14bS)-benzyl 10-(4-(methoxycarbonyl)phenyl)-2,2,6a,6b,9,9,12a-heptamethyl-1,2,3,4,4a,5,6,6a,6b,7,8,8a,9,12,12a,12b, 13,14b-octadecahydropicene-4-a-carboxylate. Intermediate B4

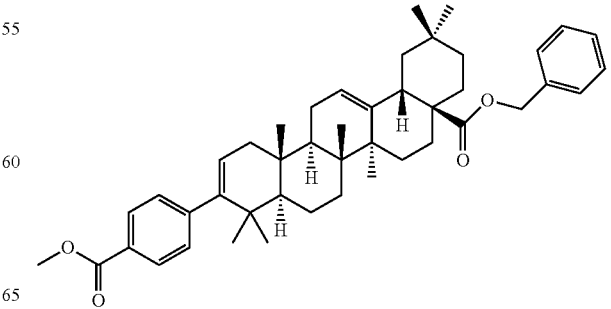

The title compound was prepared via from triflate intermediate B3 using the Suzuki coupling procedure described previously for the preparation of intermediate 4, (65%). $^1$H NMR (400 MHz, CHLOROFORM-d) δ ppm 0.70 (s, 3H), 0.92 (s, 3H), 0.95 (s, 9H), 1.04 (s, 3H), 1.08-1.15 (m, 1H), 1.17 (s, 3H), 1.19-1.25 (m, 2H), 1.27 (br. s., 2H), 1.30-1.38 (m, 2H), 1.40 (dd, J=8.03, 3.51 Hz, 1H), 1.43-1.54 (m, 2H), 1.58-1.68 (m, 3H), 1.68-1.78 (m, 3H), 1.90 (dd, J=6.15, 3.89 Hz, 1H), 1.92-2.03 (m, 2H), 2.07 (dd, J=17.07, 6.27 Hz, 1H), 2.95 (dd, J=13.80, 4.02 Hz, 1H), 3.92 (s, 3H), 5.04-5.15 (m, 2H), 5.31 (dd, J=6.15, 1.88 Hz, 1H), 5.36 (t, J=3.39 Hz, 1H), 7.21 (d, J=8.53 Hz, 2H), 7.33-7.38 (m, 5H), 7.94 (d, J=8.28 Hz, 2H).

Preparation of Intermediates A5 and B5

(1S,2R,4aS,6aS,6bR,8aR,12aS,12bR,14bS)-tert-butyldimethylsilyl 10-(4-(methoxycarbonyl)phenyl)-1,2,6a,6b,9,9,12a-heptamethyl-1,2,3,4,4a,5,6,6a,6b,7,8,8a,9,12,12a,12b,13,14b-octadecahydropicene-4-a-carboxylate. Intermediate A5

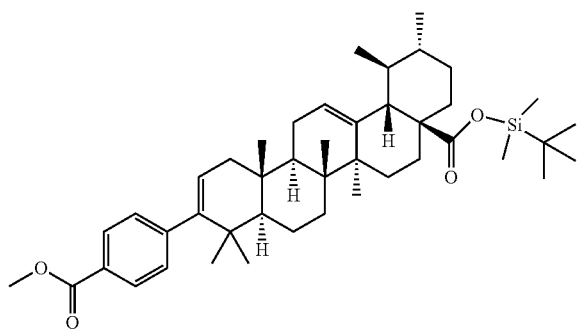

Palladium catalyzed hydrosilylation of the benzyl esters intermediate A4 as described in the preparation of intermediate 5 afforded the title compound (57%). $^1$H NMR (400 MHz, CHLOROFORM-d) δ ppm 0.24 (s, 3H), 0.25 (s, 3H), 0.87-0.90 (m, 6H), 0.93-0.98 (m, 18H), 1.09 (s, 3H), 1.12 (s, 3H), 1.16-1.51 (m, 6H), 1.52-1.59 (m, 7H), 1.59-1.88 (m, 4H), 1.88-2.07 (m, 3H), 2.11 (dd, J=17.07, 6.27 Hz, 1H), 2.22 (d, J=10.29 Hz, 1H), 3.92 (s, 3H), 5.30-5.34 (m, 2H), 7.22 (d, J=8.28 Hz, 2H), 7.94 (d, J=8.28 Hz, 2H);

(4aS,6aS,6bR,8aR,12aS,12bR,14bS)-tert-butyldimethylsilyl 10-(4-(methoxycarbonyl)phenyl)-2,2,6a,6b,9,9,12a-heptamethyl-1,2,3,4,4a,5,6,6a,6b,7,8,8a,9,12,12a,12b,13,14b-octadecahydropicene-4-a-carboxylate. Intermediate 17 B5

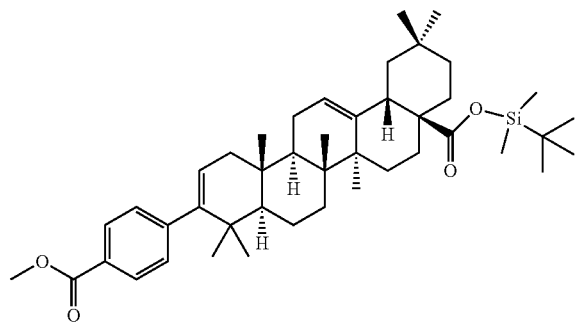

Palladium catalyzed hydrosilylation of the benzyl esters intermediate B4 as described in the preparation of intermediate 5 afforded the title compound (54%). $^1$H NMR (400 MHz, CHLOROFORM-d) δ ppm 0.25 (s, 3H), 0.26 (s, 3H), 0.87 (s, 3H), 0.92 (s, 3H), 0.93-0.97 (m, 18H), 1.07 (s, 3H), 1.12-1.17 (m, 2H), 1.18 (s, 4H), 1.21-1.30 (m, 3H), 1.30-1.53 (m, 5H), 1.62-1.80 (m, 5H), 1.82-1.95 (m, 1H), 1.95-2.03 (m, 2H), 2.07 (dd, J=17.07, 6.27 Hz, 1H), 2.88 (dd, J=13.93, 4.64 Hz, 1H), 3.92 (s, 3H), 5.31 (dd, J=6.27, 1.76 Hz, 1H), 5.35 (t, J=3.51 Hz, 1H), 7.22 (d, J=8.53 Hz, 2H), 7.94 (d, J=8.28 Hz, 2H).

Preparation of Intermediates A6 and B6

(1S,2R,4aS,6aS,6bR,8aR,12aS,12bR,14bS)-10-(4-(methoxycarbonyl)phenyl)-1,2,6a,6b,9,9,12a-heptamethyl-1,2,3,4,4a,5,6,6a,6b,7,8,8a,9,12,12a,12b,13,14b-octadecahydropicene-4-a-carboxylic acid. Intermediate A6

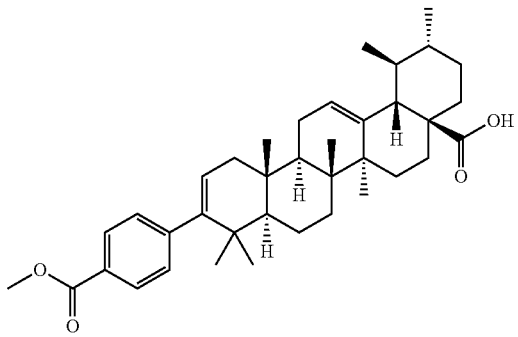

The title compound was prepared following the procedure describe for the preparation of intermediate 6 using intermediate A5 as starting material, (98%). $^1$H NMR (400 MHz, CHLOROFORM-d) δ ppm 0.87 (s, 3H), 0.89 (d, J=6.53 Hz, 3H), 0.93 (s, 3H), 0.94 (s, 3H), 0.96 (s, 3H), 0.98 (s, 3H), 1.03 (t, J=7.28 Hz, 2H), 1.08-1.11 (m, 3H), 1.13 (s, 3H), 1.19 (s, 2H), 1.22-1.82 (m, 10H), 1.84-2.06 (m, 2H), 2.06-2.15 (m, 1H), 2.23 (d, J=11.04 Hz, 1H), 3.32-3.51 (m, 1H), 3.92 (s, 3H), 5.32 (dd, J=5.90, 1.63 Hz, 2H), 7.20 (d, J=8.28 Hz, 2H), 7.94 (d, J=8.28 Hz, 2H).

(4aS,6aS,6bR,8aR,12aS,12bR,14bS)-10-(4-(methoxycarbonyl)phenyl)-2,2,6a,6b,9,9,12a-heptamethyl-1,2,3,4,4a,5,6,6a,6b,7,8,8a,9,12,12a,12b,13,14b-octadecahydropicene-4-a-carboxylic acid. Intermediate B6

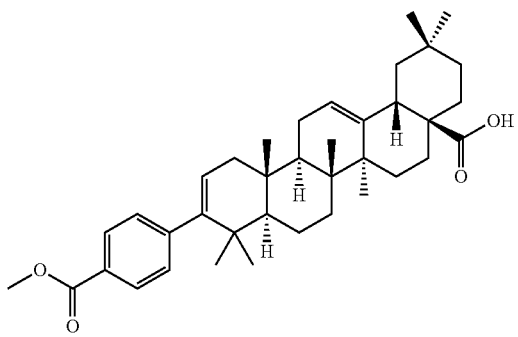

The title compound was prepared following the procedure describe for the preparation of intermediate 6 using intermediate B5 as starting material, (95%). $^1$H NMR (400 MHz, CHLOROFORM-d) δ ppm 0.85 (s, 3H), 0.91-0.97 (m, 12H), 1.03 (t, J=7.28 Hz, 2H), 1.08 (s, 3H), 1.12-1.16 (m, 1H), 1.18 (s, 3H), 1.21 (d, J=4.52 Hz, 2H), 1.26 (br. s., 2 H), 1.28 (br. s., 1H), 1.32-1.43 (m, 2H), 1.43-1.53 (m, 2H), 1.53-1.61 (m, 2H), 1.63 (d, J=4.27 Hz, 1H), 1.71 (d, J=6.02 Hz, 1H), 1.74-1.82 (m, 2H), 1.82-1.96 (m, 2H), 2.01 (dd, J=7.91, 3.64 Hz, 1H), 2.03-2.13 (m, 1H), 2.87 (dd, J=13.68, 3.89 Hz, 1H), 3.33-3.46 (m, 1H), 3.92 (s, 3H), 5.31 (dd, J=6.15, 1.63 Hz, 1H), 5.36 (t, J=3.39 Hz, 1H), 7.20 (d, J=8.28 Hz, 2H), 7.94 (d, J=8.53 Hz, 2H).

Preparation of Examples A1-2 and B1-2

Examples A1-2 and B1-2 were prepared accordingly to the previously described general procedure for C-28 amide formation using either intermediates A6 and B6 as starting materials; followed by the general procedure for hydrolysis of the benzoic acid using NaOH.

The title compound was prepared as described above using intermediate A6 as starting material and N1,N1-dimethylethane-1,2-diamine as the reactant amine. $^1$H NMR (400 MHz, Methanol-$d_4$) δ ppm 0.90 (s, 3H), 0.94 (d, J=6.53 Hz, 3H), 0.96-1.01 (m, 10H), 1.13 (s, 3H), 1.18 (s, 3H), 1.32 (dd, J=11.42, 1.88 Hz, 1H), 1.35-1.47 (m, 2H), 1.47-1.66 (m, 6H), 1.66-1.75 (m, 3H), 1.75-1.89 (m, 2H), 1.94-2.09 (m, 2H),

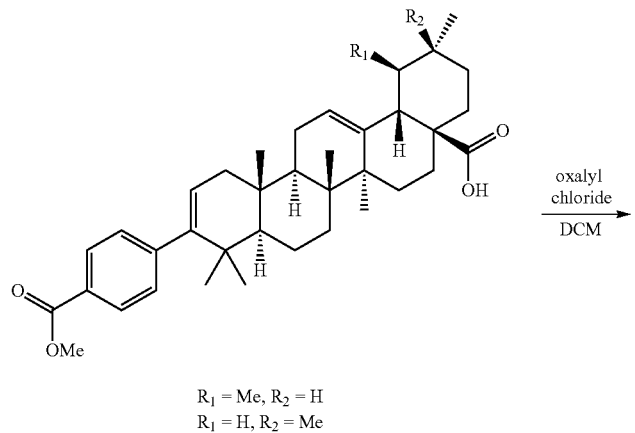

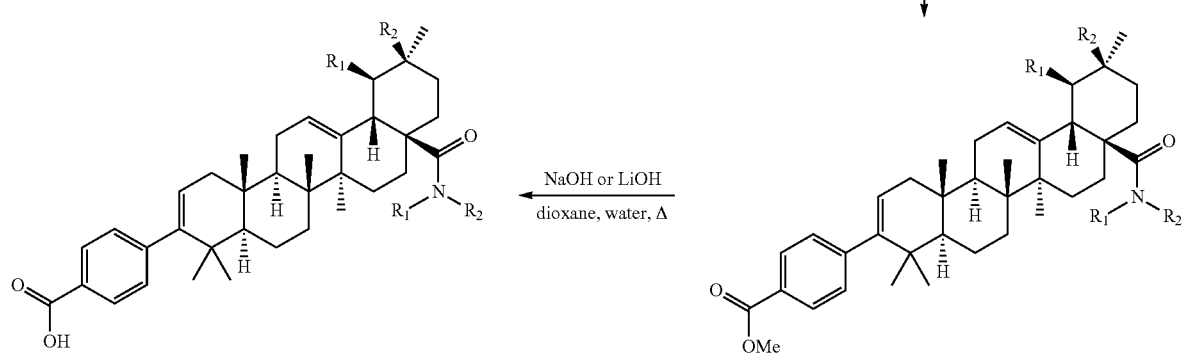

2.09-2.25 (m, 3H), 2.94 (s, 6H), 3.17-3.24 (m, 2H), 3.39-3.50 (m, 1H), 3.50-3.65 (m, 1H), 5.33 (dd, J=6.27, 1.76 Hz, 1H), 5.40 (t, J=3.39 Hz, 1H), 7.24 (d, J=8.53 Hz, 2H), 7.72 (t, J=5.65 Hz, 1H), 7.93 (d, J=8.53 Hz, 2H).

Example A1

Preparation of 4-((4aR,6aR,6bS,8aS,11R,12S,12aS,14aR,14bS)-8a-(2-(dimethylamino)ethylcarbamoyl)-4,4,6a,6b,11,12,14b-heptamethyl-1,4,4a,5,6,6a,6b,7,8,8a,9,10,11,12,12a,14,14a,14b-octadecahydropicen-3-yl)benzoic acid

Example B1

Preparation of 4-((4aR,6aR,6bS,8aS,12aS,14aR,14bS)-8a-(2-(dimethylamino)ethylcarbamoyl)-4,4,6a,6b,11,11,14b-heptamethyl-1,4,4a,5,6,6a,6b,7,8,8a,9,10,11,12,12a,14,14a,14b-octadecahydropicen-3-yl)benzoic acid

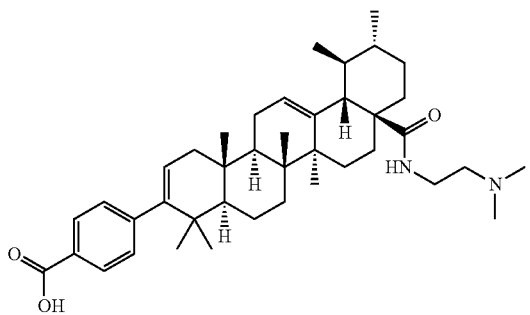

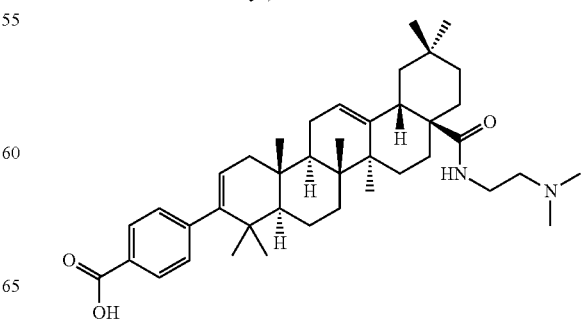

The title compound was prepared as described above using intermediate B6 as starting material and N1,N1-dimethylethane-1,2-diamine as the reactant amine ¹H NMR (400 MHz, Methanol-d₄) δ ppm 0.88 (s, 3H), 0.94 (s, 3H), 0.97 (br. s., 3H), 0.98 (s, 6H), 1.12 (s, 4H), 1.23 (s, 4H), 1.33 (d, J=11.04 Hz, 1H), 1.36-1.49 (m, 2H), 1.49-1.58 (m, 2H), 1.58-1.67 (m, 4H), 1.68 (d, J=4.02 Hz, 1H), 1.70-1.78 (m, 2H), 1.78-1.90 (m, 2H), 1.90-2.27 (m, 4H), 2.84 (dd, J=13.30, 3.51 Hz, 1H), 2.95 (s, 6H), 3.22 (t, J=6.27 Hz, 2H), 3.39-3.66 (m, 2H), 5.33 (dd, J=6.15, 1.63 Hz, 1H), 5.41 (t, J=3.39 Hz, 1H), 7.24 (d, J=8.28 Hz, 2H), 7.81 (t, J=5.40 Hz, 1H), 7.93 (d, J=8.28 Hz, 2H).

Example A2

Preparation of 4-((4aR,6aR,6bS,8aS,11R,12S,12aS,14aR,14bS)-8a-((3-(1,1-dioxido-4-thiomorpholinyl)propyl)carbamoyl)-4,4,6a,6b,11,12,14b-heptamethyl-1,4,4a,5,6,6a,6b,7,8,8a,9,10,11,12,12a,14,14a,14b-octadecahydro-3-picenyl)benzoic acid

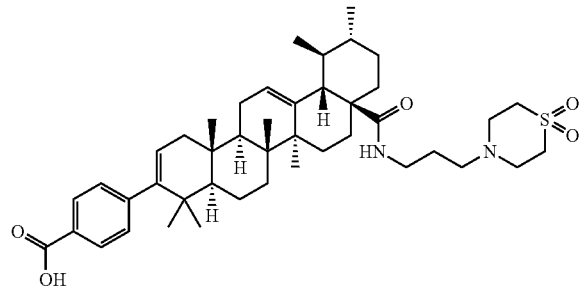

The title compound was prepared as described above using intermediate A6 as starting material and 4-(3-aminopropyl)thiomorpholine 1,1-dioxide as the reactant amine ¹H NMR (400 MHz, Methanol-d₄) δ ppm 0.87-0.90 (m, 3H), 0.95 (d, J=5.02 Hz, 3H), 0.97-1.01 (m, 6H), 1.11-1.15 (m, 3H), 1.19 (s, 3H), 1.23 (s, 3H), 1.27-1.47 (m, 4H), 1.47-1.86 (m, 10H), 1.86-1.97 (m, 3H), 1.97-2.24 (m, 5H), 2.76-2.91 (m, 1H), 3.00-3.16 (m, 2H), 3.16-3.26 (m, 1H), 3.48 (d, J=5.02 Hz, 4H), 3.64 (d, J=2.01 Hz, 4H), 5.33 (d, J=4.27 Hz, 1H), 5.37-5.50 (m, 1H), 7.24 (d, J=8.03 Hz, 2H), 7.93 (d, J=8.28 Hz, 2H).

Example B2

Preparation of 4-((4aR,6aR,6bS,8aS,12aS,14aR,14bS)-8a-((3-(1,1-dioxido-4-thiomorpholinyl)propyl)carbamoyl)-4,4,6a,6b,11,11,14b-heptamethyl-1,4,4a,5,6,6a,6b,7,8,8a,9,10,11,12,12a,14,14a,14b-octadecahydro-3-picenyl)benzoic acid

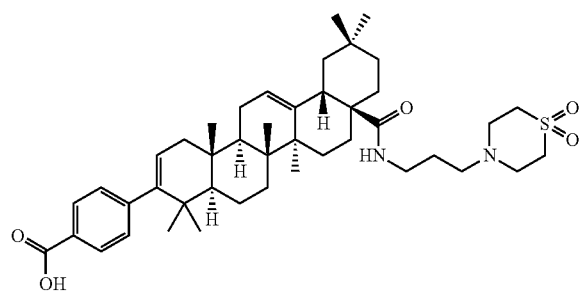

The title compound was prepared as described above using intermediate B6 as starting material and 4-(3-aminopropyl)thiomorpholine 1,1-dioxide as the reactant amine ¹H NMR (400 MHz, Methanol-d₄) δ ppm 0.88 (s, 3H), 0.94 (s, 3H), 0.98 (s, 9H), 1.12 (s, 3H), 1.15-1.22 (m, 2H), 1.23 (s, 4H), 1.32 (d, J=11.04 Hz, 1H), 1.36-1.36 (m, 1H), 1.36-1.52 (m, 3H), 1.52-1.70 (m, 7H), 1.70-1.86 (m, 3H), 1.86-2.20 (m, 7H), 2.84 (dd, J=12.92, 3.14 Hz, 1H), 3.05-3.17 (m, 2H), 3.17-3.28 (m, 1H), 3.48 (d, J=4.27 Hz, 4H), 3.64 (br. s., 4H), 5.33 (dd, J=6.15, 1.63 Hz, 1H), 5.43 (t, J=3.39 Hz, 1H), 7.24 (d, J=8.28 Hz, 2H), 7.93 (d, J=8.28 Hz, 2H).

Biology Data for the Examples

"µM" means micromolar;

"mL" means milliliter;

"µl" jar means microliter;

"mg" means milligram;

"µg" means microgram;

The materials and experimental procedures used to obtain the results reported in Tables 1-2 are described below.

HIV Cell Culture Assay—

MT-2 cells and 293T cells were obtained from the NIH AIDS Research and Reference Reagent Program. MT-2 cells were propagated in RPMI 1640 media supplemented with 10% heat inactivated fetal bovine serum, 100 µg/ml penicillin G and up to 100 units/ml streptomycin. The 293T cells were propagated in DMEM media supplemented with 10% heat inactivated fetal bovine serum (FBS), 100 units/ml penicillin G and 100 µg/ml streptomycin. The proviral DNA clone of $NL_{4-3}$ was obtained from the NIH AIDS Research and Reference Reagent Program. A recombinant $NL_{4-3}$ virus, in which a section of the nef gene from NL4-3 was replaced with the *Renilla* luciferase gene, was used as a reference virus. In addition, residue Gag P373 was converted to P373S. Briefly, the recombinant virus was prepared by transfection of the altered proviral clone of $NL_{4-3}$. Transfections were performed in 293T cells using LipofectAMINE PLUS from Invitrogen (Carlsbad, Calif.), according to manufacturer's instruction. The virus was titered in MT-2 cells using luciferase enzyme activity as a marker. Luciferase was quantitated using the Dual Luciferase kit from Promega (Madison, Wis.), with modifications to the manufacturer's protocol. The diluted Passive Lysis solution was pre-mixed with the re-suspended Luciferase Assay Reagent and the re-suspended Stop & Glo Substrate (2:1:1 ratio). Fifty (50) µL of the mixture was added to each aspirated well on assay plates and luciferase activity was measured immediately on a Wallac TriLux (Perkin-Elmer). Antiviral activities of inhibitors toward the recombinant virus were quantified by measuring luciferase activity in cells infected for 4-5 days with NLRluc recombinants in the presence serial dilutions of the inhibitor. The $EC_{50}$s data for the compounds is shown in Table 2. Table 1 is the key for the data in Table 2.

Results

TABLE 1

Biological Data Key for $EC_{50}$s

| Compounds with $EC_{50}$ > 0.1 µM | Compounds with $EC_{50}$ < 0.1 µM |
|---|---|
| Group "B" | Group "A" |

TABLE 2
| Compound | Structure | Group |
|---|---|---|
| Example 1 | 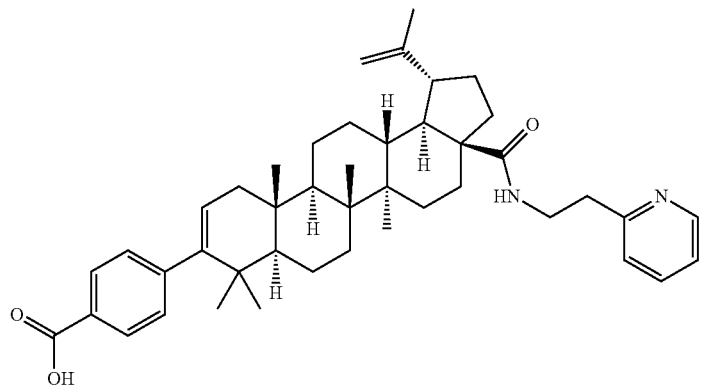 | A |
| Example 2 | 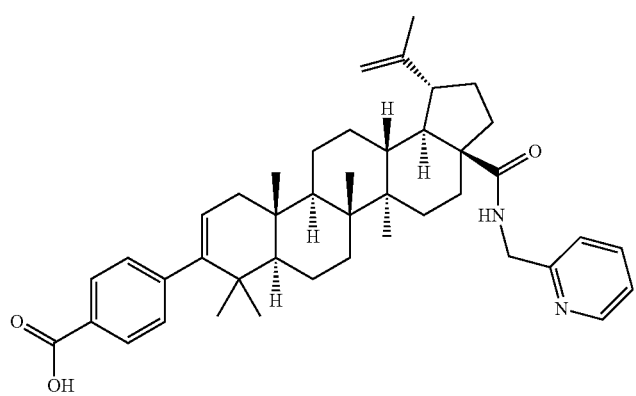 | A |
| Example 3 | 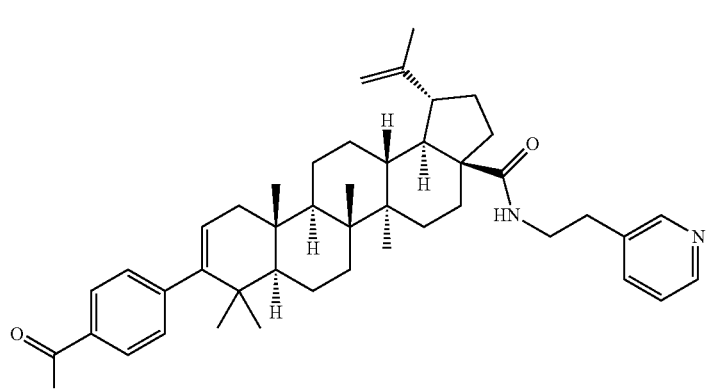 | A |
| Example 4 | 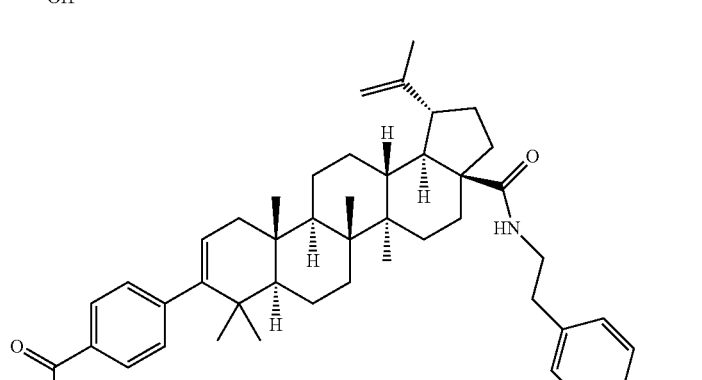 | A |

TABLE 2-continued
| Compound | Structure | Group |
|---|---|---|
| Example 5 | 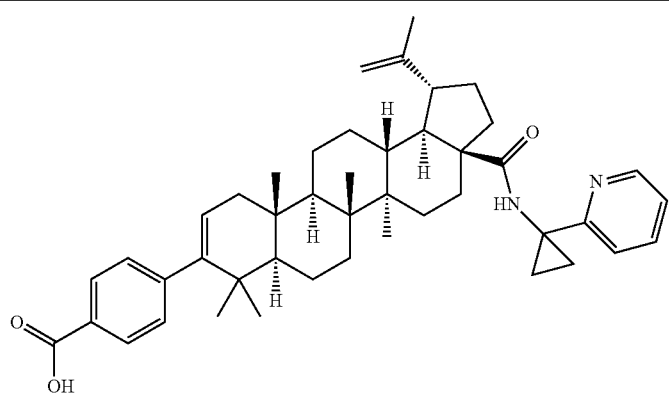 | A |
| Example 6 | 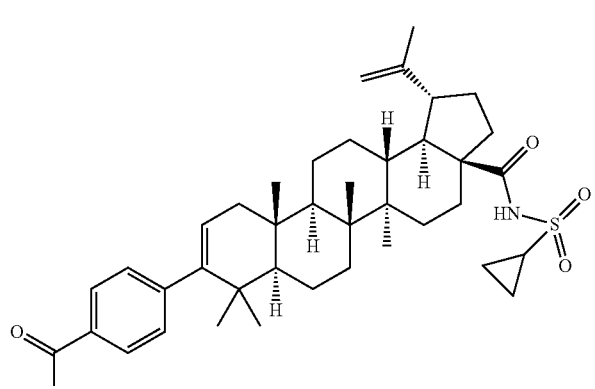 | A |
| Example 7 | 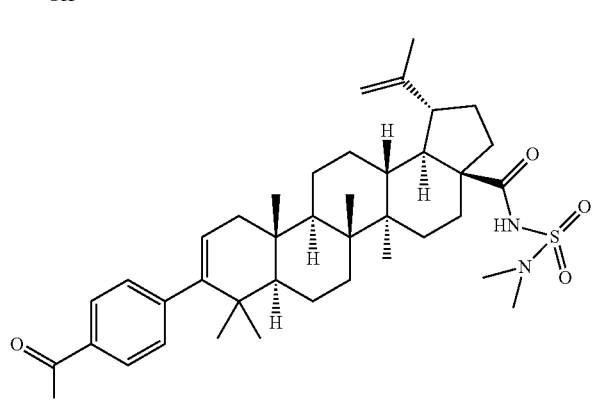 | A |
| Example 8 | 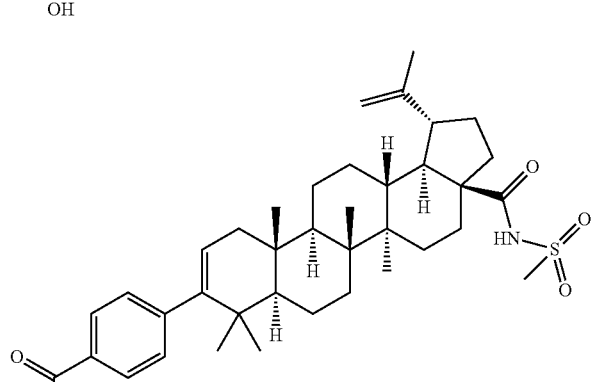 | A |

TABLE 2-continued

| Compound | Structure | Group |
|---|---|---|
| Example 9 | 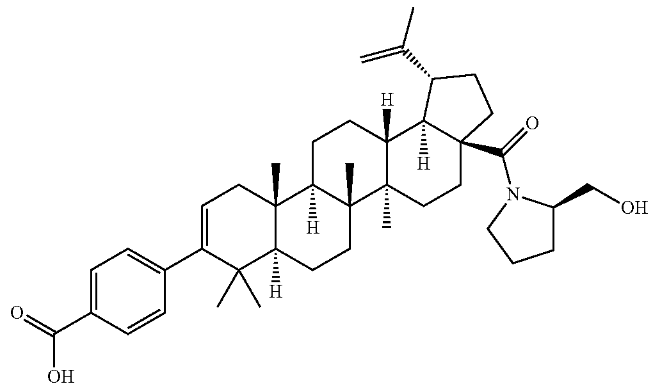 | A |
| Example 10 | 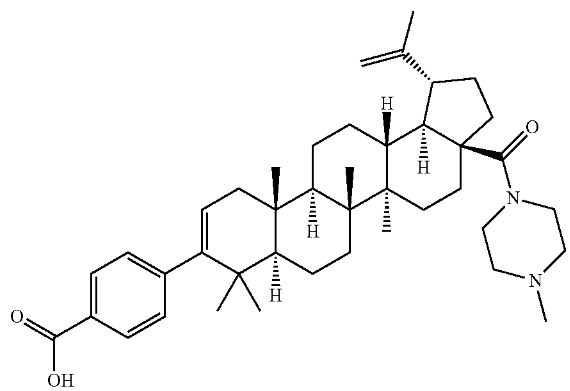 | A |
| Example 11 | 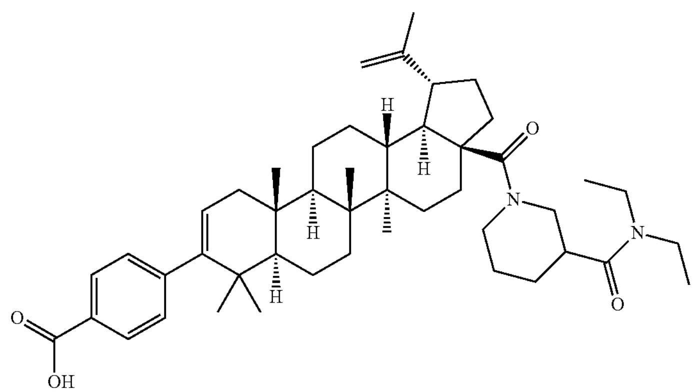 | 61 nM |
| Example 12 | 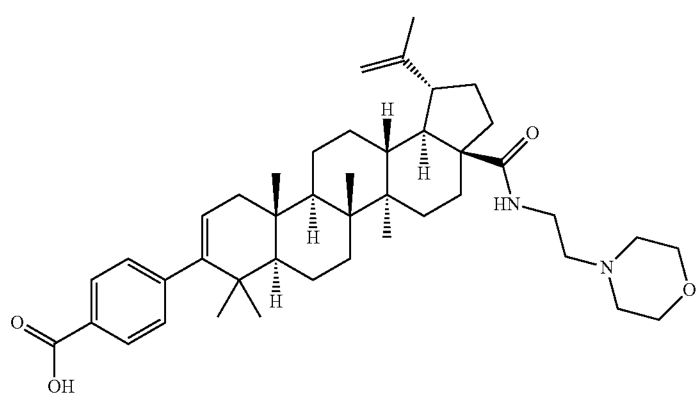 | A |

TABLE 2-continued

| Compound | Structure | Group |
|---|---|---|
| Example 13 | 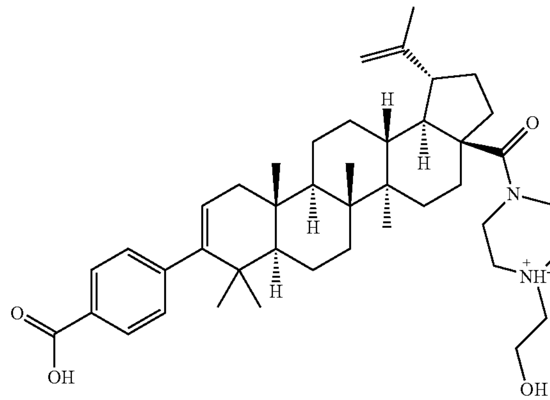 | A |
| Example 14 | 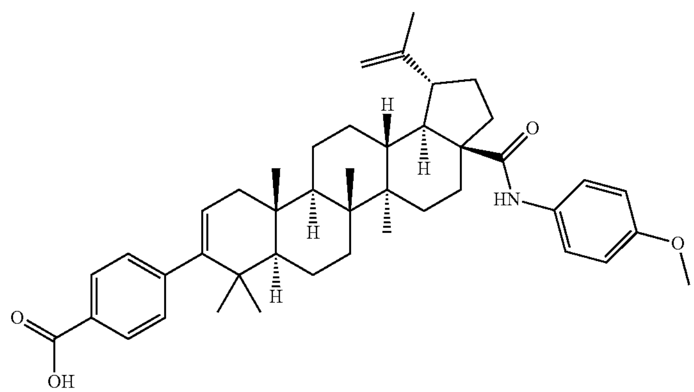 | 0.11 µM |
| Example 15 | 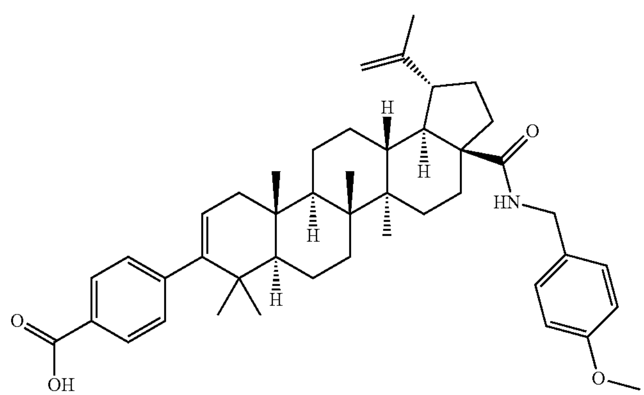 | A |
| Example 16 | 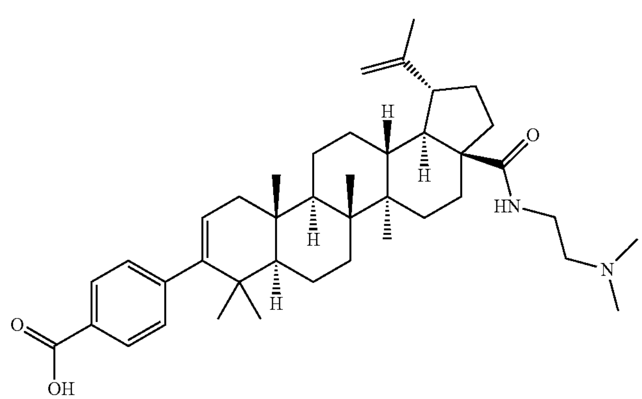 | A |

TABLE 2-continued

| Compound | Structure | Group |
|---|---|---|
| Example 17 | 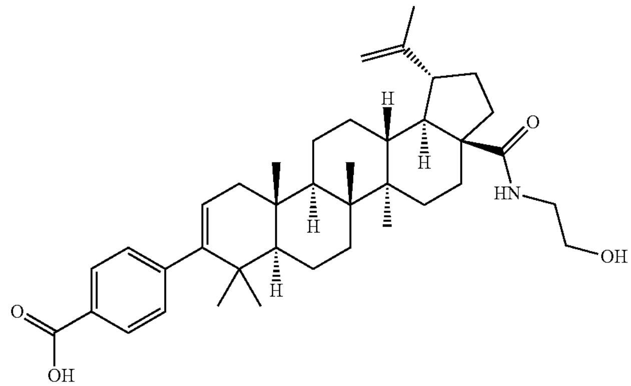 | A |
| Example 18 | 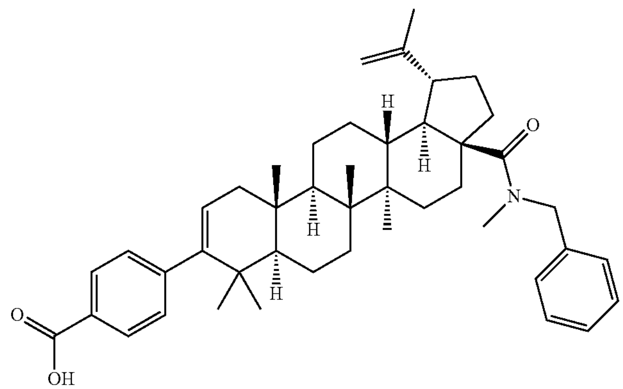 | B |
| Example 19 | 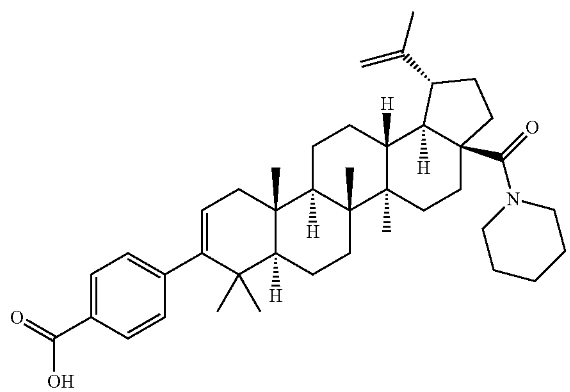 | 0.37 μM |
| Example 20 | 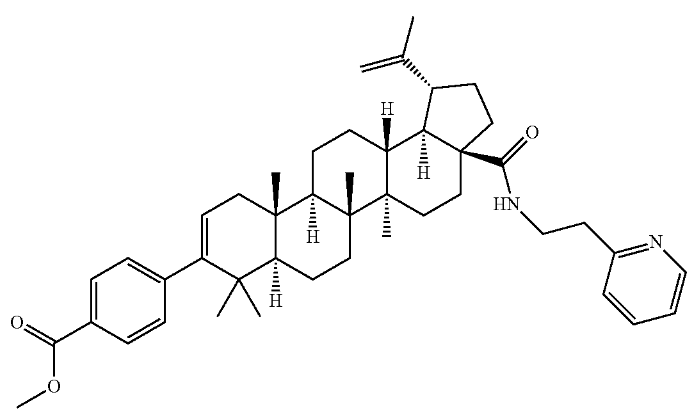 | B |

TABLE 2-continued

| Compound | Structure | Group |
|---|---|---|
| Example 21 | 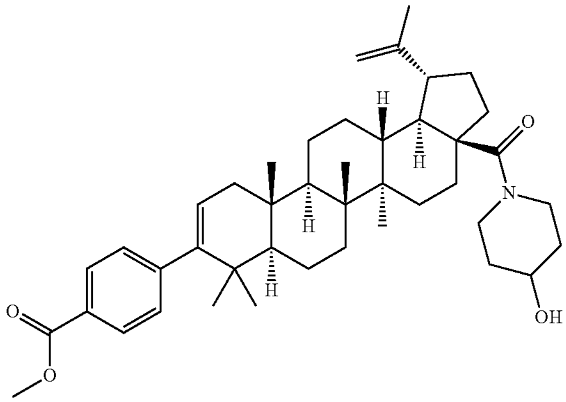 | B |
| Example 22 | 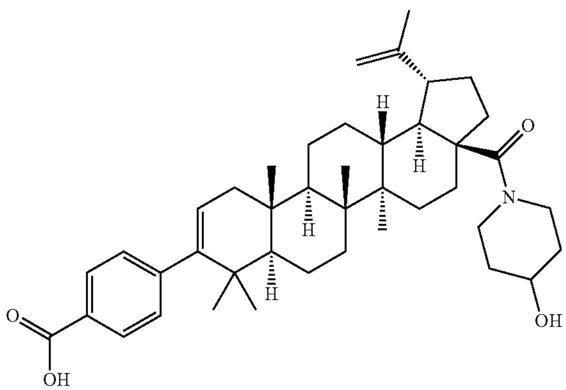 | A |
| Example 23 | 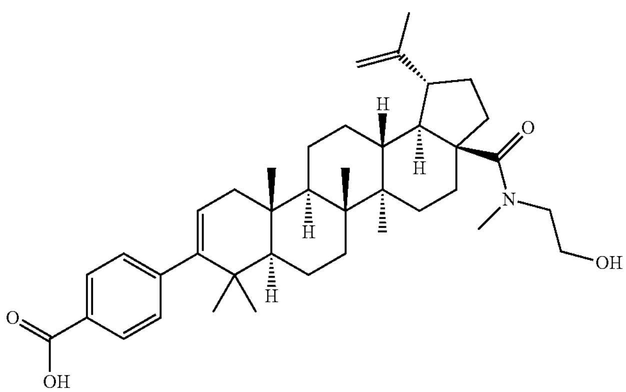 | A |
| Example 24 | 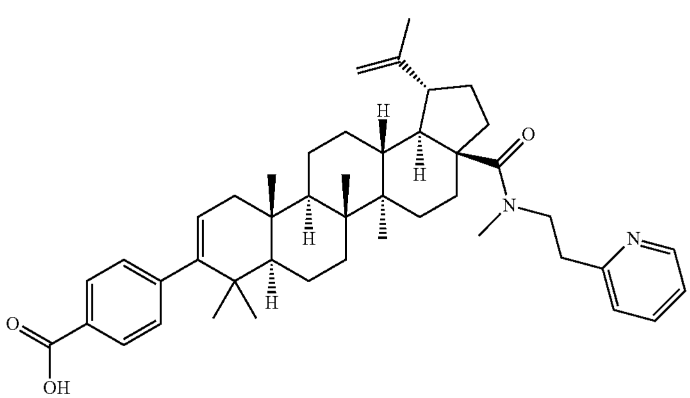 | 48 nM |

TABLE 2-continued

| Compound | Structure | Group |
|---|---|---|
| Example 25 | 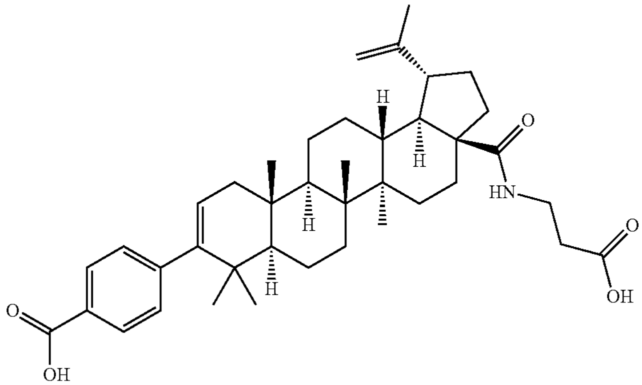 | A |
| Example 26 | 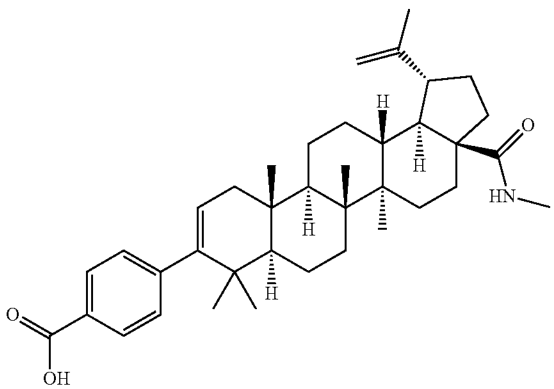 | A |
| Example 27 | 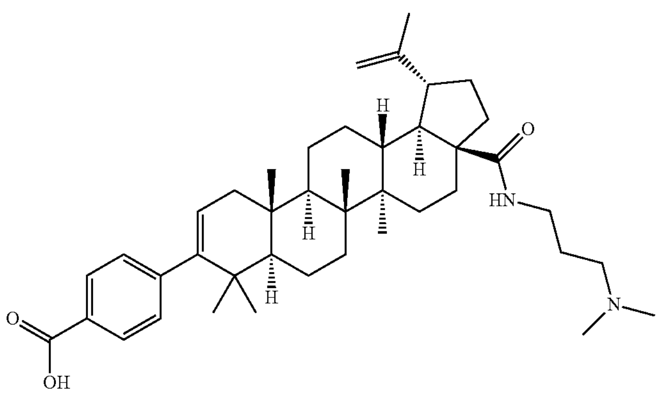 | A |
| Example 28 | 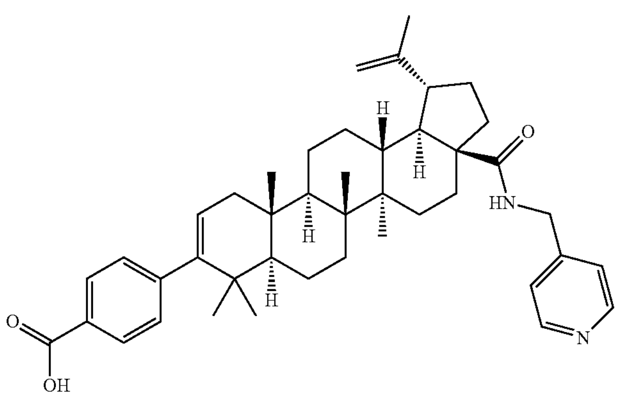 | A |

TABLE 2-continued
| Compound | Structure | Group |
|---|---|---|
| Example 29 | 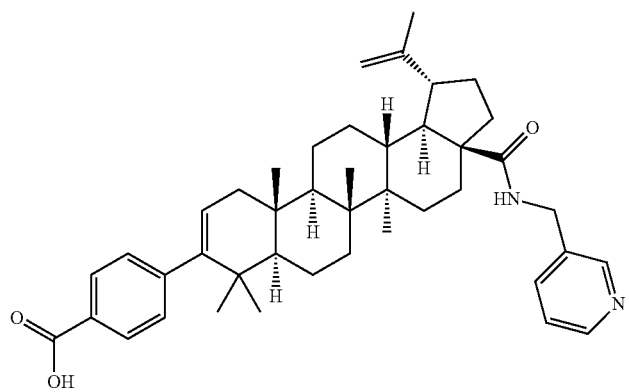 | A |
| Example 30 | 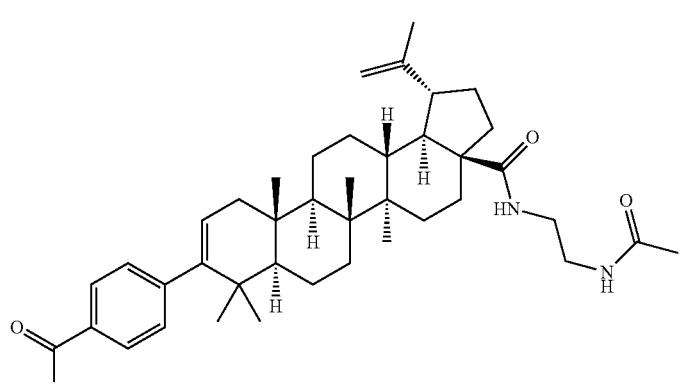 | A |
| Example 31 | 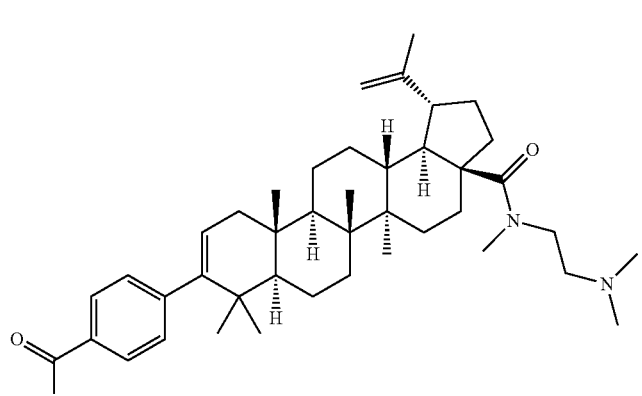 | A |
| Example 32 | 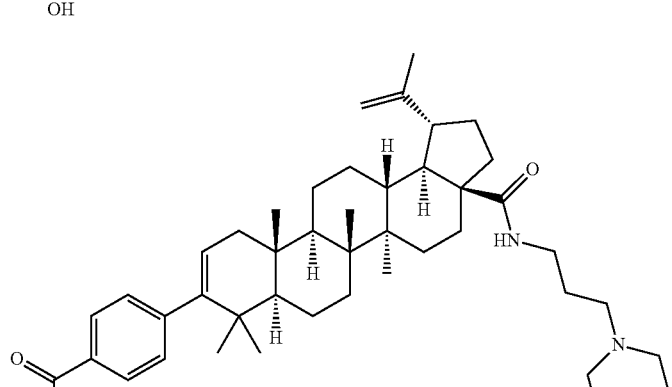 | A |

TABLE 2-continued
| Compound | Structure | Group |
|---|---|---|
| Example 33 | 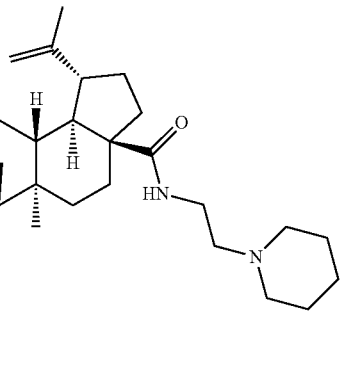 | A |
| Example 34 | 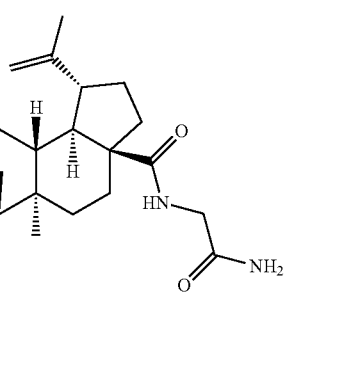 | A |
| Example 35 | 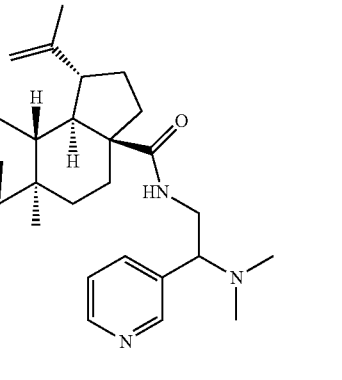 | A |
| Example 36 | 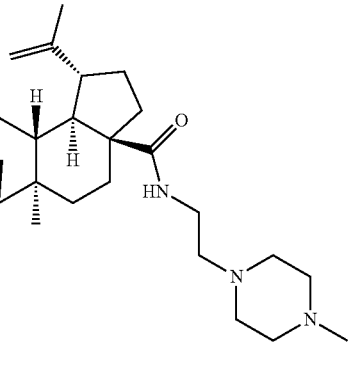 | A |

TABLE 2-continued
| Compound | Structure | Group |
|---|---|---|
| Example 37 | 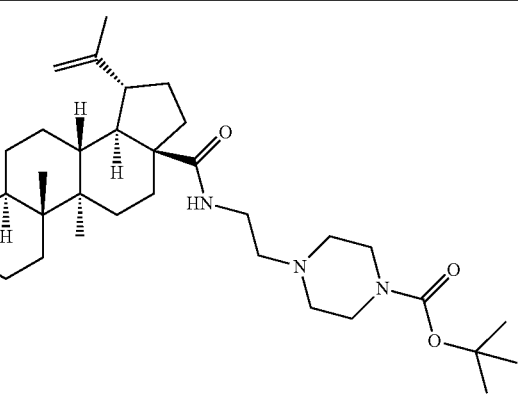 | A |
| Example 38 | 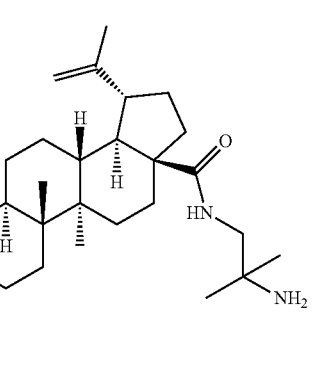 | A |
| Example 39 | 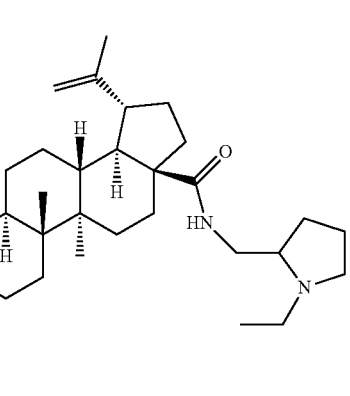 | A |
| Example 40 | 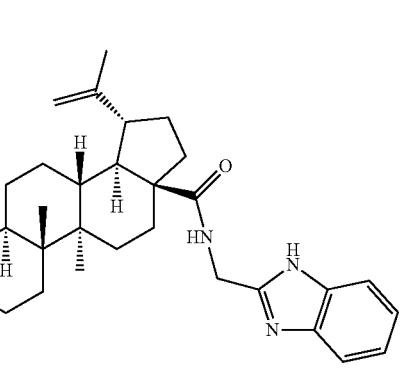 | A |

TABLE 2-continued

| Compound | Structure | Group |
|---|---|---|
| Example 41 | 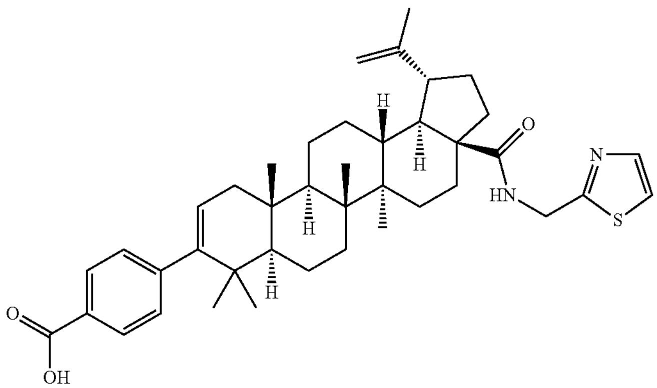 | A |
| Example 42 | 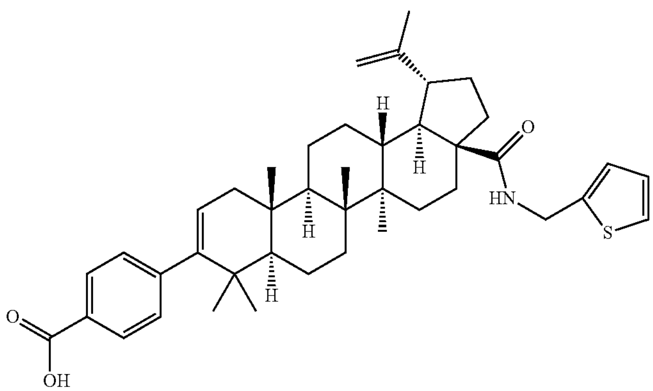 | 0.12 μM |
| Example 43 | 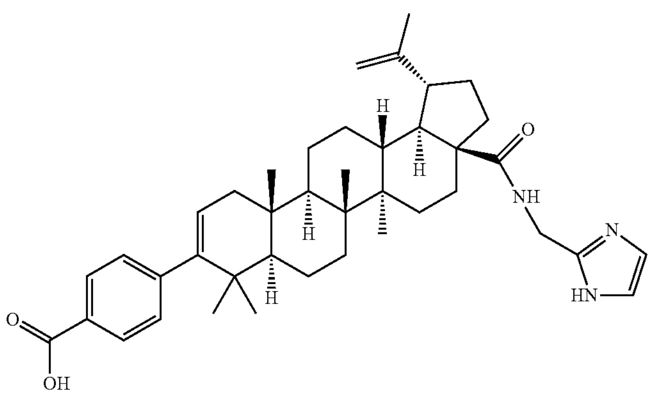 | A |
| Example 44 | 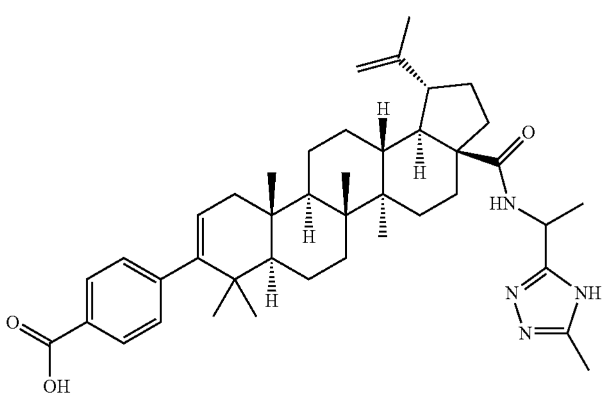 | A |

TABLE 2-continued

| Compound | Structure | Group |
|---|---|---|
| Example 45 | 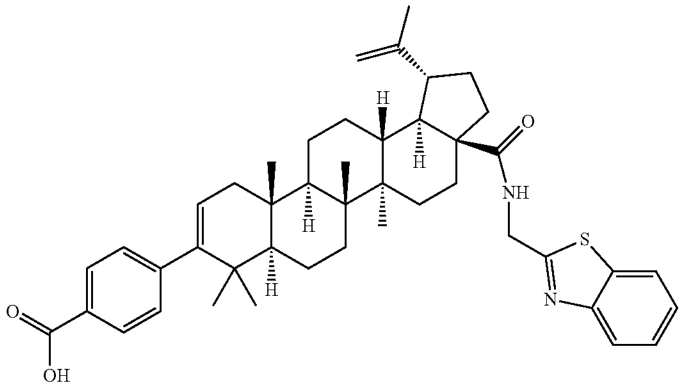 | A |
| Example 46 | 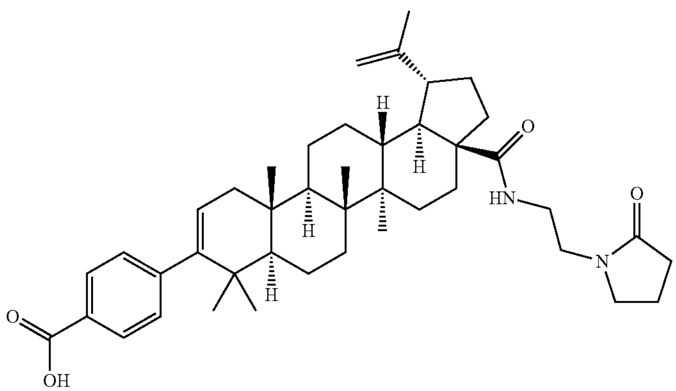 | A |
| Example 47 | 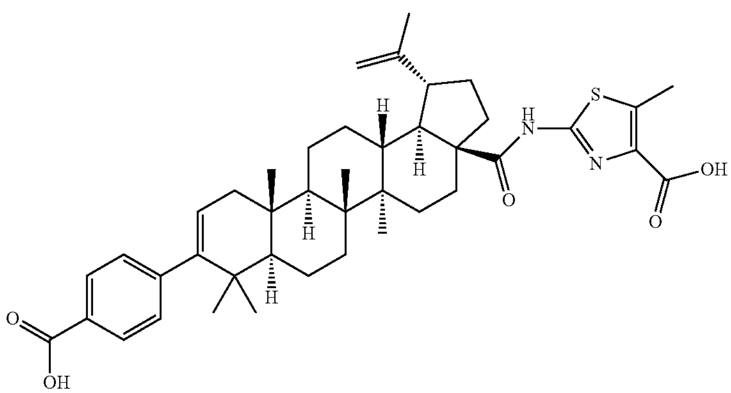 | 8.7 nM |
| Example 48 | 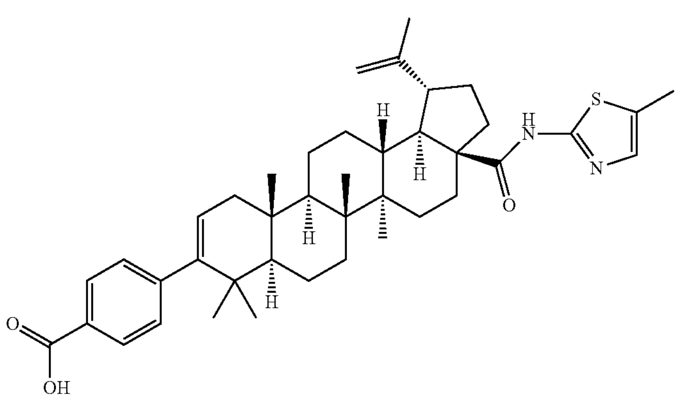 | A |

TABLE 2-continued

| Compound | Structure | Group |
|---|---|---|
| Example 49 | 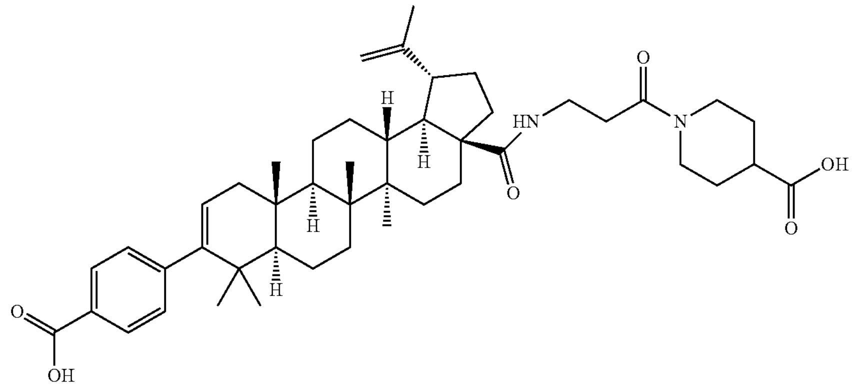 | A |
| Example 50 | 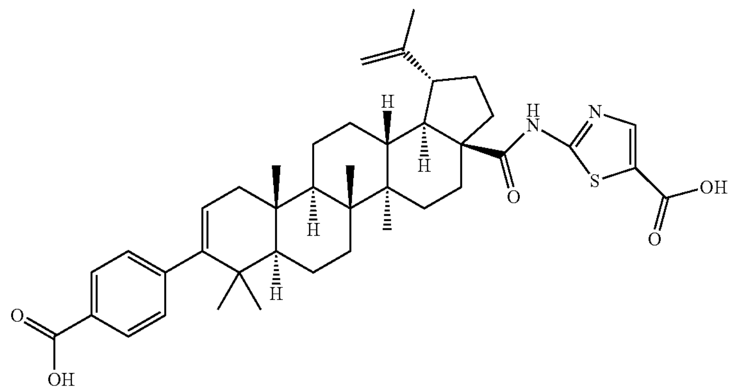 | A |
| Example 51 | 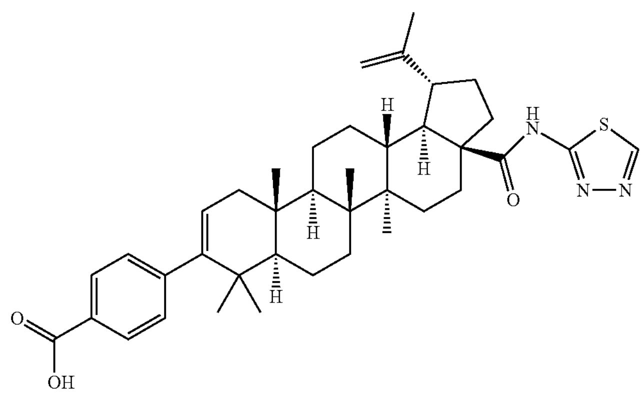 | A |
| Example 52 | 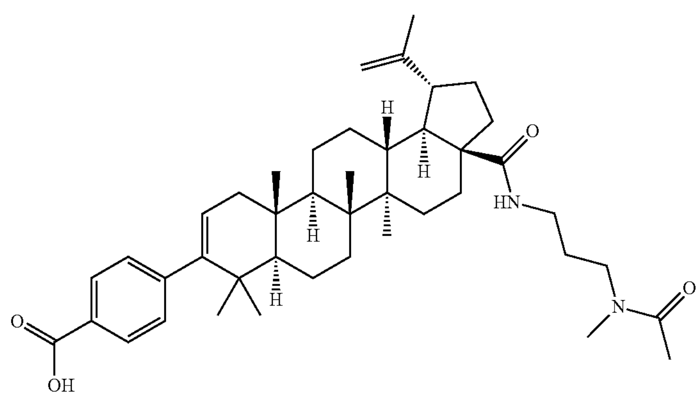 | A |

TABLE 2-continued
| Compound | Structure | Group |
|---|---|---|
| Example 53 | 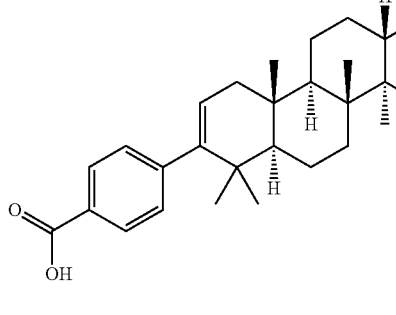 | A |
| Example 54 | 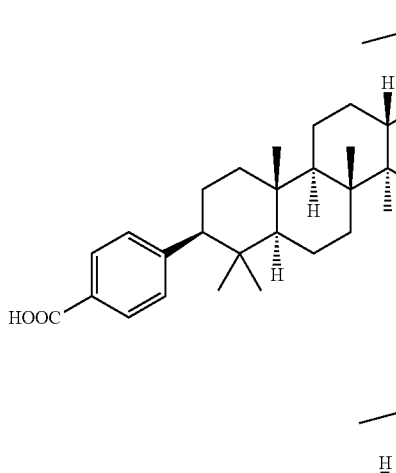 | A |
| Example 55 | 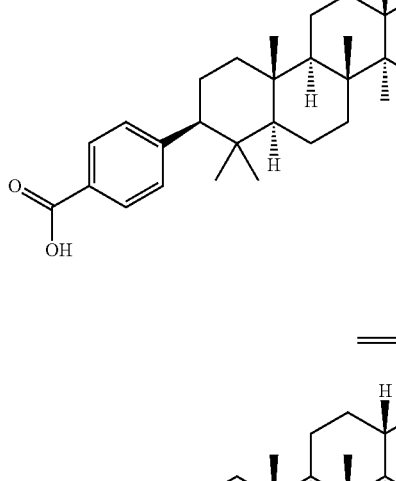 | A |
| Example 56 | 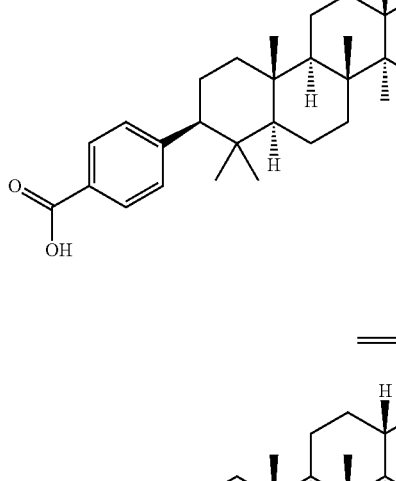 | A |

TABLE 2-continued
| Compound | Structure | Group |
|---|---|---|
| Example 57 | 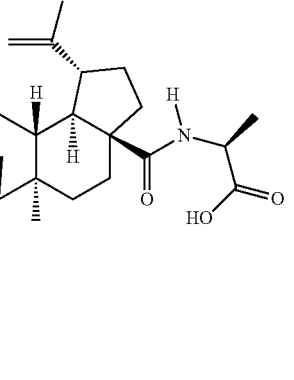 | 0.70 μM |
| Example 58 | 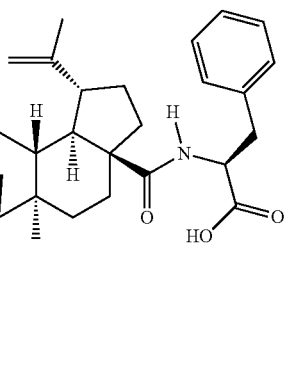 | A |
| Example 59 | 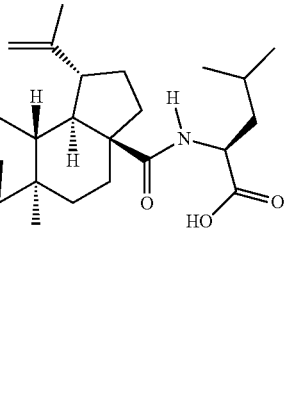 | A |
| Example 60 | 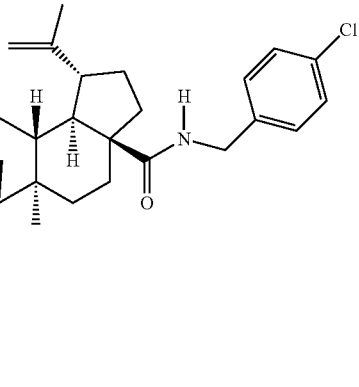 | 48 nM |

TABLE 2-continued

| Compound | Structure | Group |
|---|---|---|
| Example 61 | 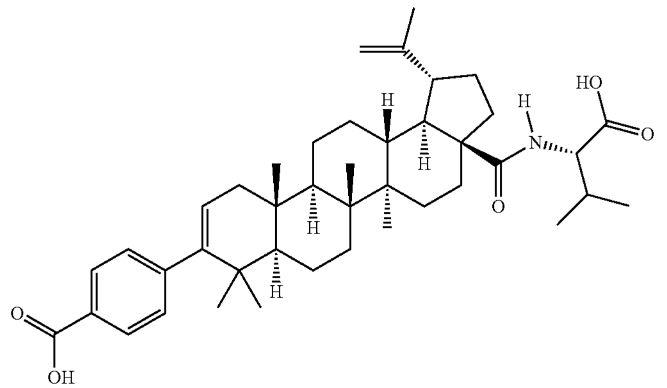 | A |
| Example 62 | 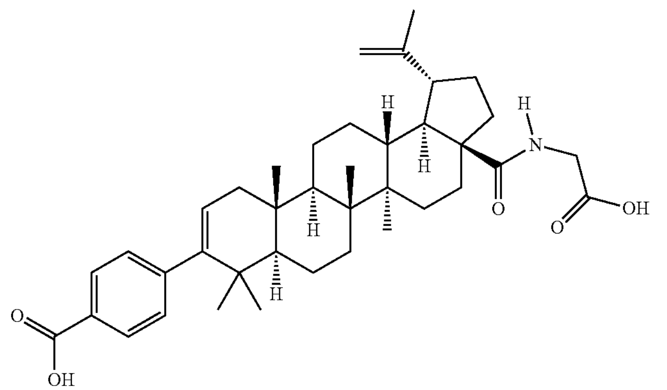 | B |
| Example 63 | 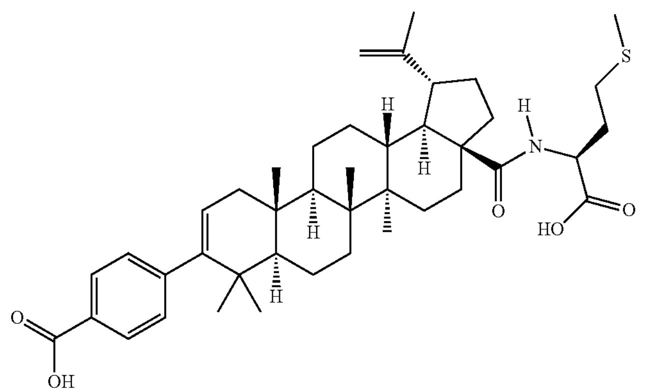 | B |
| Example 64 | 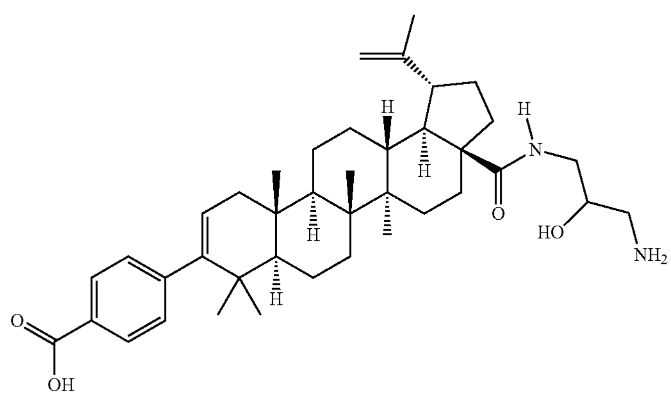 | A |

TABLE 2-continued
| Compound | Structure | Group |
|---|---|---|
| Example 65 | 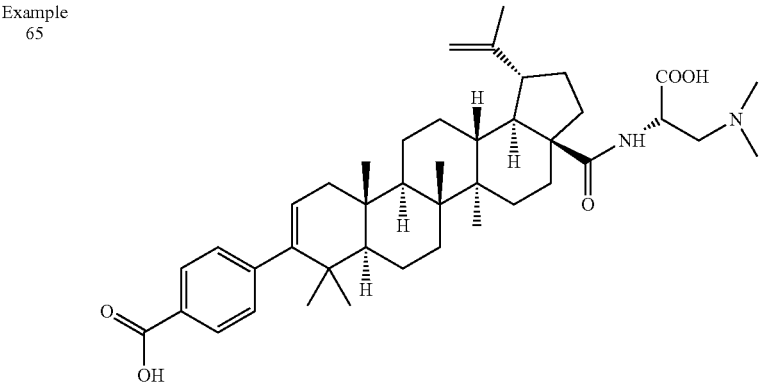 | A |
| Example 66 | 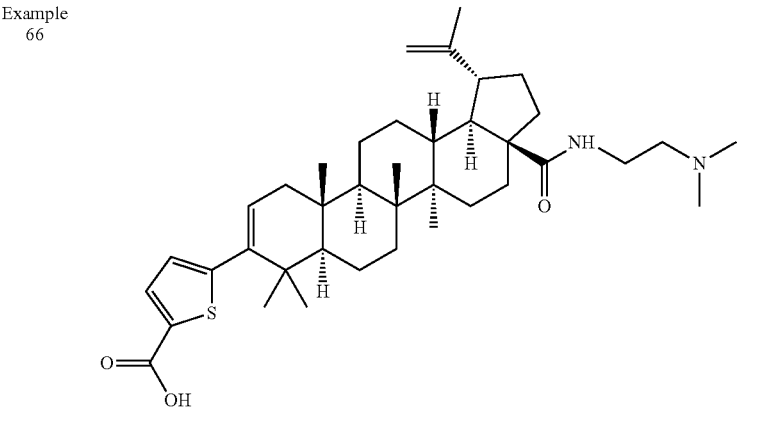 | A |
| Example 67 | 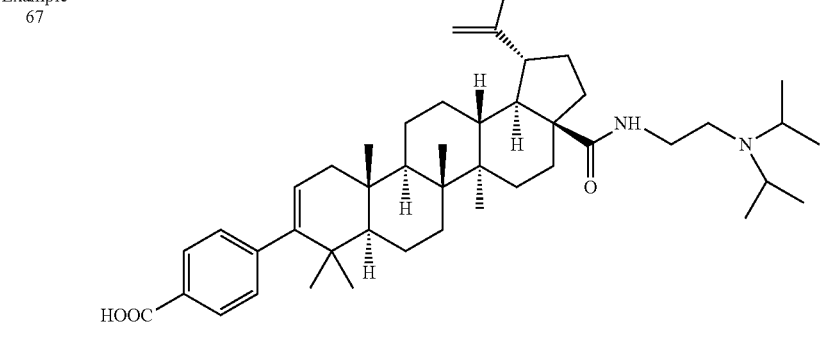 | 3.8 nM |
| Example 68 | 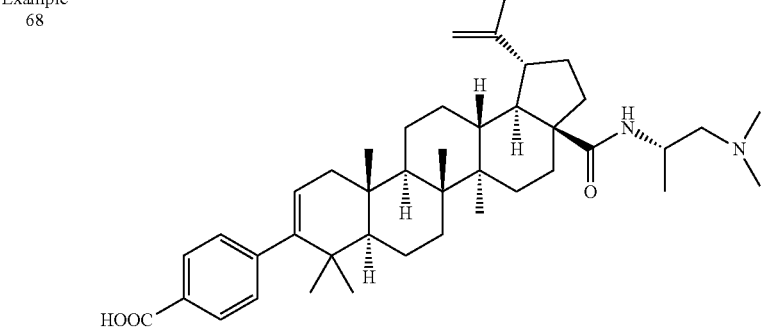 | A |

TABLE 2-continued
| Compound | Structure | Group |
|---|---|---|
| Example 69 | 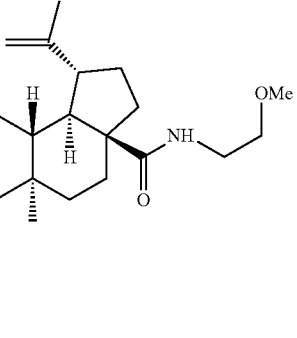 | A |
| Example 70 | 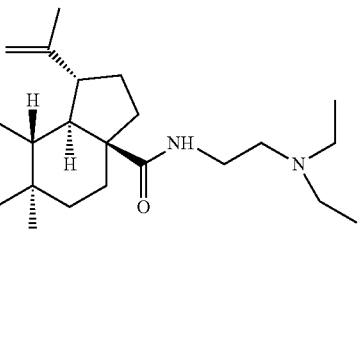 | A |
| Example 71 | 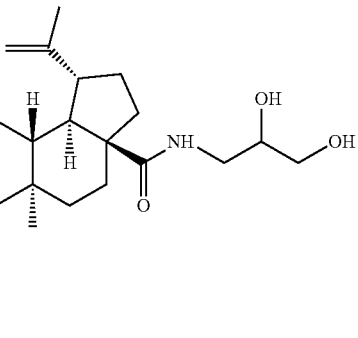 | A |
| Example 72 | 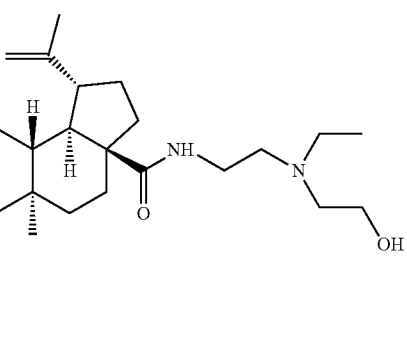 | A |

TABLE 2-continued

| Compound | Structure | Group |
|---|---|---|
| Example 73 | 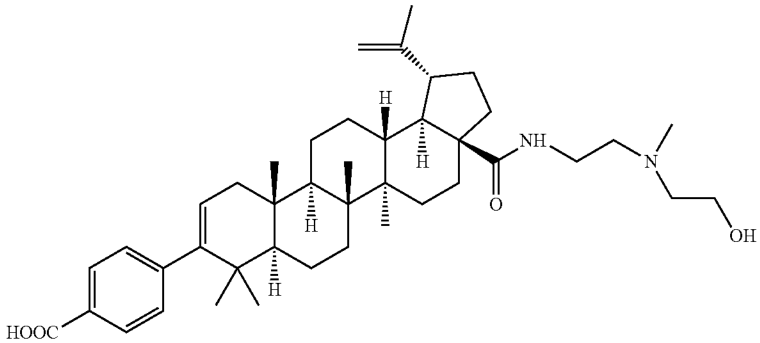 | A |
| Example 74 | 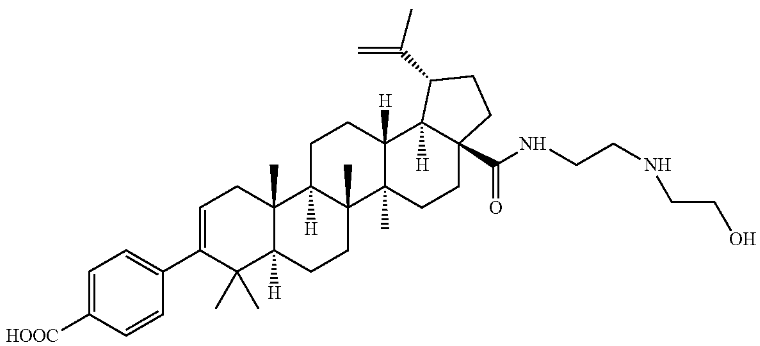 | A |
| Example 75 | 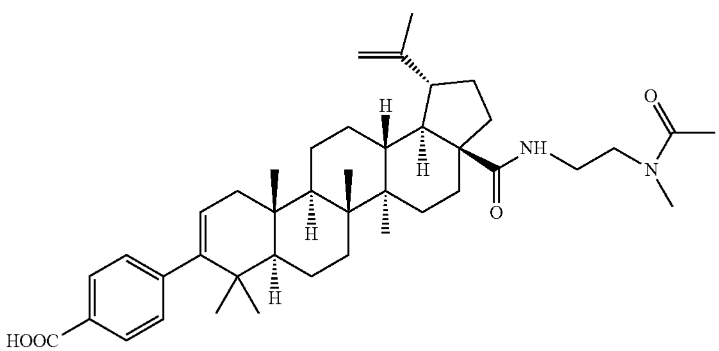 | A |
| Example 76 | 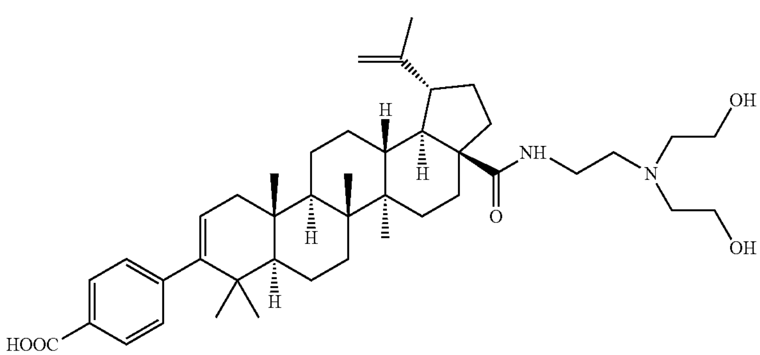 | A |

TABLE 2-continued

| Compound | Structure | Group |
|---|---|---|
| Example 77 | 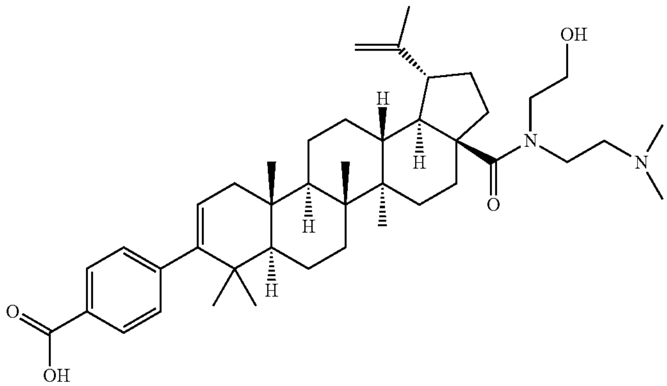 | B |
| Example 78 | 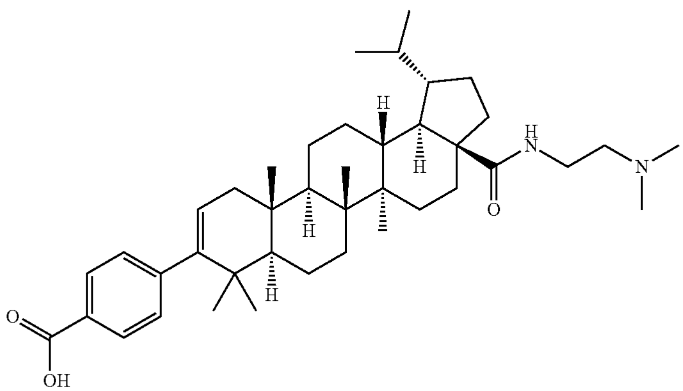 | A |
| Example 79 | 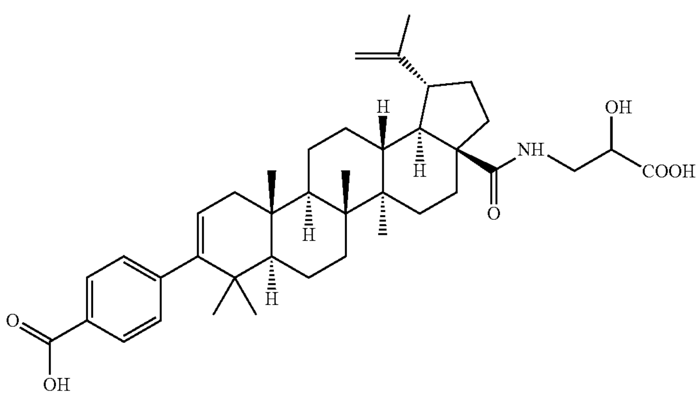 | A |
| Example 80 | 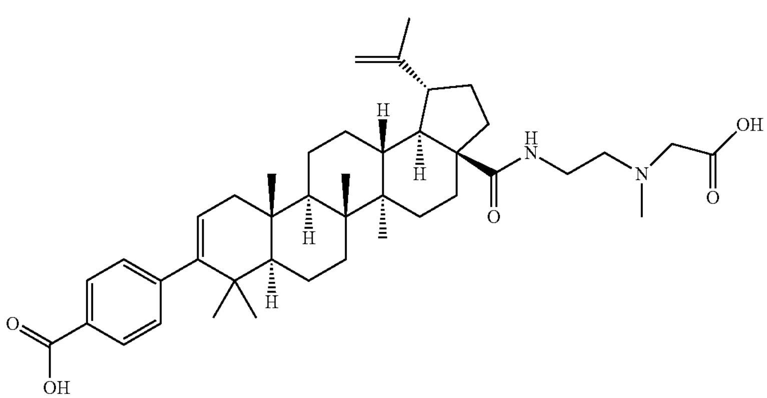 | A |

TABLE 2-continued

| Compound | Structure | Group |
|---|---|---|
| Example 81 | 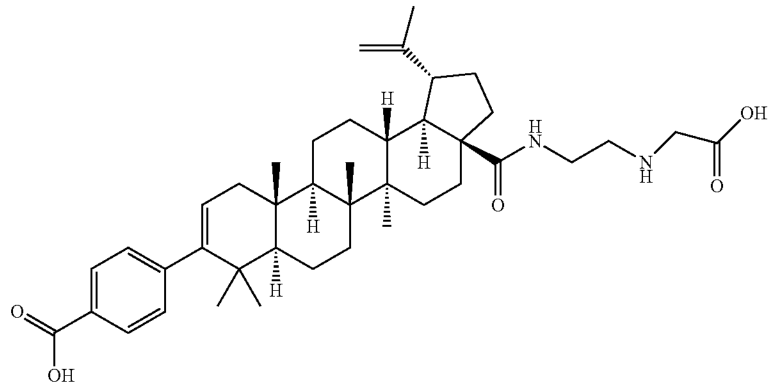 | A |
| Example 82 | 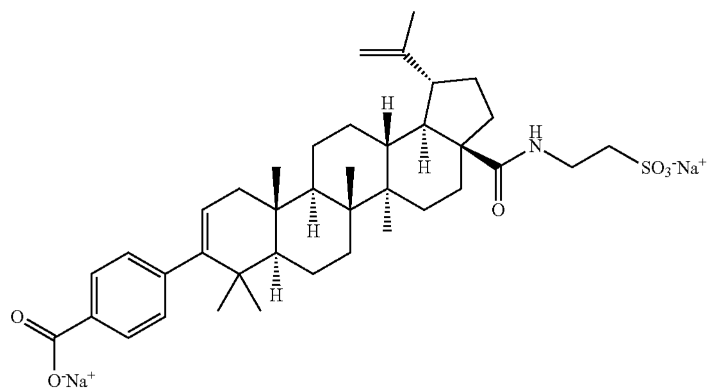 | 1.23 μM |
| Example 83 | 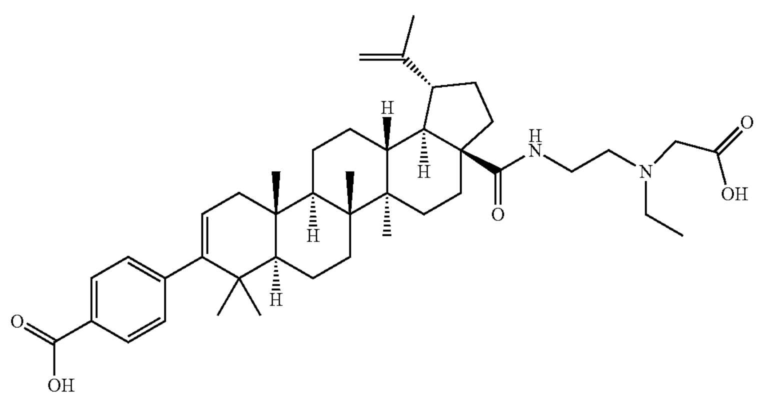 | A |
| Example 84 | 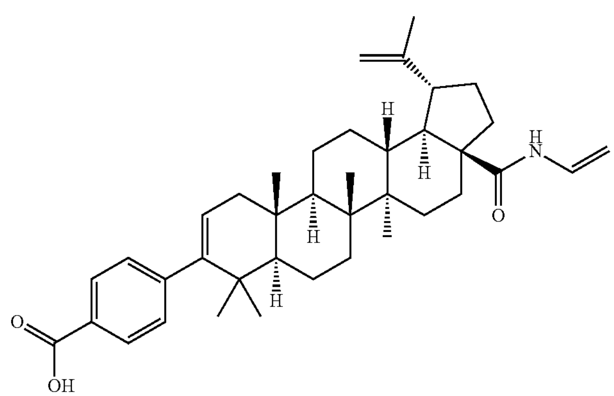 | A |

TABLE 2-continued

| Compound | Structure | Group |
|---|---|---|
| Example 85 | 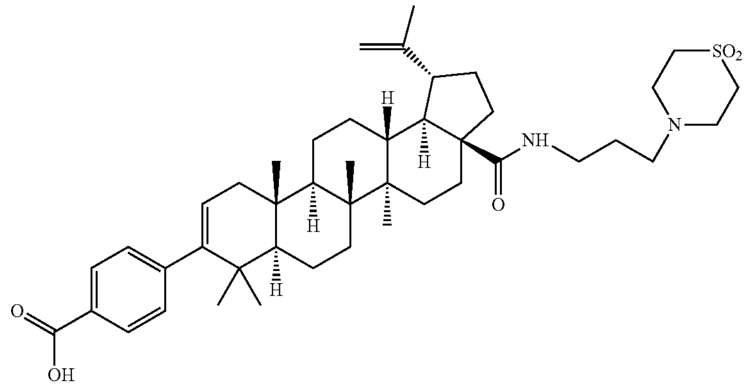 | A |
| Example 86 | 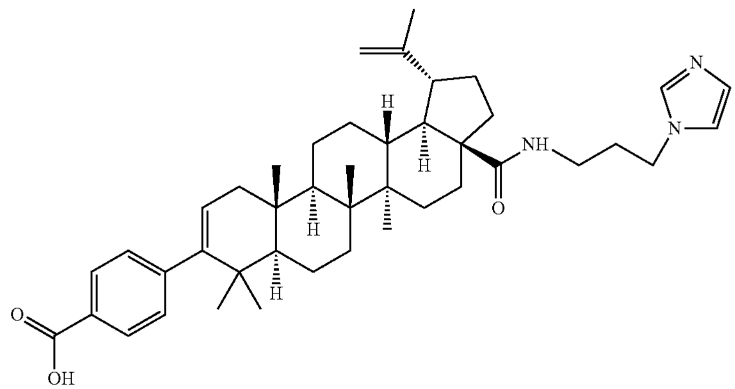 | A |
| Example 87 | 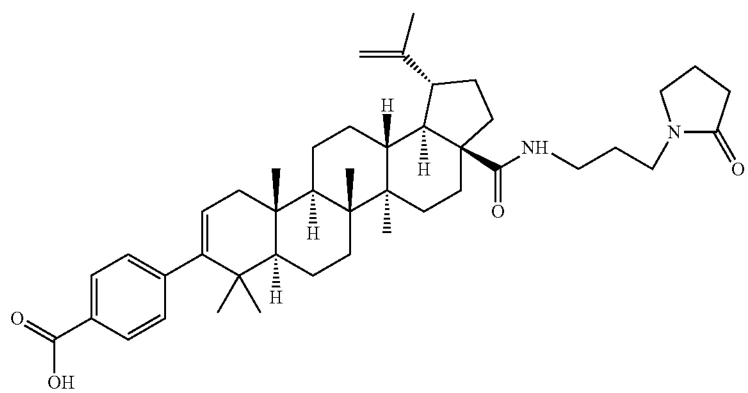 | A |
| Example 88 | 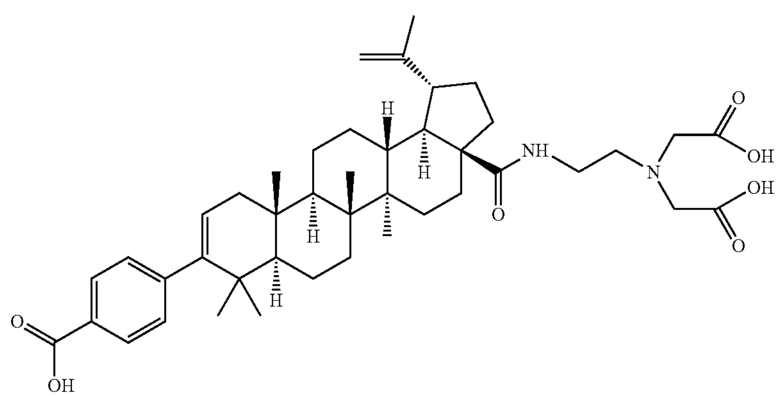 | B |

TABLE 2-continued
| Compound | Structure | Group |
|---|---|---|
| Example 89 | 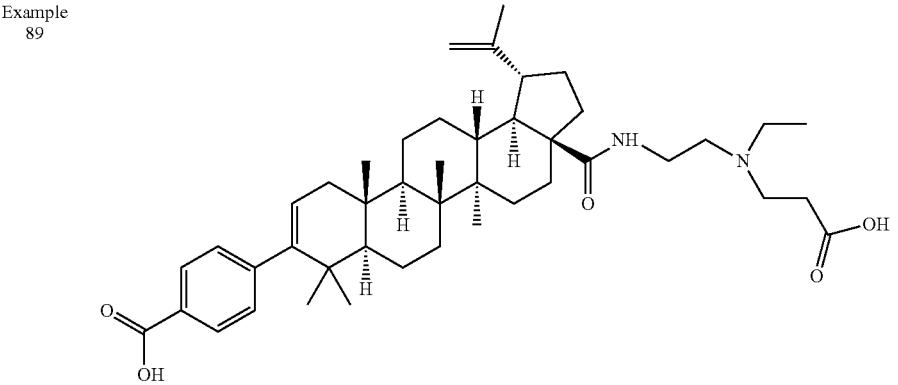 | A |
| Example 90 | 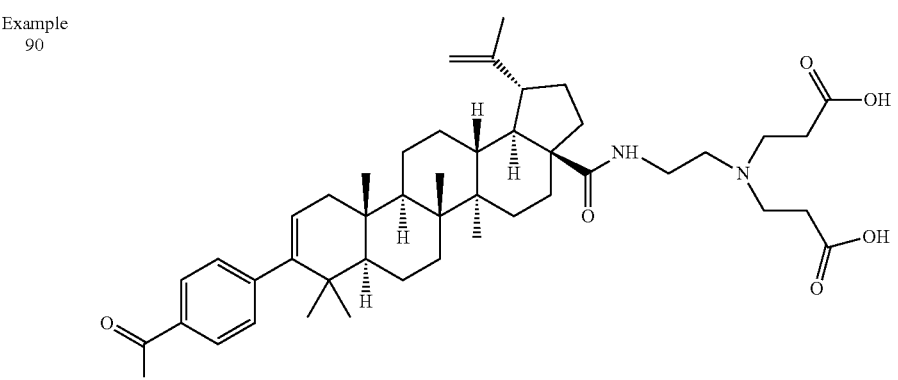 | B |
| Example 91 | 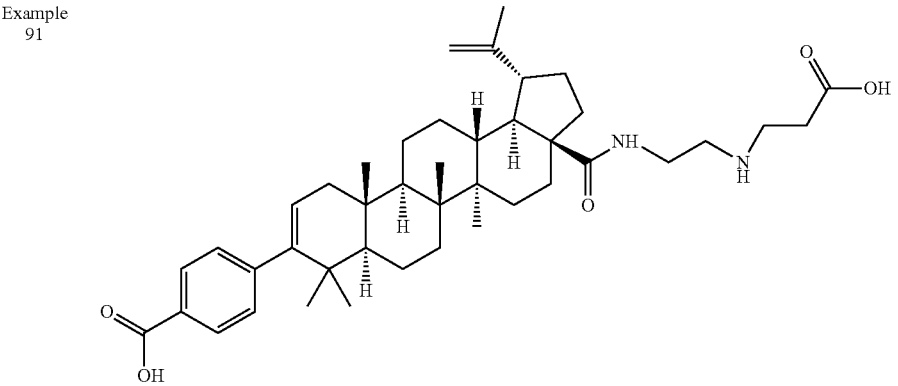 | A |
| Example 92 | 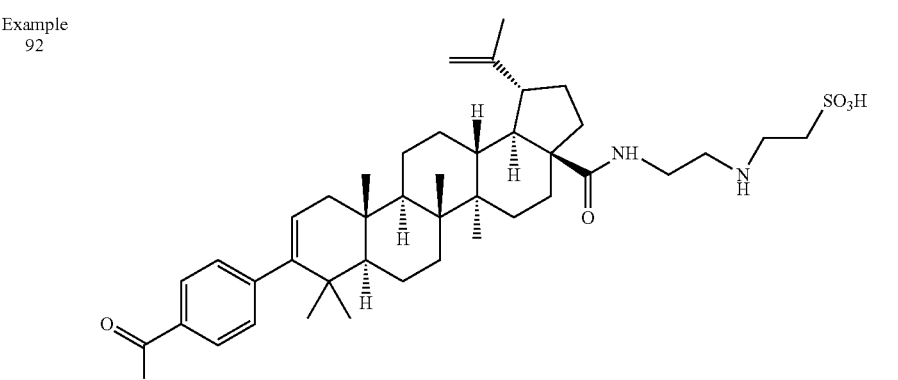 | A |

| Compound | Structure | Group |
|---|---|---|
| Example 93 | 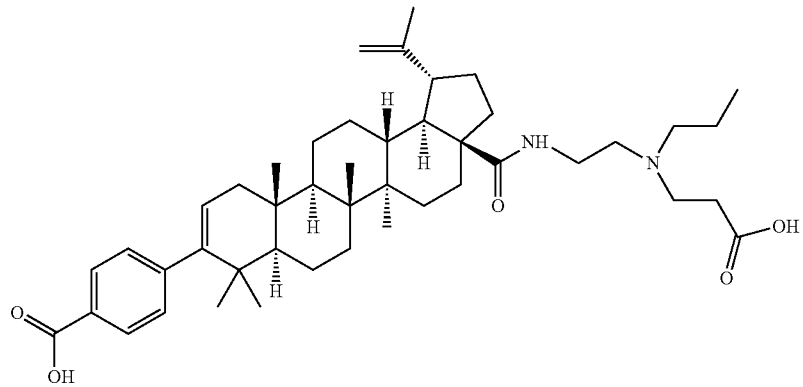 | A |
| Example 94 | 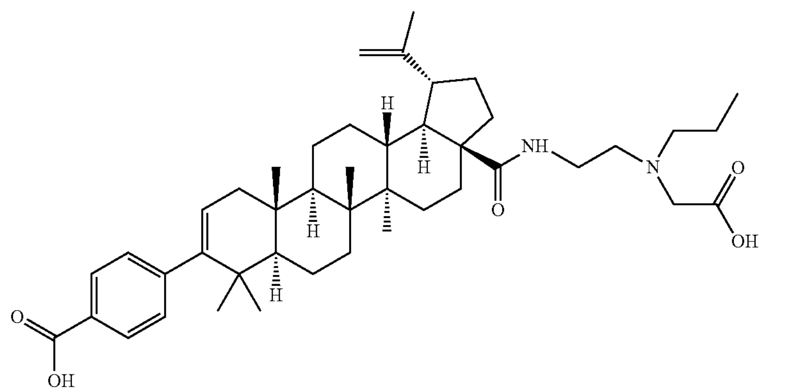 | A |
| Example 95 | 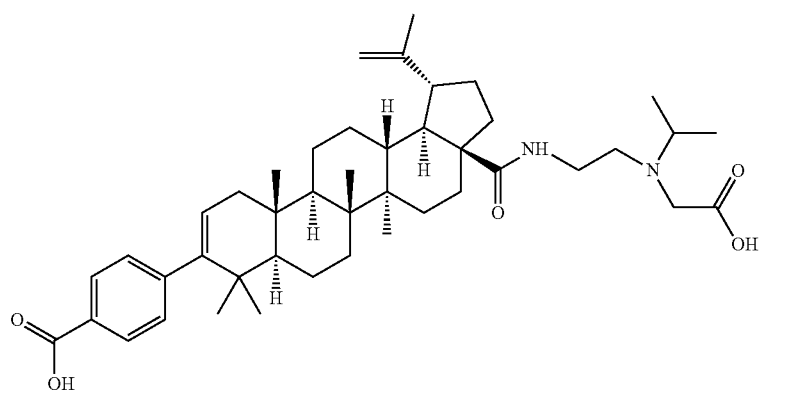 | A |
| Example 96 | 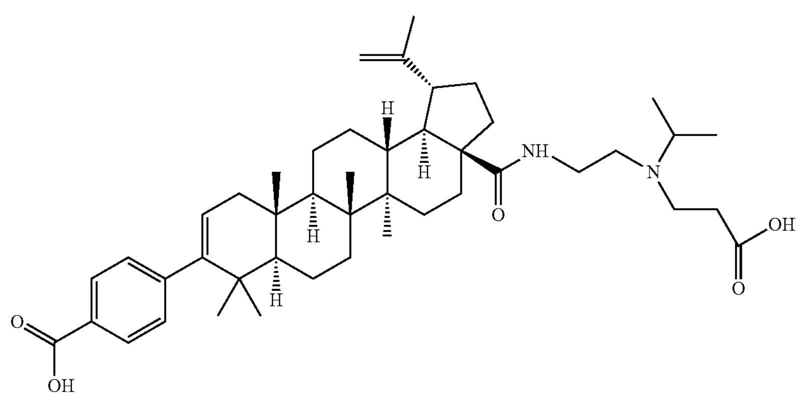 | A |

TABLE 2-continued

| Compound | Structure | Group |
|---|---|---|
| Example 97 | 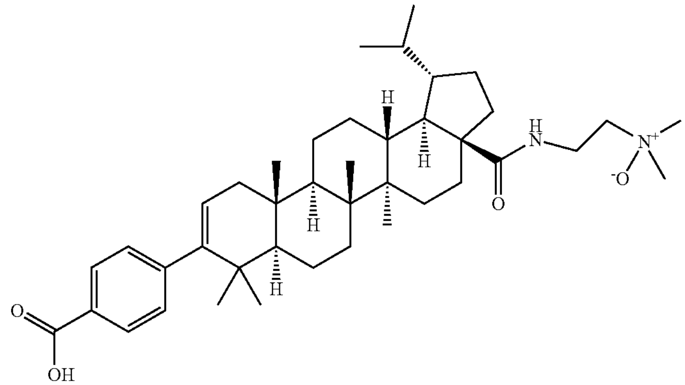 | 2.6 nM |
| Example 98 | 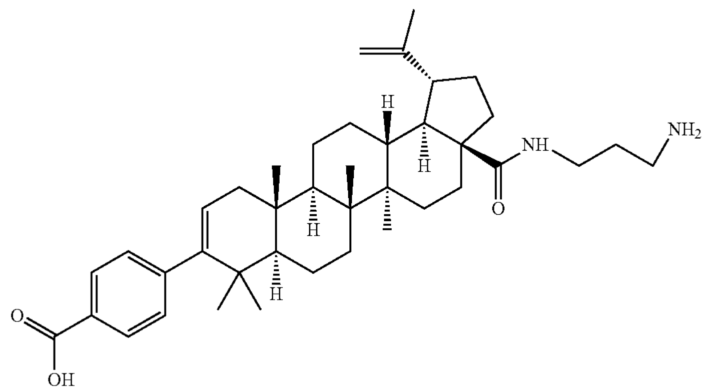 | A |
| Example 99 | 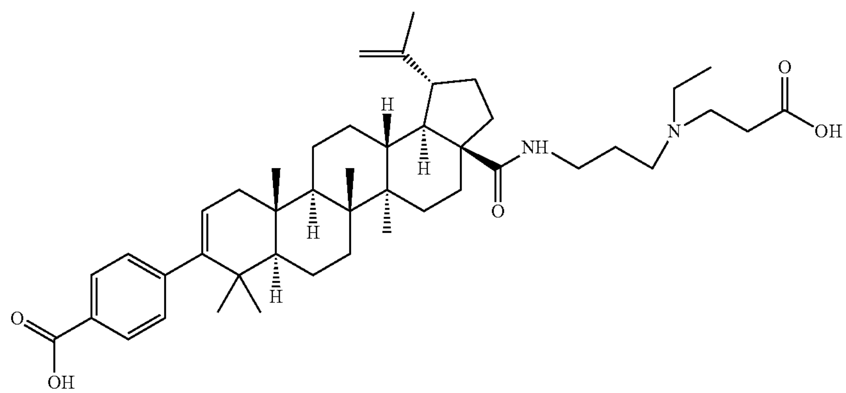 | A |
| Example 100 | 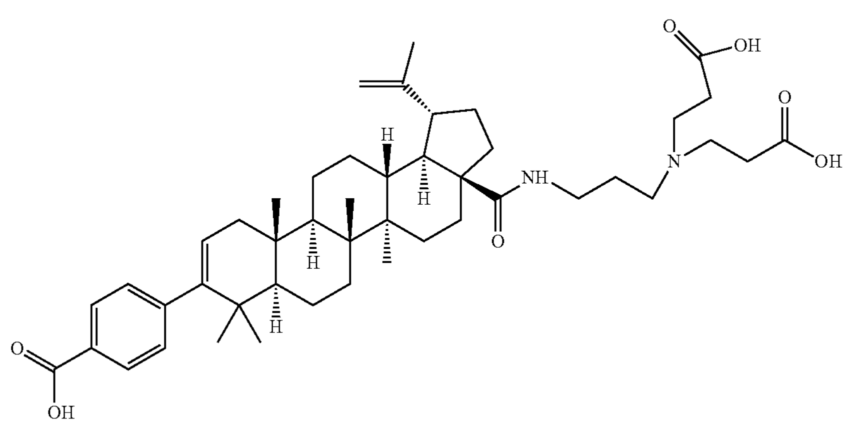 | B |

TABLE 2-continued

| Compound | Structure | Group |
|---|---|---|
| Example 101 | 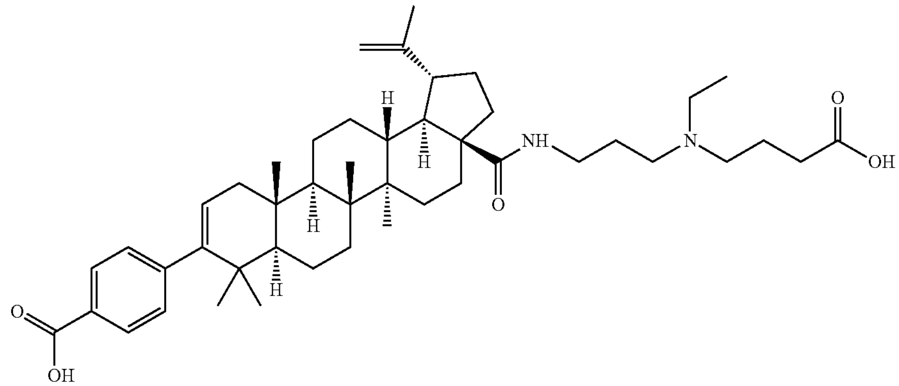 | A |
| Example 102 | 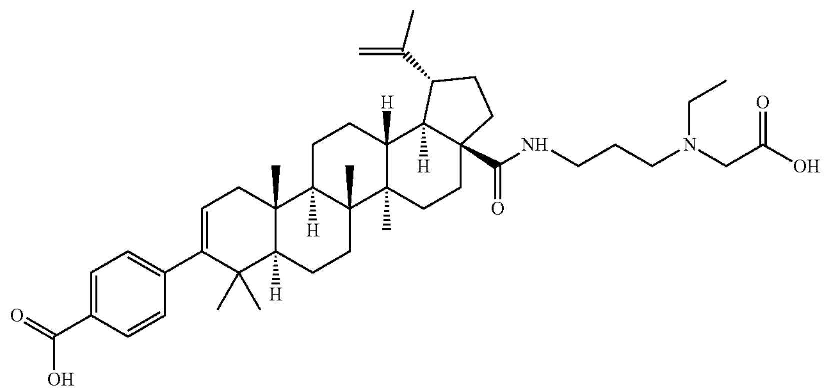 | 10.5 nM |
| Example 103 | 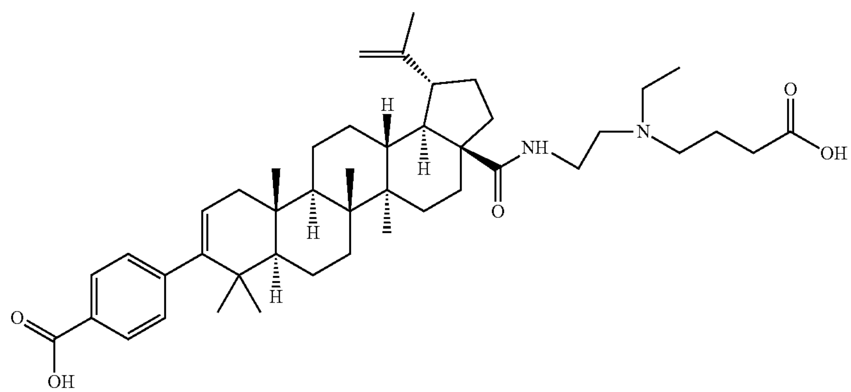 | A |
| Example 104 | 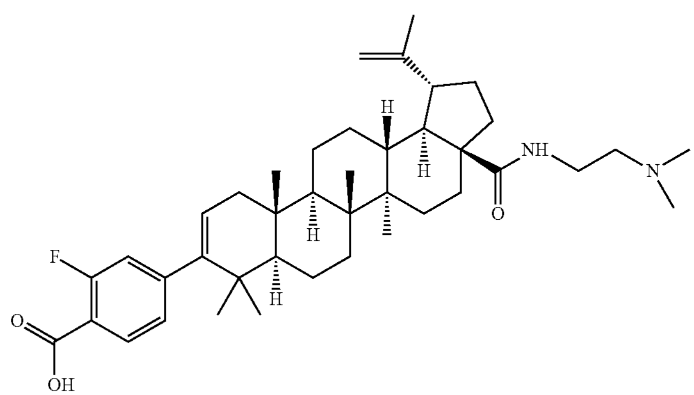 | A |

TABLE 2-continued

| Compound | Structure | Group |
|---|---|---|
| Example 105 | 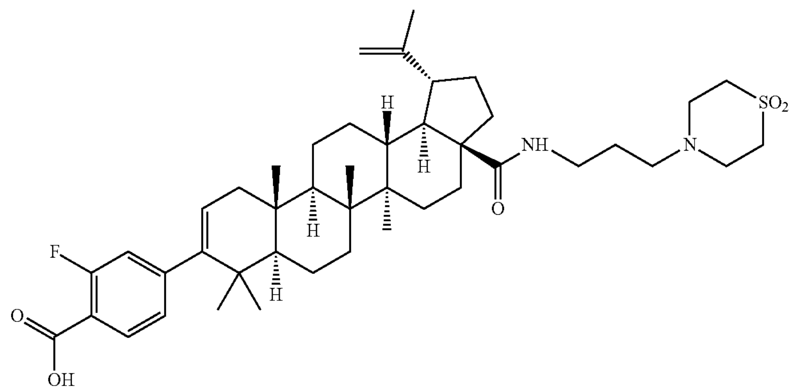 | A |
| Example 106 | 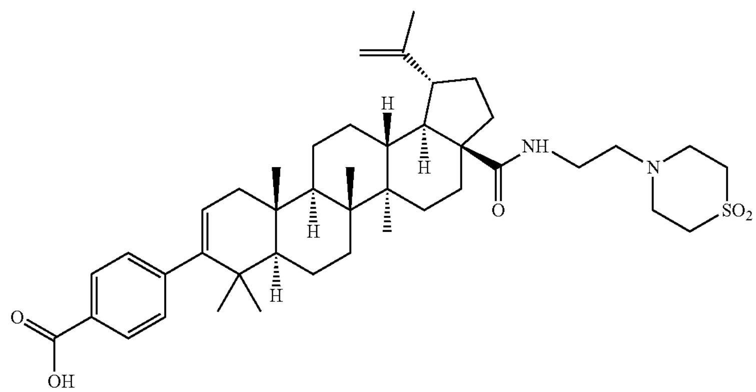 | A |
| Example 107 | 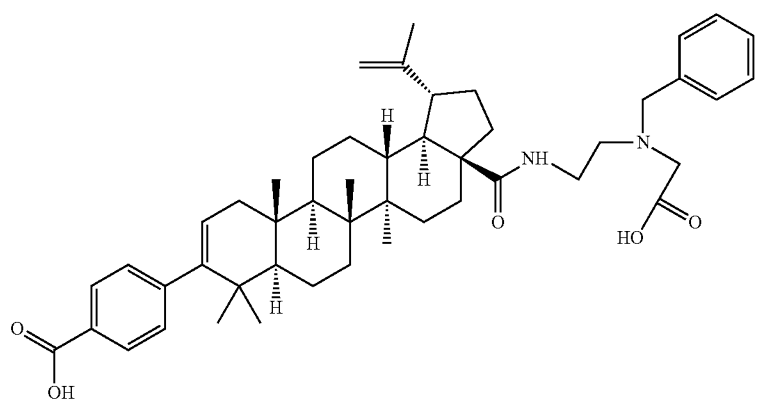 | A |
| Example 108 | 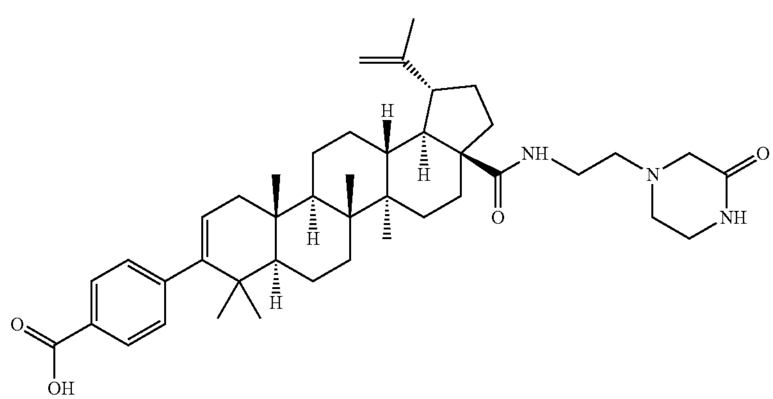 | A |

TABLE 2-continued
| Compound | Structure | Group |
|---|---|---|
| Example 109 | 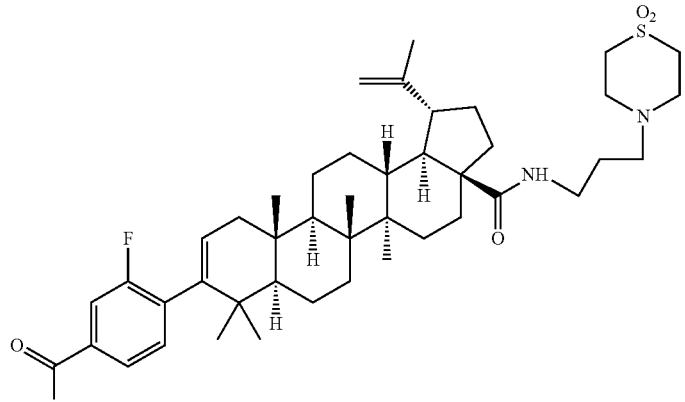 | A |
| Example 110 | 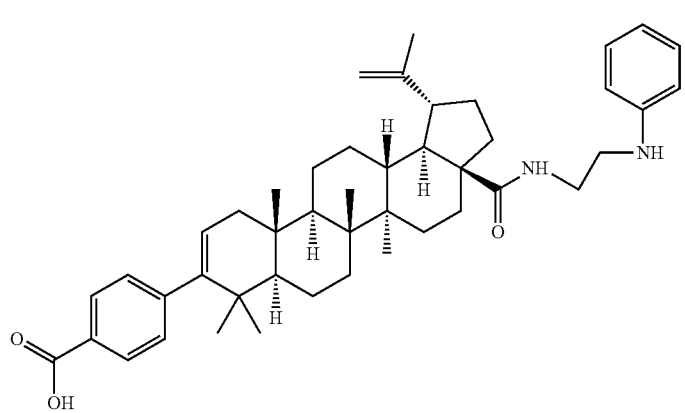 | A |
| Example 111 | 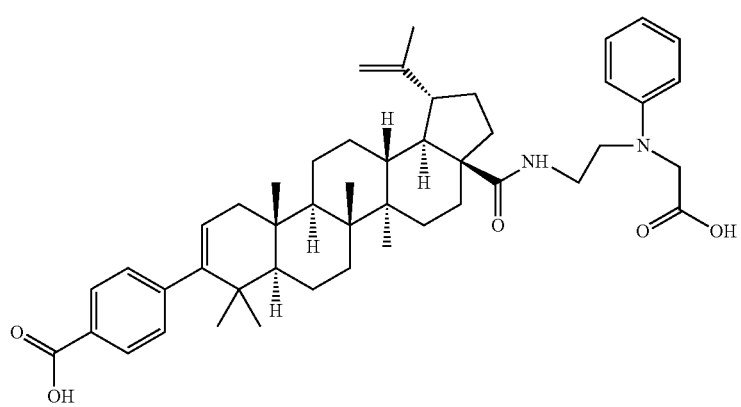 | A |
| Example 112 | 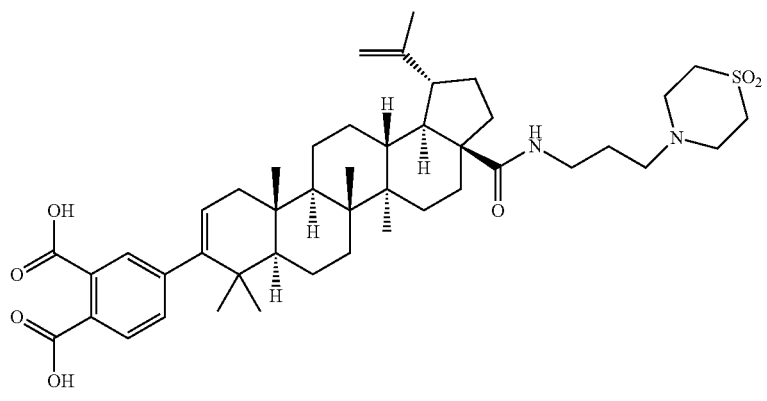 | A |

TABLE 2-continued
| Compound | Structure | Group |
|---|---|---|
| Example 113 | 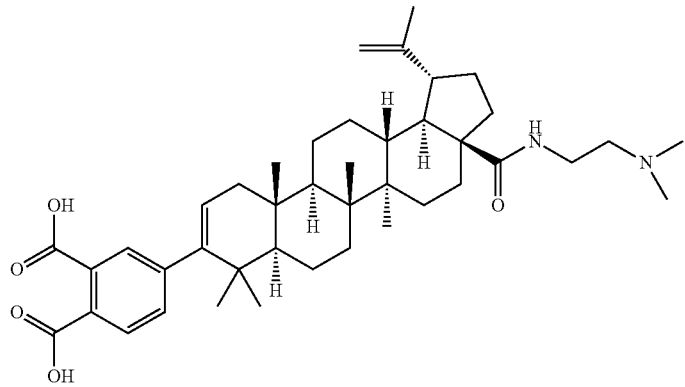 | B |
| Example 114 | 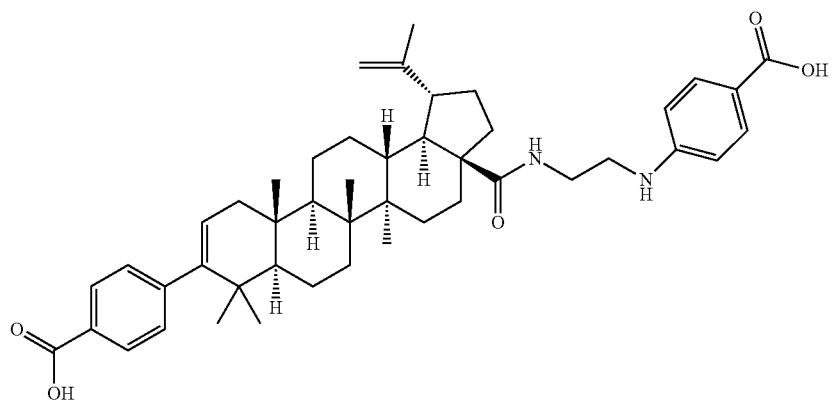 | 17.6 nM |
| Example 115 | 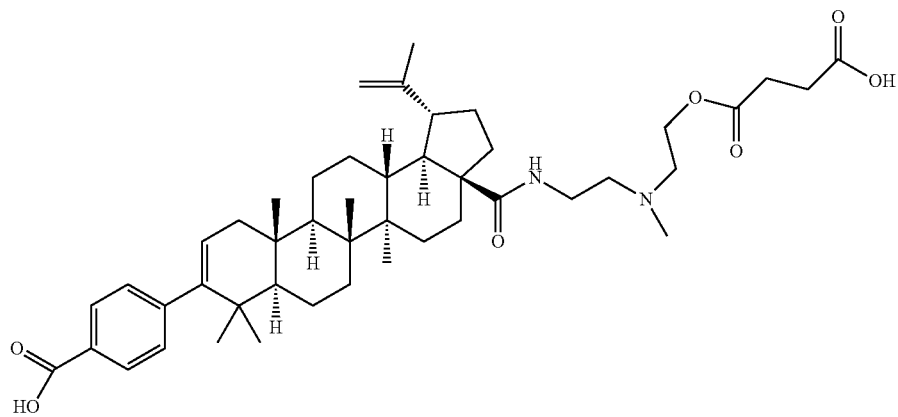 | A |
| Example 116 | 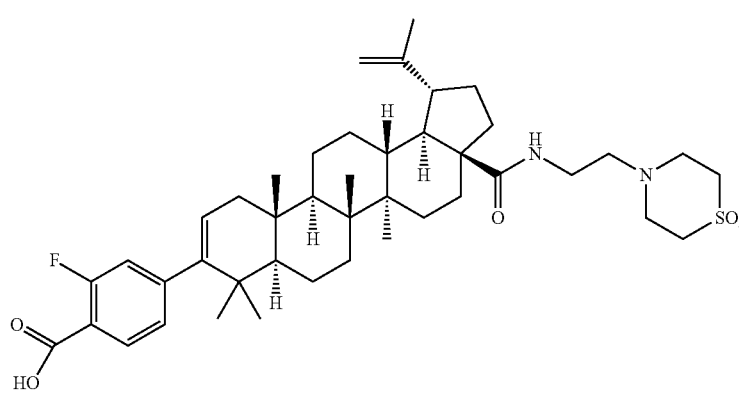 | A |

TABLE 2-continued

| Compound | Structure | Group |
|---|---|---|
| Example 117 | 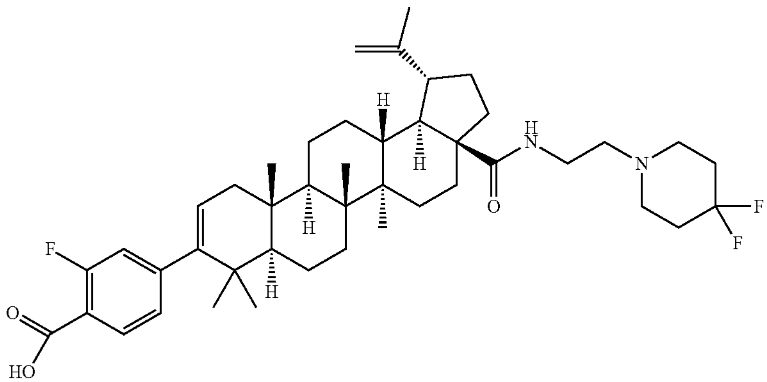 | A |
| Example 118 | 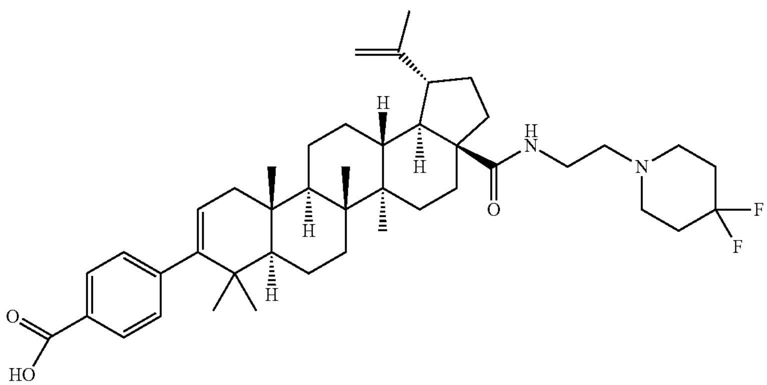 | A |
| Example 119 | 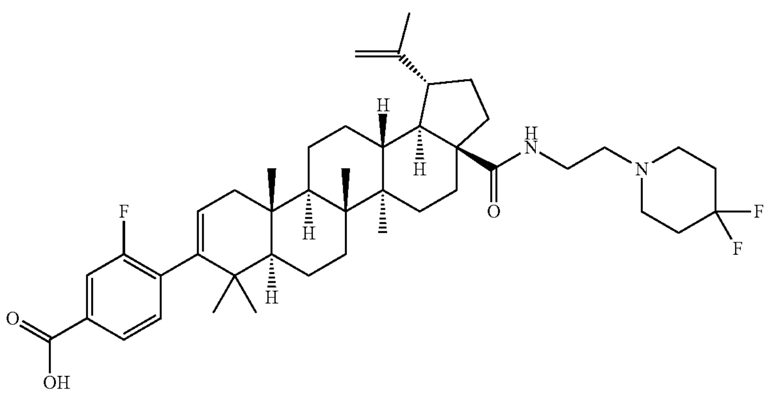 | A |
| Example 120 | 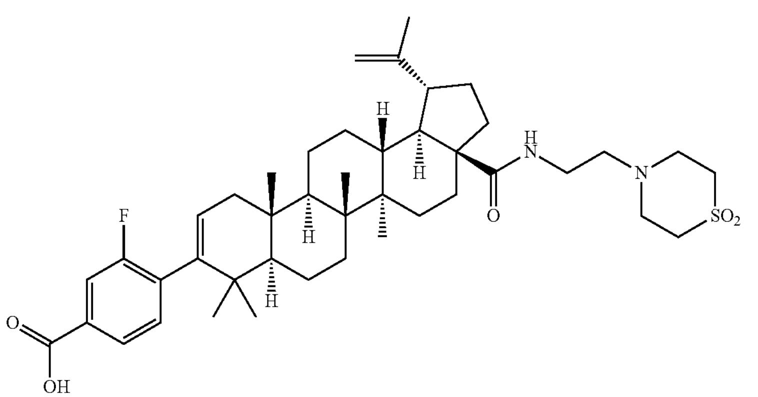 | A |

TABLE 2-continued

| Compound | Structure | Group |
|---|---|---|
| Example 121 | 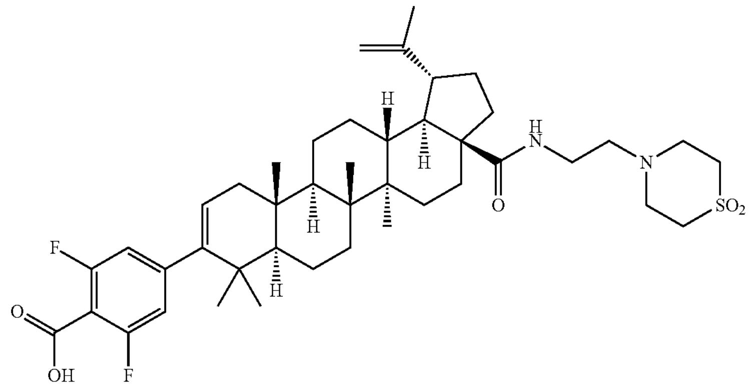 | A |
| Example 122 | 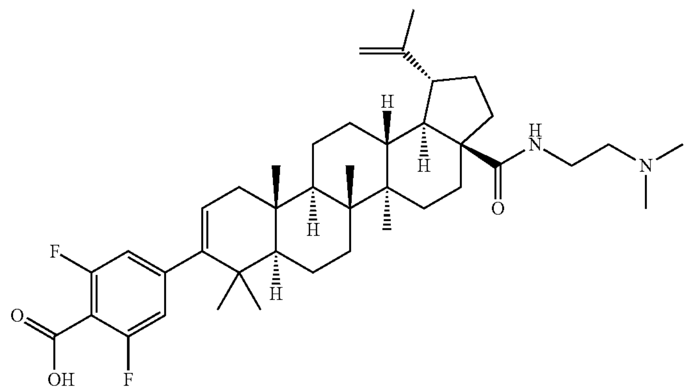 | A |
| Example 123 | 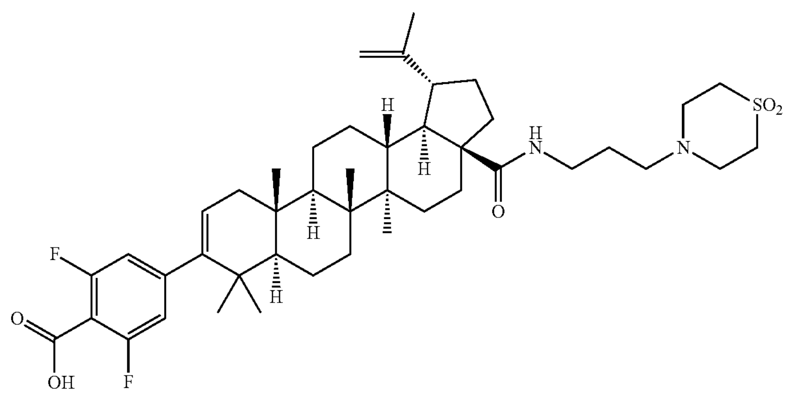 | A |
| Example 124 | 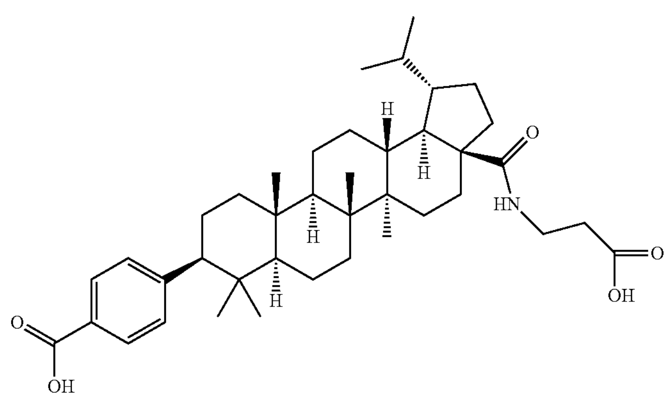 | A |

TABLE 2-continued
| Compound | Structure | Group |
|---|---|---|
| Example 125 | 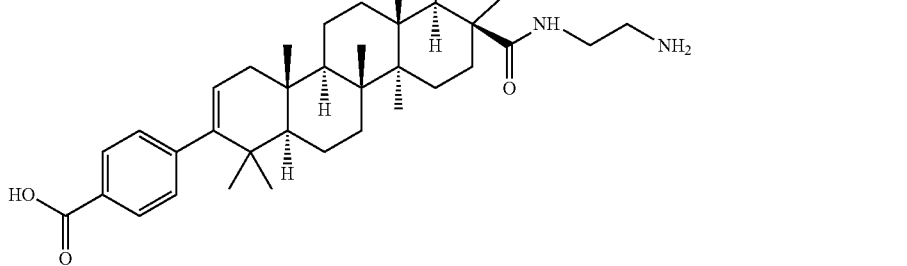 | A |
| Example 126 | 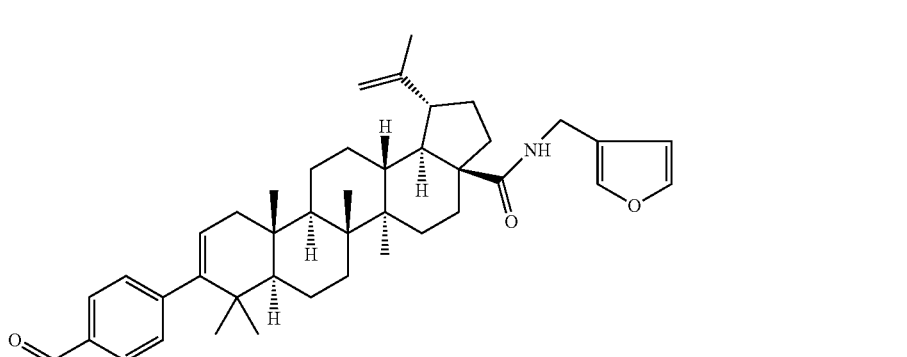 | A |
| Example 127 | 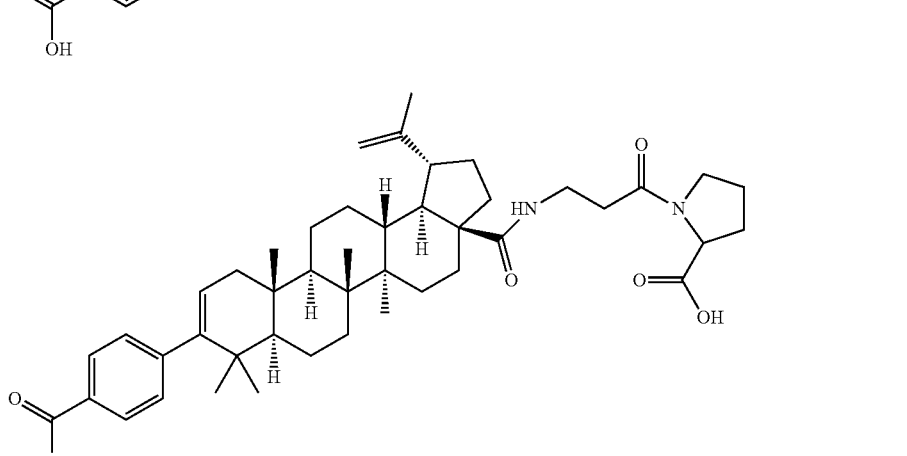 | A |
| Example 128 | 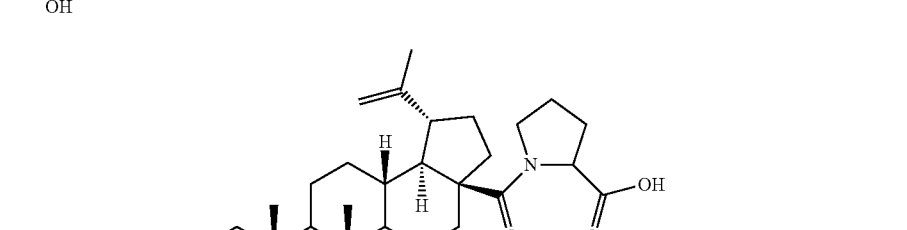 | A |

TABLE 2-continued
| Compound | Structure | Group |
|---|---|---|
| Example 129 | 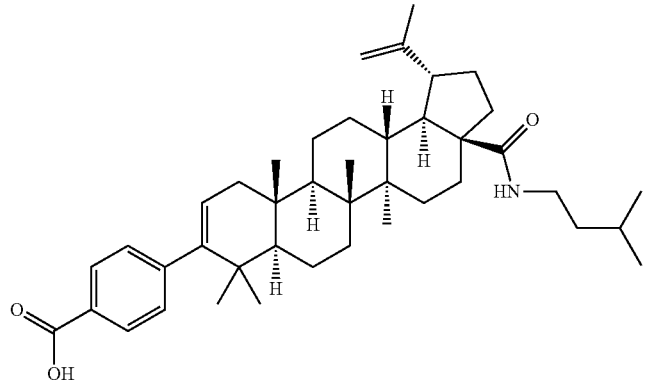 | A |
| Example 130 | 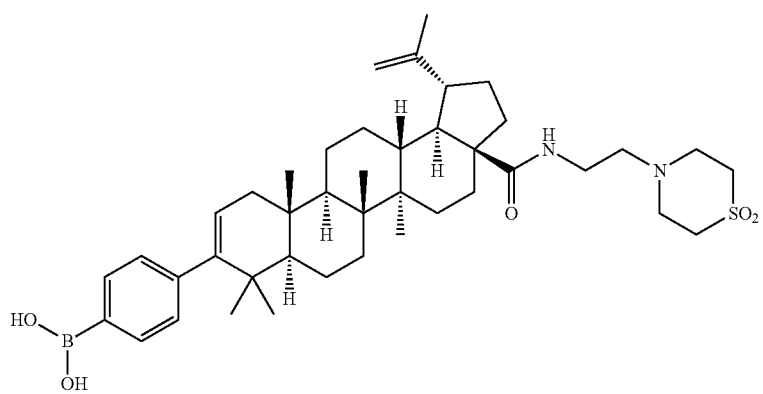 | 13.4 nM |
| Example A1 | 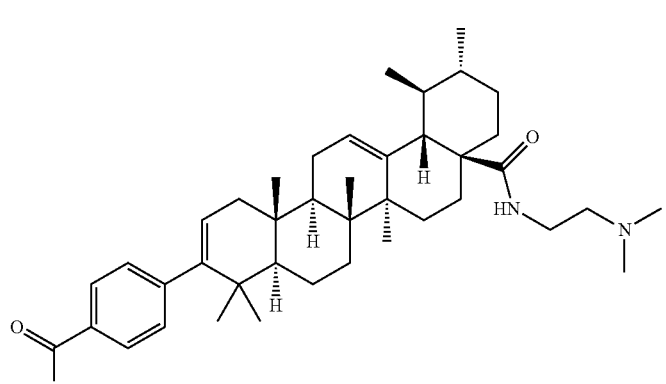 | A |
| Example B1 | 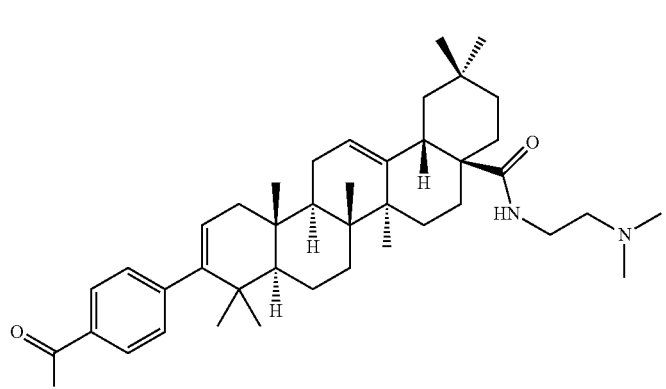 | A |

TABLE 2-continued

| Compound | Structure | Group |
|---|---|---|
| Example A2 | (steroid/triterpene structure with 4-carboxyphenyl group and propyl-thiomorpholine-1,1-dioxide amide) | A |
| Example B2 | (steroid/triterpene structure with 4-carboxyphenyl group and propyl-thiomorpholine-1,1-dioxide amide) | A |

The foregoing description is merely illustrative and should not be understood to limit the scope or underlying principles of the invention in any way. Indeed, various modifications of the invention, in addition to those shown and described herein, will become apparent to those skilled in the art from the following examples and the foregoing description. Such modifications are also intended to fall within the scope of the appended claims.

What is claimed is:

1. A compound which is selected from the group of:

a compound of formula I

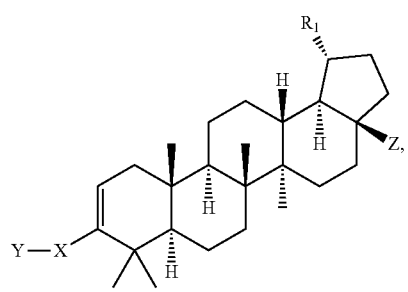

Formula I a compound of formula II

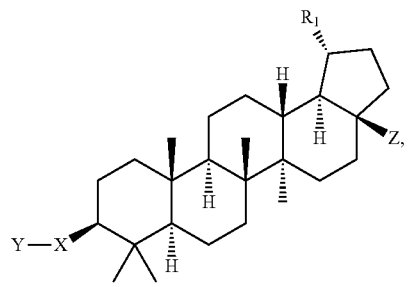

Formula II a compound of formula III

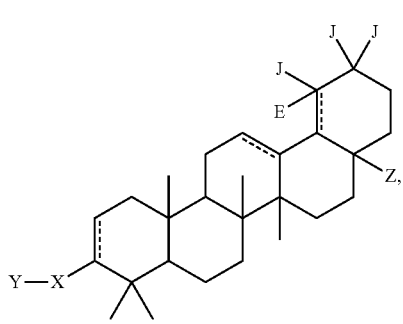

Formula III wherein $R_1$ is isopropenyl or isopropyl;

J and E are —H or —CH$_3$;

E is absent when the double bond is present;

X is a phenyl or heteroaryl ring substituted with A, wherein A is at least one member selected from the group of —H, -halo, -alkyl, -alkoxy, —COOR$_2$ and -hydroxyl wherein $R_2$ is —H—C$_{1-6}$ alkyl, or substituted —C$_{1-6}$ alkyl;

Y is selected from the group of —COOR$_2$, —C(O)NR$_2$SO$_2$R$_3$, —C(O)NR$_2$SO$_2$NR$_2$R$_2$, —SO$_2$NR$_2$R$_2$, —NR$_2$SO$_2$R$_2$, —C$_{1-6}$ cycloalkyl-COOR$_2$, —C$_{1-6}$ alkenyl-COOR$_2$, —C$_{1-6}$ alkynyl-COOR$_2$, —C$_{1-6}$ alkyl-COOR$_2$, —NHC(O)(CH$_2$)$_n$—COOR$_2$, —SO$_2$NR$_2$C(O)R$_2$, -tetrazole, B(OH)$_2$ and —CONHOH wherein n=1-6 and wherein $R_3$ is C$_{1-6}$ alkyl; and Z is —CONR$_4$R$_5$;

$R_4$ is selected from the group of H, C$_{1-6}$ alkyl, and C$_{1-6}$ alkyl-OH;

$R_5$ is selected from the group of H, C$_{1-6}$ alkyl, substituted-alkyl, C$_{1-6}$ alkyl-R$_6$, C$_{2-6}$ alkyl-R$_7$, SO$_2$R$_8$, SO$_2$NR$_9$R$_{10}$;

$R_6$ is selected from phenyl, substituted phenyl, heteroaryl, substituted heteroaryl, SO$_2$R$_{11}$, SO$_2$NR$_{12}$R$_{13}$, C$_{1-6}$ cycloalkyl, substituted C$_{1-6}$ cycloalkyl, SO$_3$H, COOR$_{14}$, C(O)NR$_{15}$R$_{16}$;

$R_7$ is selected from OR$_{17}$, N$^+$(O$^-$)R$_{18}$R$_{19}$, NR$_{20}$(COR$_{21}$) and NR$_{22}$R$_{23}$;

or $R_4$ and $R_5$ are taken together to form a cycle selected from the group of:

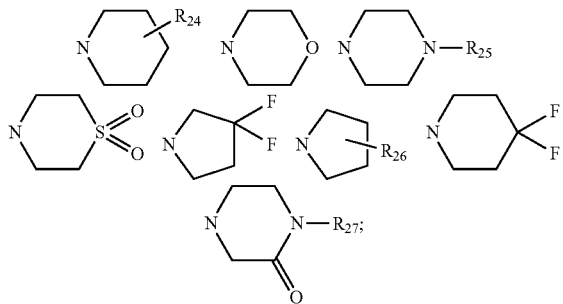

$R_{22}$ and $R_{23}$ are selected from the group of H, C$_{1-6}$ alkyl, substituted-alkyl, C$_{1-6}$ alkyl-R$_{32}$, C$_{2-6}$ alkyl-R$_{33}$, SO$_2$R$_8$, SO$_2$NR$_9$R$_{10}$;

$R_{32}$ is selected from phenyl, substituted phenyl, heteroaryl, substituted heteroaryl, SO$_2$R$_{11}$, SO$_2$NR$_{12}$R$_{13}$, C$_{1-6}$ cycloalkyl, substituted C$_{1-6}$ cycloalkyl, SO$_3$H, COOR$_{14}$, C(O)NR$_{15}$R$_{16}$, $R_{33}$ is selected from OR$_{17}$, N$^+$(O$^-$)R$_{18}$R$_{19}$, NR$_{20}$(COR$_{21}$) and NR$_9$R$_{10}$;

or $R_{22}$ and $R_{23}$ are taken together to form a cycle selected from the group of:

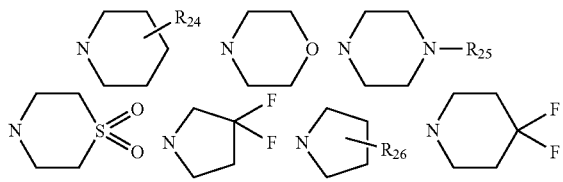

-continued

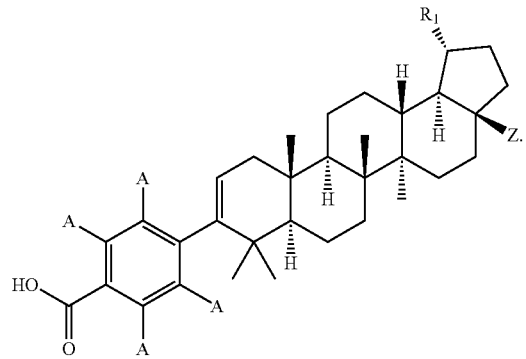

$R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{27}$, $R_{29}$, $R_{30}$ and $R_{31}$ are each independently selected from the group of H, C$_{1-6}$ alkyl, substituted-alkyl, C$_{1-6}$ cycloalkyl and substituted C$_{1-6}$ cycloalkyl;

$R_{24}$, $R_{26}$ and $R_{28}$ are selected from the group of H, alkyl, substituted alkyl, COOR$_{29}$, COONR$_{30}$R$_{31}$; and $R_{25}$ is selected from the group of alkyl, substituted alkyl, COOR$_{29}$, COONR$_{30}$R$_{31}$;

and pharmaceutically acceptable salts thereof.

2. The compound as claimed in claim 1, wherein said compound is a compound of Formula I.

3. The compound as claimed in claim 1, wherein said compound is a compound of Formula II.

4. The compound as claimed in claim 2, wherein X is a phenyl ring, and Y is in the para position.

5. The compound as claimed in claim 2, wherein X is a substituted phenyl ring.

6. The compound as claimed in claim 5, wherein said phenyl ring is substituted with A, and A is at least one member selected from the group of —H, —OH and —F.

7. The compound as claimed in claim 6, wherein Y is —COOH.

8. The compound as claimed in claim 4, wherein X is a phenyl ring and Y is —COOH in the para position according to Formula Ia:

Formula Ia

9. The compound as claimed in claim 8, wherein A is at least one member selected from the group of —H, —OH and —F.

10. The compound as claimed in claim 9, wherein A is —H or —F.

11. A compound which is selected from the group consisting of:
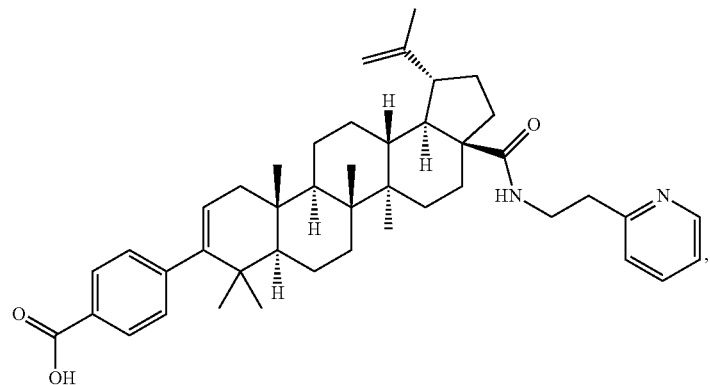
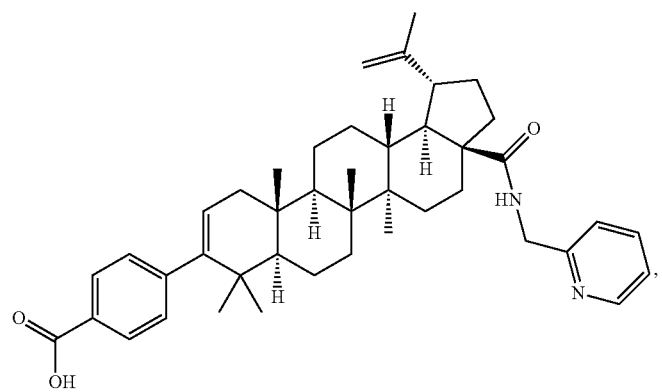
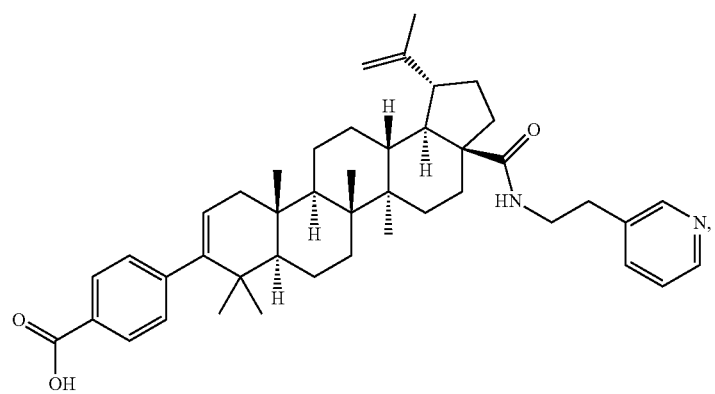
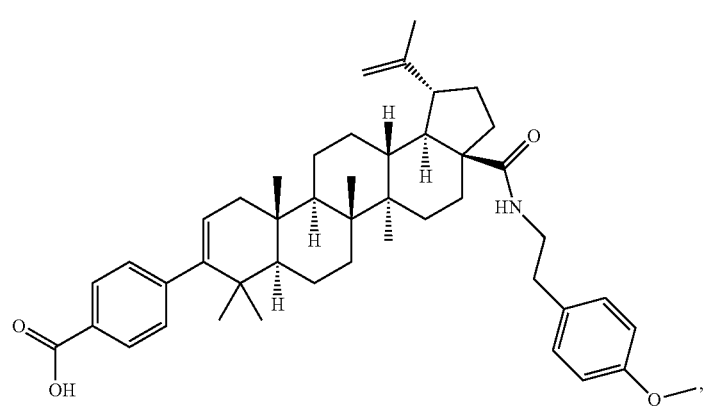

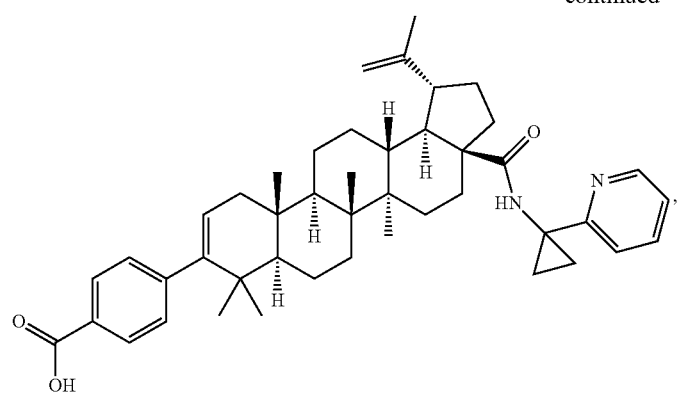
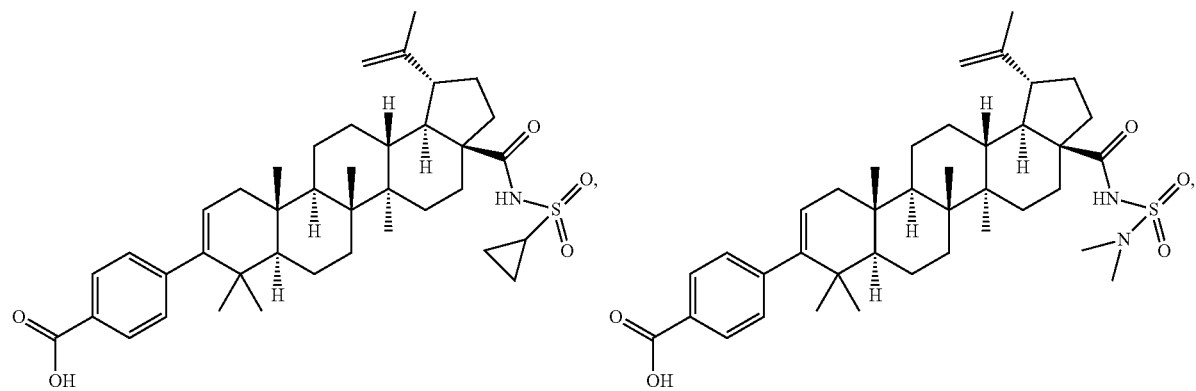
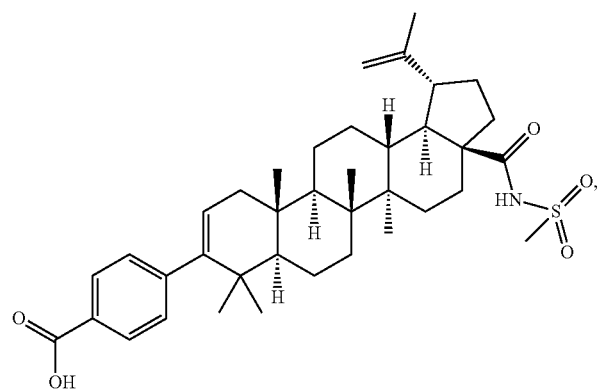
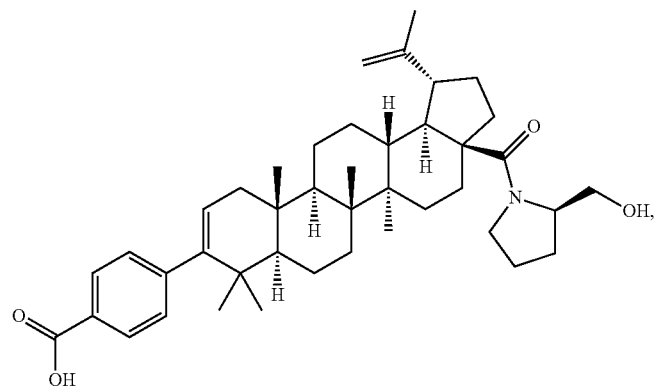

-continued
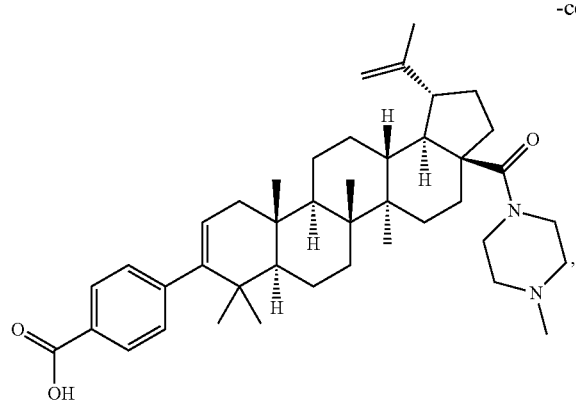
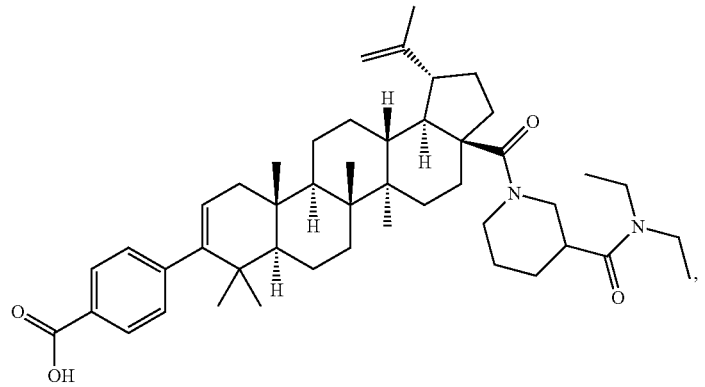
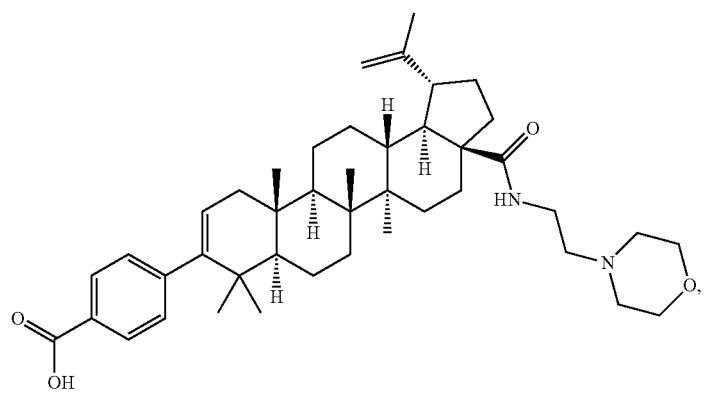
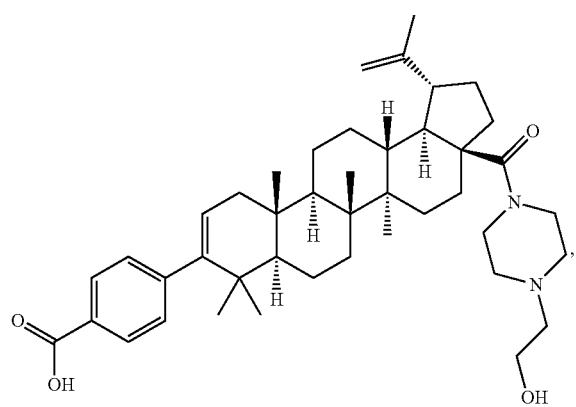

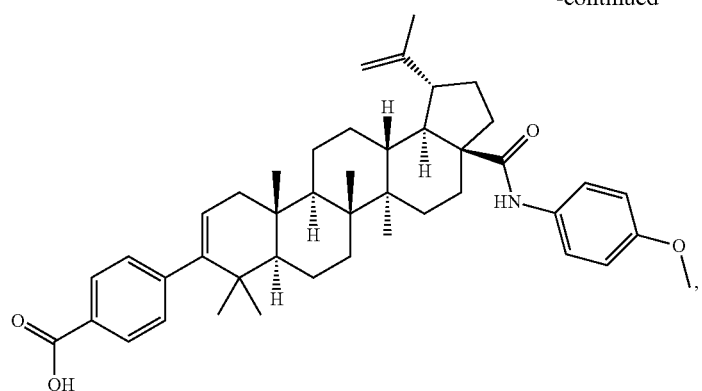
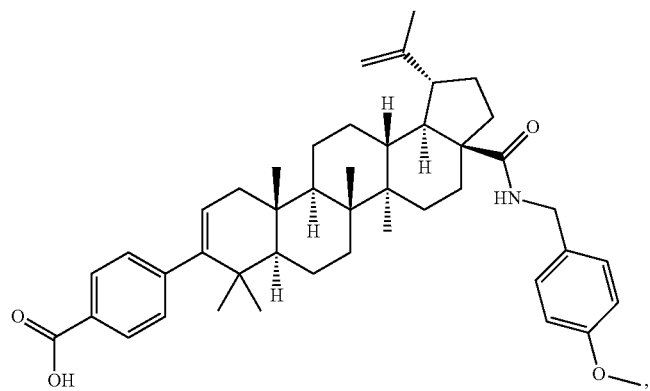
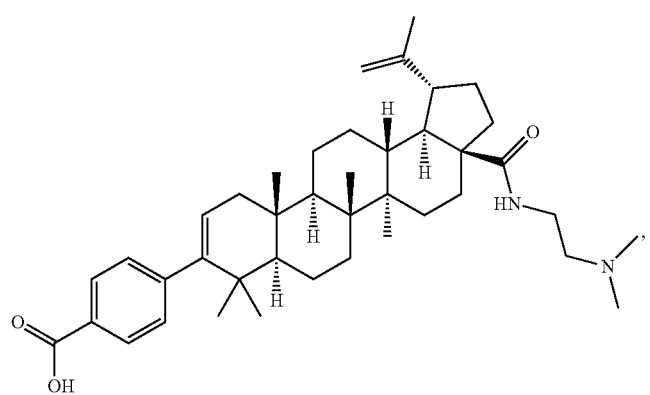
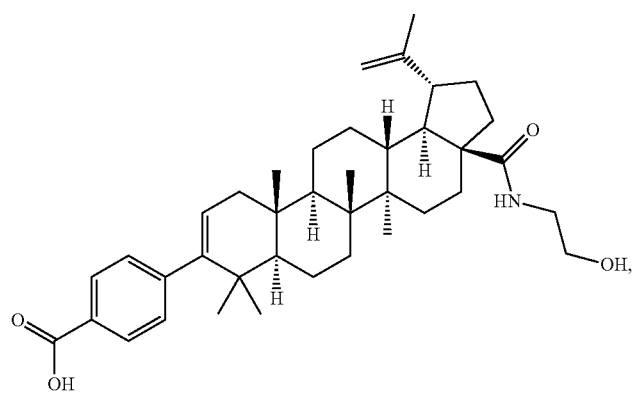

377            378
-continued
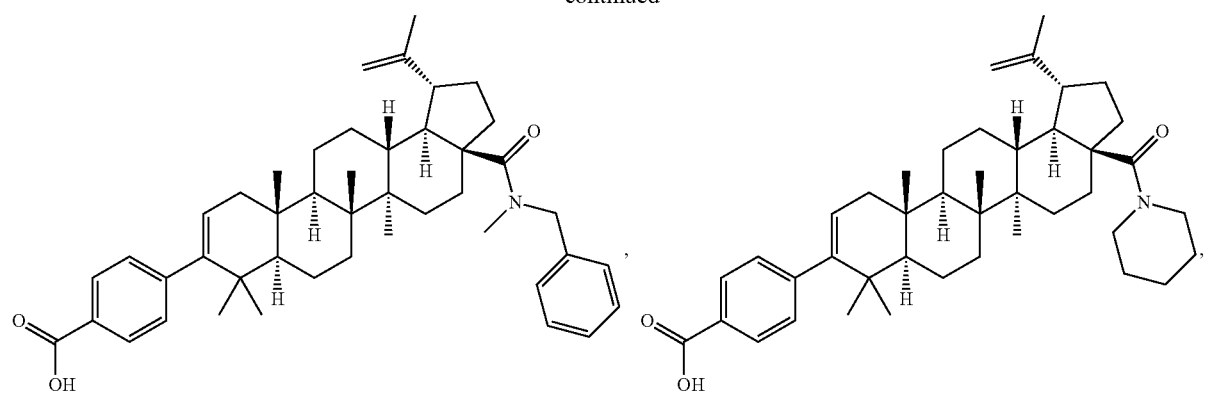
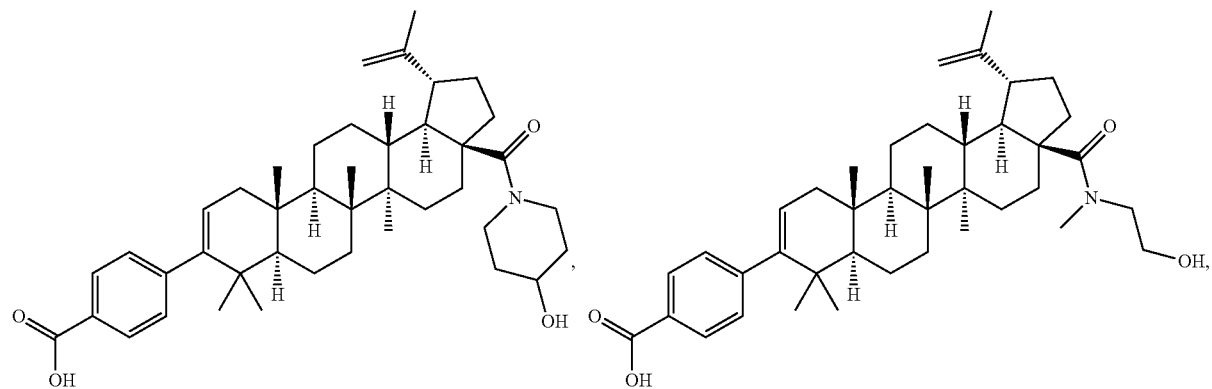
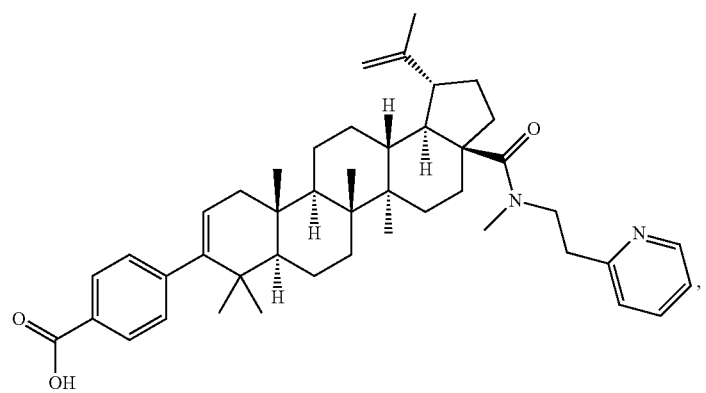
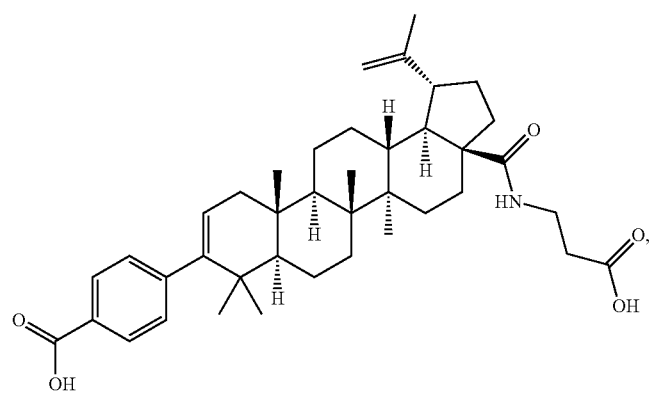

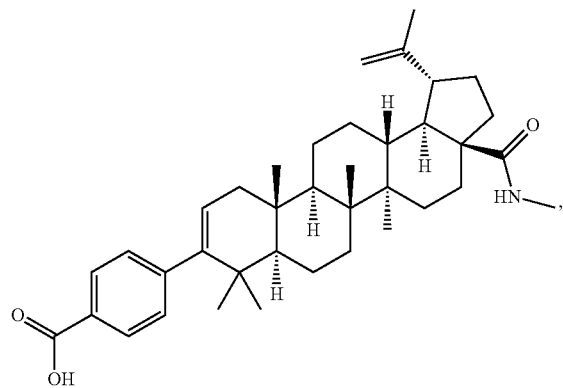
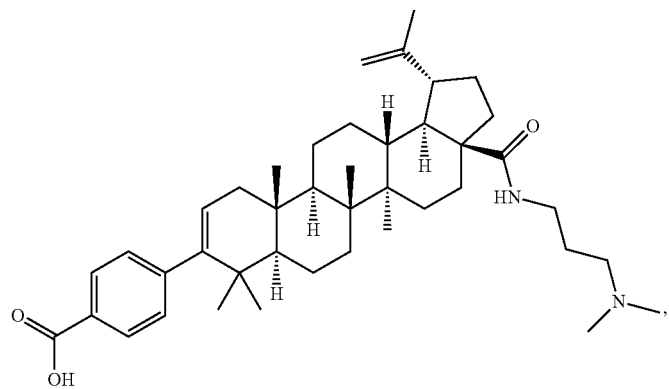
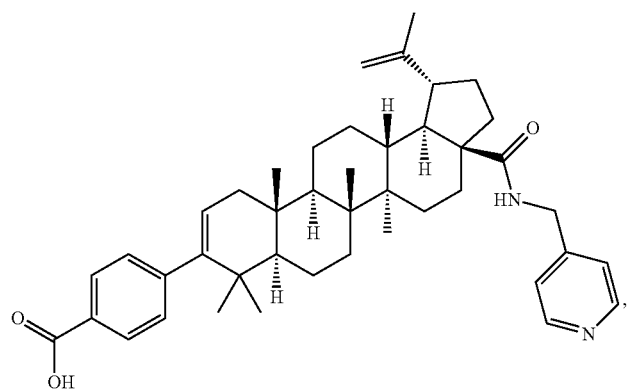
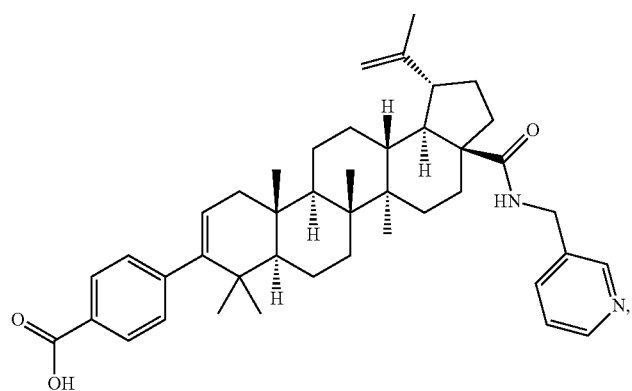

-continued
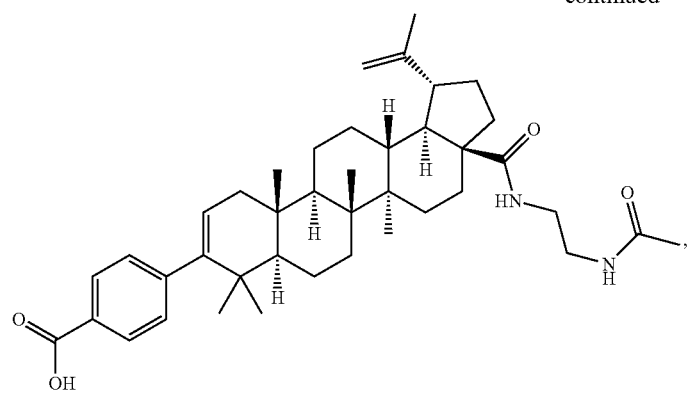
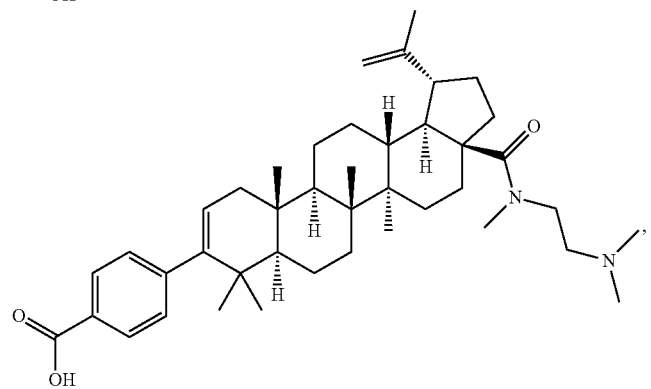
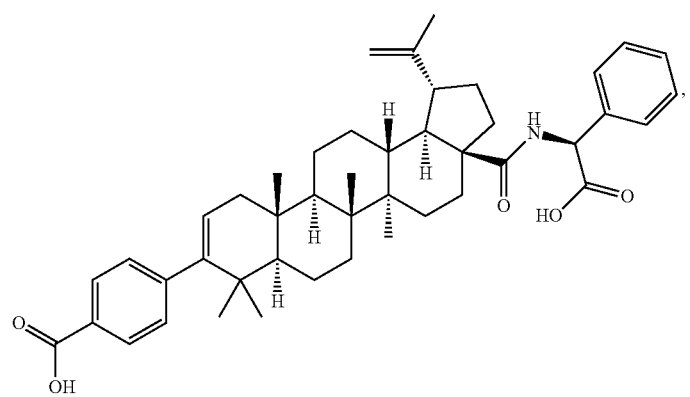
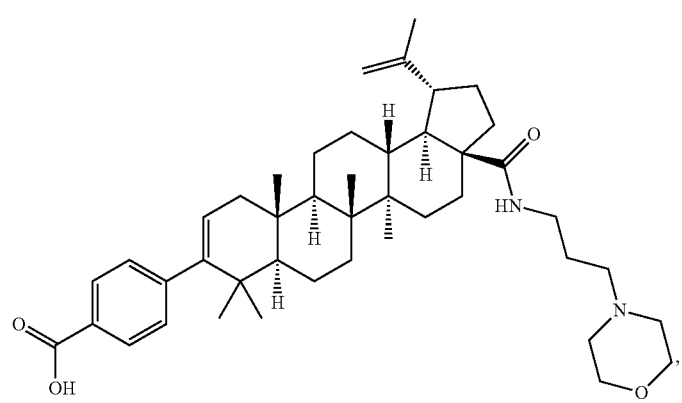

-continued
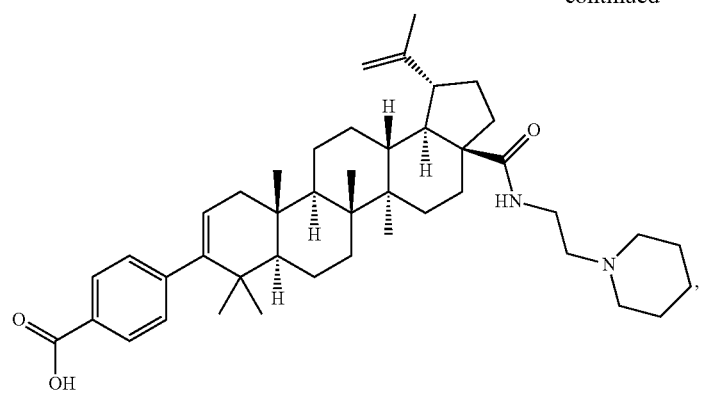
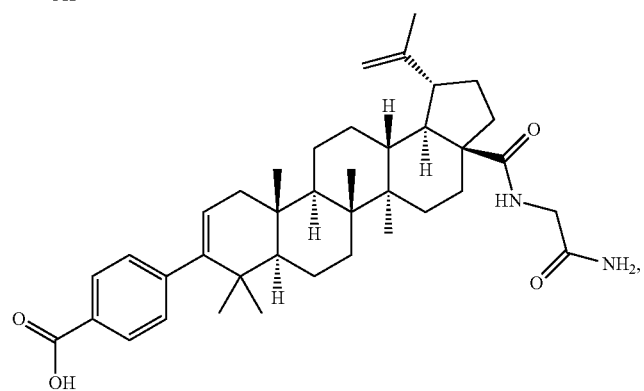
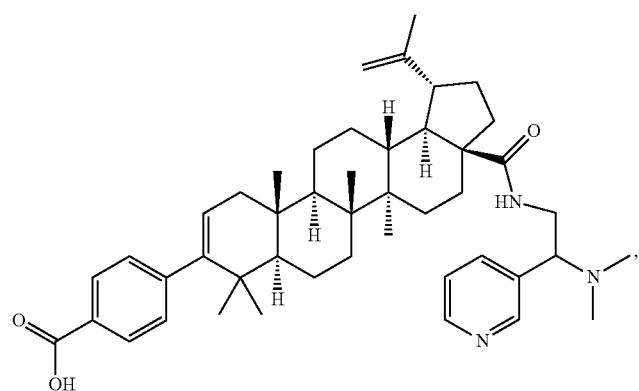
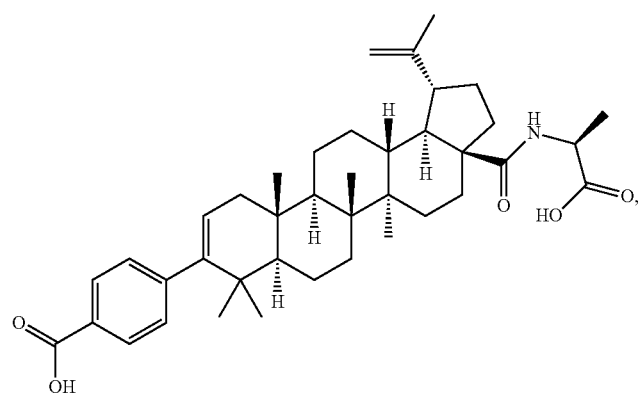

-continued
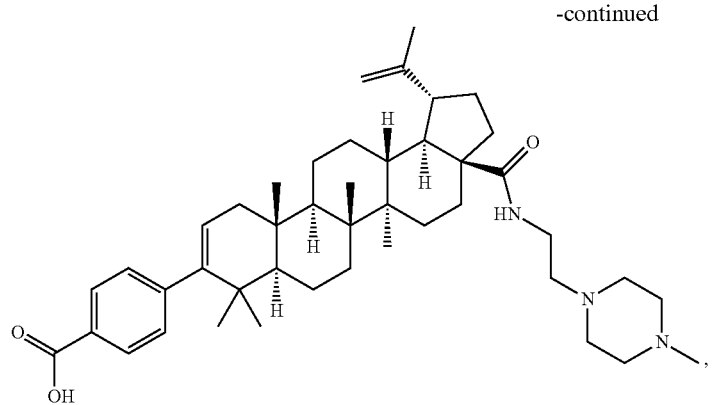
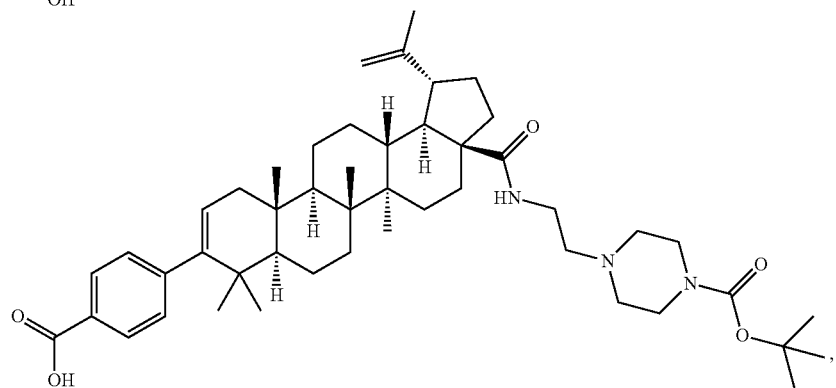
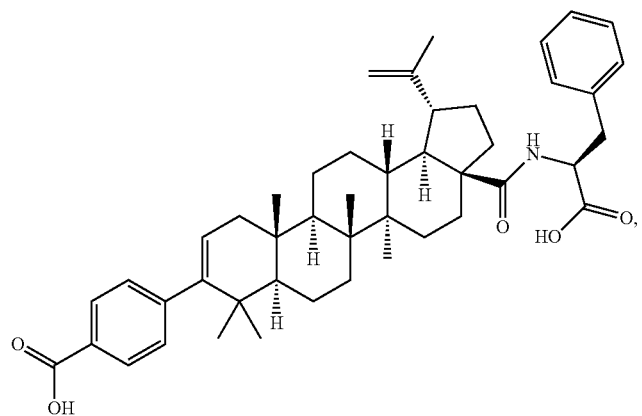
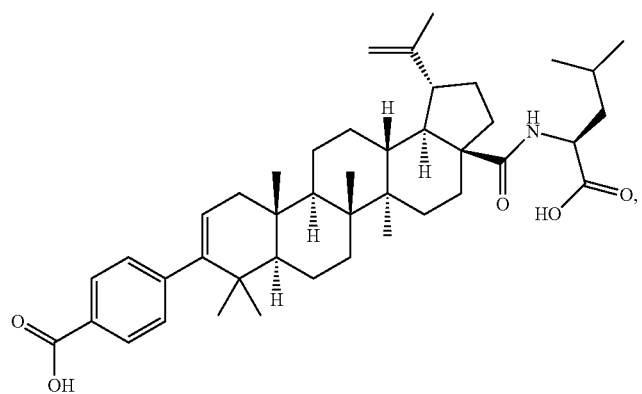

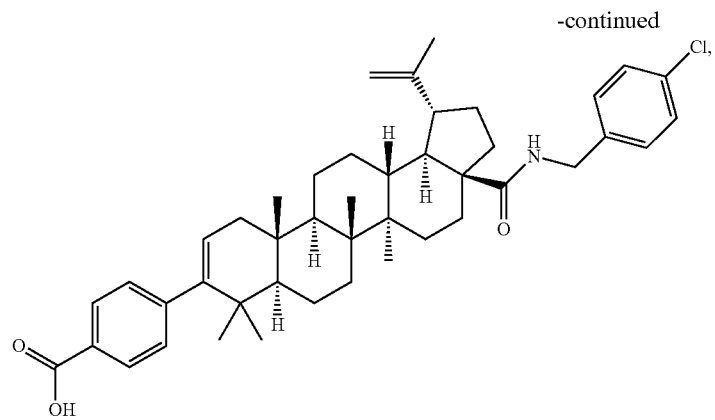
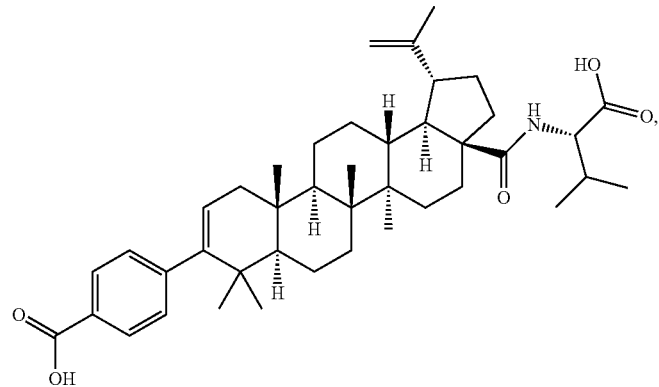
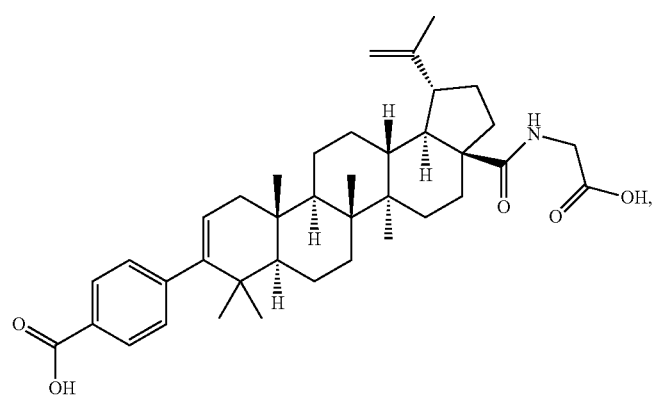
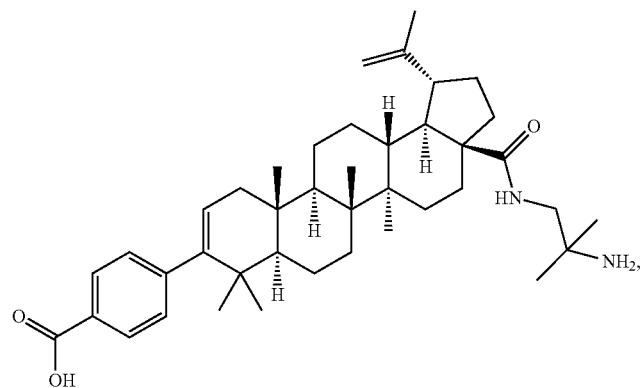

-continued
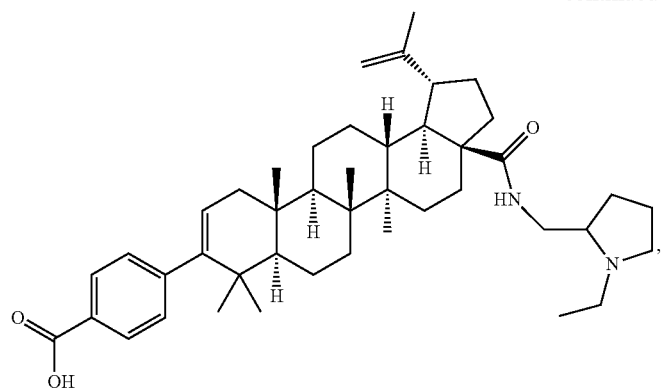
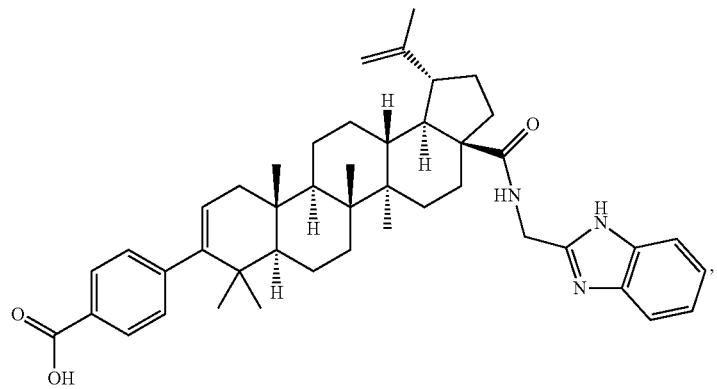
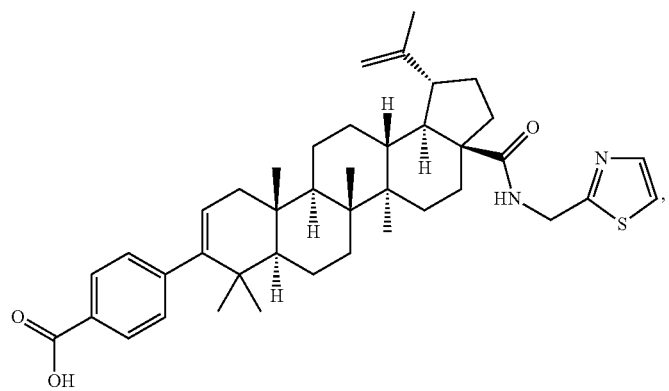
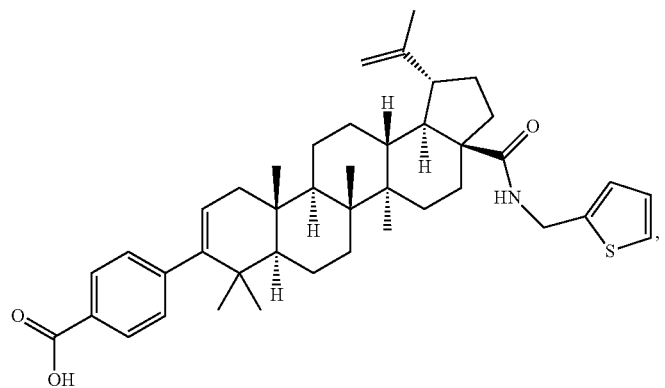

-continued
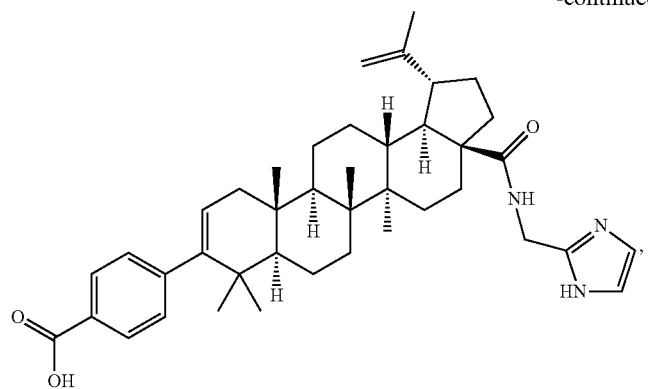
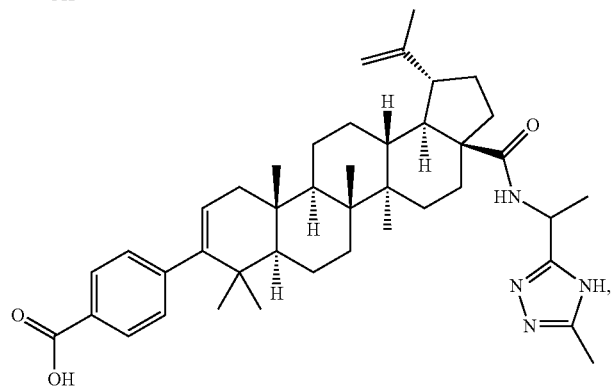
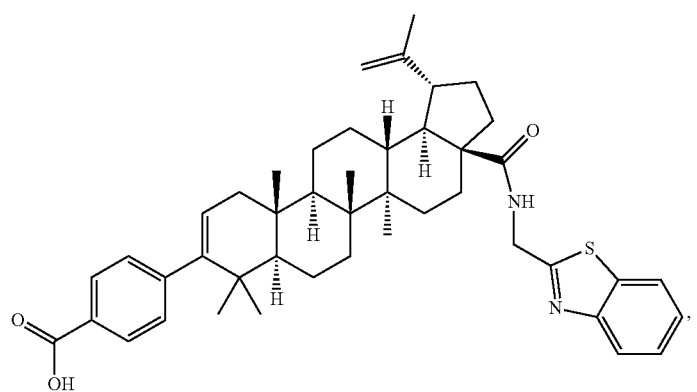
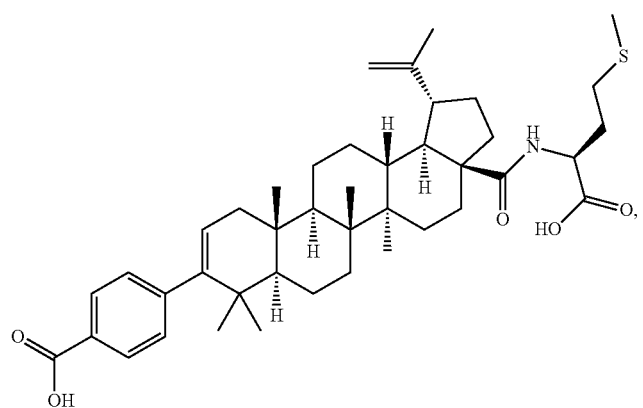

-continued
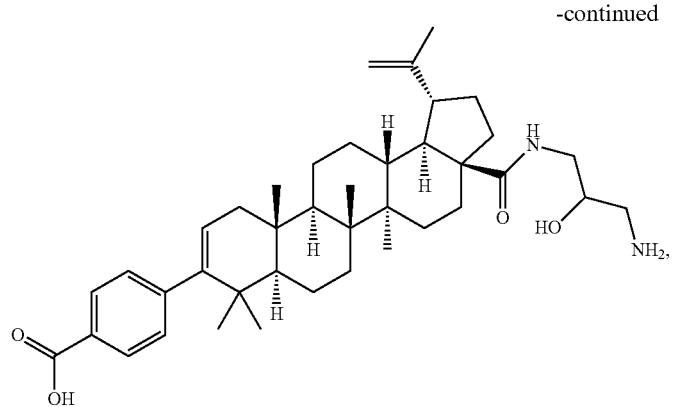
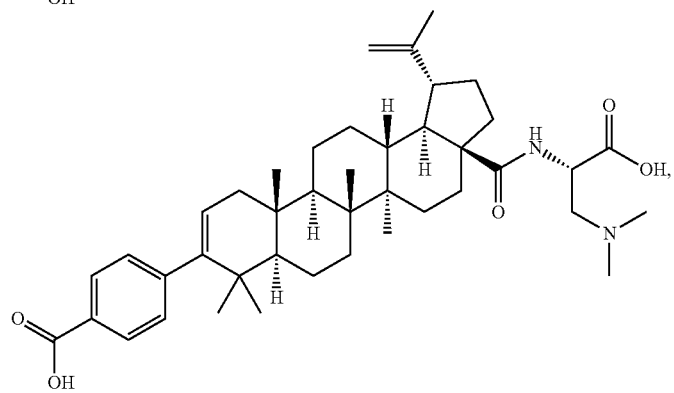
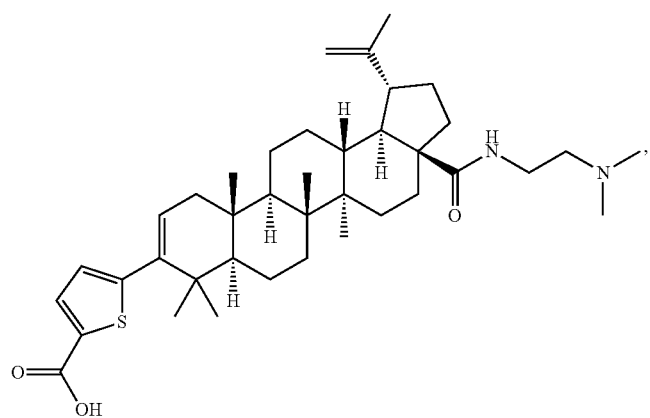
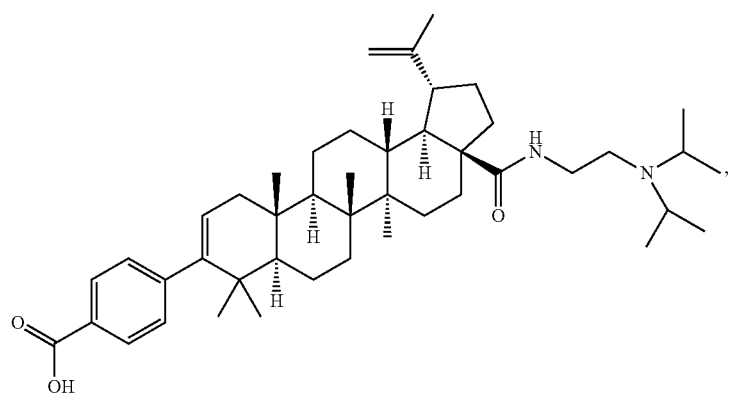

-continued
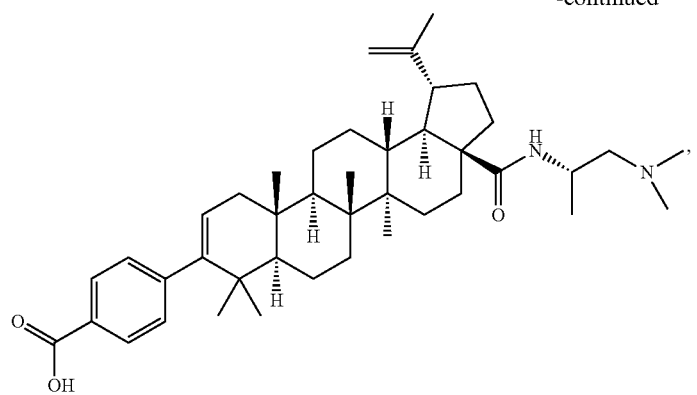
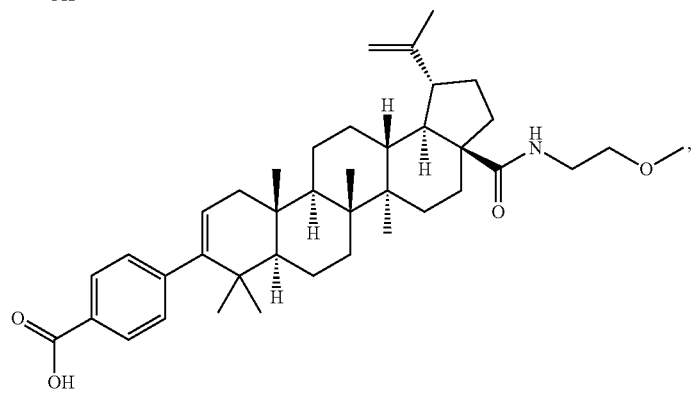
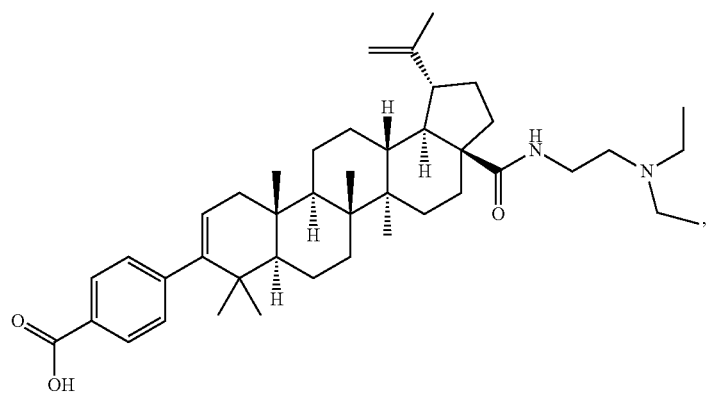
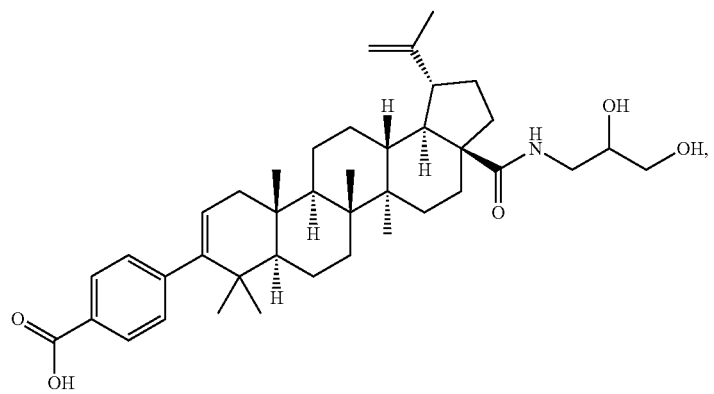

-continued
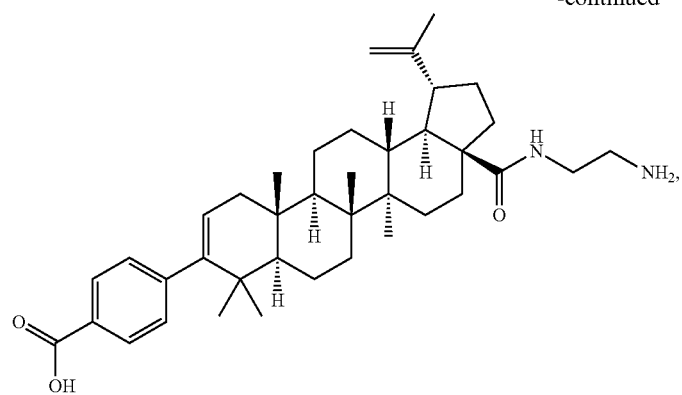
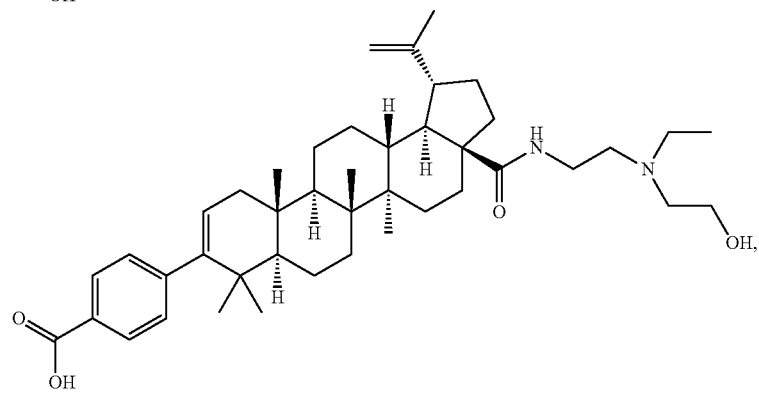
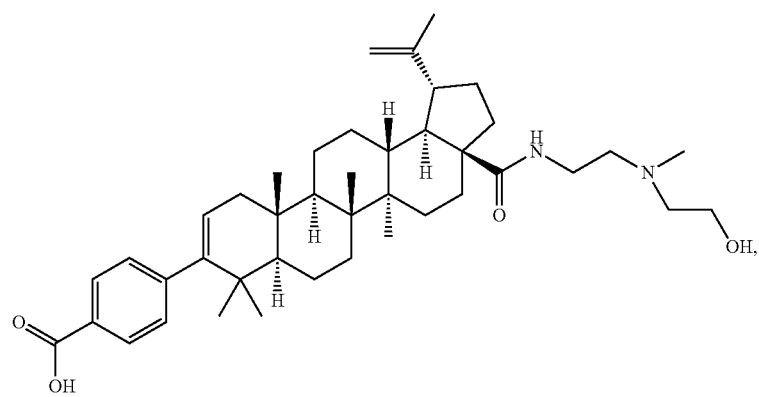
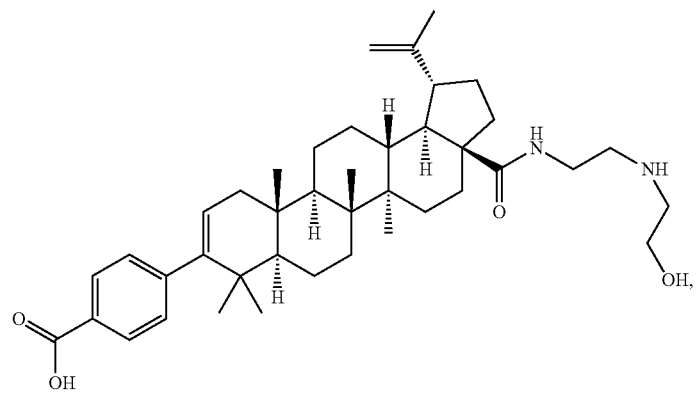

-continued
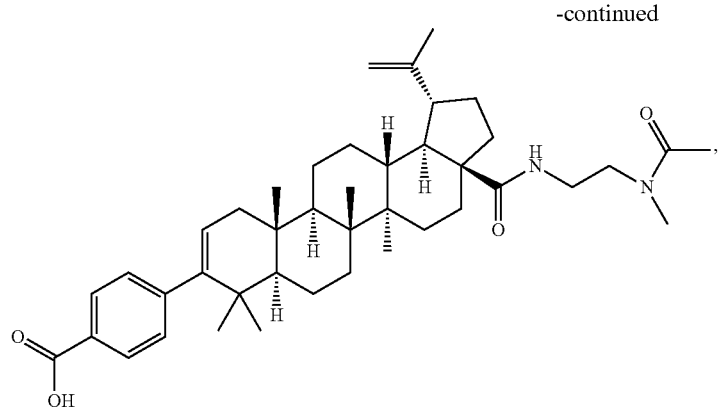
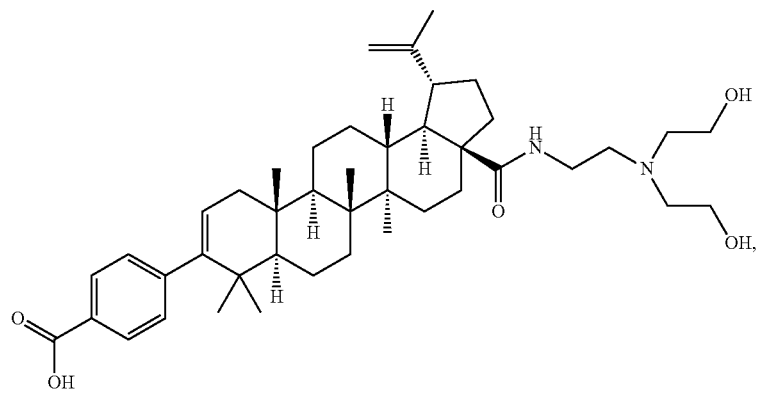
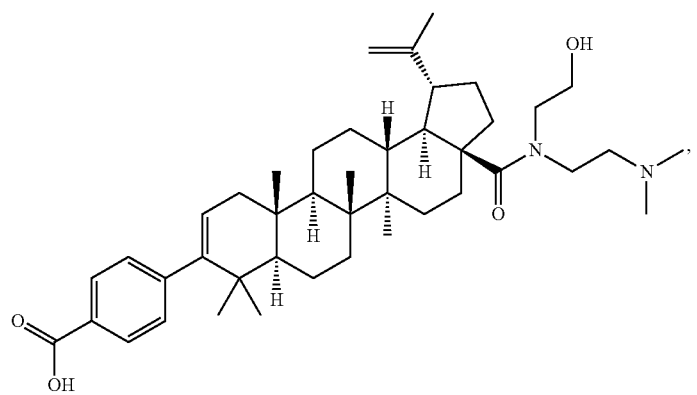
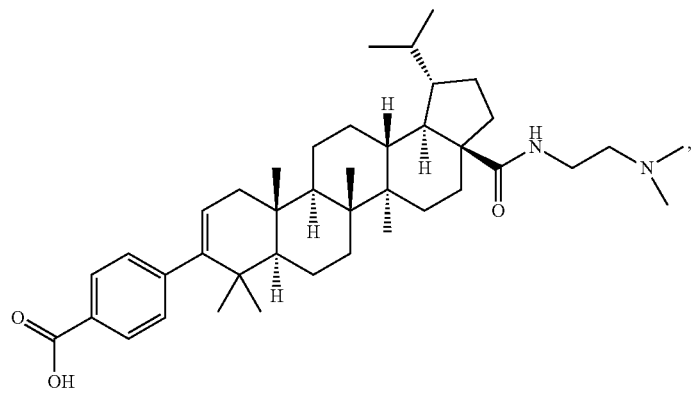

-continued
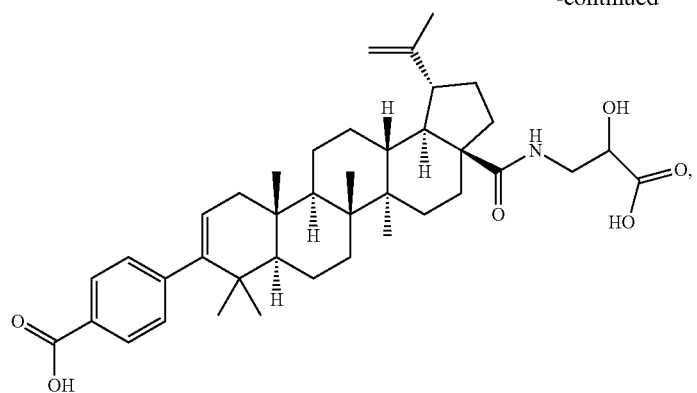
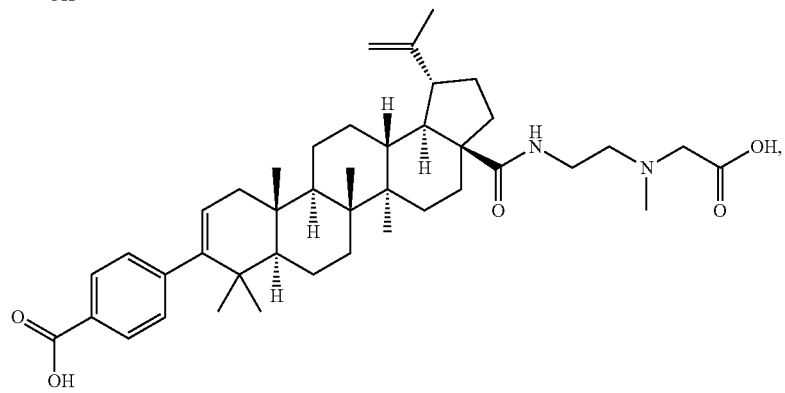
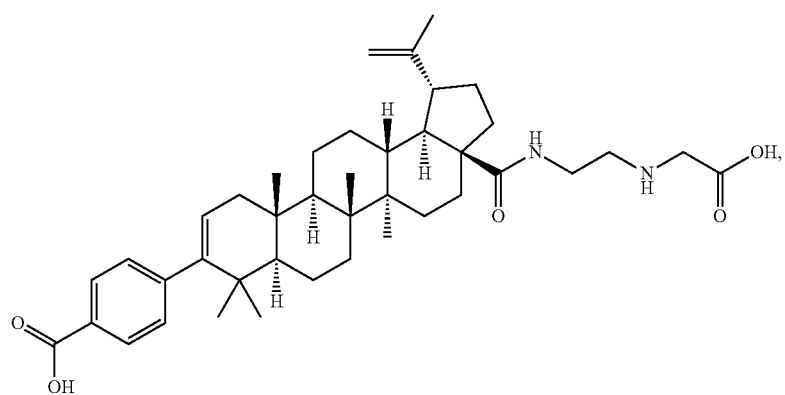
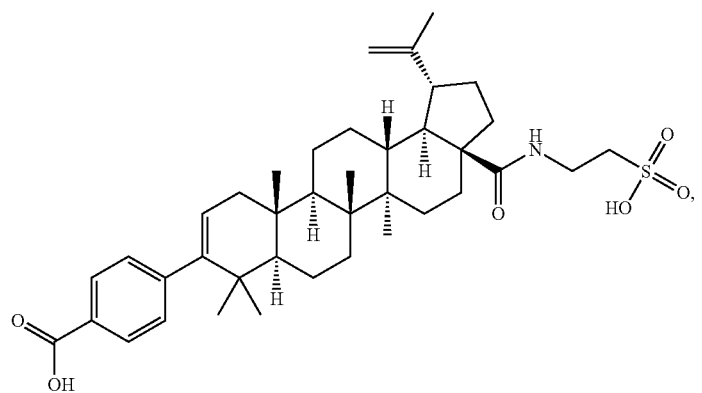

-continued
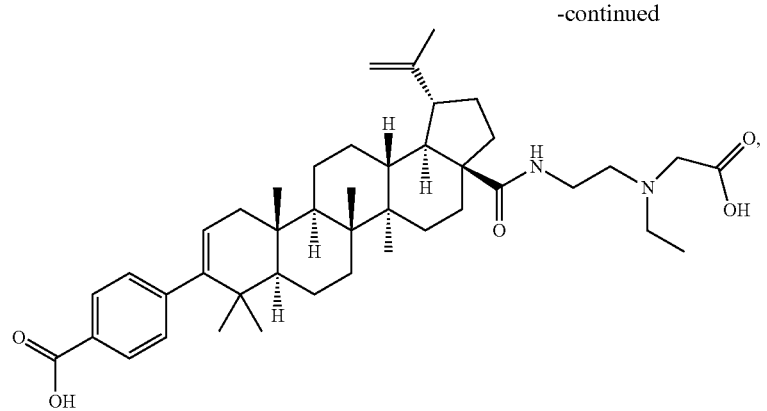
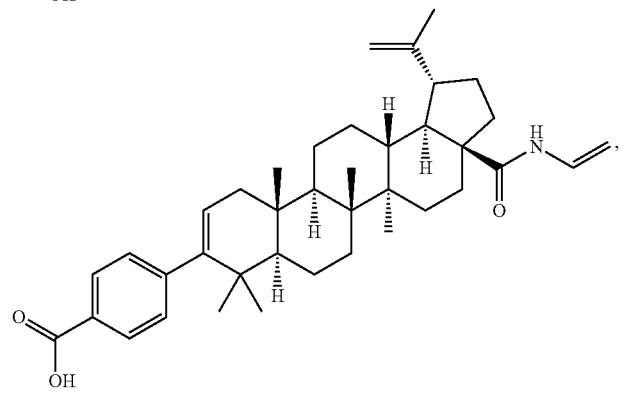
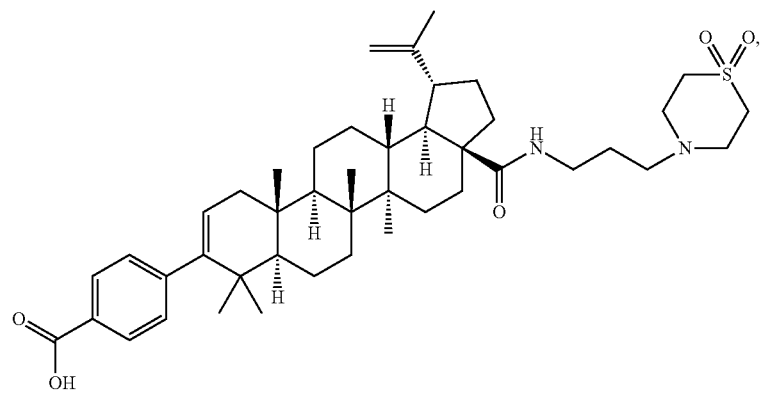
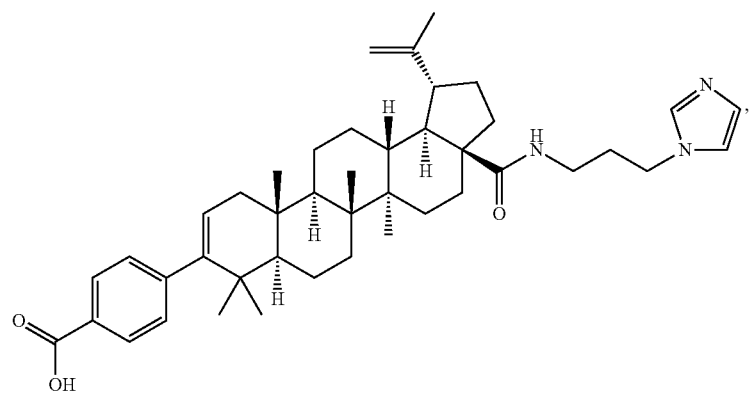

-continued
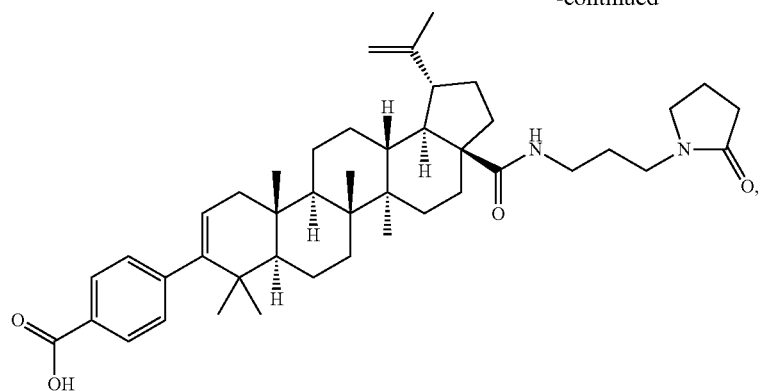
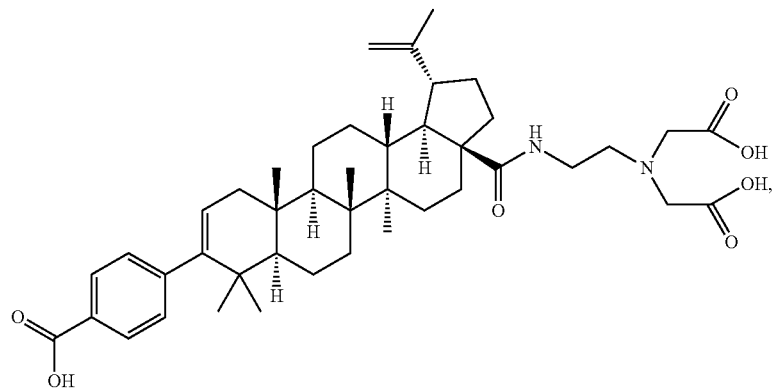
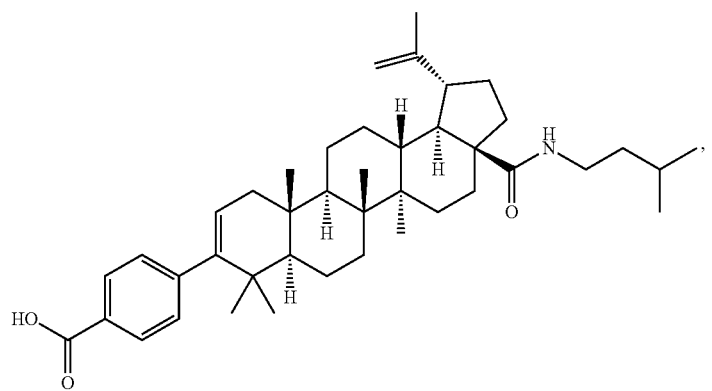
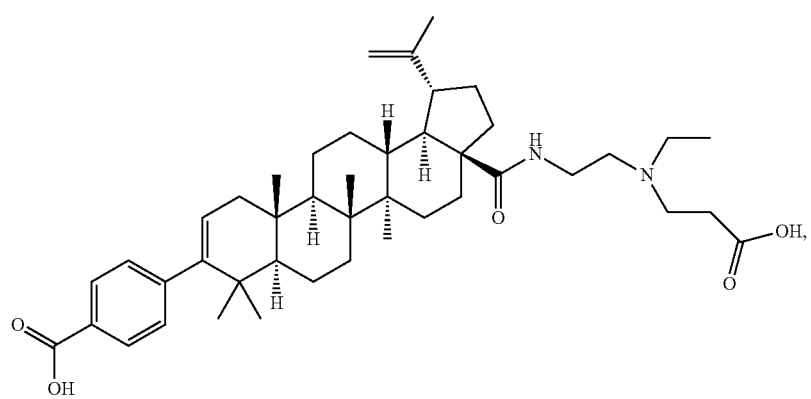

-continued
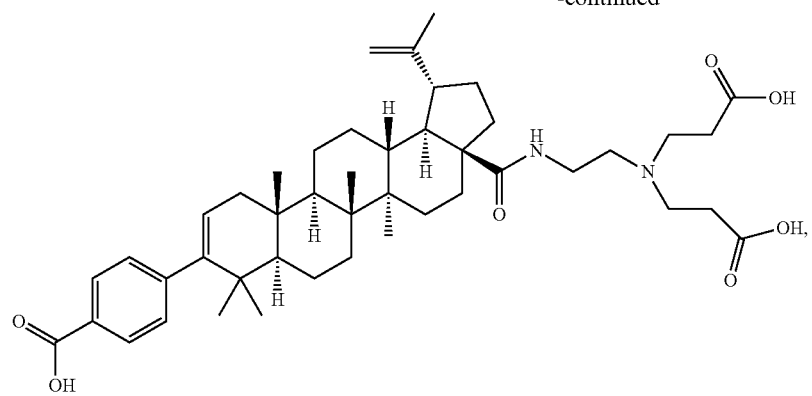
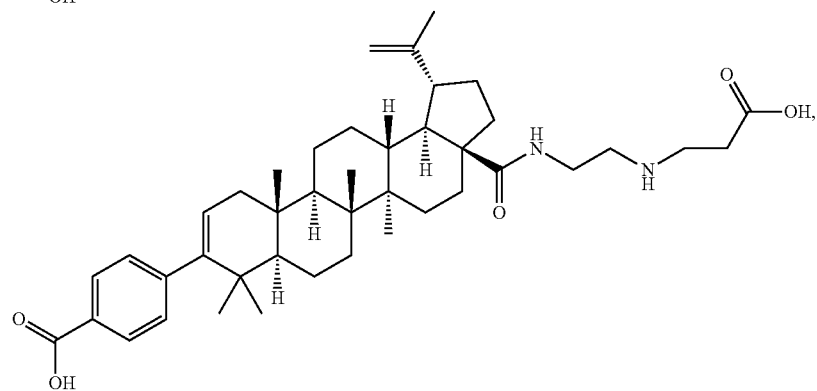
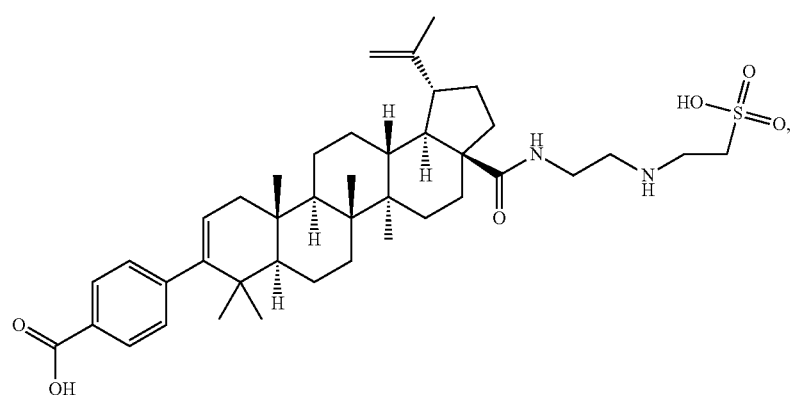
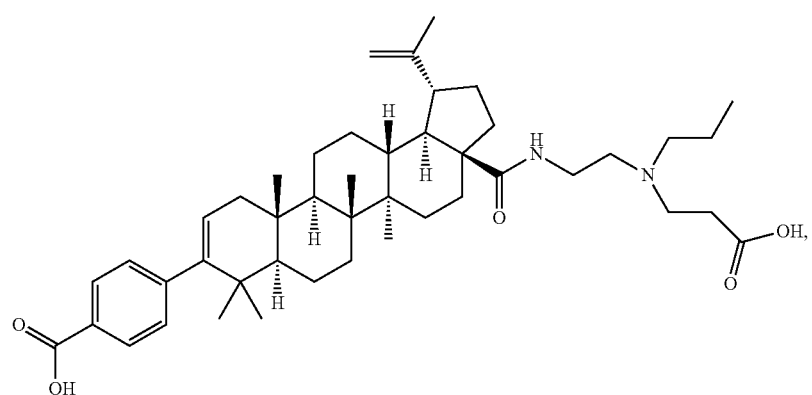

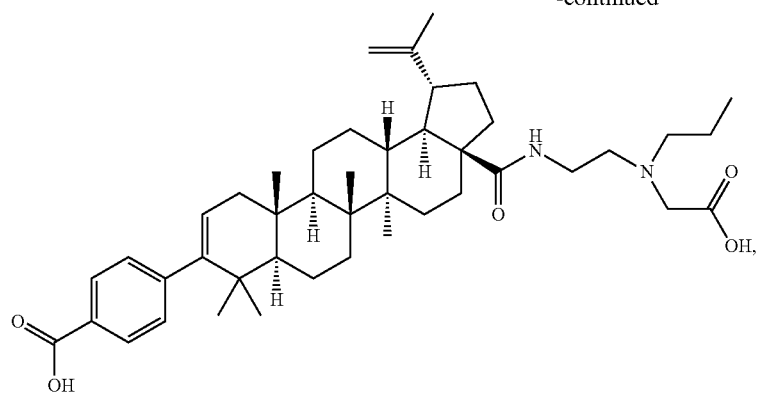
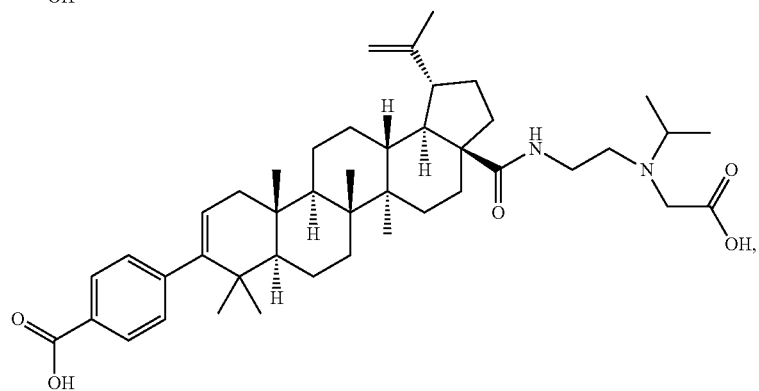
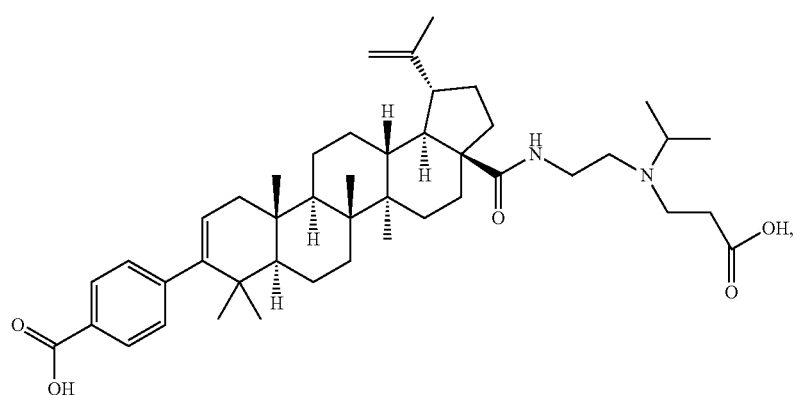
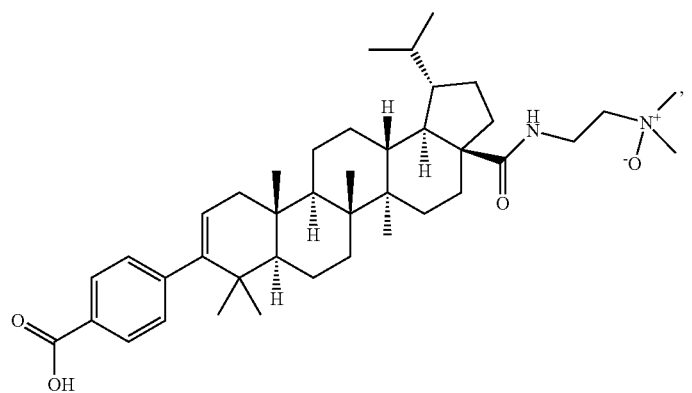

-continued
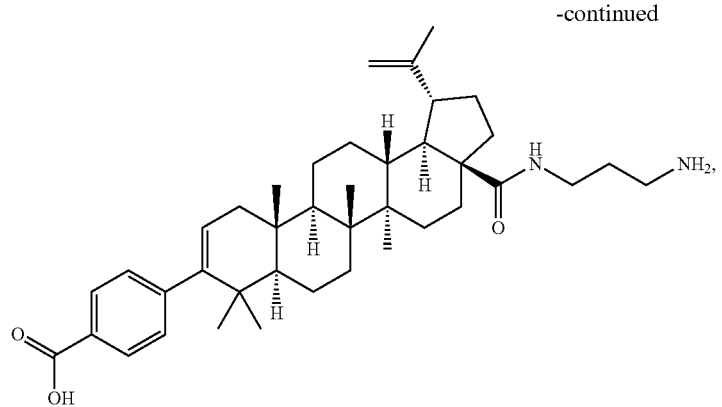
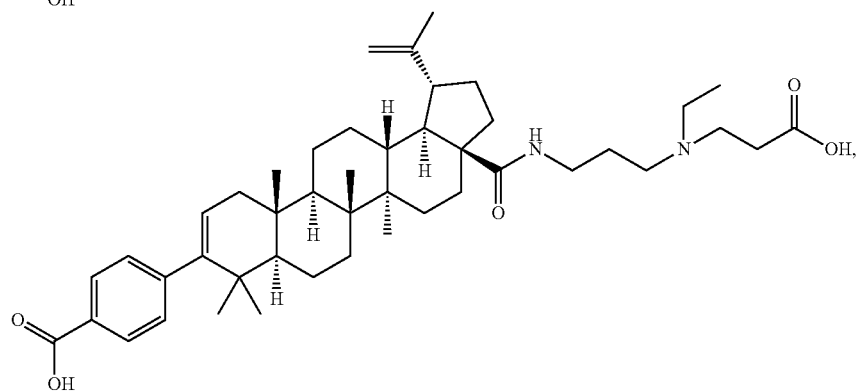
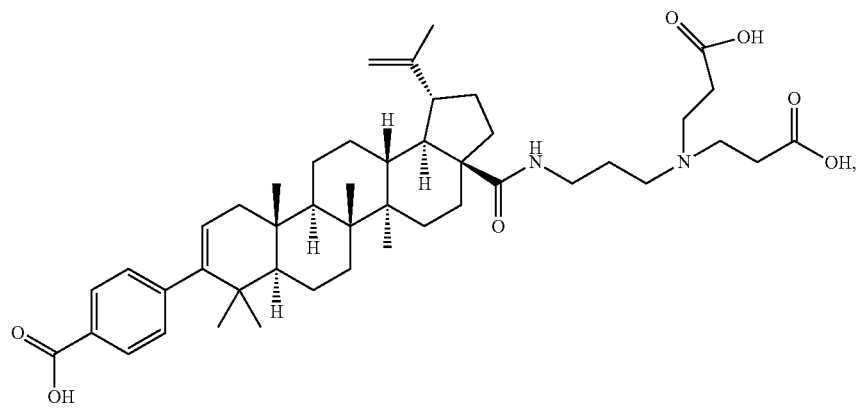
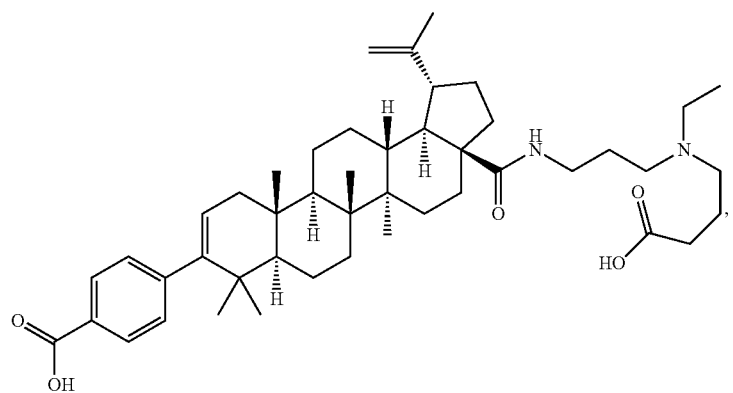

-continued
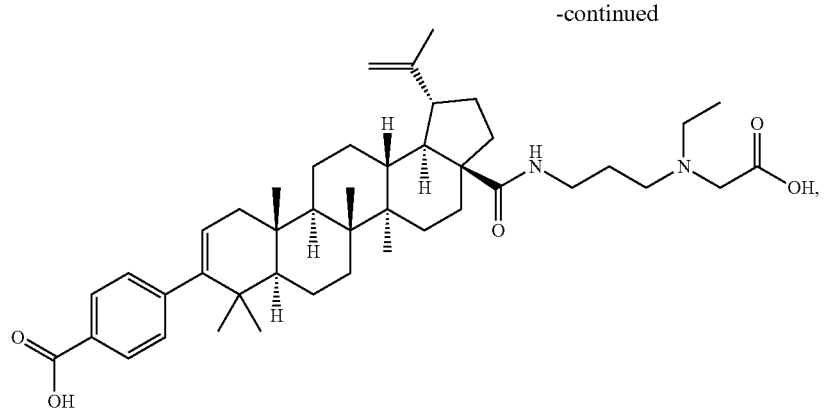
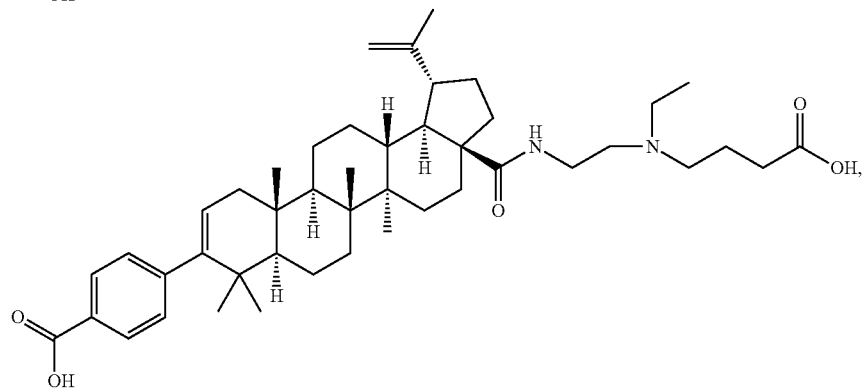
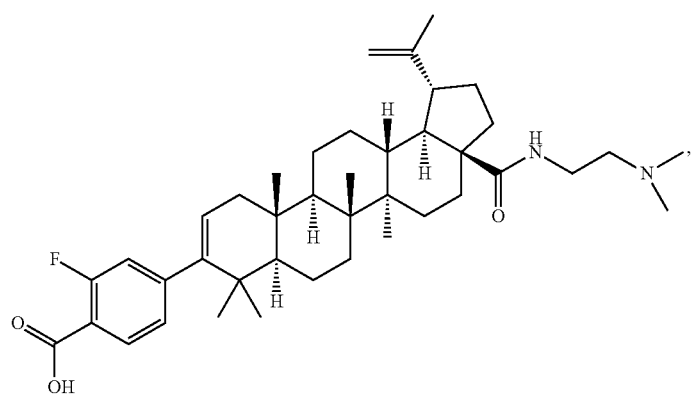
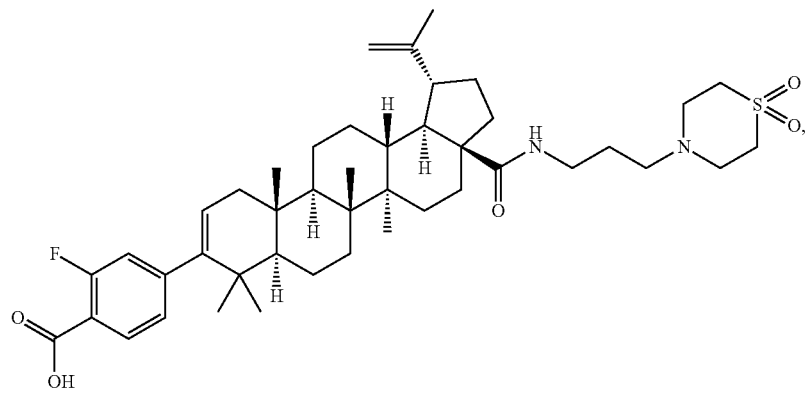

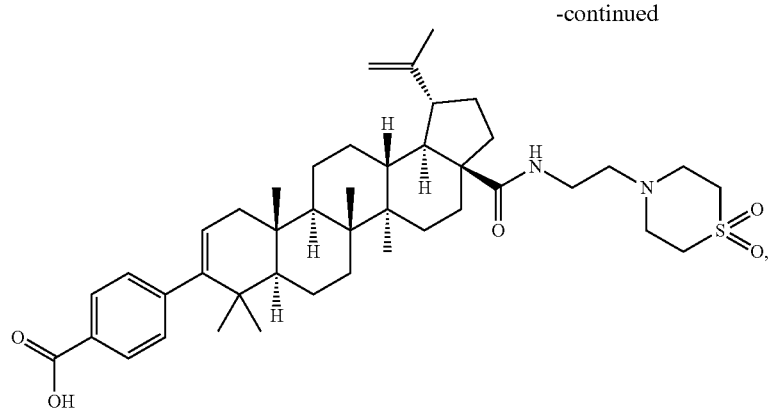
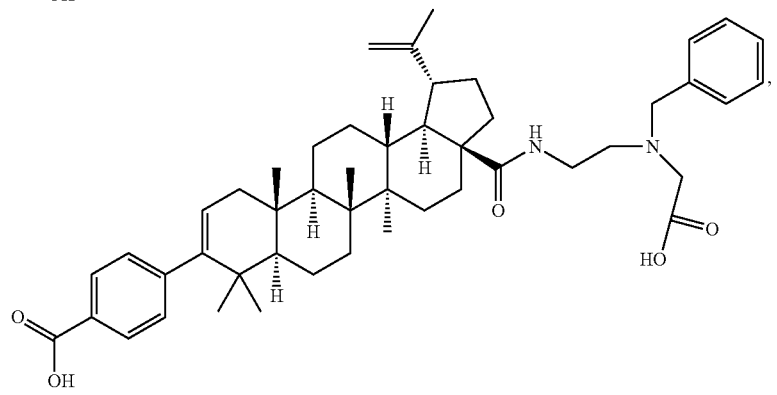
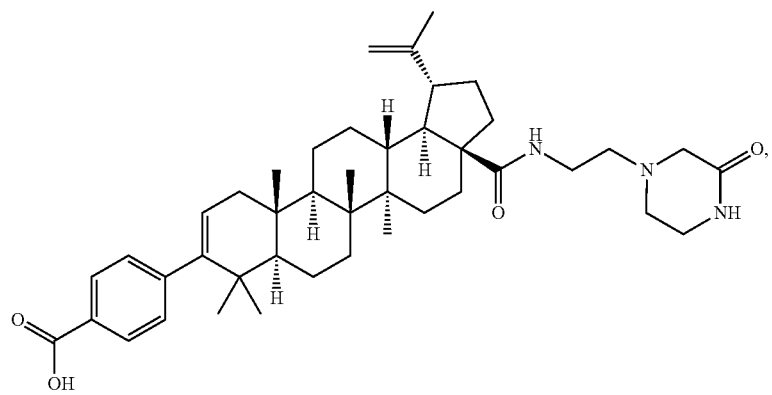
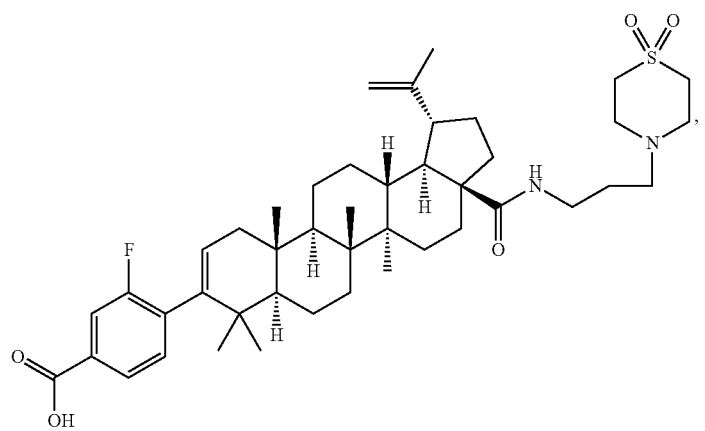

-continued
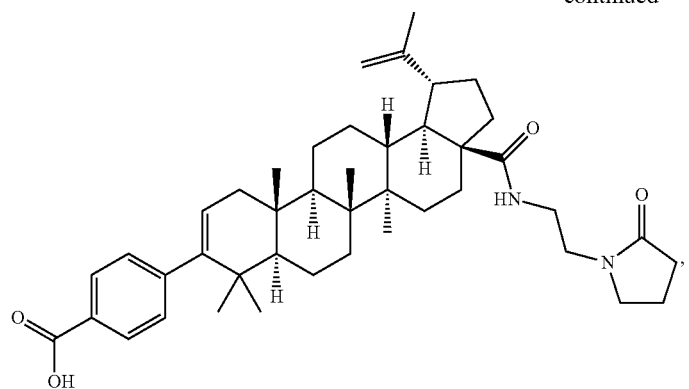
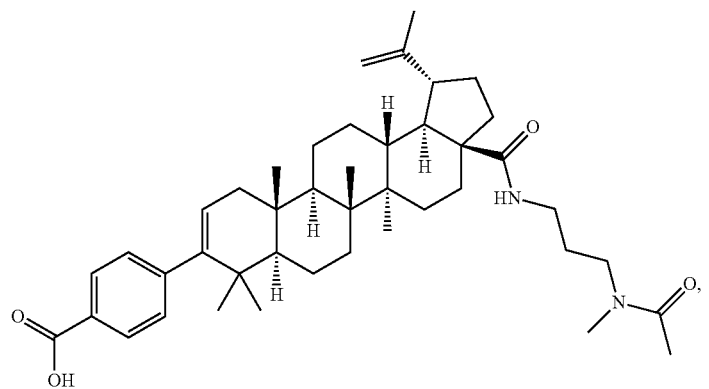
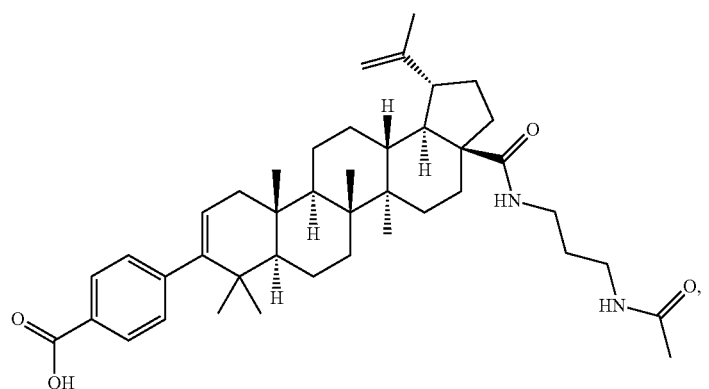
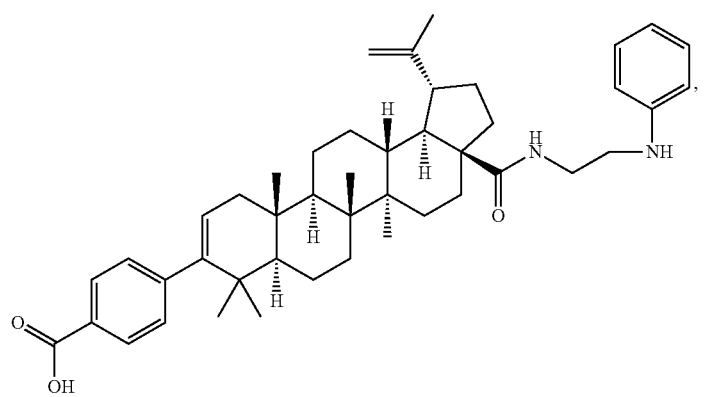

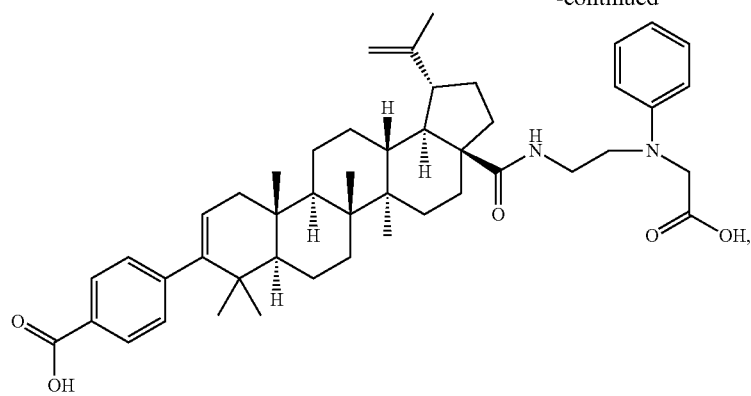
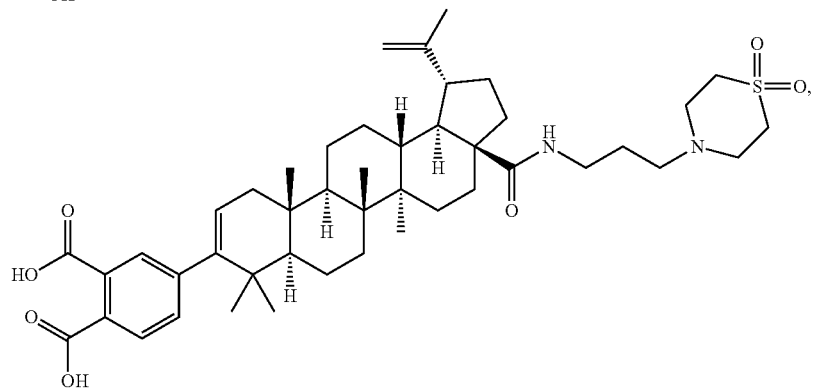
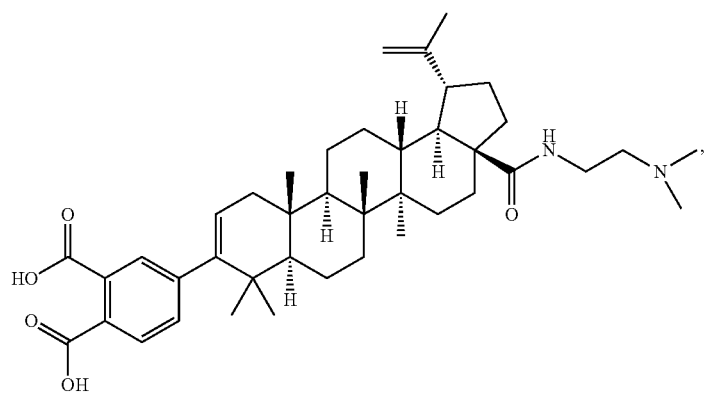
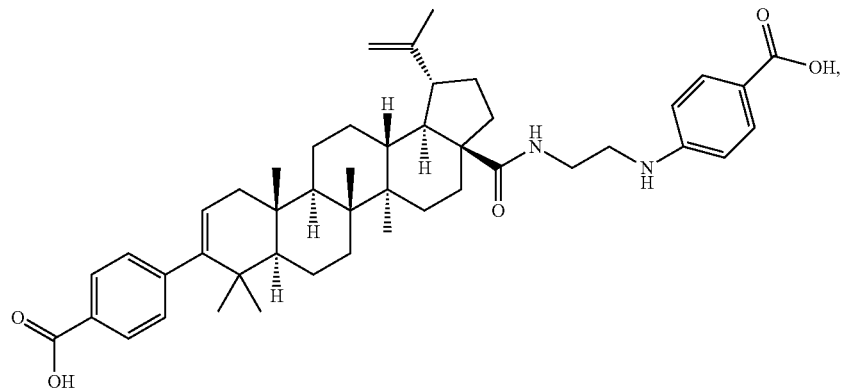

-continued
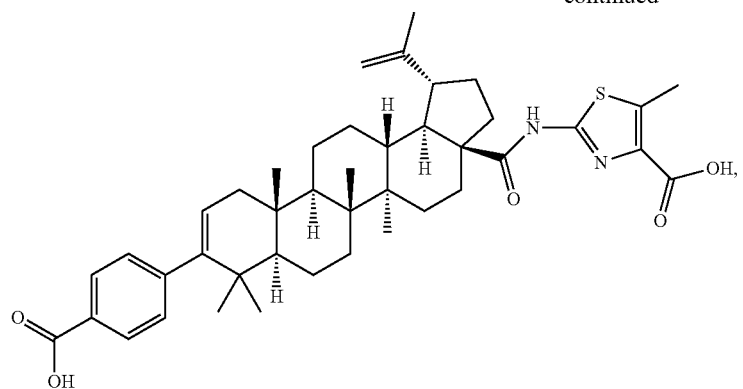
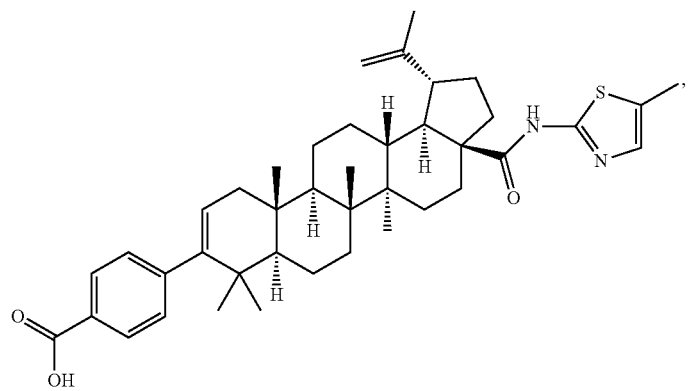
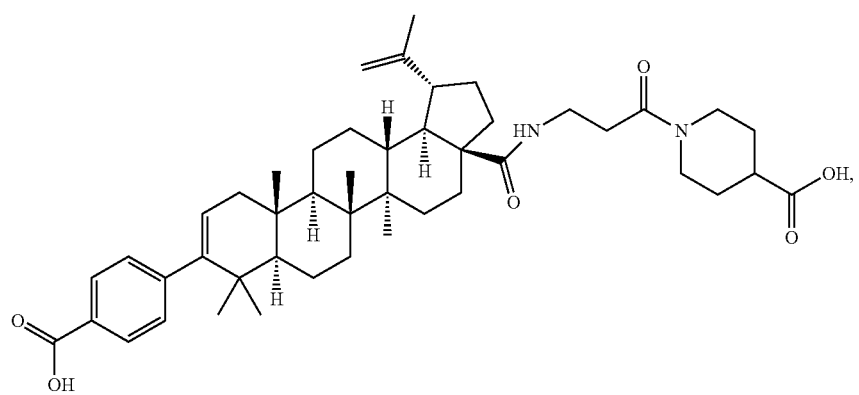
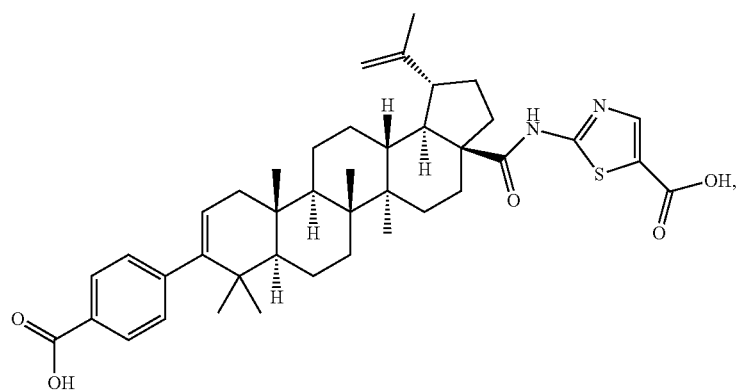

-continued
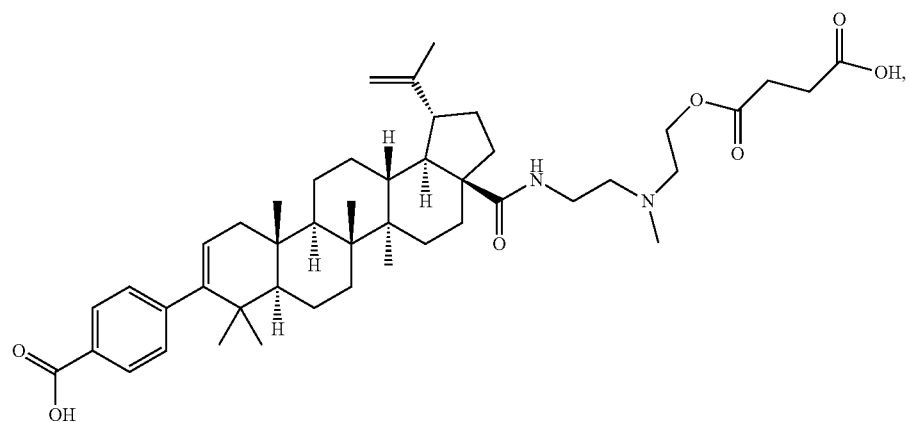
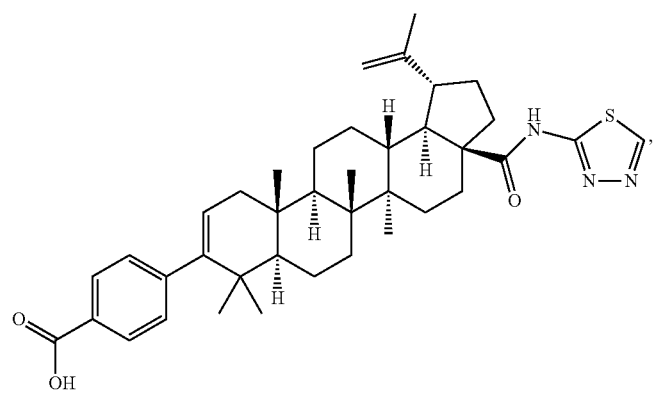
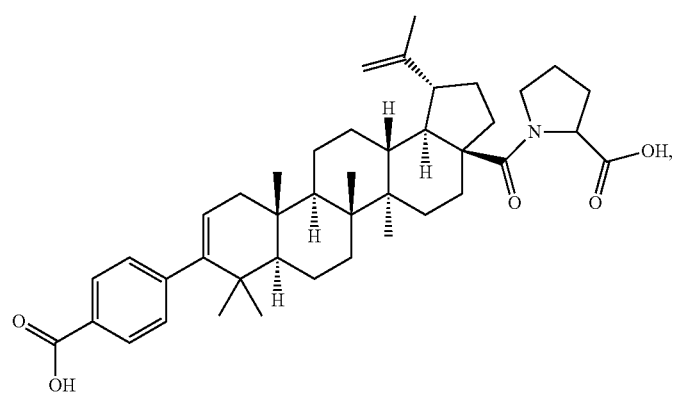
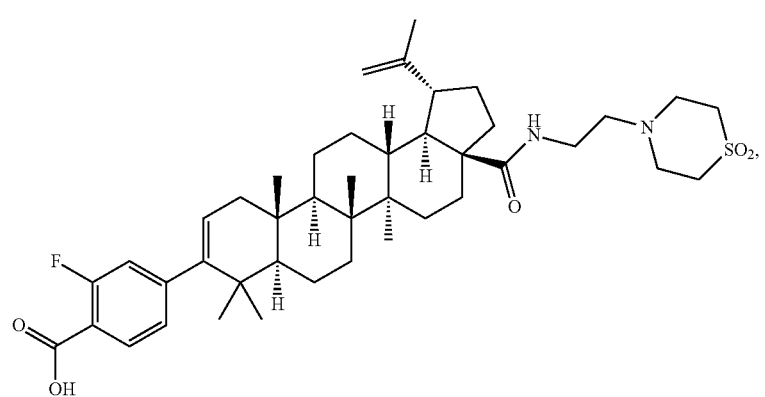

-continued
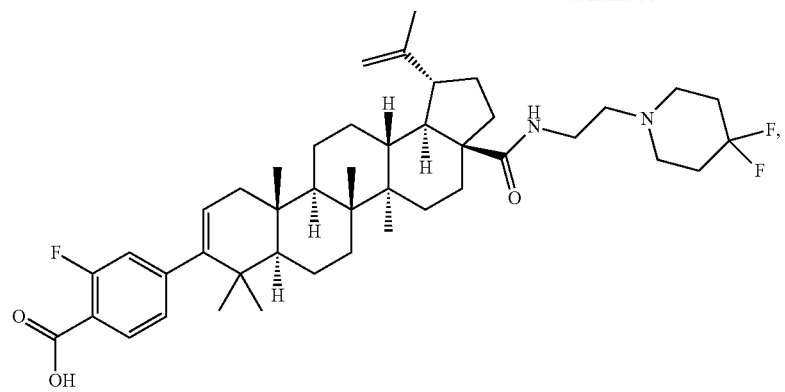
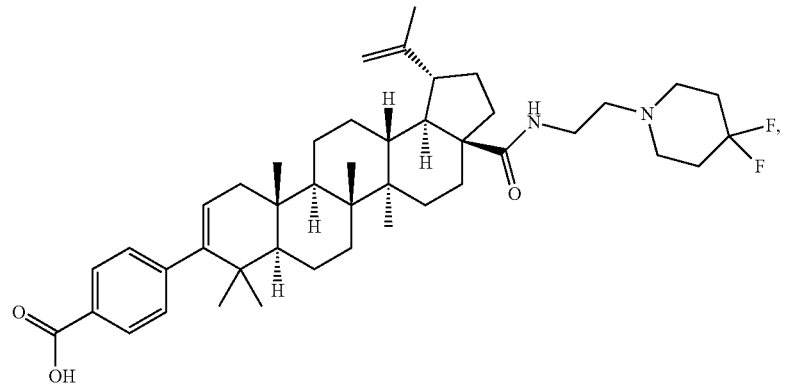
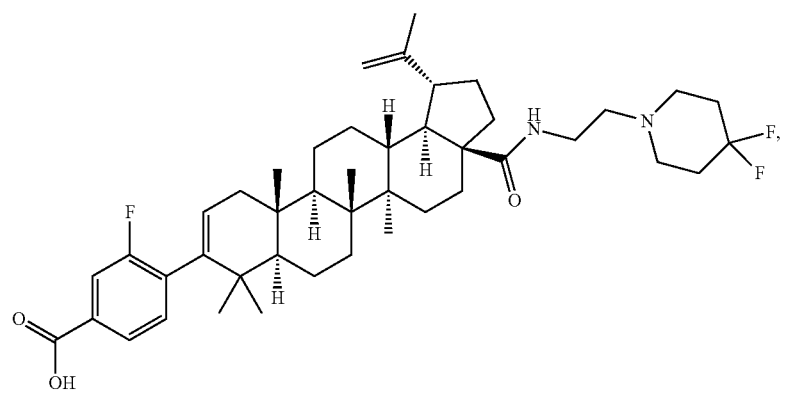
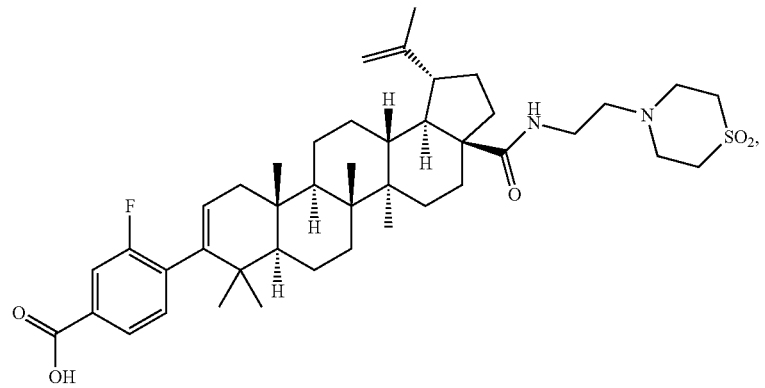

-continued
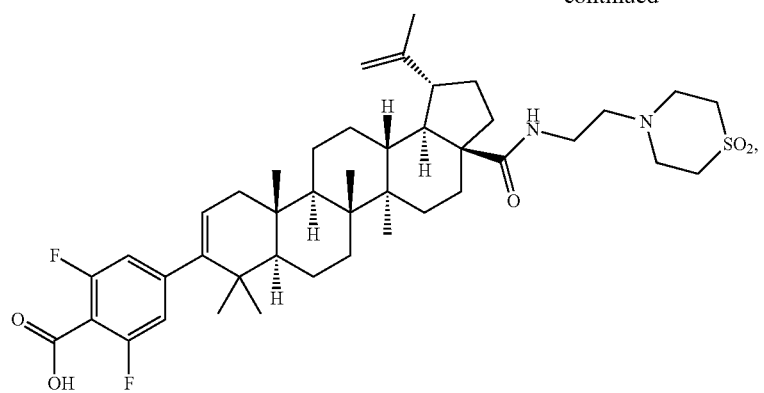
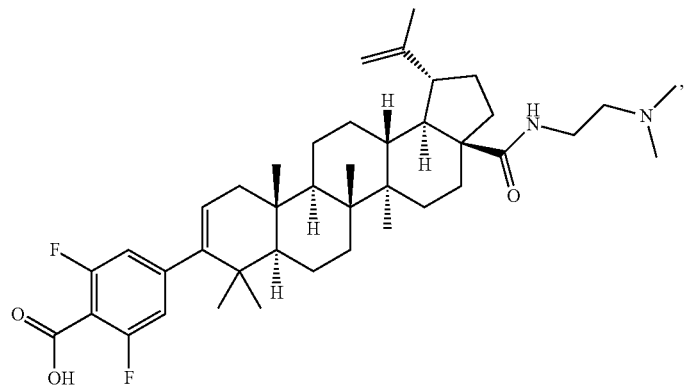
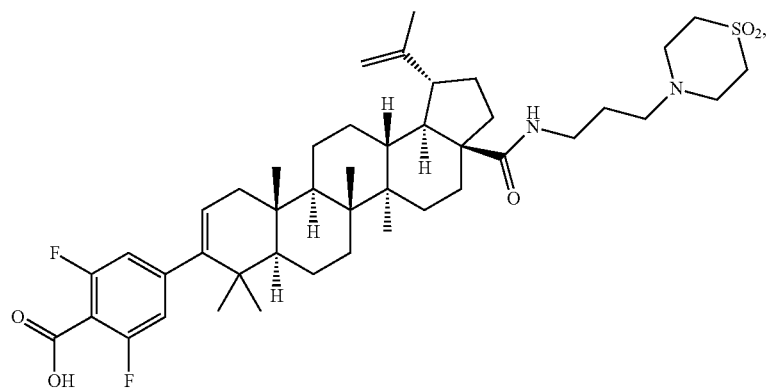
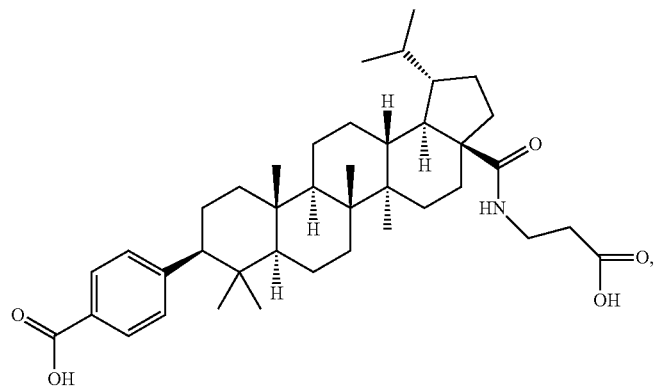

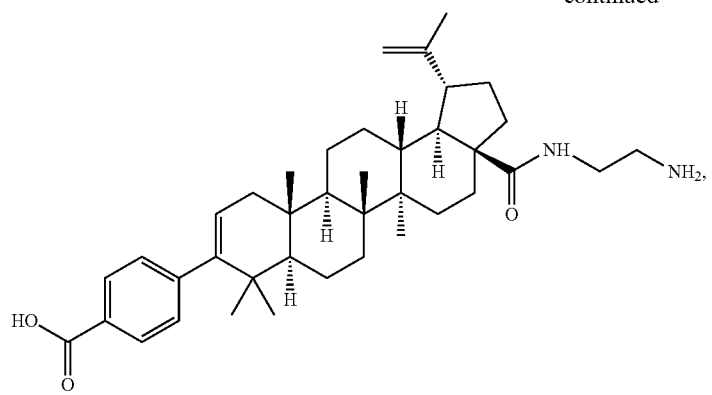
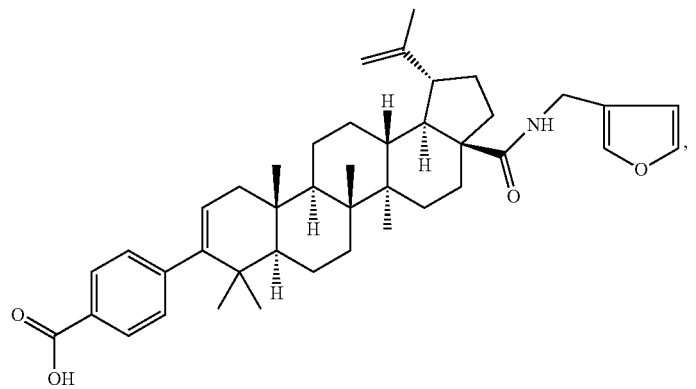
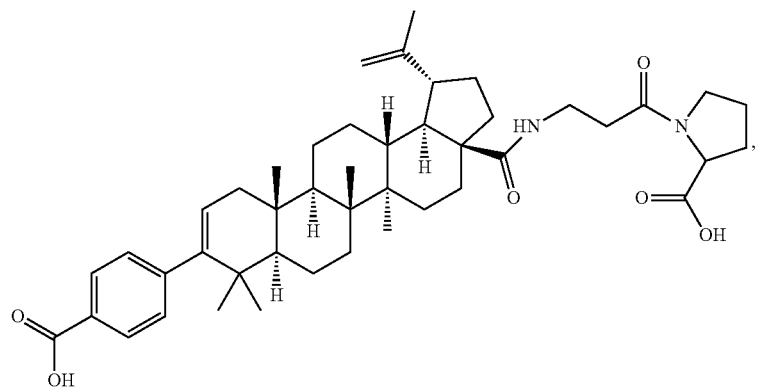
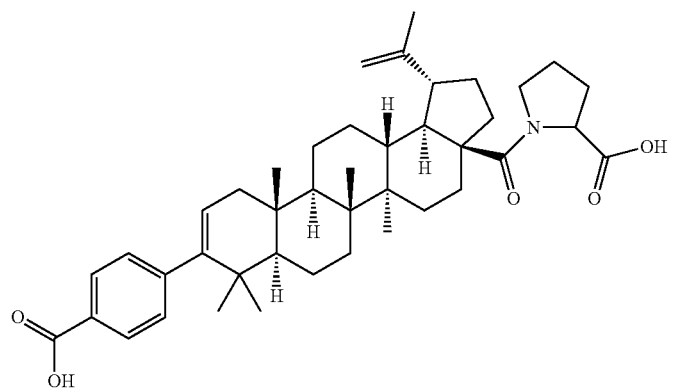

-continued
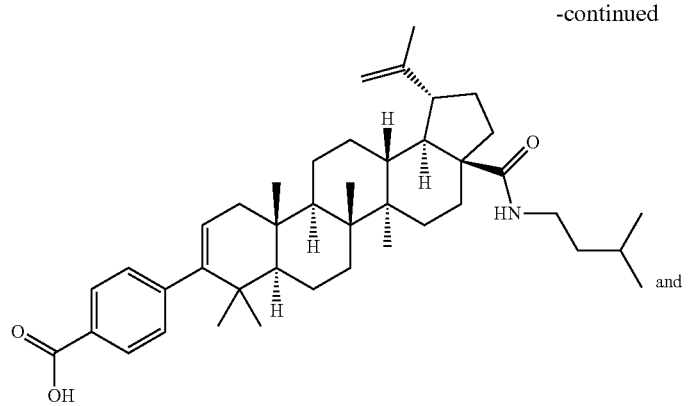
and
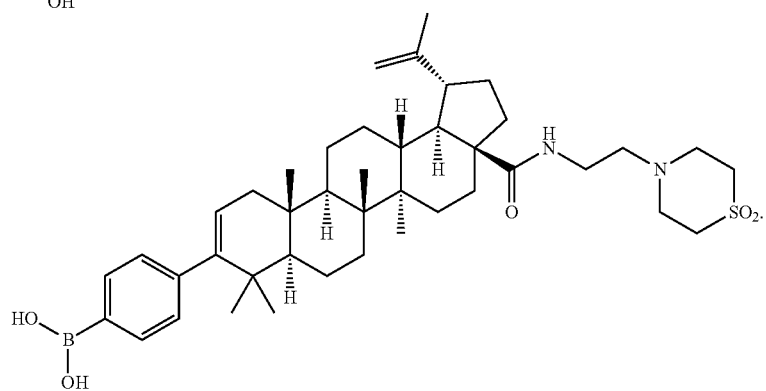
and pharmaceutically acceptable salts thereof.
12. A compound as claimed in claim 11, which is selected from the group consisting of:
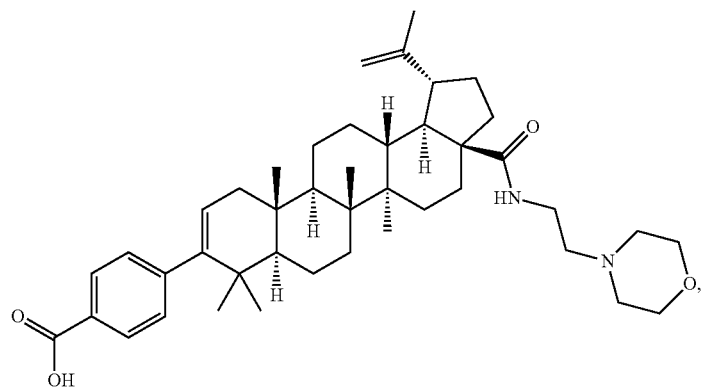
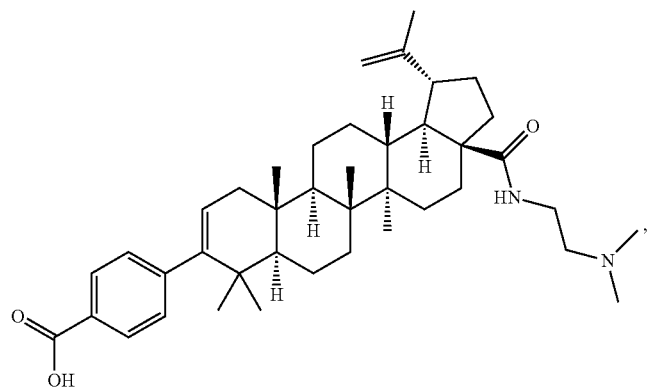

-continued
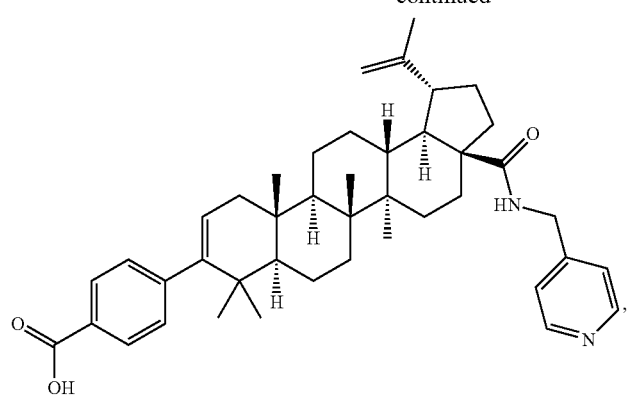
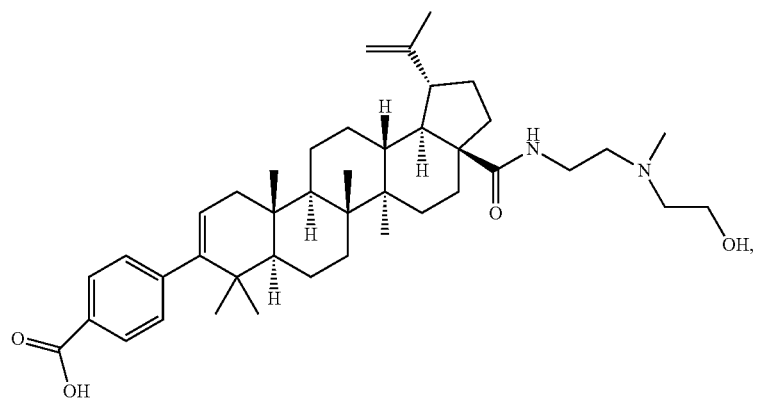
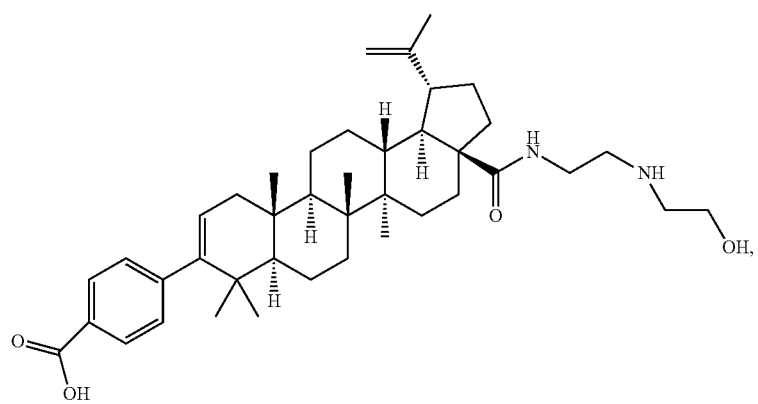
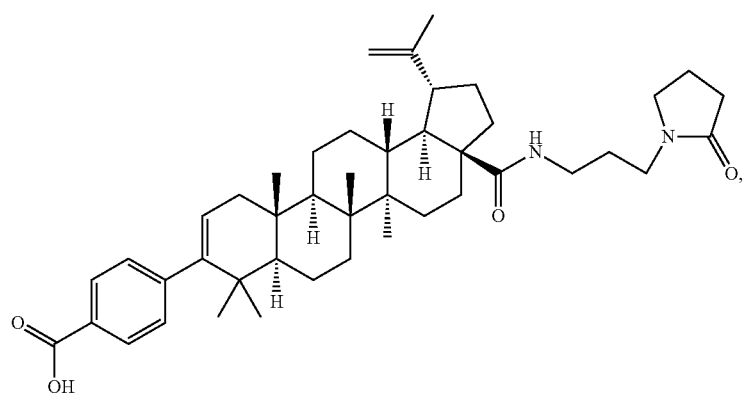

-continued
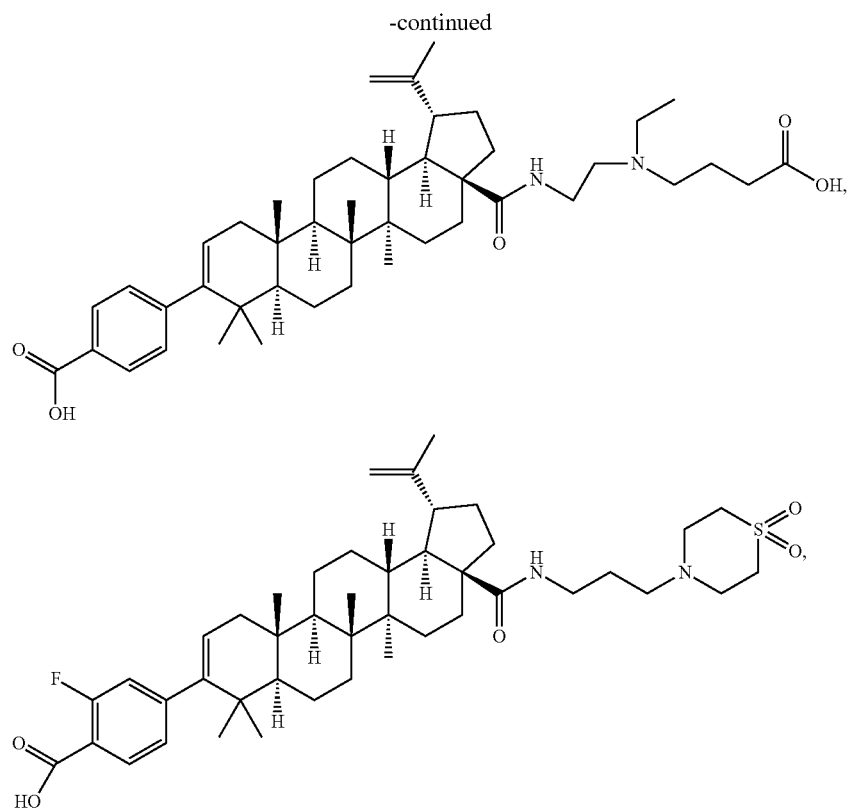
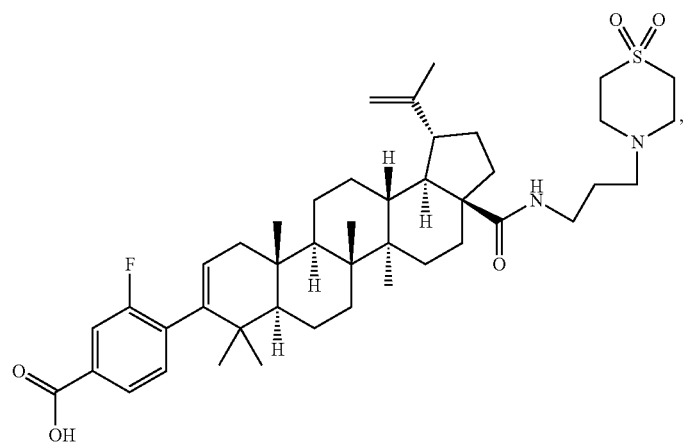
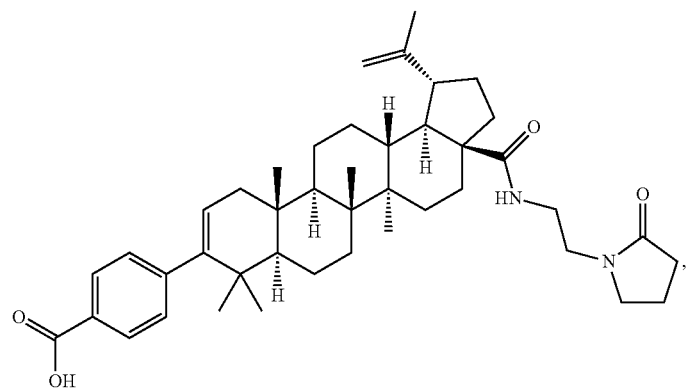

-continued
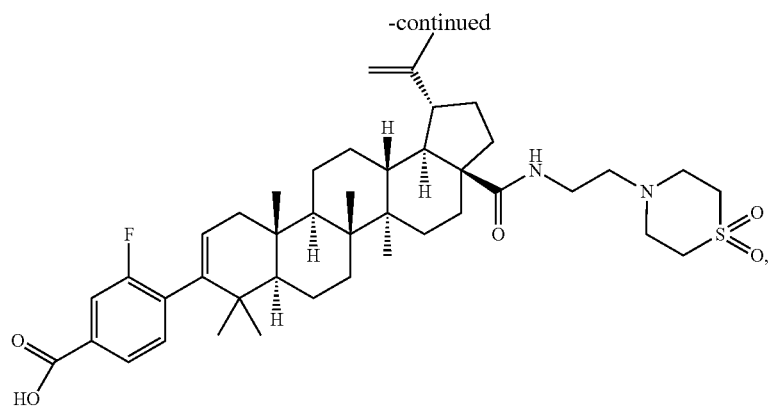
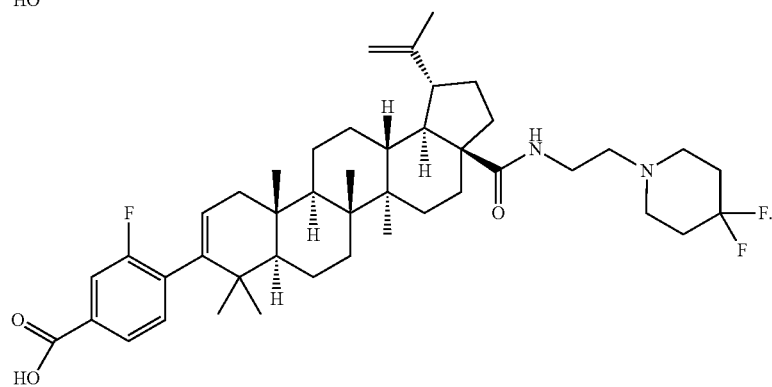
13. A compound which is selected from the group consisting of:
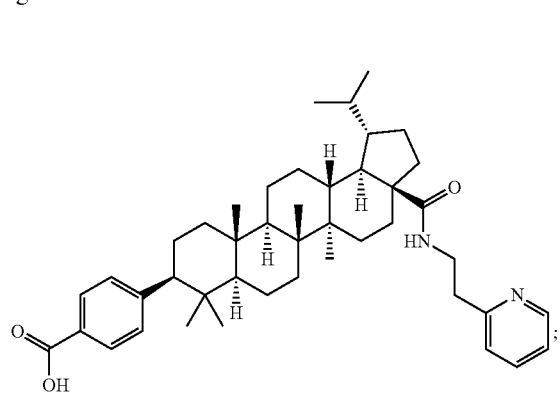
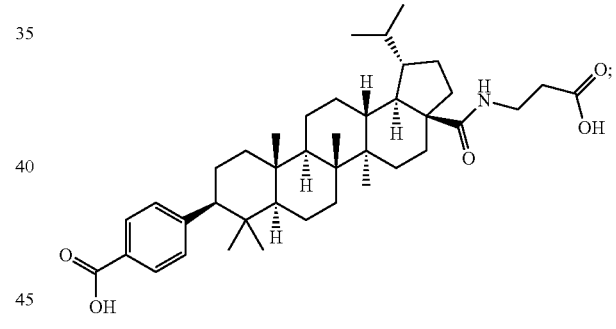
and pharmaceutically acceptable salts thereof.
14. The compound as claimed in claim 2, wherein X is a 5-membered heteroaryl ring and said compound is of the following formula:
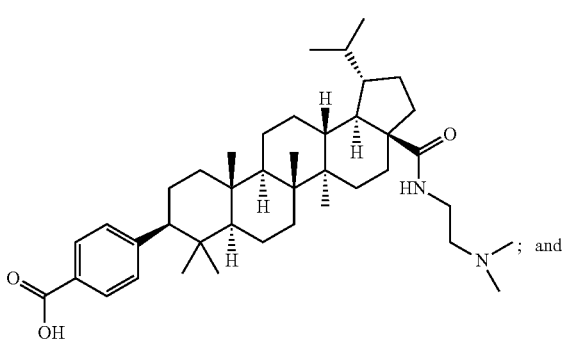
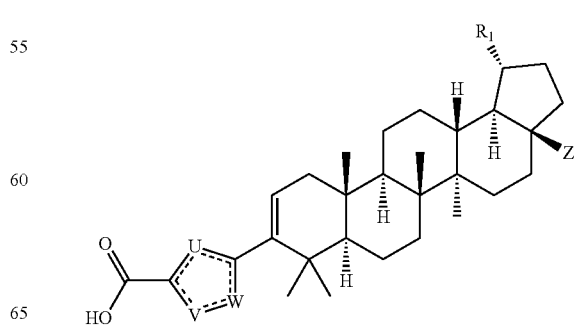

wherein each of U, V and W is selected from the group consisting of C, N, O and S, with the proviso that at least one of U, V and W is other than C.

15. The compound as claimed in claim 14, wherein X is selected from the group of thiophene, pyrazole, isoxazole, and oxadiazole groups.

16. The compound as claimed in claim 15, wherein X is thiophene.

17. The compound as claimed in claim 3, wherein X is a phenyl group and Y is —COOH in the para position according to Formula IIa below:

Formula IIa

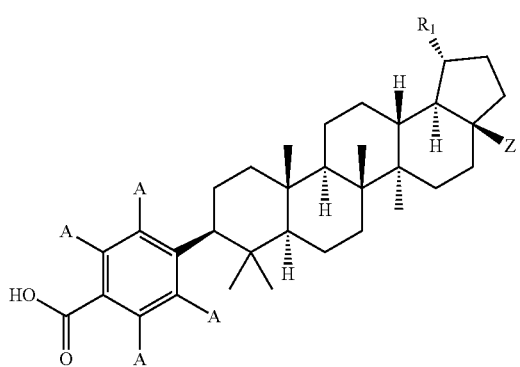

wherein A is at least one member selected from the group of —H, -halo, —OH, —$C_{1-3}$ alkyl and —$C_{1-3}$ alkoxy, and wherein -halo is selected from the group of -fluoro and -chloro.

18. The compound as claimed in claim 1, wherein said compound is a compound of formula III.

19. A compound which is selected from the group consisting of:

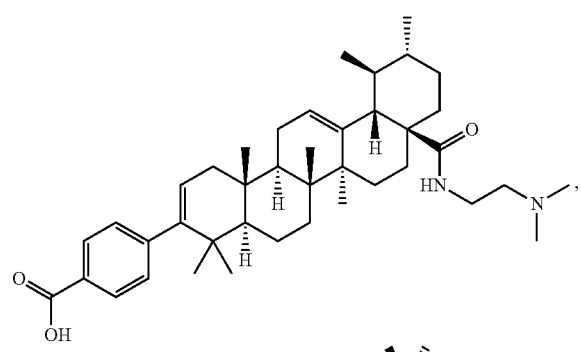

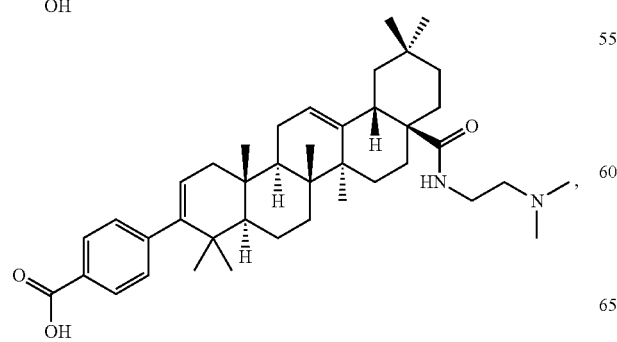

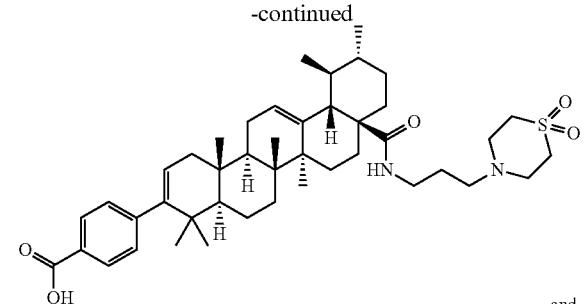

and

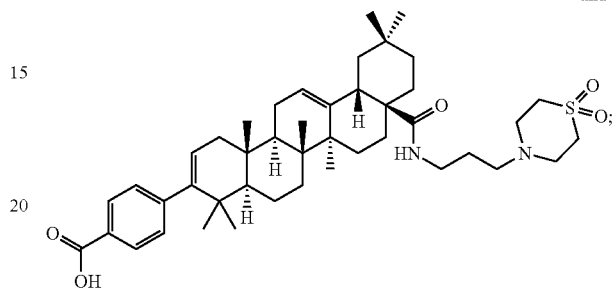

and pharmaceutically acceptable salts thereof.

20. A pharmaceutical composition which comprises an antiviral effective amount of one or more of the compounds as claimed in claim 1, together with one or more pharmaceutically acceptable carriers, excipients or diluents.

21. An intermediate compound which is selected from the group of:

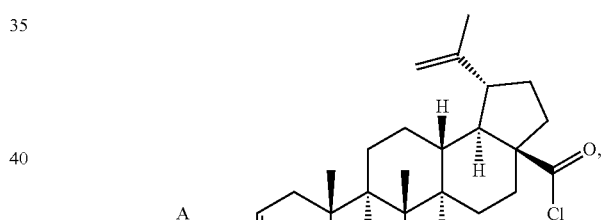

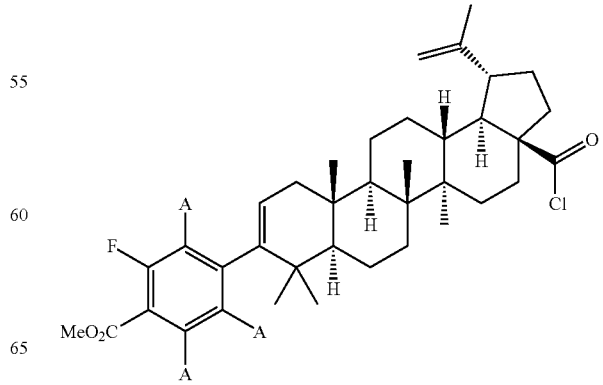

-continued

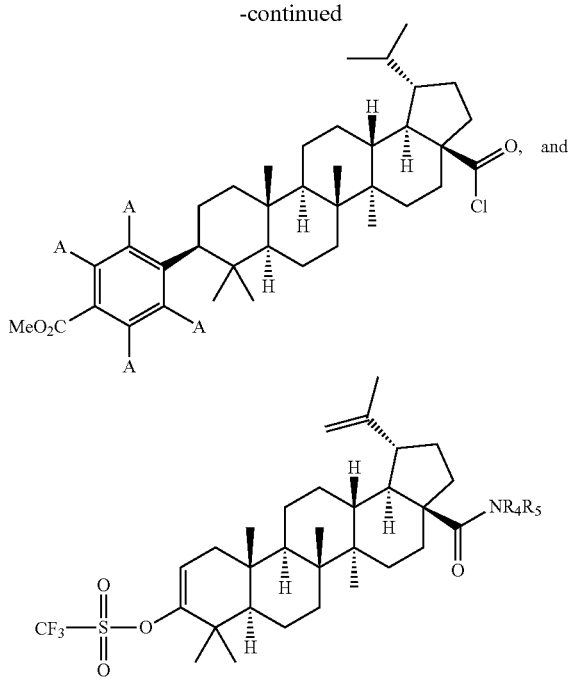

wherein A is selected from the group of —H, -halo, -alkyl, -alkoxy, —COOR$_2$ and -hydroxyl, wherein R$_2$ is —H, —C$_{1-6}$ alkyl, or substituted C$_{1-6}$ alkyl, wherein R$_4$ is selected from the group of H, C$_{1-6}$ alkyl, and C$_{1-6}$ alkyl-OH;

wherein R$_5$ is selected from the group of H, C$_{1-6}$ alkyl, substituted-alkyl, C$_{1-6}$ alkyl-R$_6$, C$_{2-6}$ alkyl-R$_7$, SO$_2$R$_8$, SO$_2$NR$_9$R$_{10}$;

wherein R$_6$ is selected from phenyl, substituted phenyl, heteroaryl, substituted heteroaryl, SO$_2$R$_{11}$, SO$_2$NR$_{12}$R$_{13}$, C$_{1-6}$ cycloalkyl, substituted C$_{1-6}$ cycloalkyl, SO$_3$H, COOR$_{14}$, C(O)NR$_{15}$R$_{16}$;

wherein R$_7$ is selected from OR$_{17}$, N$^+$(O$^-$)R$_{18}$R$_{19}$, NR$_{20}$(COR$_{21}$) and NR$_{22}$R$_{23}$;

wherein R$_8$, R$_9$, R$_{10}$, R$_{11}$, R$_{12}$, R$_{13}$, R$_{14}$, R$_{15}$, R$_{16}$, R$_{17}$, R$_{18}$, R$_{19}$, R$_{20}$, R$_{21}$ are each independently selected from the group of H, C$_{1-6}$ alkyl, substituted-alkyl, C$_{1-6}$ cycloalkyl and substituted C$_{1-6}$ cycloalkyl;

wherein R$_{22}$ and R$_{23}$ are selected from the group of H, C$_{1-6}$ alkyl, substituted-alkyl, C$_{1-6}$ alkyl-R$_{32}$, C$_{2-6}$ alkyl-R$_{33}$, SO$_2$R$_8$, SO$_2$NR$_9$R$_{10}$;

wherein R$_{32}$ is selected from phenyl, substituted phenyl, heteroaryl, substituted heteroaryl, SO$_2$R$_{11}$, SO$_2$NR$_{12}$R$_{13}$, C$_{1-6}$ cycloalkyl, substituted C$_{1-6}$ cycloalkyl, SO$_3$H, COOR$_{14}$, C(O)NR$_{15}$R$_{16}$, and wherein R$_{33}$ is selected from OR$_{17}$, N$^+$(O$^-$)R$_{18}$R$_{19}$, NR$_{20}$(COR$_{21}$) and NR$_9$R$_{10}$.

22. An intermediate compound with the structure:

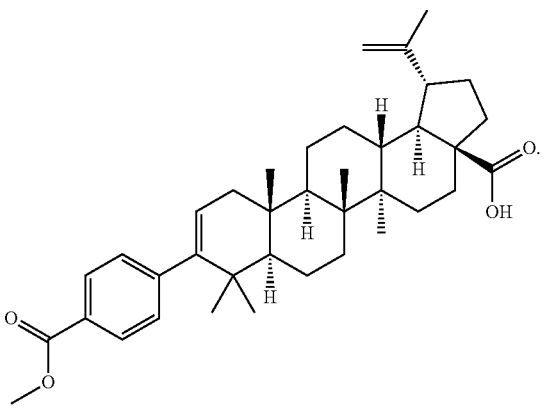

* * * * *